US011008316B2

(12) United States Patent
Bourque et al.

(10) Patent No.: US 11,008,316 B2
(45) Date of Patent: May 18, 2021

(54) GLUCOSYLCERAMIDE SYNTHASE INHIBITORS

(71) Applicant: Genzyme Corporation, Cambridge, MA (US)

(72) Inventors: Elyse Bourque, Blaine, WA (US); Mario A. Cabrera-Salazar, Brighton, MA (US); Cassandra Celatka, Hull, MA (US); Seng H. Cheng, Natick, MA (US); Bradford Hirth, Littleton, MA (US); Andrew Good, Wallingford, CT (US); Katherine Jancsics, Wilmington, MA (US); John Marshall, Charlestown, MA (US); Markus Metz, Encinitas, CA (US); Ronald K. Scheule, Hopkinton, MA (US); Renato Skerlj, W. Newton, MA (US); Yibin Xiang, Dracut, MA (US); Zhong Zhao, Wayland, MA (US); John Leonard, Manchester, NH (US); Thomas Natoli, Revere, MA (US); Elina Makino, Winchester, MA (US); Herve Husson, Boston, MA (US); Oxana Beskrovnaya, Southborough, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/490,385

(22) Filed: Apr. 18, 2017

(65) Prior Publication Data

US 2018/0065957 A1 Mar. 8, 2018

Related U.S. Application Data

(63) Continuation of application No. 14/427,275, filed as application No. PCT/US2013/058896 on Sep. 10, 2013, now abandoned.

(60) Provisional application No. 61/699,714, filed on Sep. 11, 2012.

(51) Int. Cl.

| | | |
|---|---|---|
| *C07D 453/02* | (2006.01) | |
| *C07D 471/08* | (2006.01) | |
| *A61K 31/439* | (2006.01) | |
| *A61K 31/496* | (2006.01) | |
| *A61K 31/497* | (2006.01) | |
| *A61K 31/506* | (2006.01) | |
| *A61K 31/5377* | (2006.01) | |
| *A61K 31/55* | (2006.01) | |
| *A61K 31/551* | (2006.01) | |
| *A61K 45/06* | (2006.01) | |

(52) U.S. Cl.
CPC .......... *C07D 453/02* (2013.01); *A61K 31/439* (2013.01); *A61K 31/496* (2013.01); *A61K 31/497* (2013.01); *A61K 31/506* (2013.01); *A61K 31/5377* (2013.01); *A61K 31/55* (2013.01); *A61K 31/551* (2013.01); *A61K 45/06* (2013.01); *C07D 471/08* (2013.01)

(58) Field of Classification Search
CPC .................................................. C07D 453/02
See application file for complete search history.

(56) References Cited

U.S. PATENT DOCUMENTS

| | | | |
|---|---|---|---|
| 3,119,742 A | 1/1964 | Heimlich et al. | |
| 3,492,397 A | 1/1970 | Peters et al. | |
| 3,538,214 A | 11/1970 | Polli et al. | |
| 4,060,598 A | 11/1977 | Groppenbacher et al. | |
| 4,173,626 A | 11/1979 | Dempski et al. | |
| 4,593,034 A | 6/1986 | Munson, Jr. et al. | |
| 4,983,600 A | 1/1991 | Ward et al. | |
| 5,025,022 A * | 6/1991 | Naylor ................. | A61K 31/435 514/305 |
| 5,236,838 A | 8/1993 | Rasmussen et al. | |
| 5,272,071 A | 12/1993 | Chappel | |
| 5,549,892 A | 8/1996 | Friedman et al. | |
| 5,968,502 A | 10/1999 | Treco et al. | |
| 6,066,626 A | 5/2000 | Yew et al. | |

(Continued)

FOREIGN PATENT DOCUMENTS

| | | |
|---|---|---|
| EP | 0382687 | 8/1990 |
| EP | 0505778 B1 | 10/1995 |

(Continued)

OTHER PUBLICATIONS

Aerts J.M., et al., "Elevated Globotriaosylsphingosine is a Hallmark of Fabry Disease," PNAS, Proceedings of the National Academy of Sciences, 2008, vol. 105 (8), pp. 2812-2817.

(Continued)

*Primary Examiner* — Brian E Mcdowell
(74) *Attorney, Agent, or Firm* — Hoxie & Associates LLC

(57) ABSTRACT

The invention relates to inhibitors of glucosylceramide synthase (GCS), such as Compound of Formula I, shown below, as defined herein, useful for the treatment of metabolic diseases, such as lysosomal storage diseases, either alone or in combination with enzyme replacement therapy, cystic disease and for the treatment of cancer.

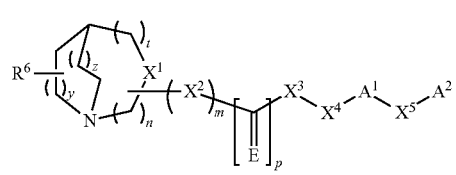

2 Claims, 3 Drawing Sheets

(56) References Cited

U.S. PATENT DOCUMENTS

| | | | |
|---|---|---|---|
| 6,468,998 | B1 | 10/2002 | Kuroita et al. |
| 6,987,106 | B1 | 1/2006 | Gallet et al. |
| 7,115,629 | B2 | 10/2006 | Farrerons Gallemi et al. |
| 7,138,410 | B2 | 11/2006 | Luithle et al. |
| 2004/0002513 | A1 | 1/2004 | Mazurov et al. |
| 2006/0058349 | A1 | 3/2006 | Ali et al. |
| 2009/0131470 | A1 | 5/2009 | Walmsley et al. |
| 2009/0163500 | A1 | 6/2009 | Lingwood et al. |
| 2011/0052559 | A1 | 3/2011 | Schuchman et al. |

FOREIGN PATENT DOCUMENTS

| | | |
|---|---|---|
| EP | 0747355 | 12/1996 |
| EP | 1300407 | 4/2003 |
| EP | 1231212 | 12/2006 |
| EP | 2119716 A1 | 11/2009 |
| EP | 2154136 | 2/2010 |
| JP | H08-198751 | 6/1996 |
| JP | 2002302490 | 10/2002 |
| JP | 2003-267977 | 9/2003 |
| WO | WO 1995/021820 | 8/1995 |
| WO | 199717348 | 5/1997 |
| WO | 98/04517 | 2/1998 |
| WO | WO 2000/026186 | 5/2000 |
| WO | WO 2000/058311 | 10/2000 |
| WO | WO 2001/085727 | 11/2001 |
| WO | 2002/015662 A2 | 2/2002 |
| WO | 2002/016356 A2 | 2/2002 |
| WO | WO 2003/078431 | 9/2003 |
| WO | 2004000840 | 12/2003 |
| WO | WO 2004/007453 | 1/2004 |
| WO | 2004/016617 A1 | 2/2004 |
| WO | WO 2004/011430 | 5/2004 |
| WO | WO 2004/052365 | 6/2004 |
| WO | 2004/056745 A2 | 7/2004 |
| WO | 2005/061510 A1 | 7/2005 |
| WO | 2005068426 A1 | 7/2005 |
| WO | 2005073183 | 8/2005 |
| WO | 2006002375 | 1/2006 |
| WO | 2006053043 A2 | 5/2006 |
| WO | WO 2006/134318 | 12/2006 |
| WO | 2007038367 A1 | 4/2007 |
| WO | 2007083978 A1 | 7/2007 |
| WO | 2007/100430 A2 | 9/2007 |
| WO | 2008/156721 A1 | 12/2008 |
| WO | 2010/015324 A1 | 2/2010 |
| WO | WO 2010/014554 | 2/2010 |
| WO | 2010091104 A1 | 8/2010 |
| WO | 2010091164 A1 | 8/2010 |
| WO | 2010121963 A1 | 10/2010 |
| WO | 2011006074 A1 | 1/2011 |
| WO | 2011073263 A1 | 6/2011 |
| WO | 2012129084 A2 | 9/2012 |
| WO | 2014/041425 A1 | 3/2014 |

OTHER PUBLICATIONS

Auray-Blais C., et al., "How Well Does Urinary Lyso-gb3 Function as a Biomarker in Fabry Disease?," Clinica Chimica Acta, 2010, vol. 411 (23-24), pp. 1906-1914.
Barton N.W., et al., "Replacement Therapy for Inherited Enzyme Deficiency—Macrophage-Targeted Glucocerebrosidase for Gaucher'S Disease," The New England Journal of Medicine, 1991, vol. 324 (21), pp. 1464-1470.
Beniaminovitz A., et al., "Prevention of Rejection in Cardiac Transplantation by Blockade of the Interleukin-2 Receptor with a Monoclonal Antibody," The New England Journal of Medicine, 2000, vol. 342 (9), pp. 613-619.
Berard J.L., et al., "A Review of Interleukin-2 Receptor Antagonists in Solid Organ Transplantation," Pharmacotherapy, 1999, vol. 19 (10), pp. 1127-1137.
Branco L., et al., "Selective Deletion of Antigen-Specific, Activated T Cells by a Humanized MAB to CD2 (Medi-507) is Mediated by NK Cells," Transplantation, 1999, vol. 68 (10), pp. 1588-1596.
Chirmule N., et al., "Readministration of Adenovirus Vector in Nonhuman Primate Lungs by Blockade of CD40-CD40 Ligand Interactions," Journal of Virology, 2000, vol. 74 (7), pp. 3345-3352.
Czartoryska B., et al., "Changes in Serum Chitotriosidase Activity with Cessation of Replacement Enzyme (Cerebrosidase) Administration in Gaucher Disease," Clinical Biochemistry, 2000, vol. 33 (2), pp. 147-149.
Czartoryska B., et al., "Serum Chitotriosidase Activity in Gaucher Patients on Enzyme Replacement Therapy (ERT)," Clinical Biochemistry, 1998, vol. 31 (5), pp. 417-420.
Den Tandt W.R., et al., "Marked Increase of Methylumbelliferyl-Tetra-N-Acetylchitotetraoside Hydrolase Activity in Plasma from Gaucher Disease Patients," Journal of Inherited Metabolic Disease, 1996, vol. 19 (3), pp. 344-350.
Dodelson De Kremer R., et al., "[Plasma Chitotriosidase Activity in Argentinian Patients with Gaucher Disease, Various Lysosomal Diseases and Other Inherited Metabolic Disorders]," Medicina, 1997, vol. 57 (6), pp. 677-684.
Eckhoff D.E., et al., "The Safety and Efficacy of a Two-Dose Daclizumab (Zenapax) Induction Therapy in Liver Transplant Recipients," Transplantation, 2000, vol. 69 (9), pp. 1867-1872.
Ekberg H., et al., "Daclizumab Prevents Acute Rejection and Improves Patient Survival Post Transplantation: 1 Year Pooled Analysis," Transplant International, 2000, vol. 13 (2), pp. 151-159.
El Alwani M., et al., "Regulation of the Sphingolipid Signaling Pathways in the Growing and Hypoxic Rat Heart," Prostaglandins & Other Lipid Mediators, 2005, vol. 78 (1-4), pp. 249-263.
Enquist I.B., et al., "Murine Models of Acute Neuronopathic Gaucher Disease," Proceedings of the National Academy of Sciences of the United States of America, 2007, vol. 104 (44), pp. 17483-17488.
Fishwild D.M., et al., "Differential Effects of Administration of a Human Anti-CD4 Monoclonal Antibody, HM6G, in Nonhuman Primates," Clinical Immunology, 1999, vol. 92 (2), pp. 138-152.
Gaziev D., et al., "Chronic Graft-Versus-Host Disease: Is there an Alternative to the Conventional Treatment?," Bone Marrow Transplantation, 2000, vol. 25 (7), pp. 689-696.
Goker-Alpan O., et al., "Phenotypic Continuum in Neuronopathic Gaucher Disease: An Intermediate Phenotype Between Type 2 and Type 3," The Journal of Pediatrics, 2003, vol. 143 (2), pp. 273-276.
Grabowski G.A., et al., "Enzyme Therapy in Type 1 Gaucher Disease: Comparative Efficacy of Mannose-Terminated Glucocerebrosidase from Natural and Recombinant Sources," Annals of Internal Medicine, 1995, vol. 122 (1), pp. 33-39.
Gummert J.F., et al., "Newer Immunosuppressive Drugs: A Review," Journal of the American Society of Nephrology : Jasn, 1999, vol. 10 (6), pp. 1366-1380.
Guo Y., et al., "Elevated Plasma Chitotriosidase Activity in Various Lysosomal Storage Disorders," Journal of Inherited Metabolic Disease, 1995, vol. 18 (6), pp. 717-722.
Henry M.L., et al., "Cyclosporine and Tacrolimus (FK506): A Comparison of Efficacy and Safety Profiles," Clinical Transplantation, 1999, vol. 13 (3), pp. 209-220.
Hers H.G.,, "Inborn Lysosomal Diseases," Gastroenterology, 1965, vol. 48, pp. 625-633.
Hollak C.E., et al., "Marked Elevation of Plasma Chitotriosidase Activity. A Novel Hallmark of Gaucher Disease," The Journal of Clinical Investigation, 1994, vol. 93 (3), pp. 1288-1292.
Hong J.C., et al., "Immunosuppressive Agents in Organ Transplantation: Past, Present, and Future," Seminars in Nephrology, 2000, vol. 20 (2), pp. 108-125.
Ideguchi M., et al., "Local Adenovirus-Mediated CTLA4-Immunoglobulin Expression Suppresses the Immune Responses to Adenovirus Vectors in the Brain," Neuroscience, 2000, vol. 95 (1), pp. 217-226.
International Preliminary Report on Patentability for Application No. PCT/US2013/058896, dated Mar. 17, 2015, 9 pages.
International Search Report and Written Opinion for Application No. PCT/US2013/058896, dated Nov. 18, 2013, 15 pages.

(56) References Cited

OTHER PUBLICATIONS

Ito D., et al., "Induction of CTL Responses by Simultaneous Administration of Liposomal Peptide Vaccine with Anti-Cd40 and Anti-CTLA-4 Mab," Journal of Immunology, 2000, vol. 164 (3), pp. 1230-1235.
Kodanko J.J., et al., "Synthesis of Diethynyltriptycene-linked Dipyridyl Ligands," Organic Letters, 2005, vol. 7 (21), pp. 4585-4588.
Kurlberg G., et al., "Blockade of the B7-CD28 Pathway by CTLA4-Ig Counteracts Rejection and Prolongs Survival in Small Bowel Transplantation," Scandinavian Journal of Immunology, 2000, vol. 51 (3), pp. 224-230.
Leonard W.J., et al., "Cytokine Receptor Signaling Pathways," Journal of Allergy and Clinical Immunology, 2000, vol. 105 (5), pp. 877-888.
Liu Y., et al., "Mice with Type 2 and 3 Gaucher Disease Point Mutations Generated by a Single Insertion Mutagenesis Procedure," Proceedings of the National Academy of Sciences, United States of America, 1998, vol. 95 (5), pp. 2503-2508.
Marinova-Mutafchieva L., et al., "A Comparative Study into the Mechanisms of Action of Anti-Tumor Necrosis Factor Alpha, Anti-Cd4, and Combined Anti-Tumor Necrosis Factor Alpha/Anti-Cd4 Treatment in Early Collagen-Induced Arthritis," Arthritis & Rheumatology, 2000, vol. 43 (3), pp. 638-644.
Mazurov A., et al., "2-(Arylmethyl)-3-Substituted Quinuclidines as Selective Alpha 7 Nicotinic Receptor Ligands," Bioorganic & Medicinal Chemistry Letters, 2005, vol. 15 (8), pp. 2073-2077.
Mistry P.K., et al., "A Practical Approach to Diagnosis and Management of Gaucher's Disease," Baillieres Clinical Haematology, 1997, vol. 10 (4), pp. 817-838.
Moder K.G., "New Medications for Use in Patients with Rheumatoid Arthritis," Annals of Allergy, Asthma & Immunology, 2000, vol. 84 (3), pp. 280-284.
Morales L.E., "Gaucher's Disease: A Review," Annals of Pharmacotherapy, 1996, vol. 30 (4), pp. 381-388.
Nevins T.E., "Overview of New Immunosuppressive Therapies," Current Opinion in Pediatrics, 2000, vol. 12 (2), pp. 146-150.
Nilsson O., et al., "Accumulation of Glucosylceramide and Glucosylsphingosine (Psychosine) in Cerebrum and Cerebellum in Infantile and Juvenile Gaucher Disease," Journal of Neurochemistry, 1982, vol. 39 (3), pp. 709-718.
Oberholzer A., et al., "Cytokine Signaling—Regulation of the Immune Response in Normal and Critically ill States," Critical Care Medicine, 2000, vol. 28 (Suppl 4), pp. N3-N12.
Pastores G.M., et al., "Enzyme Therapy in Gaucher Disease Type 1: Dosage Efficacy and Adverse Effects in 33 Patients Treated for 6 to 24 Months," Blood, 1993, vol. 82 (2), pp. 408-416.
Ponticelli C., et al., "Promising New Agents in the Prevention of Transplant Rejection," Drugs in R and D, 1999, vol. 1 (1), pp. 55-60.
Potter M.A., et al., "Review—The Use of Immunosuppressive Agents to Prevent Neutralizing Antibodies against a Transgene Product," Annals of the New York Academy of Sciences, 1999, vol. 875, pp. 159-174.
Przepiorka D., et al., "A Phase II Study of BTI-322, A Monoclonal Anti-CD2 Antibody, for Treatment of Steroid-Resistant Acute Graft-Versus-Host Disease," Blood, 1998, vol. 92 (11), pp. 4066-4071.
Qi S., et al., "Effect of Tacrolimus (FK506) and Sirolimus (rapamycin) Mono- and Combination Therapy in Prolongation of Renal Allograft Survival in the Monkey," Transplantation, 2000, vol. 69 (7), pp. 1275-1283.
Rosenthal D.I., et al., "Enzyme Replacement Therapy for Gaucher Disease: Skeletal Responses to Macrophage-Targeted Glucocerebrosidase," Pediatrics, 1995, vol. 96 (4 Pt 1), pp. 629-637.
Rubinstein M., et al., "Recent Advances in Cytokines, Cytokine Receptors and Signal Transduction," Cytokine & Growth Factor Reviews, 1998, vol. 9 (2), pp. 175-181.
Ryan E.A., et al., "Clinical Outcomes and Insulin Secretion after Islet Transplantation with the Edmonton Protocol," Diabetes, 2001, vol. 50 (4), pp. pp. 710-719.

Shapiro A.M., et al., "Islet Transplantation in Seven Patients with Type 1 Diabetes Mellitus Using a Glucocorticoid-Free Immunosuppressive Regimen," The New England Journal of Medicine, 2000, vol. 343 (4), pp. 230-238.
Slavik J.M., et al., "CD28/CTLA-4 and CD80/CD86 Families: Signaling and Function," Immunologic Research, 1999, vol. 19 (1), pp. 1-24.
Turzanski J., et al., "P-Glycoprotein is Implicated in the Inhibition of Ceramide-Induced Apoptosis in Tf-1 Acute Myeloid Leukemia Cells by Modulation of the Glucosylceramide Synthase Pathwa," Experimental Hematology, 2005, 33 (1), pp. 62-72.
Weinreb N.J., et al., "Effectiveness of Enzyme Replacement Therapy in 1028 Patients with Type 1 Gaucher Disease after 2 to 5 Years of Treatment: A Report from the Gaucher Registry," The American Journal of Medicine, 2002, vol. 113 (2), pp. 112-119.
Wiseman L.R., et al., "Daclizumab: A Review of its use in the Prevention of Acute Rejection in Renal Transplant Recipients," Drugs, 1999, vol. 58 (6), pp. 1029-1042.
Yamashita T., et al., "A Vital Role for Glycosphingolipid Synthesis during Development and Differentiation," Proceedings of the National Academy of Sciences, United States of America, 1999, vol. 96 (16), pp. 9142-9147.
Young E., et al., "Plasma Chitotriosidase Activity in Gaucher Disease Patients Who Have Been Treated either by Bone Marrow Transplantation or by Enzyme Replacement Therapy with Alglucerase," Journal of Inherited Metabolic Disease, 1997, vol. 20 (4), pp. 595-602.
Kloe, G., et al., "Surface Plasmon Resonance Biosensor Based Fragment Screening Using Acetylcholine Binding Protein Identifies Ligand Efficiency Hot Spots (LE Hot Spots) by Deconstruction of Nicotinic Acetylcholine Receptor α7 Ligands," Journal of Medicinal Chemistry, 2010, vol. 53, pp. 7192-7201.
Naito, R., et al., "Selective Muscarinic Antagonists. II.(1) Synthesis and Antimuscarinic Properties of Biphenylylcarbamate Derivatives," Chem. Pharm. Bull., 1998, vol. 46(8), pp. 1286-1294.
Barranger, Glucosylceramide lipidosis: Gaucher disease. In: Scriver CR BA, Sly WS, Valle D, editor. The Metabolic Basis of Inherited Disease. New York: McGraw-Hill. pp. 3635-3668 (2001).
Brenkert et al., Synthesis of Galactosyl Ceramide and Glucosyl Ceramideby Rat Brain: Assay Procedures and Changes With Age, Brain Research 36: 183-193 (1972).
Bundgard, Design of Prodrugs, pp. 7-9, 21-24 (1985).
Cabrera-Salazar et al., Intracerebroventricular delivery of glucocerebrosidase reduces substrates andincreases lifespan in a mouse model of neuronopathic Gaucher disease, Experimental Neurology 225: 436-444 (2010).
Conradi et al., Neuropathology of the Norrbottnian Type of Gaucher Disease, Acta Neuropathologica 65: 99-109(1984).
Conradi et al., Late-infantile Gaucher disease in a child with myoclonus andbulbar signs: neuropathological and neurochemical findings*, Acta Neuropathologica 82: 152-157 (1991).
Davidson et al., The Neuronal Ceroid Lipofuscinosis, Clinical Features and Molecular Basis of Disease, Lysosomal Storage Disorders, (2007), pp. 371-388. Springer, New York, U.S.A.
International Search Report for WO2012/0129084 dated Jul. 2, 2013.
Fernandez et al., Synthesis of Ethylenediamines-alpha, alpha-disubstituted, Anales de la Real Academia de Farmacia (1988), 54, 502.
Giri et al., Krabbe disease: psychosine-mediated activation ofphospholipase A2 in oligodendrocyte cell death, Journal of lipid research 47: 1478-1492 (2006).
Graler et al., Lysophospholipids and their G protein-coupled receptorsin inflammation and immunity, Molecular and Cell Biology of Lipids 1582: 168-174 (2002).
Hirschhorn R, Glycogen Storage Disease Type II: Acid alpha-Glucosidase (Acid Maltase) Deficiency, in: The Metabolic and Molecular Bases of Inherited Disease, Scriver et al., eds., McGraw-Hill, N.Y., 7.sup.th ed., pp. 2443-2464, (1995).
Ida et al., Clinical and genetic studies of Japanese homozygotes for the Gaucher disease L444P mutation, Human Genetics 105: 120-126 (1999).

(56) References Cited

OTHER PUBLICATIONS

Marks et al., Identification of Active Site Residues in Glucosylceramide Synthase, Journal of Biological Chemistry, (2001), 276, pp. 26492-26498.

Marshall et al., Substrate Reduction Augments the Efficacy of EnzymeTherapy in a Mouse Model of Fabry Disease, PLoS One 5:e15033 (2010).

Merrill et al., Sphingolipidomics: High-throughput, structure-speciWc,and quantitative analysis of sphingolipids by liquid chromatographytandem mass spectrometry, Methods 36: 207-224 (2005).

Orvisky et al., Glucosylsphingosine accumulation in tissues from patients with Gaucher disease: correlation with phenotype and genotype, Molecular Genetics and Metabolism 76: 262-270 (2002).

Orvisky et al., Glucosylsphingosine Accumulation in Mice and Patients with Type 2 Gaucher Disease Begins Early in Gestation, Pediatric Research 48: 233-237 (2000).

Pelled et al., The increased sensitivity of neurons with elevated glucocerebroside to neurotoxic agents can be reversed by imiglucerase, Journal of Inherited Metabolic Disease 23: 175-184 (2000).

Schueler et al., Toxicity of glucosylsphingosine (glucopsychosine) to cultured neuronalcells: a model system for assessing neuronal damage in Gaucher disease type 2 and 3, Neurobiology of Disease 14: 595-601 (2003).

Silverman, Prodrugs and Drug Delivery Systems, The Organic Chemistry of Drug Design and Drug Action, pp. 352-401, Academic Press, San Diego, Calif., (1992).

Sun et al., Neuronopathic Gaucher disease in the mouse:viable combined selective saposin C deficiency andmutant glucocerebrosidase (V394L) mice withglucosylsphingosine and glucosylceramide accumulation and progressive neurological deficits, Hum Mol Genet 19: 1088-1097 (2010).

Wong et al., Neuropathology provides clues to the pathophysiology of Gaucher disease, Molecular Genetics and Metabolism 82: 192-207 (2004).

European Search Report for EP2685986 entitled "Glucosylceraminde Synthase Inhibitors", dated Feb. 4, 2015.

O'Donnell et al., Synthesis and SAR studies of 1,4-diazabicyclo[3.2.2]nonane phenyl carbamates—subtype selective, high affinity α7 nicotinic acetylcholine receptor agonists, Bioorganic & Medicinal Chemistry Letters, vol. 19: 4747-4751 (2009).

Demain et al., Enantiomeric purity determination of 3-aminoquinuclidine by diastereomeric derivatization and high-performance liquid chromatographic separation, Journal of Chromatography, vol. 466: 415-420 (1989).

Mashkovsky, The Relationship Between the Chemical Structure and Pharmacological Activity of Some Esters of 3-Hydroxyquinuclidine (Quinuclidine-3-OL), Proc. Intern. Pharmacol. Meeting, 1st, Stockholm, 1961, 1963, vol. 7: 356-366.

Milhlina et al., New paths of synthesis of 3-quinuclidineacetic acid, Zhurnal Obshchei Khimii, 1960, vol. 30: 2970-2977.

Horak et al., Optimization of a ligand immobilization and azide group endcapping concept via "Click-Chemistry" for the preparation of adsorbents for antibody purification, Journal of Chromatography B, Analytical Technologies in the Biomedical and Life Science, 2010, vol. 878(32): 3382-3394.

Cerbai et al., Acetylene derivatives with antispastic activity. II. Amino esters of propylpropargylacetic acid, Farmaco, Edizione Scientifica, 1972, vol. 27(3): 217-234.

JP2002302490, Pfizer Products, Inc., "Medicinal Composition for Treating CNS Disorder and Other Disorder," Oct. 18, 2002, English language machine translation of abstract, Espacenet, date obtained: Apr. 5, 2019, 2 pages <https://worldwide.espacenet.com/publicationDetails/biblio?CC=JP&NR=2002302490A&KC=A&FT=D&ND=3&date=20021018&DB=&locale=en_EP>.

WO1995021820, Yamanouchi Pharma Co. Ltd., "Novel Carbamate Derivative and Medicinal Composition Containing the Same," Aug. 17, 1995, English language machine translation of abstract, Espacenet, date obtained: Apr. 5, 2019, 2 pages <https://worldwide.espacenet.com/publicationDetails/biblio?CC=WO&NR=9521820A1&KC=A1&FT=D&ND=3&date=19950817&DB=&locale=en_EP>.

WO2000026186, Yoshitomi Pharmaceutical, "Pyrrolidine Compounds and Medicinal Utilization Thereof," May 11, 2000, English language machine translation of abstract, Espacenet, date obtained: Apr. 5, 2019, 2 pages <https://worldwide.espacenet.com/publicationDetails/biblio?CC=WO&NR=0026186A1&KC=A1&FT=D&ND=3&date=20000511&DB=&locale=en_EP>.

WO2003078431, Bayer AG, "AZA-Bicyclic N-Biarylamides with Affinity for the Alpha-7 Nicotinic Acetylcholine Receptor," Sep. 25, 2003, English language machine translation of abstract, Espacenet, date obtained: Apr. 5, 2019, 2 pages <https://worldwide.espacenet.com/publicationDetails/biblio?CC=WO&NR=03078431A1&KC=A1&FT=D&ND=4&date=20030925&DB=&locale=en_EP>.

\* cited by examiner (S)-Quinuclidin-3-yl (2-(4'-(2-methoxyethoxy)-[1,1'-biphenyl]-4-yl)propan-2-yl)carbamate

GLUCOSYLCERAMIDE SYNTHASE INHIBITORS

CROSS REFERENCE TO RELATED APPLICATIONS

This application is a national application filed under 35 U.S.C. § 111, claiming priority to and the benefit of U.S. application Ser. No. 14/427,275, filed on Mar. 10, 2015, now abandoned, which is a national stage application filed under 35 U.S.C. § 371 of International Application PCT/US2013/058896, filed on Sep. 10, 2013, which claims priority to and the benefit of U.S. Provisional Application Ser. No. 61/699,714, filed on Sep. 11, 2012, the contents of each of which are hereby incorporated by reference in their entireties.

FIELD OF THE INVENTION

The present invention relates generally to the field of therapeutics for cystic, cancer and metabolic diseases. More specifically, the invention relates to inhibitors of glucosylceramide synthase (GCS) useful for the treatment of diseases, such as metabolic diseases, including lysosomal storage diseases, either alone or in combination with enzyme replacement therapy, neuropathic disease, cystic disease, or for the treatment of cancer.

SUMMARY OF THE RELATED ART

Glucosylceramide synthase (GCS) is a pivotal enzyme which catalyzes the initial glycosylation step in the biosynthesis of glucosylceramide-base glycosphingolipids (GSLs) namely via the pivotal transfer of glucose from UDP-glucose (UDP-Glc) to ceramide to form glucosylceramide (See FIG. 1). GCS is a transmembrane, type III integral protein localized in the cis/medial Golgi. Glycosphingolipids (GSLs) are believed to be integral for the dynamics of many cell membrane events, including cellular interactions, signaling and trafficking. Synthesis of GSL structures has been shown (see, Yamashita et al., Proc. Natl. Acad. Sci. USA 1999, 96(16), 9142-9147) to be essential for embryonic development and for the differentiation of some tissues. Ceramide plays a central role in sphingolipid metabolism and down regulation of GCS activity has been shown to have marked effects on the sphingolipid pattern with diminished expression of glycosphingolipids. Sphingolipids (SLs) have a biomodulatory role in physiological as well as pathological cardiovascular conditions. In particular, sphingolipids and their regulating enzymes appear to play a role in adaptive responses to chronic hypoxia in the neonatal rat heart (see, El Alwanit et al., Prostaglandins & Other Lipid Mediators 2005, 78(1-4), 249-263).

GCS inhibitors have been proposed for the treatment of a variety of diseases (see for example, WO2005068426). Such treatments include treatment of glycolipid storage diseases (e.g., Tay Sachs, Sandhoffs, GM2 Activator deficiency, GM1 gangliosidosis and Fabry diseases), diseases associated with glycolipid accumulation (e.g., Gaucher disease; Miglustat (Zavesca), a GCS inhibitor, has been approved for therapy in type 1 Gaucher disease patients, see, Treiber et al., Xenobiotica 2007, 37(3), 298-314), diseases that cause renal hypertrophy or hyperplasia such as diabetic nephropathy; diseases that cause hyperglycemia or hyperinsulemia; cancers in which glycolipid synthesis is abnormal, infectious diseases caused by organisms which use cell surface glycolipids as receptors, infectious diseases in which synthesis of glucosylceramide is essential or important, diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis) and diabetes mellitus and obesity (see, WO 2006053043).

In particular, it has been shown that overexpression of GCS is implicated in multi-drug resistance and disrupts ceramide-induced apoptosis. For example, Turzanski et al., (Experimental Hematology 2005, 33 (1), 62-72 have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-1 cells. Thus, GCS inhibitors can be useful for treatment of proliferative disorders by inducing apoptosis in diseased cells.

SUMMARY OF THE INVENTION

The present invention refers to a compound represented by the following structural formula,

I or a pharmaceutically acceptable salt or prodrug thereof, wherein:
n is 1, 2 or 3;
m is 0 or 1;
p is 0 or 1;
t is 0, 1 or 2;
y is 1 or 2;
z is 0, 1 or 2;
E is S, O, NH, NOH, $NNO_2$, NCN, NR, NOR or $NSO_2R$;
$X^1$ is $CR^1$ when m is 1 or N when m is 0;
$X^2$ is O, —NH, —$CH_2$—, $SO_2$, NH—$SO_2$; $CH(C_1-C_6)$ alkyl or —$NR^2$;
$X^3$ is a direct bond, O, —NH, —$CH_2$—, CO, —$CH(C_1-C_6)$ alkyl, $SO_2NH$, —CO—NH— or —$NR^3$;
$X^4$ is a direct bond, $CR^4R^5$, $CH_2$ $CR^4R^5$ or $CH_2$—$(C_1-C_6)$ alkyl-$CR^4R^5$;
$X^5$ is a direct bond, O, S, $SO_2$, $CR^4R^5$; $(C_1-C_6)$alkyl, $(C_1-C_6)$alkyloxy, —O—$(C_1-C_6)$alkyl, $(C_1-C_6)$alkenyl, $(C_1-C_6)$alkenyloxy, —$R^7$—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C_2-C_9)$heteroaryl, $(C_2-C_9)$heteroaryl-$R^7$—, —$R^7$—$(C_2-C_9)$heterocycloalkyl, and $(C_2-C_9)$heterocycloalkyl-$R^7$—, wherein $R^7$ is a direct bond, O, S, $SO_2$, $CR^4R^5$; $(C_1-C_6)$alkyl, $(C_1-C_6)$alkyloxy, —O—$(C_1-C_6)$alkyl, $(C_1-C_6)$alkenyl, $(C_1-C_6)$alkenyloxy; and further wherein when $X^5$ is defined as —$R^7$—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C_2-C_9)$heteroaryl, $(C_2-C_9)$heteroaryl-$R^7$—, —$R^7$—$(C_2-C_9)$heterocycloalkyl, and $(C_2-C_9)$heterocycloalkyl-R7-, wherein the $(C_3-C_{10})$cycloalkyl, $(C_6-C_{12})$aryl, $(C_2-C_9)$heteroaryl, $(C_2-C_9)$heterocycloalkyl groups are optionally substituted by one or more substituents selected from the group consisting of halo, $(C_1-C_6)$alkyl, $(C_1-C_6)$alkylenyl, amino, $(C_1$-

$C_6$) alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$alkyloxy, $(C_3-C_6)$ cycloalkyl, $(C_1-C_6)$ alkoxycarbonyl, $(C_1-C_6)$ alkylcarbonyl, $(C_1-C_6)$ haloalkyl, $(C_2-C_9)$heterocycloalkyl, $R^8R^9N-CO-$ wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$ alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy; and $(C_1-C_6)$alkyloxy substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

R is $(C_6-C_{12})$aryl, $(C_2-C_9)$heteroaryl, $(C_1-C_6)$alkyl, $(C_2-C_9)$heteroaryl$(C_1-C_6)$alkyl;

$R^1$ is H, CN, $(C_1-C_6)$alkylcarbonyl, or $(C_1-C_6)$alkyl;

$R^2$ and $R^3$ are each independently $-H$, $(C_1-C_6)$alkyl optionally substituted by one or more substituents selected from the group consisting of halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl, or optionally when $X^2$ is $-NR^2$ and $X^3$ is $-NR^3$, $R^2$ and $R^3$ may be taken together with the nitrogen atoms to which they are attached form a non-aromatic heterocyclic ring optionally substituted by with one or more substituents selected from halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl;

$R^4$ and $R^5$ are independently selected from H, $(C_1-C_6)$ alkyl, or taken together with the carbon to which they are attached to form a spiro $(C_3-C_{10})$cycloalkyl ring or spiro $(C_3-C_{10})$cycloalkoxy ring;

$R^6$ is $-H$, halogen, $-CN$, $(C_6-C_{12})$aryl, $(C_6-C_{12})$aryloxy, $(C_1-C_6)$alkyloxy; $(C_1-C_6)$alkyl optionally substituted by one to four halo or $(C_1-C_6)$alkyl;

$A^1$ is $(C_2-C_6)$alkynyl; $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkenyl, amino, $(C_1-C_6)$alkylamino, $(C_1-C_6)$dialkylamino, $(C_1-C_6)$alkoxy, nitro, CN, $-OH$, $(C_1-C_6)$alkyloxy optionally substituted by one to three halo; $(C_1-C_6)$alkoxycarbonyl, and $(C_1-C_6)$ alkylcarbonyl;

$A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkylenyl, amino, $(C_1-C_6)$ alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$alkyloxy optionally substituted by one to three halo; $(C_3-C_6)$ cycloalkyl, $(C_1-C_6)$ alkoxycarbonyl, $(C_1-C_6)$ alkylcarbonyl, $(C_1-C_6)$ haloalkyl, $(C_2-C_9)$heterocycloalkyl, $R^8R^9N-CO-$ wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

with the proviso that the sum of n+t+y+z is not greater than 6;

with the proviso that when p is 0; $X^2$ is $NH-SO_2$ and $X^3$ is NH;

with the proviso that when n is 1; t is 0; y is 1; z is 1; $X^2$ is NH; E is O; $X^3$ is NH; $A^2$ is H and $X^5$ is a direct bond; $A^1$ is not unsubstituted phenyl, halophenyl or isopropenyl phenyl;

with the proviso that when n is 1; t is 0; y is 1; z is 1; $X^2$ is O; E is O; $X^3$ is NH; $A^1$ is $(C_6-C_{12})$aryl and $X^5$ is a direct bond; $A^2$ is H and $R^4$ is H then $R^5$ is not cyclohexyl;

with the proviso that when n is 1; t is 0; y is 1; z is 1; $X^2$ is NH; E is O; $X^3$ is $CH_2$; $R^4$ and $R^5$ are both hydrogen; $A^2$ is H and $X^5$ is a direct bond; then $A^1$ is not unsubstituted phenyl; and with the proviso that when $X^3$ is O, $-NH$, $-CH_2-$, CO, $-CH(C_1-C_6)$ alkyl, $SO_2NH$, $-CO-NH-$ or $-NR^3$; and $X^4$ is $CR^4R^5$, $CH_2$ $CR^4R^5$ or $CH_2-(C_1-C_6)$ alkyl-$CR^4R^5$; then $A^2$ must be $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl substituted with one or more substituents selected from the group consisting of, $(C_2-C_9)$heterocycloalkyl, $R^8R^9N-CO-$ wherein $R^8$ and $R^9$ are each independently selected from the group consisting of hydrogen and $(C_1-C_6)$ alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$ alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

Certain aspects of the invention include administering the foregoing compound to a patient as part of combination therapy that includes an enzyme replacement therapy (ERT) and small molecule therapy (SMT) to reduce the amount of and/or inhibit substrate accumulation in a patient diagnosed with a lysosomal storage disease.

The present invention further relates to the compound of Formula I, wherein n is 1; t is 0; y is 1 and z is 1.

The present invention further relates to the compound of Formula I, wherein n is 1; t is 1; y is 1 and z is 1.

The present invention further relates to the compound of Formula I, wherein n is 2; t is 0; y is 1 and z is 1.

The present invention further relates to the compound of Formula I, wherein n is 2; t is 1; y is 1 and z is 1.

The present invention further relates to the compound of Formula I, wherein n is 3; t is 0; y is 1 and z is 1.

The present invention further relates to the compound of Formula I, wherein n is 1; t is 2; y is 1 and z is 1.

The present invention further relates to the compound of Formula I, wherein n is 1; t is 0; y is 1 and z is 0.

The present invention further relates to the compound of Formula I, wherein n is 1; t is 1; y is 1 and z is 0.

The present invention further relates to the compound of Formula I, wherein n is 2; t is 0; y is 1 and z is 0.

The present invention further relates to the compound of Formula I, wherein n is 2; t is 1; y is 1 and z is 0.

The present invention further relates to the compound of Formula I, wherein n is 3; t is 0; y is 1 and z is 0.

The present invention further relates to the compound of Formula I, wherein n is 1; t is 2; y is 1 and z is 0.

The present invention further relates to the compound of Formula I, wherein n is 1; t is 1; y is 2 and z is 0.

The present invention further relates to the compound of Formula I, wherein n is 2; t is 0; y is 2 and z is 0.

The present invention further relates to the compound of Formula I, wherein m is 1 and $X^1$ is $CR^1$.

The present invention further relates to the compound of Formula I, wherein m is 0 and $X^1$ is N.

The present invention further relates to the compound of Formula I, wherein m is 1; E is O; $X^2$ is O and $X^3$ is NH.

The present invention further relates to the compound of Formula I, wherein m is 1; E is O; $X^2$ is NH and $X^3$ is NH.

The present invention further relates to the compound of Formula I, wherein m is 1; E is O; $X^2$ is $CH^2$ and $X^3$ is NH.

The present invention further relates to the compound of Formula I, wherein m is 1; E is O; $X^2$ is NH and $X^3$ is $CH^2$.

The present invention further relates to the compound of Formula I, wherein m is 1; E is S; $X^2$ is NH and $X^3$ is NH.

The present invention further relates to the compound of Formula I, wherein m is 0; E is O; $X^1$ is NH and $X^3$ is NH.

The present invention further relates to the compound of Formula I, wherein m is 1; E is O; $X^2$ is NH and $X^3$ is CO—NH.

The present invention further relates to the compound of Formula I, wherein m is 1; p is 0; $X^2$ is NH—$SO_2$ and $X^3$ is NH.

The present invention further relates to the compound of Formula I, wherein $R^4$ and $R^5$ are each $(C_1-C_6)$alkyl or taken together with the carbon to which they are attached to form a spiro $(C_3-C_{10})$cyclo-alkyl ring or a spiro $(C_3-C_{10})$cycloalkoxy ring.

The present invention further relates to the compound of Formula I, wherein $R^4$ and $R^5$ are each methyl.

The present invention further relates to the compound of Formula I, wherein $R^4$ and $R^5$ are taken together with the carbon to which they are attached to form a spiro $(C_3-C_{10})$ cycloalkyl ring.

The present invention further relates to the compound of Formula I, wherein $R^4$ and $R^5$ are taken together with the carbon to which they are attached to form a spiro cyclopropyl ring.

The present invention further relates to the compound of Formula I, wherein $R^4$ and $R^5$ are taken together with the carbon to which they are attached to form a spiro $(C_3-C_{10})$ cycloalkoxy ring.

The present invention further relates to the compound of Formula I, wherein $A^1$ is $(C_2-C_6)$alkynyl or $(C_6-C_{12})$aryl.

The present invention further relates to the compound of Formula I, wherein $A^1$ is $(C_2-C_9)$heteroaryl.

The present invention further relates to the compound of Formula I, wherein $A^1$ is thiophene, thiazole, isothiazole, furane, oxazole, isoxazole, pyrrole, imidazole, pyrazole, triazole, pyridine, pymiridine, pyridazine, indole, benzotiazole, benzoisoxazole, benzopyrazole, benzoimidazole, benzofuran, benzooxazole or benzoisoxazole.

The present invention further relates to the compound of Formula I, wherein $A^1$ is $(C_2-C_9)$heterocycloalkyl.

The present invention further relates to the compound of Formula I, wherein $A^1$ is pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, 2,6-diazaspiro[3.3]heptane, 2-azaspiro[3.3]heptane, 2,7-diazaspiro[4.4]nonane, azepane, 1,4-diazepane, 3,6-diazabicyclo[3.1.1]heptane, 2-azabicyclo[2.2.1]heptane, 7-azabicyclo[2.2.2]octane, 3-azabicyclo[3.1.1]heptane or 6-azabicyclo[3.1.1]heptane.

The present invention further relates to the compound of Formula I, wherein $A^1$ is benzo$(C_2-C_9)$heterocycloalkyl.

The present invention further relates to the compound of Formula I, wherein $A^1$ is 2,3-dihydrobenzo[b][1,4] dioxine or 2,2-difluorobenzo[d][1,3]dioxole.

The present invention further relates to the compound of Formula I, wherein $R^6$ is H.

The present invention further relates to the compound of Formula I, $X^5$ is a direct bond.

The present invention further relates to the compound of Formula I, $X^5$ is a $CR^4R^5$.

The present invention further relates to the compound of Formula I, wherein $R^4$ and $R^5$ are each methyl.

The present invention further relates to the compound of Formula I, wherein $R^4$ and $R^5$ are taken together with the carbon to which they are attached to form a spiro $(C_3-C_{10})$ cycloalkyl ring.

The present invention further relates to the compound of Formula I, wherein $R^4$ and $R^5$ are taken together with the carbon to which they are attached to form a spiro cyclopropyl ring.

The present invention further relates to the compound of Formula I, wherein $R^4$ and $R^5$ are taken together with the carbon to which they are attached to form a spiro $(C_3-C_{10})$ cycloalkoxy ring.

The present invention further relates to the compound of Formula I, wherein $A^2$ is $(C_6-C_{12})$aryl.

The present invention further relates to the compound of Formula I, wherein $A^2$ is $(C_2-C_9)$heteroaryl.

The present invention further relates to the compound of Formula I, wherein $A^2$ is pyridine.

The present invention further relates to the compound of Formula I, wherein $A^2$ is $(C_2-C_9)$heterocycloalkyl.

The present invention further relates to the compound of Formula I, wherein $A^2$ is pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl or octahydro-1H-indolyl.

The present invention further relates to the compound of Formula I, wherein $A^2$ is benzo$(C_2-C_9)$heterocycloalkyl.

The present invention further relates to the compound of Formula I, where $R^1$ is hydrogen or methyl.

The present further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; X is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is; E is O; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; X is O; $X^3$ is NH; $R^1$ is H; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; X is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; X is O; $X^3$ is NH; $R^1$ is H; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; X is $CR^1$; m is 1; E is O; $X^2$ is NH; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; X is $CR^1$; m is 1; E is O; $X^2$ is $CH_2$; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^2$ is $(C_2-C_9)$heterocycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; $X^2$ is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; X is O; $X^3$ is NH; $R^1$ is H; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; is O; $X^2$ is NH; $X^3$ is NH; $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; X is $CR^1$; m is 1; E is O; $X^2$ is $CH_2$; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heterocycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heterocycloalkyl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2$-$C_9)$heterocycloalkyl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; is O; $X^2$ is NH; $X^3$ is NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3$-$C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; X is O; $X^3$ is NH; $R^1$ is H; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; X is O; $X^3$ is NH; $R^1$ is H; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is N; m is; E is O; $X^3$ is NH; $R^4$ and $R^5$ are each independently methyl; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_6$-$C_{12})$aryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_6$-$C_{12})$aryl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_3$-$C_{10})$cycloalkyl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; X is $CR^1$; m is 1; p is 1; E is O; $X^2$ is O; $X^3$ is NH; $R^1$ is H; $R^4$ and $R^5$ are each independently methyl; $R^6$ is a hydrogen or methyl; $A^1$ is $(C_3$-$C_{10})$cycloalkyl; $X^5$ is a direct bond, O or $CR^4R^5$ and $A^2$ is $(C_2$-$C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3$-$C_{10})$cycloalkyl ring or spiro $(C_3$-$C_{10})$cycloalkoxy ring; $R^6$ is a hydrogen or methyl; $A^1$ is $(C_2$-$C_9)$heteroaryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; X is $CR^1$; m is 1; E is O; $X^2$ is NH; $X^3$ is NH; $R^4$ and $R^5$ are each independently methyl; $R^6$ is a hydrogen or methyl; $A^1$ is $(C_2$-$C_9)$heteroaryl; $X^5$ is a direct bond, O or $CR^4R^5$ and $A^2$ is $(C_3$-$C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are taken together with the carbon to which they are attached to form a spiro $(C_3$-$C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is N; m is 0; E is O; $X^3$ is NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to the compound of Formula I, wherein $A^1$ is $(C_3-C_{10})$cycloalkyl.

The present invention further relates to the compound of Formula I, wherein $A^2$ is $(C_3-C_{10})$cycloalkyl.

The present invention further relates to the compound of Formula I, or a pharmaceutically acceptable salt or prodrug thereof, selected from the group consisting of:

1-azabicyclo[2.2.2]oct-3-yl [2-(2,4'-difluorobiphenyl-4-yl)propan-2-yl]carbamate;
1-azabicyclo[2.2.2]oct-3-yl {2-[4-(1,3-benzothiazol-6-yl)phenyl]propan-2-yl}carbamate;
1-azabicyclo[3.2.2]non-4-yl {1-[5-(4-fluorophenyl)pyridin-2-yl]cyclopropyl}carbamate;
1-azabicyclo[2.2.2]oct-3-yl {1-[3-(4-fluorophenoxy)phenyl]cyclopropyl}carbamate;
1-azabicyclo[2.2.2]oct-3-yl {1-[4-(1,3-benzothiazol-5-yl)phenyl]cyclopropyl}carbamate;
1-azabicyclo[2.2.2]oct-3-yl [1-(4'-fluoro-3'-methoxybiphenyl-4-yl)cyclopropyl]carbamate;
1-azabicyclo[2.2.2]oct-3-yl [3-(4'-fluorobiphenyl-4-yl)oxetan-3-yl]carbamate;
1-azabicyclo[2.2.2]oct-3-yl {1-[6-(4-fluorophenoxy)pyridin-2-yl]cyclopropyl}carbamate;
1-azabicyclo[2.2.2]oct-3-yl [3-(4'-fluorobiphenyl-4-yl)pentan-3-yl]carbamate;
1-azabicyclo[2.2.2]oct-3-yl {2-[2-(4-fluorophenyl)-2H-indazol-6-yl]propan-2 yl}carbamate;
1-azabicyclo[2.2.2]oct-3-yl {2-[2-(1H-pyrrol-1-yl)pyridin-4-yl]propan-2-yl}carbamate;
1-(3-ethyl-1-azabicyclo[2.2.2]oct-3-yl)-3-[1-(4'-fluorobiphenyl-4-yl)cyclopropyl]urea;
N-(1-azabicyclo[2.2.2]oct-3-yl)-N'-[1-(4'-fluorobiphenyl-4yl)cyclopropyl]ethanediamide;
1-azabicyclo[2.2.2]oct-3-yl (1-{4[(4,4difluorocyclohexyl)oxy]phenyl}cyclopropyl) carbamate;
1-(4-methyl-1-azabicyclo[3.2.2]non-4-yl)-3-[1-(5-phenylpyridin-2-yl)cyclopropyl]urea;
1-[1-(4'-fluorobiphenyl-4-yl)cyclopropyl]-1-methyl-3-(3-methyl-1-azabicyclo[2.2.2]oct-3-yl)urea;
1-[1-(4'-fluorobiphenyl-4-yl)cyclopropyl]-1-methyl-3-(3-methyl-1-azabicyclo[2.2.2]oct-3-yl)urea;
1-{2-[4'-(2-methoxyethoxy)biphenyl-4-yl]propan-2-yl}-3-(3-methyl-1-azabicyclo[2.2.2]oct-3-yl)urea;
2-(1-azabicyclo[3.2.2]non-4-yl)-N-[1-(5-phenylpyridin-2-yl)cyclopropyl]acetamide;
3-(4'-fluorobiphenyl-4-yl)-3-methyl-N-(4-methyl-1-azabicyclo[3.2.2]non-4-yl)butanamide;
N-[2-(biphenyl-4-yl)propan-2-yl]-N'-(3-methyl-1-azabicyclo[2.2.2]oct-3-yl)sulfuric diamide;
N-[2-(4'-fluorobiphenyl-4-yl)propan-2-yl]-N'-(3-methyl-1-azabicyclo[2.2.2]oct-3-yl)sulfuric diamide;
1-(3-butyl-1-azabicyclo[2.2.2]oct-3-yl)-3-{2-[1-(4-fluorophenyl)-1H-pyrazol-4-yl]propan-2-yl}urea;
1-azabicyclo[2.2.2]oct-3-yl [4-(4-fluorophenyl)-2-methylbut-3-yn-2-yl]carbamate;
1-(3-butyl-1-azabicyclo[2.2.2]oct-3-yl)-3-[4-(4-fluorophenyl)-2-methylbut-3-yn-2-yl]urea;
N-[1-(4'-fluorobiphenyl-4-yl)cyclopropyl]-1,4-diazabicyclo[3.2.2]nonane-4-carboxamide;
1-(2-(4'-fluoro-[1,1'-biphenyl]-4-yl)propan-2-yl)-3-(3-methyl-1-azabicyclo[3.2.2]nonan-3-yl)urea;
1-(2-(4'-fluoro-[1,1'-biphenyl]-4-yl)propan-2-yl)-3-(4-methyl-1-azabicyclo[4.2.2]decan-4-yl)urea;
1-(2-(4'-fluoro-[1,1'-biphenyl]-4-yl)propan-2-yl)-3-(3-methyl-1-azabicyclo[4.2.2]decan-3-yl)urea; and
1-(2-(4'-fluoro-[1,1'-biphenyl]-4-yl)propan-2-yl)-3-(5-methyl-1-azabicyclo[4.2.2]decan-5-yl)urea.

The present invention further relates to a pharmaceutical composition for treating a disease or disorder mediated by glucosylceramide synthase (GCS) or a disease or disorder in which GCS is implicated in a subject in need of such treatment comprising administering to the subject an effective amount of the compound of Formula I.

The present invention further relates to a method for treating a disease or disorder mediated by glucosylceramide synthase (GCS) or a disease or disorder in which GCS is implicated in a subject in need of such treatment comprising administering to the subject an effective amount of the compound of Formula I.

The present invention further relates to a method for treating a disease or disorder such as cancer.

The present invention further relates to a method for treating a disease or disorder such as a metabolic disorder.

The present invention further relates to a method for treating a disease or disorder such as a neuropathic disease.

The present invention further relates to a method wherein the neuropathic disease is Alzheimer's disease.

The present invention further relates to a method wherein the neuropathic disease is Parkinson's disease.

The present invention further relates to a method for treating a disease or disorder such as a cystic disease. The cystic diseases include, but are not limited to renal cystic diseases such as: acquired renal cystic disease (ARCD), dialysis-associated cystic disease, autosomal dominant polycystic kidney disease (ADPKD), autosomal recessive polycystic kidney disease (ARPKD), congenital multicystic kidney (CMK), multi cystic dysplastic kidney, end-stage renal disease (ESRD), medullary sponge kidney (MSK), nephronophthisis-medullary cystic kidney disease complex (NMCD), nephronophthisis-uremic medullary cystic disease complex, juvenile nephronophthisis, medullary cystic disease, renal cell carcinoma (RCC), tuberous sclerosis (TS), von Hippel-Lindau syndrome (VHLS).

The present invention further relates to methods for treating, ameliorating or preventing cystic diseases.

The present invention further relates to the method for inducing decreased glucosylceramide synthase catalytic activity in a cell, in vitro, comprising contacting the cell with an effect amount of the compound of Formula I.

The present invention further relates to the compound of Formula I ((S)-Quinuclidin-3-yl (2-(4'-(2-methoxyethoxy)-[1,1'-biphenyl]-4-yl)propan-2-yl)carbamate), represented by the following structural formula,

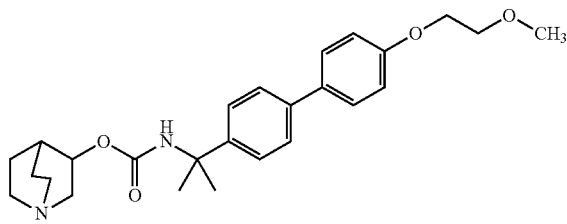 [SMILES: COCCOc1ccc(-c2ccc(C(C)(C)NC(=O)OC3CN4CCC3CC4)cc2)cc1]

or a pharmaceutically acceptable salt or prodrug thereof.

The present invention further relates to the compound of Formula I (4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide), represented by the following structural formula,

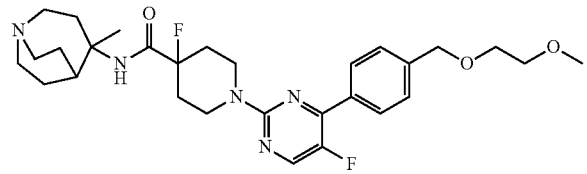 [SMILES: COCCOCc1ccc(-c2nc(N3CCC(F)(C(=O)NC4(C)CCN5CCC4CC5)CC3)ncc2F)cc1]

or a pharmaceutically acceptable salt or prodrug thereof.

The present invention further relates to the compound of Formula I, (4-Fluoro-1-(4-(4-((2-methoxyethoxy)methyl)phenyl)pyrimidin-2-yl)-N-(3-methylquinuclidin-3-yl)piperidine-4-carboxamide) represented by the following structural formula,

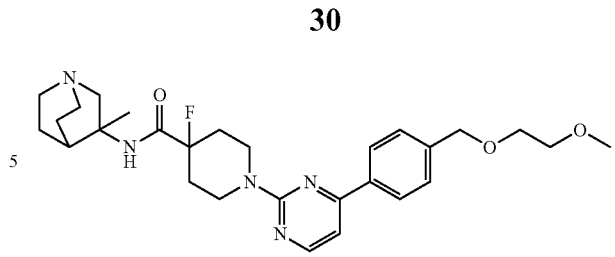

The present invention further relates to the compound of Formula I, (4-Fluoro-1-(4-(4-((2-methoxy ethoxy)methyl)phenyl)pyrimidin-2-yl)-N-(4-methyl-1-azabicyclo[3.2.2]nonan-4-yl)piperidine-4-carboxamide) represented by the following structural formula,

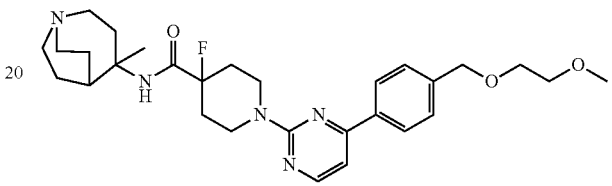

The present invention further relates to the compound of Formula I, (4-Fluoro-1-(4-(4-(methoxymethyl)phenyl)pyrimidin-2-yl)-N-(3-methylquinuclidin-3-yl)piperidine-4-carboxamide) represented by the following structural formula,

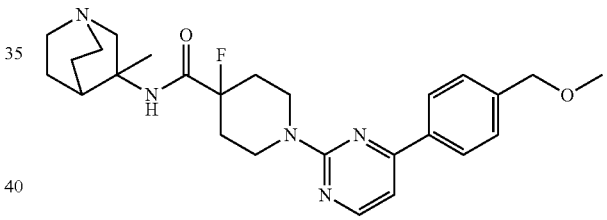

The present invention further relates to the compound of Formula I, (4-Fluoro-1-(4-(4-(methoxymethyl)phenyl)pyrimidin-2-yl)-N-(4-methyl-1-azabicyclo[3.2.2]nonan-4-yl) piperidine-4-carboxamide) represented by the following structural formula,

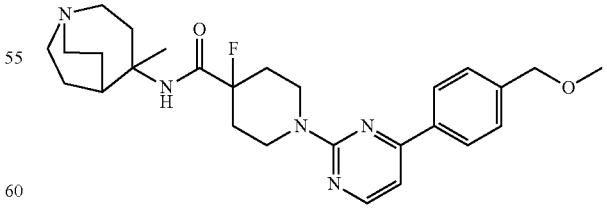

The present invention further relates to the compound of Formula I, (4-Fluoro-1-(4-(4-(2-methoxyethoxy)phenyl)pyrimidin-2-yl)-N-(3-methylquinuclidin-3-yl)piperidine-4-carboxamide) represented by the following structural formula,

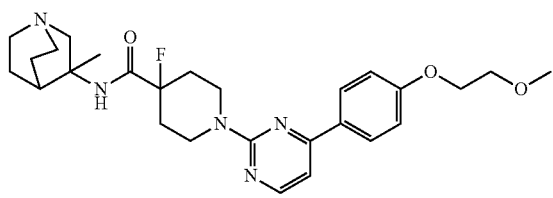 [SMILES: COCCOc1ccc(-c2ccnc(N3CCC(F)(C(=O)NC4(C)CN5CCC4CC5)CC3)n2)cc1]

The present invention further relates to the compound of Formula I, (4-Fluoro-1-(4-(4-(2-methoxyethoxy)phenyl)pyrimidin-2-yl)-N-(4-methyl-1-azabicyclo[3.2.2]nonan-4-yl)piperidine-4-carboxamide) represented by the following structural formula,

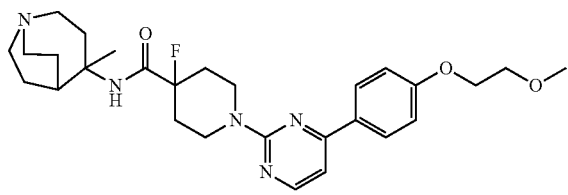 [SMILES: COCCOc1ccc(-c2ccnc(N3CCC(F)(C(=O)NC4(C)CCN5CCC4CC5)CC3)n2)cc1]

The present invention further relates to the compound of Formula I, (4-Fluoro-1-(4-(4-(2-fluoroethoxy)phenyl)pyrimidin-2-yl)-N-(quinuclidin-3-yl)piperidine-4-carboxamide) represented by the following structural formula,

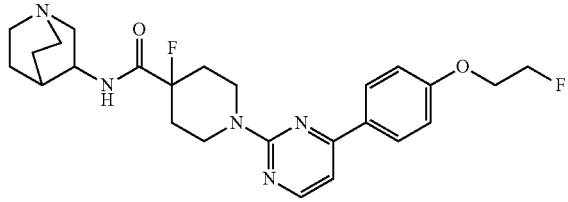 [SMILES: O=C(NC1CN2CCC1CC2)C1(F)CCN(c2nccc(-c3ccc(OCCF)cc3)n2)CC1]

The present invention further relates to the compound of Formula I, (4-Fluoro-1-(4-(4-(2-fluoroethoxy)phenyl)pyrimidin-2-yl)-N-(4-methyl-1-azabicyclo[3.2.2]nonan-4-yl)piperidine-4-carboxamide) represented by the following structural formula,

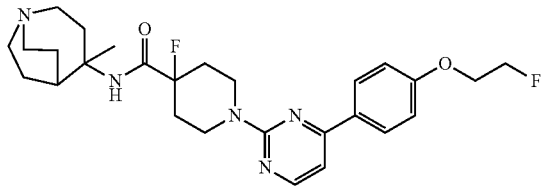 [SMILES: CC1(NC(=O)C2(F)CCN(c3nccc(-c4ccc(OCCF)cc4)n3)CC2)CCN2CCC1CC2]

The present invention further relates to a method of treating a subject diagnosed as having a lysosomal storage disease, the method including administering to the subject an effective amount of the compound of formula I, and in certain embodiments the compound is represented by following structural formula,

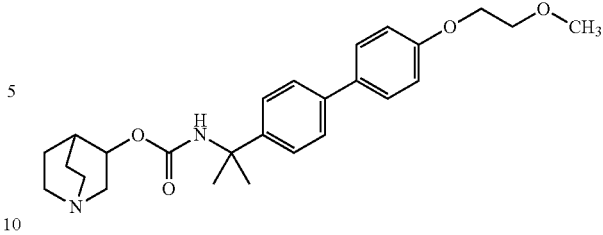

or a pharmaceutically acceptable salt or prodrug thereof.

In certain embodiments of the invention, the lysosomal storage disease results from a defect in the glycosphingolipid pathway.

In certain embodiments of the invention, the lysosomal storage disease is Gaucher, Fabry, $G_{M1}$-gangliosidosis, $G_{M2}$ Activator deficiency, Tay-Sachs or Sandhoff.

The present invention further relates to a method of treating a subject diagnosed as having a lysosomal storage disease, the method including administering to the subject an effective amount of the compound of formula I and administering to the subject a therapeutically effective amount of a lysosomal enzyme.

In certain embodiments of the invention, the lysosomal enzyme is glucocerebrosidase, alpha-galactosidase A, Hexosaminidase A, Hexosaminidase B or $G_{M1}$-ganglioside-β-galactosidase.

In certain embodiments of the invention, the subject has elevated levels of a lysosomal substrate prior to treatment and once undergoing treatment the subject has lower combined amounts of the lysosomal substrate in the urine and plasma than a subject treated with either the lysosomal enzyme or compound alone.

In certain embodiments of the invention, the substrate is globotriaosylceramide or lyso-globotriaosylceramide, and combinations thereof.

The present invention further relates to a method of reducing glucosylceramide synthase (GCS) activity in a subject diagnosed as having a lysosomal storage disease, including administering to the patient an effective amount of the compound of formula I, either alone or as a combination therapy with an enzyme replacement therapy.

The present invention further relates to a method of reducing accumulation of a GCS-derived material in a subject diagnosed as having a lysosomal storage disease, including administering to the patient an effective amount of the compound of formula I, either alone or as a combination therapy with an enzyme replacement therapy.

This invention provides a method of combination therapy for treatment of a subject diagnosed as having a lysosomal storage disease comprising alternating between administration of an enzyme replacement therapy and a small molecule therapy.

This invention provides a method of combination therapy for treatment of a subject diagnosed as having a lysosomal storage disease comprising simultaneously administering an enzyme replacement therapy and a small molecule therapy.

The present invention further relates to a method of treating a subject diagnosed as having a cystic disease, the method including administering to the subject an effective amount of the compound of Formula I, and in certain embodiments the compound is represented by following structural formula,

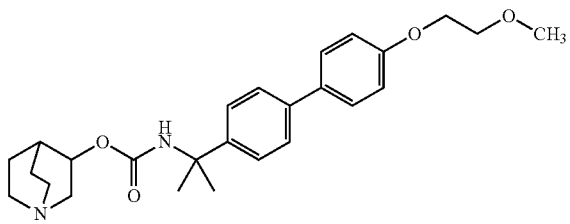 [SMILES: COCCOc1ccc(-c2ccc(C(C)(C)NC(=O)OC3CN4CCC3CC4)cc2)cc1]

In certain embodiments of the invention, the cystic diseases is acquired renal cystic disease (ARCD), dialysis-associated cystic disease, autosomal dominant polycystic kidney disease (ADPKD), autosomal recessive polycystic kidney disease (ARPKD), congenital multicystic kidney (CMK), multi cystic dysplastic kidney, end-stage renal disease (ESRD), medullary sponge kidney (MSK), nephronophthisis-medullary cystic kidney disease complex (NMCD), nephronophthisis-uremic medullary cystic disease complex, juvenile nephronophthisis, medullary cystic disease, renal cell carcinoma (RCC), tuberous sclerosis (TS), von Hippel-Lindau syndrome (VHLS).

The present invention further relates to the compound of Formula I, wherein $X^3$ is a direct bond.

The present invention further relates to the compound of Formula I, wherein $X^4$ is a direct bond.

The present invention further relates to the compound of Formula I, wherein $X^3$ and $X^4$ are each independently a direct bond.

The present invention further relates to the compound of Formula I, wherein m is 1; E is O; $X^2$ is O and $X^3$ is direct bond.

The present invention further relates to the compound of Formula I, wherein m is 1; E is O; $X^2$ is NH and $X^3$ is direct bond.

The present invention further relates to the compound of Formula I, wherein m is 1; E is O; $X^2$ is $CH_2$ and $X^3$ is direct bond.

The present invention further relates to the compound of Formula I, wherein m is 1; E is S; $X^2$ is NH and $X^3$ is direct bond.

The present invention further relates to the compound of Formula I, wherein m is 0; E is O; $X^1$ is NH and $X^3$ is direct bond.

The present invention further relates to the compound of Formula I, wherein m is 1; p is 0; $X^2$ is NH—$SO_2$ and $X^3$ is direct bond.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is O and $X^3$ is direct bond.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is NH and $X^3$ is direct bond.

The present invention further relates to the compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$ and $X^3$ is direct bond.

The present invention further relates to the compound of Formula I, wherein n is 1; 2 or 3; t is 0, 1 or 2; y is 0 or 1; z is 0, 1 or 2; $X^1$ is $CR^1$; m is 1; E is S; $X^2$ is NH and $X^3$ is direct bond.

The present invention further relates to the compound of Formula I, wherein n is 1; 2 or 3; t is 0, 1 or 2; y is 0 or 1; z is 0, 1 or 2; $X^1$ is $CR^1$; m is 0; E is O; $X^1$ is NH and $X^3$ is direct bond.

The present invention further relates to the compound of Formula I, wherein n is 1; 2 or 3; t is 0, 1 or 2; y is 0 or 1; z is 0, 1 or 2; $X^1$ is $CR^1$; m is 1; p is 0; $X^2$ is NH—$SO_2$ and $X^3$ is direct bond.

The present invention further relates to the compound of Formula I, wherein $X^5$ is a direct bond, O, S, $SO_2$, $CR^4R^5$; $(C_1-C_6)$alkyl, $(C_1-C_6)$alkyloxy, $(C_1-C_6)$alkenyl or $(C_1-C_6)$alkenyloxy.

The present invention further relates to the compound of Formula I, wherein $X^5$ is —O—$(C_1-C_6)$alkyl, —R—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C_2-C_9)$heteroaryl, $(C_2-C_9)$heteroaryl-$R^7$—, —$R^7$—$(C_2-C_9)$heterocycloalkyl, and $(C_2-C_9)$heterocycloalkyl-$R^7$—, wherein $R^7$ is a direct bond, O, S, $SO_2$, $CR^4R^5$; $(C_1-C_6)$alkyl, $(C_1-C_6)$alkyloxy, —O—$(C_1-C_6)$alkyl, $(C_1-C_6)$alkenyl or $(C_1-C_6)$alkenyloxy.

The present invention further relates to the compound of Formula I, wherein $A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkylenyl, amino, $(C_1-C_6)$ alkylamino, $(C_1-C_6)$dialkylamino, $(C_1-C_6)$alkoxy, O($C_3-C_6$ cycloalkyl), $(C_3-C_6)$cycloalkoxy, nitro, CN, OH, $(C_1-C_6)$alkyloxy optionally substituted by one to three halo; $(C_3-C_6)$ cycloalkyl, $(C_1-C_6)$ alkoxycarbonyl, $(C_1-C_6)$ alkylcarbonyl or $(C_1-C_6)$ haloalkyl.

The present invention further relates to the compound of Formula I, wherein $A^2$ is $(C_3-C_{10})$cycloalkyl, $(C_6-C_{12})$aryl, $(C_2-C_9)$heteroaryl, $(C_2-C_9)$heterocycloalkyl or benzo($C_2-C_9$)heterocycloalkyl substituted with one or more substituents selected from the group consisting of $(C_2-C_9)$heterocycloalkyl, $R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$ alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

The present invention further relates to the compound of Formula I, wherein $X^3$ is O, —NH, —$CH_2$—, CO, —CH($C_1-C_6$) alkyl, $SO_2NH$, —CO—NH— or —$NR^3$; $X^4$ is $CR^4R^5$, $CH_2$ $CR^4R^5$ or $CH_2$—$(C_1-C_6)$ alkyl-$CR^4R^5$; and $A^2$ is $(C_3-C_{10})$cycloalkyl, $(C_6-C_{12})$aryl, $(C_2-C_9)$heteroaryl, $(C_2-C_9)$heterocycloalkyl or benzo($C_2-C_9$)heterocycloalkyl substituted with one or more substituents selected from the group consisting of, $(C_2-C_9)$heterocycloalkyl, $R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

The present invention further relates to the Compound of Formula I, wherein $X^3$ is a direct bond.

The present invention further relates to the Compound of Formula I, wherein $X^4$ is a direct bond.

The present invention further relates to the Compound of Formula I, wherein $X^3$ and $X^4$ are each independently a direct bond.

The present invention further relates to the Compound of Formula I, wherein m is 1; E is O; $X^2$ is O and $X^3$ is direct bond.

The present invention further relates to the Compound of Formula I, wherein m is 1; E is O; $X^2$ is NH and $X^3$ is direct bond.

The present invention further relates to the Compound of Formula I, wherein m is 1; E is O; $X^2$ is $CH_2$ and $X^3$ is direct bond.

The present invention further relates to the Compound of Formula I, wherein m is 1; E is S; $X^2$ is NH and $X^3$ is direct bond.

The present invention further relates to the Compound of Formula I, wherein m is 0; E is O; $X^1$ is NH and $X^3$ is direct bond.

The present invention further relates to the Compound of Formula I, wherein m is 1; p is 0; $X^2$ is NH—$SO_2$ and $X^3$ is direct bond.

The present invention further relates to the Compound of Formula I, wherein n is 1; 2 or 3; t is 0, 1 or 2; y is 0 or 1; z is 0, 1 or 2; $X^1$ is $CR^1$; m is 1; E is O; $X^2$ is O and $X^3$ is direct bond.

The present invention further relates to the Compound of Formula I, wherein n is 1; 2 or 3; t is 0, 1 or 2; y is 0 or 1; z is 0, 1 or 2; $X^1$ is $CR^1$; m is 1; E is O; $X^2$ is NH and $X^3$ is direct bond.

The present invention further relates to the Compound of Formula I, wherein n is 1; 2 or 3; t is 0, 1 or 2; y is 0 or 1; z is 0, 1 or 2; $X^1$ is $CR^1$; m is 1; E is O; $X^2$ is $CH_2$ and $X^3$ is direct bond.

The present invention further relates to the Compound of Formula I, wherein n is 1; 2 or 3; t is 0, 1 or 2; y is 0 or 1; z is 0, 1 or 2; $X^1$ is $CR^1$; m is 1; E is S; $X^2$ is NH and $X^3$ is direct bond.

The present invention further relates to the Compound of Formula I, wherein n is 1; 2 or 3; t is 0, 1 or 2; y is 0 or 1; z is 0, 1 or 2; $X^1$ is $CR^1$; m is 0; E is O; $X^1$ is NH and $X^3$ is direct bond.

The present invention further relates to the Compound of Formula I, wherein n is 1; 2 or 3; t is 0, 1 or 2; y is 0 or 1; z is 0, 1 or 2; $X^1$ is $CR^1$; m is 1; p is 0; $X^2$ is NH—$SO_2$ and $X^3$ is direct bond.

The present invention further relates to the Compound of Formula I, wherein $X^5$ is a direct bond, O, S, $SO_2$, $CR^4R^5$; $(C_1-C_6)$alkyl, $(C_1-C_6)$alkyloxy, $(C_1-C_6)$alkenyl or $(C_1-C_6)$alkenyloxy.

The present invention further relates to the Compound of Formula I, wherein $X^5$ is —O—$(C_1-C_6)$alkyl, —R—$(C_3-C_{10})$cycloalkyl, $(C_3-C_{10})$cycloalkyl-$R^{7}$—, —$R^7$—$(C_6-C_{12})$aryl, $(C_6-C_{12})$aryl-$R^{7}$, —$R^7$—$(C_2-C_9)$heteroaryl, $(C_2-C_9)$heteroaryl-$R^{7}$—, —$R^7$—$(C_2-C_9)$heterocycloalkyl, and $(C_2-C_9)$heterocycloalkyl-$R^{7}$, wherein $R^7$ is a direct bond, O, S, $SO_2$, $CR^4R^5$; $(C_1-C_6)$alkyl, $(C_1-C_6)$alkyloxy, —O—$(C_1-C_6)$alkyl, $(C_1-C_6)$alkenyl or $(C_1-C_6)$alkenyloxy.

The present invention further relates to the Compound of Formula I, wherein $A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkylenyl, amino, $(C_1-C_6)$ alkylamino, $(C_1-C_6)$dialkylamino, $(C_1-C_6)$alkoxy, O$(C_3-C_6$ cycloalkyl), $(C_3-C_6)$cycloalkoxy, nitro, CN, OH, $(C_1-C_6)$alkyloxy optionally substituted by one to three halo; $(C_3-C_6)$ cycloalkyl, $(C_1-C_6)$ alkoxycarbonyl, $(C_1-C_6)$ alkylcarbonyl or $(C_1-C_6)$ haloalkyl.

The present invention further relates to the Compound of Formula I, wherein $A^2$ is $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl wherein $A^2$ is substituted with one or more substituents selected from the group consisting of $(C_2-C_9)$heterocycloalkyl, $R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy; and $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

The present invention further relates to the Compound of Formula I, wherein $X^3$ is O, —NH, —$CH_2$—, CO, —CH $(C_1-C_6)$ alkyl, $SO_2NH$, —CO—NH— or —$NR^3$; $X^4$ is $CR^4R^5$, $CH_2$ $CR^4R^5$ or $CH_2$—$(C_1-C_6)$ alkyl-$CR^4R^5$; and $A^2$ is $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl wherein $A^2$ is substituted with one or more substituents selected from the group consisting of, $(C_2-C_9)$heterocycloalkyl, $R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

The present invention further relates to the Compound of Formula I, wherein $A^1$ is phenyl.

The present invention further relates to the Compound of Formula I, wherein $X^5$ is a direct bond.

The present invention further relates to the Compound of Formula I, wherein $A^2$ is phenyl substituted by $(C_1-C_6)$alkoxy$(C_1-C_6)$ alkoxy.

The present invention further relates to the Compound of Formula I, wherein n is 1; t is 0; y is 1; z is 1; $X^1$ is $CR^1$; m is 1; p is 1; E is O; $X^2$ is O; $X^3$ is NH; $R^1$ is H; $X^4$ is $CR^4R^5$ wherein R4 and R5 are each independently methyl; $R^6$ is a hydrogen; $A^1$ is phenyl; $X^5$ is a direct bond, O or $CR^4R^5$ and A2 is phenyl substituted by $(C_1-C_6)$ alkoxy$(C_1-C_6)$ alkoxy.

The present invention further relates to a compound of the formula

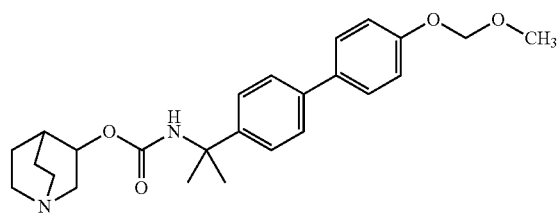 [SMILES: COCOc1ccc(-c2ccc(C(C)(C)NC(=O)OC3CN4CCC3CC4)cc2)cc1]

or a pharmaceutically acceptable salt or prodrug thereof.

The present invention further relates to the Compound of Formula I, wherein $A^1$ is piperdine optionally substituted by halo.

The present invention further relates to the Compound of Formula I, wherein $X^5$ is pyrimidine optionally substituted by halo.

In the various combination therapies of the invention, it will be understood that administering small molecule therapy may occur prior to, concurrently with, or after, administration of enzyme replacement therapy. Similarly, administering enzyme replacement therapy may occur prior to, concurrently with, or after, administration of small molecule therapy.

Definitions

As used herein, the term "pharmaceutically acceptable salt" means either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "prodrug" means a pharmacological derivative of a parent drug molecule that requires biotransformation, either spontaneous or enzymatic, within the organism to release the active drug. For example, prodrugs are variations or derivatives of the compounds of Formula I that have groups cleavable under certain metabolic conditions, which when cleaved, become the compounds of Formula I. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide or alkyl ester moiety covalently bonded to any of the above substituents disclosed herein.

As used herein, the term "$(C_1-C_6)$alkyl" means a saturated linear or branched free radical consisting essentially of 1 to 6 carbon atoms and a corresponding number of hydrogen atoms. Exemplary $(C_1-C_6)$alkyl groups include methyl, ethyl, n-propyl, isopropyl, n-butyl, isobutyl, etc. Of course, other $(C_1-C_6)$alkyl groups will be readily apparent to those of skill in the art given the benefit of the present disclosure.

As used herein, the term "$(C_3-C_{10})$cycloalkyl" means a nonaromatic saturated free radical forming at least one ring consisting essentially of 3 to 10 carbon atoms and a corresponding number of hydrogen atoms. As such, $(C_3-C_{10})$ cycloalkyl groups can be monocyclic or multicyclic. Individual rings of such multicyclic cycloalkyl groups can have different connectivities, e.g., fused, bridged, spiro, etc. in addition to covalent bond substitution. Exemplary $(C_3-C_{10})$ cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl substituted with cyclobutyl, cyclobutyl substituted with cyclopentyl, cyclohexyl substituted with cyclopropyl, etc. Of course, other $(C_3-C_{10})$cycloalkyl groups will be readily apparent to those of skill in the art given the benefit of the present disclosure.

As used herein, the term "$(C_2-C_9)$heterocycloalkyl" means a nonaromatic free radical having 3 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, $(C_2-C_9)$heterocycloalkyl groups can be monocyclic or multicyclic. Individual rings of such multicyclic heterocycloalkyl groups can have different connectivities, e.g., fused, bridged, spiro, etc. in addition to covalent bond substitution. Exemplary $(C_2-C_9)$ heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, etc. In general, the ($C_2$-$C_9$)heterocycloalkyl group typically is attached to the main structure via a carbon atom or a nitrogen atom. Of course, other ($C_2$-$C_9$)heterocycloalkyl groups will be readily apparent to those of skill in the art given the benefit of the present disclosure.

As used herein, the term "($C_2$-$C_9$)heteroaryl" means an aromatic free radical having 5 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, ($C_2$-$C_9$)heteroaryl groups can be monocyclic or multicyclic. Individual rings of such multicyclic heteroaryl groups can have different connectivities, e.g., fused, etc. in addition to covalent bond substitution. Exemplary ($C_2$-$C_9$)heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the ($C_2$-$C_9$)heteroaryl group typically is attached to the main structure via a carbon atom, however, those of skill in the art will realize when certain other atoms, e.g., hetero ring atoms, can be attached to the main structure. Of course, other ($C_2$-$C_9$)heteroaryl groups will be readily apparent to those of skill in the art given the benefit of the present disclosure.

As used herein, the term "($C_6$-$C_{10}$)aryl" means phenyl or naphthyl.

As used herein, the term "halo" means fluorine, chlorine, bromine, or iodine.

As used herein, the term "amino" means a free radical having a nitrogen atom and 1 to 2 hydrogen atoms. As such, the term amino generally refers to primary and secondary amines. In that regard, as used herein and in the appended claims, a tertiary amine is represented by the general formula RR'N—, wherein R and R' are carbon radicals that may or may not be identical. Nevertheless, the term "amino" generally may be used herein to describe a primary, secondary, or tertiary amine, and those of skill in the art will readily be able to ascertain the identification of which in view of the context in which this term is used in the present disclosure.

As used herein, the term "combination therapy" means treating a patient with two or more therapeutic platforms (e.g., enzyme replacement therapy and small molecule therapy) in rotating, alternating and/or simultaneous treatment schedules. Examples of treatment schedules may include, but are not limited to: (1) enzyme replacement therapy, then small molecule therapy; (2) small molecule therapy, then enzyme replacement therapy; (3) enzyme replacement therapy concurrent with small molecule therapy, and (4) and any combination of the foregoing. Combination therapy may provide a temporal overlap of therapeutic platforms, as needed, depending on the clinical course of a given storage disease in a given subject.

As used herein, the term "enzyme replacement therapy", or "ERT" means administering an exogenously-produced natural or recombinant enzyme to a patient who is in need thereof. In the case of a lysosomal storage disease, for example, the patient accumulates harmful levels of a substrate (i.e., material stored) in lysosomes due to a deficiency or defect in an enzyme responsible for metabolizing the substrate, or due to a deficiency in an enzymatic activator required for proper enzymatic function. Enzyme replacement therapy is provided to the patient to reduce the levels of (i.e., debulk) accumulated substrate in affected tissues. Table 1 provides a list of lysosomal storage diseases and identifies the corresponding enzyme deficiency and accumulated substrate for each disease. Enzyme replacement therapies for treating lysosomal storage diseases are known in the art. In accordance with a combination therapy of the invention, the lysosomal enzymes identified in Table 1 can be used for enzyme replacement therapy to reduce the levels of corresponding substrate in a patient diagnosed with the respective lysosomal storage disease.

As used herein, "effective amount" of an enzyme or small molecule, when delivered to a subject in a combination therapy of the invention, is an amount sufficient to improve the clinical course of a lysosomal storage disease, where clinical improvement is measured by any of the variety of defined parameters well known to the skilled artisan.

Abbreviations

ACN refers to acetonitrile.
DMF refers to N,N-dimethylformamide.
DMSO refers to dimethylsulfoxide.
EtOAc refers to ethyl acetate.
EtOH refers to ethanol.
Hunig's Base refers to diisopropylethyl amine ("DIPEA").
MeOH refers to methanol.
NaOH refers to sodium hydroxide.
THF refers to tetrahydrofuran.
TFA refers to trifluoroacetic acid.

Additional features and advantages of compounds disclosed herein will be apparent from the following detailed description of certain embodiments.

DETAILED DESCRIPTION

Figure 1:
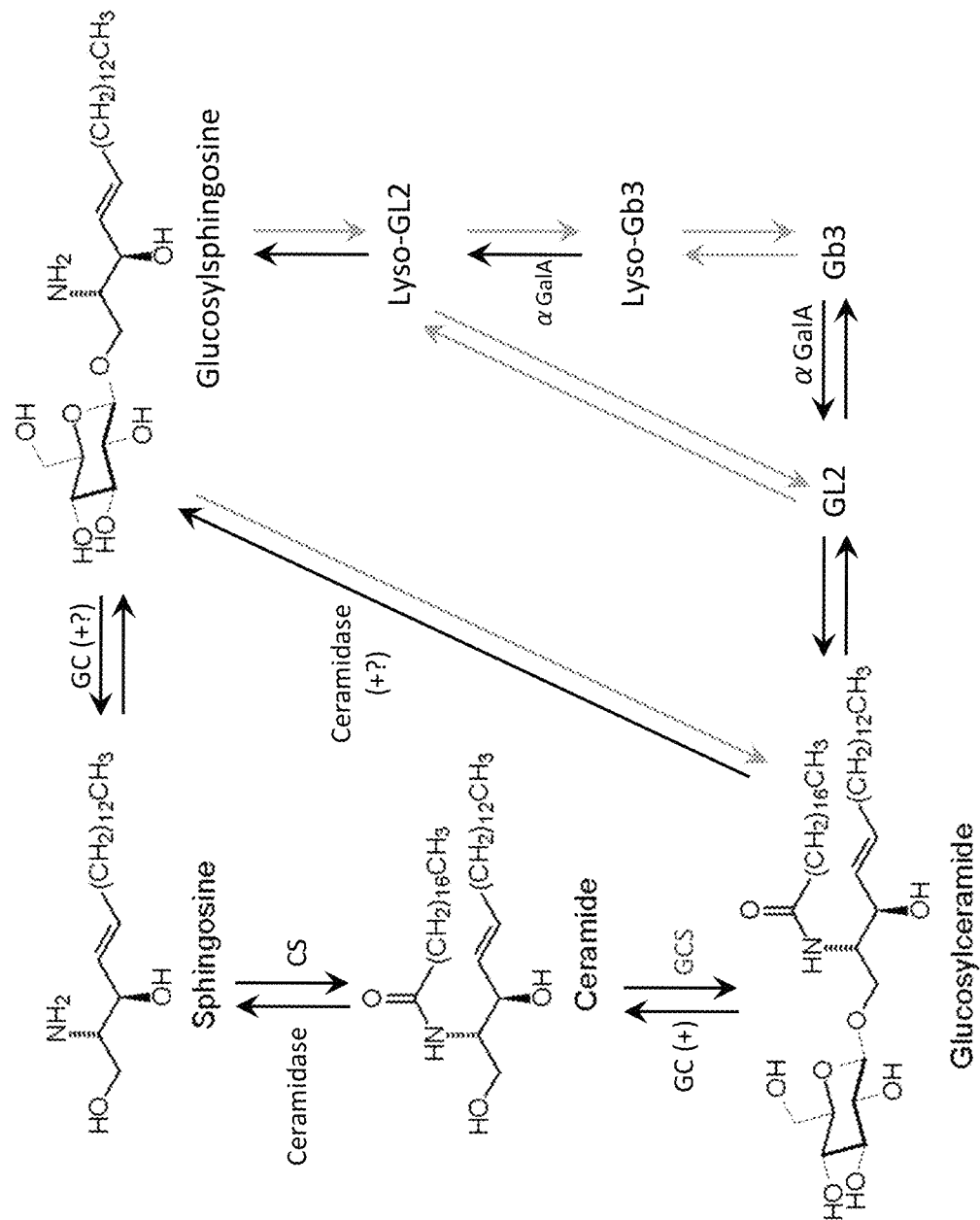
FIG. 1 presents the metabolic pathway for the potential synthesis of Gb3 and lyso-Gb3. Documented synthetic pathways are shown with black arrows and undocumented (potential) pathways are shown with grey arrows.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

The present invention refers to a compound represented by the following structural formula,

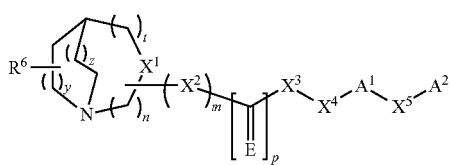

I or a pharmaceutically acceptable salt or prodrug thereof, wherein:

n is 1, 2 or 3;
m is 0 or 1;
p is 0 or 1;
t is 0, 1 or 2;
y is 1 or 2;
z is 0, 1 or 2;
E is S, O, NH, NOH, $NNO_2$, NCN, NR, NOR or $NSO_2R$;
$X^1$ is $CR^1$ when m is 1 or N when m is 0;
$X^2$ is O, —NH, —$CH_2$—, $SO_2$, NH—$SO_2$; $CH(C_1-C_6)$ alkyl or —$NR^2$;
$X^3$ is a direct bond, O, —NH, —$CH_2$—, CO, —$CH(C_1-C_6)$ alkyl, $SO_2NH$, —CO—NH— or —$NR^3$;
$X^4$ is a direct bond, $CR^4R^5$, $CH_2$ $CR^4R^5$ or $CH_2$—$(C_1-C_6)$ alkyl-$CR^4R^5$;
$X^5$ is a direct bond, O, S, $SO_2$, $CR^4R^5$; $(C_1-C_6)$alkyl, $(C_1-C_6)$alkyloxy, —O—$(C_1-C_6)$alkyl, $(C_1-C_6)$alkenyl, $(C_1-C_6)$alkenyloxy, —$R^7$—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C_2-C_9)$heteroaryl, $(C_2-C_9)$heteroaryl-$R^7$—, —$R^7$—$(C_2-C_9)$heterocycloalkyl, and $(C_2-C_9)$heterocycloalkyl-$R^7$—, wherein $R^7$ is a direct bond, O, S, $SO_2$, $CR^4R^5$; $(C_1-C_6)$alkyl, $(C_1-C_6)$alkyloxy, —O—$(C_1-C_6)$alkyl, $(C_1-C_6)$alkenyl, $(C_1-C_6)$alkenyloxy; and further wherein when $X^5$ is defined as —$R^7$—$(C_3-C_{10})$cycloalkyl, $(C_3-C_{10})$cycloalkyl-$R^7$—, —$R^7$—$(C_6-C_{12})$aryl, $(C_6-C_{12})$aryl-$R^7$—, —$R^7$—$(C_2-C_9)$heteroaryl, $(C_2-C_9)$heteroaryl-$R^7$—, —$R^7$—$(C_2-C_9)$heterocycloalkyl, and $(C_2-C_9)$heterocycloalkyl-R7—, wherein the $(C_3-C_{10})$cycloalkyl, $(C_6-C_{12})$aryl, $(C_2-C_9)$heteroaryl, $(C_2-C_9)$heterocycloalkyl groups are optionally substituted by one or more substituents selected from the group consisting of halo, $(C_1-C_6)$alkyl, $(C_1-C_6)$alkylenyl, amino, $(C_1-C_6)$alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$alkyloxy, $(C_3-C_6)$ cycloalkyl, $(C_1-C_6)$ alkoxycarbonyl, $(C_1-C_6)$ alkylcarbonyl, $(C_1-C_6)$ haloalkyl, $(C_2-C_9)$heterocycloalkyl, $R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$ alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy; and $(C_1-C_6)$alkyloxy substituted by one to four substituents selected from the group consisting of halo, hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

R is $(C_6-C_{12})$aryl, $(C_2-C_9)$heteroaryl, $(C_1-C_6)$alkyl, $(C_2-C_9)$heteroaryl$(C_1-C_6)$alkyl;
$R^1$ is H, CN, $(C_1-C_6)$alkylcarbonyl, or $(C_1-C_6)$alkyl;
$R^2$ and $R^3$ are each independently —H, $(C_1-C_6)$alkyl optionally substituted by one or more substituents selected from the group consisting of halogen, $(C_1-C_6)$alkyl, $(C_6-C_{12})$aryl, $(C_2-C_9)$heteroaryl, $(C_1-C_6)$alkyl$(C_6-C_{12})$aryl, halo $(C_6-C_{12})$aryl, and halo$(C_2-C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl;
$R^4$ and $R^5$ are independently selected from H, $(C_1-C_6)$alkyl, or taken together with the carbon to which they are attached to form a spiro $(C_3-C_{10})$cycloalkyl ring or spiro $(C_3-C_{10})$cycloalkoxy ring;
$R^6$ is —H, halogen, —CN, $(C_6-C_{12})$aryl, $(C_6-C_{12})$aryloxy, $(C_1-C_6)$alkyloxy; $(C_1-C_6)$alkyl optionally substituted by one to four halo or $(C_1-C_6)$alkyl;
$A^1$ is $(C_2-C_6)$alkynyl; $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkenyl, amino, $(C_1-C_6)$alkylamino, $(C_1-C_6)$dialkylamino, $(C_1-C_6)$alkoxy, nitro, CN, —OH, $(C_1-C_6)$alkyloxy optionally substituted by one to three halo; $(C_1-C_6)$alkoxycarbonyl, and $(C_1-C_6)$ alkylcarbonyl;
$A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkylenyl, amino, $(C_1-C_6)$ alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$alkyloxy optionally substituted by one to three halo; $(C_3-C_6)$ cycloalkyl, $(C_1-C_6)$ alkoxycarbonyl, $(C_1-C_6)$ alkylcarbonyl, $(C_1-C_6)$ haloalkyl, $(C_2-C_9)$heterocycloalkyl,
$R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$ heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

with the proviso that the sum of n+t+y+z is not greater than 6;

with the proviso that when p is 0; $X^2$ is NH—$SO_2$ and $X^3$ is NH;

with the proviso that when n is 1; t is 0; y is 1; z is 1; $X^2$ is NH; E is O; $X^3$ is NH; $A^2$ is H and $X^5$ is a direct bond; $A^1$ is not unsubstituted phenyl, halophenyl or isopropenyl phenyl;

with the proviso that when n is 1; t is 0; y is 1; z is 1; $X^2$ is O; E is O; $X^3$ is NH; $A^1$ is $(C_6-C_{12})$aryl and $X^5$ is a direct bond; $A^2$ is H and $R^4$ is H then $R^5$ is not cyclohexyl;

with the proviso that when n is 1; t is 0; y is 1; z is 1; $X^2$ is NH; E is O; $X^3$ is $CH_2$; $R^4$ and $R^5$ are both hydrogen; $A^2$ is H and $X^5$ is a direct bond; then $A^1$ is not unsubstituted phenyl; and with the proviso that when $X^3$ is O, —NH, —$CH_2$—, CO, —CH$(C_1-C_6)$ alkyl, $SO_2$NH, —CO—NH— or —$NR^3$; and $X^4$ is $CR^4R^5$, $CH_2$ $CR^4R^5$ or $CH_2$—$(C_1-C_6)$ alkyl-$CR^4R^5$; then $A^2$ must be $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl substituted with one or more substituents selected from the group consisting of, $(C_2-C_9)$heterocycloalkyl, $R^8R^9N$—CO— wherein $R^8$ and $R^9$ are each independently selected from the group consisting of hydrogen and $(C_1-C_6)$ alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$alkylsulfonyl optionally substituted by one or two groups selected from $(C_1-C_6)$ alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

The present invention further relates to a compound according to Formula I, wherein n is 1; t is 1; y is 1 and z is 1.

The present invention further relates to a compound according to Formula I, wherein n is 2; t is 0; y is 1 and z is 1.

The present invention further relates to a compound according to Formula I, wherein n is 2; t is 1; y is 1 and z is 1.

The present invention further relates to a compound according to Formula I, wherein n is 3; t is 0; y is 1 and z is 1.

The present invention further relates to a compound according to Formula I, wherein n is 1; t is 2; y is 1 and z is 1.

The present invention further relates to a compound according to Formula I, wherein n is 1; t is 0; y is 1 and z is 0.

The present invention further relates to a compound according to Formula I, wherein n is 1; t is 1; y is 1 and z is 0.

The present invention further relates to a compound according to Formula I, wherein n is 2; t is 0; y is 1 and z is 0.

The present invention further relates to a compound according to Formula I, wherein n is 2; t is 1; y is 1 and z is 0.

The present invention further relates to a compound according to Formula I, wherein n is 3; t is 0; y is 1 and z is 0.

The present invention further relates to a compound according to Formula I, wherein n is 1; t is 2; y is 1 and z is 0.

The present invention further relates to a compound according to Formula I, wherein n is 1; t is 1; y is 2 and z is 0.

The present invention further relates to a compound according to Formula I, wherein n is 2; t is 0; y is 2 and z is 0.

The present invention further relates to a compound according to Formula I, wherein m is 0 and $X^1$ is N.

The present invention further relates to a compound according to Formula I, wherein m is 1; E is O; $X^2$ is NH and $X^3$ is NH.

The present invention further relates to a compound according to Formula I, wherein m is 1; E is O; $X^2$ is CH2 and $X^3$ is NH.

The present invention further relates to a compound according to Formula I, wherein m is 1; E is O; $X^2$ is NH and $X^3$ is CH2.

The present invention further relates to a compound according to Formula I, wherein m is 1; E is S; $X^2$ is NH and $X^3$ is NH.

The present invention further relates to a compound according to Formula I, wherein m is 0; E is O; $X^1$ is NH and $X^3$ is NH.

The present invention further relates to a compound according to Formula I, wherein m is 1; E is O; $X^2$ is NH and $X^3$ is CO—NH.

The present invention further relates to a compound according to Formula I, wherein m is 1; p is 0; $X^2$ is NH—$SO_2$ and $X^3$ is NH.

The present invention further relates to a compound according to Formula I, wherein $R^4$ and $R^5$ are each $(C_1-C_6)$alkyl or taken together with the carbon to which they are attached to form a spiro $(C_3-C_{10})$cyclo-alkyl ring or a spiro $(C_3-C_{10})$cycloalkoxy ring.

The present invention further relates to a compound according to Formula I, wherein $R^4$ and $R^5$ are each $(C_1-C_6)$alkyl or taken together with the carbon to which they are attached to form a spiro $(C_3-C_{10})$cyclo-alkyl ring or a spiro $(C_3-C_{10})$cycloalkoxy ring, and further wherein $X^4$ is $CR^4R^5$ wherein $R^4$ and $R^5$ are taken together with the carbon to which they are attached to form a spiro $(C_3-C_{10})$cycloalkyl ring.

The present invention further relates to a compound according to Formula I, wherein $R^4$ and $R^5$ are each ($C_1$-$C_6$)alkyl or taken together with the carbon to which they are attached to form a spiro ($C_3$-$C_{10}$)cyclo-alkyl ring or a spiro ($C_3$-$C_{10}$)cycloalkoxy ring, and further wherein $X^4$ is $CR^4R^5$ wherein $R^4$ and $R^5$ are taken together with the carbon to which they are attached to form a spiro ($C_3$-$C_{10}$)cycloalkyl ring, and further wherein $X^4$ is $CR^4R^5$ wherein $R^4$ and $R^5$ are taken together with the carbon to which they are attached to form a spiro cyclopropyl ring.

The present invention further relates to a compound according to Formula I, wherein $R^4$ and $R^5$ are each ($C_1$-$C_6$)alkyl or taken together with the carbon to which they are attached to form a spiro ($C_3$-$C_{10}$)cyclo-alkyl ring or a spiro ($C_3$-$C_{10}$)cycloalkoxy ring, and further wherein $X^4$ is $CR^4R^5$ wherein $R^4$ and $R^5$ are taken together with the carbon to which they are attached to form a spiro ($C_3$-$C_{10}$)cycloalkoxy ring.

The present invention further relates to a compound according to Formula I, wherein $A^1$ is ($C_2$-$C_9$)heteroaryl.

The present invention further relates to a compound according to Formula I, wherein $A^1$ is ($C_2$-$C_9$)heteroaryl, and further wherein $A^1$ is thiophene, thiazole, isothiazole, furane, oxazole, isoxazole, pyrrole, imidazole, pyrazole, triazole, pyridine, pymiridine, pyridazine, indole, benzotiazole, benzoisoxazole, benzopyrazole, benzoimidazole, benzofuran, benzooxazole or benzoisoxazole.

The present invention further relates to a compound according to Formula I, wherein $A^1$ is ($C_2$-$C_9$)heterocycloalkyl.

The present invention further relates to a compound according to Formula I, wherein $A^1$ is ($C_2$-$C_9$)heterocycloalkyl, and further wherein $A^1$ is pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, 2,6-diazaspiro[3.3]heptane, 2-azaspiro[3.3]heptane, 2,7-diazaspiro[4.4]nonane, azepane, 1,4-diazepane, 3,6-diazabicyclo[3.1.1]heptane, 2-azabicyclo[2.2.1]heptane, 7-azabicyclo[2.2.2]octane, 3-azabicyclo[3.1.1]heptane or 6-azabicyclo[3.1.1]heptane.

The present invention further relates to a compound according to Formula I, wherein $A^1$ is benzo($C_2$-$C_9$)heterocycloalkyl.

The present invention further relates to a compound according to Formula I, wherein $A^1$ is benzo($C_2$-$C_9$)heterocycloalkyl, and further wherein $A^1$ is 2,3-dihydrobenzo[b][1,4] dioxine or 2,2-difluorobenzo[d][1,3]dioxole.

The present invention further relates to a compound according to Formula I, $X^5$ is a direct bond.

The present invention further relates to a compound according to Formula I, wherein $X^5$ is a $CR^4R^5$.

The present invention further relates to a compound according to Formula I, wherein $X^5$ is $CR^4R^5$ wherein $R^4$ and $R^5$ are each methyl.

The present invention further relates to a compound according to Formula I, wherein $X^5$ is $CR^4R^5$ wherein $R^4$ and $R^5$ are taken together with the carbon to which they are attached to form a spiro ($C_3$-$C_{10}$)cycloalkyl ring.

The present invention further relates to a compound according to Formula I, wherein $X^5$ is $CR^4R^5$ wherein $R^4$ and $R^5$ are taken together with the carbon to which they are attached to form a spiro ($C_3$-$C_{10}$)cycloalkyl ring, wherein $X^5$ is $CR^4R^5$ wherein $R^4$ and $R^5$ are taken together with the carbon to which they are attached to form a spiro cyclopropyl ring.

The present invention further relates to a compound according to Formula I, wherein $X^5$ is a $CR^4R^5$, wherein $R^4$ and $R^5$ are taken together with the carbon to which they are attached to form a spiro ($C_3$-$C_{10}$)cycloalkoxy ring.

The present invention further relates to a compound according to Formula I, wherein $A^2$ is ($C_6$-$C_{12}$)aryl.

The present invention further relates to a compound according to Formula I, wherein $A^2$ is ($C_2$-$C_9$)heteroaryl.

The present invention further relates to a compound according to Formula I, wherein $A^2$ is ($C_2$-$C_9$)heteroaryl, further wherein $A^2$ is pyridine.

The present invention further relates to a compound according to Formula I, wherein $A^2$ is ($C_2$-$C_9$)heterocycloalkyl.

The present invention further relates to a compound according to Formula I, wherein $A^2$ is ($C_2$-$C_9$)heterocycloalkyl, further wherein $A^2$ is ($C_2$-$C_9$)heterocycloalkyl further wherein $A^2$ is pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl or octahydro-1H-indolyl.

The present invention further relates to a compound according to Formula I, wherein $A^2$ is benzo($C_2$-$C_9$)heterocycloalkyl.

The present invention further relates to a compound according to Formula I, wherein $A^2$ is benzo($C_2$-$C_9$)heterocycloalkyl further wherein $A^2$ is 2,3-dihydrobenzo[b][1,4]dioxine or 2,2-difluorobenzo[d][1,3]dioxole.

The present invention further relates to a compound according to Formula I, where $R^1$ is hydrogen or methyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; X3 is NH; $R^1$ is H; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$) cycloalkoxy ring; $R^6$ is a hydrogen or methyl; $A^1$ is ($C_6$ $C_{12}$)aryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is ($C_6$ $C_{12}$)aryl; $X^5$ is a direct bond, 0 or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; X3 is NH; $R^1$ is H; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$ $C_{12}$)aryl; $X^5$ is a direct bond, O or $CR^4R^5$ and $A^2$ is ($C_2$-$C_9$)heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is ($C_6$ $C_{12}$)aryl; $X^5$ is a direct bond, 0 or $CR^4R^5$ and $A^2$ is ($C_2$-$C_9$)heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$) cycloalkoxy ring; $R^6$ is a hydrogen or methyl; $A^1$ is ($C_2$-$C_9$) heteroaryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$ $C_{12}$)aryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is ($C_6$ $C_{12}$)aryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$) aryl; $X^5$ is a direct bond, O or $CR^4R^5$ and $A^2$ is ($C_2$-$C_9$) heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$) heteroaryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CH2; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$ $C_{12}$)aryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CH2; $X^4$ is $CR^4R^5$ wherein $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is CR1; m is 1; E is O; $X^2$ is NH; $X^3$ is CH2; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$) aryl; $X^5$ is a direct bond, O or $CR^4R^5$ and $A^2$ is ($C_2$-$C_9$) heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CH2; $X^4$ is $CR^4R^5$ wherein $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CH2; $X^4$ is $CR^4R^5$ wherein $R^4$ and $R^5$ are taken together with the carbon to which they are attached to form a spiro ($C_3$-$C_{10}$)cycloalkyl ring or spiro ($C_3$—$C_{10}$)cycloalkoxy ring; $R^6$ is a hydrogen or methyl; $A^1$ is ($C_2$-$C_9$) heteroaryl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CH2; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is CR1; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_2-C_9)$ heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$ cycloalkyl ring or spiro $(C_3-C_{10})$cycloalkoxy ring; $R^6$ is a hydrogen or methyl; $A^1$ is $(C_6 C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$ cycloalkyl ring or spiro $(C_3-C_{10})$cycloalkoxy ring; $R^6$ is a hydrogen or methyl; $A^1$ is $(C_6 C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_6 C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$ cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$ cycloalkoxy ring; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$ cycloalkoxy ring; $R^6$ is a hydrogen or methyl; $A^1$ is $(C_6 C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$ cycloalkoxy ring; $R^6$ is a hydrogen or methyl; $A^1$ is $(C_2-C_9)$ heteroaryl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, 0 or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$ cycloalkoxy ring; $R^6$ is a hydrogen or methyl; $A^1$ is $(C_6 C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_6 C_{12})$aryl; $X^5$ is a direct bond, 0 or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$ cycloalkoxy ring; $R^6$ is a hydrogen or methyl; $A^1$ is $(C_2-C_9)$ heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is ($C_6$-$C_{12}$)aryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is ($C_2$-$C_9$)heterocycloalkyl; $X^5$ is a direct bond, 0 or $CR^4R^5$ and $A^2$ is ($C_6$-$C_{12}$)aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is ($C_2$-$C_9$)heterocycloalkyl; $X^5$ is a direct bond, O or $CR^4R^5$ and $A^2$ is ($C_2$-$C_9$)heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro ($C_3$-$C_{10}$)cycloalkyl ring or spiro ($C_3$-$C_{10}$)cycloalkoxy ring; $R^6$ is a hydrogen or methyl; $A^1$ is ($C_2$-$C_9$)heteroaryl; $X^5$ is a direct bond, O or $CR^4R^5$ and $A^2$ is ($C_2$-$C_9$)heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH^2$; $X^4$ is $CR^4R^5$ wherein $R^4$ and $R^5$ are each independently methyl; $R^6$ is a hydrogen or methyl; $A^1$ is $(C2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH^2$; $X^3$ is NH; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heterocycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heterocycloalkyl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2\text{-}C_9)$heterocycloalkyl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heterocycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heterocycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heterocycloalkyl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_2\text{-}C_9)$heterocycloalkyl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, 0 or $CR^4R^5$ and $A^2$ is $(C_2\text{-}C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_2\text{-}C_9)$heteroaryl; $X^5$ is a direct bond, 0 or $CR^4R^5$ and $A^2$ is $(C_2\text{-}C_9)$heterocycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heterocycloalkyl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_2\text{-}C_9)$heterocycloalkyl; $X^5$ is a direct bond, 0 or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{—}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are taken together with the carbon to which they are attached to form a spiro $(C_3\text{-}C_{10})$cycloalkyl ring or spiro $(C_3\text{-}C_{10})$cycloalkoxy ring; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are each independently methyl; $R^6$ is a hydrogen or methyl; $A^1$ is $(C_2\text{-}C_9)$heteroaryl; $X^5$ is a direct bond, O or $CR^4R^5$ and $A^2$ is $(C_2\text{-}C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, 0 or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3—C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$ cycloalkyl ring or spiro $(C_3-C_{10})$cycloalkoxy ring; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_6-C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_6\ C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_6\ C_{12})$aryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, 0 or $CR^4R^5$ and $A^2$ is $(C_6-C_{12})$aryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; X is $CR^1$; m is 1; p is 1; E is O; $X^2$ is O; $X^3$ is NH; $R^1$ is H; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 1; E is O; $X^2$ is O; $X^3$ is NH; $R^1$ is H; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; X is $CR^1$; m is 1; E is O; $X^2$ is NH; $X^3$ is $CH_2$; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; X is $CR^1$; m is 1; E is O; $X^2$ is NH; $X^3$ is $CH_2$; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is $CH_2$; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; X is $CR^1$; m is 1; E is O; $X^2$ is $CH_2$; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; X is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; X is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; X is $CR^1$; m is 1; E is $SO_2$; $X^2$ is NH; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is $SO_2$; $X^2$ is NH; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; $X^1$ is N; m is 0; E is O; $X^3$ is NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to a compound according to Formula I, wherein n is 1; 2 or 3; t is 0, 1 or 2; y is 0 or 1; z is 0, 1 or 2; X is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_2-C_9)$heteroaryl; $X^5$ is a direct bond, O or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_2-C_9)$heteroaryl; $X^5$ is a direct bond, 0 or $CR^4R^5$ and $A^2$ is $(C_3-C_{10})$cycloalkyl.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are taken together with the carbon to which they are attached to form a spiro $(C_3-C_{10})$cycloalkyl ring or spiro $(C_3-C_{10})$cycloalkoxy ring; $R^6$ is a hydrogen or methyl; $A^1$ is $(C_3-C_{10})$cycloalkyl; $X^5$ is a direct bond, O or $CR^4R^5$ and $A^2$ is $(C_2-C_9)$heteroaryl.

The present invention further relates to an A compound according to Formula I, wherein n is 1; 2 or 3; t is 0, 1 or 2; y is 0 or 1; z is 0, 1 or 2; $X^1$ is $CR^1$; m is 1; E is O; $X^2$ is NH; $X^3$ is CO—NH; $X^4$ is $CR^4R^5$ wherein $R^4$ and $R^5$ are each independently methyl; $R^6$ is a hydrogen or methyl; $A^1$ is $(C_3-C_{10})$cycloalkyl; $X^5$ is a direct bond, 0 or $CR^4R^5$ and $A^2$ is $(C_2-C_9)$heteroaryl.

The present invention further relates to a compound according to Formula I, wherein $A^1$ is $(C_3-C_{10})$cycloalkyl.

The present invention further relates to a compound according to Formula I, wherein $A^2$ is $(C_3-C_{10})$cycloalkyl.

The present invention further relates to a compound according to Formula I, or a pharmaceutically acceptable salt or prodrug thereof, selected from the group consisting of:

1-azabicyclo[2.2.2]oct-3-yl [2-(2,4'-difluorobiphenyl-4-yl)propan-2-yl]carbamate;

1-azabicyclo[2.2.2]oct-3-yl {2-[4-(1,3-benzothiazol-6-yl)phenyl]propan-2-yl}carbamate;

1-azabicyclo[3.2.2]non-4-yl {1-[5-(4-fluorophenyl)pyridin-2-yl]cyclopropyl}carbamate;

1-azabicyclo[2.2.2]oct-3-yl {1-[3-(4-fluorophenoxy)phenyl]cyclopropyl}carbamate;

1-azabicyclo[2.2.2]oct-3-yl {1-[4-(1,3-benzothiazol-5-yl)phenyl]cyclopropyl}carbamate;

1-azabicyclo[2.2.2]oct-3-yl [1-(4'-fluoro-3'-methoxybiphenyl-4yl)cyclopropyl]carbamate;

1-azabicyclo[2.2.2]oct-3-yl [3-(4'-fluorobiphenyl-4-yl)oxetan-3-yl]carbamate;

1-azabicyclo[2.2.2]oct-3-yl {1-[6-(4-fluorophenoxy)pyridin-2-yl]cyclopropyl}carbamate;

1-azabicyclo[2.2.2]oct-3-yl [3-(4'-fluorobiphenyl-4-yl)pentan-3-yl]carbamate;

1-azabicyclo[2.2.2]oct-3-yl {2-[2-(4-fluorophenyl)-2H-indazol-6-yl]propan-2 yl}carbamate;

1-azabicyclo[2.2.2]oct-3-yl {2-[2-(1H-pyrrol-1-yl)pyridin-4-yl]propan-2-yl}carbamate;

1-(3-ethyl-1-azabicyclo[2.2.2]oct-3-yl)-3-[1-(4'-fluorobiphenyl-4-yl)cyclopropyl]urea;

N-(1-azabicyclo[2.2.2]oct-3-yl)-N'-[1-(4'-fluorobiphenyl-4yl)cyclopropyl] ethanediamide;

1-azabicyclo[2.2.2]oct-3-yl (1-{4[(4,4difluorocyclohexyl)oxy]phenyl}cyclopropyl) carbamate;

1-(4-methyl-1-azabicyclo[3.2.2]non-4-yl)-3-[1-(5-phenylpyridin-2-yl)cyclopropyl]urea;

1-[1-(4'-fluorobiphenyl-4-yl)cyclopropyl]-1-methyl-3-(3-methyl-1-azabicyclo[2.2.2]oct-3-yl)urea;

1-[1-(4'-fluorobiphenyl-4-yl)cyclopropyl]-1-methyl-3-(3-methyl-1-azabicyclo[2.2.2]oct-3-yl)urea;

1-{2-[4'-(2-methoxyethoxy)biphenyl-4-yl]propan-2-yl}-3-(3-methyl-1-azabicyclo[2.2.2]oct-3-yl)urea;

2-(1-azabicyclo[3.2.2]non-4-yl)-N-[1-(5-phenylpyridin-2-yl)cyclopropyl]acetamide;

3-(4'-fluorobiphenyl-4-yl)-3-methyl-N-(4-methyl-1-azabicyclo[3.2.2]non-4-yl)butanamide;

N-[2-(biphenyl-4-yl)propan-2-yl]-N'-(3-methyl-1-azabicyclo[2.2.2]oct-3-yl)sulfuric diamide;

N-[2-(4'-fluorobiphenyl-4-yl)propan-2-yl]-N'-(3-methyl-1-azabicyclo[2.2.2]oct-3-yl)sulfuric diamide;

1-(3-butyl-1-azabicyclo[2.2.2]oct-3-yl)-3-{2-[1-(4-fluorophenyl)-1H-pyrazol-4-yl]propan-2-yl}urea;

1-azabicyclo[2.2.2]oct-3-yl [4-(4-fluorophenyl)-2-methylbut-3-yn-2-yl]carbamate;

1-(3-butyl-1-azabicyclo[2.2.2]oct-3-yl)-3-[4-(4-fluorophenyl)-2-methylbut-3-yn-2-yl]urea;

N-[1-(4'-fluorobiphenyl-4-yl)cyclopropyl]-1,4-diazabicyclo[3.2.2]nonane-4-carboxamide;

1-(2-(4'-fluoro-[1,1'-biphenyl]-4-yl)propan-2-yl)-3-(3-methyl-1-azabicyclo[3.2.2]nonan-3-yl)urea;

1-(2-(4'-fluoro-[1,1'-biphenyl]-4-yl)propan-2-yl)-3-(4-methyl-1-azabicyclo[4.2.2]decan-4-yl)urea;

1-(2-(4'-fluoro-[1,1'-biphenyl]-4-yl)propan-2-yl)-3-(3-methyl-1-azabicyclo[4.2.2]decan-3-yl)urea; and 1-(2-(4'-fluoro-[1,1'-biphenyl]-4-yl)propan-2-yl)-3-(5-methyl-1-azabicyclo[4.2.2]decan-5-yl)urea.

The present invention further relates to a pharmaceutical composition for treating a disease or disorder mediated by glucosylceramide synthase (GCS) or a disease or disorder in which GCS is implicated in a subject in need of such treatment comprising administering to the subject an effective amount of a compound according to Formula I.

The present invention further relates to a method for treating a disease or disorder mediated by glucosylceramide synthase (GCS) or a disease or disorder in which GCS is implicated in a subject in need of such treatment comprising administering to the subject an effective amount of a compound according to Formula I.

The present invention further relates to a method for treating a disease or disorder mediated by glucosylceramide synthase (GCS) or a disease or disorder in which GCS is implicated in a subject in need of such treatment comprising administering to the subject an effective amount of a compound according to Formula I wherein the disease or disorder is cancer.

The present invention further relates to a method for treating a disease or disorder mediated by glucosylceramide synthase (GCS) or a disease or disorder in which GCS is implicated in a subject in need of such treatment comprising administering to the subject an effective amount of a compound according to Formula I, wherein the disease or disorder is a metabolic disorder.

The present invention further relates to a method for treating a disease or disorder mediated by glucosylceramide synthase (GCS) or a disease or disorder in which GCS is implicated in a subject in need of such treatment comprising administering to the subject an effective amount of a compound according to Formula I, wherein the disease or disorder is a neuropathic disease.

The present invention further relates to a method for treating a disease or disorder mediated by glucosylceramide synthase (GCS) or a disease or disorder in which GCS is implicated in a subject in need of such treatment comprising administering to the subject an effective amount of a compound according to Formula I, wherein the disease or disorder is a neuropathic disease, wherein the neuropathic disease is Alzheimers disease.

The present invention further relates to a method for treating a disease or disorder mediated by glucosylceramide synthase (GCS) or a disease or disorder in which GCS is implicated in a subject in need of such treatment comprising administering to the subject an effective amount of a compound according to Formula I, wherein the disease or disorder is a neuropathic disease, wherein the neuropathic disease is Parkinsons disease.

The present invention further relates to a method for inducing decreased glucosylceramide synthase catalytic activity in a cell, in vitro, comprising contacting the cell with an effect amount of a compound according to Formula I.

The present invention further relates to a method of treating a subject diagnosed as having a lysosomal storage disease, comprising administering to the subject an effective amount of the compound according to Formula I.

The present invention further relates to a method of treating a subject diagnosed as having a lysosomal storage disease, comprising administering to the subject an effective amount of the compound according to Formula I, wherein the lysosomal storage disease results from a defect in the glycosphingolipid pathway.

The present invention further relates to a method of treating a subject diagnosed as having a lysosomal storage disease, comprising administering to the subject an effective amount of the compound according to Formula I, wherein the lysosomal storage disease results from a defect in the glycosphingolipid pathway, wherein the lysosomal storage disease is selected from the group consisting of Gaucher, Fabry, GM1-gangliosidosis, GM2 Activator deficiency, Tay-Sachs and Sandhoff.

The present invention further relates to a method of treating a subject diagnosed as having a lysosomal storage disease, comprising administering to the subject an effective amount of the compound according to Formula I, wherein the lysosomal storage disease results from a defect in the glycosphingolipid pathway, wherein the lysosomal storage disease is selected from the group consisting of Gaucher, Fabry, GM1-gangliosidosis, GM2 Activator deficiency, Tay-Sachs and Sandhoff, wherein the lysosomal storage disease is Fabry.

The present invention further relates to a method of treating a subject diagnosed as having a lysosomal storage disease, comprising administering to the subject an effective amount of the compound according to Formula I, further comprising the step of administering to the subject a therapeutically effective amount of a lysosomal enzyme.

The present invention further relates to a method of treating a subject diagnosed as having a lysosomal storage disease, comprising administering to the subject an effective amount of the compound according to Formula I, further comprising the step of administering to the subject a therapeutically effective amount of a lysosomal enzyme, wherein the lysosomal enzyme is selected from the group consisting of glucocerebrosidase, alpha-galactosidase A, Hexosaminidase A, Hexosaminidase B and GM1-ganglioside-β-galactosidase.

The present invention further relates to a method of treating a subject diagnosed as having a lysosomal storage disease, comprising administering to the subject an effective amount of the compound according to Formula I, further comprising the step of administering to the subject a therapeutically effective amount of a lysosomal enzyme, wherein the lysosomal enzyme is alpha-galactosidase A.

The present invention further relates to a method of treating a subject diagnosed as having a lysosomal storage disease, comprising administering to the subject an effective amount of the compound according to Formula I, further comprising the step of administering to the subject a therapeutically effective amount of a lysosomal enzyme, wherein prior to treatment the subject has elevated levels of a lysosomal substrate.

The present invention further relates to a method of treating a subject diagnosed as having a lysosomal storage disease, comprising administering to the subject an effective amount of the compound according to Formula I, further comprising the step of administering to the subject a therapeutically effective amount of a lysosomal enzyme, wherein prior to treatment the subject has elevated levels of a lysosomal substrate, wherein the subject undergoing treatment has lower combined amounts of the lysosomal substrate in the urine and plasma than a subject treated with either the lysosomal enzyme or compound alone.

The present invention further relates to a method of treating a subject diagnosed as having a lysosomal storage disease, comprising administering to the subject an effective amount of the compound according to Formula I, further comprising the step of administering to the subject a therapeutically effective amount of a lysosomal enzyme, wherein prior to treatment the subject has elevated levels of a lysosomal substrate, wherein the subject undergoing treatment has lower combined amounts of the lysosomal substrate in the urine and plasma than a subject treated with either the lysosomal enzyme or compound alone, wherein the substrate is selected from the group consisting of globotriaosylceramide and lyso-globotriaosylceramide, and combinations thereof.

The present invention further relates to a method of treating a subject diagnosed as having a lysosomal storage disease, comprising administering to the subject an effective amount of the compound according to Formula I, wherein the compound is represented by the following structural formula,

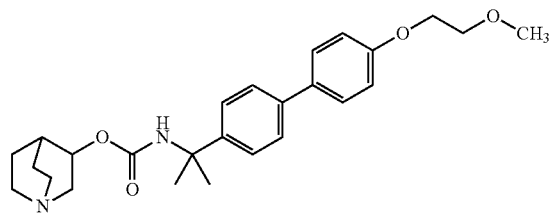 [SMILES: COCCOc1ccc(-c2ccc(C(C)(C)NC(=O)OC3CN4CCC3CC4)cc2)cc1]

or a pharmaceutically acceptable salt or prodrug thereof.

The present invention further relates to a method of reducing glucosylceramide synthase (GCS) activity in a subject diagnosed as having a lysosomal storage disease, comprising administering to the patient an effective amount of the compound according to Formula I, either alone or as a combination therapy with an enzyme replacement therapy.

The present invention further relates to a method of reducing accumulation of a GCS-derived material in a subject diagnosed as having a lysosomal storage disease, comprising administering to the patient an effective amount of the compound according to Formula I, either alone or as a combination therapy with an enzyme replacement therapy.

The present invention further relates to a compound according to Formula I, wherein $X^3$ is a direct bond.

The present invention further relates to a compound according to Formula I, wherein $X^4$ is a direct bond.

The present invention further relates to a compound according to Formula I, wherein $X^3$ and $X^4$ are each independently a direct bond.

The present invention further relates to a compound according to Formula I, wherein m is 1; E is O; $X^2$ is O and $X^3$ is direct bond.

The present invention further relates to a compound according to Formula I, wherein m is 1; E is O; $X^2$ is NH and $X^3$ is direct bond.

The present invention further relates to a compound according to Formula I, wherein m is 1; E is O; $X^2$ is $CH_2$ and $X^3$ is direct bond.

The present invention further relates to a compound according to Formula I, wherein m is 1; E is S; $X^2$ is NH and $X^3$ is direct bond.

The present invention further relates to a compound according to Formula I, wherein m is 0; E is O; $X^1$ is NH and $X^3$ is direct bond.

The present invention further relates to a compound according to Formula I, wherein m is 1; p is 0; $X^2$ is $NH-SO_2$ and $X^3$ is direct bond.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is O and $X^3$ is direct bond.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is NH and $X^3$ is direct bond.

The present invention further relates to a compound according to Formula I, wherein n is 1; 2 or 3; t is 0, 1 or 2; y is 0 or 1; z is 0, 1 or 2; $X^1$ is $CR^1$; m is 1; E is O; $X^2$ is $CH_2$ and $X^3$ is direct bond.

The present invention further relates to a compound according to Formula I, wherein n is 1; 2 or 3; t is 0, 1 or 2; y is 0 or 1; z is 0, 1 or 2; $X^1$ is $CR^1$; m is 1; E is S; $X^2$ is NH and $X^3$ is direct bond.

The present invention further relates to a compound according to Formula I, wherein n is 1; 2 or 3; t is 0, 1 or 2; y is 0 or 1; z is 0, 1 or 2; $X^1$ is $CR^1$; m is 0; E is O; $X^1$ is NH and $X^3$ is direct bond.

The present invention further relates to a compound according to Formula I, wherein n is 1; 2 or 3; t is 0, 1 or 2; y is 0 or 1; z is 0, 1 or 2; $X^1$ is $CR^1$; m is 1; p is 0; $X^2$ is $NH-SO_2$ and $X^3$ is direct bond.

The present invention further relates to a compound according to Formula I, wherein $X^5$ is a direct bond, O, S, $SO_2$, $CR^4R^5$; $(C_1-C_6)$alkyl, $(C_1-C_6)$alkyloxy, $(C_1-C_6)$alkenyl or $(C_1-C_6)$alkenyloxy.

The present invention further relates to a compound according to Formula I, wherein $A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkylenyl, amino, $(C_1-C_6)$ alkylamino, $(C_1-C_6)$dialkylamino, $(C_1-C_6)$alkoxy, $O(C_3-C_6$ cycloalkyl), $(C_3-C_6)$ cycloalkoxy, nitro, CN, OH, $(C_1-C_6)$ alkyloxy optionally substituted by one to three halo; $(C_3-C_6)$ cycloalkyl, $(C_1-C_6)$ alkoxycarbonyl, $(C_1-C_6)$ alkylcarbonyl or $(C_1-C_6)$ haloalkyl.

The present invention further relates to a compound according to Formula I, wherein $X^3$ is O, —NH, —$CH_2$—, CO, —CH($C_1-C_6$) alkyl, $SO_2NH$, —CO—NH— or —$NR^3$; $X^4$ is $CR^4R^5$, $CH_2$ $CR^4R^5$ or $CH_2$—$(C_1-C_6)$ alkyl-$CR^4R^5$; and $A^2$ is $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl wherein $A^2$ is substituted with one or more substituents selected from the group consisting of, $(C_2-C_9)$ heterocycloalkyl, $R^8R^9N$—CO— wherein $R^8$ and $R^9$ are each independently selected from the group consisting of hydrogen and $(C_1-C_6)$alkyl or $R^8$ and $R^9$ can be taken together with the nitrogen to which they are attached to form a $(C_2-C_9)$heterocycloalkyl or $(C_2-C_9)$heterocycloalkyl group optionally substituted by one to three halo groups, $(C_1-C_6)$ alkylsulfonyl optionally substituted by one or two groups selected from $(C_1-C_6)$alkoxy and $(C_3-C_{10})$cycloalkyl;

$(C_1-C_6)$alkyl substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy;

or $(C_1-C_6)$alkyloxy substituted by one to four substituents selected from the group consisting of hydroxy, cyano, $(C_1-C_6)$alkoxy, $(C_1-C_6)$alkoxy$(C_1-C_6)$alkoxy, $(C_2-C_9)$heterocycloalkyl, $(C_2-C_9)$heteroaryl optionally substituted by $(C_1-C_6)$alkoxy; or $(C_3-C_{10})$cycloalkoxy optionally substituted by $(C_1-C_6)$alkoxy.

The present invention further relates to a compound according to Formula I, wherein $A^1$ is phenyl.

The present invention further relates to a compound according to Formula I, wherein $X^5$ is a direct bond.

The present invention further relates to a compound according to Formula I, wherein $A^2$ is phenyl substituted by $(C_1-C_6)$ alkoxy$(C_1-C_6)$ alkoxy.

The present invention further relates to a compound according to Formula I, wherein $A^1$ is piperdine optionally substituted by halo.

The present invention further relates to a compound according to Formula I, wherein $X^5$ is pyrimidine optionally substituted by halo.

Preparation A

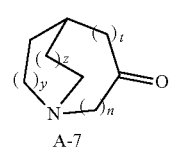

A-7

-continued
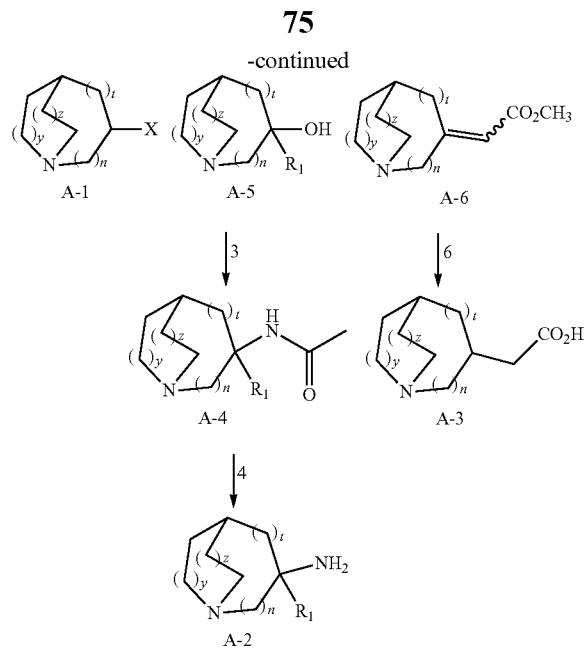
Preparation B
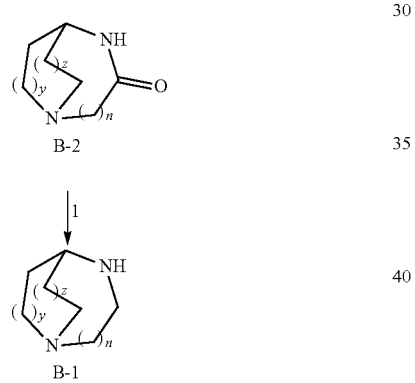
Preparation C
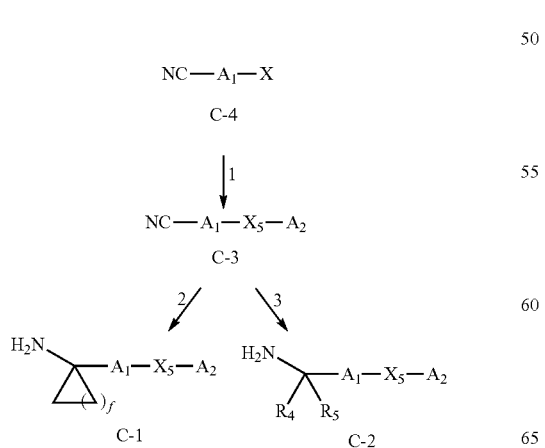
Preparation D
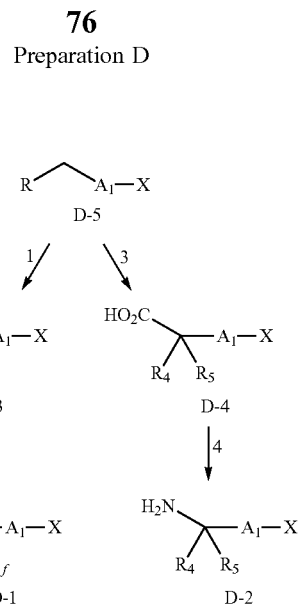
Preparation E
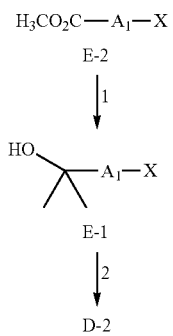
Preparation F
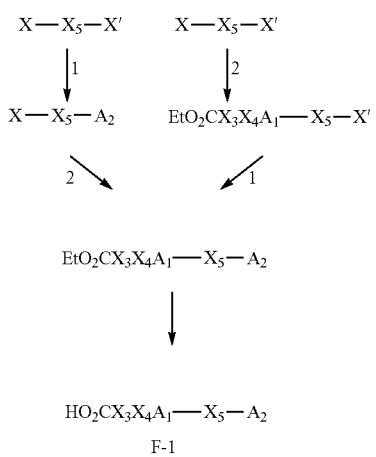

Preparation G

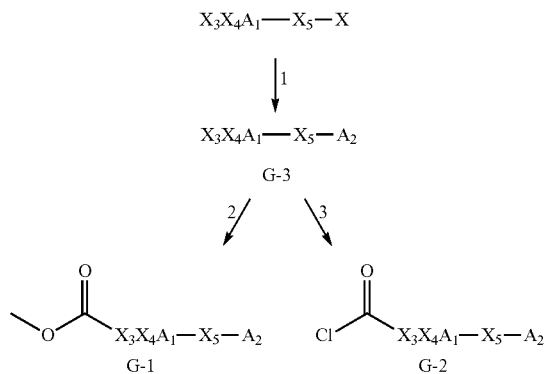

SCHEME 1

A-1 or A-2

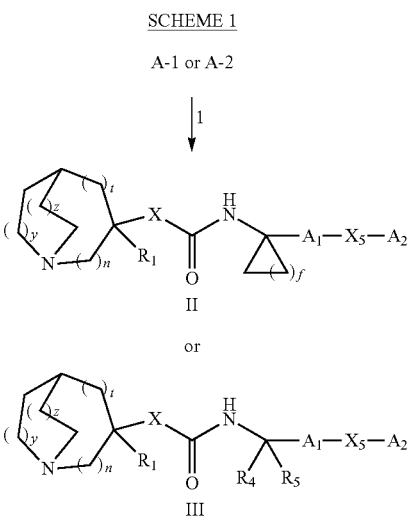

SCHEME 2

A-1 or A-2 or B-1

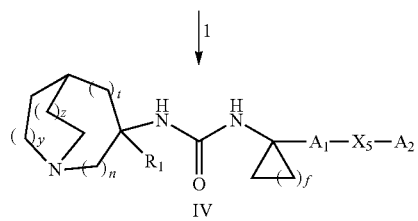

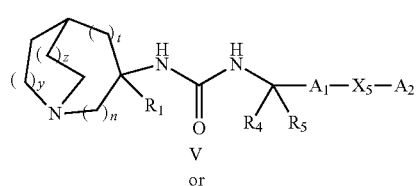

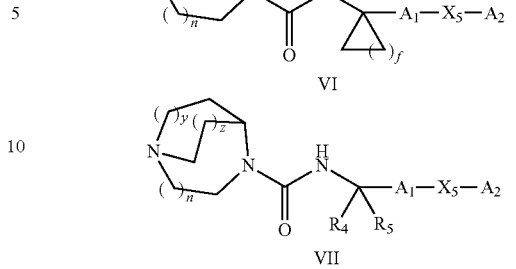

SCHEME 3

A-3

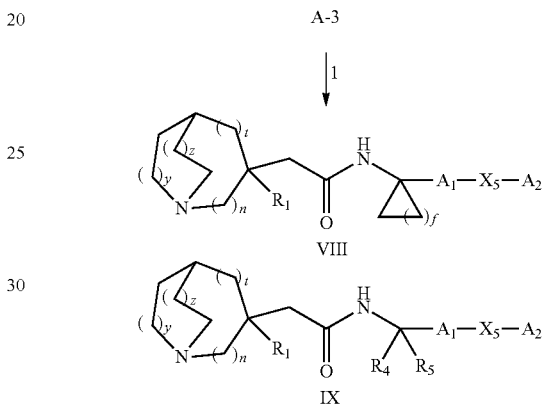

SCHEME 4

A-1 or A-2

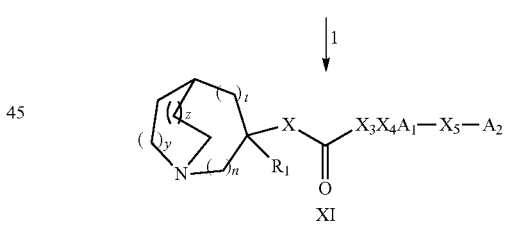

In reaction 1 of Preparation A, the compound of formula A-7 is converted to the corresponding compound of formula A-1, wherein X is OH, by reducing A-7 with a reducing agent, preferably lithium aluminum hydride in aprotic solvent such tetrahydrofuran. The reaction is stirred at a temperature between 0° C. and room temperature for a time period between about 15 minutes to about 2 hours, preferably about 30 minutes. Alternatively, the compound of formula A-7 is converted to the corresponding compound of formula A-1, wherein X is OH, by reducing A-7 under approximately 1 atmosphere of hydrogen in presence of a catalyst, preferably platinum oxide, and a polar solvent such methanol or ethanol for a period of 2 hours to 6 hours, preferably 4 hours. Alternatively, the compound of formula A-7 is converted to the corresponding compound of formula A-1, wherein X is NH, by reacting A-7 with hydroxylamine hydrochloride and sodium acetate in a polar solvent such ethanol, methanol, isopropanol, preferably isopropanol. The reaction mixture is stirred at a temperature between 50-80° C. for a period of 2 hours to 7 hours, preferably 3 hours. Subsequently, the compound so formed above is converted to compound of formula A-1 with a reducing agent, preferably sodium metallic in a polar protic solvent such ethanol, methanol, propanol, preferably n-propanol. The reaction is stirred overnight at 50-80° C., preferably solvent reflux temperature.

In reaction 2 of Preparation A, the compound of formula A-7 is converted to the corresponding compound of formula A-5, wherein R1, n and z are as defined above, by adding a solution of R1-magnesium bromide in ether to a solution of A-7 in a aprotic solvent, such as ether, at a temperature between about −60° C. to about −90° C., preferably about −78° C. for a time period between about 1 hour to about 4 hours, preferably about 2 hours. Alternatively, the compound of formula A-7 can be reacted with R1-lithium to afford the compound of formula A-5.

In reaction 3 of Preparation A, the compound of formula A-5 is converted to the corresponding compound of formula A-4, wherein R1, n and z are as defined above, by treating A-5 with a strong acid, preferably sulfuric acid, in the presence of acetonitrile. The reaction is stirred overnight at room temperature.

In reaction 4 of Preparation A, the compound of formula A-4 is converted to the corresponding compound of formula A-3, wherein R1, n and z are as defined above, by treating A-4 with an acid, preferably hydrochloric acid. The reaction is stirred at reflux for a period of 18 hours to 72 hours, preferably 24 hours and basified to pH=8 by treatment with an inorganic base in aqueous solution, such as sodium hydroxide.

In reaction 5 of Preparation A, the compound of formula A-7 is converted to the corresponding compound of formula A-6, wherein R1, n and z are as defined above, by reacting A-7 with a triphenyl phosphonium ylide to give the corresponding alkene compound of formula A-6. The reaction is stirred at room temperature for overnight.

In reaction 6 of Preparation A, the compound of formula A-6 is converted to the corresponding compound of formula A-3, wherein R1, n and z are as defined above, by reducing A-6 under approximately 1 atmosphere of hydrogen in the presence of a catalyst, preferably palladium on carbon, and a polar solvent, such as methanol, ethanol or ethyl acetate. The reaction is stirred at room temperature for a time period between about 2 hours to about 24 hour, preferably about 18 hours. Subsequently, the compound so formed is treated with a base, preferably lithium hydroxide, in a mixture of solvent such tetrahydrofuran, methanol and water to afford the compound of A-3. The reaction is stirred overnight at room temperature.

In reaction 1 of Preparation B, the compound of formula B-2 is converted to the corresponding compound of formula B-1, by reducing B-2 with a reducing agent, preferably lithium aluminum hydride in aprotic solvent such tetrahydrofuran. The reaction is stirred at a temperature between 0° C. and room temperature for a time period between about 15 minutes to about 2 hours, preferably about 30 minutes.

In reaction 1 of Preparation C, the compound of C-4 is converted to the corresponding compound of formula C-3, wherein X is bromine or chloride, by reacting C-4 with boronic acid in the presence of a catalyst, preferably 1,1′-bis(diphenylphosphino)ferrocene-palladium(II)-dichloride, and potassium carbonate. The reaction is microwaved in a mixture of dimethoxyethane and water at a temperature between about 130° C. to about 170° C., preferably about 150° C., for a time period between about 15 min to about 1 hour, preferably about 30 min. Alternatively, the reaction can be performed using solvent such dioxane and stirred overnight at 100° C. under conventional heating.

In reaction 2 of Preparation C, the compound of C-3 is converted to the corresponding compound of formula C-1, wherein f is 1 to 8 and A1, X5 and A2 are as defined above, by adding ethyl magnesium bromide dropwise to a mixture of C-3 and titanium isopropoxide in ether. The reaction is stirred at a temperature between about −50° C. to about −90° C., preferably about −70° C. The resulting reaction mixture is allowed to warm to about 20° C. to about 30° C., preferably about 25° C., and allowed to stir for an additional time period between about 30 minutes to about 2 hours, preferably about 1 hour. Boron trifluoride diethyl etherate is then added to the mixture dropwise at a temperature between about 20° C. to about 30° C., preferably about 25° C.

In reaction 3 of Preparation C, the compound of C-3 is converted to the corresponding compound of formula C-2, wherein A1, X5 and A2 are as defined above, by first stirring a suspension of cerium (III) chloride in an aprotic solvent, such as tetrahyrofuran, at room temperature for time period between about 30 minutes to about 2 hours, preferably about 1 hour. The resulting suspension is cooled to a temperature between about −60° C. to about −90° C., preferably about −78° C. and an organolithium agent is added, preferably methyl lithium in an ether solution. The resulting organocerium complex is allowed to form for a time period between about 30 minutes to about 2 hours, preferably about 1 hour, followed by the addition of C-3 in an aprotic solvent, such as tetrahydrofuran. The resulting reaction mixture is then warmed to room temperature and allowed to stir for time period between about 16 hours to about 20 hours, preferably about 18 hours.

In reaction 1 of Preparation D, the compound of D-5, wherein R is CO2Et or CN and X is bromine or chloride, is converted to the corresponding compound of formula D-3, by reacting D-5 with an alkyl dihalide such 1,2-dibromo-ethane. Subsequently, the compound so formed is treated with an inorganic base such lithium hydroxide or potassium hydroxide, in a mixture of solvent such tetrahydrofuran, methanol, glycol and water to afford the compound of D-3, wherein f is 1 to 8. The reaction is stirred overnight at a temperature between 25° C. and 130° C. Alternatively, to form the corresponding compound of formula D-3, wherein X is X5-A2, D-5 must first be reacted according to the procedure discussed above in reaction 1 of Preparation C.

In reaction 2 of Preparation D, the compound of D-3 is converted to the corresponding compound of formula D-1 by reacting D-3 with a base such triethylamine and diphenylphosphoryl azide in aprotic solvent such toluene. The reaction was heated to a temperature range between 80° C.-110° C., preferably at 110° C. for 15 min to 1 hour, preferably 30 minutes. The so formed intermediate is then treated with tert-butyl alcohol for overnight period at 60-110° C., preferably 90° C. Subsequently, the so formed carbamate is converted to the corresponding compound of formula D-1, wherein f is 1 to 8, by a treatment under acidic media using preferably trifluoroacetic acid in dichloromethane at room temperature for a period of 30 min to 5 hours, preferably 2 hours.

In reaction 3 of Preparation D, the compound of D-5, wherein R is CO2Et or CN and X is bromine or chloride, is converted to the corresponding compound of formula D-4, by reacting D-5 with an alkyl halide such MeI. Subsequently, the compound so formed is treated with an inorganic base such lithium hydroxide or potassium hydroxide, in a mixture of solvent such tetrahydrofuran, methanol, glycol and water to afford the compound of D-4. The reaction is stirred overnight at a temperature between 25° C. and 130° C. Alternatively, to form the corresponding compound of formula D-4, wherein X is X5-A2, D-5 must first be reacted according to the procedure discussed above in reaction 1 of Preparation C.

In reaction 4 of Preparation D, the compound of D-4 is converted to the corresponding compound of formula D-2, by reacting D-4 with a base such triethylamine and diphenylphosphoryl azide in aprotic solvent such toluene. The reaction was heated to a temperature range between 80° C.-110° C., preferably at 110° C. for 15 min to 1 hour, preferably 30 minutes. The so formed intermediate is then treated with tert-butyl alcohol for overnight period at 60-110° C., preferably 90° C. Subsequently, the so formed carbamate is converted to the corresponding compound of formula D-1 by a treatment under acidic media using preferably trifluoroacetic acid in dichloromethane at room temperature for a period of 30 min to 5 hours, preferably 2 hours.

In reaction 1 of Preparation E, the compound of formula E-2, wherein X is bromide or chloride, is converted to the corresponding compound of formula E-1, by reacting E-2 with methyl magnesium bromide in ether, at a temperature between about −60° C. to about −90° C., preferably about −78° C. for a time period between about 30 min to about 3 hours, preferably about 2 hours. Alternatively, to form the corresponding compound of formula E-1, wherein X is X5-A2, E-2 must first be reacted according to the procedure discussed above in reaction 1 of Preparation C.

In reaction 2 of Preparation E, the compound of formula E-1 is converted to the corresponding compound of D-2 by treating E-1 with a strong acid, preferably sulfuric acid, in the presence of chloroacetonitrile. The reaction is stirred overnight at room temperature. Subsequently, the so formed compound is treated with thiourea in a polar protic solvent such ethanol for an overnight period at 80° C. to form the corresponding compound of formula D-2. Alternatively, E-1 is treated with sodium azide and trifluoroacetic acid in an aprotic solvent such dichloromethane at a temperature range of −10° C. to room temperature, preferably 0° C. The so formed compound is reduced in presence of triphenylphosphine in a solution of tetrahydrofuran and water to form corresponding compound of formula D-2. The reaction is stirred at a temperature range 25-80° C., preferably at room temperature for a period of 2 hours to 24 hours, preferably 18 hours.

In Reaction 1 of Preparation F, by adding an arylboronate or arylboronic acid component, sodium carbonate and a catalyst, such as [1,1'-bis(diphenylphosphino)ferrocene]dichloropalladium(II), to a solution of the aryl halide component in 5:1 (v/v) dioxane/water (~0.15 M) or 5:1 (v/v) N,N-dimethylformamide. The mixture so formed is heated to a temperature between about 80° C. to about 100° C., preferably to about 90° C., for a time period between 8 hours to about 16 hours, preferably about 14 hours.

In Reaction 2 of Preparation F, the compound of formula X—X5-A2 so formed is converted to the corresponding compound of formula EtO2CX3X3X4A1-X5-A2 by a (1) transition metal catalyzed coupling or (2) nucloephilic aromatic substitution reaction between the aryl halide and amine.

In Reaction 3 of Preparation F, the compound of formula X—X5-A2 so formed is converted to the corresponding compound of formula EtO2CX3X3X4A1-X5-X' by a (1) transition metal catalyzed coupling or (2) nucloephilic aromatic substitution reaction between the aryl halide and amine.

In reaction 4 of Preparation F, by adding an arylboronate or arylboronic acid component, sodium carbonate and a catalyst, such as [1,1'-bis(diphenylphosphino)ferrocene]dichloropalladium(II), to a solution of the aryl halide component in 5:1 (v/v) dioxane/water (~0.15 M) or 5:1 (v/v) N,N-dimethylformamide. The mixture so formed is heated to a temperature between about 80° C. to about 100° C., preferably to about 90° C., for a time period between 8 hours to about 16 hours, preferably about 14 hours.

In reaction 5 of Preparation F, the compound of formula EtO2CX3X3X4A1-X5-A2 so formed is converted to the corresponding compound of formula F-1 by an ester hydrolysis reaction.

In reaction 1 of Preparation G, the compound of formula X3X4A1-X5-X is converted to the corresponding compound of formula G-3 by adding an arylboronate or arylboronic acid component, sodium carbonate and a catalyst, such as [1,1'-bis(diphenylphosphino)dichloropalladium(II), to a solution of the aryl halide component in 5:1 (v/v) dioxane/water (~0.15 M) or 5:1 (v/v) N,N-dimethylformamide. The mixture so formed is heated to a temperature between about 80° C. to about 100° C., preferably to about 90° C., for a time period between 8 hours to about 16 hours, preferably about 14 hours.

In reaction 2 of Preparation G, the compound of Formula G-3 is converted to the corresponding compound of G-1 by cooling (0° C.) a solution of the secondary amine component and triethylamine in methylene chloride and adding methyl chloroformate. The reaction is then allowed to warm to room temperature and stirred for time period between about 4 hours to about 8 hours, preferably about 6 hours. The reaction solution is then washed with aqueous sodium bicarbonate solution and brine, dried ($Na_2SO_4$) and concentrated. The crude methyl carbamate is used, without purification, in the next step. To a solution of this intermediate in toluene is added, in order, activated 4 Å molecular sieves, the alcohol component and sodium hydride. The reaction is heated at reflux overnight, filtered and concentrated.

In reaction 3 of Preparation G, the compound of Formula G-3 is converted to the corresponding compound of G-2 by adding triphosgene in toluene to a solution of the amine component in chloroform. The reaction is stirred for a time period between about 1 hour to about 4 hours, preferably 2 hours, and then concentrated. The residue is taken up in chloroform and cooled (0° C.). With stirring, the second amine component and triethylamine (2 equivalents) are added, in order. The reaction is stirred overnight at room temperature and then concentrated.

In reaction 1 of Scheme 1, the compounds of formula A-1 or A-2 are converted to the corresponding compounds of Formula II, wherein f is 1 to 8, or III, respectively, by adding triphosgene to a suspension of C-1 or C-2 and triethylamine in a aprotic solvent, such as tetrahydrofuran. The reaction is stirred at room temperature for a time period between about 5 minutes to about 20 minutes, preferably about 15 minutes, and a small amount of ether was added. The triethylammonium salt generated is filtered off. Separately, sodium hydride is added to a suspension of A-1 or A-2, wherein X is OH or NH, in an aprotic solvent, such as tetrahydrofuran, at 0° C. or room temperature. The reaction is stirred at room temperature for a time period between about 5 minutes to about 20 minutes, preferably about 15 minutes, and the isocyanate tetrahydrofuran/ether solution so formed above is added dropwise. Alternatively, the compounds of Formula II and III may be formed by reacting the compounds of D3 or D4 with A-1 and A-2 in presence of a base such triethylamine and diphenylphosphoryl azide in aprotic solvent such toluene as described in procedure discussed above in reaction 4 of Preparation D.

In reaction 1 of Scheme 2, the compounds of formula A-1, A-2 or B-1 are converted to the corresponding compounds of Formula IV, V, VI and VII, wherein f is 1 to 8, respectively, by adding triphosgene to a suspension of C-1, C-2, D-1 or D-2 and triethylamine in a aprotic solvent, such as tetrahydrofuran or toluene. The reaction is stirred at room temperature for a time period between about 5 minutes to about 20 minutes, preferably about 15 minutes, and a small amount of ether was added. Subsequently, A-1 or A-2, wherein X is NH, is added to the isocyanate solution so formed above and the reaction is stirred at a temperature range of 25-100° C., preferably at room temperature for a period of about 2 hours to 24 hours, preferably 18 hours.

In reaction 1 of Scheme 3, the compound of formula A-3 is converted to the corresponding compounds of Formula VIII, wherein f is 1 to 8, and IX, respectively by reacting A3 with C1, C-2, D-1 or D-2 via peptidic coupling using carbodiimide coupling agent such 1-ethyl-3-(3-dimethylaminopropyl) carbodiimide and 1-hydroxy-benzotriazole or 2-(1H-7-Azabenzotriazol-1-yl)-1,1,3,3-tetramethyl uronium hexafluorophosphate in solvent such tetrahydrofuran or dimethylformamide. The reaction is stirred at room temperature for overnight.

In reaction 1 of Scheme 4, the compound of formula A-2 is converted to the corresponding compound of formula XI by reacting, via amide coupling, the compound of formula A-2 and the compound of formula F-1. Specifically, to a solution of the primary amine component in chloroform was added 4-dimethylaminopyridine (0.1 equivalent) and di-tert-butyl dicarbonate. The mixture was stirred for 1 hour before adding the secondary amine component and heating to reflux overnight.

In reaction 1 of Scheme 4, the tert-butoxy carbonyl protected compound of formula A-2 is converted to the corresponding compound of formula XI by a reacting, via condensation reaction, the compound of formula A-2 and the compound of formula G-3.

Specifically, to a solution of the primary amine component in chloroform (concentration ~0.1 M) was added 4-dimethylaminopyridine and di-tert-butyl dicarbonate. The mixture was stirred for 1 hour before adding the secondary amine component and heating to reflux overnight.

In reaction 1 of Scheme 4, the compound of formula A-1 is converted to the corresponding compound of formula XI by a reacting, via acylation reaction, the compound of formula A-1 and the compound of formula G-1 by cooling (0° C.) a solution of the secondary amine component and triethylamine in methylene chloride and adding methyl chloroformate. The reaction is then allowed to warm to room temperature and stirred for time period between about 4 hours to about 8 hours, preferably about 6 hours. The reaction solution is then washed with aqueous sodium bicarbonate solution and brine, dried ($Na_2SO_4$) and concentrated. The crude methyl carbamate is used, without purification, in the next step. To a solution of this intermediate in toluene is added, in order, activated 4 Å molecular sieves, the alcohol component and sodium hydride. The reaction is heated at reflux overnight, filtered and concentrated.

In reaction 1 of Scheme 4, the compound of formula A-2 is converted to the corresponding compound of formula XI by a reacting, via acylation reaction, the compound of formula A-2 and the compound of formula G-2 by adding triphosgene in toluene to a solution of the amine component in chloroform. The reaction is stirred for a time period between about 1 hour to about 4 hours, preferably 2 hours, and then concentrated. The residue is taken up in chloroform and cooled (0° C.). With stirring, the second amine component and triethylamine (2 equivalents) are added, in order. The reaction is stirred overnight at room temperature and then concentrated.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

All pharmaceutically acceptable salts, prodrugs, tautomers, hydrates and solvates of the compounds presently disclosed are also within the scope of the present disclosure.

Presently disclosed compounds that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

Acids which can be used to prepare the pharmaceutically acceptable acid addition salts of the base compounds are those which can form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Presently disclosed compounds that are acidic in nature, e.g., contain a COOH or tetrazole moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields of the desired solid salt.

Bases which can be used to prepare the pharmaceutically acceptable base addition salts of the base compounds are those which can form non-toxic base addition salts, i.e., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine-(meglumine), lower alkanolammonium and other such bases of organic amines.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

By isotopically-labeling the presently disclosed compounds, the compounds may be useful in drug and/or substrate tissue distribution assays. Tritiated (3H) and carbon-14 ($^{14}$C) labeled compounds are particularly preferred for their ease of preparation and detectability. Further, substitution with heavier isotopes such as deuterium ($^2$H) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts and prodrugs thereof, can be prepared by any means known in the art.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The compounds, salts, prodrugs, hydrates, and solvates presently disclosed can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Atropisomers are also within the scope of the present disclosure. Atropisomers refer to compounds that can be separated into rotationally restricted isomers.

The present disclosure also provides pharmaceutical compositions comprising at least one presently disclosed compound and at least one pharmaceutically acceptable carrier. The pharmaceutically acceptable carrier can be any such carrier known in the art including those described in, for example, Remington's Pharmaceutical Sciences, Mack Publishing Co., (A. R. Gennaro edit. 1985). Pharmaceutical compositions of the compounds presently disclosed may be prepared by conventional means known in the art including, for example, mixing at least one presently disclosed compound with a pharmaceutically acceptable carrier.

Presently disclosed pharmaceutical compositions can be used in an animal or human. Thus, a presently disclosed compound can be formulated as a pharmaceutical composition for oral, buccal, parenteral (e.g., intravenous, intramuscular or subcutaneous), topical, rectal or intranasal administration or in a form suitable for administration by inhalation or insufflation.

The compounds presently disclosed may also be formulated for sustained delivery according to methods well known to those of ordinary skill in the art. Examples of such formulations can be found in U.S. Pat. Nos. 3,119,742, 3,492,397, 3,538,214, 4,060,598, and 4,173,626.

For oral administration, the pharmaceutical composition may take the form of, for example, a tablet or capsule prepared by conventional means with a pharmaceutically acceptable excipient(s) such as binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); and/or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive(s) such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and/or preservative (e.g., methyl or propyl p-hydroxybenzoates or sorbic acid).

For buccal administration, the composition may take the form of tablets or lozenges formulated in a conventional manner.

Presently disclosed compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent recognized by those of skill in the art. Alternatively, the active ingredient may be in powder form for reconstitution with a suitable vehicle, e.g., sterile pyrogen-free water, before use.

For topical administration, a presently disclosed compound may be formulated as an ointment or cream.

Presently disclosed compounds may also be formulated in rectal compositions such as suppositories or retention enemas, e.g., containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

A proposed dose of a presently disclosed compound for oral, parenteral or buccal administration to the average adult human for the treatment or prevention of a TPO-related disease state is about 0.1 mg to about 2000 mg. In certain embodiments, the proposed dose is from about 0.1 mg to about 200 mg of the active ingredient per unit dose. Irrespective of the amount of the proposed dose, administration of the compound can occur, for example, 1 to 4 times per day.

Aerosol formulations for the treatment or prevention of the conditions referred to above in the average adult human are preferably arranged so that each metered dose or "puff" of aerosol contains about 20 mg to about 10,000 mg, preferably, about 20 mg to about 1000 mg of a presently disclosed compound. The overall daily dose with an aerosol will be within the range from about 100 mg to about 100 mg. In certain embodiments, the overall daily dose with an aerosol generally will be within the range from about 100 mg to about 10 mg. Administration may be several times daily, for example 2, 3, 4 or 8 times, giving for example, 1, 2 or 3 doses each time.

Aerosol combination formulations for the treatment or prevention of the conditions referred to above in the average adult human are preferably arranged so that each metered dose or "puff" of aerosol contains from about 0.01 mg to about 1000 mg of a combination comprising a presently disclosed compound. In certain embodiments, each metered dose or "puff" of aerosol contains about 0.01 mg to about 100 mg of a combination comprising a presently disclosed compound. In certain embodiments, each metered dose or "puff" of aerosol contains about 1 mg to about 10 mg of a combination comprising a presently disclosed compound. Administration may be several times daily, for example 2, 3, 4 or 8 times, giving for example, 1, 2 or 3 doses each time.

Pharmaceutical compositions and methods of treatment or prevention comprising administering prodrugs of at least one presently disclosed compound are also within the scope of the present disclosure.

Glucosylceramide Synthase Assays

Inhibition of glucosylceramide synthase activity can be measured with one or more assays. A first assay is a microsomal assay that directly measures the conversion of ceramide to glucosylceramide by HPLC. Microsomes are a source of glucosylceramide synthase activity in the microsomal assay. A second assay is a cell based, phenotypic assay that monitors cell surface expression of the downstream lipid GM3 by antibody mediated immunofluorescence. Specific protocols are provided below.

Glucosylceramide Synthase Activity Microsomal Assay:

An enzyme assay using microsomes as a source of glucosylceramide synthase activity. Fluorescent ceramide substrate is delivered to membrane-bound enzyme as a complex with albumin. After reaction, ceramide and glucosylceramide are separated and quantitated by reverse-phase HPLC with fluorescence detection. Enzymatic activity was assessed using a fluorescent labeled substrate and microsomes as a source of glucosylceramide synthase. $C_6$ NBD-Ceramide was complexed with albumin for delivery to microsomes that were isolated according to the procedure described below. The final concentration of $C_6$ NBD-Ceramide in the stock was 0.5 mM; the final concentration of BSA was 0.5 mM. Separation and quantitation of substrate and product (glucosylceramide) were achieved by reverse-phase HPLC with fluorescence detection.

Procedure

Preparation of Microsomes from A375 Human Melanoma Cells:

Microsomes were isolated from A375 human melanoma cells. Eight to ten million cells were harvested by trypsinization and washed with ice cold PBS. Cells were resuspended in the ice cold lysis buffer, containing protease inhibitors. Cell lysate was sonicated on ice using a probe sonicator. After sonication the cell lysate was separated from debris by centrifugation at 10,000 g for 10 minutes at 4° C. The supernatant was removed and cleared by additional centrifugation at 100,000 g for 1 hour at 4° C. The pellet was then resuspended in the lysis buffer, aliquoted and stored at −80° C. prior to use.

Glucosylceramide Synthase Assay

To determine glucosylceramide synthase inhibition, substrates at 2× of their Km (fluorescent ceramide and UDP-glucose, 3 µM and 4 µM respectively) and microsomes (1:50 dilution) were combined 1:1 and incubated at room temperature for 1 hour in the dark on a plate shaker. The reaction was stopped by the addition of 150 µl of 100 µM $C_8$ ceramide in 50% aq. isopropanol; 10 µl of the final mix was analyzed on HPLC (with fluorescence detector). The mobile phase was performed in 1% formic acid in 81% methanol, 19% water with flow rate 0.5 mL/min. Fluorescence was detected with $\lambda_{ex}$=470 nm and $\lambda_{em}$=530 nm. Under these conditions, NBD $C_6$ GluCer had a retention time of about 1.7 min and NBD $C_6$ Cer elutes from the column after about 2.1 min. Both peaks were separated from each other and the baseline and were integrated automatically by the HPLC software. The percent conversion of substrate to product was used as the readout for inhibitor testing.

GM3 Fluorescent-Linked Immunosorbent Assay (FLISA):

This is phenotypic assay that measures both GM3 expression in conjunction with the viability of B16 or C32 cells following treatment with compounds. Cell surface GM3 expression was determined by antibody mediated fluorescence and cell viability was assessed in each well.

Procedure

Compounds were diluted in media and plated in 384 well plates in DMSO. B16 and C32 cells were assayed at densities of 20,000 cells/ml and 62,500 cells/ml respectively per well. Each titration curve contained 10 points that were assayed in duplicate on each test run. The plates were incubated for 48 hours at 37° C., 5% CO2 and were then washed once with TBS. Anti GM3 antibody was added to each well and the plates were then incubated for an additional one hour at room temperature. Plates were subsequently washed twice and incubated for an additional hour with the labeled secondary antibody. Following the final incubation, the plates were washed twice and the fluorescence at $\lambda_{ex}$=D640/20 nm and $\lambda_{em}$=657 nm detected on fluorescent reader. After GM3 fluorescence had been determined, cell viability was assessed using the ATPlite assay (Perkin Elmer) according to the manufacturer's instructions.

Assay Results:

Individual assay results of certain exemplified compounds in these assays are presented in Table 1. The results of the microsomal assay are expressed as "GCS IC50", which represents the concentration of the compound causing 50% inhibition of glucosylceramide synthase activity. The results of the cell based assays (performed in two different cell systems, i.e. B16 mouse melanoma or C32 human melanoma cells) are expressed as "GM3 B16 IC50" or "GM3 C32 IC50" for the B16 assay and the C32 assay, respectively. These values represent the concentration of the compound causing 50% inhibition of GM3 expression on the cell surface.

Glucosylceramide Synthase Inhibition in a Model of Polycystic Kidney Disease.

Mice homozygous for the Nek8jck mutation develop polycystic kidney disease ("jck mice". Histology reveals that the kidneys of some 3 day old pups from heterozygous parents had small isolated cysts lined by cuboidal epithelial cells, and 15 day old pups had cysts lined by flattened epithelia. Disease is progressive but not evident by kidney palpation until at least 4 to 5 weeks of age. Homozygotes generally remain active until shortly before death and usually die between 20 and 25 weeks of age. Homozygous females are fertile but do not consistently care for their litters; homozygous males are fertile but decreased fertility is reported after 15 weeks of age. No histologic abnormalities are found in the liver, spleen, or pancreas. (Atala et al., 1993).

To evaluate the effects of a GCS inhibitor on polycystic kidney disease, a compound of interest can be administered in the feed of jck mice at one or more dose levels. Administration of the compound can be started at anytime after birth, e.g. starting administration between 3 and 4 weeks of age, and can continue for as long as desired. The effect of the compound on the disease phenotype can be evaluated by measurement of body weight, blood urea nitrogen ("BUN"), and serum GL1 during the in-life phase. Additional effects on kidney/body weight (K/BW), cyst volume, BUN, kidney GL1, and serum GL1 can be measured at the end of life time point of the study.

Glucosylceramide Synthase Inhibition in a Fabry Mouse Model.

A study can be designed to evaluate whether substrate inhibition (i.e. "substrate reduction therapy" or "SRT") using a compounds of the invention types could reduce the accumulation of the storage material globotriaosylceramide (Gb3) and lysoglobotriaosylceramide (lyso-Gb3). A Fabry mouse model can be used to evaluate substrate reduction therapy (SRT) with the GCS inhibitor compounds in reducing the levels of both Gb3 and lyso-Gb3 in the plasma, kidney and urine of Fabry mice. Recently it has been proposed that urinary lyso-Gb3 may represent a reliable biomarker of clinical relevance for Fabry disease (Aerts et al., PNAS USA 105:2812-2817 (2008); and Auray-Blais et al., Clin Chim Acta 411:1906-1914 (2010)). The metabolic origin of the lyso-Gb3 is not known and can conceivably be derived through either deacylation of Gb3 or through anabolic synthesis from glucosylsphingosine.

In FIG. 1, black arrows indicate demonstrated pathways, gray arrows are undocumented pathways. Enzyme replacement therapy using α-galactosidase is known to degrade both Gb3 and lyso-Gb3. Accordingly, SRT using a GCS inhibitor would be most effective at limiting lyso-Gb3 accumulation if the lyso-Gb3 is generated primarily through deacylation of Gb3, a GCS dependent pathway. These experiments can be used to demonstrate that SRT using GCS inhibitors in a mouse model of Fabry disease reduces both Gb3 and lyso-Gb3, thus supporting the use of compounds of the invention as viable therapeutic options for Fabry patients.

EXPERIMENTAL

Several approaches are being used or pursued for the treatment of LSDs, most of which focus on enzyme replacement therapy for use alone in disease management. Numerous approved enzyme replacement therapies are commercially available for treating LSDs (e.g., Myozyme® for Pompe disease, Aldurazyme® for Mucopolysaccharidosis I, Cerezyme® for Gaucher disease and Fabrazyme® for Fabry disease). Additionally, the inventors have identified a number of small molecules for use alone in the management of LSDs. The therapeutic methods of the invention described herein provide treatment options for the practitioner faced with management of various lysosomal storage diseases, as described in detail below.

In certain aspects of the invention, the compounds of the present invention may be used to treat a metabolic disease, such as a lysosomal storage disease (LSD), either alone or as a combination therapy with an enzyme replacement therapy. In other aspects of the invention, the compounds of the present invention may be used to inhibit or reduce GCS activity in a subject diagnosed with a metabolic disease, such as an LSD, either alone or as a combination therapy with an enzyme replacement therapy. In other aspects of the invention, the compounds of the present invention may be used to reduce and/or inhibit the accumulation of a stored material (e.g., lysosomal substrate) in a subject diagnosed with a metabolic disease, such as an LSD. In certain embodiments of the foregoing aspects, the LSD is Gaucher (type 1, type 2 or type 3), Fabry, $G_{M1}$-gangliosidosis or $G_{M2}$-gangliosidoses (e.g., GM2 Activator Deficiency, Tay-Sachs and Sandhoff). Table 1 lists numerous LSDs and identifies the corresponding deficient enzyme that may be used as an ERT in the foregoing aspects of the invention.

In other scenarios it may be necessary to provide SMT to a patient whose condition requires the reduction of substrates in the brain and thus is not treatable by systemic administration of ERT. While direct intracerebroventricular or intrathecal administration can reduce substrate levels in the brain, systemic administration of ERT is not amenable for LSD's with Central Nervous System (CNS) involvement due to its incapacity to cross the Blood Brain Barrier (BBB) and SMT may prove beneficial in patients having residual enzymatic activities in the CNS.

In accordance with the present invention, SMT is provided to a patient to treat a cancer and/or metabolic disease, such as, a lysosomal storage disease. The SMT may include one or more small molecules. The SMT includes administering to the patient compounds of the present invention. In particular embodiments, the compound is (S)-Quinuclidin-3-yl (2-(2-(4-fluorophenyl)thiazol-4-yl)propan-2-yl)carbamate or Quinuclidin-3-yl (2-(4'-fluoro-[1,1'-biphenyl]-3-yl)propan-2-yl)carbamate, or combinations thereof.

In certain embodiments, compounds of the invention, such as, for example, (S)-Quinuclidin-3-yl (2-(2-(4-fluorophenyl)thiazol-4-yl)propan-2-yl)carbamate and Quinuclidin-3-yl (2-(4'-fluoro-[1,1'-biphenyl]-3-yl)propan-2-yl)carbamate may be used for treatment of virtually any storage disease resulting from a defect in the glycosphingolipid pathway (e.g. Gaucher (i.e., type 1, type 2 type 3), Fabry, GM1-gangliosidosis, $G_{M2}$-gangliosidoses (e.g., GM2 Activator Deficiency, Tay-Sachs and Sandhoff)). In a particularly preferred embodiment, (S)-Quinuclidin-3-yl (2-(2-(4-fluorophenyl)thiazol-4-yl)propan-2-yl)carbamate or a pharmaceutically acceptable salt or prodrug thereof is used to inhibit and/or reduce the accumulation of Gb3 and/or lyso-Gb3 in a patient with Fabry disease, either alone or as a combination therapy with enzyme replacement therapy (see Examples). In a preferred embodiment, the enzyme replacement therapy includes administering alpha-galactosidase A to the Fabry patient. Indeed, the Examples below demonstrate that a GCS inhibitor of the invention effectively reduces Gb3 and lyso-Gb3 storage in a mouse model of Fabry disease, thus supporting its use as a viable approach for the treatment of Fabry disease. Furthermore, in vivo combination therapy data provided in the Examples strongly suggest that a combined therapeutic approach could be both additive and complementary.

In certain embodiments, compounds of the invention, such as, for example, (S)-Quinuclidin-3-yl (2-(2-(4-fluorophenyl)thiazol-4-yl)propan-2-yl)carbamate and Quinuclidin-3-yl (2-(4'-fluoro-[1,1'-biphenyl]-3-yl)propan-2-yl)carbamate may be used for reducing the level of GluCer and GluSph in the brain of a subject diagnosed with neuropathic Gaucher disease, either alone or in combination with ERT (e.g., glucocerebrosidase administration).

Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT of the invention for the treatment of any storage disease are well known to the skilled artisan. Guidance for dosage regimens can be obtained from any of the many well known references in the art on this topic. Further guidance is available, inter alia, from a review of the specific references cited herein. In certain embodiments, such dosages may range from about 0.5 mg/kg to about 300 mg/kg, preferably from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred oral dose range is from about 50 mg to about 100 mg, wherein the dose is administered twice daily. A particular oral dose range for a compound of the present invention is from about 5 mg/kg/day to about 600 mg/kg/day. In a particular oral dose range for a compound of the present invention is from about 1 mg/kg/day to about 120 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day, 100 mg/kg/day, 105 mg/kg/day, 110 mg/kg/day, 115 mg/kg/day or 120 mg/kg/day.

In certain embodiments, the invention relates to combination therapies of SMT using compounds of the invention and ERT therapy for the treatment of lysosomal storage diseases. A partial list of known lysosomal storage diseases that can be treated in accordance with the invention is set forth in Table 1, including common disease name, material stored, and corresponding enzyme deficiency (adapted from Table 38-4 of Kolodny et al., 1998, Id.).

TABLE 1

| Lysosomal Storage Diseases | | |
| --- | --- | --- |
| Disease | Material Stored | Enzyme Deficiency |
| Sphingolipidoses | | |
| Gaucher | Glucocerebroside, glucosylsphingosine | Glucocerebrosidase |
| Niemann-Pick | Sphingomyelin | Sphingomyelinase |
| Niemann-Pick B | Sphingomyelin | Sphingomyelinase |
| Farber | Ceramide | Ceramidase |
| $G_{M1}$-gangliosidosis | $G_{M1}$-ganglioside, glycoprotein | $G_{M1}$-ganglioside-$\beta$-galactosidase |
| $G_{M2}$-gangliosidosis (Sandhoff) | $G_{M2}$-ganglioside, globoside | Hexosaminidase A and B |
| Tay-Sachs | $G_{M2}$-ganglioside | Hexosaminidase A |
| Krabbe | Galactosylceramide | $\beta$-Galactocerebrosidase |
| Mucopolysaccharidoses | | |
| Hurler-Scheie (MPS I) | Dermatan sulfate, heparin Sulfate | $\alpha$-L-iduronidase |
| Hunter (MPS II) | Dermatan sulfate, heparin sulfate | Iduronate sulfatase |
| Sanfilippo (MPS III) | | |
| Type A | Heparan sulfate | Heparan-N-sulfatase |
| Type B | Heparan sulfate | N-acetyl-$\alpha$-glucosaminidase |
| Type C | Heparan sulfate | Acetyl CoA: $\alpha$-glucosaminide acetyl-transferase |
| Type D | Heparan sulfate | N-acetyl-$\alpha$-glucosamine-6-sulfatase |

TABLE 1-continued

| Disease | Material Stored | Enzyme Deficiency |
|---|---|---|
| Marquio (MPS IV) | | |
| Type A | Keratan sulfate | Galactosamine-6-sulfatase |
| Type B | Keratan sulfate | β-galactosidase |
| Maroteaux-Lamy (MPS VI) | Dermatan sulfate | Galactosamine-4-sulfatase (arylsulfatase B) |
| Sly (MPS VII) | Dermatan sulfate, heparan Sulfate | β-glucuronidase |
| Mucosulfatidosis | Sulfatides, mucopolysaccharides | Arylsulfatase A, B and C, other sulfatases |
| Mucolipidoses | | |
| Sialidoses | Sialyloligosaccharides, glycoproteins | α-neuraminidase |
| Mucolipidosis II | Sialyloligosaccharides, glycoproteins, glycolipids | High serum, low fibroblast enzymes; N-acetyl-glucosamine-1-phosphate transferase |
| Mucolipidosis III | Glycoproteins, glycolipids | Same as above |
| Mucolipidosis IV | Glycolipids, glycoproteins | Mcoln1 transm protein |
| Other Diseases of Complex Carbohydrate Metabolism | | |
| Fabry | Globotriaosylceramide(Gb3), lyso-Gb3 | α-galactosidase A |
| Schindler | O-linked glycopeptides | α-N-acetylgalactosaminidase |
| Pompe | Glycogen | α-glucosidase |
| Sialic acid storage disease | Free sialic acid | Unknown |
| Fucosidosis | Fucoglycolipids, fucosyloligosaccharides | α-fucosidase |
| Mannosidosis | Mannosyloligosaccharides | α-mannosidase |
| Aspartylglucosaminuria | Aspartylglucosamine | Aspartylglucosamine amidase |
| Wolman | Cholesteryl esters, Triglycerides | Acid lipase |
| Neuronal Ceroid Lipofuscinoses (NCLs)* | | |
| Infantile NCL | Granular osmophilic deposits, Saposins A and D thioesterase | Palmitoyl-protein thioesterase (PPT1) |
| Late Infantile | Curvilinear profiles, ATP synthase subunit c | Tripeptidyl protease 1 (TPP1) |
| Finnish variant | Fingerprint/Rectilinear profiles, ATP synthase subunit c | CLN5 |
| Variant | Fingerprint/Rectilinear profiles, ATP synthase subunit c | CLN6 |
| Juvenile | Fingerprint profile, ATP synthase subunit c | CLN3 |
| Adult | Variable | Unknown |
| Northern Epilepsy | Rectilinear profile, ATP synthase subunit c | CLN8 |
| Turkish variant | Fingerprint/Rectilinear profiles - constituents unknown | Unknown |
| Lysosomal diseases of cholesterol transport and metabolism | | |
| Niemann-Pick type C | Unesterified cholesterol | NPC1 or NPC2 |

*Davidson et al., The Neuronal Ceroid Lipofuscinosis, Clinical Features and Molecular Basis of Disease. In Barranger J A and Cabrera-Salazar M A (Eds) Lysosomal Storage Disorders. 2007. pp. 371-388. Springer, New York, U.S.A.

Any method known to the skilled artisan may be used to monitor disease status and the effectiveness of a combination therapy of the invention. Clinical monitors of disease status may include but are not limited to organ volume (e.g. liver, spleen), hemoglobin, erythrocyte count, hematocrit, thrombocytopenia, cachexia (wasting), and plasma chitinase levels (e.g. chitotriosidase). Chitotriosidase, an enzyme of the chitinase family, is known to be produced by macrophages in high levels in subjects with lysosomal storage diseases (see Guo et al., 1995, J. Inherit. Metab. Dis. 18, 717-722; den Tandt et al., 1996, J. Inherit. Metab. Dis. 19, 344-350; Dodelson de Kremer et al., 1997, Medicina (Buenos Aires) 57, 677-684; Czartoryska et al., 2000, Clin. Biochem. 33, 147-149; Czartoryska et al., 1998, Clin. Biochem. 31, 417-420; Mistry et al., 1997, Baillieres Clin. Haematol. 10, 817-838; Young et al., 1997, J. Inherit. Metab. Dis. 20, 595-602; Hollak et al., 1994, J. Clin. Invest. 93, 1288-1292). Chitotriosidase is preferably measured in conjunction with angiotensin converting enzyme and non tartrate resistant acid phosphatase to monitor response to treatment of Gaucher patients.

Methods and formulations for administering the combination therapies of the invention include all methods and formulations well known in the art (see, e.g., Remington's Pharmaceutical Sciences, 1980 and subsequent years, 16th ed. and subsequent editions, A. Oslo editor, Easton Pa.; Controlled Drug Delivery, 1987, 2nd rev., Joseph R. Robinson & Vincent H. L. Lee, eds., Marcel Dekker, ISBN:

0824775880; Encyclopedia of Controlled Drug Delivery, 1999, Edith Mathiowitz, John Wiley & Sons, ISBN: 0471148288; U.S. Pat. No. 6,066,626 and references cited therein; see also, references cited in sections below).

According to the invention, the following general approaches are provided for combination therapy in the treatment of lysosomal storage diseases. Each general approach involves combining enzyme replacement therapy with small molecule therapy in a manner consistent with optimizing clinical benefit while minimizing disadvantages associated with using each therapy alone.

In one embodiment of the invention, enzyme replacement therapy (alone or in combination with small molecule therapy) is administered to initiate treatment (i.e., to debulk the subject), and small molecule therapy is administered after the de-bulking phase to achieve and maintain a stable, long-term therapeutic effect without the need for frequent intravenous ERT injections. For example, enzyme replacement therapy may be administered intravenously (e.g. over a one to two hour period) once, on a weekly basis, once every two weeks, or once every two months, for several weeks or months, or longer (e.g., until an involved indicator organ such as spleen or liver shows a decrease in size). Moreover, the ERT phase of initial de-bulking treatment can be performed alone or in combination with a small molecule therapy. A small molecule therapeutic component is particularly preferred where the small molecule is compatible with oral administration, thus providing further relief from frequent intravenous intervention.

Alternating among ERT and SMT, or supplementing SMT with ERT as needed, provides a strategy for simultaneously taking advantage of the strengths and addressing the weaknesses associated with each therapy when used alone. An advantage of ERT, whether used for de-bulking and/or for more long-term care, is the much broader clinical experience available to inform the practitioner's decisions. Moreover, a subject can be effectively titrated with ERT during the de-bulking phase by, for example, monitoring biochemical metabolites in urine or other body samples, or by measuring affected organ volume. A disadvantage of ERT, however, is the frequency of the administration required, typically involving intravenous injection on a weekly or bi-weekly basis due to the constant re-accumulation of the substrate. The use of small molecule therapy to reduce the amount of or inhibit substrate accumulation in a patient can in turn reduce the administration frequency of ERT. For example, a bi-weekly enzyme replacement therapy dosing regimen can be offered an "ERT holiday" (e.g., using a SMT) so that frequent enzyme injections are not required therapy. Furthermore, treating a lysosomal storage disease with combination therapy can provide complementary therapeutic approaches. Indeed, as demonstrated in the Examples below, a combination therapy of SMT and ERT can provide significant improvements over either therapeutic platform alone. These data suggest that combination therapy using SMT and ERT can be both additive and complementary. In one embodiment, ERT may be used as a de-bulking strategy (i.e., to initiate treatment), followed by or simultaneously supplemented with SMT using a compound of the present invention. In another embodiment, a patient is first treated with SMT using a compound of the present invention, followed by or simultaneously supplemented with ERT. In other embodiments, a SMT is used to inhibit or reduce further accumulation of substrate (or re-accumulation of substrate if used after debulking with ERT) in a patient with a lysosomal storage disease, and optionally provided ERT as needed to reduce any further substrate accumulation. In one embodiment, this invention provides a method of combination therapy for treatment of a subject diagnosed as having a lysosomal storage disease comprising alternating between administration of an enzyme replacement therapy and a small molecule therapy. In another embodiment, this invention provides a method of combination therapy for treatment of a subject diagnosed as having a lysosomal storage disease comprising simultaneously administering an enzyme replacement therapy and a small molecule therapy. In the various combination therapies of the invention, it will be understood that administering small molecule therapy may occur prior to, concurrently with, or after, administration of enzyme replacement therapy. Similarly, administering enzyme replacement therapy may occur prior to, concurrently with, or after, administration of small molecule therapy.

In any of the embodiments of the invention, the lysosomal storage disease is selected from the group consisting of Gaucher (types 1, 2 and 3), Niemann-Pick, Farber, $G_{M1}$-gangliosidosis, $G_{M2}$-gangliosidoses (e.g., GM2 Activator Deficiency, Tay-Sachs and Sandhoff), Krabbe, Hurler-Scheie (MPS I), Hunter (MPS II), Sanfilippo (MPS III) Type A, Sanfilippo (MPS III) Type B, Sanfilippo (MPS III) Type C, Sanfilippo (MPS III) Type D, Marquio (MPS IV) Type A, Marquio (MPS IV) Type B, Maroteaux-Lamy (MPS VI), Sly (MPS VII), mucosulfatidosis, sialidoses, mucolipidosis II, mucolipidosis III, mucolipidosis IV, Fabry, Schindler, Pompe, sialic acid storage disease, fucosidosis, mannosidosis, aspartylglucosaminuria, Wolman, and neuronal ceroid lipofucsinoses.

Further, the ERT provides an effective amount of at least one of the following enzymes; glucocerebrosidase, sphingomyelinase, ceramidase, $G_{M1}$-ganglioside-beta-galactosidase, hexosaminidase A, hexosaminidase B, beta-galactocerebrosidase, alpha-L-iduronidase, iduronate sulfatase, heparan-N-sulfatase, N-acetyl-alpha-glucosaminidase, acetyl CoA:alpha-glucosaminide acetyl-transferase, N-acetyl-alpha-glucosamine-6-sulfatase, galactosamine-6-sulfatase, beta-galactosidase, galactosamine-4-sulfatase (arylsulfatase B), beta-glucuronidase, arylsulfatase A, arylsulfatase C, alpha-neuraminidase, N-acetyl-glucosamine-1-phosphate transferase, alpha-galactosidase A, alpha-N-acetylgalactosaminidase, alpha-glucosidase, alpha-fucosidase, alpha-mannosidase, aspartylglucosamine amidase, acid lipase, palmitoyl-protein thioesterase (CLN-1), PPT1, TPP1, CLN3, CLN5, CLN6, CLN8, NPC1 or NPC2.

In accordance with the invention, the SMT and/or ERT produce a diminution in at least one of the following stored materials; glucocerebroside, sphingomyelin, ceramide, $G_{M1}$-ganglioside, $G_{M2}$-ganglioside, globoside, galactosylceramide, dermatan sulfate, heparan sulfate, keratan sulfate, sulfatides, mucopolysaccharides, sialyloligosaccharides, glycoproteins, sialyloligosaccharides, glycolipids, globotriaosylceramide, O-linked glycopeptides, glycogen, free sialic acid, fucoglycolipids, fucosyloligosaccharides, mannosyloligosaccharides, aspartylglucosamine, cholesteryl esters, triglycerides, granular osmophilic deposits—Saposins A and D, ATP synthase subunit c, NPC1 or NPC2.

Figure 2:
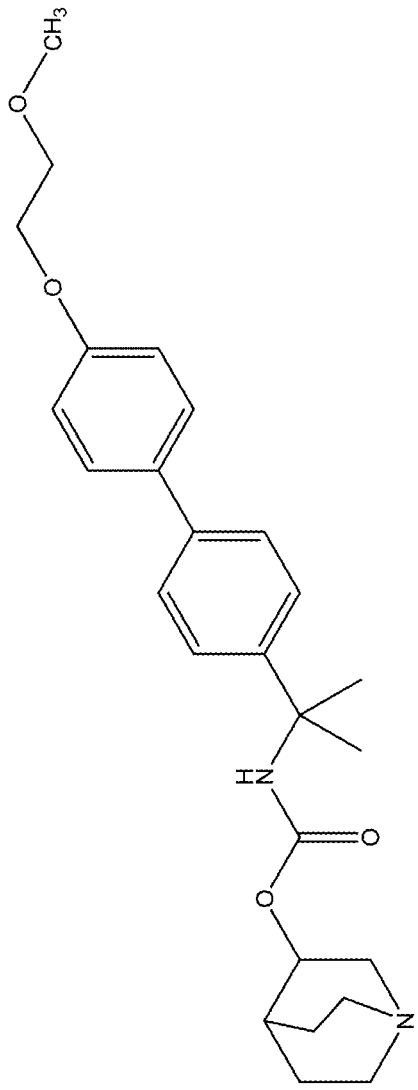
FIG. 2 presents the chemical structure of (S)-Quinuclidin-3-yl (2-(4'-(2-methoxyethoxy)-[1,1'-biphenyl]-4-yl)propan-2-yl)carbamate.

In certain embodiments of the invention, the small molecule therapy comprises administering to the subject an effective amount of (S)-Quinuclidin-3-yl (2-(2-(4-fluorophenyl)thiazol-4-yl)propan-2-yl)carbamate (see FIG. 2A). In other embodiments, the small molecule therapy comprises administering to the subject an effective amount of Quinuclidin-3-yl (2-(4'-fluoro-[1,1'-biphenyl]-3-yl)propan-2-yl)carbamate (see FIG. 2B). The small molecule therapy may include administering to a subject one or more compounds. In certain embodiments, at least one of the compounds is a compound of the present invention, such as those shown in FIGS. 2A and/or 2B.

Enzyme replacement therapy can provoke unwanted immune responses. Accordingly, immunosuppressant agents may be used together with an enzyme replacement therapy component of a combination therapy of the invention. Such agents may also be used with a small molecule therapy component, but the need for intervention here is generally less likely. Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Any combination of immunosuppressant agents known to the skilled artisan can be used together with a combination therapy of the invention. One immunosuppressant agent combination of particular utility is tacrolimus (FK506) plus sirolimus (rapamycin) plus daclizumab (anti-IL2 receptor .alpha.-subunit antibody). This combination is proven effective as an alternative to steroids and cyclosporine, and when specifically targeting the liver. Moreover, this combination has recently been shown to permit successful pancreatic islet cell transplants. See Denise Grady, The New York Times, Saturday, May 27, 2000, pages A1 and A11. See also A. M. Shapiro et al., Jul. 27, 2000, "Islet Transplantation In Seven Patients With Type 1 Diabetes Mellitus Using A Glucocorticoid-Free Immunosuppressive Regimen", N. Engl. J. Med. 343, 230-238; Ryan et al., 2001, Diabetes 50, 710-719. Plasmaphoresis by any method known in the art may also be used to remove or deplete antibodies that may develop against various components of a combination therapy.

Immune status indicators of use with the invention include but are not limited to antibodies and any of the cytokines known to the skilled artisan, e.g., the interleukins, CSFs and interferons (see generally, Leonard et al., 2000, J. Allergy Clin. Immunol. 105, 877-888; Oberholzer et al., 2000, Crit. Care Med. 28 (4 Suppl.), N3-N12; Rubinstein et al., 1998, Cytokine Growth Factor Rev. 9, 175-181). For example, antibodies specifically immunoreactive with the replacement enzyme can be monitored to determine immune status of the subject. Among the two dozen or so interleukins known, particularly preferred immune status indicators are IL-1.alpha., IL-2, IL-4, IL-8 and IL-10. Among the colony stimulating factors (CSFs), particularly preferred immune status indicators are G-CSF, GM-CSF and M-CSF. Among the interferons, one or more alpha, beta or gamma interferons are preferred as immune status indicators.

In the sections which follow, various components that may be used for eight specific lysosomal storage diseases are provided (i.e., Gaucher (including types 1, 2 and 3), Fabry, Niemann-Pick B, Hunter, Morquio, Maroteaux-Lamy, Pompe, and Hurler-Scheie). In subsequent sections, further enabling disclosure for enzyme replacement therapy and small molecule therapy components of a combination therapy of the invention are provided.

Gaucher

As noted above, Gaucher's disease is caused by the deficiency of the enzyme glucocerebrosidase (beta-D-glucosyl-N-acylsphingosine glucohydrolase, EC 3.2.1.45) and accumulation of glucocerebroside (glucosylceramide). For an enzyme replacement therapy component of a combination therapy of the invention for the treatment of Gaucher's disease, a number of references are available which set forth satisfactory dosage regimens and other useful information relating to treatment (see Morales, 1996, Gaucher's Disease: A Review, The Annals of Pharmacotherapy 30, 381-388; Rosenthal et al., 1995, Enzyme Replacement Therapy for Gaucher Disease: Skeletal Responses to Macrophage-targeted Glucocerebrosidase, Pediatrics 96, 629-637; Barton et al., 1991, Replacement Therapy for Inherited Enzyme Deficiency—Macrophage-targeted Glucocerebrosidase for Gaucher's Disease, New England Journal of Medicine 324, 1464-1470; Grabowski et al., 1995, Enzyme Therapy in Type 1 Gaucher Disease: Comparative Efficacy of Mannose-terminated Glucocerebrosidase from Natural and Recombinant Sources, Annals of Internal Medicine 122, 33-39; Pastores et al., 1993, Enzyme Therapy in Gaucher Disease Type 1: Dosage Efficacy and Adverse Effects in 33 Patients treated for 6 to 24 Months, Blood 82, 408-416); and Weinreb et al., Am. J. Med.; 113(2):112-9 (2002).

In one embodiment, an ERT dosage regimen of from 2.5 units per kilogram (U/kg) three times a week to 60 U/kg once every two weeks is provided, where the enzyme is administered by intravenous infusion over 1-2 hours. A unit of glucocerebrosidase is defined as the amount of enzyme that catalyzes the hydrolysis of one micromole of the synthetic substrate para-nitrophenyl-p-D-glucopyranoside per minute at 37° C. In another embodiment, a dosage regimen of from 1 U/kg three times a week to 120 U/kg once every two weeks is provided. In yet another embodiment, a dosage regimen of from 0.25 U/kg daily or three times a week to 600 U/kg once every two to six weeks is provided.

Since 1991, alglucerase (Ceredase®) has been available from Genzyme Corporation. Alglucerase is a placentally-derived modified form of glucocerebrosidase. In 1994, imiglucerase (Cerezyme®) also became available from Genzyme Corporation. Imiglucerase is a modified form of glucocerebrosidase derived from expression of recombinant DNA in a mammalian cell culture system (Chinese hamster ovary cells). Imiglucerase is a monomeric glycoprotein of 497 amino acids containing four N-linked glycosylation sites. Imiglucerase has the advantages of a theoretically unlimited supply and a reduced chance of biological contaminants relative to placentally-derived aglucerase. These enzymes are modified at their glycosylation sites to expose mannose residues, a maneuver which improves lysosomal targeting via the mannose-6-phosphate receptor. Imiglucerase differs from placental glucocerebrosidase by one amino acid at position 495 where histidine is substituted for arginine. Several dosage regimens of these products are known to be effective (see Morales, 1996, Id.; Rosenthal et al., 1995, Id.; Barton et al., 1991, Id.; Grabowski et al., 1995, Id.; Pastores et al., 1993, Id.). For example, a dosage regimen of 60 U/kg once every two weeks is of clinical benefit in subjects with moderate to severe disease. The references cited above and the package inserts for these products should be consulted by the skilled practitioner for additional dosage regimen and administration information. See also U.S. Pat. Nos. 5,236,838 and 5,549,892 assigned to Genzyme Corporation.

As noted above, Gaucher Disease results from a deficiency of the lysosomal enzyme glucocerebrosidase (GC). In the most common phenotype of Gaucher disease (type 1), pathology is limited to the reticuloendothelial and skeletal systems and there are no neuropathic symptoms. See Barranger, Glucosylceramide lipidosis: Gaucher disease. In: Scriver C R B A, Sly W S, Valle D, editor. The Metabolic Basis of Inherited Disease. New York: McGraw-Hill. pp. 3635-3668 (2001). In neuropathic Gaucher disease (nGD), subdivided into type 2 and type 3 Gaucher disease, the deficiency of glucocerebrosidase (GC) causes glucosylceramide (GluCer; GL-1) and glucosylsphingosine (GluSph) to accumulate in the brain, leading to neurologic impairment. Type 2 Gaucher disease is characterized by early onset, rapid progression, extensive pathology in the viscera and central nervous system, and death usually by 2 years of age. Type 3 Gaucher disease, also known as subacute nGD, is an intermediate phenotype with varying age of onset and different degrees of severity and rates of progression. Goker-Alpan et al., The Journal of Pediatrics 143: 273-276 (2003). A recent development has produced the K14 lnl/lnl mouse model of type 2 Gaucher disease (hereinafter, the "K14 mouse"); this mouse model closely recapitulates the human disease showing ataxia, seizures, spasticity and a reduced median lifespan of only 14 days. Enquist et al., PNAS 104: 17483-17488 (2007).

As in patients with nGD, several mouse models of the disease have increased levels of GluCer and GluSph in the brain due to the deficiency in GC activity. Liu et al., PNAS 95: 2503-2508 (1998) and Nilsson, J. Neurochem 39: 709-718 (1982). The "K14" mice display a neuropathic phenotype that shares many pathologic features with type 2 Gaucher disease, such as neurodegeneration, astrogliosis, microglial proliferation, and increased levels of GluCer and GluSph in specific brain regions. Enquist et al. (2007).

Clinical management of patients affected by nGD poses a challenge for treating physicians both because of the severity of type 2 disease and the inability of the current therapies to cross the blood brain barrier (BBB). Current treatment of non-nGD relies on the intravenous delivery of recombinant human glucocerebrosidase (Imiglucerase; Cerezyme™) to replace the missing enzyme or the administration of glucosylceramide synthase inhibitors to attenuate substrate (GL-1) production. However, these drugs do not cross the blood brain barrier, and thus are not expected to provide therapeutic benefit for nGD patients. Current small molecule glucosylceramide synthase inhibitors in the clinic are not likely to address the neuropathic phenotypes of nGD. An evaluation of a compound of the present invention, Quinuclidin-3-yl (2-(4'-fluoro-[1,1'-biphenyl]-3-yl)propan-2-yl)carbamate (hereinafter, "Gzl61"), in the K14 mouse model of type 2 Gaucher disease demonstrated that it could indeed reduce brain GluCer and GluSph (see Examples 122-125). It also reduced brain neuropathology and extended the lifespan of this model. Moreover, a combined approach using both enzyme replacement and small molecule substrate reduction may represent a superior therapy for type 2 Gaucher disease.

Fabry

As noted previously, Fabry's disease is caused by the deficiency of the lysosomal enzyme alpha-galactosidase A. The enzymatic defect leads to systemic deposition of glycosphingolipids having terminal alpha-galactosyl moieties, predominantly globotriaosylceramide (GL3 or Gb3) and, to a lesser extent, galabiosylceramide and blood group B glycosphingolipids.

Several assays are available to monitor disease progression and to determine when to switch from one treatment modality to another. In one embodiment, an assay to determine the specific activity of alpha-galactosidase A in a tissue sample may be used. In another embodiment, an assay to determine the accumulation of Gb3 may be used. In another embodiment, the practitioner may assay for deposition of glycosphingolipid substrates in body fluids and in lysosomes of vascular endothelial, perithelial and smooth muscle cells of blood vessels. Other clinical manifestations which may be useful indicators of disease management include proteinuria, or other signs of renal impairment such as red cells or lipid globules in the urine, and elevated erythrocyte sedimentation rate. One can also monitor anemia, decreased serum iron concentration, high concentration of beta-thromboglobulin, and elevated reticulocyte counts or platelet aggregation. Indeed, any approach for monitoring disease progression which is known to the skilled artisan may be used (See generally Desnick R J et al., 1995, .alpha.-Galactosidase A Deficiency: Fabry Disease, In: The Metabolic and Molecular Bases of Inherited Disease, Scriver et al., eds., McGraw-Hill, N.Y., 7.sup.th ed., pages 2741-2784). A preferred surrogate marker is pain for monitoring Fabry disease management. Other preferred methods include the measurement of total clearance of the enzyme and/or substrate from a bodily fluid or biopsy specimen. A preferred dosage regimen for enzyme replacement therapy in Fabry disease is 1-10 mg/kg i.v. every other day. A dosage regimen from 0.1 to 100 mg/kg i.v. at a frequency of from every other day to once weekly or every two weeks can be used.

Niemann-Pick B

As previously noted, Niemann-Pick B disease is caused by reduced activity of the lysosomal enzyme acid sphingomyelinase and accumulation of membrane lipid, primarily sphingomyelin. An effective dosage of replacement acid sphingomyelinase to be delivered may range from about 0.01 mg/kg to about 10 mg/kg body weight at a frequency of from every other day to weekly, once every two weeks, or once every two months. In other embodiments an effective dosage may range from about 0.03 mg/kg to about 1 mg/kg; from about 0.03 mg/kg to about 0.1 mg/kg; and/or from about 0.3 mg/kg to about 0.6 mg/kg. In a particular embodiment, a patient is administering acid sphingomyelinase in an escalating dose regimen at the following sequential doses: 0.1 mg/kg; 0.3 mg/kg; 0.6 mg/kg; and 1.0 mg/kg, wherein each dose of acid sphingomyelinase is administered at least twice, and each dose is administered at two week intervals, and wherein the patient is monitored for toxic side effects before elevating the dose to the next level (See U.S. Patent Application Publication No. 2011/0052559.

Hurler-Scheie (MPS I)

Hurler, Scheie, and Hurler-Scheie disease, also known as MPS I, are caused by inactivation of alpha-iduronidase and accumulation of dermatan sulfate and heparan sulfate. Several assays are available to monitor MPS I disease progression. For example, alpha-iduronidase enzyme activity can be monitored in tissue biopsy specimens or cultured cells obtained from peripheral blood. In addition, a convenient measure of disease progression in MPS I and other mucopolysaccharidoses is the urinary excretion of the glycosaminoglycans dermatan sulfate and heparan sulfate (see Neufeld et al., 1995, Id.). In a particular embodiment, alpha-iduronidase enzyme is administered once weekly as an intravenous infusion at a dosage of 0.58 mg/kg of body weight.

Hunter (MPS II)

Hunter's disease (a.k.a. MPS II) is caused by inactivation of iduronate sulfatase and accumulation of dermatan sulfate and heparan sulfate. Hunter's disease presents clinically in severe and mild forms. A dosage regimen of therapeutic enzyme from 1.5 mg/kg every two weeks to 50 mg/kg every week is preferred.

Morquio (MPS IV)

Morquio's syndrome (a.k.a. MPS IV) results from accumulation of keratan sulfate due to inactivation of either of two enzymes. In MPS IVA the inactivated enzyme is galactosamine-6-sulfatase and in MPS IVB the inactivated enzyme is beta-galactosidase. A dosage regimen of therapeutic enzyme from 1.5 mg/kg every two weeks to 50 mg/kg every week is preferred.

Maroteaux-Lamy (MPS VI)

Maroteaux-Lamy syndrome (a.k.a. MPS VI) is caused by inactivation of alactosamine-4-sulfatase (arylsulfatase B) and accumulation of dermatan sulfate. A dosage regimen of from 1.5 mg/kg every two weeks to 50 mg/kg every week is a preferred range of effective therapeutic enzyme provided by ERT. Optimally, the dosage employed is less than or equal to 10 mg/kg per week. A preferred surrogate marker for MPS VI disease progression is proteoglycan levels.

Pompe

Pompe's disease is caused by inactivation of the acid alpha-glucosidase enzyme and accumulation of glycogen. The acid alpha-glucosidase gene resides on human chromosome 17 and is designated GAA. H. G. Hers first proposed the concept of inborn lysosomal disease based on his studies of this disease, which he referred to as type II glycogen storage disease (GSD II) and which is now also termed acid maltase deficiency (AMD) (see Hers, 1965, Gastroenterology 48, 625). In a particular embodiment, GAA is administered every 2 weeks as an intravenous infusion at a dosage of 20 mg/kg body weight.

Several assays are available to monitor Pompe disease progression. Any assay known to the skilled artisan may be used. For example, one can assay for intra-lysosomal accumulation of glycogen granules, particularly in myocardium, liver and skeletal muscle fibers obtained from biopsy. Alpha-glucosidase enzyme activity can also be monitored in biopsy specimens or cultured cells obtained from peripheral blood. Serum elevation of creatine kinase (CK) can be monitored as an indication of disease progression. Serum CK can be elevated up to ten-fold in infantile-onset patients and is usually elevated to a lesser degree in adult-onset patients. See Hirschhorn R, 1995, Glycogen Storage Disease Type II: Acid alpha-Glucosidase (Acid Maltase) Deficiency, In: The Metabolic and Molecular Bases of Inherited Disease, Scriver et al., eds., McGraw-Hill, N.Y., 7.sup.th ed., pages 2443-2464.

Enzyme Replacement Therapy

The following sections set forth specific disclosure and alternative embodiments available for the enzyme replacement therapy component of a combination therapy of the invention. Generally, dosage regimens for an enzyme replacement therapy component of a combination therapy of the invention are generally determined by the skilled clinician. Several examples of dosage regimens for the treatment of Gaucher's disease with glucocerebrosidase are provided above. The general principles for determining a dosage regimen for any given ERT component of a combination therapy of the invention for the treatment of any LSD will be apparent to the skilled artisan from publically available information, such as, for example, a review of the specific references cited in the sections for each specific LSD. An ERT may be administered to a patient by intravenous infusion. Intracerebroventricular and/or intrathecal infusion may be used (e.g., in addition to intravenous infusion) to administer ERT to a patient diagnosed with a lysosomal storage disease having CNS manifestations.

Any method known in the art may be used for the manufacture of the enzymes to be used in an enzyme replacement therapy component of a combination therapy of the invention. Many such methods are known and include but are not limited to the Gene Activation technology developed by Shire plc (see U.S. Pat. Nos. 5,968,502 and 5,272,071).

Renal cysts occur in one third of people older than 50 years. While most are simple cysts, renal cystic disease has multiple etiologies. Broad categories of the cystic disease include the following:

Congenital—Congenital cystic dysplasia;

Genetic—Autosomal recessive polycystic kidney disease (ARPKD), autosomal dominant polycystic kidney disease (ADPKD), nephronophthisis-medullary cystic kidney disease complex (NMCD);

Acquired—Simple cysts, acquired cystic disease;

Cysts associated with systemic disease—Von Hippel-Lindau syndrome (VHLS), tuberous sclerosis (TS) and Malignancy—Renal cell carcinoma (RCC).

The most common larger cysts are acquired cysts, simple cysts, and cysts with ADPKD. Smaller cysts are associated with ARPKD, NMCD, and medullary sponge kidney (MSK). In adults, renal angiomyolipomas and RCC also may demonstrate cystic lesions.

Polycystic Kidney Disease (PKD)

Polycystic kidney disease (PKD) describes several conditions in which fluid-filled cysts form in the kidneys. Cysts generally develop in weak segments of the tubules that carry urine from the glomeruli. The cyst's growth displaces healthy kidney tissue. The kidneys expand to accommodate the cyst, which can weigh as much as 20 pounds. There are many forms of PKD, both inherited forms and noninherited.

Autosomal dominant PKD (ADPKD) is the most common, inherited form. Symptoms of ADPKD usually develop between the ages of 30 and 40, but they can begin earlier, even in childhood. About 90 percent of all PKD cases are autosomal dominant PKD. ADPKD results from mutation in the PKD1 gene that encodes polycystin-1 (85% of the cases) or PKD2 gene that encodes polycystin-1 (15% of the cases).

Autosomal recessive PKD (ARPKD) is a rare, inherited form. Symptoms of autosomal recessive PKD begin in the earliest months of life, even in the womb.

Acquired cystic kidney disease (ACKD) develops in association with long-term kidney problems, especially in patients who have kidney failure and who have been on dialysis for a long time. Therefore it tends to occur in later years of life. It is not an inherited form of PKD.

The renal cystic diseases include, but are not limited to renal cyctic diseases such as: acquired renal cystic disease (ARCD), dialysis-associated cystic disease, autosomal dominant polycystic kidney disease (ADPKD), autosomal recessive polycystic kidney disease (ARPKD), congenital multicystic kidney (CMK), multicystic dysplastic kidney, end-stage renal disease (ESRD), medullary sponge kidney, MSK, nephronophthisis-medullary cystic kidney disease complex (NMCD), nephronophthisisuremic medullary cystic disease complex, juvenile nephronophthisis, medullary cystic disease, renal cell carcinoma (RCC), tuberous sclerosis (TS), von Hippel-Lindau syndrome (VHLS).

When PKD causes kidneys to fail, which usually happens after many years, the patient requires dialysis or kidney transplantation. About one-half of people with the major type of PKD progress to kidney failure. PKD can cause cysts in the liver and problems in other organs, such as the heart and blood vessels in the brain. These complications distinguish PKD from the usually harmless "simple" cysts that often form in the kidneys in later years of life.

In the United States, about 600,000 people, and worldwide about 12.5 million people have PKD, and it is a leading cause of kidney failure. Three factors determine cyst classification: its cause (acquired, inherited), its features (complicated, simple, multiple, single), and its location (outer (cortical) or inner (medullary) kidney tissue).

At this time, PKD has no cure. The treatments for PKD include medicine and surgery to reduce pain, antibiotics to resolve infections, dialysis to replace functions of failed kidneys and kidney transplantation. Therefore, there is a need for developing more efficient treatments of PKD.

SUMMARY

In one embodiment, provided herein are methods for treating, ameliorating or preventing multiple cystic diseases. The cystic diseases include, but are not limited to renal cyctic diseases such as: acquired renal cystic disease (ARCD), dialysis-associated cystic disease, autosomal dominant polycystic kidney disease (ADPKD), autosomal recessive polycystic kidney disease (ARPKD), congenital multicystic kidney (CMK), multi cystic dysplastic kidney, end-stage renal disease (ESRD), medullary sponge kidney (MSK), nephronophthisis-medullary cystic kidney disease complex (NMCD), nephronophthisis-uremic medullary cystic disease complex, juvenile nephronophthisis, medullary cystic disease, renal cell carcinoma (RCC), tuberous sclerosis (TS), von Hippel-Lindau syndrome (VHLS). In one embodiment, provided herein are methods for treatment, amelioration or prevention of polycystic kidney disease.

Small Molecule Therapy

The following section also sets forth specific disclosures and alternative embodiments available for the small molecule therapy component of a combination therapy of the invention. Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT component of any combination therapy of the invention for the treatment of any storage disease are well known to the skilled artisan. Guidance for dosage regimens can be obtained from any of the many well-known references in the art on this topic. Further guidance is available, inter alia, from a review of the specific references cited herein.

Generally, compounds of the present invention, such as, for example, (S)-Quinuclidin-3-yl (2-(2-(4-fluorophenyl) thiazol-4-yl)propan-2-yl)carbamate and Quinuclidin-3-yl (2-(4'-fluoro-[1,1'-biphenyl]-3-yl)propan-2-yl)carbamate may be used in the combination therapies of the invention for treatment of virtually any storage disease resulting from a lesion in the glycosphingolipid pathway (e.g. Gaucher, Fabry, $G_{M1}$-gangliosidosis and $G_{M2}$-gangliosidoses (e.g., GM2 Activator Deficiency, Tay-Sachs and Sandhoff)). Likewise, aminoglycosides (e.g. gentamicin, G418) may be used in the combination therapies of the invention for any storage disease individual having a premature stop-codon mutation (i.e., nonsense mutation). Such mutations are particularly prevalent in Hurler syndrome. A small molecule therapy component of a combination therapy of the invention is particularly preferred where there is a central nervous system manifestation to the storage disease being treated (e.g., Sandhoff, Tay-Sachs, Niemann-Pick Type A, and Gaucher types 2 and 3), since small molecules can generally cross the blood-brain barrier with ease when compared to other therapies.

Preferred dosages of substrate inhibitors used in a combination therapy of the invention are easily determined by the skilled artisan. In certain embodiments, such dosages may range from about 0.5 mg/kg to about 300 mg/kg, preferably from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred oral dose range is from about 50 mg to about 100 mg, wherein the dose is administered twice daily. A particular oral dose range for a compound of the present invention is from about 5 mg/kg/day to about 600 mg/kg/day. In a particular oral dose range for a compound of the present invention is from about 1 mg/kg/day to about 100 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day or 100 mg/kg/day.

A rotating combination of therapeutic platforms (i.e., enzyme replacement and small molecule therapy) is preferred. However, subjects may also be treated by overlapping both approaches as needed, as determined by the skilled clinician. Examples of treatment schedules may include but are not limited to: (1) SMT followed by ERT; (2) ERT followed by SMT; and (3) ERT and SMT provided at about the same time. As noted previously, temporal overlap of therapeutic platforms may also be performed, as needed, depending on the clinical course of a given storage disease in a given subject.

Treatment intervals for various combination therapies can vary widely and may generally be different among different storage diseases and different individuals depending on how aggressively storage products are accumulated. For example, Fabry storage product accumulation may be slow compared to rapid storage product accumulation in Pompe. Titration of a particular storage disease in a particular individual is carried out by the skilled artisan by monitoring the clinical signs of disease progression and treatment success.

The various macromolecules that accumulate in lysosomal storage diseases are not uniformly distributed, but instead are deposited in certain preferred anatomic sites for each disease. However, an exogenously supplied enzyme is generally taken up by cells of the reticuloendothelial system and sorted to the lysosomal compartment where it acts to hydrolyze the accumulated substrate. Moreover, cellular uptake of therapeutic enzyme can be augmented by certain maneuvers to increase lysosomal targeting (see e.g. U.S. Pat. No. 5,549,892 by Friedman et al., assigned to Genzyme Corporation, which describes recombinant glucocerebrosidase having improved pharmacokinetics by virtue of remodeled oligosaccharide side chains recognized by cell surface mannose receptors which are endocytosed and transported to lysosomes).

Some treatment modalities target some affected organs better than others. In Fabry, for example, if ERT does not reach the kidney well enough for a satisfactory clinical outcome, SMT can be used to reduce the substrate levels in the kidney. As demonstrated in Example 112 and FIG. 6B, SMT effectively reduced Gb3 levels (i.e., the substrate accumulated in Fabry patients) in the urine of a Fabry mouse model to a greater extent than ERT. The kidneys are believed to be the major source of urine Gb3. In contrast, FIG. 6B shows ERT effectively reduced the Gb3 levels in the plasma to a greater extent than SMT. These results demonstrate that a combination therapy of ERT and SMT provides a complementary therapeutic strategy that takes advantage of the strengths and addresses the weaknesses associated with each therapy employed alone. SMT is able to cross the BBB, providing a powerful approach, when combined with ERT, for treating LSDs having CNS manifestations, such as Niemann Pick Type A and Neuropathic Gaucher disease (nGD). Moreover, substrate reduction by SMT combined with enzyme replacement address the storage problem at separate and distinct intervention points which may enhance clinical outcome.

It will be understood that reference to simultaneous or concurrent administration of two or more therapies does not require that they be administered at the same time, just that they be acting in the subject at the same time.

General Procedure A: Trisubstituted Urea Formation Via N-t-Butoxycarbonyl Functionalized Primary Amine Component To a stirred solution of the primary amine component (1 equivalent) in chloroform (concentration ~0.1 M) was added 4-dimethylaminopyridine (0.1 equivalent) and di-tert-butyl dicarbonate (1 equivalent). The mixture was stirred for 1 hour before adding the secondary amine component (1 equivalent) and heating to reflux overnight. The reaction was then concentrated and the residue purified by preparative HPLC.

General Procedure B: Tetrasubstituted Urea Formation with Triphosgene

To a stirred solution of triphosgene (0.7 equivalent) in toluene (~0.7 M) was added a solution of the first amine component (1 equivalent) in chloroform (~0.5 M). The reaction was stirred for 2 hours and then concentrated. The residue was taken up in chloroform (~0.3 M) and cooled (0° C.). With stirring, the second amine component (1.1 equivalent) and triethylamine (2 equivalents) were added, in order. The reaction was stirred overnight at room temperature and then concentrated. The residue taken up in aqueous sodium carbonate solution and extracted with chloroform. The combined extracts were dried ($Na_2SO_4$) and concentrated. The crude material was purified by preparative HPLC or flash chromatography over $C_{18}$-reversed phase silica.

General Procedure C: Trisubstituted Carbamate Formation Via N-Methoxycarbonyl Functionalized Amine Component To a stirred and cooled (0° C.) solution of the secondary amine component (1 equivalent) and triethylamine (4 equivalents) in methylene chloride (~0.2 M) was added methyl chloroformate (3 equivalents). The reaction was allowed to warm to room temperature and stirred for 6 hours. The reaction solution was then washed with aqueous sodium bicarbonate solution and brine, dried ($Na_2SO_4$) and concentrated. The crude methyl carbamate was used, without purification, in the next step. To a solution of this intermediate (1 equivalent) in toluene (~0.2 M) was added, in order, activated 4 Å molecular sieves, the alcohol component (1.4 equivalents) and sodium hydride (60% dispersion in mineral oil; 0.25 equivalent). The reaction was heated at reflux overnight, filtered and concentrated. The residue was purified by flash chromatography over $C_{18}$-reversed phase silica.

General Procedure D: Amide Formation Using N-(3-Dimethylaminopropyl)-N'-Ethylcarbodiimide Hydrochloride To a stirred solution of the carboxylic acid component (1 equivalent) in N,N-dimethylformamide (~0.1 M) was added the amine component (1.1 equivalent), N,N-diisopropylethylamine (2.2 equivalents), N-(3-dimethylaminopropyl)-N'-ethylcarbodiimide hydrochloride (1.1 equivalents) and 1-hydroxybenzotriazole hydrate (1.1 equivalents). Stirring was continued overnight and then the reaction solution was diluted with water and extracted with chloroform. The combined extracts were washed brine, dried ($Na_2SO_4$) and concentrated. The residue was purified by preparative HPLC.

General Procedure E: Amide Formation Using O-(7-Azabenzotriazol-1-yl)-N,N,N',N'-Tetramethyluronium Hexafluorophosphate To a stirred solution of the carboxylic acid component (1.1 equivalents) in N,N-dimethylformamide (~0.25 M) was added the amine component (1 equivalent) and O-(7-azabenzotriazol-1-yl)-N,N,N',N'-tetramethyluronium hexafluorophosphate (1.1 equivalents). The mixture was cooled (0° C.) and treated, dropwise, with triethylamine (2.2 equivalents). The reaction was allowed to warm to room temperature, stirred overnight and then concentrated. The residue was taken up in aqueous sodium carbonate and extracted with ethyl acetate. The combined organic layers were dried ($Na_2SO_4$) and concentrated and the crude material was purified by flash chromatography over silica using a chloroform/methanol/ammonia eluant.

General Procedure F: Biaryl Coupling Using Suzuki Conditions

To a stirred solution of the aryl halide component (1 equivalent) in 5:1 (v/v) dioxane/water (~0.15 M) or 5:1 (v/v) N,N-dimethylformamide (~0.15 M), was added the arylboronate or arylboronic acid component (1-1.5 equivalents), sodium carbonate (2-3 equivalents) and [1,1'-bis(diphenylphosphino)ferrocene]dichloropalladium(II) (0.05 equivalents). The mixture was heated (90° C.) overnight and then filtered through a plug of Celite. The Celite was rinsed with ethyl acetate and the combined filtrate was washed with brine, dried ($Na_2SO_4$) and concentrated. The residue was purified by flash chromatography over silica.

General Procedure G: Deprotection of t-Butoxycarbonylamino Group with Trifluoroacetic Acid To stirred solution of the t-butoxycarbonylamino protected starting material in dichloromethane (~0.15 M), was added trifluoroacetic acid (20-50 equivalents). The reaction was stirred at room temperature until TLC monitoring indicated the reaction was complete (generally 30-120 minutes). The reaction was concentrated and the residue taken up in aqueous sodium hydroxide and extracted with ethyl acetate. The combined extracts were washed with brine, dried ($Na_2SO_4$) and concentrated to afford the product, which could be used without purification or, optionally, subjected to flash chromatography over silica.

General Procedure H: Urea/Carbamate Formation Using an Isocyanate Generated Via a Mixed Anhydride/Curtius Rearrangement Route To a stirred solution of the carboxylic acid component (1 equivalent) in tetrahydrofuran (~0.1 M) was added triethylamine (2 equivalents). The reaction was cooled (0° C.) and treated with isobutyl chloroformate (1.5 equivalents). After 1 hour at 0° C., a solution of sodium azide (2 equivalents) in water (~1 M) was added and the reaction was allowed to warm to room temperature. After overnight stirring, the reaction was diluted with water and extracted with ethyl acetate. The combined extracts were washed with aqueous sodium bicarbonate solution and brine, dried (Na2SO4) and concentrated. The crude acyl azide was further dried via coevaporation with toluene and then taken up in toluene (~0.1 M). The stirred solution was refluxed for 2-2.5 hours, cooled and treated with either an amine component (1-1.5 equivalents) or alcohol component (1.25-2 equivalents). The reaction was heated at reflux overnight and then concentrated. The residue was taken up in either ethyl acetate or chloroform and washed with aqueous sodium carbonate, (Na2SO4) and concentrated. The crude product was purified by flash chromatography over silica using chloroform/methanol (less polar carbamates) or chloroform/methanol/ammonia (more polar carbamates and ureas) solvent gradients.

General Procedure I: Urea/Carbamate Formation Using an Isocyanate Generated Via a Diphenylphosphoryl Azide/Curtius Rearrangement Route To a stirred solution of the carboxylic acid component (1 equivalent) in toluene (~0.25 M) was added triethylamine (2.5 equivalents) and diphenyl phosphoryl azide (1.25 equivalents). The mixture was heated at reflux for 30 minutes and then cooled to room temperature. The amine or alcohol component (1.2-1.5 equivalents) was added and the reaction was heated at reflux for another 3-18 hours (less time for ureas, more time for carbamates). After this time, the reaction was concentrated and the residue partitioned between ethyl acetate and aqueous sodium carbonate solution. The organic layer was dried (Na2SO4) and concentrated and the resulting crude product was purified by flash chromatography over reversed phase silica using a water/acetonitrile gradient.

General Procedure J: Urea/Carbamate Formation Using an Isocyanate Generated with Phosgene To a stirred solution of the benzylamine component (1 equivalent) in toluene (~0.2 M) was added a 1.9 M solution of phosgene in toluene (4 equivalents). The reaction was heated at reflux for 4 hours and then concentrated. In the case of urea targets, the crude isocyanate was taken up in chloroform (~0.2 M), treated with the second amine component and stirred overnight at room temperature. In the case of the carbamate targets, the crude isocyanate was dissolved in toluene (~0.2 M), treated with the alcohol component and heated at reflux overnight. The urea or carbamate reaction solution was then concentrated, partitioned between aqueous sodium carbonate solution and chloroform. The organic solution was dried (Na2SO4) and concentrated. Crude product was purified by flash chromatography over silica using chloroform/methanol (less polar carbamates) or chloroform/methanol/ammonia (more polar carbamates and ureas) solvent gradients.

Preparation A

Intermediate 1

3-Methylquinuclidin-3-amine

A well-stirred 3.0 M solution of methyllithium in diethyl ether (67.0 mL, 201 mmol) was diluted with additional diethyl ether (150 mL), cooled to −78° C. and treated, dropwise, with a solution of quinuclidin-3-one (12.5 g, 100 mmol) in diethyl ether (100 mL). The resulting solution was maintained at −78° C. for 1 hour and then allowed to warm to room temperature. After overnight stirring, the reaction was recooled (0° C.) and treated, dropwise, with water (60 mL). The mixture was concentrated and the resulting residue was purified by flash chromatography over neutral aluminum oxide using a chloroform/methanol gradient (0-20% methanol) to give 3-methylquinuclidin-3-ol (10.0 g, 71%) as a light yellow solid. To stirred acetonitrile (250 mL) at 0° C., was slowly added concentrated sulfuric acid (100 mL). The resulting solution was added dropwise to a mixture of 3-methylquinuclidin-3-ol (9.10 g, 64.5 mmol) in acetonitrile (250 mL) at 0° C. The reaction mixture was stirred at room temperature for 60 hours, cooled to (0° C.) and then basified (pH~10) with aqueous sodium hydroxide solution. The mixture was extracted with 5:1 (v/v) chloroform/isopropanol. The combined organic layers were concentrated and the residue was diluted with 2N hydrochloric acid. After washing with 5:1 (v/v) chloroform/isopropanol, the aqueous layer was basified with 2N aqueous sodium hydroxide and extracted with 5:1 (v/v) chloroform/isopropanol. The combined organic layers were washed with water, dried ($Na_2SO_4$) and concentrated to afford N-(3-methylquinuclidin-3-yl)acetamide as a light yellow oil (9.50 g, 82%). A solution of the above acetamide intermediate (9.50 g, 52.0 mmol) in concentrated hydrochloric acid (100 mL) was refluxed for 3 days. After cooling in an ice bath, the reaction was treated with enough aqueous sodium hydroxide solution to achieve pH~1. The mixture was washed with 5:1 (v/v) chloroform/isopropanol. The aqueous layer was then basified with 2N aqueous sodium hydroxide solution and extracted with 5:1 (v/v) chloroform/isopropanol. The combined extracts were washed with water, dried ($Na_2SO_4$) and concentrated to afford the title compound as a light yellow semi-solid (5.00 g, 69%). $^1$H NMR (500 MHz, DMSO-$d_6$) δ 2.72-2.39 (m, 6H), 2.01-1.96 (m, 1H), 1.67-1.61 (m, 1H), 1.43-1.36 (m, 2H), 1.23-1.17 (m, 1H), 1.09 (s, 3H) ppm. $^{13}$C NMR (125 MHz, DMSO-$d_6$) δ 65.3, 48.3, 46.6, 46.4, 34.2, 30.0, 24.8, 22.8 ppm.

Preparation B

Intermediate 2

3-Ethylquinuclidin-3-amine

A cooled (0° C.) and well-stirred 0.5 M solution of ethyllithium in benzene/cyclohexane (100 mL, 50 mmol) was diluted with tetrahydrofuran (50 mL) and treated, dropwise over ~5 minutes, with a solution of quinuclidin-3-one (3.13 g, 25.0 mmol) in tetrahydrofuran (20 mL). After 2 hours, the cooling bath was removed and the reaction was stirred overnight. The reaction was quenched by the slow addition of water (10 mL). The resulting mixture was concentrated onto silica and purified by flash chromatography over silica using a chloroform/methanol/ammonia eluant to afford 3-ethylquinuclidin-3-ol as a waxy, amber solid (2.43 g, 63%). To a stirred and cooled (0° C.) solution of this product (2.31 g, 14.9 mmol) in acetonitrile (20 mL) was added, dropwise over ~20 minutes, concentrated sulfuric acid (40 mL). The mixture was stirred overnight and allowed to slowly warm to room temperature. The reaction was then poured over crushed ice. While stirring, concentrated ammonium hydroxide (~110 mL) was slowly added (final pH~10). The solution was extracted with 4:1 (v/v) chloroform/isopropanol and the combined extracts were dried ($Na_2SO_4$) and concentrated onto silica. The crude product was purified by flash chromatography using a chloroform/methanol/ammonia gradient to afford N-(3-ethylquinuclidin-3-yl)acetamide as a waxy, amber solid (2.16 g, 74%). A solution of this product (5.48 g, 28.0 mmol) in a mixture of water (60 mL) and concentrated hydrochloric acid (60 mL) was heated at reflux for 3 days. After this time, the solution was concentrated to provide the dihydrochloride of title compound, which was used without purification, as a light brown solid (4.75 g, 75%). $^1$H NMR (400 MHz, $CD_3OD$) δ 3.65-3.55 (m, 2H), 3.52-3.27 (m, 4H), 2.51-2.45 (m, 1H), 2.27-2.00 (m, 6H), 1.06 (t, J=7.5 Hz, 3H) ppm. In reactions which require liberation of the free base, an equimolar quantity of triethylamine was added with the dihydrochloride salt. Alternatively, the product could be isolated as a free base by dissolving the dihydrochloride salt in aqueous sodium hydroxide solution and extracting with 4:1 (v/v) chloroform/isopropanol. After drying ($Na_2SO_4$), the combined extracts were concentrated to afford the product as a pale amber oil. $^1$H NMR (400 MHz, $CD_3OD$) δ 2.94-2.84 (m, 1H), 2.83-2.55 (m, 5H), 2.05-1.94 (m, 1H), 1.83-1.73 (m, 1H), 1.73-1.60 (m, 2H), 0.91 (t, J=7.4 Hz, 3H) ppm.

Preparation C

Intermediate 3

1-Azabicyclo[3.2.2]nonan-4-ol

A stirred and cooled (0° C.) 2.0 M solution of trimethylsilyldiazomethane in hexanes (43.9 mL, 87.9 mmol) was treated, dropwise, with a solution of 3-quinuclidinone (10.0 g, 79.9 mmol) in THF (80 mL). Methanol (44 mL) was added and the reaction was stirred overnight and allowed to warm to room temperature. The reaction was then treated with acetic acid (1.0 mL). After a few minutes, a saturated solution of aqueous sodium carbonate (40 mL) was added and the layers were separated. The organic layer was combined with additional ethyl acetate extracts, dried ($Na_2SO_4$) and concentrated. The resulting yellow oil was purified by flash chromatography over neutral alumina using a methylene chloride/methanol eluant to afford 1-azabicyclo[3.2.2]nonan-4-one as a white solid (6.80 g, 61%). To a stirred and cooled (0° C.) solution of this product (6.80 g, 48.8 mmol) in tetrahydrofuran (100 mL) was added, portion wise, lithium aluminum hydride (1.85 g, 48.8 mmol). After vigorous hydrogen gas evolution ceased, the reaction was allowed to warm to room temperature and then heated at reflux for 1 hour. The solution was then cooled (0° C.) and quenched by the successive, dropwise, addition of water (1.8 mL), 10% sodium hydroxide solution (1.8 mL), and water again (5.5 mL). The colorless precipitate was removed by filtration through Celite, which was then washed with tetrahydrofuran. The combined filtrate was dried ($Na_2SO_4$) and concentrated to afford the title compound as a white solid (5.60 g, 81%). $^1$H NMR (400 MHz, $CDCl_3$) 03.90-3.86 (m, 1H), 3.09-3.03 (m, 1H), 2.96-2.91 (dd, J=9.2, 6.8 Hz, 1H), 2.86-2.75 (m, 3H), 2.71-2.64 (m, 1H), 2.34-2.27 (br s, 1H), 1.98-1.86 (m, 3H), 1.71-1.59 (m, 3H), 1.51-1.35 (m, 1H) ppm.

Preparation D

Intermediate 4

1-Azabicyclo[3.2.2]nonan-4-amine

To a stirred solution of 1-azabicyclo[3.2.2]nonan-4-one (Preparation C) (10.0 g, 71.8 mmol) in isopropanol (50 mL) was added sodium acetate (11.80 g, 143.7 mmol) and hydroxylamine hydrochloride (5.50 g, 79.1 mmol). The mixture was heated at reflux for 3 hours and then cooled to room temperature. The reaction was filtered and concentrated to afford the oxime intermediate, which was used in the next step without purification, as a white solid (11.00 g, 99%). A stirred solution of this product (11.0 g, 71.3 mmol) in n-propanol (120 mL) was heated to reflux temperature. Sodium metal (16.5 g, 718 mmol) was added, portion wise, over 30 minutes. Reflux was continued overnight and then the reaction was then cooled to room temperature and treated with brine (20 mL). The mixture was extracted with n-propanol (2×50 mL) and the combined organic layers were concentrated. The residue was diluted with chloroform and the remaining solids were filtered off. The filtrate was dried ($Na_2SO_4$) and concentrated to afford the title compound as a light yellow semi-solid (6.70 g, 74%). $^1$H NMR (500 MHz, $CDCl_3$) δ 3.17-3.13 (m, 1H), 3.10-3.07 (m, 1H), 3.05-3.01 (m, 1H), 2.91-2.88 (m, 3H), 2.77-2.70 (m, 1H), 1.92-1.87 (m, 1H), 1.83-1.80 (m, 1H), 1.71-1.68 (m, 3H), 1.59-1.48 (m, 2H), 1.33 (br s, 2H) ppm.

Preparation E

Intermediate 5

4-Methyl-1-azabicyclo[3.2.2]nonan-4-amine

The title compound was prepared from 1-azabicyclo[3.2.2]nonan-4-one (Preparation C) by the same procedure used to convert quinuclidin-3-one to 3-methylquinuclidin-3-amine in Preparation A. $^1$H NMR (500 MHz, DMSO-$d_6$) δ 2.84-2.65 (m, 6H), 2.01-1.97 (m, 1H), 1.69-1.24 (m, 8H), 1.09 (s, 3H) ppm.

Preparation F

Intermediate 6

1,4-Diazabicyclo[3.2.2]nonane

To a stirred solution of 1,4-diazabicyclo[3.2.2]nonan-3-one (1.00 g, 7.13 mmol) in 1,4-dioxane (7.2 mL) at room temperature was added lithium aluminum hydride [2.0M/THF] (4.1 mL, 8.2 mmol). The reaction mixture was then heated at reflux for 6 hours. After cooling to room temperature, the reaction was quenched by the sequential addition of water (200 DL), 15% aqueous NaOH (200 DL) and water again (600 DL).

The mixture was filtered through Celite which was subsequently washed with ethyl acetate. The combined filtrate was concentrated to afford the title compound as a light brown solid (0.82 g, 90%) which was used without purification. $^1$H NMR (400 MHz, CDCl$_3$) ☐ 3.28-3.25 (m, 1H), 2.99-2.95 (m, 8H), 1.86-1.80 (m, 3H), 1.69-1.64 (m, 2H) ppm.

Preparation G

Intermediate 7

1-Azabicyclo[3.2.2]nonan-3-ol

To a stirred and cooled (0° C.) solution of ethyl 2-hydroxyacetate (20.0 g, 19.0 mmol) in tetrahydrofuran (250 mL) was added tetrabutylammonium iodide (7.01 g, 19.0 mmol) and sodium hydride (60% in mineral oil, 7.60 g, 19.0 mmol). The mixture was stirred at 0° C. for 30 minutes before adding benzyl bromide (32.3 g, 19.0 mmol). The reaction was stirred overnight and allowed to warm to room temperature. The mixture was then cooled (0° C.), quenched with aqueous ammonium chloride (100 mL) and extracted with ethyl acetate. The combined organic layers were washed with water and brine, dried (Na$_2$SO$_4$) and concentrated. The residue was purified by flash chromatography over silica using a hexane/ethyl acetate eluant to afford ethyl 2-(benzyloxy)acetate as a yellow oil (14.7 g, 57%). To a stirred and cooled (0° C.) solution of this product (13.6 g, 70.0 mmol) in tetrahydrofuran (150 mL) was added dimethyl methylphosphonate (11.3 g, 91.1 mmol) followed by a 2.0 M solution of lithium diisopropylamide in tetrahydrofuran/heptane/ethylbenzene (74.0 mL, 148 mmol). The reaction was stirred at 0° C. for 3 hours before quenching with enough 5.0 M aqueous hydrochloric acid to bring the pH to ~4. The resulting mixture was then extracted with ethyl acetate. The combined organic layers were washed with brine, dried (Na$_2$SO$_4$) and concentrated. The residue was purified by flash chromatography over silica using a hexane/ethyl acetate eluant to afford dimethyl (3-(benzyloxy)-2-oxopropyl)phosphonate as a light yellow oil (10.1 g, 54%). To a stirred and cooled (0° C.) solution of this intermediate (9.89 g, 36.4 mmol) in tetrahydrofuran (100 mL) was added sodium hydride (60% in mineral oil; 1.60 g, 40.0 mmol). The mixture was stirred at 0° C. for 30 minutes before adding, dropwise, a solution of tert-butyl 4-oxo-piperidine-1-carboxylate (5.79 g, 29.1 mmol) in tetrahydrofuran (50 mL). The resulting mixture was stirred at 0° C. for 2 hours, then quenched with saturated aqueous ammonium chloride and extracted with ethyl acetate. The combined organic layers were washed with brine, dried (Na$_2$SO$_4$), and concentrated. The residue was purified by flash chromatography over silica using a hexane/ethyl acetate eluant to afford tert-butyl 4-(3-(benzyloxy)-2-oxopropylidene)piperidine-1-carboxylate as a light yellow oil (6.50 g, 52%). This material (6.50 g, 18.8 mmol), 10% Pd/C (1.00 g) and ethyl acetate (50 mL) were placed in a Parr bottle and hydrogenated for 5 hours at room temperature. The mixture was filtered through Celite and concentrated to afford tert-butyl 4-(3-hydroxy-2-oxopropyl)piperidine-1-carboxylate as a yellow oil (4.80 g, 99%). To a stirred solution of this product (4.80 g, 18.7 mmol) in methylene chloride (8 mL) was added carbon tetrabromide (12.4 g, 37.4 mmol) and triphenylphosphine (9.80 g, 37.4 mmol). After 3 hours, the reaction was concentrated and the residue purified by flash chromatography over silica using a hexane/ethyl acetate eluant to afford tert-butyl 4-(3-bromo-2-oxopropyl)piperidine-1-carboxylate as a white solid (3.30 g, 56%). To a stirred and cooled (0° C.) solution of this product (3.30 g, 10.3 mmol) in methylene chloride (50 mL) was added trifluoroacetic acid (12.0 mL, 145 mmol). The mixture was stirred at 0° C. for min before concentrating to afford crude 1-bromo-3-(piperidin-4-yl)acetone trifluoroacetate, which was used without purification in the next step. To a stirred solution of diisopropylethylamine (20 mL) in acetonitrile (800 mL) at reflux was added a solution of the crude intermediate in acetonitrile (150 mL), dropwise over 4 hours (syringe pump). Reflux was continued overnight and then the mixture was concentrated. The resulting residue was partitioned between aqueous potassium carbonate solution and 9:1 (v/v) chloroform/methanol. The organic layer was combined with a second extract using the same solvent mixture, dried (Na$_2$SO$_4$) and concentrated. The crude material was purified flash chromatography over silica using a 95/4.5/0.5 (v/v) chloroform/methanol/ammonium hydroxide eluant to afford 1-azabicyclo[3.2.2]nonan-3-one as a brown solid (770 mg, 54%). To a stirred and cooled (0° C.) solution of this intermediate (770 mg, 5.54 mmol) in tetrahydrofuran (10 mL), was added lithium aluminum hydride (211 mg, 5.54 mmol), portion wise. After vigorous hydrogen gas evolution ceased, the reaction mixture was allowed to warm to room temperature and then heated at reflux for 1 hour. The solution was cooled to 0° C. and quenched by the successive dropwise addition of water (0.2 mL), 10% aqueous sodium hydroxide solution (0.2 mL) and water again (0.6 mL). The colorless precipitate was removed by filtration through Celite, which was subsequently washed with tetrahydrofuran. The combined filtrate was dried (Na$_2$SO$_4$) and concentrated to afford the title compound as yellow solid (770 mg, 99%).

Preparation H

Intermediate 8

1-Azabicyclo[3.2.2]nonan-3-amine

The title compound was prepared from 1-azabicyclo[3.2.2]nonan-3-one (Preparation G) by the same procedure used to convert 1-azabicyclo[3.2.2]nonan-4-one to 1-azabicyclo[3.2.2]nonan-4-amine in Preparation D.

Preparation I

Intermediates 9, 10

Enantiomers of 4-Methyl-1-azabicyclo[3.2.2]nonan-4-amine

Racemic N-(4-methyl-1-azabicyclo[3.2.2]nonan-4-yl)acetamide (Preparation E) was resolved into its component enantiomers using a Thar SFC Prep 80 instrument and the following separation conditions: CHIRALCEL OZ-H column (30×250 mm, 5 mm particle size) with a carbon dioxide/acetonitrile/isopropanol/diethylamine (55/30/15/0.2) mobile phase and a flow rate of 60 g/min. The enantiomers eluted at 6.34 and 9.55 minutes. Using the acetamide hydrolysis conditions described in Preparation A, the early eluting isomer was deacetylated to generate Intermediate 9 and the later eluting isomer was deacetylated to generate Intermediate 10. The absolute stereochemistry of the enantiomers was not determined.

Preparation J

Intermediates 11, 12

Enantiomers of 3-Methylquinuclidin-3-amine

Racemic N-(3-methylquinuclidin-3-yl)acetamide (Preparation A) was resolved into its component enantiomers using a Thar SFC Prep 80 instrument and the following separation conditions: CHIRALCEL IC-H column (30×250 mm, 5 μm particle size) with a carbon dioxide/isopropanol/diethylamine (50/50/0.1) mobile phase and a flow rate of 60 g/min. The enantiomers eluted at 3.12 and 8.17 minutes. Using the acetamide hydrolysis conditions described in Preparation A, the early eluting isomer was deacetylated to generate Intermediate 11 and the later eluting isomer was deacetylated to generate Intermediate 10. Intermediate 12 was then amide coupled (General Procedure D) to (S)-(+)-2-phenylpropionic acid to generate a single enantiomer of (2S)—N-(3-methylquinuclidin-3-yl)-2-phenylpropanamide. A crystal of this compound was produced and subjected to X-ray crystallography, revealing the amide to be in the (2'R,3S)-configuration. Thus, it was determined that Intermediate 11 is (S)-3-methylquinuclidin-3-amine and Intermediate 12 is (R)-3-methylquinuclidin-3-amine.

Preparation K

Intermediates 13, 14

Enantiomers of 3-Ethylquinuclidin-3-amine

Racemic N-(3-ethylquinuclidin-3-yl)acetamide (Preparation B) was resolved into its component enantiomers using a Thar SFC Prep 80 instrument and the following separation conditions: CHIRALCEL IC-H column (30×250 mm, 5 μm particle size) with a carbon dioxide/ethanol/diethylamine (60/40/0.2) mobile phase and a flow rate of 80 g/min. The enantiomers eluted at 3.31 and 4.70 minutes. Using the acetamide hydrolysis conditions described in Preparation A, the early eluting isomer was deacetylated to generate Intermediate 13 and the later eluting isomer was deacetylated to generate Intermediate 14. The absolute stereochemistry of the enantiomers was not determined.

Preparation L

Intermediates 15, 16

Enantiomers of 1-Azabicyclo[3.2.2]nonan-4-ol

A stirred solution of racemic 1-azabicyclo[3.2.2]nonan-4-ol (Preparation C; 23.0 g, 16.3 mmol) in acetic anhydride (100 mL) was heated at reflux for 1 hour. The mixture was concentrated and the residue was taken up in aqueous sodium bicarbonate solution and extracted with 5:1 (v/v) chloroform/isopropanol. The combined extracts were washed with brine, dried (Na2SO4) and concentrated to afford 1-azabicyclo[3.2.2]nonan-4-yl acetate. This material was resolved into its component enantiomers using a Thar SFC Prep 80 instrument and the following separation conditions: CHIRALCEL OZ-H column (30×250 mm, 5 μm particle size) with a carbon dioxide/acetonitrile/isopropanol/diethylamine (55/30/15/0.2) mobile phase and a flow rate of 60 g/min. The enantiomers eluted at 3.39 minutes (10.5 g collected) and 6.54 minutes (11.3 g collected). The later eluting acetate enantiomer (11.0 g, 60.0 mmol) was taken up in 2N aqueous sodium hydroxide solution. The stirred mixture was heated at 50° C. for 1 hour before cooling and extracting with 5:1 (v/v) chloroform/isopropanol. The combined extracts were dried (Na2SO4) and concentrated to afford Intermediate 16 as light yellow solid (8.00 g, 94%). The early eluting acetate isomer was deprotected in the same manner to afford Intermediate 15. The absolute stereochemistry of the enantiomers was not determined.

Preparation M

Intermediate 17

3-Propylquinuclidin-3-amine dihydrochloride

A stirred and cooled (−78° C.) 2.0 M solution of propylmagnesium chloride in diethyl ether (100 mL, 200 mmol) was diluted with tetrahydrofuran (150 mL) and treated, dropwise over ~20 minutes, with a solution of quinuclidin-3-one (13.45 g, 107.5 mmol) in tetrahydrofuran (90 mL). The cooling bath was allowed to slowly warm to room temperature and the mixture was stirred overnight. The reaction was then heated at reflux for 30 minutes, cooled (0° C.) and quenched by the slow addition of water (60 mL). The mixture was concentrated to remove organic solvent, diluted with aqueous ammonium chloride solution (250 mL) and extracted with 4:1 (v/v) chloroform/isopropanol. The combined extracts were dried (Na2SO4) and concentrated onto silica. Flash chromatography over silica using a chloroform/methanol/ammonia gradient provided 3-propylquinuclidin-3-ol as a white solid (5.57 g, 31%). To a stirred and cooled (0° C.) solution of this product (5.55 g, 32.8 mmol) in acetonitrile (30 mL) was added, dropwise over 15 minutes, concentrated sulfuric acid (40 mL). The cooling bath was allowed to slowly warm to room temperature and the mixture was stirred overnight. The reaction was then poured over crushed ice. The resulting ice slurry was stirred and slowly treated with concentrated ammonium hydroxide solution (100 mL). After the ice fully melted, the mixture was extracted with 4:1 (v/v) chloroform/isopropanol. The combined extracts were dried (Na2SO4) and concentrated onto silica. Flash chromatography over silica using a chloroform/methanol/ammonia gradient provided N-(3-propylquinuclidin-3-yl)acetamide as a faint amber gum (6.94 g, 100%). A solution of this product (6.94 g, 32.8 mmol) in a mixture of water (90 mL) and concentrated hydrochloric acid (90 mL) was heated at reflux for 4 days. After this time, the solution was concentrated to provide the title compound as a white solid (6.44 g, 81%) which was used without purification. In reactions which require liberation of the free base, an equimolar quantity of triethylamine was added with the dihydrochloride salt. 1H NMR (400 MHz, DMSO-d6) □ 11.27 (br s, 1H), 8.91 (br s, 3H), 3.52-3.30 (m, 2H), 3.28-3.06 (m, 4H), 2.35-2.24 (m, 1H), 2.24-2.08 (m, 1H), 1.97-1.71 (m, 5H), 1.48-1.21 (m, 2H), 0.89 (t, J=7.1 Hz, 3H) ppm.

Example 1

4-([1,1'-Biphenyl]-4-yl)-N-(3-methylquinuclidin-3-yl)piperazine-1-carboxamide

Using General Procedure A and the reaction inputs 1-([1,1'-biphenyl]-4-yl)piperazine and Intermediate 1, the title compound was prepared. $^1$H NMR (500 MHz, DMSO-d$_6$) δ 7.56 (d, J=7.5 Hz, 2H), 7.54 (d, J=8.0 Hz, 2H), 7.41 (t, J=7.5 Hz, 2H), 7.27 (t, J=7.5 Hz, 1H), 7.05 (d, J=8.5 Hz, 2H), 5.99 (s, 1H), 3.44 (t, J=5.0 Hz, 4H), 3.15 (t, J=5.0 Hz, 4H), 2.96-2.93 (m, 1H), 2.67-2.57 (m, 5H), 2.12-2.11 (m, 1H), 1.75-1.64 (m, 2H), 1.41-1.23 (m, 5H) ppm. $^{13}$C NMR (125 MHz, CDCl$_3$) δ 157.0, 150.2, 140.7, 132.9, 128.7, 127.9, 126.6, 126.6, 116.4, 63.5, 52.7, 50.8, 48.9, 46.6, 43.9, 31.3, 25.3, 23.3, 22.6 ppm. Purity: >99% (214 & 254 nm) LCMS; retention time: 1.99 min; (M+H⁺) 405.3.

Example 2

4-([1,1'-Biphenyl]-4-yl)-N-(quinuclidin-3-yl)piperazine-1-carboxamide

Using General Procedure A and the reaction inputs 1-([1,1'-biphenyl]-4-yl)piperazine and quinuclidin-3-amine, the title compound was prepared. ¹H NMR (500 MHz, CDCl₃) δ 7.57-7.52 (m, 4H), 7.41 (t, J=8.0 Hz, 2H), 7.29 (t, J=7.5 Hz, 1H), 7.00 (d, J=8.5 Hz, 2H), 4.61 (s, 1H), 3.88 (m, 1H), 3.57 (t, J=5.0 Hz, 4H), 3.41-3.36 (m, 1H), 3.26 (t, J=5.0 Hz, 4H), 2.90-2.80 (m, 4H), 2.53-2.50 (m, 1H), 1.95-1.94 (m, 1H), 1.74-1.66 (m, 3H), 1.49 (m, 1H) ppm. ¹³C NMR (125 MHz, CDCl₃) δ 157.4, 150.2, 140.7, 133.0, 128.7, 127.9, 126.6, 126.5, 116.5, 56.6, 48.9, 47.9, 47.4, 46.7, 43.7, 26.1, 25.9, 20.2 ppm. Purity: >99% (214 & 254 nm) LCMS; retention time: 1.44 min; (M+H⁺⁾ 391.2.

Example 3

4-([1,1'-Biphenyl]-4-yl)-N-(1-azabicyclo[3.2.2]nonan-4-yl)piperazine-1-carboxamide Using General Procedure A and the reaction inputs 1-([1,1'-biphenyl]-4-yl)piperazine and Intermediate 4, the title compound was prepared. ¹H NMR (500 MHz, CDCl₃) δ 7.56-7.52 (m, 4H), 7.41 (t, J=8.0 Hz, 2H), 7.29 (t, J=8.0 Hz, 1H), 7.00-6.98 (d, J=9.0 Hz, 2H), 4.50 (d, J=7.0 Hz, 1H), 4.01-3.96 (m, 1H), 3.55 (t, J=5.0 Hz, 4H), 3.25 (t, J=5.0 Hz, 4H), 3.19-2.76 (m, 6H), 2.05-1.57 (m, 7H) ppm. ¹³C NMR (125 MHz, CDCl₃) δ 156.8, 150.2, 140.7, 133.0, 128.7, 128.7, 127.9, 126.6, 116.5, 56.1, 53.0, 49.0, 48.9, 44.3, 43.7, 34.8, 32.0, 26.6, 22.4 ppm. Purity: >98% (214 & 254 nm) LCMS; retention time: 1.45 min; (M+H⁺) 405.2.

Example 4

4-([1,1'-Biphenyl]-4-yl)-N-(4-methyl-1-azabicyclo[3.2.2]nonan-4-yl)piperazine-1-carboxamide Using General Procedure A and the reaction inputs 1-([1,1'-biphenyl]-4-yl)piperazine and Intermediate 5, the title compound was prepared. ¹H NMR (500 MHz, CDCl₃) δ 7.56-7.52 (m, 4H), 7.41 (t, J=7.5 Hz, 2H), 7.29 (t, J=7.5 Hz, 1H), 7.00-6.98 (d, J=8.5 Hz, 2H), 4.40 (s, 1H), 3.54-3.26 (m, 4H), 3.25-3.02 (m, 4H), 3.00-2.81 (m, 6H), 2.39-2.37 (m, 1H), 2.17 (m, 1H), 1.96-1.51 (m, 8H) ppm. ¹³C NMR (125 MHz, CDCl₃) δ 157.0, 150.2, 140.7, 132.9, 128.7, 127.9, 126.6, 126.6, 116.4, 59.1, 53.2, 48.9, 47.6, 46.4, 43.9, 39.8, 36.5, 25.8, 24.5, 24.2 ppm. Purity: >98% (214 & 254 nm) LCMS; retention time: 1.29 min; (M+H⁺) 419.2.

Example 5

(4-([1,1'-Biphenyl]-4-yl)piperazin-1-yl)(1,4-diazabicyclo[3.2.2]nonan-4-yl)methanone Using General Procedure B and the reaction inputs 1-([1,1'-biphenyl]-4-yl)piperazine and Intermediate 6, the title compound was prepared. ¹H NMR (400 MHz, CDCl₃) δ 7.57-7.52 (m, 4H), 7.40 (t, J=8.0 Hz, 2H), 7.28 (t, J=7.2 Hz, 1H), 7.01-6.98 (d, J=8.8 Hz, 2H), 4.12-4.11 (m, 1H), 3.52 (t, J=6.0 Hz, 2H), 3.38-3.36 (m, 4H), 3.25-3.23 (m, 4H), 3.07-2.96 (m, 6H), 2.07-2.00 (m, 2H), 1.80-1.72 (m, 2H) ppm. ¹³C NMR (100 MHz, CDCl₃) δ 163.7, 150.5, 140.8, 132.8, 128.7, 127.8, 126.5, 116.4, 56.5, 49.2, 49.0, 47.2, 46.4, 45.7, 27.2 ppm. Purity: >99% (214 & 254 nm) LCMS; retention time: 1.26 min; (M+H⁺) 391.2.

Example 6

Quinuclidin-3-yl 4-([1,1'-biphenyl]-4-yl)piperazine-1-carboxylate

Using General Procedure C and the reaction inputs 1-([1,1'-biphenyl]-4-yl)piperazine and quinuclidin-3-ol, the title compound was prepared. ¹H NMR (500 MHz, CDCl₃) δ 7.58-7.54 (m, 4H), 7.43 (t, J=7.5 Hz, 2H), 7.31 (t, J=7.5 Hz, 1H), 7.02 (d, J=8.0 Hz, 2H), 4.81 (m, 1H), 3.68 (t, J=4.5 Hz, 4H), 3.31-3.24 (m, 5H), 2.95-2.78 (m, 5H), 2.11-2.10 (m, 1H), 1.87-1.46 (m, 4H) ppm. ¹³C NMR (125 MHz, CDCl₃) δ 155.0, 150.4, 140.7, 133.1, 128.7, 127.8, 126.6, 126.5, 116.7, 72.1, 55.7, 49.2, 47.4, 46.4, 43.6, 25.5, 24.5, 19.7 ppm. Purity: >99% (214 & 254 nm) LCMS; retention time: 1.32 min; (M+H⁺) 392.2.

Example 7

4-Phenyl-N-(quinuclidin-3-yl)piperazine-1-carboxamide

Using General Procedure A and the reaction inputs 1-phenylpiperazine and quinuclidin-3-amine, the title compound was prepared. ¹H NMR (500 MHz, CDCl₃) δ 7.31-7.28 (m, 2H), 6.95-6.89 (m, 3H), 4.74-4.72 (m, 1H), 3.91-3.89 (m, 1H), 3.56 (t, J=5.0 Hz, 4H), 3.38-3.37 (m, 1H), 3.21 (t, J=5.0 Hz, 4H), 2.87-2.82 (m, 4H), 2.60-2.59 (m, 1H), 1.97-1.96 (m, 1H), 1.72-1.25 (m, 4H) ppm. ¹³C NMR (125 MHz, CDCl₃) δ 157.4, 151.0, 129.2, 120.3, 116.5, 56.4, 49.1, 47.8, 47.4, 46.6, 43.8, 26.1, 25.7, 20.1 ppm. Purity: >98% (214 & 254 nm) LCMS; retention time: 1.04 min; (M+H⁺) 315.1.

Example 8

N-(1-Azabicyclo[3.2.2]nonan-4-yl)-4-phenylpiperazine-1-carboxamide

Using General Procedure A and the reaction inputs 1-phenylpiperazine and Intermediate 4, the title compound was prepared. ¹H NMR (500 MHz, CDCl₃) δ 7.31-7.28 (m, 2H), 6.95-6.90 (m, 3H), 4.58 (d, J=7.0 Hz, 1H), 4.04-3.99 (m, 1H), 3.55-3.53 (m, 4H), 3.28-3.19 (m, 5H), 3.11-3.05 (m, 1H), 2.99-2.96 (m, 3H), 2.87-2.81 (m, 1H), 2.09-1.59 (m, 7H) ppm. ¹³C NMR (125 MHz, CDCl₃) δ 156.8, 151.0, 129, 120.3, 116.4, 56.0, 53.0, 49.1, 49.0, 44.4, 43.7, 34.8, 31.9, 26.5, 22.2 ppm. Purity: >96% (214 & 254 nm) LCMS; retention time: 1.60 min; (M+H⁺) 329.3.

Example 9

N-(3-Methylquinuclidin-3-yl)-4-phenylpiperazine-1-carboxamide

Using General Procedure A and the reaction inputs 1-phenylpiperazine and Intermediate 1, the title compound was prepared. ¹H NMR (500 MHz, CDCl₃) δ 7.30-7.27 (m, 2H), 6.94-6.88 (m, 3H), 4.41 (s, 1H), 3.51 (t, J=5.0 Hz, 4H), 3.19 (t, J=5.0 Hz, 4H), 3.01-2.92 (m, 2H), 2.84-2.79 (m, 4H), 2.07-2.06 (m, 1H), 1.86-1.78 (m, 2H), 1.56-1.44 (m, 5H) ppm. ¹³C NMR (100 MHz, CDCl₃) δ 157.1, 151.0, 129.2, 120.3, 116.4, 63.5, 52.6, 49.1, 46.5, 46.4, 43.9, 31.3, 25.3, 23.3, 22.6 ppm. Purity: >98% (214 & 254 nm) LCMS; retention time 1.63 min; (M+H$^+$) 329.3.

Example 10

N-(4-Methyl-1-azabicyclo[3.2.2]nonan-4-yl)-4-phenylpiperazine-1-carboxamide Using General Procedure A and the reaction inputs 1-phenylpiperazine and Intermediate 5, the title compound was prepared. $^1$H NMR (500 MHz, CDCl$_3$) δ 7.31-7.26 (m, 2H), 6.95-6.89 (m, 3H), 4.42 (s, 1H), 3.54-3.51 (m, 4H), 3.22-3.20 (m, 4H), 3.07-2.96 (m, 4H), 2.90-2.84 (m, 2H), 2.42-2.40 (m, 1H), 1.97-1.92 (m, 1H), 1.88-1.82 (m, 2H), 1.73-1.50 (m, 6H) ppm. $^{13}$C NMR (125 MHz, CDCl$_3$) δ 157.0, 151.0, 129.2, 120.3, 116.4, 59.0, 53.1, 49.1, 47.6, 46.3, 44.0, 39.5, 36.5, 25.7, 24.2, 24.0 ppm. Purity: >99% (214 & 254 nm) LCMS; retention time: 1.63 min; (M+H$^+$) 343.3.

Example 11

1,4-Diazabicyclo[3.2.2]nonan-4-yl(4-phenylpiperazin-1-yl)methanone

Using General Procedure B and the reaction inputs 1-phenylpiperazine and Intermediate 6, the title compound was prepared. $^1$H NMR (500 MHz, CDCl$_3$) δ 7.25 (t, J=8.0 Hz, 2H), 6.92 (d, J=8.0 Hz, 2H), 6.86 (t, J=7.5 Hz, 1H), 4.09 (m, 1H), 3.48 (t, J=5.5 Hz, 2H), 3.30-3.32 (m, 4H), 3.18-3.17 (m, 4H), 3.03-2.96 (m, 6H), 2.01 (m, 2H), 1.75-1.71 (m, 2H) ppm. $^{13}$C NMR (100 MHz, CDCl$_3$) δ 163.7, 151.2, 129.1, 120.1, 116.3, 56.4, 49.1, 47.2, 46.3, 45.6, 27.2 ppm. Purity: >99% (214 & 254 nm) LCMS; retention time: 1.70 min; (M+H$^+$) 315.3.

Example 12

Quinuclidin-3-yl 4-phenylpiperazine-1-carboxylate

Using General Procedure C and the reaction inputs 1-phenylpiperazine and quinuclidin-3-ol, the title compound was prepared. $^1$H NMR (500 MHz, CDCl$_3$) δ 7.31-7.28 (m, 2H), 6.96-6.90 (m, 3H), 4.79-4.78 (m, 1H), 3.66 (t, J=5.0 Hz, 4H), 3.28-3.25 (m, 1H), 3.17 (m, 4H), 2.93-2.74 (m, 5H), 2.08-2.07 (m, 1H), 1.85-1.44 (m, 4H) ppm. $^{13}$C NMR (125 MHz, CDCl$_3$) δ 155.0, 151.2, 129.2, 120.5, 116.7, 72.1, 55.8, 49.4, 47.4, 46.5, 43.7, 25.5, 24.5, 19.7 ppm. Purity: >99% (214 & 254 nm) LCMS; retention time: 1.11 min; (M+H$^+$) 316.1.

Example 13

4-([1,1'-Biphenyl]-3-yl)-N-(quinuclidin-3-yl)piperazine-1-carboxamide

Using General Procedure A and the reaction inputs 1-([1,1'-biphenyl]-3-yl)piperazine and quinuclidin-3-amine, the title compound was prepared. $^1$H NMR (500 MHz, CDCl$_3$) δ 7.59 (d, J=7.5 Hz, 2H), 7.45 (t, J=7.5 Hz, 2H), 7.37 (dd, J=8.5, 1.0 Hz, 2H), 7.14-7.13 (m, 2H), 6.95-6.93 (m, 1H), 4.62 (d, J=6.0 Hz, 1H), 3.89-3.88 (m, 1H), 3.58 (m, J=5.5 Hz, 4H), 3.42-3.38 (m, 1H), 3.28 (t, J=5.5 Hz, 4H), 2.89-2.81 (m, 4H), 2.53-2.50 (m, 1H), 1.96-1.94 (m, 1H), 1.70-1.48 (m, 4H) ppm. $^{13}$C NMR (125 MHz, CDCl$_3$) δ 157.4, 151.4, 142.5, 141.6, 129.6, 128.7, 127.3, 127.2, 119.4, 115.5, 115.4, 56.8, 49.2, 47.9, 47.5, 46.7, 43.8, 26.1, 26.0, 20.3 ppm. Purity: >99% (214 & 254 nm) LCMS; retention time: 1.27 min; (M+H$^+$) 391.3.

Example 14

4-([1,1'-Biphenyl]-3-yl)-N-(1-azabicyclo[3.2.2]nonan-4-yl)piperazine-1-carboxamide Using General Procedure A and the reaction inputs 1-([1,1'-biphenyl]-3-yl)piperazine and Intermediate 4, the title compound was prepared. $^1$H NMR (500 MHz, CDCl$_3$) δ 7.59-7.57 (d, J=8.5 Hz, 2H), 7.45 (t, J=7.5 Hz, 2H), 7.36 (t, J=8.0 Hz, 2H), 7.14-7.13 (m, 2H), 6.94-6.92 (m, 1H), 4.57-4.55 (d, J=7.0 Hz, 1H), 4.01-3.98 (m, 1H), 3.56 (t, J=5.0 Hz, 4H), 3.27 (t, J=5.0 Hz, 4H), 3.20-3.17 (m, 1H), 3.07-3.04 (m, 1H), 2.97-2.78 (m, 4H), 2.11-1.58 (m, 7H) ppm. $^{13}$C NMR (125 MHz, CDCl$_3$) δ 156.8, 151.4, 142.5, 141.6, 129.6, 128.7, 127.3, 127.2, 119.4, 115.5, 115.4, 56, 53.0, 49.2, 49.0, 44.4, 43.7, 34.7, 31.9, 26.4, 22.2 ppm. Purity: >98% (214 & 254 nm) LCMS; retention time 1.27 min; (M+H$^+$) 405.2.

Example 15

4-([1,1'-Biphenyl]-3-yl)-N-(3-methylquinuclidin-3-yl)piperazine-1-carboxamide Using General Procedure A and the reaction inputs 1-([1,1'-biphenyl]-3-yl)piperazine and Intermediate 1, the title compound was prepared. $^1$H NMR (500 MHz, CDCl$_3$) δ 7.59-7.58 (dd, J=7.5, 1.5 Hz, 2H), 7.44 (t, J=7.5 Hz, 2H), 7.36 (t, J=7.5 Hz, 2H), 7.14-7.12 (m, 2H), 6.94 (m, 1H), 4.44 (s, 1H), 3.55 (t, J=5.0 Hz, 4H), 3.27 (t, J=5.0 Hz, 4H), 3.00-2.83 (m, 6H), 2.08 (m, 1H), 1.85-1.83 (m, 2H), 1.57-1.45 (m, 5H) ppm. $^{13}$C NMR (125 MHz, CDCl$_3$) δ 157.0, 151.4, 142.5, 141.6, 129.6, 128.7, 127.3, 127.3, 119.4, 115.4, 115.3, 63.5, 52.6, 49.2, 46.5, 46.5, 43.9, 31.3, 25.3, 23.3, 22.6 ppm. Purity: >96% (214 & 254 nm) LCMS; retention time: 1.97 min; (M+H$^+$) 405.3.

Example 16

4-([1,1'-Biphenyl]-3-yl)-N-(4-methyl-1-azabicyclo[3.2.2]nonan-4-yl)piperazine-1-carboxamide Using General Procedure A and the reaction inputs 1-([1,1'-biphenyl]-3-yl)piperazine and Intermediate 5, the title compound was prepared. $^1$H NMR (500 MHz, CDCl$_3$) δ 7.60-7.35 (m, 6H), 7.14-7.13 (m, 2H), 6.94-6.93 (m, 1H), 4.41 (s, 1H), 3.56-3.54 (m, 4H), 3.29-3.27 (m, 4H), 3.02-2.85 (m, 6H), 2.42-2.40 (m, 1H), 1.98-1.53 (m, 9H) ppm. $^{13}$C NMR (125 MHz, CDCl$_3$) δ 157.0, 151.4, 142.4, 141.6, 129.6, 128.7, 127.3, 127.2, 119.3, 115.4, 115.3, 55.0, 53.2, 49.2, 47.5, 46.3, 44.0, 39.7, 36.5, 25.7, 24.4, 24.2 ppm. Purity: >99% (214 & 254 nm) LCMS; retention time 1.29 min; (M+H$^+$) 419.2.

Example 17

(4-([1,1'-Biphenyl]-3-yl)piperazin-1-yl)(1,4-diazabicyclo[3.2.2]nonan-4-yl)methanone Using General Procedure B and the reaction inputs 1-([1,1'-biphenyl]-3-yl)piperazine and Intermediate 6, the title compound was prepared. $^1$H NMR (500 MHz, CDCl$_3$) δ 7.60-7.58 (m, 2H), 7.46-7.43 (m, 2H), 7.36 (t, J=8.0 Hz, 2H), 7.15-7.12 (m, 2H), 6.95-6.93 (m, 1H), 4.14-4.13 (m, 1H), 3.54-3.52 (m, 2H), 3.53 (t, J=5.0 Hz, 4H), 3.27 (t, J=5.0 Hz, 4H), 3.09-3.01 (m, 6H), 2.06-2.04 (m, 2H), 1.80-1.76 (m, 2H) ppm. $^{13}$C NMR (125 MHz, CDCl$_3$) δ 163.7, 155.5, 151.6, 142.4, 141.6, 129.5, 128.7, 128.5, 127.3, 119.3, 115.4, 56.4, 50.8, 49.3, 49.1, 47.3, 46.4, 45.6, 27.1 ppm. Purity: >99% (214 & 254 nm) LCMS; retention time: 2.01 min; (M+H$^+$) 391.3.

Example 18

Quinuclidin-3-yl 4-([1,1'-biphenyl]-3-yl)piperazine-1-carboxylate

Using General Procedure C and the reaction inputs 1-([1,1'-biphenyl]-3-yl)piperazine and quinuclidin-3-ol, the title compound was prepared. $^1$H NMR (500 MHz, CDCl$_3$) δ 7.59 (d, J=7.0 Hz, 2H), 7.45 (t, J=7.5 Hz, 2H), 7.38-7.35 (m, 2H), 7.15-7.14 (m, 2H), 6.95-6.93 (m, 1H), 4.80-4.78 (m, 1H), 3.68 (t, J=5.5 Hz, 4H), 3.28-3.24 (m, 5H), 2.92-2.75 (m, 5H), 2.08-2.08 (m, 1H), 1.85-1.44 (m, 4H) ppm. $^{13}$C NMR (125 MHz, CDCl$_3$) δ 155.0, 151.6, 142.4, 141.5, 129.6, 128.7, 127.3, 127.2, 119.6, 115.8, 115.7, 72.1, 55.8, 49.5, 47.4, 46.4, 43.8, 43.6, 25.5, 24.5, 19.7 ppm. Purity: >99% (214 & 254 nm) LCMS; retention time: 1.33 min; (M+H$^+$) 392.2.

Example 19

1-Azabicyclo[3.2.2]nonan-4-yl 4-([1,1'-biphenyl]-3-yl)piperazine-1-carboxylate

Using General Procedure C and the reaction inputs 1-([1,1'-biphenyl]-3-yl)piperazine and Intermediate 3, the title compound was prepared. $^1$H NMR (500 MHz, CDCl$_3$) δ 7.59-7.58 (d, J=7.5 Hz, 2H), 7.45 (t, J=7.5 Hz, 2H), 7.36 (t, J=7.5 Hz, 2H), 7.15-7.13 (m, 2H), 6.95-6.93 (m, 1H), 4.96 (m, 1H), 3.68-3.66 (m, 4H), 3.23-2.86 (m, 10H), 2.17-1.55 (m, 7H) ppm. $^{13}$C NMR (100 MHz, CDCl$_3$) δ 154.8, 151.6, 142.4, 141.5, 129.6, 128.7, 127.3, 127.2, 119.5, 115.7, 115.6, 79.0, 51.6, 49.5, 47.8, 45.2, 43.7, 33.4, 30.4, 24.5, 22.0 ppm. Purity: >99% (214 & 254 nm) LCMS; retention time 1.16 min; (M+H$^+$) 406.2.

Example 20

1-Azabicyclo[3.2.2]nonan-3-yl 4-([1,1'-biphenyl]-3-yl)piperazine-1-carboxylate

Using General Procedure C and the reaction inputs 1-([1,1'-biphenyl]-3-yl)piperazine and Intermediate 7, the title compound was prepared. $^1$H NMR (500 MHz, CDCl$_3$) δ 7.60 (d, J=8.0 Hz, 2H), 7.46 (t, J=7.5 Hz, 2H), 7.37 (t, J=8.0 Hz, 2H), 7.15 (m, 2H), 6.95 (dd, J=9.0 Hz, 1.5 Hz, 1H), 5.15 (m, 1H), 3.67 (m, 4H), 3.50 (m, 1H), 3.24-2.83 (m, 9H), 2.35 (m, 1H), 2.13 (m, 1H), 1.80-1.72 (m, 5H) ppm. $^{13}$C NMR (125 MHz, CDCl$_3$) δ 154.9, 151.6, 142.4, 141.6, 129.6, 128.7, 127.3, 127.2, 119.5, 115.8, 115.6, 72.1, 61.2, 49.5, 48.5, 45.4, 43.7, 39.1, 28.9, 26.9, 24.2 ppm. Purity: >99% (214 & 254 nm) LCMS; retention time 1.40 min; (M+H$^+$) 406.2.

Example 21

4-([1,1'-Biphenyl]-3-yl)-N-(3-ethylquinuclidin-3-yl)piperazine-1-carboxamide

Using General Procedure A and the reaction inputs 1-([1,1'-biphenyl]-3-yl)piperazine and Intermediate 2, the title compound was prepared. $^1$H NMR (500 MHz, CDCl$_3$) δ 7.59-7.58 (d, J=7.5 Hz, 2H), 7.45 (d, J=7.5 Hz, 2H), 7.37-7.35 (m, 2H), 7.14-7.12 (m, 2H), 6.94-6.92 (m, 1H), 4.43 (s, 1H), 3.56-3.56 (m, 4H), 3.29-3.27 (m, 4H), 3.06-2.79 (m, 6H), 2.19-2.10 (m, 2H), 1.92-1.74 (m, 3H), 1.55-1.46 (m, 2H), 0.82 (t, J=7.5 Hz, 3H) ppm. $^{13}$C NMR (125 MHz, CDCl$_3$) δ 156.8, 151.4, 142.4, 141.6, 129.6, 128.7, 127.3, 127.2, 119.4, 115.4, 115.3, 63.2, 55.1, 50.5, 49.3, 46.9, 46.7, 44.0, 28.4, 28.1, 22.9, 22.5, 8.2 ppm. Purity: >99% (214 & 254 nm) LCMS; retention time 1.51 min; (M+H$^+$) 419.3.

Example 22

4-(4'-Fluoro-[1,1'-biphenyl]-3-yl)-N-(4-methyl-1-azabicyclo[3.2.2]nonan-4-yl)piperazine-1-carboxamide Using General Procedure F and the reaction inputs 1-(3-bromophenyl)piperazine and 4-fluorophenylboronic acid, 1-(4'-fluoro-[1,1'-biphenyl]-3-yl)piperazine was prepared. This compound was reacted with Intermediate 5 using General Procedure A to generate the title compound. $^1$H NMR (500 MHz, CDCl$_3$) δ 9.22 (s, 1H), 8.94 (s, 2H), 7.44 (t, J=7.5 Hz, 1H), 7.10-7.02 (m, 3H), 4.43 (s, 1H), 3.58-3.56 (m, 4H), 3.31-3.29 (m, 4H), 3.06-2.85 (m, 6H), 2.42 (m, 1H), 1.95-1.57 (m, 9H) ppm. $^{13}$C NMR (100 MHz, CDCl$_3$) δ 157.5, 156.9, 154.9, 151.7, 135.4, 134.7, 130.3, 118.7, 116.6, 114.6, 59.1, 53.2, 48.8, 47.5, 46.3, 43.9, 39.7, 36.5, 25.7, 24.4, 24.2 ppm. Purity: >99% (214 & 254 nm) LCMS; retention time: 1.01 min; (M+H$^+$) 421.3.

Example 23

N-(3-Ethylquinuclidin-3-yl)-4-(4'-fluoro-[1,1'-biphenyl]-3-yl)piperazine-1-carboxamide Using General Procedure A and the reaction inputs 1-(4'-fluoro-[1,1'-biphenyl]-3-yl)piperazine (prepared as described in Example 22) and Intermediate 2, the title compound was prepared. $^1$H NMR (500 MHz, CDCl$_3$) δ 7.54-7.52 (m, 2H), 7.35-7.33 (m, 1H), 7.14-7.06 (m, 4H), 6.93-6.91 (d, J=8.0 Hz, 1H), 4.39 (s, 1H), 3.55 (m, 4H), 3.28-3.26 (m, 4H), 2.99-2.83 (m, 6H), 2.18-2.08 (m, 2H), 1.89-1.73 (m, 3H), 1.52-1.46 (m, 2H), 0.81 (t, J=7.5 Hz, 3H) ppm. $^{13}$C NMR (125 MHz, CDCl$_3$) δ 163.5, 161.4, 156.9, 151.4, 141.4, 137.1, 129.6, 128.8, 128.7, 119.1, 115.7, 115.6, 115.4, 115.4, 63.2, 55.2, 49.2, 46.9, 46.7, 44.0, 28.4, 23.1, 23.0, 22.6, 8.2 ppm. Purity: >99% (214 & 254 nm) LCMS; retention time: 1.54 min; (M+H$^+$) 437.3.

Example 24

1-Azabicyclo[3.2.2]nonan-4-yl 4-(4'-fluoro-[1,1'-biphenyl]-3-yl)piperazine-1-carboxylate Using General Procedure C and the reaction inputs 1-(4'-fluoro-[1,1'-biphenyl]-3-yl)piperazine (prepared as described in Example 22) and Intermediate 3, the title compound was prepared. $^1$H NMR (500 MHz, CDCl$_3$) δ 7.55-7.52 (m, 2H), 7.35 (t, J=8.5 Hz, 1H), 7.14-7.07 (m, 4H), 6.94-6.92 (m, 1H), 4.96 (m, 1H), 3.67 (t, J=5.0 Hz, 4H), 3.23-2.80 (m, 10H), 2.16-1.53 (m, 7H) ppm. $^{13}$C NMR (125 MHz, CDCl$_3$) δ 162.5 (d, J=245.0 Hz), 154.8, 151.6, 141.4, 137.6 (d, J=2.5 Hz), 129.6, 128.7 (d, J=8.4 Hz), 119.3, 115.5 (d, J=21.9 Hz), 79.1, 51.8, 49.5, 47.9, 45.3, 43.7, 33.5, 30.6, 24.7, 22.2 ppm. Purity: >95% (214 & 254 nm) LCMS; retention time: 1.27 min; (M+H$^+$) 424.2.

Example 25

1-Azabicyclo[3.2.2]nonan-3-yl 4-(4'-fluoro-[1,1'-biphenyl]-3-yl)piperazine-1-carboxylate Using General Procedure C and the reaction inputs 1-(4'-fluoro-[1,1'-biphenyl]-3-yl)piperazine (prepared as described in Example 22) and Intermediate 7, the title compound was prepared. $^1$H NMR (500 MHz, CDCl$_3$) δ 7.57-7.47 (m, 6H), 7.13 (t, J=8.5 Hz, 2H), 5.11 (br s, 1H), 5.00 (m, 1H), 3.43-2.75 (m, 6H), 2.35-2.05 (m, 2H), 1.71-1.56 (m, 11H) ppm. $^{13}$C NMR (100 MHz, CDCl$_3$) δ 163.4, 161.4, 138.5, 136.9, 128.6, 128.5, 127.0, 125.3, 115.6, 115.5, 70.5, 61.0, 55.0, 48.9, 44.9, 38.9, 29.5, 29.2, 26.4, 23.9 ppm. Purity: >93% (214 & 254 nm) LCMS; retention time: 1.42 min; (M+H$^+$) 397.2.

Example 26

N-(4-Methyl-1-azabicyclo[3.2.2]nonan-4-yl)-4-(3-(pyrimidin-2-yl)phenyl)piperazine-1-carboxamide Using General Procedure F and the reaction inputs 2-chloropyrimidine and t-butyl 4-(3-(4,4,5,5-tetramethyl-1,3,2-dioxaborolan-2-yl)phenyl)piperazine-1-carboxylate, t-butyl 4-(3-(pyrimidin-2-yl)phenyl)piperazine-1-carboxylate was prepared. The N-t-butoxycarbonyl protecting group was removed from this compound using General Procedure G to afford 2-(3-(piperazin-1-yl)phenyl)pyrimidine. This product was, in turn, was reacted with Intermediate 5 using General Procedure A to generate the title compound. $^1$H NMR (500 MHz, CDCl$_3$) δ 8.82-8.81 (d, J=4.5 Hz, 2H), 8.07-8.06 (d, J=2.0 Hz, 1H), 8.00-7.98 (d, J=7.5 Hz, 1H), 7.42 (t, J=7.5 Hz, 1H), 7.20 (t, J=4.5 Hz, 1H), 7.08-7.06 (m, 1H), 4.40 (s, 1H), 3.56-3.54 (m, 4H), 3.33-3.31 (m, 4H), 3.00-2.86 (m, 6H), 2.39 (m, 1H), 1.97-1.54 (m, 9H) ppm. $^{13}$C NMR (125 MHz, CDCl$_3$) δ 164.8, 157.2, 156.9, 151.3, 138.5, 129.5, 120.1, 119.1, 118.8, 115.8, 59.0, 53.3, 49.1, 47.6, 46.4, 44.0, 39.8, 36.5, 25.7, 24.5, 24.3 ppm. Purity: >99% (214 & 254 nm) LCMS; retention time: 1.30 min; (M+H$^+$) 421.3.

Example 27

N-(4-Methyl-1-azabicyclo[3.2.2]nonan-4-yl)-4-(3-(pyrimidin-5-yl)phenyl)piperazine-1-carboxamide Using General Procedure F and the reaction inputs 5-bromopyrimidine and t-butyl 4-(3-(4,4,5,5-tetramethyl-1,3,2-dioxaborolan-2-yl)phenyl)piperazine-1-carboxylate, t-butyl 4-(3-(pyrimidin-5-yl)phenyl)piperazine-1-carboxylate was prepared. The t-butoxycarbonyl protecting group was removed from this compound using General Procedure G to afford 5-(3-(piperazin-1-yl)phenyl)pyrimidine. This product was, in turn, was reacted with Intermediate 5 using General Procedure A to generate the title compound. $^1$H NMR (500 MHz, CDCl$_3$) δ 9.20 (s, 1H), 8.93 (s, 2H), 7.39 (t, J=8.0 Hz, 1H), 7.07-7.02 (m, 3H), 5.41 (s, 1H), 3.83-3.81 (m, 2H), 3.01-2.81 (m, 8H), 2.39-2.24 (m, 2H), 1.96-1.51 (m, 13H) ppm. $^{13}$C NMR (125 MHz, CDCl$_3$) δ 174.0, 157.4, 154.9, 152.1, 135.2, 134.9, 130.2, 118.0, 116.9, 114.8, 59.5, 53.1, 49.1, 49.1, 47.6, 46.1, 43.8, 39.2, 36.1, 28.9, 28.6, 25.1, 24.2, 24.1 ppm. Purity: >99% (214 & 254 nm) LCMS; retention time: 0.90 min; (M+H$^+$) 420.2.

Example 28

4-(3-Isopropylphenyl)-N-(4-methyl-1-azabicyclo[3.2.2]nonan-4-yl)piperazine-1-carboxamide Using General Procedure F and the reaction inputs 1-(3-bromophenyl)piperazine and 4,4,5,5-tetramethyl-2-(prop-1-en-2-yl)-1,3,2-dioxaborolane, 1-(3-(prop-1-en-2-yl)phenyl)piperazine was prepared. A stirred suspension of this compound (0.500 g, 2.50 mmol) and 10% palladium on carbon (0.100 g) in ethylacetate (50 mL) was cycled between vacuum and a nitrogen purge several times. After the last evacuation, the reaction was refilled with hydrogen gas. The mixture was stirred overnight and then filtered through Celite. The filtrate was combined with ethyl acetate rinsings of the Celite and concentrated to afford 1-(3-isopropylphenyl)piperazine as a yellow oil (0.360 g, 72%). This compound was reacted with Intermediate 5 using General Procedure A to generate the title compound. $^1$H NMR (500 MHz, CDCl$_3$) δ 7.13 (t, J=8.0 Hz, 1H), 6.73-6.66 (m, 3H), 4.36 (s, 1H), 3.46-3.42 (m, 4H), 3.41-3.10 (m, 4H), 2.97-2.75 (m, 7H), 2.31-2.30 (m, 1H), 1.87-1.72 (m, 3H), 1.63-1.42 (m, 6H), 1.18-1.16 (d, J=7.0 Hz, 6H) ppm. $^{13}$C NMR (125 MHz, CDCl$_3$) δ 157.0, 151.1, 150.1, 129.1, 118.6, 115.0, 113.8, 59.0, 53.3, 49.4, 47.6, 46.3, 44.1, 39.8, 36.5, 34.5, 25.8, 24.5, 24.2, 24.1 ppm. Purity: 100% (214 & 254 nm) LCMS; retention time: 1.88 min; (M+H$^+$) 385.4.

Example 29

4-(3-Cyclohexylphenyl)-N-(4-methyl-1-azabicyclo[3.2.2]nonan-4-yl)piperazine-1-carboxamide Exchanging 4,4,5,5-tetramethyl-2-(prop-1-en-2-yl)-1,3,2-dioxaborolane for 2-(cyclohex-1-en-1-yl)-4,4,5,5-tetramethyl-1,3,2-dioxaborolane, the same reaction sequence outlined in Example 28 was used to generate the title compound. $^1$H NMR (500 MHz, CDCl$_3$) δ 7.20 (t, J=8.0 Hz, 1H), 6.79-6.73 (m, 3H), 4.40 (s, 1H), 3.53-3.47 (m, 4H), 3.19-3.18 (m, 4H), 3.06-2.83 (m, 6H), 2.48-2.39 (m, 2H), 1.95-1.23 (m, 19H) ppm. $^{13}$C NMR (125 MHz, CDCl$_3$) δ 157.0, 151.0, 149.3, 129.1, 119.0, 115.4, 113.9, 59.0, 53.3, 49.4, 47.6, 46.3, 45.0, 44.1, 39.7, 36.5, 34.5, 26.9, 26.2, 25.8, 24.4, 24.2 ppm. Purity: >99% (214 & 254 nm) LCMS; retention time: 1.57 min; (M+H$^+$) 425.4.

Example 30

4-([1,1'-Biphenyl]-3-yl)-2-methyl-N-(4-methyl-1-azabicyclo[3.2.2]nonan-4-yl)piperazine-1-carboxamide To a stirred solution of 3-bromobiphenyl (0.70 g, 3.00 mmol) in toluene (10 mL) was added t-butyl 2-methylpiperazine-1-carboxylate (0.720 g, 3.60 mmol), potassium t-butoxide (0.504 g, 4.50 mmol), tris(dibenzylideneacetone)dipalladium(0) (0.090 g, 98.3 mmol) and tri-t-butylphosphine (0.018 g, 89.0 mmol). The mixture was heated at 90° C. for 5 hours. At this time the reaction was cooled, diluted with water and extracted with ethyl acetate. The combined extracts were washed with brine, dried (Na$_2$SO$_4$) and concentrated. The residue was purified by flash chromatography over silica using a hexane/ethyl acetate eluant to afford t-butyl 4-([1,1'-biphenyl]-3-yl)-2-methylpiperazine-1-carboxylate (0.750 g, 71%) as a brown oil. The t-butoxycarbonyl protecting group was removed from this compound using General Procedure G to afford 1-([1,1'-biphenyl]-3-yl)-3-methylpiperazine. This intermediate was, in turn, was reacted with Intermediate 5 using General Procedure A to generate the title compound. $^1$H NMR (500 MHz, CDCl$_3$) δ 7.60-7.34 (m, 6H), 7.12-7.11 (m, 2H), 6.92-6.90 (m, 1H), 4.40-4.39 (d, J=6.5 Hz, 1H), 4.19-4.14 (m, 1H), 3.87-3.33 (m, 4H), 3.09-2.88 (m, 8H), 2.46-2.43 (m, 1H), 1.99-1.55 (m, 9H), 1.38 (t, J=7.0 Hz, 3H) ppm. $^{13}$C NMR (125 MHz, CDCl$_3$) δ 156.7, 156.7, 151.9, 142.5, 141.6, 129.5, 128.7, 127.3, 127.2, 119.1, 115.4, 115.4, 115.3, 115.3, 59.0, 54.3, 54.3, 53.2, 53.3, 49.1, 49.1, 47.9, 47.8, 47.7, 47.7, 46.1, 46.0, 39.8, 39.5, 39.1, 39.0, 36.7, 36.4, 25.9, 25.8, 25.4, 24.3, 24.3, 24.1, 24.0, 15.8, 15.7 ppm. Purity: >99% (214 & 254 nm) LCMS; retention time: 1.29 min; (M+H$^+$) 433.3.

Example 31

4-([1,1'-Biphenyl]-3-yl)-3-methyl-N-(4-methyl-1-azabicyclo[3.2.2]nonan-4-yl)piperazine-1-carboxamide Exchanging t-butyl 2-methylpiperazine-1-carboxylate for t-butyl 3-methylpiperazine-1-carboxylate, the same reaction sequence outlined in Example 30 was used to generate the title compound. $^1$H NMR (500 MHz, CDCl$_3$) δ 7.60-7.58 (d, J=7.5 Hz, 2H), 7.45 (t, J=7.5 Hz, 2H), 7.37-7.34 (m, 2H), 7.12-7.11 (m, 2H), 6.91-6.90 (m, 1H), 4.39-4.37 (d, J=9.0 Hz, 1H), 3.93-2.85 (m, 13H), 2.41 (m, 1H), 1.98-1.55 (m, 9H), 1.12-1.11 (m, 3H) ppm. $^{13}$C NMR (100 MHz, CDCl$_3$) δ 156.8, 150.2, 142.4, 141.6, 129.6, 128.7, 127.3, 127.3, 119.0, 119.0, 116.0, 116.0, 115.9, 115.8, 59.0, 59.0, 53.3, 53.2, 51.9, 51.8, 49.1, 49.0, 47.7, 47.7, 46.2, 44.1, 44.1, 44.0, 43.8, 39.8, 39.6, 36.6, 36.5, 25.9, 25.8, 24.4, 24.3, 24.1, 24.1, 13.7, 13.6 ppm. Purity: >98% (214 & 254 nm) LCMS; retention time: 1.47 min; (M+H$^+$) 433.4.

Example 32

4-([1,1'-Biphenyl]-3-yl)-3-methyl-N-(4-methyl-1-azabicyclo[3.2.2]nonan-4-yl)piperazine-1-carboxamide Exchanging t-butyl 2-methylpiperazine-1-carboxylate for t-butyl 3,3-dimethylpiperazine-1-carboxylate, the same reaction sequence outlined in Example 30 was used to generate the title compound. $^1$H NMR (500 MHz, CDCl$_3$) δ 7.59-7.57 (d, J=7.5 Hz, 2H), 7.45 (t, J=7.5 Hz, 2H), 7.37-7.33 (m, 4H), 7.11-7.09 (m, 1H), 4.54 (s, 1H), 3.59-2.97 (m, 12H), 2.58 (m, 1H), 2.01-1.55 (m, 9H), 1.12 (s, 6H) ppm. $^{13}$C NMR (125 MHz, CDCl$_3$) δ 156.8, 149.1, 141.3, 141.1, 128.7, 128.5, 127.3, 127.1, 126.3, 126.1, 123.5, 58.8, 56.5, 55.1, 53.0, 48.0, 46.9, 45.7, 44.9, 38.2, 36.1, 26.0, 23.2, 22.8, 22.1, 22.0 ppm. Purity: >99% (214 & 254 nm) LCMS; retention time: 1.00 min; (M+H$^+$) 447.3.

Example 33

1-(4'-Fluoro-[1,1'-biphenyl]-3-yl)-N-(3-methylquinuclidin-3-yl)piperidine-4-carboxamide To a stirred solution of ethyl piperidine-4-carboxylate (1.60 g, 10.0 mmol) in methylene chloride (50 mL) was added 3-bromophenylboronic acid (4.10 g, 20.4 mmol), triethylamine (5.00 g, 49.4 mmol), copper(II) acetate (2.70 g, 1.49 mmol) and 4 Å molecular sieves (2.00 g). The mixture, which was left open to the air, was stirred at room temperature for 24 hours. The reaction was then diluted with methylene chloride and filtered through a plug of Celite. The filtrate was concentrated and the residue purified by flash chromatography over silica using a hexane/ethyl acetate eluant to afford ethyl 1-(3-bromophenyl)piperidine-4-carboxylate as a yellow oil (0.930 g, 30%). Using General Procedure F and the boronic acid component, 4-fluorophenylboronic acid (0.420 g, 3.00 mmol), this intermediate (0.642 g, 2.00 mmol) was subjected to Suzuki coupling to give ethyl 1-(4'-fluoro-[1,1'-biphenyl]-3-yl)piperidine-4-carboxylate as a black oil (0.589 g, 90%). A stirred solution of this compound (0.589 g, 1.80 mmol) in 1:1 (v/v) methanol/water was treated with solid sodium hydroxide (0.360 g, 9.00 mmol). After overnight stirring, the reaction was concentrated. The residue was dissolved in water, made acidic (pH~6) with the addition of 1N hydrochloric acid and extracted with ethyl acetate. The combined organic layers were washed with brine, dried (Na$_2$SO$_4$) and concentrated to afford 1-(4'-fluoro-[1,1'-biphenyl]-3-yl)piperidine-4-carboxylic acid as a white solid (0.520 g, 96%). Using General Procedure D and Intermediate 1, this carboxylic acid was subjected to amide coupling to generate the title compound as a white solid (0.033 g, 24%). $^1$H NMR (500 MHz, CDCl$_3$) δ 7.54-7.52 (m, 2H), 7.32 (t, J=8.0 Hz, 1H), 7.13-6.92 (m, 5H), 5.55 (s, 1H), 3.81-3.79 (m, 2H), 3.01-2.78 (m, 8H), 2.25-2.20 (m, 2H), 1.97-1.77 (m, 6H), 1.59-1.51 (m, 5H) ppm. $^{13}$C NMR (125 MHz, CDCl$_3$) δ 174.3, 163.4, 161.4, 151.9, 141.3, 137.9, 137.9, 129.5, 128.8, 128.7, 118.6, 115.5, 115.4, 115.4, 63.3, 52.9, 49.5, 46.6, 46.4, 43.7, 30.2, 29.0, 28.8, 24.4, 22.9, 22.4 ppm. Purity: >99% (214 & 254 nm) LCMS; retention time 1.10 min; (M+H$^+$) 422.2.

Example 34

1-(4'-Fluoro-[1,1'-biphenyl]-3-yl)-N-(4-methyl-1-azabicyclo[3.2.2]nonan-4-yl)piperidine-4-carboxamide Using General Procedure A and the reaction inputs, 1-(4'-fluoro-[1,1'-biphenyl]-3-yl)piperidine-4-carboxylic acid (prepared as described in Example 33) and Intermediate 5, the title compound was prepared. $^1$H NMR (500 MHz, CDCl$_3$) δ 7.53-7.51 (m, 2H), 7.31 (t, J=8.0 Hz, 1H), 7.12-7.02 (m, 3H), 7.02-7.00 (d, J=7.5 Hz, 1H), 6.93-6.91 (m, 1H), 5.48 (s, 1H), 3.80-3.78 (m, 2H), 3.05-2.76 (m, 8H), 2.40 (m, 1H), 2.24-2.20 (m, 1H), 1.95-1.50 (m, 13H) ppm. $^{13}$C NMR (125 MHz, CDCl$_3$) δ 174.2, 163.4, 161.4, 151.9, 141.3, 137.9, 137.9, 129.5, 128.8, 128.7, 118.6, 115.6, 115.5, 115.5, 115.4, 59.4, 531, 49.5, 49.5, 47.7, 46.0, 44.0, 39.0, 36.0, 29.1, 28.9, 25.2, 24.1, 24.0 ppm. Purity: >99% (214 & 254 nm) LCMS; retention time: 1.97 min; (M+H$^+$) 436.4.

Example 35

1-([1,1'-Biphenyl]-3-yl)-N-(3-methylquinuclidin-3-yl)piperidine-4-carboxamide

Exchanging 4-fluorophenylboronic acid for phenylboronic acid, the same reaction sequence outlined in Example 33 was used to generate the title compound. $^1$H NMR (500 MHz, CDCl$_3$) δ 7.59-7.58 (d, J=7.0 Hz, 2H), 7.44 (t, J=7.0 Hz, 2H), 7.36-7.31 (m, 2H), 7.14 (s, 1H), 7.09-7.07 (d, J=7.5 Hz, 1H), 6.95-6.93 (m, 1H), 5.85 (br s, 1H), 3.82-3.79 (m, 2H), 3.21-3.18 (m, 1H), 3.03-2.79 (m, 7H), 2.34-2.29 (m, 2H), 1.96-1.82 (m, 6H), 1.65-1.47 (m, 5H) ppm. $^{13}$C NMR (125 MHz, CDCl$_3$) δ 174.4, 151.9, 142.3, 141.8, 129.4, 128.6, 127.2, 127.2, 118.7, 115.6, 115.6, 63.2, 52.9, 49.5, 46.6, 46.5, 43.7, 30.2, 29.0, 24.4, 22.9, 22.4 ppm. Purity: >99% (214 & 254 nm) LCMS; retention time: 1.08 min; (M+H$^+$) 404.2.

Example 36

1-([1,1'-Biphenyl]-3-yl)-N-(4-methyl-1-azabicyclo[3.2.2]nonan-4-yl)piperidine-4-carboxamide Exchanging 4-fluorophenylboronic acid for phenylboronic acid and Intermediate 1 for Intermediate 5, the same reaction sequence outlined in Example 33 was used to generate the title compound. $^1$H NMR (400 MHz, CDCl$_3$) δ 7.60-7.58 (d, J=8.0 Hz, 2H), 7.44 (t, J=7.6 Hz, 2H), 7.37-7.32 (m, 2H), 7.15 (s, 1H), 7.10-7.08 (d, J=7.2 Hz, 1H), 6.96-6.94 (d, J=8.0 Hz, 1H), 5.46 (s, 1H), 3.83-3.80 (m, 2H), 3.08-2.78 (m, 8H), 2.41 (m, 1H), 2.24-2.21 (m, 1H), 2.01-1.52 (m, 13H) ppm. $^{13}$C NMR (100 MHz, CDCl$_3$) δ 174.2, 151.9, 142.3, 141.8, 129.4, 128.6, 127.2, 127.2, 118.8, 115.7, 115.6, 59.4, 53.1, 49.6, 49.5, 47.7, 46.1, 44.0, 39.1, 36.1, 29.1, 289, 25.1, 24.2, 24.1 ppm. Purity: >95% (214 & 254 nm) LCMS; retention time: 1.38 min; (M+H$^+$) 418.3.

Example 37

1-([1,1'-Biphenyl]-4-yl)-N-(3-methylquinuclidin-3-yl)piperidine-4-carboxamide

Exchanging 4-fluorophenylboronic acid for phenylboronic acid and 3-bromophenylboronic acid for 4-bromophenylboronic acid, the same reaction sequence outlined in Example 33 was used to generate the title compound. $^1$H NMR (500 MHz, CDCl$_3$) δ 7.57-7.51 (m, 4H), 7.41 (t, J=7.5 Hz, 2H), 7.29 (t, J=7.5 Hz, 1H), 7.02-7.00 (d, J=8.5 Hz, 2H), 5.75 (br s, 1H), 3.81-3.79 (m, 2H), 3.14-2.78 (m, 8H), 2.29-2.25 (m, 2H), 1.99-1.80 (m, 6H), 1.63-1.50 (m, 5H) ppm. $^{13}$C NMR (125 MHz, CDCl$_3$) δ 174.5, 150.7, 140.9, 132.1, 128.7, 127.7, 126.5, 126.4, 116.6, 62.7, 52.8, 49.2, 46.6, 46.3, 43.6, 29.9, 28.9, 28.8, 24.3, 22.6, 22.2 ppm. Purity: >98% (214 & 254 nm) LCMS; retention time 1.97 min; (M+H$^+$) 404.4.

Example 38

1-([1,1'-Biphenyl]-4-yl)-N-(4-methyl-1-azabicyclo[3.2.2]nonan-4-yl)piperidine-4-carboxamide Exchanging 4-fluorophenylboronic acid for phenylboronic acid, 3-bromophenylboronic acid for 4-bromophenylboronic acid and Intermediate 1 for Intermediate 5, the same reaction sequence outlined in Example 33 was used to generate the title compound. $^1$H NMR (500 MHz, CDCl$_3$) δ 7.60-7.56 (m, 4H), 7.45 (t, J=7.5 Hz, 2H), 7.35 (t, J=7.5 Hz, 1H), 7.30-7.29 (d, J=8.0 Hz, 2H), 4.43 (s, 1H), 4.10-4.05 (m, 2H), 3.08-2.85 (m, 8H), 2.76-2.71 (m, 1H), 2.44-2.42 (m, 1H), 1.97-1.53 (m, 13H) ppm. $^{13}$C NMR (125 MHz, CDCl$_3$) δ 157.0, 144.6, 140.9, 139.4, 128.7, 127.3, 127.1, 127.0, 58.9, 53.2, 47.7, 46.2, 45.0, 44.9, 42.3, 39.7, 36.5, 33.1, 33.1, 25.9, 24.4, 24.1 ppm. Purity: >99% (214 & 254 nm) LCMS; retention time: 1.99 min; (M+H$^+$) 418.4.

Example 39

N-(4-Methyl-1-azabicyclo[3.2.2]nonan-4-yl)-1-(3-(pyrimidin-2-yl)phenyl)piperidine-4-carboxamide To a stirred solution of ethyl 1-(3-bromophenyl)piperidine-4-carboxylate (prepared as described in Example 33; 0.800 g, 2.68 mmol) in dioxane (10 mL) was added bis(pinacolato)diboron (0.817 g, 3.22 mmol), potassium acetate (0.790 g, 8.04 mmol) and [1,1'-bis(diphenylphosphino)ferrocene]dichloropalladium(II) (0.060 g, 73.5 mmol). The mixture was heated at 90° C. overnight. After cooling, the reaction was filtered through Celite and concentrated. The residue was purified by flash chromatography over silica using a hexane/ethyl acetate eluant to afford ethyl 1-(3-(4,4,5,5-tetramethyl-1,3,2-dioxaborolan-2-yl)phenyl)piperidine-4-carboxylate as a yellow solid (0.84 g, 91%). Using General Procedure F and the aryl halide component, 2-chloropyrimidine (0.137 g, 1.20 mmol), this intermediate (0.430 g, 1.20 mmol) was subjected to Suzuki coupling to give ethyl 1-(3-(pyrimidin-2-yl)phenyl)piperidine-4-carboxylate as a colorless oil (0.200 g, 54%). To a stirred solution of this product (0.200 g, 0.642 mmol) in 1:1 methanol/water (4 mL) was added solid sodium hydroxide (0.128 g, 3.20 mmol). After overnight stirring, the reaction was concentrated. The residue was dissolved in water, made acidic (pH~6) with the addition of 1N hydrochloric acid and extracted with ethyl acetate. The combined organic layers were washed with brine, dried (Na$_2$SO$_4$) and concentrated to afford 1-(3-(pyrimidin-2-yl)phenyl)piperidine-4-carboxylic acid as a white solid (0.150 g, 82%). Using General Procedure D and Intermediate 5, this carboxylic acid was subjected to amide coupling to generate the title compound as a white solid (0.060 g, 27%). $^1$H NMR (500 MHz, CDCl$_3$) δ 8.80-8.79 (d, J=4.5 Hz, 2H), 8.06 (s, 1H), 7.94-7.92 (d, J=8.0 Hz, 1H), 7.38 (t, J=8.0 Hz, 1H), 7.18 (t, J=5.0 Hz, 1H), 7.09-7.07 (dd, J=8.0 Hz & 2.0 Hz, 1H), 5.49 (s, 1H), 3.87-3.85 (m, 2H), 3.05-2.79 (m, 8H), 2.41-2.23 (m, 2H), 1.98-1.51 (m, 13H) ppm. $^{13}$C NMR (125 MHz, CDCl$_3$) δ 174.3, 164.9, 157.1, 151.8, 138.3, 129.3, 119.6, 119.2, 119.0, 116.0, 59.3, 53.0, 49.5, 49.4, 47.6, 46.0, 44.0, 38.9, 36.0, 29.1, 28.9, 25.1, 24.9, 23.9 ppm. Purity: >96% (214 & 254 nm) LCMS; retention time: 1.23 min; (M+H$^+$) 420.3.

Example 40

N-(4-Methyl-1-azabicyclo[3.2.2]nonan-4-yl)-1-(3-(pyrimidin-5-yl)phenyl)piperidine-4-carboxamide Exchanging 2-chloropyrimidine for 5-bromopyrimidine, the same reaction sequence outlined in Example 39 was used to generate the title compound. $^1$H NMR (500 MHz, CDCl$_3$) δ 9.20 (s, 1H), 8.93 (s, 2H), 7.39 (t, J=8.0 Hz, 1H), 7.07-7.02 (m, 3H), 5.41 (s, 1H), 3.83-3.81 (m, 2H), 3.01-2.81 (m, 8H), 2.39-2.24 (m, 2H), 1.96-1.51 (m, 13H) ppm. $^{13}$C NMR (125 MHz, CDCl$_3$) δ 174.0, 157.4, 154.9, 152.1, 135.2, 134.9, 130.2, 118.0, 116.9, 114.8, 59.5, 53.1, 49.1, 49.1, 47.6, 46.1, 43.8, 39.2, 36.1, 28.9, 28.6, 25.1, 24.2, 24.1 ppm. Purity: >99% (214 & 254 nm) LCMS; retention time: 0.90 min; (M+H$^+$) 420.2.

Example 41

1-(4-(4-Fluorophenyl)pyrimidin-2-yl)-N-(4-methyl-1-azabicyclo[3.2.2]nonan-4-yl)piperidine-4-carboxamide To a stirred solution of 2,4-dichloropyrimidine (3.00 g, 20.1 mmol) in toluene (25 mL) was added 4-fluorophenylboronic acid (2.82 g, 20.1 mmol), potassium carbonate (8.32 g, 60.3 mmol), tetrakis(triphenylphosphine)palladium(0) (0.630 g, 0.545 mmol) and 1:1 (v/v) ethanol/water (36 mL). The mixture was heated at 55° C. for 12 hours and then concentrated. The residue was diluted with water and extracted with ethyl acetate. The combined extracts were washed with brine, dried ($Na_2SO_4$) and concentrated. The crude material was purified by flash chromatography over silica using a hexane/ethyl acetate eluant to afford 2-chloro-4-(4-fluorophenyl)pyrimidine as a yellow solid (2.50 g, 61%). To a stirred solution of this compound (1.27 g, 6.09 mmol) in N,N-dimethylformamide (8 mL) was added ethyl piperidine-4-carboxylate (0.959 g, 6.10 mmol) and cesium carbonate (2.10 g, 6.44 mmol). The mixture was heated at 100° C. for 12 hours and then concentrated. The residue was diluted with water and extracted with ethyl acetate. The combined extracts were washed with brine, dried ($Na_2SO_4$) and concentrated. The crude material was purified by flash chromatography over silica using a hexane/ethyl acetate eluant to afford ethyl 1-(4'-fluoro-[1,1'-biphenyl]-3-yl)piperidine-4-carboxylate as a yellow oil (1.60 g, 80%). To a stirred solution of this intermediate (1.60 g, 4.80 mmol) in 1:1 (v/v) methanol/water (20 mL) was added solid sodium hydroxide (0.968 g, 24.2 mmol). After 2 hours, the reaction was concentrated. The residue was dissolved in water, made acidic (pH~6) with the addition of 1N hydrochloric acid and extracted with ethyl acetate. The combined organic layers were washed with brine, dried ($Na_2SO_4$) and concentrated to afford 1-(4'-fluoro-[1,1'-biphenyl]-3-yl)piperidine-4-carboxylic acid as a white solid (1.40 g, 97%). Using General Procedure D and Intermediate 5, this carboxylic acid was subjected to amide coupling to generate the title compound as a white solid (0.118 g, 27%). $^1$H NMR (500 MHz, $CDCl_3$) δ 8.37 (d, J=5.0 Hz, 1H), 8.07-8.04 (m, 2H), 7.15 (t, J=9.0 Hz, 2H), 6.89 (d, J=10.0 Hz, 1H), 5.38 (s, 1H), 4.97-4.95 (m, 2H), 3.02-2.83 (m, 8H), 2.39-2.37 (m, 2H), 1.96-1.51 (m, 13H) ppm. $^{13}$C NMR (100 MHz, $CDCl_3$) δ 174.1, 165.3, 163.3, 163.2, 161.7, 158.4, 133.8, 129.0, 128.9, 115.7, 115.5, 105.2, 59.4, 53.1, 47.6, 46.1, 44.6, 43.5, 39.3, 36.1, 28.9, 28.7, 25.1, 24.3, 24.2 ppm. Purity: >96% (214 & 254 nm) LCMS; retention time: 1.44 min; (M+H$^+$) 438.3.

Example 42

1-(4-(4-Fluorophenyl)pyrimidin-2-yl)-N-(4-methyl-1-azabicyclo[3.2.2]nonan-4-yl)piperidine-4-carboxamide (Single Enantiomer A)

Using General Procedure D and the reaction inputs 1-(4'-fluoro-[1,1'-biphenyl]-3-yl)piperidine-4-carboxylic acid (prepared as described in Example 41) and Intermediate 9, the title compound was generated as single enantiomer of unknown absolute stereochemistry. NMR data matched that of the Example 41 product. Purity: 96.9%, 97.2% (210 & 254 nm) UPLCMS; retention time: 0.78 min; (M+H$^+$) 438.3.

Example 43

1-(4-(4-Fluorophenyl)pyrimidin-2-yl)-N-(4-methyl-1-azabicyclo[3.2.2]nonan-4-yl)piperidine-4-carboxamide (Single Enantiomer B)

Using General Procedure D and the reaction inputs 1-(4'-fluoro-[1,1'-biphenyl]-3-yl)piperidine-4-carboxylic acid (prepared as described in Example 41) and Intermediate 10, the title compound was generated as single enantiomer of unknown absolute stereochemistry. NMR data matched that of the Example 41 product. Purity: 100%, 99.4% (210 & 254 nm) UPLCMS; retention time: 0.78 min; (M+H$^+$) 438.3.

Example 44

1-(4-(4-Fluorophenyl)pyrimidin-2-yl)-N-(3-methylquinuclidin-3-yl)piperidine-4-carboxamide Using General Procedure D and the reaction inputs 1-(4'-fluoro-[1,1'-biphenyl]-3-yl)piperidine-4-carboxylic acid (prepared as described in Example 41) and Intermediate 1, the title compound was prepared. $^1$H NMR (500 MHz, $CDCl_3$) δ 8.30 (d, J=4.5 Hz, 1H), 8.07-8.04 (m, 2H), 7.16 (t, J=8.5 Hz, 2H), 6.89 (d, J=5.0 Hz, 1H), 5.57 (s, 1H), 4.97-4.94 (m, 2H), 3.04-2.84 (m, 8H), 2.40-2.21 (m, 2H), 1.97-1.51 (m, 11H) ppm. $^{13}$C NMR (125 MHz, $CDCl_3$) δ 174.3, 165.3, 163.3, 163.2, 161.7, 158.4, 133.8, 129.0, 128.9, 115.7, 115.5, 105.2, 63.2, 52.9, 46.6, 46.4, 44.3, 43.5, 30.2, 28.8, 28.7, 24.3, 22.9, 22.4 ppm. Purity: >99% (214 & 254 nm) LCMS; retention time: 1.27 min; (M+H$^+$) 424.2.

Example 45

1-(4-(4-Fluorophenyl)pyrimidin-2-yl)-N-(quinuclidin-3-yl)piperidine-4-carboxamide Using General Procedure E and the reaction inputs 1-(4'-fluoro-[1,1'-biphenyl]-3-yl)piperidine-4-carboxylic acid (prepared as described in Example 41) and quinuclidin-3-amine, the title compound was prepared as an off-white solid. $^1$H NMR (400 MHz, DMSO-d$_6$) δ 8.43 (d, J=5.0 Hz, 1H), 8.26-8.13 (m, 2H), 7.86 (d, J=7.1 Hz, 2H), 7.38-7.29 (m, 2H), 7.17 (d, J=5.1 Hz, 1H), 4.89-4.72 (m, 2H), 3.75-3.62 (m, 1H), 3.09-2.87 (m, 3H), 2.85-2.72 (m, 1H), 2.72-2.36 (m, 5H), 1.84-1.64 (m, 4H), 1.64-1.40 (m, 4H), 1.35-1.19 (m, 1H) ppm. $^{13}$C NMR (100 MHz, DMSO-d$_6$) δ 174.1, 163.7 (d, J=248.3 Hz), 162.1, 161.3, 158.9, 133.4 (d, J=2.9 Hz), 129.1 (d, J=8.7 Hz), 115.6 (d, J=21.7 Hz), 105.0, 54.4, 46.9, 46.3, 45.9, 43.1, 43.1, 42.1, 28.4, 28.1, 25.6, 25.6, 19.8 ppm. Purity: 95.2%, 99.6% (210 & 254 nm) UPLCMS; retention time: 0.73 min; (M+H$^+$) 410.3.

Example 46

1-(6-(4-Fluorophenyl)pyrazin-2-yl)-N-(4-methyl-1-azabicyclo[3.2.2]nonan-4-yl)piperidine-4-carboxamide To a stirred solution of 2,6-dichloropyrazine (5.00 g, 33.6 mmol) in 1,4-dioxane (150 mL) was added ethyl piperidine-4-carboxylate (5.54 g, 35.2 mmol) and triethylamine (5.2 mL, 37 mmol). The mixture heated at reflux overnight and then concentrated. The residue was taken up in aqueous sodium bicarbonate solution and extracted with ethyl acetate. The combined extracts were dried ($Na_2SO_4$) and concentrated. The residue was purified by flash chromatography over silica using a hexane/ethyl acetate eluant to afford ethyl 1-(6-chloropyrazin-2-yl)piperidine-4-carboxylate as a yellow oil (8.50 g, 94%). To a stirred solution of this compound (1.00 g, 3.71 mmol) in 10:1 (v/v) 1,4-dioxane/water (11 mL) was added 4-fluorophenylboronic acid (0.622 g, 4.44 mmol), sodium carbonate (0.785 g, 7.41 mmol) and [1,1'-bis(diphenylphosphino)ferrocene]dichloropalladium (II) (0.136 g, 0.185 mmol). The mixture was heated at reflux overnight. After cooling, the reaction was diluted with water and extracted with ethyl acetate. The combined extracts were washed with brine, dried ($Na_2SO_4$) and concentrated.

The residue was purified by flash chromatography over silica using a hexane/ethyl acetate eluant to afford ethyl 1-(6-(4-fluorophenyl)pyrazin-2-yl)piperidine-4-carboxylate as a yellow oil (1.20 g, 98%). To a stirred solution of this product in 1:1:1 (v/v/v) tetrahydrofuran/methanol/water was added solid sodium hydroxide (0.730 g, 18.3 mmol). After overnight stirring, the reaction was concentrated. The residue was dissolved in water, made acidic (pH~6) with the addition of 1N hydrochloric acid and extracted with ethyl acetate. The combined organic layers were washed with brine, dried ($Na_2SO_4$) and concentrated to afford 1-(6-(4-fluorophenyl)pyrazin-2-yl)piperidine-4-carboxylic acid as a yellow solid (0.600 g, 54%). Using General Procedure D and Intermediate 5, this carboxylic acid was subjected to amide coupling to generate the title compound as a white solid (0.100 g, 34%). $^1$H NMR (500 MHz, $CDCl_3$) δ 8.25 (s, 1H), 8.07 (s, 1H), 7.98-7.95 (m, 2H), 7.13 (t, J=8.0 Hz, 2H), 5.54 (s, 1H), 4.50-4.47 (m, 2H), 3.05-2.83 (m, 8H), 2.38-2.34 (m, 2H), 1.96-1.48 (m, 13H) ppm. $^{13}$C NMR (125 MHz, $CDCl_3$) δ 173.9, 164.6, 162.7, 153.9, 148.3, 133.2, 129.0, 128.6, 115.7, 115.6, 59.5, 53.1, 47.6, 46.0, 44.2, 44.1, 44.0, 39.0, 36.0, 28.5, 28.2, 25.1, 24.1, 24.0 ppm. Purity: >99% (214 & 254 nm) LCMS; retention time: 1.23 min; (M+H$^+$) 438.0.

Example 47

1-(6-(4-Fluorophenyl)pyrazin-2-yl)-N-(4-methyl-1-azabicyclo[3.2.2]nonan-4-yl)piperidine-4-carboxamide (Single Enantiomer A)

Using General Procedure D and the reaction inputs 1-(6-(4-fluorophenyl)pyrazin-2-yl)piperidine-4-carboxylic acid (prepared as described in Example 46) and Intermediate 9, the title compound was generated as single enantiomer of unknown absolute stereochemistry. NMR data matched that of Example 46. Purity: 100%, 98.6% (214 & 254 nm) UPLCMS; retention time: 0.79 min; (M+H$^+$) 438.4.

Example 48

1-(6-(4-Fluorophenyl)pyrazin-2-yl)-N-(4-methyl-1-azabicyclo[3.2.2]nonan-4-yl)piperidine-4-carboxamide (Single Enantiomer B)

Using General Procedure D and the reaction inputs 1-(6-(4-fluorophenyl)pyrazin-2-yl)piperidine-4-carboxylic acid (prepared as described in Example 46) and Intermediate 10, the title compound was generated as single enantiomer of unknown absolute stereochemistry. NMR data matched that of Example 46. Purity: 100%, 100% (214 & 254 nm) UPLCMS; retention time: 0.79 min; (M+H$^+$) 438.4.

Example 49

1-(6-(4-Fluorophenyl)pyrazin-2-yl)-N-(3-methylquinuclidin-3-yl)piperidine-4-carboxamide Using General Procedure E and the reaction inputs 1-(6-(4-fluorophenyl)pyrazin-2-yl)piperidine-4-carboxylic acid (prepared as described in Example 46) and Intermediate 1, the title compound was prepared as a light brown solid. $^1$H NMR (400 MHz, DMSO-$d_6$) δ 8.41 (s, 1H), 8.29 (m, 1H), 8.16-8.08 (m, 2H), 7.47 (br s, 1H), 7.36-7.28 (m, 2H), 4.54-4.41 (m, 2H), 3.02-2.85 (m, 3H), 2.73-2.41 (m, 6H), 2.16-2.08 (m, 1H), 1.84-1.51 (m, 6H), 1.45-1.20 (m, 5H) ppm. $^{13}$C NMR (100 MHz, DMSO-$d_6$) δ 173.9, 162.9 (d, J=246.8 Hz), 153.6, 146.9, 133.1 (d, J=2.9 Hz), 129.8, 128.6 (d, J=8.7 Hz), 128.3, 115.6 (d, J=21.6 Hz), 62.1, 51.8, 46.2, 45.9, 43.8, 43.7, 42.1, 29.1, 27.9, 27.7, 24.2, 22.7, 22.3 ppm. Purity: 100%, 97.7% (210 & 254 nm) UPLCMS; retention time: 0.77 min; (M+H$^+$) 424.2.

Example 50

1-(4-(4-Fluorophenyl)-1,3,5-triazin-2-yl)-N-(4-methyl-1-azabicyclo[3.2.2]nonan-4-yl)piperidine-4-carboxamide Exchanging 2,6-dichloropyrazine for 2,4-dichloro-1,3,5-triazine, the same reaction sequence outlined in Example 46 was used to generate the title compound. $^1$H NMR (500 MHz, $CDCl_3$) δ 8.60 (s, 1H), 8.43-8.40 (m, 2H), 7.12 (t, J=8.5 Hz, 2H), 5.43 (s, 1H), 5.02-4.88 (m, 2H), 3.04-2.82 (m, 8H), 2.40-2.36 (m, 2H), 1.95-1.48 (m, 13H) ppm. $^{13}$C NMR (125 MHz, $CDCl_3$) δ 173.6, 169.6, 166.4, 166.1, 164.4, 163.7, 132.5, 132.4, 130.8, 130.7, 115.5, 115.3, 59.5, 53.0, 47.5, 46.1, 44.0, 42.8, 42.6, 39.1, 36.0, 28.8, 28.6, 25.0, 24.2, 24.1 ppm. Purity: >98% (214 & 254 nm) LCMS; retention time: 1.20 min; (M+H$^+$) 439.0.

Example 51

1-(2-(4-Fluorophenyl)pyrimidin-4-yl)-N-(4-methyl-1-azabicyclo[3.2.2]nonan-4-yl)piperidine-4-carboxamide To a stirred solution of 2,4-dichloropyrimidine (2.00 g, 13.4 mmol) in methanol (30 mL) was added ethyl piperidine-4-carboxylate (1.73 g, 12.1 mmol) and triethylamine (1.49 g, 14.8 mmol). The mixture was heated at 65° C. overnight. After cooling, the reaction was filtered free of solids and concentrated. The residue was purified by flash chromatography over silica using a hexane/ethyl acetate eluant to afford ethyl 1-(2-chloropyrimidin-4-yl)piperidine-4-carboxylate as a yellow oil (2.50 g, 69%). To a stirred solution of this product in a mixture of N,N-dimethylformamide (15 mL) and water (8 mL) was added 4-fluorophenylboronic acid (0.780 g, 5.60 mmol), sodium carbonate (2.37 g, 22.4 mmol) and [1,1'-bis(diphenylphosphino)ferrocene]dichloropalladium(II) (0.204 g, 0.279 mmol). The mixture was heated at 90° C. for 6 hours and then concentrated. The residue was purified by flash chromatography over silica using a methylene chloride/methanol eluant to afford ethyl 1-(2-(4-fluorophenyl)pyrimidin-4-yl)piperidine-4-carboxylate as a white solid (0.500 g, 27%). To a stirred solution of this intermediate in 1:1 (v/v) methanol/water (20 mL) was added solid sodium hydroxide (0.303 g, 7.58 mmol). After 3 hours, the reaction was concentrated. The residue was dissolved in water, made acidic (pH~6) with the addition of 1N hydrochloric acid and extracted with ethyl acetate. The combined organic layers were washed with brine, dried ($Na_2SO_4$) and concentrated to afford 1-(2-(4-fluorophenyl)pyrimidin-4-yl)piperidine-4-carboxylic acid as a white solid (0.430 g, 94%). Using General Procedure D and Intermediate 5, this carboxylic acid was subjected to amide coupling to generate the title compound as a white solid (0.096 g, 22%). $^1$H NMR (500 MHz, $CDCl_3$) δ 8.37 (d, J=5.0 Hz, 1H), 8.07-8.04 (m, 2H), 7.15 (t, J=9.0 Hz, 2H), 6.89 (d, J=10.0 Hz, 1H), 5.38 (s, 1H), 4.97-4.95 (m, 2H), 3.02-2.83 (m, 8H), 2.39-2.37 (m, 2H), 1.96-1.51 (m, 13H) ppm. $^{13}$C NMR (125 MHz, $CDCl_3$) δ 174.1, 165.3, 163.3, 163.2, 161.7, 158.4, 133.8, 129.0, 128.9, 115.7, 115.5, 105.2, 59.4, 53.1, 47.6, 46.1, 44.6, 43.5, 39.3, 36.1, 28.9, 28.7, 25.1, 24.3, 24.2 ppm. Purity: >96% (214 & 254 nm) LCMS; retention time: 1.44 min; (M+H+) 438.3.

Example 52

4-([1,1'-Biphenyl]-3-yl)-N-(4-methyl-1-azabicyclo[3.2.2]nonan-4-yl)piperidine-1-carboxamide To a stirred solution of tert-butyl 4-(4,4,5,5-tetramethyl-1,3,2-dioxaborolan-2-yl)-5,6-dihydropyridine-1(2H)-carboxylate (1.05 g, 3.40 mmol) in 5:1 (v/v) 1,4-dioxane/water (30 mL) was added 3-bromobiphenyl (0.660 g, 2.80 mmol), potassium carbonate (1.16 g, 8.39 mmol) and [1,1'-bis(diphenylphosphino)ferrocene]dichloropalladium(II) (0.102 g, 0.139 mmol). The mixture was heated at 80° C. overnight. After cooling, the reaction was diluted with water and extracted with ethyl acetate. The combined extracts were washed with brine, dried ($Na_2SO_4$) and concentrated. The residue was purified by flash chromatography over neutral alumina using a hexane/ethyl acetate eluant to afford tert-butyl 4-([1,1'-biphenyl]-3-yl)-5,6-dihydropyridine-1(2H)-carboxylate as a light yellow oil (0.900 g, 64%). A stirred suspension of this compound (0.900 g, 2.50 mmol) and 10% palladium on carbon (50% water; 0.180 g) in ethyl acetate (30 mL) was cycled between vacuum and a nitrogen several times. After the last evacuation, the reaction was refilled with hydrogen gas. The mixture was stirred overnight and then filtered through Celite. The filtrate was combined with ethyl acetate rinsings of the Celite and concentrated to afford tert-butyl 4-([1,1'-biphenyl]-3-yl)piperidine-1-carboxylate as a yellow oil (0.898 g, 90%). To a stirred solution of this product (0.898 g, 2.66 mmol) in methylene chloride (10 mL) was added trifluoroacetic acid (2.5 mL). The mixture was stirred overnight and then concentrated. The residue was taken up in aqueous sodium carbonate solution and extracted with methylene chloride. The combined extracts were dried ($Na_2SO_4$) and concentrated to afford 4-([1,1'-biphenyl]-3-yl)piperidine as a light yellow oil (0.569 g, 90%). This compound was reacted with Intermediate 5 using General Procedure A to generate the title compound. $^1$H NMR (500 MHz, $CDCl_3$) δ 7.60-7.58 (d, J=7.5 Hz, 2H), 7.47-7.35 (m, 6H), 7.21-7.20 (d, J=7.5 Hz, 1H), 4.45 (s, 1H), 4.11-4.05 (m, 2H), 3.06-2.98 (m, 4H), 2.94-2.88 (m, 4H), 2.76-1.75 (m, 1H), 2.45 (m, 1H), 1.96-1.87 (m, 5H), 1.78-1.55 (m, 8H) ppm. $^{13}$C NMR (125 MHz, $CDCl_3$) δ 157.1, 146.0, 141.5, 141.2, 129.0, 128.7, 127.3, 127.2, 125.7, 125.7, 125.3, 58.8, 53.1, 47.7, 46.0, 45.0, 45.0, 42.7, 39.0, 36.3, 33.2, 25.9, 23.9, 23.6 ppm. Purity: >99% (214 & 254 nm) LCMS; retention time: 1.99 min; (M+H+) 418.4.

Example 53

4-([1,1'-Biphenyl]-4-yl)-N-(4-methyl-1-azabicyclo[3.2.2]nonan-4-yl)piperidine-1-carboxamide Exchanging 4-bromobiphenyl for 3-bromobiphenyl, the same reaction sequence outlined in Example 52 was used to generate the title compound. $^1$H NMR (500 MHz, $CDCl_3$) δ 7.60-7.56 (m, 4H), 7.45 (t, J=7.5 Hz, 2H), 7.35 (t, J=7.5 Hz, 1H), 7.30-7.289 (d, J=8.0 Hz, 2H), 4.43 (s, 1H), 4.10-4.05 (m, 2H), 3.08-2.85 (m, 8H), 2.76-2.71 (m, 1H), 2.44-2.42 (m, 1H), 1.97-1.53 (m, 13H) ppm. $^{13}$C NMR (125 MHz, $CDCl_3$) δ 157.0, 144.6, 140.9, 139.4, 128.7, 127.3, 127.1, 127.0, 58.9, 53.2, 47.7, 46.2, 45.0, 44.9, 42.3, 39.7, 36.5, 33.1, 33.1, 25.9, 24.4, 24.1 ppm. Purity: >99% (214 & 254 nm) LCMS; retention time: 1.99 min; (M+H+) 418.4.

Example 54

1-(5-Fluoro-4-(4-fluorophenyl)pyrimidin-2-yl)-N-(3-methylquinuclidin-3-yl)piperidine-4-carboxamide Exchanging 2,4-dichloropyrimidine for 2,4-dichloro-5-fluoropyrimidine and Intermediate 5 for Intermediate 1, the same reaction sequence outlined in Example 41 was used to generate the title compound. $^1$H NMR (500 MHz, $CDCl_3$) δ 8.25 (d, J=3.5 Hz, 1H), 8.14-8.11 (m, 2H), 7.20-7.16 (m, 2H), 5.41 (br s, 1H), 4.84-4.81 (m, 2H), 3.02-2.78 (m, 8H), 2.38-2.33 (m, 1H), 2.18-2.16 (m, 1H), 1.95-1.92 (m, 2H), 1.80-1.70 (m, 4H), 1.56-1.46 (m, 5H) ppm. $^{13}$C NMR (125 MHz, $CDCl_3$) δ 174.2, 165.1, 163.1, 158.3, 158.2, 150.5, 150.2, 150.1, 148.5, 146.8, 146.6, 131.12, 131.05, 131.0, 130.3, 130.25, 130.23, 130.21, 115.6, 115.4, 63.4, 52.9, 46.6, 46.4, 44.14, 44.09, 30.3, 28.7, 28.6, 24.4, 23.1, 22.5 ppm. Purity: >99% LCMS (214 nm & 254 nm); retention time 1.50 min; (M+H+) 442.2.

Example 55

1-(5-Fluoro-4-(4-fluorophenyl)pyrimidin-2-yl)-N-(4-methyl-1-azabicyclo[3.2.2]nonan-4-yl)piperidine-4-carboxamide Exchanging 2,4-dichloropyrimidine for 2,4-dichloro-5-fluoropyrimidine, the same reaction sequence outlined in Example 41 was used to generate the title compound. $^1$H NMR (500 MHz, $CDCl_3$) δ 8.25 (d, J=3.0 Hz, 1H), 8.14-8.11 (m, 2H), 7.18 (t, J=8.5 Hz, 2H), 5.36 (s, 1H), 4.85-4.82 (m, 2H), 3.04-2.83 (m, 8H), 2.39-2.34 (m, 2H), 1.96-1.92 (m, 3H), 1.82-1.53 (m, 10H) ppm. $^{13}$C NMR (125 MHz, $CDCl_3$) δ 174.0, 165.1, 163.1, 158.27, 158.25, 150.5, 150.23, 150.16, 148.5, 146.8, 146.6, 131.1, 131.04, 130.99, 130.3, 130.25, 130.23, 130.20, 115.6, 115.4, 59.5, 53.1, 47.6, 46.1, 44.4, 44.12, 44.09, 39.3, 36.1, 28.8, 28.5, 25.1, 24.3, 24.2 ppm. Purity: >99% LCMS (214 nm & 254 nm); retention time 1.52 min; (M+H+) 456.2.

Example 56

1-(5-Fluoro-4-(4-(2-methoxyethoxy)phenyl)pyrimidin-2-yl)-N-(4-methyl-1-azabicyclo[3.2.2]nonan-4-yl)piperidine-4-carboxamide Exchanging 2,4-dichloropyrimidine for 2,4-dichloro-5-fluoropyrimidine and 4-fluorophenylboronic acid for (4-(2-methoxyethoxy)phenyl)boronic acid, the same reaction sequence outlined in Example 41 was used to generate the title compound. $^1$H NMR (500 MHz, $CDCl_3$) δ 8.21 (d, J=4.0 Hz, 1H), 8.10 (d, J=8.5 Hz, 2H), 7.03 (dd, J=7.0 Hz & 2.0 Hz, 2H), 5.37 (s, 1H), 4.85-4.82 (m, 2H), 4.21 (t, J=4.5 Hz, 2H), 3.80 (t, J=4.5 Hz, 2H), 3.49 (s, 3H), 3.06-2.83 (m, 8H), 2.38-2.31 (m, 2H), 1.95-1.92 (m, 3H), 1.77-1.51 (m, 10H) ppm. $^{13}$C NMR (125 MHz, $CDCl_3$) δ 174.1, 160.7, 158.3, 150.9, 150.8, 150.7, 148.5, 146.3, 146.1, 130.6, 130.5, 126.8, 114.5, 70.9, 67.3, 59.4, 59.2, 53.1, 47.6, 46.1, 44.5, 44.2, 44.1, 39.3, 36.1, 28.9, 28.6, 25.1, 24.3, 24.2 ppm. Purity: >99% LCMS (214 nm & 254 nm); retention time 1.33 min; (M+H+) 512.3.

Example 57

1-(5-Fluoro-4-(4-(2-methoxyethoxy)phenyl)pyrimidin-2-yl)-N-(3-methylquinuclidin-3-yl)piperidine-4-carboxamide Exchanging 2,4-dichloropyrimidine for 2,4-dichloro-5-fluoropyrimidine, 4-fluorophenylboronic acid for (4-(2- methoxyethoxy)phenyl)boronic acid and Intermediate 5 for Intermediate 1, the same reaction sequence outlined in Example 41 was used to generate the title compound. $^1$H NMR (400 MHz, CDCl$_3$) δ 8.09 (d, J=2.4 Hz, 1H), 7.53 (dd, J=8.8 Hz & 1.6 Hz, 2H), 7.02 (dd, J=7.2 Hz & 2.0 Hz, 2H), 6.68 (d, J=5.2 Hz, 1H), 5.61 (br s, 1H), 4.30-4.17 (m, 4H), 3.80-3.78 (m, 2H), 3.48 (s, 3H), 3.07-2.83 (m, 8H), 2.32-2.18 (m, 2H), 1.94-1.50 (m, 11H) ppm. $^{13}$C NMR (100 MHz, CDCl$_3$) δ 174.3, 159.3, 156.7, 152.2, 137.8, 137.6, 135.5, 135.3, 130.0, 126.8, 114.7, 107.4, 70.9, 67.4, 63.0, 59.2, 52.9, 46.6, 46.4, 46.0, 43.9, 30.9, 30.1, 28.5, 28.4, 24.3, 22.8, 22.3 ppm. Purity: >99% LCMS (214 nm & 254 nm); retention time 1.27 min; (M+H$^+$) 497.3.

Example 58

1-(5-Fluoro-4-(4-((2-methoxyethoxy)methyl)phenyl)pyrimidin-2-yl)-N-(4-methyl-1-azabicyclo[3.2.2]nonan-4-yl)piperidine-4-carboxamide Exchanging 2,4-dichloropyrimidine for 2,4-dichloro-5-fluoropyrimidine and 4-fluorophenylboronic acid for 2-(4-((2-methoxyethoxy)methyl)phenyl)-4,4,5,5-tetramethyl-1,3,2-dioxaborolane, the same reaction sequence outlined in Example 41 was used to generate the title compound. $^1$H NMR (400 MHz, CDCl$_3$) δ 8.23 (d, J=3.6 Hz, 1H), 8.06 (d, J=8.3 Hz, 2H), 7.46 (d, J=8.3 Hz, 2H), 5.49 (s, 1H), 4.87-4.77 (m, 2H), 4.64 (s, 2H), 3.67-3.62 (m, 2H), 3.62-3.57 (m, 2H), 3.41 (s, 3H), 3.10-2.80 (m, 8H), 2.44-2.30 (m, 2H), 1.97-1.45 (m, 13H) ppm. Purity: 99.1% (214 & 254 nm) UPLCMS; retention time: 0.89 min; (M+H$^+$) 526.4.

Example 59

1-(5-Fluoro-4-(4-((2-methoxyethoxy)methyl)phenyl)pyrimidin-2-yl)-N-(3-methylquinuclidin-3-yl)piperidine-4-carboxamide Exchanging 2,4-dichloropyrimidine for 2,4-dichloro-5-fluoropyrimidine, 4-fluorophenylboronic acid for 2-(4-((2-methoxyethoxy)methyl)phenyl)-4,4,5,5-tetramethyl-1,3,2-dioxaborolane and Intermediate 5 for Intermediate 1, the same reaction sequence outlined in Example 41 was used to generate the title compound. $^1$H NMR (400 MHz, CDCl$_3$) δ 8.23 (d, J=3.6 Hz, 1H), 8.06 (d, J=8.3 Hz, 2H), 7.46 (d, J=8.3 Hz, 2H), 5.43 (s, 1H), 4.86-4.78 (m, 2H), 4.64 (s, 2H), 3.67-3.62 (m, 2H), 3.62-3.57 (m, 2H), 3.41 (s, 3H), 3.00-2.88 (m, 4H), 2.88-2.71 (m, 4H), 2.38-2.28 (m, 1H), 2.16-2.11 (m, 1H), 1.96-1.86 (m, 2H), 1.82-1.66 (m, 2H), 1.57-1.38 (m, 5H) ppm. Purity: >99.9% (214 & 254 nm) UPLCMS; retention time: 0.87 min; (M+H$^+$) 512.4.

Example 60

1-(5-Fluoro-4-(4-(methoxymethyl)phenyl)pyrimidin-2-yl)-N-(4-methyl-1-azabicyclo[3.2.2]nonan-4-yl)piperidine-4-carboxamide Exchanging 2,4-dichloropyrimidine for 2,4-dichloro-5-fluoropyrimidine and 4-fluorophenylboronic acid for 2-(4-(methoxymethyl)phenyl)-4,4,5,5-tetramethyl-1,3,2-dioxaborolane, the same reaction sequence outlined in Example 41 was used to generate the title compound. $^1$H NMR (500 MHz, CDCl$_3$) δ 8.26 (d, J=3.5 Hz, 1H), 8.09 (d, J=7.5 Hz, 2H), 7.48 (d, J=8.5 Hz, 2H), 5.44 (s, 1H), 4.86-4.83 (m, 2H), 4.55 (s, 2H), 3.44 (s, 3H), 3.09-2.83 (m, 8H), 2.42-2.18 (m, 2H), 1.98-1.93 (m, 3H), 1.83-1.51 (m, 10H) ppm. $^{13}$C NMR (100 MHz, CDCl$_3$) δ 174.1, 158.4, 151.2, 151.1, 150.9, 148.4, 146.7, 146.4, 140.9, 133.5, 133.4, 129.0, 127.5, 74.2, 59.4, 58.2, 53.1, 47.7, 46.0, 44.5, 44.1, 39.0, 36.0, 30.9, 28.8, 28.6, 25.1, 24.1, 23.9 ppm. Purity: >99% LCMS (214 nm & 254 nm); retention time 1.40 min; (M+H$^+$) 482.2.

Example 61

1-(5-Fluoro-4-(4-(methoxymethyl)phenyl)pyrimidin-2-yl)-N-(3-methylquinuclidin-3-yl)piperidine-4-carboxamide Exchanging 2,4-dichloropyrimidine for 2,4-dichloro-5-fluoropyrimidine, 4-fluorophenylboronic acid for 2-(4-(methoxymethyl)phenyl)-4,4,5,5-tetramethyl-1,3,2-dioxaborolane and Intermediate 5 for Intermediate 1, the same reaction sequence outlined in Example 41 was used to generate the title compound. $^1$H NMR (500 MHz, CDCl$_3$) δ 8.26 (d, J=3.5 Hz, 1H), 8.09 (d, J=8.0 Hz, 2H), 7.47 (d, J=8.5 Hz, 2H), 5.58 (br s, 1H), 4.86-4.83 (m, 2H), 4.55 (s, 2H), 3.44 (s, 3H), 3.01-2.84 (m, 8H), 2.40-2.22 (m, 2H), 1.94-1.92 (m, 2H), 1.80-1.48 (m, 9H) ppm. $^{13}$C NMR (100 MHz, CDCl$_3$) δ 174.3, 158.3, 151.2, 151.1, 150.9, 148.4, 146.7, 146.4, 140.9, 133.4, 129.0, 128.9, 127.5, 74.2, 63.2, 58.2, 52.9, 46.6, 46.4, 44.2, 44.1, 30.9, 30.1, 28.7, 28.6, 24.3, 22.9, 22.4 ppm. Purity: >99% LCMS (214 nm & 254 nm); retention time 1.38 min; (M+H$^+$) 468.3.

Example 62

1-(5-Fluoro-4-(4-(3-methoxypropoxy)phenyl)pyrimidin-2-yl)-N-(4-methyl-1-azabicyclo[3.2.2]nonan-4-yl)piperidine-4-carboxamide Exchanging 2,4-dichloropyrimidine for 2,4-dichloro-5-fluoropyrimidine and 4-50 fluorophenylboronic acid for 2-(4-(3-methoxypropoxy)phenyl)-4,4,5,5-tetramethyl-1,3,2-dioxaborolane, the same reaction sequence outlined in Example 41 was used to generate the title compound. $^1$H NMR (400 MHz, CDCl$_3$) δ 8.17 (d, J=3.8 Hz, 1H), 8.06 (d, J=9.0 Hz, 2H), 6.97 (d, J=9.0 Hz, 2H), 5.65 (s, 1H), 4.85-4.75 (m, 2H), 4.12 (t, J=6.3 Hz, 2H), 3.57 (t, J=6.3 Hz, 2H), 3.36 (s, 3H), 3.18-2.89 (m, 8H), 2.52-2.46 (m, 1H), 2.45-2.35 (m, 1H), 2.12-2.01 (m, 2H), 2.01-1.53 (m, 10H), 1.47 (s, 3H) ppm. Purity: >99.9% (214 & 254 nm) UPLCMS; retention time: 0.96 min; (M+H$^+$) 526.3.

Example 63

1-(5-Fluoro-4-(4-(3-methoxypropoxy)phenyl)pyrimidin-2-yl)-N-(3-methylquinuclidin-3-yl)piperidine-4-carboxamide Exchanging 2,4-dichloropyrimidine for 2,4-dichloro-5-fluoropyrimidine, 4-fluorophenylboronic acid for 2-(4-(3-methoxypropoxy)phenyl)-4,4,5,5-tetramethyl-1,3,2-dioxaborolane and Intermediate 5 for Intermediate 1, the same reaction sequence outlined in Example 41 was used to generate the title compound. $^1$H NMR (400 MHz, CDCl$_3$) δ 8.19 (d, J=3.8 Hz, 1H), 8.07 (d, J=8.9 Hz, 2H), 6.98 (d, J=8.9 Hz, 2H), 5.38 (s, 1H), 4.85-4.77 (m, 2H), 4.13 (t, J=6.3 Hz, 2H), 3.57 (t, J=6.3 Hz, 2H), 3.36 (s, 3H), 3.00-2.88 (m, 4H), 2.88-2.71 (m, 4H), 2.37-2.27 (m, 1H), 2.16-2.04 (m, 3H), 1.96-1.86 (m, 2H), 1.82-1.65 (m, 4H), 1.56-1.38 (m, 5H) ppm. Purity: >99.9% (214 & 254 nm) UPLCMS; retention time: 0.95 min; (M+H$^+$) 512.3.

Example 64

1-(4-(3,4-Difluorophenyl)pyrimidin-2-yl)-N-(4-methyl-1-azabicyclo[3.2.2]nonan-4-yl)piperidine-4-carboxamide Exchanging 4-fluorophenylboronic acid for 3,4-difluorophenylboronic acid, the same reaction sequence outlined in Example 41 was used to generate the title compound. $^1$H NMR (500 MHz, CDCl$_3$) δ 8.39 (d, J=5.0 Hz, 1H), 7.94-7.93 (m, 1H), 7.78-7.77 (m, 1H), 7.27-7.24 (m, 1H), 6.87 (d, J=5.0 Hz, 1H), 5.44 (br, 1H), 4.96-4.93 (m, 2H), 3.06-2.87 (m, 8H), 2.41-2.39 (m, 2H), 1.97-1.52 (m, 13H) ppm. $^{13}$C NMR (125 MHz, CDCl$_3$) δ 174.1, 162.1, 161.7, 158.9, 152.9, 152.8, 151.6, 151.5, 150.9, 150.8, 149.7, 149.6, 134.9, 123.2, 123.1, 117.4, 117.3, 117.1, 116.2, 116.0, 105.0, 59.4, 53.0, 47.6, 46.0, 44.5, 43.7, 43.5, 39.0, 36.0, 28.9, 28.7, 25.1, 24.1, 23.9 ppm. Purity: >99% LCMS (214 nm & 254 nm); retention time 1.23 min; (M+H$^+$) 456.2.

Example 65

1-(4-(3,5-Difluorophenyl)pyrimidin-2-yl)-N-(4-methyl-1-azabicyclo[3.2.2]nonan-4-yl)piperidine-4-carboxamide Exchanging 4-fluorophenylboronic acid for 3,5-difluorophenylboronic acid, the same reaction sequence outlined in Example 41 was used to generate the title compound. $^1$H NMR (500 MHz, CDCl$_3$) δ 8.42 (d, J=5.5 Hz, 1H), 7.60-7.57 (m, 2H), 6.95-6.90 (m, 1H), 6.87 (d, J=5.5 Hz, 1H), 5.49 (s, 1H), 4.96-4.93 (m, 2H), 3.06-2.87 (m, 8H), 2.44-2.37 (m, 2H), 1.99-1.93 (m, 3H), 1.94-1.52 (m, 10H) ppm. $^{13}$C NMR (125 MHz, CDCl$_3$) δ 174.1, 164.3, 164.2, 162.3, 162.2, 161.8, 161.7, 158.9, 141.3, 141.2, 109.9, 109.7, 105.7, 105.5, 105.3, 59.4, 53.0, 47.6, 46.0, 44.4, 43.5, 39.0, 36.0, 28.9, 28.6, 25.1, 24.1, 23.9 ppm. Purity: >99% LCMS (214 nm & 254 nm); retention time 2.00 min; (M+H$^+$) 456.3.

Example 66

1-(4-(4-(2-Methoxyethoxy)phenyl)pyrimidin-2-yl)-N-(4-methyl-1-azabicyclo[3.2.2]nonan-4-yl)piperidine-4-carboxamide Exchanging 4-fluorophenylboronic acid for (4-(2-methoxyethoxy)phenyl)boronic, the same reaction sequence outlined in Example 41 was used to generate the title compound. $^1$H NMR (500 MHz, CDCl$_3$) δ 8.33-8.32 (d, J=5.0 Hz, 1H), 8.02 (d, J=9.0 Hz, 2H), 7.01 (d, J=8.5 Hz, 2H), 6.88 (d, J=5.0 Hz, 1H), 5.37 (s, 1H), 4.98-4.95 (m, 2H), 4.20 (t, J=5.0 Hz, 2H), 3.79 (t, J=5.0 Hz, 2H), 3.48 (s, 3H), 3.01-2.83 (m, 8H), 2.38-2.36 (m, 2H), 1.96-1.93 (m, 3H), 1.78-1.50 (m, 10H) ppm. $^{13}$C NMR (125 MHz, CDCl$_3$) δ 174.1, 163.8, 161.8, 160.8, 158.0, 130.3, 128.4, 114.6, 104.9, 70.9, 67.4, 59.4, 59.2, 53.1, 47.6, 46.1, 44.7, 43.5, 39.3, 36.1, 28.9, 28.7, 25.1, 24.3, 24.2 ppm. Purity: >99% LCMS (214 nm & 254 nm); retention time 1.13 min; (M+H$^+$) 494.3.

Example 67

1-(4-(4-(3-Methoxypropoxy)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(3-methoxypropoxy)phenyl)-4,4,5,5-tetramethyl-1,3,2-dioxaborolane, the same reaction sequence outlined in Example 41 was used to generate the title compound. $^1$H NMR (500 MHz, CDCl$_3$) δ 8.34 (d, J=5.0 Hz, 1H), 8.03 (d, J=9.0 Hz, 2H), 7.00 (d, J=9.0 Hz, 2H), 6.89 (d, J=5.0 Hz, 1H), 5.38 (s, 1H), 4.99-4.96 (m, 2H), 4.14 (t, J=6.0 Hz, 2H), 3.60 (t, J=5.0 Hz, 2H), 3.39 (s, 3H), 3.02-2.83 (m, 8H), 2.39-2.36 (m, 2H), 2.11-2.08 (m, 2H), 1.98-1.52 (m, 13H) ppm. $^{13}$C NMR (125 MHz, CDCl$_3$) δ 174.1, 163.9, 161.8, 161.0, 158.0, 130.1, 128.5, 114.5, 104.9, 69.1, 65.0, 59.4, 58.7, 53.1, 47.6, 46.1, 44.7, 43.5, 39.2, 36.1, 29.6, 29.0, 28.8, 25.1, 24.3, 24.1 ppm. Purity: >99% LCMS (214 nm & 254 nm); retention time 1.28 min; (M+H$^+$) 508.3.

Example 68

1-(4'-(2-Methoxyethoxy)-[1,1'-biphenyl]-3-yl)-N-(4-methyl-1-azabicyclo[3.2.2]nonan-4-yl)piperidine-4-carboxamide Exchanging 4-fluorophenylboronic acid for (4-(2-methoxyethoxy)phenyl)boronic acid and Intermediate 1 for Intermediate 5, the same reaction sequence outlined in Example 33 was used to generate the title compound. $^1$H NMR (500 MHz, CDCl$_3$) δ 7.52 (d, J=8.5 Hz, 2H), 7.31 (t, J=8.0 Hz, 1H), 7.12 (t, J=2.0 Hz, 1H), 7.05 (d, J=7.5 Hz, 1H), 7.01 (d, J=8.5 Hz, 2H), 6.92 (dd, J=8.0 Hz & 2.0 Hz, 1H), 5.38 (s, 1H), 4.20-4.17 (m, 2H), 3.81-3.79 (m, 4H), 3.49 (s, 3H), 3.01-2.79 (m, 8H), 2.40 (m, 1H), 2.25-2.20 (m, 1H), 1.97-1.53 (m, 13H) ppm. $^{13}$C NMR (125 MHz, CDCl$_3$) δ 174.2, 158.3, 151.9, 141.8, 134.5, 129.4, 128.2, 118.5, 115.3, 115.1, 114.8, 71.1, 67.4, 59.4, 59.2, 53.1, 49.6, 49.5, 47.6, 46.1, 44.1, 39.2, 36.1, 29.1, 28.9, 25.1, 24.3, 24.2 ppm. Purity: >99% LCMS (214 nm & 254 nm); retention time 1.19 min; (M+H$^+$) 492.3.

Example 69

1-(4'-((2-Methoxyethoxy)methyl)-[1,1'-biphenyl]-3-yl)-N-(4-methyl-1-azabicyclo[3.2.2]nonan-4-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane and Intermediate 1 for Intermediate 5, the same reaction sequence outlined in Example 33 was used to generate the title compound. $^1$H NMR (500 MHz, CDCl$_3$) δ 8.38 (d, J=5.5 Hz, 1H), 8.04 (d, J=8.0 Hz, 2H), 7.47 (d, J=8.0 Hz, 2H), 6.95 (d, J=5.5 Hz, 1H), 5.46 (s, 1H), 4.99-4.96 (m, 2H), 4.66 (s, 2H), 3.66-3.60 (m, 4H), 3.43 (s, 3H), 3.05-2.84 (m, 8H), 2.42-2.37 (m, 2H), 1.97-1.95 (m, 3H), 1.94-1.51 (m, 10H) ppm. $^{13}$C NMR (125 MHz, CDCl$_3$) δ 174.2, 164.1, 161.8, 158.3, 140.7, 137.1, 127.9, 127.1, 105.5, 72.9, 72.0, 69.4, 59.4, 59.1, 53.1, 47.7, 46.0, 44.6, 43.5, 38.9, 36.0, 31.0, 29.0, 28.7, 25.1, 24.0, 23.9 ppm. Purity: >98% LCMS (214 nm & 254 nm); retention time 1.29 min; (M+H$^+$) 508.3. $^1$H NMR (400 MHz, CDCl$_3$) δ 7.60-7.58 (d, J=8.0 Hz, 2H), 7.44 (t, J=7.6 Hz, 2H), 7.37-7.32 (m, 2H), 7.15 (s, 1H), 7.10-7.08 (d, J=7.2 Hz, 1H), 6.96-6.94 (d, J=8.0 Hz, 1H), 5.46 (s, 1H), 3.83-3.80 (m, 2H), 3.08-2.78 (m, 8H), 2.41 (m, 1H), 2.24-2.21 (m, 1H), 2.01-1.52 (m, 13H) ppm. Purity: >95% (214 & 254 nm) LCMS; retention time: 1.38 min; (M+H$^+$) 418.3.

Example 70

1-(4-(4-(Methoxymethyl)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(methoxymethyl)phenyl)-4,4,5,5-tetramethyl-1,3,2-dioxaborolane, the same reaction sequence outlined in Example 41 was used to generate the title compound. $^1$H NMR (500 MHz, CDCl$_3$) δ 8.37 (d, J=5.0 Hz, 1H), 8.04 (d, J=8.0 Hz, 2H), 7.44 (d, J=8.0 Hz, 2H), 6.94 (d, J=5.0 Hz, 1H), 5.39 (s, 1H), 4.99-4.96 (m, 2H), 4.54 (s, 2H), 3.43 (s, 3H), 3.02-2.85 (m, 8H), 2.39-2.37 (m, 2H), 1.96-1.51 (m, 13H) ppm. $^{13}$C NMR (125 MHz, CDCl$_3$) δ 174.1, 164.1, 161.8, 158.3, 140.7, 137.1, 127.7, 127.0, 105.5, 74.2, 59.4, 58.2, 53.1, 47.6, 46.1, 44.6, 43.5, 39.2, 36.1, 29.0, 28.7, 25.1, 24.2, 24.1 ppm. Purity: >99% LCMS (214 nm & 254 nm); retention time 1.82 min; (M+H$^+$) 464.4.

Example 71

1-(4-(4-(2-Fluoroethoxy)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(2-fluoroethoxy)phenyl)-4,4,5,5-tetramethyl-1,3,2-dioxaborolane, the same reaction sequence outlined in Example 41 was used to generate the title compound. $^1$H NMR (500 MHz, CDCl$_3$) δ 8.34 (d, J=5.0 Hz, 1H), 8.04 (d, J=9.0 Hz, 2H), 7.02 (d, J=9.0 Hz, 2H), 6.89 (d, J=5.5 Hz, 1H), 5.36 (s, 1H), 4.98-4.95 (m, 2H), 4.86-4.74 (dt, J=48 Hz & 4.0 Hz, 1H), 4.33-4.26 (dt, J=27 Hz & 4.0 Hz, 1H), 3.03-2.83 (m, 8H), 2.39-2.36 (m, 2H), 1.97-1.51 (m, 13H) ppm. $^{13}$C NMR (125 MHz, CDCl$_3$) δ 174.1, 163.7, 161.8, 160.4, 158.1, 130.8, 128.5, 114.6, 104.9, 82.5, 81.1, 67.2, 67.1, 59.4, 53.1, 47.6, 46.1, 44.7, 43.5, 39.3, 36.1, 29.0, 28.7, 25.1, 24.3, 24.2 ppm. Purity: >99% LCMS (214 nm & 254 nm); retention time 1.47 min; (M+H$^+$) 482.2.

Example 72

1-(4-(4-(3-Methoxypropoxy)phenyl)pyrimidin-2-yl)-N-(quinuclidin-3-yl)piperidine-4-carboxamide Exchanging 4-fluorophenylboronic acid for 2-(4-(3-methoxypropoxy)phenyl)-4,4,5,5-tetramethyl-1,3,2-dioxaborolane and Intermediate 5 for quinuclidin-3-amine, the same reaction sequence outlined in Example 41 was used to generate the title compound. $^1$H NMR (500 MHz, CDCl$_3$) δ 8.34 (d, J=5.0 Hz, 1H), 8.03 (d, J=9.0 Hz, 2H), 7.00 (d, J=9.0 Hz, 2H), 6.89 (d, J=5.0 Hz, 1H), 6.14 (br s, 1H), 4.99 (d, J=13.0 Hz, 2H), 4.16 (t, J=6.5 Hz, 2H), 4.07 (m, 1H), 3.61 (t, J=6.0 Hz, 2H), 3.40-3.37 (m, 4H), 3.08-2.71 (m, 7H), 2.50-2.46 (m, 1H), 2.11-1.56 (m, 11H) ppm. $^{13}$C NMR (100 MHz, CDCl$_3$) δ 174.8, 163.8, 161.7, 161.1, 158.0, 130.0, 128.4, 114.5, 104.8, 69.1, 64.9, 58.7, 55.3, 47.3, 46.6, 46.0, 43.8, 43.5, 30.9, 29.6, 28.9, 28.6, 25.4, 25.1, 19.7 ppm. Purity: >99% LCMS (214 nm & 254 nm); retention time 1.26 min; (M+H$^+$) 480.3.

Example 73

1-(4-(4-(Methoxymethyl)phenyl)pyrimidin-2-yl)-N-(3-methylquinuclidin-3-yl)piperidine-4-carboxamide Exchanging 4-fluorophenylboronic acid for 2-(4-(methoxymethyl)phenyl)-4,4,5,5-tetramethyl-1,3,2-dioxaborolane and Intermediate 5 for Intermediate 1, the same reaction sequence outlined in Example 41 was used to generate the title compound. $^1$H NMR (400 MHz, CDCl$_3$) δ 8.36-8.34 (d, J=5.2 Hz, 1H), 8.02 (d, J=8.4 Hz, 2H), 7.43 (d, J=8.0 Hz, 2H), 6.92 (d, J=5.2 Hz, 1H), 5.45 (s, 1H), 4.95 (d, J=13.2 Hz, 2H), 4.52 (s, 2H), 3.41 (s, 3H), 3.00-2.76 (m, 8H), 2.40-2.35 (m, 1H), 2.15-2.13 (m, 1H), 1.95-1.47 (m, 11H) ppm. $^{13}$C NMR (100 MHz, CDCl$_3$) δ 174.3, 164.1, 161.8, 158.3, 140.7, 137.1, 127.8, 127.1, 105.5, 74.3, 63.4, 58.2, 52.9, 46.6, 46.4, 44.4, 43.5, 30.3, 28.8, 28.7, 24.4, 23.1, 22.5 ppm. Purity: >96% LCMS (214 nm & 254 nm); retention time 1.25 min; (M+H$^+$) 450.3.

Example 74

1-(4-(4-((2-Methoxyethoxy)methyl)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane, the same reaction sequence outlined in Example 41 was used to generate the title compound. $^1$H NMR (500 MHz, CDCl$_3$) δ 8.38 (d, J=5.5 Hz, 1H), 8.04 (d, J=8.0 Hz, 2H), 7.47 (d, J=8.0 Hz, 2H), 6.95 (d, J=5.5 Hz, 1H), 5.46 (s, 1H), 4.99-4.96 (m, 2H), 4.66 (s, 2H), 3.66-3.60 (m, 4H), 3.43 (s, 3H), 3.05-2.84 (m, 8H), 2.42-2.37 (m, 2H), 1.97-1.95 (m, 3H), 1.94-1.51 (m, 10H) ppm. $^{13}$C NMR (125 MHz, CDCl$_3$) δ 174.2, 164.1, 161.8, 158.3, 140.7, 137.1, 127.9, 127.1, 105.5, 72.9, 72.0, 69.4, 59.4, 59.1, 53.1, 47.7, 46.0, 44.6, 43.5, 38.9, 36.0, 31.0, 29.0, 28.7, 25.1, 24.0, 23.9 ppm. Purity: >98% LCMS (214 nm & 254 nm); retention time 1.29 min; (M+H$^+$) 508.3.

Example 75

4-Fluoro-1-(4-(4-(methoxymethyl)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(methoxymethyl)phenyl)-4,4,5,5-tetramethyl-1,3,2-dioxaborolane and ethyl piperidine-4-carboxylate for ethyl 4-fluoropiperidine-4-carboxylate hydrochloride, the same reaction sequence outlined in Example 41 was used to generate the title compound. $^1$H NMR (400 MHz, CDCl$_3$) δ 8.36 (d, J=5.6 Hz, 1H), 8.01 (d, J=8.0 Hz, 2H), 7.42 (d, J=8.0 Hz, 2H), 6.94 (d, J=5.6 Hz, 1H), 6.35 (m, 1H), 4.89-4.85 (m, 2H), 4.51 (s, 2H), 3.40 (s, 3H), 3.31-3.25 (m, 2H), 3.04-2.83 (m, 6H), 2.34-2.21 (m, 4H), 1.95-1.61 (m, 10H) ppm. $^{13}$C NMR (100 MHz, CDCl$_3$) δ 171.1, 170.9, 164.1, 161.7, 158.3, 140.7, 140.0, 127.8, 127.1, 105.8, 96.2 (d, J=185.6 Hz), 74.2, 59.3, 58.2, 53.1, 47.6, 46.0, 39.2, 39.0, 36.2, 32.2, 32.0, 31.7, 25.0, 24.3, 24.1 ppm. Purity: >97% LCMS (214 nm & 254 nm); retention time 1.37 min; (M+H$^+$) 482.2.

Example 76

4-Fluoro-1-(4-(4-(3-methoxypropoxy)phenyl)pyrimidin-2-yl)-N-(3-methylquinuclidin-3-yl)piperidine-4-carboxamide Exchanging 4-fluorophenylboronic acid for 2-(4-(3-methoxypropoxy)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for Intermediate 1, the same reaction sequence outlined in Example 41 was used to generate the title compound. $^1$H NMR (400 MHz, CDCl$_3$) δ 8.33 (d, J=5.2 Hz, 1H), 8.01 (d, J=8.8 Hz, 2H), 6.98 (d, J=9.2 Hz, 2H), 6.91 (d, J=5.2 Hz, 1H), 6.39 (d, J=6.4 Hz, 1H), 4.89-4.85 (m, 2H), 4.13 (t, J=6.4 Hz, 2H), 3.59 (t, J=6.4 Hz, 2H), 3.38 (s, 3H), 3.01-3.26 (m, 2H), 3.05-2.82 (m, 6H), 2.31-2.05 (m, 6H), 1.86-

1.51 (m, 8H) ppm. $^{13}$C NMR (100 MHz, CDCl$_3$) δ 171.4, 171.2, 163.9, 161.7, 161.1, 158.0, 130.0, 128.5, 114.5, 105.2, 97.1, 69.1, 64.9, 63.0, 58.7, 52.7, 46.5, 46.4, 39.3, 32.1, 32.0, 31.9, 31.8, 30.1, 29.6, 24.2, 22.8, 22.3 ppm. Purity: >96% LCMS (214 nm & 254 nm); retention time 1.54 min; (M+H$^+$) 512.3.

Example 77

4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane, ethyl piperidine-4-carboxylate for ethyl 4-fluoropiperidine-4-carboxylate hydrochloride, and 2,4-dichloropyrimidine for 2,4-dichloro-5-fluoropyrimidine, the same reaction sequence outlined in Example 41 was used to generate the title compound. $^1$H NMR (400 MHz, CDCl$_3$) δ 8.24 (d, J=3.6 Hz, 1H), 8.05 (d, J=8.2 Hz, 2H), 7.46 (d, J=8.2 Hz, 2H), 6.34 (d, J=7.2 Hz, 1H), 4.75-4.72 (m, 2H), 4.65 (s, 2H), 3.66-3.58 (m, 4H), 3.41 (s, 3H), 3.31-3.24 (m, 2H), 3.05-2.85 (m, 6H), 2.35-2.17 (m, 3H), 1.96-1.50 (m, 11H) ppm. $^{13}$C NMR (100 MHz, CDCl$_3$) δ 171.1, 170.9, 158.2, 151.3, 146.8, 140.9, 133.3, 129.0, 127.6, 97.0, 72.8, 72.0, 69.5, 59.3, 59.1, 53.0, 47.6, 46.0, 39.9, 38.8, 36.2, 35.1, 31.8, 31.7, 25.0, 24.2, 24.0 ppm. Purity: >99% LCMS (214 nm & 254 nm); retention time 1.57 min; (M+H$^+$) 544.3.

Example 78

4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide (Single Enantiomer A)

Exchanging 4-fluorophenylboronic acid for 2-(4-((2-methoxyethoxy)methyl)phenyl)-4,4,5,5-tetramethyl-1,3,2-dioxaborolane, ethyl piperidine-4-carboxylate for ethyl 4-fluoropiperidine-4-carboxylate hydrochloride, 2,4-dichloropyrimidine for 2,4-dichloro-5-fluoropyrimidine and Intermediate 5 for Intermediate 9, the same reaction sequence outlined in Example 41 was used to generate the title compound. $^1$H NMR (400 MHz, CDCl$_3$) δ 8.24 (d, J=3.5 Hz, 1H), 8.05 (d, J=8.4 Hz, 2H), 7.46 (d, J=8.4 Hz, 2H), 6.34 (d, J=7.3 Hz, 1H), 4.78-4.70 (m, 2H), 4.65 (s, 2H), 3.67-3.63 (m, 2H), 3.62-3.57 (m, 2H), 3.41 (s, 3H), 3.33-3.22 (m, 2H), 3.09-2.78 (m, 6H), 2.36-2.10 (m, 3H), 2.00-1.70 (m, 6H), 1.67-1.46 (m, 5H) ppm. Purity: >99.9% (214 & 254 nm) UPLCMS; retention time: 0.92 min; (M+H$^+$) 544.5.

Example 79

4-Fluoro-1-(5-fluoro-4-(4-((2-methoxyethoxy)methyl)phenyl)pyrimidin-2-yl)-N-(4-50 methyl-1-azabicyclo[3.2.2]nonan-4-yl)piperidine-4-carboxamide Single Enantiomer B Exchanging 4-fluorophenylboronic acid for 2-(4-((2-methoxyethoxy)methyl)phenyl)-4,4,5,5-tetramethyl-1,3,2-dioxaborolane, ethyl piperidine-4-carboxylate for ethyl 4-fluoropiperidine-4-carboxylate hydrochloride, 2,4-dichloropyrimidine for 2,4-dichloro-5-fluoropyrimidine and Intermediate 5 for Intermediate 10, the same reaction sequence outlined in Example 41 was used to generate the title compound. $^1$H NMR (400 MHz, CDCl$_3$) δ 8.24 (d, J=3.5 Hz, 1H), 8.05 (d, J=8.4 Hz, 2H), 7.46 (d, J=8.4 Hz, 2H), 6.34 (d, J=7.3 Hz, 1H), 4.78-4.70 (m, 2H), 4.65 (s, 2H), 3.67-3.63 (m, 2H), 3.62-3.57 (m, 2H), 3.41 (s, 3H), 3.33-3.22 (m, 2H), 3.09-2.78 (m, 6H), 2.36-2.10 (m, 3H), 2.00-1.70 (m, 6H), 1.67-1.46 (m, 5H) ppm. Purity: >99.9% (214 & 254 nm) UPLCMS; retention time: 0.92 min; (M+H$^+$) 544.5.

Example 80

4-Fluoro-1-(4-(4-(methoxymethyl)phenyl)pyrimidin-2-yl)-N-(3-methylquinuclidin-3-yl)piperidine-4-carboxamide Exchanging 4-fluorophenylboronic acid for 2-(4-(methoxymethyl)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for Intermediate 1, the same reaction sequence outlined in Example 41 was used to generate the title compound. $^1$H NMR (500 MHz, CDCl$_3$) δ 8.40 (d, J=5.5 Hz, 1H), 8.05 (d, J=8.0 Hz, 2H), 7.45 (d, J=8.0 Hz, 2H), 6.98 (d, J=4.5 Hz, 1H), 6.44 (d, J=7.0 Hz, 1H), 4.90 (d, J=13.5 Hz, 2H), 4.55 (s, 2H), 3.44 (s, 3H), 3.31 (t, J=13.0 Hz, 2H), 3.08-2.88 (m, 6H), 2.34-2.20 (m, 5H), 1.91-1.53 (m, 7H) ppm. $^{13}$C NMR (125 MHz, CDCl$_3$) δ 171.4, 171.3, 164.2, 161.7, 158.4, 140.7, 137.0, 127.8, 127.1, 105.9, 96.9, 95.4, 74.2, 62.6, 58.2, 52.7, 46.4, 46.2, 39.3, 32.1, 31.9, 31.8, 31.0, 30.1, 24.2, 22.6, 22.0 ppm. Purity: >97% LCMS (214 nm & 254 nm); retention time 1.50 min; (M+H$^+$) 468.3.

Example 81

(S)-4-Fluoro-1-(4-(4-(methoxymethyl)phenyl)pyrimidin-2-yl)-N-(3-methylquinuclidin-3-yl)piperidine-4-carboxamide Exchanging 4-fluorophenylboronic acid for 2-(4-(methoxymethyl)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for Intermediate 11, the same reaction sequence outlined in Example 41 was used to generate the title compound. $^1$H NMR (500 MHz, CDCl$_3$) δ 8.39 (d, J=5.5 Hz, 1H), 8.04 (d, J=8.5 Hz, 2H), 7.45 (d, J=8.5 Hz, 2H), 6.97 (d, J=5.5 Hz, 1H), 6.40 (d, J=6.5 Hz, 1H), 4.90-4.87 (m, 2H), 4.54 (s, 2H), 3.43 (s, 3H), 3.34-3.28 (m, 2H), 3.02-2.82 (m, 6H), 2.34-2.20 (m, 5H), 1.91-1.51 (m, 7H) ppm. $^{13}$C NMR (125 MHz, CDCl$_3$) δ 171.3, 171.2, 164.2, 161.7, 158.3, 140.7, 137.0, 127.8, 127.1, 105.9, 96.9, 95.4, 74.2, 63.2, 58.2, 52.8, 46.6, 46.4, 39.3, 32.1, 32.0, 31.9, 31.8, 30.1, 24.2, 23.0, 22.4 ppm. Purity: >99% LCMS (214 nm & 254 nm); retention time 1.38 min; (M+H$^+$) 468.2.

Example 82

4-Fluoro-1-(4-(4-(3-methoxypropoxy)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(3-methoxypropoxy)phenyl)-4,4,5,5-tetramethyl-1,3,2-dioxaborolane and ethyl piperidine-4-carboxylate for ethyl 4-fluoropiperidine-4-carboxylate hydrochloride, the same reaction sequence outlined in Example 41 was used to generate the title compound. $^1$H NMR (400 MHz, CDCl$_3$) δ 8.33 (d, J=5.2 Hz, 1H), 8.01 (d, J=8.8 Hz, 2H), 6.98 (d, J=8.4 Hz, 2H), 6.91 (d, J=5.2 Hz, 1H), 6.36 (d, J=7.6 Hz, 1H), 4.89-4.86 (m, 2H), 4.13 (t, J=6.4 Hz, 2H), 3.59 (t, J=6.4 Hz, 2H), 3.38 (s, 3H), 3.32-3.26 (m, 2H), 3.05-2.91 (m, 6H), 2.41-1.59 (m, 16H) ppm. $^{13}$C NMR (100 MHz, CDCl$_3$) δ 171.3, 171.1, 163.9, 161.7, 161.1, 158.0, 129.9, 128.5, 114.5, 105.2, 97.2, 69.1, 64.9, 59.2, 58.7, 52.8, 47.5, 45.9, 39.3, 38.2, 36.0, 32.2, 32.0, 31.9, 31.7, 29.6, 25.0, 23.6, 23.4, 23.3 ppm. Purity: >96% LCMS (214 nm & 254 nm); retention time 1.57 min; (M+H$^+$) 526.4.

Example 83

4-Fluoro-1-(4-(4-((2-methoxyethoxy)methyl)phenyl)pyrimidin-2-yl)-N-(3-methylquinuclidin-3-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for Intermediate 1, the same reaction sequence outlined in Example 41 was used to generate the title compound. $^1$H NMR (500 MHz, CDCl$_3$) δ 8.39 (d, J=5.5 Hz, 1H), 8.04 (d, J=8.0 Hz, 2H), 7.47 (d, J=8.0 Hz, 2H), 6.97 (d, J=5.0 Hz, 1H), 6.39 (d, J=7.5 Hz, 1H), 4.89 (d, J=13.0 Hz, 2H), 4.66 (s, 2H), 3.67-3.60 (m, 4H), 3.43 (s, 3H), 3.30 (t, J=12.0 Hz, 2H), 2.97-2.83 (m, 6H), 2.35-2.19 (m, 3H), 1.91-1.51 (m, 9H) ppm. $^{13}$C NMR (125 MHz, CDCl$_3$) δ 171.3, 171.2, 164.2, 161.7, 158.4, 140.7, 137.0, 127.9, 127.1, 105.9, 96.9, 95.4, 72.9, 72.0, 69.4, 63.2, 59.1, 52.8, 46.5, 46.4, 39.3, 32.1, 32.0, 31.9, 31.8, 31.0, 30.1, 24.2, 23.0, 22.4 ppm. Purity: >99% LCMS (214 nm & 254 nm); retention time 1.34 min; (M+H$^{+)}$ 512.3.

Example 84

(S)-4-Fluoro-1-(4-(4-((2-methoxyethoxy)methyl)phenyl)pyrimidin-2-yl)-N-(3-methylquinuclidin-3-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for Intermediate 11, the same reaction sequence outlined in Example 41 was used to generate the title compound. $^1$H NMR (500 MHz, CDCl$_3$) δ 8.38 (d, J=5.0 Hz, 1H), 8.03 (d, J=8.0 Hz, 2H), 7.46 (d, J=8.0 Hz, 2H), 6.96 (d, J=5.5 Hz, 1H), 6.41 (d, J=7.0 Hz, 1H), 4.88 (m, 2H), 4.65 (s, 2H), 3.67-3.59 (m, 4H), 3.42 (s, 3H), 3.33-3.27 (m, 2H), 3.03-2.81 (m, 6H), 2.33-2.20 (m, 4H), 1.92-1.85 (m, 3H), 1.59-1.49 (m, 5H) ppm. $^{13}$C NMR (100 MHz, CDCl$_3$) δ 171.4, 171.2, 164.2, 161.7, 158.3, 140.8, 137.0, 127.8, 127.1, 105.9, 96.9, 95.4, 72.9, 72.0, 69.4, 63.1, 59.1, 52.8, 46.5, 46.4, 39.3, 32.1, 32.0, 31.9, 31.8, 30.1, 24.2, 22.9, 22.3 ppm. Purity: >99% LCMS (214 nm & 254 nm); retention time 1.34 min; (M+H$^+$) 512.3.

Example 85

4-Fluoro-1-(4-(4-(2-methoxyethoxy)phenyl)pyrimidin-2-yl)-N-(3-methylquinuclidin-3-yl)piperidine-4-carboxamide Exchanging 4-fluorophenylboronic acid for (4-(2-methoxyethoxy)phenyl)boronic acid, ethyl piperidine-4-carboxylate for ethyl 4-fluoropiperidine-4-carboxylate hydrochloride and Intermediate 5 for Intermediate 1, the same reaction sequence outlined in Example 41 was used to generate the title compound. $^1$H NMR (500 MHz, CDCl$_3$) δ 8.35 (d, J=5.0 Hz, 1H), 8.03 (d, J=9.0 Hz, 2H), 7.02 (d, J=9.0 Hz, 2H), 6.92 (d, J=5.5 Hz, 1H), 6.58 (d, J=6.5 Hz, 1H), 4.89-4.86 (m, 2H), 4.21 (t, J=5.0 Hz, 2H), 3.81 (t, J=5.0 Hz, 2H), 3.49 (s, 3H), 3.35-3.27 (m, 2H), 3.07-2.98 (m, 6H), 2.38-2.20 (m, 3H), 1.94-1.56 (m, 9H) ppm. $^{13}$C NMR (125 MHz, CDCl$_3$) δ 171.7, 171.5, 163.9, 161.7, 160.8, 158.1, 130.2, 128.5, 114.6, 105.3, 96.9, 95.4, 70.9, 67.3, 61.4, 59.3, 54.8, 52.5, 46.2, 45.9, 39.2, 32.1, 31.9, 31.8, 31.7, 30.9, 29.8, 24.2, 24.1, 21.8, 21.3 ppm. Purity: >99% LCMS (214 nm & 254 nm); retention time 1.32 min; (M+H$^+$) 497.9.

Example 86

(S)-4-Fluoro-1-(4-(4-(2-methoxyethoxy)phenyl)pyrimidin-2-yl)-N-(3-methylquinuclidin-3-yl)piperidine-4-carboxamide Exchanging 4-fluorophenylboronic acid for (4-(2-methoxyethoxy)phenyl)boronic acid, ethyl piperidine-4-carboxylate for ethyl 4-fluoropiperidine-4-carboxylate hydrochloride and Intermediate 5 for Intermediate 11, the same reaction sequence outlined in Example 41 was used to generate the title compound. $^1$H NMR (500 MHz, CDCl$_3$) δ 8.34 (d, J=4.5 Hz, 1H), 8.02 (dd, J=11.0 Hz & 2.5 Hz, 2H), 7.02 (dd, J=11.0 Hz & 2.5 Hz, 2H), 6.91 (d, J=5.5 Hz, 1H), 6.38 (d, J=7.0 Hz, 1H), 4.89-4.86 (m, 2H), 4.20 (t, J=5.0 Hz, 2H), 3.80 (t, J=5.0 Hz, 2H), 3.48 (s, 3H), 3.32-3.26 (m, 2H), 2.95-2.74 (m, 6H), 2.33-2.18 (m, 3H), 1.92-1.75 (m, 4H), 1.58-1.43 (m, 5H) ppm. $^{13}$C NMR (125 MHz, CDCl$_3$) δ 171.3, 171.2, 163.9, 161.7, 160.8, 158.1, 130.3, 128.5, 114.6, 105.2, 96.9, 95.4, 70.9, 67.3, 63.3, 59.2, 52.8, 46.5, 46.4, 39.3, 32.1, 32.0, 31.9, 31.8, 30.1, 24.2, 23.0, 22.4 ppm. Purity: >99% LCMS (214 nm & 254 nm); retention time 1.35 min; (M+H$^+$) 498.2.

Example 87

4-Fluoro-1-(4-(4-(2-fluoroethoxy)phenyl)pyrimidin-2-yl)-N-(quinuclidin-3-yl)piperidine-4-carboxamide Exchanging 4-fluorophenylboronic acid for 2-(4-(2-fluoroethoxy)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for quinuclidin-3-amine, the same reaction sequence outlined in Example 41 was used to generate the title compound. $^1$H NMR (500 MHz, CDCl$_3$) δ 8.36 (d, J=4.5 Hz, 1H), 8.05 (d, J=9.0 Hz, 2H), 7.03 (d, J=8.5 Hz, 2H), 6.93 (d, J=5.5 Hz, 1H), 6.85 (m, 1H), 4.91-4.76 (m, 4H), 4.32-4.06 (dt, J=19.5 Hz & 4.5 Hz, 2H), 4.07-4.06 (m, 1H), 3.47-3.30 (m, 3H), 3.12-2.80 (m, 5H), 2.32-1.62 (m, 9H) ppm. $^{13}$C NMR (125 MHz, CDCl$_3$) δ 171.9, 171.7, 163.8, 161.6, 160.4, 158.2, 130.7, 128.6, 114.6, 105.2, 96.8, 82.5, 81.1, 67.2, 67.0, 55.1, 47.1, 46.5, 45.8, 39.2, 32.2, 32.1, 31.9, 25.4, 24.9, 19.5 ppm. Purity: >95% LCMS (214 nm & 254 nm); retention time 1.31 min; (M+H$^+$) 472.0.

Example 88

(S)-4-Fluoro-1-(4-(4-(2-fluoroethoxy)phenyl)pyrimidin-2-yl)-N-(quinuclidin-3-yl)piperidine-4-carboxamide Exchanging 4-fluorophenylboronic acid for 2-(4-(2-fluoroethoxy)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for (S)-quinuclidin-3-amine, the same reaction sequence outlined in Example 41 was used to generate the title compound. $^1$H NMR (500 MHz, CDCl$_3$) δ 8.36 (d, J=5.5 Hz, 1H), 8.04 (dd, J=7.0 Hz & 2.0 Hz, 2H), 7.03 (d, J=8.5 Hz, 2H), 6.93 (d, J=5.0 Hz, 1H), 6.65 (t, J=6.5 Hz, 1H), 4.91-4.86 (m, 3H), 4.77 (t, J=4.0 Hz, 1H), 4.34-4.26 (m, 2H), 4.00 (m, 1H), 3.45-3.34 (m, 1H), 3.35-3.30 (m, 2H), 2.89-2.83 (m, 4H), 2.61-2.58 (m, 1H), 2.35-2.20 (m, 2H), 2.00-1.87 (m, 3H), 1.75-1.70 (m, 3H), 1.58-1.55 (m, 1H) ppm. $^{13}$C NMR (100 MHz, CDCl$_3$) δ 171.8, 171.6, 163.8, 161.6, 160.4, 158.2, 130.6, 128.6, 114.6, 105.2, 97.1, 95.2, 82.7, 81.0, 67.2, 67.0, 55.7, 47.3, 46.6, 46.0, 39.2, 32.2, 32.1, 32.0, 31.9, 25.5, 25.4, 19.8 ppm. Purity: >95% LCMS (214 nm & 254 nm); retention time 1.35 min; (M+H$^+$) 472.2.

Example 89

4-Fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane and ethyl piperidine-4-carboxylate for ethyl 4-fluoropiperidine-4-carboxylate hydrochloride, the same reaction sequence outlined in Example 41 was used to generate the title compound. $^1$H NMR (500 MHz, CDCl$_3$) δ 8.39 (d, J=5.5 Hz, 1H), 8.04 (d, J=8.5 Hz, 2H), 7.47 (d, J=8.0 Hz, 2H), 6.95 (d, J=5.0 Hz, 1H), 6.67 (d, J=7.5 Hz, 1H), 4.90-4.87 (m, 2H), 4.66 (s, 2H), 3.67-3.61 (m, 4H), 3.43 (s, 3H), 3.33-3.27 (m, 2H), 3.04-2.87 (m, 6H), 2.38-2.24 (m, 3H), 1.89-1.52 (m, 11H) ppm. $^{13}$C NMR (125 MHz, CDCl$_3$) δ 171.1, 171.0, 164.2, 161.7, 158.4, 140.7, 137.0, 127.9, 127.1, 124.8, 105.9, 96.9, 95.5, 72.9, 72.0, 69.4, 59.3, 59.1, 53.0, 47.5, 46.0, 39.3, 38.9, 36.2, 32.2, 32.0, 31.9, 31.7, 31.0, 25.0, 24.2, 24.0 ppm. Purity: >99% LCMS (214 nm & 254 nm); retention time 1.36 min; (M+H$^+$) 526.3.

Example 90

4-Fluoro-1-(4-(4-(2-fluoroethoxy)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(2-fluoroethoxy)phenyl)-4,4,5,5-tetramethyl-1,3,2-dioxaborolane and ethyl piperidine-4-carboxylate for ethyl 4-fluoropiperidine-4-carboxylate hydrochloride, the same reaction sequence outlined in Example 41 was used to generate the title compound. $^1$H NMR (500 MHz, CDCl$_3$) δ 8.36 (d, J=5.5 Hz, 1H), 8.04 (d, J=9.0 Hz, 2H), 7.03 (d, J=8.5 Hz, 2H), 6.93 (d, J=5.0 Hz, 1H), 6.38 (d, J=7.0 Hz, 1H), 4.90-4.76 (m, 4H), 4.34-4.27 (m, 2H), 3.33-3.27 (m, 2H), 3.11-2.88 (m, 6H), 2.40-2.21 (m, 3H), 2.04-1.53 (m, 11H) ppm. $^{13}$C NMR (125 MHz, CDCl$_3$) δ 171.2, 171.1, 163.8, 161.7, 160.4, 158.2, 130.7, 128.6, 114.6, 105.3, 97.0, 95.5, 82.5, 81.1, 67.2, 67.1, 59.2, 52.8, 47.5, 45.9, 39.3, 38.4, 36.1, 32.2, 32.0, 31.7, 25.0, 23.8, 23.6 ppm. Purity: >96% LCMS (214 nm & 254 nm); retention time 1.33 min; (M+H$^+$) 500.0.

Example 91

4-Fluoro-1-(5-fluoro-4-(4-(2-methoxyethoxy)phenyl)pyrimidin-2-yl)-N-(4-methyl-1-azabicyclo[3.2.2]nonan-4-yl)piperidine-4-carboxamide Exchanging 4-fluorophenylboronic acid for (4-(2-methoxyethoxy)phenyl)boronic acid, ethyl piperidine-4-carboxylate for ethyl 4-fluoropiperidine-4-carboxylate hydrochloride and 2,4-dichloropyrimidine for 2,4-dichloro-5-fluoropyrimidine, the same reaction sequence outlined in Example 41 was used to generate the title compound. $^1$H NMR (500 MHz, CDCl$_3$) δ 8.22 (d, J=3.5 Hz, 1H), 8.10 (d, J=9.0 Hz, 2H), 7.03 (d, J=8.0 Hz, 2H), 6.37 (d, J=7.5 Hz, 1H), 4.75 (m, 2H), 4.21 (t, J=4.5 Hz, 2H), 3.80 (t, J=4.5 Hz, 2H), 3.49 (s, 3H), 3.31-3.26 (m, 2H), 3.10-2.91 (m, 6H), 2.41-2.22 (m, 3H), 2.01-1.53 (m, 11H) ppm. $^{13}$C NMR (125 MHz, CDCl$_3$) δ 171.4, 171.2, 160.8, 158.1, 151.0, 150.9, 150.7, 148.7, 146.4, 146.2, 130.6, 130.5, 126.7, 114.5, 96.8, 95.3, 70.9, 67.3, 63.7, 59.3, 59.1, 52.2, 47.1, 45.4, 39.9, 37.3, 35.7, 32.0, 31.8, 31.7, 31.5, 25.0, 22.8, 22.6 ppm. Purity: >99% LCMS (214 nm & 254 nm); retention time 1.44 min; (M+H$^+$) 530.2.

Example 92

4-Fluoro-1-(4-(4-(2-fluoroethoxy)phenyl)pyrimidin-2-yl)-N-(3-methylquinuclidin-3-yl)piperidine-4-carboxamide Exchanging 4-fluorophenylboronic acid for 2-(4-(2-fluoroethoxy)phenyl)-4,4,5,5-tetramethyl-1,3,2-dioxaborolane, ethyl piperidine-4-carboxylate for ethyl 4-fluoropiperidine-4-carboxylate hydrochloride and Intermediate 5 for Intermediate 1, the same reaction sequence outlined in Example 41 was used to generate the title compound. $^1$H NMR (400 MHz, CDCl$_3$) δ 8.35 (d, J=5.2 Hz, 1H), 8.04 (d, J=8.8 Hz, 2H), 7.02 (d, J=8.4 Hz, 2H), 6.92 (d, J=5.6 Hz, 1H), 6.41 (d, J=6.8 Hz, 1H), 4.88-4.74 (m, 4H), 4.35-4.26 (m, 2H), 3.31-3.29 (m, 2H), 3.00-2.85 (m, 6H), 2.41-2.19 (m, 3H), 1.96-1.52 (m, 9H) ppm. $^{13}$C NMR (100 MHz, CDCl$_3$) δ 171.4, 171.2, 163.8, 161.7, 160.4, 158.1, 130.7, 128.6, 114.6, 105.3, 97.1, 95.2, 82.6, 80.9, 67.3, 67.1, 63.0, 52.8, 46.5, 46.3, 39.3, 32.1, 32.0, 31.9, 31.8, 30.9, 30.1, 24.2, 22.8, 22.3 ppm. Purity: >99% LCMS (214 nm & 254 nm); retention time 1.32 min; (M+H$^+$) 486.0.

Example 93

4-Fluoro-1-(4-(4-(2-methoxyethoxy)phenyl)pyrimidin-2-yl)-N-(4-methyl-1-azabicyclo[3.2.2]nonan-4-yl)piperidine-4-carboxamide Exchanging 4-fluorophenylboronic acid for (4-(2-methoxyethoxy)phenyl)boronic acid and ethyl piperidine-4-carboxylate for ethyl 4-fluoropiperidine-4-carboxylate hydrochloride, the same reaction sequence outlined in Example 41 was used to generate the title compound. $^1$H NMR (500 MHz, CDCl$_3$) δ 8.35 (d, J=5.0 Hz, 1H), 8.03 (d, J=9.0 Hz, 2H), 7.02 (d, J=9.0 Hz, 2H), 6.92 (d, J=5.5 Hz, 1H), 6.37 (d, J=7.0 Hz, 1H), 4.88 (m, 2H), 4.21 (t, J=4.5 Hz, 2H), 3.81 (t, J=4.5 Hz, 2H), 3.49 (s, 3H), 3.32-3.27 (m, 2H), 3.09-2.89 (m, 6H), 2.40-2.21 (m, 3H), 2.01-1.53 (m, 11H) ppm. $^{13}$C NMR (100 MHz, CDCl$_3$) δ 171.2, 171.0, 163.9, 161.7, 160.8, 158.1, 130.3, 128.5, 114.6, 105.2, 97.2, 95.3, 70.9, 67.3, 59.3, 53.0, 47.5, 46.0, 39.3, 38.7, 36.2, 32.2, 32.0, 31.9, 31.7, 25.0, 24.1, 23.8 ppm. Purity: >99% LCMS (214 nm & 254 nm); retention time 1.33 min; (M+H$^+$) 512.0.

Example 94

4-Fluoro-1-(4-(4-fluorophenyl)pyrimidin-2-yl)-N-(4-methyl-1-azabicyclo[3.2.2]nonan-4-yl)piperidine-4-carboxamide Exchanging ethyl piperidine-4-carboxylate for ethyl 4-fluoropiperidine-4-carboxylate hydrochloride, the same reaction sequence outlined in Example 41 was used to generate the title compound. $^1$H NMR (400 MHz, CDCl$_3$) δ 8.36 (d, J=5.2 Hz, 1H), 8.07-7.96 (m, 2H), 7.14 (t, J=8.7 Hz, 2H), 6.89 (d, J=5.2 Hz, 1H), 6.35 (d, J=7.2 Hz, 1H), 4.92-4.76 (m, 2H), 3.36-3.19 (m, 2H), 3.10-2.73 (m, 6H), 2.38-2.12 (m, 3H), 2.02-1.68 (m, 6H), 1.67-1.40 (m, 5H) ppm. Purity: 99.7% (214 & 254 nm) UPLCMS; retention time: 0.87 min; (M+H$^+$) 456.5.

Example 95

4-Fluoro-1-(4-(4-fluorophenyl)pyrimidin-2-yl)-N-(3-methylquinuclidin-3-yl)piperidine-4-carboxamide Exchanging ethyl piperidine-4-carboxylate for ethyl 4-fluoropiperidine-4-carboxylate hydrochloride and Intermediate 5 for Intermediate 1, the same reaction sequence outlined in Example 41 was used to generate the title compound. $^1$H NMR (400 MHz, CDCl$_3$) δ 8.36 (d, J=5.1 Hz, 1H), 8.07-7.97 (m, 2H), 7.18-7.06 (m, 2H), 6.89 (d, J=5.1 Hz, 1H), 6.37 (d, J=6.9 Hz, 1H), 4.93-4.75 (m, 2H), 3.37-3.18 (m, 2H), 2.99-2.67 (m, 6H), 2.37-2.09 (m, 3H), 1.95-1.67 (m, 4H), 1.60-1.34 (m, 5H) ppm. Purity: 99.7% (214 & 254 nm) UPLCMS; retention time: 0.92 min; (M+H$^+$) 442.5.

Example 96

1-(4-(4-(Methoxymethyl)phenyl)pyrimidin-2-yl)-4-methyl-N-(4-methyl-1-azabicyclo[3.2.2]nonan-4-yl)piperidine-4-carboxamide Exchanging 4-fluorophenylboronic acid for 2-(4-(methoxymethyl)phenyl)-4,4,5,5-tetramethyl-1,3,2-dioxaborolane and ethyl 4-piperidine-4-carboxylate for ethyl 4-methylpiperidine-4-carboxylate hydrochloride, the same reaction sequence outlined in Example 41 was used to generate the title compound. $^1$H NMR (400 MHz, CDCl$_3$) δ 8.35 (d, J=5.1 Hz, 1H), 8.03 (d, J=8.2 Hz, 2H), 7.43 (d, J=8.2 Hz, 2H), 6.92 (d, J=5.1 Hz, 1H), 5.48 (s, 1H), 4.52 (s, 2H), 4.27-4.16 (m, 2H), 3.75-3.64 (m, 2H), 3.41 (s, 3H), 3.09-2.74 (m, 6H), 2.44-2.32 (m, 1H), 2.11-2.01 (m, 2H), 2.00-1.89 (m, 1H), 1.87-1.45 (m, 10H), 1.27 (s, 3H) ppm. Purity: >99.9% (214 & 254 nm) UPLCMS; retention time: 0.83 min; (M+H$^+$) 478.4.

Example 97

1-(4-(4-((2-Methoxyethoxy)methyl)phenyl)pyrimidin-2-yl)-4-methyl-N-(4-methyl-1-azabicyclo[3.2.2]nonan-4-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane and ethyl 4-piperidine-4-carboxylate for ethyl 4-methylpiperidine-4-carboxylate hydrochloride, the same reaction sequence outlined in Example 41 was used to generate the title compound. $^1$H NMR (400 MHz, CDCl$_3$) δ 8.36-8.35 (d, J=5.2 Hz, 1H), 8.03 (d, J=8.0 Hz, 2H), 7.45 (d, J=8.0 Hz, 2H), 6.92 (d, J=4.8 Hz, 1H), 5.50 (s, 1H), 4.64 (s, 2H), 4.23-4.19 (m, 2H), 3.72-3.58 (m, 6H), 3.41 (s, 3H), 3.08-2.84 (m, 6H), 2.42 (m, 1H), 2.07-1.50 (m, 13H), 1.27 (s, 3H) ppm. $^{13}$C NMR (100 MHz, CDCl$_3$) δ 175.9, 164.0, 161.8, 158.3, 140.7, 137.0, 127.8, 127.0, 105.4, 72.9, 72.0, 69.4, 59.3, 59.1, 53.2, 47.8, 45.9, 41.9, 40.9, 39.2, 36.2, 34.9, 25.8, 25.1, 24.3, 24.2 ppm. Purity: >95% LCMS (214 nm & 254 nm); retention time: 1.35 min; (M+H$^+$) 522.3.

Example 98

1-(4-(4-((2-Methoxyethoxy)methyl)phenyl)pyrimidin-2-yl)-4-methyl-N-(3-methylquinuclidin-3-yl)piperidine-4-carboxamide Exchanging 4-fluorophenylboronic acid for 2-(4-((2-methoxyethoxy)methyl)phenyl)-4,4,5,5-tetramethyl-1,3,2-dioxaborolane, ethyl 4-piperidine-4-carboxylate for ethyl 4-methylpiperidine-4-carboxylate hydrochloride and Intermediate 5 for Intermediate 1, the same reaction sequence outlined in Example 41 was used to generate the title compound. $^1$H NMR (500 MHz, CDCl$_3$) δ 8.37 (d, J=4.5 Hz, 1H), 8.04 (d, J=8.0 Hz, 2H), 7.46 (d, J=8.5 Hz, 2H), 6.93 (d, J=5.5 Hz, 1H), 5.62 (s, 1H), 4.66 (s, 2H), 4.26-4.23 (m, 2H), 3.71-3.60 (m, 6H), 3.43 (s, 3H), 3.04-2.82 (m, 6H), 2.20 (m, 1H), 2.10-2.07 (m, 2H), 1.82-1.49 (m, 9H), 1.29 (s, 3H) ppm. $^{13}$C NMR (125 MHz, CDCl$_3$) δ 176.0, 164.0, 161.8, 158.3, 140.7, 137.1, 127.8, 127.1, 105.4, 72.9, 72.0, 69.4, 63.2, 59.1, 52.8, 48.8, 46.6, 46.5, 41.8, 41.0, 34.9, 30.6, 25.8, 24.2, 23.0, 22.6 ppm. Purity: >99% LCMS (214 nm & 254 nm); retention time 1.33 min; (M+H$^+$) 508.3.

Example 99

1-(4-(4-Fluorophenyl)pyrimidin-2-yl)-4-hydroxy-N-(4-methyl-1-azabicyclo[3.2.2]nonan-4-yl)piperidine-4-carboxamide To a stirred solution of 2,4-dichloropyrimidine (3.00 g, 20.1 mmol) in toluene (25 mL) was added 4-fluorophenylboronic acid (2.82 g, 20.1 mmol), potassium carbonate (8.32 g, 60.3 mmol), tetrakis(triphenylphosphine)palladium(0) (0.630 g, 0.545 mmol) and 1:1 (v/v) ethanol/water (36 mL). The mixture was heated at 55° C. for 12 hours and then concentrated. The residue was diluted with water and extracted with ethyl acetate. The combined extracts were washed with brine, dried (Na$_2$SO$_4$) and concentrated. The crude material was purified by flash chromatography over silica using a hexane/ethyl acetate eluant to afford 2-chloro-4-(4-fluorophenyl)pyrimidine as a yellow solid (2.50 g, 61%). To a stirred solution of this compound (1.04 g, 5.00 mmol) in N,N-dimethylformamide (15 mL) was added 4-hydroxypiperidine-4-carboxylic acid (0.910 g, 5.00 mmol) and cesium carbonate (3.43 g, 10.5 mmol). The mixture was heated overnight at 100° C. and then concentrated. The residue was purified by flash chromatography over silica using a hexane/ethyl acetate eluant to afford 1-(4-(4-fluorophenyl)pyrimidin-2-yl)-4-hydroxypiperidine-4-carboxylic acid as a yellow solid (1.02 g, 64%). Using General Procedure D and Intermediate 5, this carboxylic acid was subjected to amide coupling to generate the title compound as a white solid (0.071 g, 39%). $^1$H NMR (500 MHz, CDCl$_3$) δ 8.37 (d, J=5.0 Hz, 1H), 8.07-8.04 (m, 2H), 7.15 (t, J=8.5 Hz, 2H), 6.89 (d, J=5.0 Hz, 1H), 6.74 (s, 1H), 4.82 (d, J=12.5 Hz, 2H), 3.99 (br s, 1H), 3.34-3.30 (m, 2H), 3.01-2.84 (m, 6H), 2.39 (m, 1H), 2.17-2.14 (m, 2H), 1.95-1.49 (m, 11H) ppm. $^{13}$C NMR (125 MHz, CDCl$_3$) δ 175.3, 165.3, 163.3, 163.2, 161.7, 158.4, 133.8, 129.0, 128.9, 115.7, 115.5, 105.2, 73.5, 59.0, 53.0, 47.8, 45.8, 39.5, 38.7, 36.1, 34.3, 34.1, 25.1, 24.1, 23.9 ppm. Purity: >98% LCMS (214 nm & 254 nm); retention time 1.52 min; (M+H$^+$) 454.3.

Example 100

1-(4-(4-Fluorophenyl)pyrimidin-2-yl)-4-methoxy-N-(4-methyl-1-azabicyclo[3.2.2]nonan-4-yl)piperidine-4-carboxamide To a stirred solution of 2,4-dichloropyrimidine (3.00 g, 20.1 mmol) in toluene (25 mL) was added 4-fluorophenylboronic acid (2.82 g, 20.1 mmol), potassium carbonate (8.32 g, 60.3 mmol), tetrakis(triphenylphosphine)palladium(0) (0.630 g, 0.545 mmol) and 1:1 (v/v) ethanol/water (36 mL). The mixture was heated at 55° C. for 12 hours and then concentrated. The residue was diluted with water and extracted with ethyl acetate. The combined extracts were washed with brine, dried ($Na_2SO_4$) and concentrated. The crude material was purified by flash chromatography over silica using a hexane/ethyl acetate eluant to afford 2-chloro-4-(4-fluorophenyl)pyrimidine as a yellow solid (2.50 g, 61%). To a stirred and cooled solution of this compound (0.317 g, 1.00 mmol) in N,N-dimethylformamide (15 mL) was added sodium hydride (60% dispersion in mineral oil; 0.120 g, 3.00 mmol). The mixture was stirred for 30 minutes before adding iodomethane (0.187 mL, 3.00 mmol) and then allowed to slowly warm to room temperature and stirred overnight. The reaction was concentrated and the residue was partitioned between water and ethyl acetate. The organic layer was combined with an additional ethyl acetate extract, dried ($Na_2SO_4$) and concentrated. The residue was purified by flash chromatography over silica using a hexane/ethyl acetate eluant to afford methyl 1-(4-(4-fluorophenyl)pyrimidin-2-yl)-4-methoxypiperidine-4-carboxylate as a yellow oil (0.210 g, 61%). To a stirred solution of this compound (0.165 g, 0.500 mmol) in methanol (3 mL) and water (1 mL) was added sodium hydroxide (0.100 g, 2.50 mmol). After overnight stirring, the solution was acidified with 2.0 M hydrochloric acid and extracted with ethyl acetate. The combined extracts were dried ($Na_2SO_4$) and concentrated to afford 1-(4-(4-fluorophenyl)pyrimidin-2-yl)-4-methoxypiperidine-4-carboxylic acid as a white solid (0.157 g, 95%). Using General Procedure D and Intermediate 5, this carboxylic acid was subjected to amide coupling to generate the title compound as a white solid (0.061 g, 44%). $^1$H NMR (500 MHz, $CDCl_3$) δ 8.37 (d, J=5.5 Hz, 1H), 8.07-8.05 (m, 2H), 7.16 (t, J=8.5 Hz, 2H), 6.90 (d, J=5.5 Hz, 1H), 6.46 (s, 1H), 4.70-4.67 (m, 2H), 3.36-3.29 (m, 5H), 3.08-2.87 (m, 6H), 2.39 (m, 1H), 2.13-1.51 (m, 13H) ppm. $^{13}$C NMR (100 MHz, $CDCl_3$) δ 173.5, 165.6, 163.2, 163.1, 161.8, 158.4, 133.9, 133.8, 129.0, 128.9, 115.7, 115.5, 105.2, 79.3, 59.0, 53.1, 51.7, 47.6, 46.1, 39.6, 38.8, 36.4, 31.4, 30.4, 25.0, 24.1, 24.0 ppm. Purity: >98% LCMS (214 nm & 254 nm); retention time 1.38 min; (M+H$^+$) 468.3.

Example 101

4-Methoxy-1-(4-(4-(3-methoxypropoxy)phenyl)pyrimidin-2-yl)-N-(4-methyl-1-azabicyclo[3.2.2]nonan-4-yl)piperidine-4-carboxamide Exchanging 4-fluorophenylboronic acid for 2-(4-(3-methoxypropoxy)phenyl)-4,4,5,5-tetramethyl-1,3,2-dioxaborolane, the same reaction sequence outlined in Example 100 was used to generate the title compound. $^1$H NMR (500 MHz, $CDCl_3$) δ 8.34 (d, J=5.0 Hz, 1H), 8.02 (d, J=8.5 Hz, 2H), 6.99 (d, J=9.0 Hz, 2H), 6.89 (d, J=5.0 Hz, 1H), 6.46 (s, 1H), 4.69 (s, 2H), 4.14 (t, J=6.5 Hz, 2H), 3.60 (t, J=6.0 Hz, 2H), 3.39-3.31 (m, 8H), 3.12-2.91 (m, 6H), 2.43 (m, 1H), 2.12-1.52 (m, 15H) ppm. $^{13}$C NMR (125 MHz, $CDCl_3$) δ 173.7, 163.9, 161.8, 161.0, 158.0, 130.1, 128.5, 114.5, 104.9, 79.4, 69.1, 64.9, 58.9, 58.8, 53.0, 51.8, 47.6, 46.0, 39.6, 38.3, 36.2, 31.5, 30.4, 29.6, 25.0, 23.7, 23.6 ppm. Purity: >96% LCMS (214 nm & 254 nm); retention time 1.36 min; (M+H$^+$) 538.3.

Example 102

1-(5-Fluoro-4-(4-(2-fluoroethoxy)phenyl)pyrimidin-2-yl)-4-methoxy-N-(4-methyl-1-azabicyclo[3.2.2]nonan-4-yl)piperidine-4-carboxamide Exchanging 4-fluorophenylboronic acid for 2-(4-(2-fluoroethoxy)phenyl)-4,4,5,5-tetramethyl-1,3,2-dioxaborolane and 2,4-dichloropyrimidine for 2,4-dichloro-5-fluoropyrimidine, the same reaction sequence outlined in Example 100 was used to generate the title compound. $^1$H NMR (500 MHz, $CDCl_3$) δ 8.22 (d, J=4.0 Hz, 1H), 8.11 (d, J=8.5 Hz, 2H), 7.03 (d, J=8.5 Hz, 2H), 6.45 (s, 1H), 4.87-4.75 (dt, J=47.5 Hz & 4.0 Hz, 2H), 4.58-4.56 (m, 2H), 4.33-4.27 (dt, J=27.5 Hz & 4.0 Hz, 2H), 3.34 (s, 3H), 3.31-3.27 (m, 2H), 3.03-2.87 (m, 6H), 2.37 (m, 1H), 2.09-1.50 (m, 13H) ppm. $^{13}$C NMR (125 MHz, $CDCl_3$) δ 173.5, 160.3, 158.3, 150.8, 150.7, 150.5, 148.5, 146.4, 146.2, 130.7, 130.6, 127.3, 127.2, 114.4, 82.5, 81.1, 79.2, 67.2, 67.0, 59.0, 53.2, 51.7, 47.6, 46.1, 40.2, 39.0, 36.4, 31.3, 30.3, 25.0, 24.3, 24.1 ppm. Purity: >97% LCMS (214 nm & 254 nm); retention time 1.49 min; (M+H$^+$) 530.3.

Example 103

1-(4-(4-(2-Fluoroethoxy)phenyl)pyrimidin-2-yl)-4-methoxy-N-(4-methyl-1-azabicyclo[3.2.2]nonan-4-yl)piperidine-4-carboxamide Exchanging 4-fluorophenylboronic acid for 2-(4-(2-fluoroethoxy)phenyl)-4,4,5,5-tetramethyl-1,3,2-dioxaborolane, the same reaction sequence outlined in Example 100 was used to generate the title compound. $^1$H NMR (500 MHz, $CDCl_3$) δ 8.33 (d, J=5.0 Hz, 1H), 8.03 (d, J=9.0 Hz, 2H), 7.01 (d, J=9.0 Hz, 2H), 6.88 (d, J=4.5 Hz, 1H), 6.44 (s, 1H), 4.85-4.73 (dt, J=47.5 Hz & 4.0 Hz, 2H), 4.68-4.66 (m, 2H), 4.32-4.24 (dt, J=27.5 Hz & 4.0 Hz, 2H), 3.33-3.27 (m, 5H), 3.07-2.84 (m, 6H), 2.37 (s, 1H), 2.12-1.49 (m, 13H) ppm. $^{13}$C NMR (125 MHz, $CDCl_3$) δ 173.6, 163.7, 161.8, 160.4, 158.1, 130.8, 128.6, 114.6, 105.0, 82.5, 81.2, 79.4, 67.2, 67.1, 59.0, 53.2, 51.8, 47.6, 46.1, 39.6, 38.8, 36.4, 31.5, 30.4, 25.0, 24.1, 24.0 ppm. Purity: >96% LCMS (214 nm & 254 nm); retention time 1.35 min; (M+H$^+$) 512.3.

Example 104

1-(4-(4-Fluorophenyl)-5-(2-methoxyethoxy)pyrimidin-2-yl)-N-(4-methyl-1-azabicyclo[3.2.2]nonan-4-yl)piperidine-4-carboxamide Exchanging 2,4-dichloropyrimidine for 2,4-dichloro-5-methoxypyrimidine, the first two steps of the reaction sequence outlined in Example 41 were used to generate the intermediate, ethyl 1-(4-(4-fluorophenyl)-5-methoxypyrimidin-2-yl)piperidine-4-carboxylate. To a stirred and cooled (−70° C.) solution of this compound (2.20 g, 6.13 mmol) in dichloromethane (30 mL) was added a 4.0 M solution of boron tribromide in dichloromethane (6.13 mL, 24.5 mmol). The reaction was stirred at −70° C. for 1 hour, warmed to 0° C., and then stirred for another 2 hours. After quenching with added methanol, the reaction mixture was partitioned between water and dichloromethane. The aqueous phase was extracted again with dichloromethane and the combined organic layers were dried ($Na_2SO_4$) and concentrated. The residue was purified by flash chromatography over silica using a dichloromethane/methanol eluant to afford ethyl 1-(4-(4-fluorophenyl)-5-hydroxypyrimidin-2-yl)piperidine- 4-carboxylate as a brown oil (1.50 g, 71%). To a stirred solution of this compound (0.900 g, 2.61 mmol) in N,N-dimethylformamide (10 mL) was added 1-bromo-2-methoxyethane (0.725 g, 5.22 mmol) and cesium carbonate (2.55 g, 7.83 mmol). The reaction was stirred at 60° C. for 4 hours before diluting with water and extracting with ethyl acetate. The combined organic layers were washed with water and aqueous sodium chloride solution, dried ($Na_2SO_4$) and concentrated. The residue was purified by flash chromatography over silica using a hexane/ethyl acetate eluant to afford ethyl 1-(4-(4-fluorophenyl)-5-(2-methoxyethoxy)pyrimidin-2-yl)piperidine-4-carboxylate as a brown oil (0.550 g, 52%). To a stirred solution of this ester (0.550 g, 1.36 mmol) in 1:1:1 tetrahydrofuran/water/methanol (9 mL) was added sodium hydroxide (0.273 g, 6.82 mmol). After 3 hours, the reaction was concentrated and the residue was taken up in water. The solution was made acidic (~pH 3) with the addition of 1.0 N hydrochloric acid and then extracted with ethyl acetate. The combined extracts were dried ($Na_2SO_4$) and concentrated to afford 1-(4-(4-fluorophenyl)-5-(2-methoxyethoxy)pyrimidin-2-yl)piperidine-4-carboxylic acid as a light yellow solid (0.450 g, 88%). Using General Procedure D and Intermediate 5, this carboxylic acid was subjected to amide coupling to generate the title compound as a light yellow solid (0.090 g, 44%). $^1$H NMR (500 MHz, $CDCl_3$) δ 8.22-8.19 (m, 3H), 7.15-7.11 (m, 2H), 5.37 (s, 1H), 4.82 (d, J=13.5 Hz, 2H), 4.03 (t, J=4.5 Hz, 2H), 3.66 (t, J=5.0 Hz, 2H), 3.41 (s, 3H), 3.07-2.81 (m, 8H), 2.38-2.30 (m, 2H), 1.97-1.51 (m, 13H) ppm. $^{13}$C NMR (125 MHz, $CDCl_3$) δ 174.2, 164.7, 162.7, 157.7, 154.1, 148.0, 143.2, 132.2, 131.6, 131.5, 115.1, 114.9, 71.1, 71.0, 59.4, 59.1, 53.1, 47.6, 46.1, 44.6, 44.1, 39.3, 36.1, 28.9, 28.6, 25.1, 24.3, 24.2 ppm. Purity: >98% LCMS (214 nm & 254 nm); retention time 1.55 min; (M+H$^+$) 512.3.

Example 105

1-(4-(4-Fluorophenyl)-6-(2-methoxyethoxy)pyrimidin-2-yl)-N-(4-methyl-1-azabicyclo[3.2.2]nonan-4-yl)piperidine-4-carboxamide Exchanging 2,4-dichloropyrimidine for 2,4,6-trichloropyrimidine, the first step of the reaction sequence outlined in Example 41 was used to generate the intermediate 2,4-dichloro-6-(4-fluorophenyl)pyrimidine. To a stirred solution of this compound (0.800 g, 3.30 mmol) in acetonitrile (20 mL) was added cesium carbonate (3.23 g, 9.90 mmol). The suspension was stirred at 0° C. for 30 minutes before adding 2-methoxyethanol (0.201 g, 2.64 mmol), dropwise over 2-3 minutes. The mixture was allowed to slowly warm to room temperature, stirred for two more hours and then concentrated. The residue was purified by flash chromatography over silica using a hexane/ethyl acetate eluant to afford 2-chloro-4-(4-fluorophenyl)-6-(2-methoxyethoxy)pyrimidine as a colorless oil (0.470 g, 51%). To a stirred solution of this compound (0.300 g, 1.06 mmol) in ethanol (5 mL) was added trifluoroacetic acid (0.081 mL, 1.06 mmol) and ethyl piperidine-4-carboxylate (0.200 g, 1.28 mmol). The reaction was heated overnight at 80° C., cooled and concentrated. The residue was purified by flash chromatography over silica using a hexane/ethyl acetate eluant to afford ethyl 1-(4-(4-fluorophenyl)-6-(2-methoxyethoxy)pyrimidin-2-yl)piperidine-4-carboxylate as a colorless oil (0.400 g, 94%). To a stirred solution of this intermediate (0.400 g, 0.990 mmol) in methanol (2 mL), tetrahydrofuran (1 mL) and water (1 mL) was added sodium hydroxide (0.199 g, 4.96 mmol). After overnight stirring, the reaction was concentrated. The residue was taken up in water and the solution was made acidic (~pH 3) with 1.0 N hydrochloric acid. The resulting suspension was extracted with ethyl acetate. The combined extracts were dried ($Na_2SO_4$) and concentrated to afford 1-(4-(4-fluorophenyl)-6-(2-methoxyethoxy)pyrimidin-2-yl)piperidine-4-carboxylic acid as a white solid (0.320 g, 86%). Using General Procedure D and Intermediate 5, this carboxylic acid was subjected to amide coupling to generate the title compound as a white solid (0.100 g, 49%). $^1$H NMR (500 MHz, $CDCl_3$) δ 8.02-7.98 (m, 2H), 7.15-7.11 (m, 2H), 6.44 (s, 1H), 5.37 (s, 1H), 4.95 (d, J=12.5 Hz, 2H), 4.52 (t, J=4.5 Hz, 2H), 3.77 (t, J=4.5 Hz, 2H), 3.47 (s, 3H), 3.07-2.94 (m, 6H), 2.88-2.84 (m, 2H), 2.40-2.33 (m, 2H), 1.95-1.51 (m, 13H) ppm. $^{13}$C NMR (125 MHz, $CDCl_3$) δ 174.1, 170.6, 165.0, 164.2, 163.1, 161.4, 134.2, 134.1, 128.8, 115.5, 115.3, 92.0, 70.8, 64.8, 59.4, 59.1, 53.1, 47.7, 46.1, 44.7, 43.6, 39.2, 36.1, 30.9, 28.9, 28.7, 25.1, 24.3, 24.1 ppm. Purity: >97% LCMS (214 nm & 254 nm); retention time 1.40 min; (M+H$^+$) 512.4.

Example 106

1-(4-(4-Fluorophenyl)pyridin-2-yl)-N-(4-methyl-1-azabicyclo[3.2.2]nonan-4-yl)piperidine-4-carboxamide To a stirred solution of 4-bromo-2-fluoropyridine (1.76 g, 10.0 mmol) in acetonitrile (10 mL) was added ethyl piperidine-4-carboxylate (2.36 g, 15.0 mmol) and potassium carbonate (2.76 g, 20.0 mmol). The reaction was heated at 60° C. overnight and then concentrated. The residue was purified by flash chromatography over silica using a hexane/ethyl acetate eluant to afford ethyl 1-(4-bromopyridin-2-yl)piperidine-4-carboxylate as a colorless oil (2.40 g, 76%). To a stirred solution of this compound in 10:1 1,4-dioxane/water (20 mL) was added 4-fluorophenylboronic acid (0.536 g, 3.83 mmol) potassium carbonate (1.10 g, 7.98 mmol) and [1,1'-bis(diphenylphosphino)ferrocene]dichloropalladium (II) (0.117 g, 0.160 mmol). The reaction was heated overnight at 95° C. After diluting with water, the reaction mixture extracted with ethyl acetate. The combined extracts were dried ($Na_2SO_4$) and concentrated. The residue was purified by flash chromatography over silica using a hexane/ethyl acetate eluant to afford ethyl 1-(4-(4-fluorophenyl)pyridin-2-yl)piperidine-4-carboxylate as a white solid (1.00 g, 95%). Using the final two steps described in Example 41, this intermediate was used to prepare the title compound. $^1$H NMR (500 MHz, $CDCl_3$) δ 8.23 (d, J=5.0 Hz, 1H), 7.60-7.55 (m, 2H), 7.18-7.14 (m, 2H), 6.80-6.78 (m, 2H), 5.37 (s, 1H), 4.45-4.42 (m, 2H), 3.07-2.80 (m, 8H), 2.39-2.30 (m, 2H), 1.98-1.50 (m, 13H) ppm. $^{13}$C NMR (125 MHz, $CDCl_3$) δ 174.0, 164.1, 162.2, 159.9, 149.1, 148.4, 135.7, 128.7, 115.9, 115.7, 111.7, 105.1, 59.5, 53.1, 47.6, 46.1, 45.2, 44.4, 39.2, 36.1, 28.7, 28.4, 25.1, 24.3, 24.2 ppm. Purity: >99% LCMS (214 nm & 254 nm); retention time 1.04 min; (M+H$^+$) 437.2.

Example 107

1-(5-(4-Fluorophenyl)pyridin-3-yl)-N-(4-methyl-1-azabicyclo[3.2.2]nonan-4-yl)piperidine-4-carboxamide A stirred mixture of 3,5-dibromopyridine (0.500 g, 2.11 mmol), ethyl piperidine-4-carboxylate (1.60 g, 10.2 mmol) and cesium carbonate (0.729 g, 2.24 mmol) was heated in a microwave reactor at 150° C. for 1 hour. The reaction was cooled and concentrated. The residue was purified by flash chromatography over silica using a hexane/ethyl acetate eluant to afford ethyl 1-(5-bromopyridin-3-yl)piperidine-4-carboxylate as a yellow oil (0.078 g, 12%). Using the final three steps described in Example 106, this intermediate was used to prepare the title compound. $^1$H NMR (500 MHz, CDCl$_3$) δ 8.30 (d, J=2.0 Hz, 1H), 8.27 (s, 1H), 7.55-7.52 (m, 2H), 7.30 (s, 1H), 7.16 (t, J=8.5 Hz, 2H), 5.43 (s, 1H), 3.85-3.82 (m, 2H), 3.06-2.85 (m, 8H), 2.40-2.23 (m, 2H), 1.99-1.54 (m, 13H) ppm. $^{13}$C NMR (125 MHz, CDCl$_3$) δ 173.8, 163.8, 161.8, 146.9, 139.0, 137.6, 135.8, 134.5, 128.9, 121.1, 116.0, 115.8, 59.5, 53.1, 48.6, 47.6, 46.1, 43.7, 39.2, 36.1, 28.8, 28.5, 25.1, 24.3, 24.2 ppm. Purity: >99% LCMS (214 nm & 254 nm); retention time 1.19 min; (M+H$^+$) 437.3.

Example 108

1-(2-(4-Fluorophenyl)pyridin-4-yl)-N-(4-methyl-1-azabicyclo[3.2.2]nonan-4-yl)piperidine-4-carboxamide To a stirred solution of 2,4-dichloropyridine (4.00 g, 27.0 mmol) in a mixture of N,N-dimethylformamide (50 mL) and water (25 mL) was added 4-fluorophenylboronic acid (3.78 g, 27.0 mmol), sodium bicarbonate (2.27 g, 27.03 mmol) and bis(triphenylphosphine)palladium(II) dichloride (0.948 g, 1.35 mmol). The reaction was heated overnight at 80° C. and then concentrated. The residue was taken up in ethyl acetate, washed with water and aqueous sodium chloride solution, dried (Na2SO4) and concentrated. The residue was purified by flash chromatography over silica using a hexane/ethyl acetate eluant to afford 4-chloro-2-(4-fluorophenyl)pyridine as a colorless solid (2.21 g, 39%). This intermediate (2.18 g, 10.5 mmol) was combined with ethyl piperidine-4-carboxylate (3.30 g, 21.0 mmol), N,N-diisopropylethylamine (4.4 mL, 25 mmol) and acetonitrile (12 mL) in a sealed microwave reaction vessel. With stirring, the mixture was heated in a microwave reactor for 5 hours at 180° C. The reaction was then concentrated and the residue was taken up in ethyl acetate and washed with an aqueous sodium bicarbonate solution. The aqueous layer was back-extracted with ethyl acetate and the combined organic layers were dried (Na$_2$SO$_4$) and concentrated. The residue was purified by flash chromatography over silica using a hexane/ethyl acetate eluant to afford ethyl 1-(2-(4-fluorophenyl)pyridin-4-yl)piperidine-4-carboxylate as a pale amber oil (2.88 g, 84%). Using the final two steps described in Example 41, this intermediate was used to prepare the title compound. $^1$H NMR (400 MHz, CDCl$_3$) δ 8.22 (d, J=6.0 Hz, 1H), 8.15-8.09 (m, 2H), 7.42 (s, 1H), 7.33-7.22 (m, 3H), 6.79 (dd, J=6.0, 2.5 Hz, 1H), 4.15-4.05 (m, 2H), 3.03-2.69 (m, 8H), 2.55-2.43 (m, 1H), 2.34-2.27 (m, 1H), 1.82-1.44 (m, 9H), 1.41-1.27 (m, 4H) ppm. Purity: 95% (214 & 254 nm) UPLCMS; retention time: 0.46 min; (M+H$^+$) 437.4.

Example 109

1-(4-(4-Fluorophenyl)pyrimidin-2-yl)-N-methyl-N-(quinuclidin-3-yl)piperidine-4-carboxamide Using General Procedure D and the reaction inputs 1-(4-(4-fluorophenyl)pyrimidin-2-yl)piperidine-4-carboxylic acid (prepared as described in Example 41) and N-methylquinuclidin-3-amine, the title compound was prepared. $^1$H NMR (500 MHz, CDCl$_3$) δ 8.39 (d, J=5.5 Hz, 1H), 8.08-8.05 (m, 2H), 7.17 (t, J=8.5 Hz, 2H), 6.90 (d, J=5.0 Hz, 1H), 4.99-4.96 (m, 2H), 4.58-4.54 (m, 1H), 3.33-2.83 (m, 12H), 2.08-1.55 (m, 9H) ppm. $^{13}$C NMR (125 MHz, CDCl$_3$) δ 175.6, 165.3, 163.3, 163.2, 161.8, 158.4, 133.9, 129.0, 128.9, 115.7, 115.5, 105.2, 51.1, 47.5, 46.8, 43.5, 28.4, 21.8 ppm. Purity: >96% LCMS (214 nm & 254 nm); retention time 1.24 min; (M+H$^+$) 424.2.

Example 110

1-Azabicyclo[3.2.2]nonan-4-yl 1-(4-(4-fluorophenyl)pyrimidin-2-yl)piperidine-4-carboxylate To a stirred solution of ethyl 1-(4-(4-fluorophenyl)pyrimidin-2-yl)piperidine-4-carboxylate (prepared as described in Example 41; 0.200 g, 0.607 mmol) and Intermediate 3 (0.094 g, 0.666 mmol) in toluene (10 mL) was added a 60% dispersion of sodium hydride in mineral oil (0.097 g, 2.43 mmol) and 4 Å molecular sieves. The mixture was heated at reflux for two nights before filtering off the solids and concentrating. The residue was purified by reverse phase preparative HPLC to afford the title compound as yellow oil (0.066 g, 27%). $^1$H NMR (500 MHz, CDCl$_3$) δ 8.38 (d, J=5.0 Hz, 1H), 8.09-8.05 (m, 2H), 7.17 (t, J=8.5 Hz, 2H), 6.90 (d, J=5.0 Hz, 1H), 5.05-5.00 (m, 1H), 4.83-4.80 (m, 2H), 3.22-2.85 (m, 8H), 2.66-2.59 (m, 1H), 2.06-1.56 (m, 11H) ppm. $^{13}$C NMR (125 MHz, CDCl$_3$) δ 174.0, 165.3, 163.3, 163.2, 161.7, 158.4, 133.8, 129.0, 128.9, 115.7, 115.5, 105.1, 78.1, 51.8, 47.9, 45.2, 43.2, 41.8, 33.4, 30.3, 28.0, 24.9, 22.3 ppm. Purity: >98% LCMS (214 nm & 254 nm); retention time 1.47 min; (M+H$^+$) 425.2.

Example 111

1-(5-Fluoro-4-(4-(3-methoxypropoxy)phenyl)pyrimidin-2-yl)-N-(4-methyl-1-50 azabicyclo[3.2.2]nonan-4-yl)azetidine-3-carboxamide Exchanging 4-fluorophenylboronic acid for 2-(4-(3-methoxypropoxy)phenyl)-4,4,5,5-tetramethyl-1,3,2-dioxaborolane, ethyl piperidine-4-carboxylate for methyl azetidine-3-carboxylate hydrochloride and 2,4-dichloropyrimidine for 2,4-dichloro-5-fluoropyrimidine, the same reaction sequence outlined in Example 41 was used to generate the title compound. $^1$H NMR (500 MHz, CDCl$_3$) δ 8.23 (d, J=4.5 Hz, 1H), 8.10 (d, J=8.5 Hz, 2H), 7.00 (d, J=9.0 Hz, 2H), 5.55 (s, 1H), 4.33-4.30 (m, 4H), 4.15 (t, J=6.0 Hz, 2H), 3.59 (t, J=6.0 Hz, 2H), 3.39-3.36 (m, 4H), 3.07-2.99 (m, 4H), 2.89-2.86 (m, 2H), 2.43 (s, 1H), 2.12-2.07 (m, 2H), 1.99-1.54 (m, 9H) ppm. $^{13}$C NMR (125 MHz, CDCl$_3$) δ 171.5, 161.1, 160.0, 151.5, 151.4, 149.5, 146.4, 146.2, 130.7, 130.6, 126.1, 114.4, 69.1, 64.9, 59.9, 58.8, 53.3, 53.0, 47.2, 46.4, 39.0, 36.1, 35.2, 30.9, 29.5, 24.9, 24.0 ppm. Purity: >98% LCMS (214 nm & 254 nm); retention time 1.41 min; (M+H$^+$) 498.3.

Example 112

1-(5-Fluoro-4-(4-fluorophenyl)pyrimidin-2-yl)-N-(4-methyl-1-azabicyclo[3.2.2]nonan-4-yl)azetidine-3-carboxamide Exchanging ethyl piperidine-4-carboxylate for methyl azetidine-3-carboxylate hydrochloride and 2,4-dichloropyrimidine for 2,4-dichloro-5-fluoropyrimidine, the same reaction sequence outlined in Example 41 was used to generate the title compound. $^1$H NMR (500 MHz, CDCl$_3$) δ 8.25 (d, J=3.0 Hz, 1H), 8.12-8.09 (m, 2H), 7.17-7.13 (m, 2H), 5.42

(s, 1H), 4.32-4.27 (m, 4H), 3.36-3.33 (m, 1H), 3.01-2.80 (m, 6H), 2.38 (m, 1H), 1.97-1.52 (m, 9H) ppm. $^{13}$C NMR (125 MHz, CDCl$_3$) δ 171.3, 165.3, 163.3, 160.0, 159.9, 151.4, 150.7, 149.4, 146.9, 146.7, 131.2, 131.1, 129.9, 129.8, 115.7, 115.5, 59.9, 53.2, 53.0, 47.1, 46.5, 39.2, 36.2, 35.1, 24.8, 24.2, 24.1 ppm. Purity: >98% LCMS (214 nm & 254 nm); retention time 1.34 min; (M+H$^+$) 428.2.

Example 113

1-(4-(4-Fluorophenyl)pyrimidin-2-yl)-N-(4-methyl-1-azabicyclo[3.2.2]nonan-4-yl)azetidine-3-carboxamide Exchanging ethyl piperidine-4-carboxylate for methyl azetidine-3-carboxylate, the same reaction sequence outlined in Example 41 was used to generate the title compound. $^1$H NMR (500 MHz, CDCl$_3$) δ 8.36 (d, J=5.5 Hz, 1H), 8.06-8.03 (m, 2H), 7.14 (t, J=8.5 Hz, 2H), 6.96 (d, J=4.5 Hz, 1H), 5.44 (s, 1H), 4.35-4.33 (m, 4H), 3.38-3.35 (m, 1H), 3.00-2.81 (m, 6H), 2.38 (m, 1H), 1.97-1.52 (m, 9H) ppm. $^{13}$C NMR (125 MHz, CDCl$_3$) δ 171.2, 163.5, 163.4, 163.2, 158.4, 133.5, 129.1, 115.8, 115.6, 106.3, 60.0, 53.0, 52.9, 52.8, 47.2, 46.5, 39.2, 36.2, 35.4, 24.9, 24.2, 24.1 ppm. Purity: >99% LCMS (214 nm & 254 nm); retention time 1.26 min; (M+H$^+$) 410.2.

Example 114

1-(4'-Fluoro-[1,1'-biphenyl]-3-yl)-N-(4-methyl-1-azabicyclo[3.2.2]nonan-4-yl)azetidine-3-carboxamide Exchanging ethyl piperidine-4-carboxylate for methyl azetidine-3-carboxylate, the same reaction sequence outlined in Example 33 was used to generate the title compound. $^1$H NMR (500 MHz, CDCl$_3$) δ 7.55-7.52 (m, 2H), 7.30 (t, J=8.0 Hz, 1H), 7.12 (t, J=8.5 Hz, 2H), 6.96 (d, J=7.5 Hz, 1H), 6.63 (s, 1H), 6.50 (d, J=8.0 Hz, 1H), 5.75 (s, 1H), 4.12-4.02 (m, 4H), 3.39-3.35 (m, 1H), 3.03-2.84 (m, 6H), 2.40 (s, 1H), 1.98-1.55 (m, 9H) ppm. $^{13}$C NMR (125 MHz, CDCl$_3$) δ 171.6, 163.4, 161.4, 151.9, 141.2, 137.7, 129.4, 128.8, 128.7, 117.2, 115.5, 115.4, 110.8, 110.4, 59.8, 55.1, 55.0, 53.1, 47.3, 46.4, 39.1, 36.3, 36.2, 24.9, 24.2 ppm. Purity: >98% LCMS (214 nm & 254 nm); retention time 1.42 min; (M+H$^+$) 408.3.

Example 115

1-(4-(4-Fluorophenoxy)pyrimidin-2-yl)-N-(4-methyl-1-azabicyclo[3.2.2]nonan-4-yl)piperidine-4-carboxamide To a stirred solution of 4-fluorophenol (0.448 g, 4.00 mmol) in tetrahydrofuran (35 mL) was added potassium tert-butoxide (0.493 g, 4.40 mmol). After 30 minutes, 2,4-dichloropyrimidine (0.596 g, 4.00 mmol) was added and the reaction was left to stir for another 6 hours. At this time, the reaction was filtered to remove the suspended solids and the filtrate was concentrated to afford crude 2-chloro-4-(4-fluorophenoxy)pyrimidine as a white solid (0.827 g, 92%). This intermediate (0.548 g, 2.40 mmol), which was clean enough to use without purification, was combined with ethyl piperidine-4-carboxylate (0.452 g, 2.88 mmol) and triethylamine (1.0 mL, 7.2 mL) in ethanol (10 mL). The stirred mixture was heated overnight at 80° C. and then concentrated. The residue was purified by flash chromatography over silica using a hexane/ethyl acetate eluant to afford ethyl 1-(4-(4-fluorophenoxy)pyrimidin-2-yl)piperidine-4-carboxylate as a light yellow oil (0.639 g, 76%). To a stirred solution of this intermediate (0.330 g, 0.960 mmol) in 1:1 (v/v) methanol/water (4 mL) was added solid sodium hydroxide (0.192 g, 4.80 mmol). After overnight stirring, the reaction was concentrated. The residue was dissolved in water, made acidic (pH~3) with the addition of 1N hydrochloric acid and extracted with ethyl acetate. The combined organic layers were washed with brine, dried (Na$_2$SO$_4$) and concentrated to afford 1-(4-(4-fluorophenoxy)pyrimidin-2-yl)piperidine-4-carboxylic acid as a white solid (0.288 g, 95%). Using General Procedure D and Intermediate 5, this carboxylic acid was subjected to amide coupling to generate the title compound as a white solid (0.019 g, 7%). $^1$H NMR (500 MHz, CDCl$_3$) δ 8.16 (d, J=5.5 Hz, 1H), 7.12-7.05 (m, 4H), 5.99 (d, J=5.5 Hz, 1H), 5.28 (s, 1H), 4.62-4.60 (m, 2H), 3.01-2.80 (m, 8H), 2.34-2.26 (m, 2H), 1.91-1.47 (m, 13H) ppm. $^{13}$C NMR (125 MHz, CDCl$_3$) δ 173.9, 169.9, 161.5, 160.9, 159.5, 158.9, 148.5, 123.2, 116.1, 115.9, 95.5, 59.5, 53.2, 47.6, 46.2, 44.5, 43.4, 39.4, 36.1, 28.8, 28.5, 25.1, 24.4, 24.2 ppm. Purity: >99% LCMS (214 nm & 254 nm); retention time 1.32 min; (M+H$^+$) 454.3.

Example 116

4-Fluoro-1-(4-(4-fluorophenoxy)pyrimidin-2-yl)-N-(4-methyl-1-azabicyclo[3.2.2]nonan-4-yl)piperidine-4-carboxamide Exchanging ethyl piperidine-4-carboxylate for ethyl 4-fluoropiperidine-4-carboxylate hydrochloride, the same reaction sequence outlined in Example 115 was used to generate the title compound. $^1$H NMR (400 MHz, CDCl$_3$) δ 8.17 (d, J=5.5 Hz, 1H), 7.15-7.02 (m, 4H), 6.31 (d, J=7.3 Hz, 1H), 6.03 (d, J=5.5 Hz, 2H), 4.62-4.41 (m, 2H), 3.22-2.76 (m, 8H), 2.36-2.28 (m, 1H), 2.26-2.02 (m, 2H), 2.00-1.89 (m, 1H), 1.87-1.67 (m, 5H), 1.67-1.42 (m, 5H) ppm. Purity: >99.9% (214 & 254 nm) UPLCMS; retention time: 0.82 min; (M+H$^+$) 472.4.

Example 117

4-Fluoro-1-(4-(4-fluorophenoxy)-1,3,5-triazin-2-yl)-N-(4-methyl-1-azabicyclo[3.2.2]nonan-4-yl)piperidine-4-carboxamide Exchanging 2,4-dichloropyrimidine for 2,4-dichlorotriazine and ethyl piperidine-4-carboxylate for ethyl 4-fluoropiperidine-4-carboxylate hydrochloride, the same reaction sequence outlined in Example 115 was used to generate the title compound. $^1$H NMR (400 MHz, CDCl$_3$) δ 8.37 (s, 1H), 7.20-7.03 (m, 4H), 6.32 (d, J=7.1 Hz, 1H), 4.85-4.72 (m, 1H), 4.60-4.47 (m, 1H), 3.34-3.11 (m, 2H), 3.10-2.74 (m, 6H), 2.37-2.05 (m, 3H), 2.02-1.43 (m, 11H) ppm. Purity: >99.9% (214 & 254 nm) UPLCMS; retention time: 0.74 min; (M+H$^+$) 473.5.

Example 118

4-Fluoro-1-(5-fluoro-4-(4-(2-methoxyethoxy)phenoxy)pyrimidin-2-yl)-N-(3-methylquinuclidin-3-yl)piperidine-4-carboxamide Exchanging 4-fluorophenol for 4-(2-methoxyethoxy)phenol, ethyl piperidine-4-carboxylate for ethyl 4-fluoropiperidine-4-carboxylate hydrochloride and Intermediate 5 for Intermediate 1, the same reaction sequence outlined in Example 115 was used to generate the title compound. $^1$H NMR (500 MHz, CDCl$_3$) δ 8.08 (d, J=3.0 Hz, 1H), 7.11-7.08 (m, 2H), 6.96-6.93 (m, 2H), 6.32 (d, J=7.0 Hz, 1H), 4.34-4.32 (m, 2H), 4.14 (t, J=4.5 Hz, 2H), 3.79 (t, J=4.5 Hz, 2H), 3.49 (s, 3H), 3.09-2.75 (m, 8H), 2.18-2.02 (m, 3H), 1.87-1.27 (m, 9H) ppm. $^{13}$C NMR (100 MHz, CDCl$_3$) δ 171.2, 171.0, 157.8, 157.7, 156.8, 156.1, 145.6, 144.7, 144.5, 140.8, 138.3, 122.5, 114.9, 96.7, 94.8, 71.0, 67.6, 63.2, 59.3, 52.8, 46.5, 46.3, 39.6, 31.7, 31.6, 31.5, 31.4, 30.1, 24.1, 23.0, 22.4 ppm. Purity: >99% LCMS (214 nm & 254 nm); retention time 1.44 min; (M+H$^+$) 532.2.

Example 119

1-(4-(4-Cyanophenoxy)pyrimidin-2-yl)-4-fluoro-N-(3-methylquinuclidin-3-yl)piperidine-4-carboxamide Exchanging 4-fluorophenol for 4-cyanophenol, ethyl piperidine-4-carboxylate for ethyl 4-fluoropiperidine-4-carboxylate hydrochloride and Intermediate 5 for Intermediate 1, the same reaction sequence outlined in Example 115 was used to generate the title compound. $^1$H NMR (500 MHz, CDCl$_3$) δ 8.24 (d, J=6.5 Hz, 1H), 7.71 (d, J=8.5 Hz, 2H), 7.29 (d, J=8.0 Hz, 2H), 6.35 (d, J=6.5 Hz, 1H), 6.17 (d, J=6.0 Hz, 1H), 4.52-4.46 (m, 2H), 3.14-3.12 (m, 2H), 2.93-2.77 (m, 6H), 2.18-2.02 (m, 3H), 1.79-1.47 (m, 9H) ppm. $^{13}$C NMR (125 MHz, CDCl$_3$) δ 171.1, 168.8, 161.1, 160.1, 156.2, 133.5, 122.7, 118.5, 108.7, 96.5, 63.2, 52.9, 46.5, 46.4, 39.2, 31.9, 31.8, 31.7, 31.6, 30.1, 24.1, 23.0, 22.4 ppm. Purity: >99% LCMS (214 nm & 254 nm); retention time 1.39 min; (M+H$^+$) 465.2.

Example 120

1-(4-(4-Cyanophenoxy)pyrimidin-2-yl)-4-fluoro-N-(4-methyl-1-azabicyclo[3.2.2]nonan-4-yl)piperidine-4-carboxamide Exchanging 4-fluorophenol for 4-cyanophenol and ethyl piperidine-4-carboxylate for ethyl 4-fluoropiperidine-4-carboxylate, the same reaction sequence outlined in Example 115 was used to generate the title compound. $^1$H NMR (500 MHz, CDCl$_3$) δ 8.24 (d, J=5.0 Hz, 1H), 7.70 (d, J=9.0 Hz, 2H), 7.29 (d, J=8.5 Hz, 2H), 6.33 (d, J=7.5 Hz, 1H), 6.16 (d, J=5.5 Hz, 1H), 4.47 (m, 2H), 3.15-2.82 (m, 8H), 2.34-2.31 (m, 1H), 2.17-1.49 (m, 13H) ppm. $^{13}$C NMR (125 MHz, CDCl$_3$) δ 170.9, 170.7, 168.8, 161.1, 160.1, 156.2, 133.5, 122.7, 118.5, 108.7, 96.8, 96.4, 94.9, 59.4, 53.0, 47.5, 45.9, 39.2, 38.8, 36.2, 32.0, 31.7, 31.5, 24.9, 24.2, 24.0 ppm. Purity: >99% LCMS (214 nm & 254 nm); retention time 1.43 min; (M+H$^+$) 478.9.

Example 121

1-(4-(4-Fluorophenoxy)pyrimidin-2-yl)-N-(3-methylquinuclidin-3-yl)piperidine-4-carboxamide Exchanging 2,4-dichloropyrimidine for 2,4-dichloro-5-fluoropyrimidine and Intermediate 5 for Intermediate 1, the same reaction sequence outlined in Example 115 was used to generate the title compound. $^1$H NMR (500 MHz, CDCl$_3$) δ 8.10 (d, J=2.5 Hz, 1H), 7.17-7.07 (m, 4H), 5.36 (s, 1H), 4.41 (d, J=13.0 Hz, 2H), 2.90-2.74 (m, 8H), 2.27-2.13 (m, 2H), 1.79-1.71 (m, 3H), 1.64-1.28 (m, 8H) ppm. $^{13}$C NMR (125 MHz, CDCl$_3$) δ 174.0, 160.9, 160.0, 157.3, 157.3, 156.9, 147.8, 145.0, 144.9, 140.3, 138.3, 123.2, 123.1, 115.9, 115.7, 63.4, 52.9, 46.6, 46.4, 44.0, 43.8, 30.3, 28.4, 28.3, 24.4, 23.0, 22.5 ppm. Purity: >97% LCMS (214 nm & 254 nm); retention time 1.40 min; (M+H$^+$) 458.0.

Example 122

1-(5-Cyano-4-(4-fluorophenoxy)pyrimidin-2-yl)-4-fluoro-N-(3-methylquinuclidin-3-yl)piperidine-4-carboxamide Exchanging 2,4-dichloropyrimidine for 2,4-dichloro-5-cyanopyrimidine, ethyl piperidine-4-carboxylate for ethyl 4-fluoropiperidine-4-carboxylate and Intermediate 5 for Intermediate 1, the same reaction sequence outlined in Example 115 was used to generate the title compound. $^1$H NMR (500 MHz, CDCl$_3$) δ 8.45 (s, 1H), 7.15-7.08 (m, 4H), 6.34 (d, J=6.5 Hz, 1H), 4.80 (d, J=12.5 Hz, 1H), 4.18 (d, J=12.0 Hz, 1H), 3.25 (t, J=12.5 Hz, 1H), 3.07 (t, J=12.5 Hz, 1H), 2.94-2.79 (m, 6H), 2.18-1.72 (m, 7H), 1.58-1.49 (m, 5H) ppm. $^{13}$C NMR (100 MHz, CDCl$_3$) δ 170.6, 170.4, 169.0, 163.3, 161.4, 160.5, 159.0, 147.3, 123.3, 123.2, 116.1, 115.8, 115.0, 96.1, 94.3, 83.3, 63.0, 52.9, 46.5, 46.3, 39.5, 39.3, 32.1, 32.0, 31.9, 31.8, 31.7, 30.1, 24.1, 22.9, 22.3 ppm. Purity: >99% LCMS (214 nm & 254 nm); retention time 1.89 min; (M+H$^+$) 483.1.

Example 123

4-Fluoro-N-(4-methyl-1-azabicyclo[3.2.2]nonan-4-yl)-1-(4-((tetrahydro-2H-pyran-4-yl)oxy)pyrimidin-2-yl)piperidine-4-carboxamide To a stirred and cooled (0° C.) solution of tetrahydro-2H-pyran-4-ol (1.12 g, 11.0 mmol) in N,N-dimethylformamide (20 mL) was added a 60% dispersion of sodium hydride in mineral oil (660 mg, 16.5 mmol). The mixture was stirred at 0° C. for 20 minutes before adding 2,4-dichloropyrimidine (1.98 g, 13.2 mmol) in one portion. The reaction was then left to slowly warm to room temperature and stir overnight. After this time, the reaction was quenched with water (~80 mL) and extracted with ethyl acetate. The combined organic layers were washed with brine, dried (Na$_2$SO$_4$) and concentrated. The residue was purified by flash chromatography over silica using a hexane/ethyl acetate eluant to afford 2-chloro-4-((tetrahydro-2H-pyran-4-yl)oxy)pyrimidine as a light yellow oil (1.13 g, 53%). Exchanging 2-chloro-4-(4-fluorophenyl)pyrimidine for the present intermediate, the final three steps of Example 41 were used to prepare the title compound. $^1$H NMR (500 MHz, CDCl$_3$) δ 8.08 (d, J=6.0 Hz, 1H), 6.35 (d, J=7.5 Hz, 1H), 6.00 (d, J=5.5 Hz, 1H), 5.25-5.20 (m, 1H), 4.68-4.65 (m, 2H), 4.00-3.96 (m, 2H), 3.63-3.59 (m, 2H), 3.25-3.20 (m, 2H), 3.00-2.81 (m, 6H), 2.40-2.39 (m, 1H), 2.25-2.14 (m, 2H), 2.07-1.51 (m, 15H) ppm. $^{13}$C NMR (100 MHz, CDCl$_3$) δ 171.1, 170.9, 168.8, 161.3, 158.2, 97.4, 97.0, 95.2, 69.6, 65.3, 59.3, 52.8, 47.5, 45.9, 39.3, 38.4, 36.1, 32.0, 31.8, 31.7, 31.6, 25.0, 23.9, 23.6 ppm. Purity: >99% LCMS (214 nm & 254 nm); retention time 1.13 min; (M+H$^+$) 462.0.

Example 124

4-Fluoro-1-(4-((4-fluorobenzyl)oxy)pyrimidin-2-yl)-N-(4-methyl-1-azabicyclo[3.2.2]nonan-4-yl)piperidine-4-carboxamide Exchanging tetrahydro-4-pyranol for 4-fluorobenzyl alcohol, the same reaction sequence outlined in Example 123 was used to generate the title compound. $^1$H NMR (400 MHz, CDCl$_3$) δ 8.07 (d, J=5.6 Hz, 1H), 7.42-7.34 (m, 2H), 7.09-7.01 (m, 2H), 6.33 (d, J=7.4 Hz, 1H), 6.03 (d, J=5.6 Hz, 1H), 5.29 (s, 2H), 4.73-4.63 (m, 2H), 3.28-3.16 (m, 2H), 3.09-2.78 (m, 6H), 2.37-2.30 (m, 1H), 2.30-2.08 (m, 2H), 2.01-1.90 (m, 1H), 1.89-1.69 (m, 5H), 1.67-1.45 (m, 5H) ppm. Purity: >99.9% (214 & 254 nm) UPLCMS; retention time: 0.75 min; (M+H$^+$) 486.3.

Example 125

4-Fluoro-1-(4-((4-fluorobenzyl)oxy)pyrimidin-2-yl)-N-(3-methylquinuclidin-3-yl)piperidine-4-carboxamide Exchanging tetrahydro-4-pyranol for 4-fluorobenzyl alcohol and Intermediate 5 for Intermediate 1, the same reaction sequence outlined in Example 123 was used to generate the title compound. $^1$H NMR (400 MHz, CDCl$_3$) δ 8.07 (d, J=5.6 Hz, 1H), 7.42-7.35 (m, 2H), 7.09-7.01 (m, 2H), 6.34 (d, J=6.8 Hz, 1H), 6.03 (d, J=5.6 Hz, 1H), 5.29 (s, 2H), 4.73-4.63 (m, 2H), 3.27-3.17 (m, 2H), 2.93 (s, 2H), 3.09-2.78 (m, 4H), 2.30-2.07 (m, 3H), 1.89-1.68 (m, 4H), 1.59-1.40 (n, 5H) ppm. Purity: >99.9% (214 & 254 nm) UPLCMS; retention time: 0.73 min; (M+H$^+$) 472.3.

Example 126

4-Fluoro-1-(6-(4-fluorophenoxy)pyrazin-2-yl)-N-(4-methyl-1-azabicyclo[3.2.2]nonan-4-yl)piperidine-4-carboxamide To a stirred solution of 2,6-dichloropyrazine (4.44 g, 29.8 mmol) and 4-fluorophenol (3.00 g, 26.8 mmol) in N,N-dimethylformamide (100 mL) was added potassium tert-butoxide (6.01 g, 53.6), portion wise over ~5 minutes. The reaction was heated overnight at 90° C. and then concentrated. The residue was purified by flash chromatography over silica using a hexane/ethyl acetate eluant to afford 2-chloro-6-(4-fluorophenoxy)pyrazine as a white solid (5.70 g, 95%). To a stirred solution of this product (0.850 g, 3.78 mmol) in N,N-dimethylformamide (15 mL) was added ethyl 4-fluoropiperidine-4-carboxylate (0.960 g, 4.54 mmol) and cesium carbonate (2.46 g, 7.55 mmol). The mixture was heated overnight at 60° C. and then concentrated. The residue was purified by flash chromatography over silica using a hexane/ethyl acetate eluant to afford ethyl 4-fluoro-1-(6-(4-fluorophenoxy)pyrazin-2-yl)piperidine-4-carboxylate as a yellow solid (0.190 g, 14%). To a stirred solution of this intermediate (0.300 g, 0.826 mmol) in 2:1:1 methanol/tetrahydrofuran/water (8 mL) was added solid sodium hydroxide (0.165 g, 4.13 mmol). The mixture was stirred overnight and then concentrated. The residue was dissolved in water, made acidic (pH~3) with the addition of 1N hydrochloric acid and extracted with ethyl acetate. The combined organic layers were washed with brine, dried (Na$_2$SO$_4$) and concentrated to afford 4-fluoro-1-(6-(4-fluorophenoxy)pyrazin-2-yl)piperidine-4-carboxylic acid as a yellow solid (0.176 g, 64%). Exchanging ethyl 1-(4-(4-fluorophenyl)pyrimidin-2-yl)piperidine-4-carboxylate for the present intermediate, the final two steps of Example 41 were used to prepare the title compound. $^1$H NMR (500 MHz, CDCl$_3$) δ 7.85 (s, 1H), 7.58 (s, 1H), 7.14-7.07 (m, 4H), 6.32 (d, J=7.0 Hz, 1H), 4.12 (d, J=13.5 Hz, 2H), 3.19 (t, J=11.0 Hz, 2H), 3.17-2.83 (m, 6H), 2.35 (m, 1H), 2.24-1.97 (m, 3H), 1.85-1.51 (m, 10H) ppm. $^{13}$C NMR (125 MHz, CDCl$_3$) δ 170.7, 170.5, 160.6, 158.7, 158.3, 152.6, 149.2, 123.5, 122.8, 122.7, 120.5, 116.1, 115.9, 96.3, 94.8, 59.4, 53.0, 47.5, 46.0, 40.1, 38.8, 36.2, 31.6, 31.4, 31.2, 24.9, 24.2, 24.0 ppm. Purity: >99% LCMS (214 nm & 254 nm); retention time 1.36 min; (M+H$^+$) 472.0.

Example 127

4-Fluoro-1-(5-(4-fluorophenoxy)pyridin-3-yl)-N-(4-methyl-1-azabicyclo[3.2.2]nonan-4-yl)piperidine-4-carboxamide To a stirred and cooled (0° C.) suspension of a 60% dispersion of sodium hydride in mineral oil (1.30 g, 32.5 mmol) in N,N-dimethylformamide (20 mL) was added 4-fluorophenol (2.00 g, 17.8 mmol). After 1 hour at 0° C., 3,5-dibromopyridine (4.00 g, 16.9 mmol) was added. The mixture was heated overnight at 90° C. and then diluted with water (100 mL) and extracted with ethyl acetate. The combined extracts were dried (Na$_2$SO$_4$) and concentrated. The residue was purified by flash chromatography over silica using a hexane/ethyl acetate eluant to afford 3-bromo-5-(4-fluorophenoxy)pyridine as a light yellow oil (0.660 g, 13%). To a stirred mixture of this intermediate (600 mg, 2.24 mmol) and ethyl 4-fluoropiperidine-4-carboxylate hydrochloride (0.566 g, 2.68 mmol) in toluene (15 mL) was added tris(dibenzylideneacetone)dipalladium(0) (0.204 g, 0.223 mmol), 2,2'-bis(diphenylphosphino)-1,1'-binaphthalene (0.278 g, 0.446 mmol) and potassium tert-butoxide (0.860 g, 4.48 mmol). The reaction was heated overnight at 90° C., cooled and filtered through Celite. The filtrate was concentrated to afford a residue which was diluted with 2.0 N hydrochloric acid (40 mL) and extracted with ethyl acetate. The combined organic layers were washed with brine, dried (Na$_2$SO$_4$) and concentrated to afford 4-fluoro-1-(5-(4-fluorophenoxy)pyridin-3-yl)piperidine-4-carboxylic acid (expected ester product hydrolyzed in the course of the catalytic amination reaction/workup) as a white solid (420 mg, 57%). Using General Procedure E and Intermediate 5, this carboxylic acid was subjected to amide coupling to generate the title compound as a brown solid (0.031 g, 16%). $^1$H NMR (500 MHz, CDCl$_3$) δ 8.10 (d, J=2.0 Hz, 1H), 7.81 (d, J=2.0 Hz, 1H), 7.10-7.02 (m, 4H), 6.82-6.81 (m, 1H), 6.34 (d, J=7.5 Hz, 1H), 3.64-3.62 (m, 2H), 3.16-2.82 (m, 8H), 2.40-2.32 (m, 3H), 1.99-1.52 (m, 11H) ppm. $^{13}$C NMR (125 MHz, CDCl$_3$) δ 170.8, 170.6, 160.0, 158.1, 154.6, 152.2, 147.5, 133.4, 131.0, 120.5, 120.4, 116.6, 116.4, 112.1, 95.8, 94.3, 59.4, 53.1, 47.5, 46.0, 44.1, 38.9, 36.3, 31.8, 31.6, 31.5, 31.4, 25.0, 24.3, 24.1 ppm. Purity: >99% LCMS (214 nm & 254 nm); retention time: 1.22 min; (M+H$^+$) 471.3.

Example 128

4-Fluoro-1-(4-((4-fluorobenzyl)oxy)-1,3,5-triazin-2-yl)-N-(4-methyl-1-azabicyclo[3.2.2]nonan-4-yl)piperidine-4-carboxamide To a stirred solution of 2,4-dichloro-1,3,5-triazine (1.00 g, 6.71 mmol) in 1,4-dioxane (10 mL) was added N,N-diisopropylethylamine (2.50 mL, 14.4 mmol) and ethyl 4-fluoropiperidine-4-carboxylate hydrochloride (1.14 g, 5.37 mmol). The reaction was stirred at 55° C. for 1 hour and then concentrated. The residue was purified by flash chromatography over silica gel using a hexane/ethyl acetate eluant to afford ethyl 1-(4-chloro-1,3,5-triazin-2-yl)-4-fluoropiperidine-4-carboxylate as a colorless oil (1.40 g, 72%). To a stirred and cooled (0° C.) solution of (4-fluorophenyl)methanol (0.131 g, 1.04 mmol) in anhydrous tetrahydrofuran (1 mL) was added a 60% dispersion of sodium hydride in mineral oil (0.046 g, 1.15 mmol). After 1 hour at the same temperature, the product of step 1 (0.300 g, 1.04 mmol) was added in a single portion. The reaction was then stirred at room temperature for 2 hours before diluting with water (10 mL) and extracting with ethyl acetate. The combined organic layers were dried ($Na_2SO_4$) and concentrated to afford crude product which was purified by reversed-phase flash chromatography over C-18 silica using an acetonitrile/water/trifluoroacetic acid eluant to afford ethyl 4-fluoro-1-(4-((4-fluorobenzyl)oxy)-1,3,5-triazin-2-yl)piperidine-4-carboxylate (0.120 g, 30%) as a colorless oil. Exchanging ethyl 1-(4-(4-fluorophenyl)pyrimidin-2-yl)piperidine-4-carboxylate for the present intermediate, the final two steps of Example 41 were used to prepare the title compound. $^1$H NMR (500 MHz, $CDCl_3$) δ 8.38 (s, 1H), 7.45-7.42 (m, 2H), 7.07 (t, J=8.5 Hz, 2H), 6.35 (d, J=6.5 Hz, 1H), 5.37 (s, 2H), 4.81-4.73 (m, 2H), 3.30-2.94 (m, 8H), 2.47 (m, 1H), 2.24-2.03 (m, 6H), 1.87-1.53 (m, 7H) ppm. $^{13}$C NMR (100 MHz, $CDCl_3$) δ 170.5, 170.0, 167.5, 165.2, 131.8, 130.2, 130.1, 129.5, 115.5, 115.3, 68.1, 59.3, 52.5, 47.3, 45.9, 39.0, 38.5, 37.6, 35.8, 32.1, 24.9, 23.1, 22.9 ppm. Purity: >99% LCMS (214 nm & 254 nm); retention time 1.36 min; (M+H$^+$) 487.2.

Example 129

4-Fluoro-1-(5-(4-fluorophenoxy)pyrimidin-2-yl)-N-(3-methylquinuclidin-3-yl)piperidine-4-carboxamide To a stirred solution of 2-chloropyrimidin-5-ol (1.50 g, 11.6 mmol) in dichloromethane (20 mL) was added 4-fluorophenylboronic acid (3.30 g, 23.2 mmol), copper(II) acetate (2.49 g, 13.9 mmol) and triethylamine (8.0 mL, 57 mmol). The mixture was left open to the air and stirred overnight. The suspension was then filtered through a pad of Celite and concentrated. The residue was purified by flash chromatography over silica using a hexane/ethyl acetate eluant to afford 2-chloro-5-(4-fluorophenoxy)pyrimidine as a light yellow solid (0.400 g, 17%). Exchanging 2-chloro-4-(4-fluorophenyl)pyrimidine for this intermediate, ethyl piperidine-4-carboxylate for ethyl 4-fluoropiperidine-4-carboxylate hydrochloride and Intermediate 5 for Intermediate 1, the final three steps of Example 41 were used to prepare the title compound. $^1$H NMR (400 MHz, $CD_3OD$) δ 8.20 (s, 2H), 7.09-6.99 (m, 4H), 4.70-4.66 (m, 2H), 3.33-3.16 (m, 3H), 2.90-2.83 (m, 5H), 2.30-2.01 (m, 3H), 1.92-1.89 (m, 4H), 1.70-1.50 (m, 5H) ppm. $^{13}$C NMR (100 MHz, $CD_3OD$) δ 172.4, 172.2, 159.8, 158.5, 157.4, 154.4, 150.0, 143.3, 118.2, 118.1, 116.1, 115.8, 95.7, 93.8, 60.7, 52.8, 45.6, 45.5, 39.6, 31.5, 31.4, 31.3, 31.2, 29.3, 23.0, 21.8, 21.3 ppm. Purity: >99% LCMS (214 nm & 254 nm); retention time 1.39 min; (M+H$^+$) 458.0.

Example 130

1-(5-(4-Fluorophenoxy)pyrimidin-2-yl)-N-(4-methyl-1-azabicyclo[3.2.2]nonan-4-yl)piperidine-4-carboxamide Exchanging 2-chloro-4-(4-fluorophenyl)pyrimidine for 2-chloro-5-(4-fluorophenoxy)pyrimidine (prepared as described in Example 129), the final three steps of Example 41 were used to prepare the title compound. $^1$H NMR (500 MHz, $CDCl_3$) δ 8.14 (s, 2H), 7.02-6.98 (m, 2H), 6.91-6.88 (m, 2H), 5.44 (s, 1H), 4.76-4.73 (m, 2H), 3.06-2.84 (m, 8H), 2.41-2.34 (m, 2H), 1.95-1.49 (m, 13H) ppm. $^{13}$C NMR (125 MHz, $CDCl_3$) δ 174.1, 159.4, 158.8, 157.5, 154.3, 150.3, 142.6, 118.0, 117.9, 116.4, 116.2, 59.4, 53.1, 47.6, 46.1, 44.4, 44.0, 39.2, 36.1, 31.0, 28.8, 28.5, 25.1, 24.2, 24.1 ppm. Purity: >99% LCMS (214 nm & 254 nm); retention time 1.38 min; (M+H$^+$) 454.2.

Example 131

4-Fluoro-1-(5-(4-(2-methoxyethoxy)phenoxy)pyrimidin-2-yl)-N-(3-methylquinuclidin-3-yl)piperidine-4-carboxamide Exchanging 4-fluorophenylboronic acid for (4-(2-methoxyethoxy)phenyl)boronic acid, the first step of Example 129 was used to prepare 2-chloro-5-(4-(2-methoxyethoxy)phenoxy)pyrimidine. Exchanging 2-chloro-4-(4-fluorophenyl)pyrimidine for this intermediate, ethyl piperidine-4-carboxylate for ethyl 4-fluoropiperidine-4-carboxylate hydrochloride and Intermediate 5 for Intermediate 1, the final three steps of Example 41 were used to prepare the title compound. $^1$H NMR (500 MHz, $CDCl_3$) δ 8.16 (s, 2H), 6.91 (m, 4H), 6.38 (d, J=7.0 Hz, 1H), 4.67 (d, J=13.5 Hz, 1H), 4.11 (t, J=5.0 Hz, 2H), 3.76 (t, J=4.5 Hz, 2H), 3.48 (s, 3H), 3.25 (t, J=13.5 Hz, 2H), 3.01-2.83 (m, 6H), 2.31-2.20 (m, 3H), 1.87-1.80 (m, 5H), 1.61-1.52 (m, 5H) ppm. $^{13}$C NMR (100 MHz, $CDCl_3$) δ 171.3, 171.1, 158.4, 154.7, 151.9, 149.8, 143.6, 118.2, 115.8, 96.9, 95.0, 71.1, 67.8, 63.1, 59.2, 52.8, 46.5, 46.4, 39.8, 31.9, 31.8, 31.7, 31.6, 30.1, 24.2, 23.0, 22.3 ppm. Purity: >99% LCMS (214 nm & 254 nm); retention time 1.39 min; (M+H$^+$) 514.0.

Example 132

4-Fluoro-1-(5-((4-fluorobenzyl)oxy)pyrimidin-2-yl)-N-(4-methyl-1-azabicyclo[3.2.2]nonan-4-yl)piperidine-4-carboxamide To a stirred solution of 5-bromo-2-chloropyrimidine (2.00 g, 10.3 mmol) in N,N-dimethylformamide (30 mL) was added ethyl 4-fluoropiperidine-4-carboxylate hydrochloride (2.63 g, 12.4 mmol) and cesium carbonate (3.37 g, 10.3 mmol). The suspension was heated overnight at 50° C. and then concentrated. The residue was taken up in ethyl acetate and washed with several portions of water. The organic layer was dried ($Na_2SO_4$) and concentrated. The crude product was purified by flash chromatography over silica using a hexane/ethyl acetate eluant to afford ethyl 1-(5-bromopyrimidin-2-yl)-4-fluoropiperidine-4-carboxylate as a white solid (2.93 g, 85%). To a stirred solution this intermediate (2.89 g, 8.70 mmol) in N,N-dimethylformamide (32 mL) was added bis(pinacolato)diboron (2.65 g, 10.4 mmol), potassium acetate (4.27 g, 43.5 mmol) and [1,1'-bis(diphenylphosphino)ferrocene]dichloropalladium(II) (318 mg, 435 mol). The mixture was heated overnight at 90° C. and then cooled and concentrated. The residue taken up in water and ethyl acetate, resulting in an unresolved emulsion. After suction filtering the mixture through a plug of Celite, the organic layer was separated and washed with additional portions of water. The solution was then dried ($Na_2SO_4$) and concentrated to afford ethyl 4-fluoro-1-(5-(4,4,5,5-tetramethyl-1,3,2-dioxaborolan-2-yl)pyrimidin-2-yl)piperidine-4-carboxylate as a dark brown solid (3.32 g, 101%). The crude product was used without purification in the next step. To a stirred solution of the boronate (3.31 g, 8.73 mmol) in 1:1 tetrahydrofuran/water (80 mL) was added sodium perborate monohydrate (2.21 g, 21.0 mmol). The reaction was stirred overnight and then diluted with aqueous ammonium chloride solution (~100 mL). The mixture was extracted with ethyl acetate. The combined extracts were then washed with aqueous sodium chloride solution, dried (Na$_2$SO$_4$) and concentrated. The crude product was purified by flash chromatography over silica using an ethyl acetate/chloroform eluant to afford ethyl 4-fluoro-1-(5-hydroxypyrimidin-2-yl)piperidine-4-carboxylate as a gray-green solid (1.64 g, 70%). To a stirred solution of this intermediate (0.828 g, 3.07 mmol) in N,N-dimethylformamide (15 mL) was added 1-(bromomethyl)-4-fluorobenzene (0.639 g, 3.38 mmol) and cesium carbonate (2.00 g, 6.15 mmol). The mixture was heated overnight at 40° C. and then concentrated. The residue was taken up in ethyl acetate and washed with several portions of water. The organic layer was then dried (Na$_2$SO$_4$) and concentrated. The crude product was purified by flash chromatography over silica using a hexane/ethyl acetate eluant to afford ethyl 4-fluoro-1-(5-((4-fluorobenzyl)oxy)pyrimidin-2-yl)piperidine-4-carboxylate as white solid (0.909 g, 78%). To a stirred solution of this ester (880 mg, 2.33 mmol) in 1:1:1 tetrahydrofuran/ethanol/water (21 mL) was added lithium hydroxide monohydrate (0.294 g, 7.01 mmol). The reaction was stirred overnight and then concentrated. The residue was taken up in water. The resulting suspension was treated with 1.0 N aqueous HCl (7.0 mL) and then extracted with chloroform. The combined extracts were dried (Na$_2$SO$_4$) and concentrated to afford 4-fluoro-1-(5-((4-fluorobenzyl)oxy)pyrimidin-2-yl)piperidine-4-carboxylic acid as a white solid (0.736 g, 90%). Using General Procedure E and Intermediate 5, this carboxylic acid was subjected to amide coupling to generate the title compound as a yellow solid (0.395 g, 81%). $^1$H NMR (400 MHz, CDCl$_3$) δ 8.09 (s, 2H), 7.42-7.33 (m, 2H), 7.11-7.03 (m, 2H), 6.33 (d, J=7.2 Hz, 1H), 4.98 (s, 2H), 4.63-4.53 (m, 2H), 3.25-3.15 (m, 2H), 3.08-2.90 (m, 4H), 2.89-2.78 (m, 2H), 2.36-2.30 (m, 1H), 2.30-2.09 (m, 1H), 2.00-1.89 (m, 1H), 1.88-1.68 (m, 5H), 1.67-1.44 (m, 5H) ppm. Purity: >99.9% UPLCMS (214 nm & 254 nm); retention time 0.73 min; (M+H$^+$) 472.3.

Example 133

4-Fluoro-1-(5-(4-fluorophenoxy)pyrazin-2-yl)-N-(3-methylquinuclidin-3-yl)piperidine-4-carboxamide To a stirred solution of 2,5-dibromopyrazine (0.500 g, 2.10 mmol) in N,N-dimethylformamide (15 mL) was added ethyl 4-fluoropiperidine-4-carboxylate (0.444 g, 2.10 mmol) and cesium carbonate (1.37 g, 4.20 mmol). The mixture was heated overnight at 60° C. and then concentrated. The residue was purified by flash chromatography over silica using a hexane/ethyl acetate eluant to afford ethyl 1-(5-bromopyrazin-2-yl)-4-fluoropiperidine-4-carboxylate as a yellow solid (0.330 g, 47%). This intermediate (0.400 g, 1.20 mmol) was combined with 4-fluorophenol (0.175 g, 1.56 mmol), copper oxide (0.052 g, 0.363 mmol) imidazole-4-carboxylic acid (0.081 g, 0.723 mmol), cesium carbonate (1.17 g, 3.59 mmol) and acetonitrile (12 mL) in a sealed microwave reaction vessel. The stirred mixture was heated in a microwave reactor at 120° C. for 6 hours. The reaction was then cooled and filtered to remove the solids. The filtrate was concentrated and the residue was purified by flash chromatography over silica using a hexane/ethyl acetate eluant to afford ethyl 4-fluoro-1-(5-(4-fluorophenoxy)pyrazin-2-yl)piperidine-4-carboxylate as a yellow oil (0.120 g, 28%). To a stirred solution of this intermediate (0.120 g, 0.330 mmol) in 1:1 (v/v) methanol/water (4 mL) was added solid sodium hydroxide (0.066 g, 1.65 mmol). After overnight stirring, the reaction was concentrated. The residue was dissolved in water, made acidic (pH~3) with the addition of 1N hydrochloric acid and extracted with ethyl acetate. The combined organic layers were washed with brine, dried (Na$_2$SO$_4$) and concentrated to afford 4-fluoro-1-(5-(4-fluorophenoxy)pyrazin-2-yl)piperidine-4-carboxylic acid as a white solid (0.090 g, 81%). Using General Procedure E and Intermediate 5, this carboxylic acid was subjected to amide coupling to generate the title compound as a yellow solid (0.019 g, 36%). $^1$H NMR (500 MHz, CDCl$_3$) δ 7.99 (d, J=1.0 Hz, 1H), 7.76 (d, J=1.5 Hz, 1H), 7.07-7.06 (m, 4H), 6.37 (d, J=6.5 Hz, 1H), 4.17-4.15 (m, 2H), 3.27-3.20 (m, 2H), 2.88-2.83 (m, 6H), 2.37-2.20 (m, 3H), 1.90-1.52 (m, 9H) ppm. $^{13}$C NMR (100 MHz, CDCl$_3$) δ 158.0, 152.6, 152.0, 151.1, 148.0, 131.9, 126.6, 121.2, 121.1, 116.3, 116.1, 96.4, 94.6, 63.1, 52.9, 46.5, 46.4, 41.2, 31.5, 31.4, 31.3, 31.2, 30.1, 24.2, 22.9, 22.3 ppm. Purity: >98% LCMS (214 nm & 254 nm); retention time 1.41 min; (M+H$^+$) 458.2.

Example 134

4-Fluoro-1-(6-(4-fluorophenoxy)pyridazin-3-yl)-N-(4-methyl-1-azabicyclo[3.2.2]nonan-4-yl)piperidine-4-carboxamide To a stirred solution of 3,6-dichloropyridazine (0.400 g, 2.68 mmol) in N,N-dimethylformamide (15 mL) was added ethyl 4-fluoropiperidine-4-carboxylate (0.567 g, 2.68 mmol) and cesium carbonate (2.62 g, 8.04 mmol). The mixture was heated overnight at 60° C. and then concentrated. The residue was purified by flash chromatography over silica using a hexane/ethyl acetate eluant to afford ethyl 1-(6-chloropyridazin-3-yl)-4-fluoropiperidine-4-carboxylate as a white solid (0.400 g, 52%). This intermediate (0.400 g, 1.39 mmol) was combined with 4-fluorophenol (0.203 g, 1.81 mmol), copper iodide (0.026 g, 0.137 mmol), N,N-dimethylglycine (0.029 g, 0.281 mmol), potassium carbonate (0.576 g, 4.17 mmol) and 1-methyl-2-pyrrolidinone (8 mL) in a sealed microwave reaction vessel. The stirred mixture was heated in a microwave reactor at 160° C. for 6 hours. The reaction was then cooled and filtered to remove the solids. The filtrate was concentrated and the residue was purified by flash chromatography over silica using a hexane/ethyl acetate eluant to afford ethyl 4-fluoro-1-(6-(4-fluorophenoxy)pyridazin-3-yl)piperidine-4-carboxylate as a white solid (0.120 g, 24%). Exchanging ethyl 4-fluoro-1-(6-(4-fluorophenoxy)pyrazin-2-yl)piperidine-4-carboxylate for the present intermediate, the final two steps of Example 133 were used to prepare the title compound. $^1$H NMR (500 MHz, CDCl$_3$) δ 7.17-7.05 (m, 6H), 6.36 (d, J=7.5 Hz, 1H), 4.21-4.18 (m, 2H), 3.31-3.26 (m, 2H), 3.10-3.03 (m, 4H), 2.94-2.90 (m, 2H), 2.41-2.22 (m, 3H), 1.99-1.51 (m, 11H) ppm. $^{13}$C NMR (125 MHz, CDCl$_3$) δ 171.0, 170.8, 160.5, 160.4, 158.6, 157.7, 149.9, 122.4, 119.7, 118.5, 116.2, 116.0, 96.4, 94.9, 59.3, 52.7, 47.4, 45.9, 41.6, 38.1, 36.0, 31.6, 31.5, 31.4, 31.2, 31.2, 25.0, 23.5, 23.3 ppm. Purity: >96% LCMS (214 nm & 254 nm); retention time 1.84 min; (M+H$^+$) 472.2.

Example 135

4-Fluoro-1-(4-((4-fluorophenoxy)methyl)pyrimidin-2-yl)-N-(3-methylquinuclidin-3-yl)piperidine-4-carboxamide To a stirred solution of (2-chloropyrimidin-4-yl)methanol (0.600 g, 4.14 mmol) in dichloromethane (10 mL) was added thionyl chloride (0.488 g, 4.14 mmol). The mixture was stirred at room temperature overnight and then concentrated to afford 2-chloro-4-(chloromethyl)pyrimidine as a yellow oil (0.500 g, 74%). To a stirred solution of this intermediate (0.500 g, 3.07 mmol) and 4-fluorophenol (0.378 g, 3.37 mmol) in acetonitrile (10 mL) was added potassium carbonate (0.847 g, 6.14 mmol). The reaction was heated at reflux for 1.5 hours and then concentrated. The residue was purified by flash chromatography over silica gel using a hexane/ethyl acetate eluant to afford 2-chloro-4-((4-fluorophenoxy)methyl)pyrimidine as a white solid (0.300 g, 41%). To a stirred solution of this compound (0.490 g, 2.06 mmol) in acetonitrile (15 mL) was added ethyl 4-fluoropiperidine-4-carboxylate hydrochloride (0.480 g, 2.26 mmol) and potassium carbonate (0.569 g, 4.12 mmol). The reaction was heated at reflux overnight, diluted with water (20 mL) and extracted with ethyl acetate. The combined organic layers were washed with brine, dried ($Na_2SO_4$) and concentrated. The residue was purified by flash chromatography over silica gel using a hexane/ethyl acetate eluant to afford ethyl 4-50 fluoro-1-(4-((4-fluorophenoxy)methyl)pyrimidin-2-yl)piperidine-4-carboxylate as a white solid (0.400 g, 53%). Exchanging ethyl 1-(4-(4-fluorophenyl)pyrimidin-2-yl)piperidine-4-carboxylate for the present intermediate, the final two steps of Example 41 were used to prepare the title compound. $^1$H NMR (400 MHz, $CDCl_3$) δ 8.30 (d, J=4.8 Hz, 1H), 7.01-6.97 (m, 2H), 6.90-6.87 (m, 2H), 6.69 (d, J=4.8 Hz, 1H), 6.38 (d, J=6.8 Hz, 1H), 4.93 (s, 2H), 4.75 (d, J=12.8 Hz, 2H), 3.26-3.20 (m, 2H), 3.00-2.80 (m, 6H), 2.32-2.12 (m, 3H), 1.88-1.77 (m, 4H), 1.59-1.50 (m, 5H) ppm. $^{13}$C NMR (100 MHz, $CDCl_3$) δ 171.3, 171.1, 166.7, 161.1, 158.6, 158.4, 156.3, 154.3, 154.3, 116.0, 115.8, 115.7, 115.6, 106.5, 96.9, 95.1, 70.3, 63.0, 52.8, 46.5, 46.3, 39.1, 32.0, 31.9, 31.8, 31.7, 30.1, 24.2, 22.9, 22.3 ppm. Purity: >95% LCMS (214 nm & 254 nm); retention time 1.42 min; (M+H$^+$) 472.2.

Example 136

4-Fluoro-1-(5-(4-fluorobenzyl)pyrimidin-2-yl)-N-(3-methylquinuclidin-3-yl)piperidine-4-carboxamide To a stirred solution of 4-hydroxybenzaldehyde (6.00 g, 49.1 mmol) in acetonitrile (200 mL) was added cesium carbonate (40.0 g, 123 mmol) and 1-chloro-2-methoxyethane (6.90 g, 73.7 mmol). The solution was heated at reflux overnight and then diluted with water (100 mL). The mixture was extracted with ethyl acetate and the combined organic layers were washed with water and brine, dried ($Na_2SO_4$) and concentrated. The residue was purified by flash chromatography over silica gel using a hexane/ethyl acetate eluant to afford 4-(2-methoxyethoxy)benzaldehyde as a light yellow oil (6.00 g, 67%). To a stirred solution of this compound (2.70 g, 15.0 mmol) in 1,4-dioxane (50 mL) was added 4-methylbenzenesulfonohydrazide (2.79 g, 15.0 mmol). The solution was heated at 90° C. for 1 hour and then concentrated to afford crude N'-(4-(2-methoxyethoxy)benzylidene)-4-methylbenzenesulfonohydrazide as a yellow solid (5.22 g, 99%). This material was used without purification in the next step. To a stirred solution of the hydrazone (5.22 g, 15.0 mmol) in 1,4-dioxane (50 mL) was added potassium carbonate (6.20 g, 44.9 mmol) and 2-chloropyrimidin-5-ylboronic acid (2.37 g, 15.0 mmol). Mixture was heated at 90° C. for 3 hours, diluted with water (100 mL) and extracted with ethyl acetate. The combined organic layers were washed with water and brine, dried ($Na_2SO_4$) and concentrated. The residue was purified by flash chromatography over silica gel using a hexane/ethyl acetate eluant to afford 2-chloro-5-(4-(2-methoxyethoxy)benzyl)pyrimidine as a light yellow oil (0.700 g, 17%). To a stirred solution of this intermediate (0.700 g, 2.52 mmol) in acetonitrile (15 mL) was added ethyl 4-fluoropiperidine-4-carboxylate hydrochloride (0.453 g, 2.59 mmol) and cesium carbonate (2.46 g, 7.55 mmol). The mixture was heated at 80° C. overnight, diluted with water (50 mL) and extracted with ethyl acetate. The combined organic layers were washed with brine, dried ($Na_2SO_4$) and concentrated. The residue purified by flash chromatography over silica gel using a dichloromethane/methanol eluant to afford ethyl 4-fluoro-1-(5-(4-(2-methoxyethoxy)benzyl)pyrimidin-2-yl)piperidine-4-carboxylate as a light yellow solid (0.667 g, 74%). Exchanging ethyl 1-(4-(4-fluorophenyl)pyrimidin-2-yl)piperidine-4-carboxylate for the present intermediate, the final two steps of Example 41 were used to prepare the title compound. $^1$H NMR (400 MHz, $CDCl_3$) δ 8.16 (s, 2H), 7.08 (d, J=8.8 Hz, 2H), 6.87 (d, J=8.8 Hz, 2H), 6.37 (d, J=7.2 Hz, 1H), 4.70-4.66 (m, 2H), 4.11 (t, J=4.4 Hz, 2H), 3.76-3.74 (m, 4H), 3.46 (s, 3H), 3.26-3.19 (m, 2H), 2.96-2.79 (m, 6H), 2.28-2.15 (m, 3H), 1.87-1.77 (m, 4H), 1.58-1.50 (m, 5H) ppm. $^{13}$C NMR (100 MHz, $CDCl_3$) δ 171.3, 171.1, 160.5, 157.9, 157.4, 132.4, 129.5, 122.4, 114.8, 97.0, 95.1, 71.0, 67.3, 63.0, 59.2, 52.8, 46.5, 46.3, 39.3, 34.7, 31.9, 31.8, 31.7, 31.6, 30.1, 24.2, 22.9, 22.3 ppm. Purity: >93% LCMS (214 nm & 254 nm); retention time 1.36 min; (M+H$^+$) 512.3.

Example 137

(3R)-3-Methyl-N-(4-methyl-1-azabicyclo[3.2.2]nonan-4-yl)-4-(4-phenylpyrimidin-2-yl)piperazine-1-carboxamide (Single Enantiomer B)

To a stirred solution of 2,4-dichloropyrimidine (3.00 g, 20.1 mmol) in toluene (25 mL) was added phenylboronic acid (2.47 g, 20.3 mmol), potassium carbonate (8.40 g, 60.9 mmol), tetrakis(triphenylphosphine)palladium(0) (1.26 g, 1.02 mmol) and 1:1 (v/v) ethanol/water (36 mL). The mixture was heated overnight at 55° C. and then concentrated. The residue was diluted with water and extracted with ethyl acetate. The combined extracts were washed with brine, dried ($Na_2SO_4$) and concentrated. The crude material was purified by flash chromatography over silica using a hexane/ethyl acetate eluant to afford 2-chloro-4-phenylpyrimidine as a yellow solid (3.20 g, 83%). To a stirred solution of this intermediate (1.10 g, 5.77 mmol) in butyronitrile (20 mL) was added (R)-tert-butyl 3-methylpiperazine-1-carboxylate (2.31 g, 11.5 mmol) and potassium carbonate (2.07 g, 15.0 mmol). The mixture was heated at reflux for 48 hours and then concentrated. The residue was taken up in ethyl acetate and washed with water. The aqueous layer was back-extracted with ethyl acetate and the combined organic layers were dried ($Na_2SO_4$) and concentrated. The crude product was purified by flash chromatography over silica using a methanol/dichloromethane eluant to afford (R)-tert-butyl 3-methyl-4-(4-phenylpyrimidin-2-yl)piperazine-1-carboxylate as amber solid (1.72 g, 84%). The t-butoxycarbonyl protecting group was removed from this compound using General Procedure G to afford (R)-2-(2-methylpiperazin-1-yl)-4-phenylpyrimidine. The intermediate was, in turn, reacted with Intermediate 10 using General Procedure A to generate the title compound. $^1$H NMR (400 MHz, DMSO-d$_6$) δ 8.46 (d, J=5.1 Hz, 1H), 8.18-8.10 (m, 2H), 7.57-7.48 (m, 3H), 7.22 (d, J=5.1 Hz, 1H), 5.72 (s, 1H), 4.93-4.82 (m, 1H), 4.54-4.42 (m, 1H), 4.13-4.02 (m, 1H), 3.94-3.84 (m, 1H), 3.27-3.06 (m, 2H), 2.98-2.64 (m, 7H), 2.43-2.33 (m, 1H), 1.83-1.63 (m, 4H), 1.57-1.24 (m, 5H), 1.16 (d, J=6.6 Hz, 3H) ppm. Purity: 99.7% (214 & 254 nm) UPLCMS; retention time: 0.82 min; (M+H$^+$) 435.5.

Example 138

(3R)-3-Methyl-N-(4-methyl-1-azabicyclo[3.2.2] nonan-4-yl)-4-(4-phenylpyrimidin-2-yl)piperazine-1-carboxamide (Single Enantiomer A)

Exchanging Intermediate 10 for Intermediate 9, the same reaction sequence outlined in Example 137 was used to generate the title compound. $^1$H NMR (400 MHz, DMSO-d$_6$) δ 8.46 (d, J=5.2 Hz, 1H), 8.19-8.09 (m, 2H), 7.58-7.47 (m, 3H), 7.22 (d, J=5.2 Hz, 1H), 5.70 (s, 1H), 4.91-4.80 (m, 1H), 4.54-4.42 (m, 1H), 4.07-3.88 (m, 2H), 3.27-3.14 (m, 1H), 3.14-3.04 (m, 1H), 3.00-2.67 (m, 7H), 2.40-2.31 (m, 1H), 1.87-1.64 (m, 4H), 1.57-1.43 (m, 1H), 1.42-1.26 (m, 4H), 1.15 (d, J=6.6 Hz, 3H) ppm. Purity: 99.4% (214 & 254 nm) UPLCMS; retention time: 0.83 min; (M+H$^+$) 435.5.

Example 139

(3S)-3-Methyl-N-(4-methyl-1-azabicyclo[3.2.2] nonan-4-yl)-4-(4-phenylpyrimidin-2-yl)piperazine-1-carboxamide (Single Enantiomer B)

Exchanging (R)-tert-butyl 3-methylpiperazine-1-carboxylate for (S)-tert-butyl 3-methylpiperazine-1-carboxylate, the same reaction sequence outlined in Example 137 was used to generate the title compound. $^1$H NMR (400 MHz, DMSO-d$_6$) δ 8.46 (d, J=5.2 Hz, 1H), 8.18-8.09 (m, 2H), 7.57-7.47 (m, 3H), 7.22 (d, J=5.2 Hz, 1H), 5.70 (s, 1H), 4.91-4.80 (m, 1H), 4.53-4.42 (m, 1H), 4.05-3.87 (m, 2H), 3.26-3.14 (m, 1H), 3.09 (dd, J=13.4, 3.8 Hz, 1H), 2.99-2.67 (m, 7H), 2.40-2.31 (m, 1H), 1.87-1.63 (m, 4H), 1.56-1.43 (m, 1H), 1.42-1.26 (m, 4H), 1.15 (d, J=6.6 Hz, 3H) ppm. Purity: >99.9% (214 & 254 nm) UPLCMS; retention time: 0.83 min; (M+H$^+$) 435.5.

Example 140

(3S)-3-Methyl-N-(4-methyl-1-azabicyclo[3.2.2] nonan-4-yl)-4-(4-phenylpyrimidin-2-yl)piperazine-1-carboxamide (Single Enantiomer A)

Exchanging (R)-tert-butyl 3-methylpiperazine-1-carboxylate for (S)-tert-butyl 3-methylpiperazine-1-carboxylate and Intermediate 10 for Intermediate 9, the same reaction sequence outlined in Example 137 was used to generate the title compound. $^1$H NMR (400 MHz, DMSO-d$_6$) δ 8.46 (d, J=5.2 Hz, 1H), 8.18-8.10 (m, 2H), 7.56-7.48 (m, 3H), 7.22 (d, J=5.2 Hz, 1H), 5.73 (s, 1H), 4.93-4.81 (m, 1H), 4.54-4.43 (m, 1H), 4.12-4.02 (m, 1H), 3.94-3.84 (m, 1H), 3.26-3.07 (m, 1H), 3.00-2.69 (m, 7H), 2.43-2.35 (m, 1H), 1.84-1.64 (m, 4H), 1.57-1.44 (m, 1H), 1.43-1.26 (m, 4H), 1.16 (d, J=6.5 Hz, 3H) ppm. Purity: 99.6% (214 & 254 nm) UPLCMS; retention time: 0.82 min; (M+H$^+$) 435.5.

Example 141

3-Methyl-N-(4-methyl-1-azabicyclo[3.2.2]nonan-4-yl)-4-(4-phenylpyrimidin-2-yl)piperazine-1-carboxamide Exchanging (R)-tert-butyl 3-methylpiperazine-1-carboxylate for racemic tert-butyl 3-methylpiperazine-1-carboxylate and Intermediate 10 for Intermediate 5, the same reaction sequence outlined in Example 137 was used to generate the title compound. $^1$H NMR (500 MHz, CDCl$_3$) δ 8.41 (d, J=5.5 Hz, 1H), 8.08-8.06 (m, 2H), 7.50-7.49 (m, 3H), 7.00 (d, J=5.5 Hz, 1H), 5.06-4.98 (m, 1H), 4.66-4.58 (m, 1H), 4.37-4.35 (m, 1H), 4.00-3.89 (m, 1H), 3.78-3.66 (m, 1H), 3.50-3.37 (m, 2H), 3.116-3.01 (m, 5H), 2.85-2.82 (m, 2H), 2.47-2.39 (m, 1H), 2.00-1.96 (m, 3H), 1.75-1.52 (m, 6H), 1.31 (d, J=6.5 Hz, 3H) ppm. $^{13}$C NMR (125 MHz, CDCl$_3$) δ 164.3, 161.4, 158.3, 157.2, 137.5, 130.5, 128.7, 127.0, 105.9, 59.0, 53.24, 53.21, 47.9, 47.7, 47.6, 47.4, 47.2, 46.22, 46.18, 43.9, 43.6, 39.8, 39.6, 38.4, 36.7, 36.5, 25.9, 25.8, 24.44, 24.42, 24.2, 24.1, 15.2, 15.1 ppm. Purity: >99% LCMS (214 nm & 254 nm); retention time 1.32 min; (M+H$^+$) 435.3.

Example 142

3-Ethyl-N-(4-methyl-1-azabicyclo[3.2.2]nonan-4-yl)-4-(4-phenylpyrimidin-2-yl)piperazine-1-carboxamide Exchanging (R)-tert-butyl 3-methylpiperazine-1-carboxylate for tert-butyl 3-ethylpiperazine-1-carboxylate and Intermediate 10 for Intermediate 5, the same reaction sequence outlined in Example 137 was used to generate the title compound. $^1$H NMR (400 MHz, CDCl$_3$) δ 7.60-7.58 (d, J=8.0 Hz, 2H), 7.44 (t, J=7.6 Hz, 2H), 7.37-7.32 (m, 2H), 7.15 (s, 1H), 7.10-7.08 (d, J=7.2 Hz, 1H), 6.96-6.94 (d, J=8.0 Hz, 1H), 5.46 (s, 1H), 3.83-3.80 (m, 2H), 3.08-2.78 (m, 8H), 2.41 (m, 1H), 2.24-2.21 (m, 1H), 2.01-1.52 (m, 13H) ppm. Purity: 97.7% (214 & 254 nm) UPLCMS; retention time: 0.89 min; (M+H$^+$) 449.5.

Example 143

3-Ethyl-N-(4-methyl-1-azabicyclo[3.2.2]nonan-4-yl)-4-(4-phenylpyrimidin-2-yl)piperazine-1-carboxamide Exchanging 2,4-dichloropyrimidine for 2,4-dichloro-5-fluoropyrimidine, (R)-tert-butyl 3-methylpiperazine-1-carboxylate for racemic tert-butyl 3-methylpiperazine-1-carboxylate and Intermediate 10 for Intermediate 5, the same reaction sequence outlined in Example 137 was used to generate the title compound. $^1$H NMR (500 MHz, CDCl$_3$) δ 8.29 (d, J=3.5 Hz, 1H), 8.12-8.09 (m, 2H), 7.53-7.50 (m, 3H), 4.91-4.87 (m, 1H), 4.53-4.48 (m, 1H), 4.36-4.34 (m, 1H), 4.00-3.90 (m, 1H), 3.75-3.66 (m, 1H), 3.45-3.35 (m, 2H), 3.15-2.84 (m, 7H), 2.44-2.39 (m, 1H), 1.99-1.85 (m, 3H), 1.74-1.52 (m, 6H), 1.29 (dd, J=6.5 Hz & 2.0 Hz, 3H) ppm. $^{13}$C NMR (125 MHz, CDCl$_3$) δ 157.8, 157.1, 151.5, 151.4, 150.9, 148.9, 146.8, 146.6, 134.0, 130.6, 128.9, 128.5, 59.0, 53.3, 47.9, 47.7, 47.6, 46.3, 46.2, 43.8, 43.6, 39.9, 39.7, 38.9, 36.7, 36.5, 25.9, 25.8, 24.5, 24.3, 24.2, 15.0, 14.9 ppm. Purity: >99% LCMS (214 nm & 254 nm); retention time 1.37 min; (M+H$^+$) 453.3.

Example 144

3-(Methoxymethyl)-N-(4-methyl-1-azabicyclo[3.2.2] nonan-4-yl)-4-(4-phenylpyrimidin-2-yl)piperazine-1-carboxamide 2-Chloro-4-phenylpyrimidine (prepared as described in Example 137; 0.332 g, 1.74 mmol), tert-butyl 3-(methoxymethyl)piperazine-1-carboxylate (0.400 g, 1.74 mmol), N,N- diisopropylethylamine (0.61 mL, 3.49 mmol) and acetonitrile (8 mL) were loaded into a sealed microwave reaction vial. The mixture was heated with stirring in a microwave reactor for 36 hours at 140° C. The reaction was then concentrated and the residue was partitioned between water and ethyl acetate. The organic layer was combined with a second ethyl acetate extract, dried ($Na_2SO_4$) and concentrated. The crude product was purified by flash chromatography over silica using a dichloromethane/methanol eluant to afford tert-butyl 3-(methoxymethyl)-4-(4-phenylpyrimidin-2-yl)piperazine-1-carboxylate as a glassy, faint amber solid (0.397 g, 60%). The t-butoxycarbonyl protecting group was removed from this compound using General Procedure G to afford 2-(2-(methoxymethyl)piperazin-1-yl)-4-phenylpyrimidine. The intermediate was, in turn, reacted with Intermediate 5 using General Procedure A to generate the title compound. $^1$H NMR (400 MHz, DMSO-$d_6$) δ 8.47 (d, J=5.1 Hz, 1H), 8.18-8.09 (m, 2H), 7.57-7.47 (m, 3H), 7.24 (d, J=5.1 Hz, 1H), 5.65 (s, 0.5H), 5.61 (s, 0.5H), 4.99-4.84 (m, 1H), 4.58-4.42 (m, 1H), 4.13-3.93 (m, 2H), 3.56-3.35 (m, 2H), 3.29 (s, 1.5H), 3.28 (s, 1.5H), 3.25-3.03 (m, 2H), 3.01-2.65 (m, 7H), 2.37-2.28 (m, 1H), 1.86-1.61 (m, 4H), 1.55-1.21 (m, 5H) ppm. Purity: 99.4% (214 & 254 nm) UPLCMS; retention time: 0.83 min; (M+H$^+$) 465.4.

Example 145

4-(4-(4-Fluorophenyl)pyrimidin-2-yl)-3-methyl-N-(4-methyl-1-azabicyclo[3.2.2]nonan-4-yl)piperazine-1-carboxamide Exchanging 2-chloro-4-phenylpyrimidine for 2-chloro-4-(4-fluorophenyl)pyrimidine, (R)-tert-butyl 3-methylpiperazine-1-carboxylate for racemic tert-butyl 3-methylpiperazine-1-carboxylate and Intermediate 10 for Intermediate 5, the final three steps of Example 137 were used to generate the title compound. $^1$H NMR (500 MHz, CDCl$_3$) δ 8.38 (d, J=5.5 Hz, 1H), 8.06-8.03 (m, 2H), 7.15 (t, J=8.5 Hz, 2H), 6.92 (d, J=5.5 Hz, 1H), 4.99-4.96 (m, 1H), 4.60-4.56 (m, 1H), 4.34 (d, J=6.0 Hz, 1H), 3.98-3.88 (m, 1H), 3.73-3.64 (m, 1H), 3.45-3.34 (m, 2H), 3.13-2.84 (m, 7H), 2.40-2.37 (m, 1H), 1.96-1.53 (m, 9H), 1.29 (dd, J=7.0 Hz & 2.5 Hz, 3H) ppm. $^{13}$C NMR (125 MHz, CDCl$_3$) δ 165.4, 163.4, 163.2, 161.3, 158.4, 157.2, 133.7, 139.0, 128.9, 115.7, 115.6, 105.5, 59.1, 53.3, 47.9, 47.7, 47.6, 47.4, 47.2, 46.3, 43.9, 43.6, 40.0, 39.8, 38.4, 36.8, 36.6, 25.9, 25.8, 24.5, 24.3, 24.2, 15.3. 15.1 ppm. Purity: >97% LCMS (214 nm & 254 nm); retention time 1.37 min; (M+H$^{+)}$ 453.3.

Example 146

4-(4-(4-Fluorophenyl)pyrimidin-2-yl)-3-methyl-N-(4-methyl-1-azabicyclo[3.2.2]nonan-4-yl)piperazine-1-carboxamide Exchanging phenylboronic acid for (4-(2-methoxyethoxy)phenyl)boronic acid, 2,4-dichloropyrimidine for 2,4-dichloro-5-fluoropyrimidine, (R)-tert-butyl 3-methylpiperazine-1-carboxylate for racemic tert-butyl 3-methylpiperazine-1-carboxylate and Intermediate 10 for Intermediate 5, the same reaction sequence outlined in Example 137 was used to generate the title compound. $^1$H NMR (400 MHz, CDCl$_3$) δ 8.21 (d, J=3.8 Hz, 1H), 8.09 (d, J=8.9 Hz, 2H), 7.02 (d, J=8.9 Hz, 2H), 4.91-4.81 (m, 1H), 4.50-4.36 (m, 2H), 4.22-4.16 (m, 2H), 4.01-3.87 (m, 1H), 3.82-3.63 (m, 3H), 3.47 (s, 3H), 3.43-3.30 (m, 2H), 3.14-2.80 (m, 7H), 2.47-2.38 (m, 1H), 1.99-1.78 (m, 3H), 1.78-1.48 (m, 6H), 1.26 (d, J=2.2 Hz, 1.5H), 1.25 (d, J=2.2 Hz, 1.5H) ppm. Purity: 98.7% (214 & 254 nm) UPLCMS; retention time: 0.91 min; (M+H$^+$) 527.5.

Example 147 cis-3,5-Dimethyl-N-(4-methyl-1-azabicyclo[3.2.2]nonan-4-yl)-4-(4-phenylpyrimidin-2-yl)piperazine-1-carboxamide A stirred mixture of 2-chloro-4-phenylpyrimidine (prepared as described in Example 137; 0.190 g, 0.999 mmol), 2,2,6,6-tetramethylpiperidine and tert-butyl cis-3,5-dimethylpiperazine-1-carboxylate was heated at 140° for 48 hours and then concentrated. The residue was purified by flash chromatography over silica using a hexane/ethyl acetate eluant to afford tert-butyl cis-3,5-dimethyl-4-(4-phenylpyrimidin-2-yl)piperazine-1-carboxylate as a white solid (0.094 g, 26%). To a stirred and cooled (0° C.) solution of this intermediate (0.185 g, 0.500 mmol) in dichloromethane (1 mL) was added trifluoroacetic acid (4 mL). The reaction was allowed to warm to room temperature and stirred for an additional 2 hours. At this time, the mixture was diluted with a saturated aqueous sodium carbonate solution (enough to make the solution basic) and extracted with dichloromethane. The combined extracts were dried ($Na_2SO_4$) and concentrated to afford 2-(cis-2,6-dimethylpiperazin-1-yl)-4-phenylpyrimidine as a yellow oil (0.136 g, 100%). Using General Procedure A and Intermediate 5, this intermediate was used to generate the title compound as a white solid (0.068 g, 31%). $^1$H NMR (500 MHz, CDCl$_3$) δ 8.43 (d, J=5.0 Hz, 1H), 8.09-8.06 (m, 2H), 7.51-7.49 (m, 3H), 7.01 (d, J=5.5 Hz, 1H), 4.98-4.96 (m, 2H), 4.44 (s, 1H), 3.97 (d, J=12.0 Hz, 1H), 3.78 (d, J=12.0 Hz, 1H), 3.28-2.90 (m, 8H), 2.48 (m, 1H), 1.98-1.57 (m, 9H), 1.38 (t, J=7.5 Hz, 6H) ppm. $^{13}$C NMR (125 MHz, CDCl$_3$) δ 164.2, 160.8, 158.3, 157.2, 137.7, 130.5, 128.7, 126.9, 105.7, 59.0, 53.3, 48.8, 48.2, 48.0, 46.4, 46.3, 46.0, 39.6, 36.6, 26.0, 24.3, 24.0, 19.4 ppm. Purity: >95% LCMS (214 nm & 254 nm); retention time 1.99 min; (M+H$^+$) 449.4.

Example 148

4-(5-Fluoro-4-(4-(methoxymethyl)phenyl)pyrimidin-2-yl)-3-isopropyl-N-(4-methyl-1-azabicyclo[3.2.2]nonan-4-yl)piperazine-1-carboxamide Exchanging 2,4-dichloropyrimidine for 2,4-dichloro-5-fluoropyrimidine and phenylboronic acid for 2-(4-(methoxymethyl)phenyl)-4,4,5,5-tetramethyl-1,3,2-dioxaborolane, the first step of Example 137 was used to prepare 2-chloro-5-fluoro-4-(4-(methoxymethyl)phenyl)pyrimidine. To a stirred solution of this intermediate (0.400 g, 1.58 mol) in toluene (8 mL) was added tert-butyl 3-isopropylpiperazine-1-carboxylate (0.434 g, 1.90 mmol), bis(tri-tert-butylphosphine)palladium(0) (0.081 g, 0.158 mmol), trimethylhexadecylammonium chloride (0.101 g, 0.316 mmol) and a 50% aqueous sodium hydroxide solution (0.25 mL, 4.73 mmol). The mixture was heated at 100° C. overnight and concentrated. The residue was purified by flash chromatography over silica using a hexane/ethyl acetate eluant to afford partially purified tert-butyl 4-(5-fluoro-4-(4-(methoxymethyl)phenyl)pyrimidin-2-yl)-3-isopropylpiperazine-1-carboxylate as light yellow oil (0.500 g). This material was taken up in dichloromethane (5 mL), stirred and treated with trifluoroacetic acid (3.0 mL). After 3 hours, the reaction was concentrated and the residue was purified by reversed-phase flash chromatography over C18 silica using a acetonitrile/water/trifluoroacetic acid eluant. 5-Fluoro-2-(2-isopropylpiperazin-1-yl)-4-(4-(methoxymethyl)phenyl)pyrimidine was afforded as a light yellow oil (0.200 g, 36% for two steps). Using General Procedure A and Intermediate 5, this intermediate was used to generate the title compound as a white solid (0.105 g, 63%). $^1$H NMR (500 MHz, CDCl$_3$) δ 8.24 (d, J=3.5 Hz, 1H), 8.08 (d, J=8.0 Hz, 2H), 7.48 (d, J=8.5 Hz, 2H), 4.75-4.72 (m, 1H), 4.59-4.55 (m, 3H), 4.33-4.31 (m, 1H), 3.94-3.86 (m, 2H), 3.45 (s, 3H), 3.28-3.19 (m, 2H), 3.07-2.85 (m, 7H), 2.43-2.40 (m, 1H), 2.26-2.19 (m, 1H), 1.94-1.50 (m, 9H), 1.13 (t, J=7.5 Hz, 3H), 0.87 (d, J=7.5 Hz, 3H) ppm. $^{13}$C NMR (125 MHz, CDCl$_3$) δ 158.4, 157.0, 151.1, 151.0, 150.4, 148.4, 146.7, 146.4, 140.9, 133.4, 129.0, 128.9, 127.5, 74.2, 59.0, 58.3, 57.5, 57.3, 53.2, 47.8, 47.6, 46.4, 46.1, 44.0, 43.9, 43.5, 43.3, 39.9, 39.7, 39.1, 36.7, 36.4, 27.1, 27.0, 25.9, 25.7, 24.4, 24.1, 20.4, 20.2, 19.1, 19.0 ppm. Purity: >99% LCMS (214 nm & 254 nm); retention time 1.54 min; (M+H$^+$) 525.3.

Example 149

4-(4-(4-(Methoxymethyl)phenyl)pyrimidin-2-yl)-N-(4-methyl-1-azabicyclo[3.2.2]nonan-4-yl)-3-(trifluoromethyl)piperazine-1-carboxamide Exchanging phenylboronic acid for 2-(4-(methoxymethyl)phenyl)-4,4,5,5-tetramethyl-1,3,2-dioxaborolane, the first step of Example 137 was used to prepare 2-chloro-4-(4-(methoxymethyl)phenyl)pyrimidine. To a stirred solution of this intermediate (880 mg, 3.75 mmol) in toluene (30 mL) was added tert-butyl 3-(trifluoromethyl)piperazine-1-carboxylate (1.10 g, 4.33 mmol), cesium carbonate (6.11 g, 18.75 mmol), 2,2'-bis(diphenylphosphino)-1,1'-binaphthalene (700 mg, 1.12 mmol and palladium(II) acetate (0.168 g, 0.748 mmol). The mixture was heated at reflux overnight, cooled and diluted with water (~100 mL). The mixture was extracted with ethyl acetate and the combined organic layers were dried (Na$_2$SO$_4$) and concentrated. The crude product was purified by flash chromatography over silica using a hexane/ethyl acetate eluant to afford tert-butyl 4-(4-(4-(methoxymethyl)phenyl)pyrimidin-2-yl)-3-(trifluoromethyl)piperazine-1-carboxylate as a colorless gum (0.179 g, 11%). The t-butoxycarbonyl protecting group was removed from this compound using General Procedure G to afford 4-(4-(methoxymethyl)phenyl)-2-(2-(trifluoromethyl)piperazin-1-yl)pyrimidine. This intermediate was, in turn, reacted with Intermediate 5 using General Procedure A to generate the title compound. $^1$H NMR (400 MHz, CDCl$_3$) δ 8.42 (dd, J=5.2, 1.4 Hz, 1H), 8.02 (d, J=7.8 Hz, 2H), 7.45 (d, J=7.8 Hz, 2H), 7.27 (s, 1H), 7.09 (dd, J=5.2, 1.4 Hz, 1H), 5.72-5.58 (m, 1H), 4.93-4.79 (m, 1H), 4.53 (s, 1H), 4.43-4.36 (m, 1H), 4.26-4.18 (m, 0.5H), 4.16-4.08 (m, 0.5H), 4.05-3.89 (m, 1H), 3.59-3.40 (m, 5H), 3.15-2.75 (m, 7H), 2.44-2.35 (m, 1H), 1.98-1.41 (m, 9H) ppm. Purity: >99.9% (214 & 254 nm) UPLCMS; retention time: 0.90 min; (M+H$^+$) 533.3.

Example 150

3-(Difluoromethyl)-4-(4-(4-(methoxymethyl)phenyl)pyrimidin-2-yl)-N-(4-methyl-1-azabicyclo[3.2.2]nonan-4-yl)piperazine-1-carboxamide Exchanging tert-butyl 3-isopropylpiperazine-1-carboxylate for tert-butyl 3-(difluoromethyl)piperazine-1-carboxylate, the final three steps of Example 148 were used to generate the title compound. $^1$H NMR (500 MHz, CDCl$_3$) δ 8.43 (d, J=5.5 Hz, 1H), 8.04 (d, J=8.0 Hz, 2H), 7.476 (d, J=8.0 Hz, 2H), 7.09 (d, J=5.0 Hz, 1H), 6.17 (t, J=56 Hz, 1H), 5.14-5.10 (m, 1H), 4.79 (m, 1H), 4.55 (s, 2H), 4.41-4.39 (m, 1H), 4.05-3.95 (m, 2H), 3.58-3.45 (m, 5H), 3.18-2.84 (m, 7H), 2.41-2.38 (m, 1H), 1.95-1.50 (m, 9H) ppm. $^{13}$C NMR (100 MHz, CDCl$_3$) δ 164.3, 161.5, 158.4, 156.4, 141.2, 136.4, 132.1, 131.9, 128.5, 128.4, 114.7 (td, J=246 Hz & 7.4 Hz), 107.0, 74.2, 59.1, 58.3, 53.2, 52.9, 52.6, 52.4, 52.1, 47.7, 47.5, 46.3, 46.1, 43.4, 43.2, 39.7, 39.6, 39.5, 39.4, 36.7, 36.5, 30.9, 25.8, 25.6, 24.4, 24.0 ppm. Purity: >99% LCMS (214 nm & 254 nm); retention time 1.29 min; (M+H$^+$) 515.3.

Example 151

3-Isopropyl-4-(4-(4-(methoxymethyl)phenyl)-1,3,5-triazin-2-yl)-N-(4-methyl-1-azabicyclo[3.2.2]nonan-4-yl)piperazine-1-carboxamide To a stirred and cooled (0° C.) suspension of 2,4-dichloro-1,3,5-triazine (0.800 g, 5.33 mmol) and potassium carbonate (1.47 g, 10.7 mmol) in tetrahydrofuran (20 mL) was added, dropwise over 30 minutes, a solution of tert-butyl 3-isopropylpiperazine-1-carboxylate (1.22 mg, 5.33 mmol) in tetrahydrofuran (10 mL). The mixture was stirred at 0° C. for 2 hours and then at room temperature overnight. The reaction was then concentrated and the residue was purified by column chromatography over neutral alumina using a hexane/ethyl acetate eluant to afford tert-butyl 4-(4-chloro-1,3,5-triazin-2-yl)-3-isopropylpiperazine-1-carboxylate as a white solid (1.10 g, 60%). To a stirred solution of this intermediate a (0.450 g, 1.32 mmol) in 1,4-dioxane was added 2-(4-((2-methoxyethoxy)methyl)phenyl)-4,4,5,5-tetramethyl-1,3,2-dioxaborolane (0.391 g, 1.58 mmol), tris(dibenzylideneacetone)dipalladium(0) (0.119 g, 0.130 mmol), 2-dicyclohexylphosphino-2',4',6'-triisopropylbiphenyl (0.124 g, 0.260 mmol) and cesium carbonate (1.08 g, 3.31 mmol). The mixture was heated overnight at 140° C. for 16 hours, filtered through Celite, and concentrated. The residue was purified by flash chromatography over silica gel using a dichloromethane/methanol eluant to afford tert-butyl 3-isopropyl-4-(4-(4-(methoxymethyl)phenyl)-1,3,5-triazin-2-yl)piperazine-1-carboxylate as a white solid (200 mg, 35%). To a stirred and cooled (0° C.) solution of this intermediate (200 mg, 0.470 mmol) in dichloromethane (10 mL) was added trifluoroacetic acid (10 mL). The reaction was stirred for another 3 hours at 0° C. before diluting with 2.0 N aqueous potassium carbonate solution (enough to render the mixture basic) and extracting with dichloromethane. The combined organic phases were washed with brine, dried (Na$_2$SO$_4$) and concentrated to afford 2-(2-isopropylpiperazin-1-yl)-4-(4-(methoxymethyl)phenyl)-1,3,5-triazine as a white solid (150 mg, crude). Using General Procedure A and Intermediate 5, this intermediate was used to generate the title compound as a light yellow solid (0.040 g, 15%). $^1$H NMR (500 MHz, CDCl$_3$) δ 8.65 (d, J=3.0 Hz, 1H), 8.41-8.37 (m, 2H), 7.47-7.45 (m, 2H), 4.99 (m, 0.5H), 4.80 (m, 1H), 4.63 (m, 0.5H), 4.56 (s, 2H), 4.35 (d, J=12.5 Hz, 1H), 4.08-3.89 (m, 2H), 3.44 (s, 3H), 3.19-2.84 (m, 9H), 2.42-2.40 (m, 1H), 2.24 (m, 1H), 1.98-1.56 (m, 9H), 1.19-1.13 (m, 3H), 0.89-0.85 (m, 3H) ppm. $^{13}$C NMR (125 MHz, CDCl$_3$) δ 170.5, 170.2, 166.2, 166.0, 164.5, 156.8, 142.5, 135.6, 135.5, 128.6, 128.5, 127.5, 74.2, 59.2, 59.1, 58.3, 56.8, 56.7, 56.6, 53.1, 47.6, 47.5, 46.4, 46.2, 44.5, 44.1, 44.0, 43.6, 43.5, 43.4, 43.3, 39.8, 39.6, 38.6, 38.4, 36.6, 36.4, 27.0, 26.6, 26.5, 25.8, 25.6, 24.3, 24.0, 20.5, 20.4, 20.3, 20.2, 19.0, 18.7 ppm. Purity: >95% LCMS (214 nm & 254 nm); retention time 1.90 min; (M+H$^+$) 508.3.

Example 152

(3R)-4-(5-(4-Fluorophenoxy)pyrimidin-2-yl)-3-methyl-N-(4-methyl-1-azabicyclo[3.2.2]nonan-4-yl)piperazine-1-carboxamide Exchanging 2-chloro-5-fluoro-4-(4-(methoxymethyl)phenyl)pyrimidine for 2-chloro-5-(4-fluorophenoxy)pyrimidine (prepared as described in Example 129) and tert-butyl 3-isopropylpiperazine-1-carboxylate for (R)-tert-butyl 3-methylpiperazine-1-carboxylate, the final three steps of Example 148 were used to generate the title compound. $^1$H NMR (500 MHz, CDCl$_3$) δ 8.17 (s, 2H), 7.02-6.99 (m, 2H), 6.92-6.89 (m, 2H), 4.85-4.73 (m, 1H), 4.45-4.32 (m, 2H), 3.97-3.88 (m, 1H), 3.73-3.62 (m, 1H), 3.37-3.32 (m, 2H), 3.10-2.79 (m, 7H), 2.43-2.38 (m, 1H), 1.99-1.48 (m, 9H), 1.25-1.23 (m, 3H) ppm. $^{13}$C NMR (100 MHz, CD$_3$OD) δ 160.2, 159.3, 158.5, 158.4, 157.8, 155.7, 152.0, 143.5, 119.4, 119.3, 117.8, 117.6, 59.6, 54.4, 54.3, 49.4, 49.0, 48.7, 48.5, 48.4, 48.2, 46.8, 46.5, 44.7, 44.4, 39.9, 39.8, 37.1, 36.9, 27.3, 27.1, 25.8, 25.7, 25.4, 25.3, 15.5, 15.4 ppm. Purity: >96% LCMS (214 nm & 254 nm); retention time 1.37 min; (M+H$^+$) 469.2.

Example 153

3-Ethynyl-4-(4-(4-(methoxymethyl)phenyl)pyrimidin-2-yl)-N-(4-methyl-1-azabicyclo[3.2.2]nonan-4-yl)piperazine-1-carboxamide To a stirred solution of 2-chloro-4-(4-(methoxymethyl)phenyl)pyrimidine (prepared as described in Example 149; 0.936 g, 4.00 mmol) in N,N-dimethylformamide (10 mL) was added tert-butyl 3-(hydroxymethyl)piperazine-1-carboxylate (1.73 g, 8.00 mmol). The reaction was heated at 90° C. for 5 days and then concentrated. The residue was purified by flash chromatography over silica gel using a hexane/ethyl acetate eluant to afford tert-butyl 3-(hydroxymethyl)-4-(4-(4-(methoxymethyl)phenyl)pyrimidin-2-yl)piperazine-1-carboxylate as a white solid (1.066 g, 65%). To a stirred solution of this intermediate (0.543 g, 1.32 mmol) in ethyl acetate (10 mL) was added 2-iodoxybenzoic acid (1.10 g, 3.93 mmol). The reaction was heated at 80° C. for 3 hours and then concentrated. The residue was purified by flash chromatography over silica gel using a hexane/ethyl acetate eluant to afford tert-butyl 3-ethynyl-4-(4-(4-(methoxymethyl)phenyl)pyrimidin-2-yl)piperazine-1-carboxylate as a yellow oil (0.480 g, 89%). The t-butoxycarbonyl protecting group was removed from this compound using General Procedure G to afford 2-(2-ethynylpiperazin-1-yl)-4-(4-(methoxymethyl)phenyl)pyrimidine. This intermediate was, in turn, reacted with Intermediate 5 using General Procedure A to generate the title compound. $^1$H NMR (500 MHz, CDCl$_3$) δ 8.46 (d, J=5.5 Hz, 1H), 8.07 (d, J=8.0 Hz, 2H), 7.47 (d, J=8.0 Hz, 2H), 7.10 (d, J=5.0 Hz, 1H), 5.78 (s, 1H), 4.67-4.50 (m, 4H), 4.29-3.99 (m, 2H), 3.44 (s, 3H), 3.42-3.30 (m, 2H), 3.09-2.84 (m, 7H), 2.47-2.41 (m, 1H), 2.23-2.22 (m, 1H), 1.99-1.55 (m, 9H) ppm. $^{13}$C NMR (125 MHz, CDCl$_3$) δ 164.3, 161.3, 158.5, 156.8, 156.7, 141.1, 136.5, 127.8, 127.2, 107.2, 81.2, 81.1, 74.2, 71.8, 71.7, 59.1, 59.0, 53.3, 53.2, 48.9, 48.5, 47.9, 47.8, 46.2, 46.1, 44.0, 39.7, 39.6, 36.7, 36.6, 25.8, 24.4, 24.1 ppm. Purity: >99% LCMS (214 nm & 254 nm); retention time 1.35 min; (M+H$^+$) 489.3.

Example 154

1-Azabicyclo[3.2.2]nonan-4-yl 3-methyl-4-(4-phenylpyrimidin-2-yl)piperazine-1-carboxylate Exchanging (R)-tert-butyl 3-methylpiperazine-1-carboxylate for racemic tert-butyl 3-methylpiperazine-1-carboxylate, the first three steps of Example 137 were used to prepare 2-(2-methylpiperazin-1-yl)-4-phenylpyrimidine. The intermediate was, in turn, reacted with Intermediate 3 using General Procedure C to generate the title compound. $^1$H NMR (500 MHz, CDCl$_3$) δ 8.40 (d, J=5.5 Hz, 1H), 8.07-8.04 (m, 2H), 7.49-7.47 (m, 3H), 6.99 (d, J=5.5 Hz, 1H), 5.08 (m, 1H), 4.98 (m, 1H), 4.67 (m, 1H), 4.25-4.02 (m, 2H), 3.30-2.82 (m, 9H), 2.36-1.57 (m, 7H), 1.26 (d, J=7.0 Hz, 3H) ppm. $^{13}$C NMR (125 MHz, CDCl$_3$) δ 164.3, 161.5, 158.4, 155.4, 137.6, 130.5, 128.7, 126.9, 105.9, 79.2. 79.1, 51.8, 48.3, 48.0, 47.9, 47.6, 46.6, 46.3, 45.4, 45.3, 43.8, 43.6, 38.2, 33.5, 30.8, 30.7, 24.8, 22.4, 22.3, 14.5, 14.2 ppm. Purity: >99% LCMS (214 nm & 254 nm); retention time 1.48 min; (M+H$^+$) 422.2.

Example 155

Quinuclidin-3-yl (2-(4'-(2-methoxyethoxy)-[1,1'-biphenyl]-4-yl)propan-2-yl)carbamate Using General Procedure F and the reaction inputs ethyl 2-(4-bromophenyl)-2-methylpropanoate and 4-(2-methoxyethoxy)phenylboronic acid, ethyl 2-(4'-(2-methoxyethoxy)-[1,1'-biphenyl]-4-yl)-2-methylpropanoate was prepared as an off-white solid. To a stirred solution of this compound (3.01 g, 8.78 mmol) in 1:1:1 (v/v/v) tetrahydrofuran/ethanol/water (45 mL) was added lithium hydroxide monohydrate (1.47 g, 61.4 mmol). The mixture was heated at reflux overnight and then concentrated. The residue was dissolved in water, treated with 1N hydrochloric acid (65 mL) and extracted with ethyl acetate. The combined organic layers were washed with brine, dried (Na$_2$SO$_4$) and concentrated to afford 2-(4'-(2-methoxyethoxy)-[1,1'-biphenyl]-4-yl)-2-methylpropanoic acid as a white solid (2.75 g, 100%). This intermediate and quinuclidin-3-ol were reacted according to General Procedure H to generate the title compound as a colorless, glassy solid (23%). $^1$H NMR (400 MHz, DMSO-d$_6$) δ 7.62-7.29 (m, 7H), 7.01 (d, J=8.9 Hz, 2H), 4.47-4.37 (m, 1H), 4.17-4.08 (m, 2H), 3.72-3.62 (m, 2H), 3.32 (s, 3H), 3.09-2.25 (m, 6H), 2.05-1.18 (m, 11H) ppm. $^{13}$C NMR (100 MHz, DMSO-d$_6$) δ 157.9, 154.5, 146.7, 137.4, 132.5, 127.5, 125.7, 125.2, 114.8, 70.4, 70.0, 66.9, 58.2, 55.4, 54.2, 46.9, 45.9, 29.4, 25.3, 24.2, 19.2 ppm. Purity: 100%, 99.1% (210 & 254 nm) UPLCMS; retention time: 0.87 min; (M+H$^+$) 439.0.

Example 156

(S)-Quinuclidin-3-yl (2-(4'-(2-methoxyethoxy)-[1,1'-biphenyl]-4-yl)propan-2-yl)carbamate Using General Procedure H and the reaction inputs 2-(4'-(2-methoxyethoxy)-[1,1'-biphenyl]-4-yl)-2-methylpropanoic (prepared as described in Example 1) and (S)-quinuclidin-3-ol, the title compound was prepared as a colorless, glassy solid. NMR data matched that of Example 1. Purity: 100%, 100% (210 & 254 nm) UPLCMS; retention time: 0.87 min; (M+H$^+$) 439.5.

Example 157

(R)-1-(2-(4'-(2-Methoxyethoxy)-[1,1'-biphenyl]-4-yl)propan-2-yl)-3-(3-methylquinuclidin-3-yl)urea Using General Procedure H and the reaction inputs 2-(4'-(2-methoxyethoxy)-[1,1'-biphenyl]-4-yl)-2-methylpropanoic (prepared as described in Example 155) and Intermediate 12, the title compound was prepared as a white solid. $^1$H NMR (400 MHz, DMSO-$d_6$) δ 7.57 (d, J=8.8 Hz, 2H), 7.51 (d, J=8.4 Hz, 2H), 7.38 (d, J=8.4 Hz, 2H), 7.01 (d, J=8.8 Hz, 2H), 6.15 (s, 1H), 5.76 (s, 1H), 4.15-4.08 (m, 2H), 3.74-3.64 (m, 2H), 3.32 (s, 3H), 2.74-2.44 (m, 6H), 1.93-1.85 (m, 1H), 1.85-1.73 (m, 1H), 1.67-1.56 (m, 1H), 1.53 (d, J=11.9 Hz, 6H), 1.42-1.31 (m, 1H), 1.29 (s, 2H), 1.29-1.20 (m, 1H) ppm. $^{13}$C NMR (100 MHz, DMSO-$d_6$) δ 157.9, 156.9, 147.8, 137.2, 132.5, 127.5, 125.6, 125.3, 114.8, 70.4, 66.9, 63.6, 58.2, 53.8, 50.7, 46.2, 46.1, 30.4, 30.3, 29.9, 25.1, 23.0, 22.3 ppm. Purity: 100%, 99.9% (210 & 254 nm) UPLCMS; retention time: 0.97 min; (M+H$^+$) 452.4.

Example 158

(S)-1-(2-(4'-(2-Methoxyethoxy)-[1,1'-biphenyl]-4-yl)propan-2-yl)-3-(3-methylquinuclidin-3-yl)urea Using General Procedure H and the reaction inputs 2-(4'-(2-methoxyethoxy)-[1,1'-biphenyl]-4-yl)-2-methylpropanoic (prepared as described in Example 155) and Intermediate 11, the title compound was prepared as a white solid. NMR data matched that of Example 3. Purity: 100%, 99.9% (210 & 254 nm) UPLCMS; retention time: 0.97 min; (M+H$^+$) 452.4.

Example 159

1-(3-Ethylquinuclidin-3-yl)-3-(2-(4'-(2-methoxyethoxy)-[1,1'-biphenyl]-4-yl)propan-2-yl)urea Using General Procedure H and the reaction inputs 2-(4'-(2-methoxyethoxy)-[1,1'-biphenyl]-4-yl)-2-methylpropanoic (prepared as described in Example 155) and Intermediate 2, the title compound was prepared as a white solid. $^1$H NMR (400 MHz, DMSO-$d_6$) δ 7.56 (d, J=8.8 Hz, 2H), 7.50 (d, J=8.5 Hz, 2H), 7.39 (d, J=8.5 Hz, 2H), 7.01 (d, J=8.8 Hz, 2H), 6.18 (s, 1H), 5.73 (s, 1H), 4.32-3.96 (m, 2H), 3.87-3.63 (m, 2H), 3.32 (s, 3H), 2.75-2.45 (m, 6H), 1.93-1.58 (m, 4H), 1.53 (d, J=16.2 Hz, 7H), 1.42-1.13 (m, 2H), 0.75 (t, J=7.3 Hz, 3H) ppm. $^{13}$C NMR (100 MHz, DMSO-$d_6$) δ 157.9, 156.8, 147.8, 137.2, 132.5, 127.5, 125.6, 125.3, 114.8, 70.4, 66.9, 62.9, 58.1, 53.7, 53.2, 46.5, 46.3, 30.4, 29.8, 27.8, 27.7, 22.6, 22.3, 8.0 ppm. Purity: 100%, 99.9% (210 & 254 nm) UPLCMS; retention time: 1.00 min; (M+H$^+$) 466.4.

Example 160

1-(2-(4'-(2-Methoxyethoxy)-[1,1'-biphenyl]-4-yl)propan-2-yl)-3-(4-methyl-1-azabicyclo[3.2.2]nonan-4-yl)urea Using General Procedure H and the reaction inputs 2-(4'-(2-methoxyethoxy)-[1,1'-biphenyl]-4-yl)-2-methylpropanoic (prepared as described in Example 155) and Intermediate 5, the title compound was prepared as a white solid. $^1$H NMR (400 MHz, DMSO-$d_6$) δ 7.56 (d, J=8.8 Hz, 2H), 7.50 (d, J=8.5 Hz, 2H), 7.39 (d, J=8.5 Hz, 2H), 7.01 (d, J=8.8 Hz, 2H), 6.22 (br s, 1H), 5.72 (br s, 1H), 4.20-4.07 (m, 2H), 3.85-3.60 (m, 2H), 3.32 (s, 3H), 2.93-2.66 (m, 6H), 2.11-2.05 (m, 1H), 1.83-1.36 (m, 10H), 1.33-1.19 (m, 4H) ppm. $^{13}$C NMR (100 MHz, DMSO-$d_6$) δ 157.9, 156.8, 147.8, 137.2, 132.5, 127.5, 125.6, 125.3, 114.8, 70.4, 66.9, 58.2, 57.2, 53.7, 52.8, 48.1, 45.0, 36.2, 30.4, 29.8, 26.2, 24.4, 23.9 ppm. Purity: 100%, 99.0% (210 & 254 nm) UPLCMS; retention time: 0.98 min; (M+H$^+$) 466.4.

Example 161

N-(2-(4'-(2-Methoxyethoxy)-[1,1'-biphenyl]-4-yl)propan-2-yl)-1,4-diazabicyclo[3.2.2]nonane-4-carboxamide Using General Procedure H and the reaction inputs 2-(4'-(2-methoxyethoxy)-[1,1'-biphenyl]-4-yl)-2-methylpropanoic (prepared as described in Example 155) and Intermediate 6, the title compound was prepared as a white solid. $^1$H NMR (400 MHz, DMSO-$d_6$) δ 7.56 (d, J=8.8 Hz, 2H), 7.49 (d, J=8.4 Hz, 2H), 7.36 (d, J=8.4 Hz, 2H), 7.01 (d, J=8.8 Hz, 2H), 6.12 (s, 1H), 4.19 (s, 1H), 4.12 (dd, J=5.4, 3.8 Hz, 2H), 3.75-3.62 (m, 2H), 3.48 (t, J=5.6 Hz, 2H), 3.32 (s, 3H), 2.96-2.70 (m, 6H), 1.93-1.83 (m, 2H), 1.68-1.40 (m, 8H) ppm. $^{13}$C NMR (100 MHz, DMSO-$d_6$) δ 157.8, 155.4, 148.1, 136.9, 132.7, 127.5, 125.5, 125.2, 114.8, 70.4, 66.9, 58.1, 57.5, 54.5, 46.6, 46.0, 41.4, 30.2, 27.0 ppm. Purity: 100%, 100% (210 & 254 nm) UPLCMS; retention time: 0.85 min; (M+H$^+$) 438.5.

Example 162

1-(1-(4'-(2-Methoxyethoxy)-[1,1'-biphenyl]-4-yl)cyclopropyl)-3-(quinuclidin-3-yl)urea Exchanging ethyl 2-(4-bromophenyl)-2-methylpropanoate for ethyl 1-(4-bromophenyl)cyclopropanecarboxylate, the reaction sequence outlined in Example 155 was used to prepare 1-(4'-(2-methoxyethoxy)-[1,1'-biphenyl]-4-yl)cyclopropanecarboxylic acid. This intermediate and quinuclidin-3-amine were reacted according to General Procedure H to generate the title compound as a white solid. $^1$H NMR (400 MHz, DMSO-$d_6$) δ 7.55 (d, J=8.8 Hz, 2H), 7.50 (d, J=8.5 Hz, 2H), 7.18 (d, J=8.4 Hz, 2H), 7.01 (d, J=8.8 Hz, 2H), 6.68 (br s, 1H), 5.99 (br s, 1H), 4.15-4.09 (m, 2H), 3.75-3.63 (m, 2H), 3.61-3.50 (m, 1H), 3.32 (s, 3H), 3.06 (dd, J=13.6, 9.5 Hz, 1H), 2.73-2.54 (m, 4H), 2.35-2.22 (m, 1H), 1.71-1.40 (m, 4H), 1.36-1.24 (m, 1H), 1.21-1.08 (m, 4H) ppm. $^{13}$C NMR (100 MHz, DMSO-$d_6$) δ 157.9, 157.5, 143.4, 136.9, 132.4, 127.5, 125.7, 125.0, 114.8, 70.4, 66.9, 58.2, 56.1, 46.9, 46.3, 46.1, 33.9, 26.1, 25.6, 19.8, 18.6 ppm. Purity: 100%, 99.9% (210 & 254 nm) UPLCMS; retention time: 0.82 min; (M+H$^+$) 436.3.

Example 163

1-(1-(4'-(2-Methoxyethoxy)-[1,1'-biphenyl]-4-yl)cyclopropyl)-3-(3-methylquinuclidin-3-yl)urea Using General Procedure H and the reaction inputs 1-(4'-(2-methoxyethoxy)-[1,1'-biphenyl]-4-yl)cyclopropanecarboxylic acid (prepared as described in Example 162) and Intermediate 1, the title compound was prepared as a white solid. $^1$H NMR (400 MHz, DMSO-$d_6$) δ 7.56 (d, J=8.8 Hz, 2H), 7.51 (d, J=8.4 Hz, 2H), 7.18 (d, J=8.4 Hz, 2H), 7.00 (d, J=8.8 Hz, 2H), 6.63 (s, 1H), 5.61 (s, 1H), 4.17-4.06 (m, 2H), 3.80-3.61 (m, 2H), 3.32 (s, 3H), 2.82-2.52 (m, 6H), 1.99-

1.82 (m, 1H), 1.78-1.54 (m, 2H), 1.46-1.30 (m, 4H), 1.29-1.19 (m, 1H), 1.19-1.11 (m, 4H) ppm. $^{13}$C NMR (100 MHz, DMSO-d$_6$) δ 157.9, 157.3, 143.5, 136.9, 132.4, 127.5, 125.7, 124.8, 114.8, 70.4, 66.9, 63.4, 58.2, 50.9, 46.2, 46.0, 33.8, 30.4, 25.0, 23.0, 22.3, 18.8 ppm. Purity: 100%, 99.9% (210 & 254 nm) UPLCMS; retention time: 0.85 min; (M+H$^+$) 450.4.

Example 164

1-(3-Ethylquinuclidin-3-yl)-3-(1-(4'-(2-methoxyethoxy)-[1,1'-biphenyl]-4-yl)cyclopropyl)urea Using General Procedure H and the reaction inputs 1-(4'-(2-methoxyethoxy)-[1,1'-biphenyl]-4-yl)cyclopropanecarboxylic acid (prepared as described in Example 162) and Intermediate 2, the title compound was prepared as a white solid. $^1$H NMR (400 MHz, DMSO-d$_6$) δ 7.56 (d, J=8.8 Hz, 2H), 7.50 (d, J=8.4 Hz, 2H), 7.19 (d, J=8.3 Hz, 2H), 7.00 (d, J=8.8 Hz, 2H), 6.65 (s, 1H), 5.57 (s, 1H), 4.17-4.03 (m, 2H), 3.77-3.61 (m, 2H), 3.32 (s, 3H), 2.77-2.51 (m, 6H), 1.97-1.83 (m, 2H), 1.78-1.49 (m, 3H), 1.43-1.30 (m, 1H), 1.30-1.20 (m, 1H), 1.20-1.04 (m, 4H), 0.73 (t, J=7.2 Hz, 3H) ppm. $^{13}$C NMR (100 MHz, DMSO-d$_6$) δ 157.9, 157.1, 143.4, 136.9, 132.4, 127.5, 125.7, 124.7, 114.8, 70.4, 66.9, 62.8, 58.2, 53.4, 46.4, 46.3, 33.8, 27.8, 27.7, 22.6, 22.3, 18.9, 7.9 ppm. Purity: 99.9%, 99.5% (210 & 254 nm) UPLCMS; retention time: 0.89 min; (M+H$^+$) 464.4.

Example 165

1-(1-(4'-(2-Methoxyethoxy)-[1,1'-biphenyl]-4-yl)cyclopropyl)-3-(4-methyl-1-azabicyclo[3.2.2]nonan-4-yl)urea Using General Procedure H and the reaction inputs 1-(4'-(2-methoxyethoxy)-[1,1'-biphenyl]-4-yl)cyclopropanecarboxylic acid (prepared as described in Example 162) and Intermediate 5, the title compound was prepared as a white solid. $^1$H NMR (400 MHz, DMSO-d$_6$) δ 7.55 (d, J=8.6 Hz, 2H), 7.50 (d, J=8.2 Hz, 2H), 7.20 (d, J=8.1 Hz, 2H), 7.00 (d, J=8.6 Hz, 2H), 6.70 (s, 1H), 5.56 (s, 1H), 4.20-4.05 (m, 2H), 3.72-3.62 (m, 2H), 3.32 (s, 3H), 2.94-2.54 (m, 6H), 2.18-2.06 (m, 1H), 1.83-1.57 (m, 3H), 1.57-1.00 (m, 10H) ppm. $^{13}$C NMR (100 MHz, DMSO-d$_6$) δ 157.9, 157.2, 143.5, 136.9, 132.4, 127.5, 125.7, 124.8, 114.8, 70.4, 66.9, 58.2, 57.4, 52.7, 47.9, 45.0, 39.1, 36.4, 33.8, 26.1, 24.4, 24.0, 18.9, 18.7 ppm. Purity: 100%, 99.3% (210 & 254 nm) UPLCMS; retention time: 0.85 min; (M+H$^+$) 464.4.

Example 166

Quinuclidin-3-yl (1-(4'-(2-methoxyethoxy)-[1,1'-biphenyl]-4-yl)cyclopropyl)carbamate Using General Procedure H and the reaction inputs 1-(4'-(2-methoxyethoxy)-[1,1'-biphenyl]-4-yl)cyclopropanecarboxylic acid (prepared as described in Example 162) and quinuclidin-3-ol, the title compound was prepared as a glassy, purple solid. $^1$H NMR (400 MHz, DMSO-d$_6$) δ 8.02 (br s, 1H), 7.60-7.46 (m, 4H), 7.29-7.13 (m, 2H), 7.01 (d, J=8.7 Hz, 2H), 4.58-4.46 (m, 1H), 4.17-4.07 (m, 2H), 3.72-3.61 (m, 2H), 3.32 (s, 3H), 3.13-2.89 (m, 1H), 2.83-2.24 (m, 5H), 1.84-1.01 (m, 9H) ppm. $^{13}$C NMR (100 MHz, DMSO-d$_6$) δ 157.9, 156.0, 142.4, 137.1, 132.4, 127.5, 125.8, 125.1, 114.8, 70.4, 70.4, 66.9, 58.1, 55.5, 46.9, 46.0, 34.3, 25.3, 24.2, 19.2, 18.1 ppm. Purity: 100%, 99.9% (210 & 254 nm) UPLCMS; retention time: 0.83 min; (M+H$^+$) 437.0.

Example 107

Quinuclidin-3-yl (2-(3'-(2-methoxyethoxy)-[1,1'-biphenyl]-4-yl)propan-2-yl)carbamate Exchanging 4-(2-methoxyethoxy)phenylboronic acid for 3-(2-methoxyethoxy)phenylboronic acid for, the reaction sequence outlined in Example 155 was used to prepare 2-(3'-(2-methoxyethoxy)-[1,1'-biphenyl]-4-yl)-2-methylpropanoic acid. This intermediate and quinuclidin-3-ol were reacted according to General Procedure H to generate the title compound as a glassy, colorless solid. $^1$H NMR (400 MHz, DMSO-d$_6$) δ 7.63-7.31 (m, 6H), 7.24-7.10 (m, 2H), 6.92 (dd, J=8.2, 1.9 Hz, 1H), 4.51-4.34 (m, 1H), 4.21-4.08 (m, 2H), 3.72-3.64 (m, 2H), 3.32 (s, 3H), 3.09-2.26 (m, 5H), 2.04-1.22 (m, 9H) ppm. $^{13}$C NMR (100 MHz, DMSO-d$_6$) δ 158.9, 154.6, 147.6, 141.5, 137.6, 129.9, 126.3, 125.2, 118.9, 113.2, 112.5, 70.4, 70.0, 66.9, 58.2, 55.4, 54.2, 46.9, 45.9, 29.4, 25.3, 24.2, 19.2 ppm. Purity: 100%, 100% (210 & 254 nm) UPLCMS; retention time: 0.91 min; (M+H$^+$) 439.4.

Example 168

1-Azabicyclo[3.2.2]nonan-4-yl (2-(3'-(2-methoxyethoxy)-[1,1'-biphenyl]-4-yl)propan-2-yl)carbamate Using General Procedure H and the reaction inputs 2-(3'-(2-methoxyethoxy)-[1,1'-biphenyl]-4-yl)-2-methylpropanoic acid (prepared as described in Example 167) and Intermediate 3, the title compound was prepared as a glassy, amber solid. $^1$H NMR (400 MHz, DMSO-d$_6$) δ 7.58 (d, J=8.5 Hz, 2H), 7.53-7.31 (m, 4H), 7.24-7.12 (m, 2H), 6.92 (dd, J=8.2, 1.8 Hz, 1H), 4.65-4.55 (m, 1H), 4.26-4.08 (m, 2H), 3.83-3.60 (m, 2H), 3.32 (s, 3H), 3.00-2.45 (m, 6H), 1.97-1.34 (m, 13H) ppm. $^{13}$C NMR (100 MHz, DMSO-d$_6$) δ 158.9, 154.2, 147.7, 141.5, 137.6, 129.9, 126.3, 125.2, 118.9, 113.2, 112.5, 77.1, 70.4, 66.8, 58.2, 54.1, 51.4, 47.7, 44.6, 33.5, 30.6, 29.6, 24.7, 22.2 ppm. Purity: 100%, 100% (210 & 254 nm) UPLCMS; retention time: 0.92 min; (M+H$^+$) 453.4.

Example 169

N-(2-(3'-(2-Methoxyethoxy)-[1,1'-biphenyl]-4-yl)propan-2-yl)-1,4-diazabicyclo[3.2.2]nonane-4-carboxamide Using General Procedure H and the reaction inputs 2-(3'-(2-methoxyethoxy)-[1,1'-biphenyl]-4-yl)-2-methylpropanoic acid (prepared as described in Example 167) and Intermediate 6, the title compound was prepared as an off-white solid. $^1$H NMR (400 MHz, DMSO-d$_6$) δ 7.55 (d, J=8.5 Hz, 2H), 7.44-7.28 (m, 3H), 7.25-7.09 (m, 2H), 6.14 (br s, 1H), 4.22-4.12 (m, 3H), 3.70-3.65 (m, 2H), 3.52-3.45 (m, 2H), 3.32 (s, 3H), 2.95-2.75 (m, 6H), 1.93-1.82 (m, 2H), 1.64-1.52 (m, 8H) ppm. $^{13}$C NMR (100 MHz, DMSO-d$_6$) δ 158.9, 155.4, 149.0, 141.7, 137.1, 129.9, 126.1, 125.2, 118.9, 113.1, 112.5, 70.4, 66.8, 58.2, 57.5, 54.5, 46.6, 46.0, 41.5, 30.2, 27.0 ppm. Purity: 100%, 100% (210 & 254 nm) UPLCMS; retention time: 0.86 min; (M+H$^+$) 438.4.

Example 170

Quinuclidin-3-yl (2-(4'-(2-methoxyethoxy)-[1,1'-biphenyl]-3-yl)propan-2-yl)carbamate Exchanging ethyl 2-(4-bromophenyl)-2-methylpropanoate for ethyl 2-(3-bromophenyl)-2-methylpropanoate, the reaction sequence outlined in Example 155 was used to prepare 2-(4'-(2-methoxyethoxy)-[1,1'-biphenyl]-3-yl)-2-methylpropanoic acid. This intermediate and quinuclidin-3-ol were reacted according to General Procedure H to generate the title compound as a yellow solid. $^1$H NMR (400 MHz, DMSO-d$_6$) δ 7.62-7.20 (m, 7H), 7.03 (d, J=8.7 Hz, 2H), 4.48-4.35 (m, 2H), 4.18-4.08 (m, 2H), 3.72-3.62 (m, 2H), 3.32 (s, 3H), 3.10-2.19 (m, 6H), 2.10-1.10 (m, 11H) ppm. $^{13}$C NMR (100 MHz, DMSO-d$_6$) δ 158.0, 154.6, 148.8, 139.5, 133.1, 128.5, 127.7, 123.8, 123.2, 122.7, 114.8, 70.4, 69.9, 67.0, 58.2, 55.3, 54.5, 47.0, 45.9, 29.4, 25.3, 24.2, 19.2 ppm. Purity: 97.4%, 94.6% (210 & 254 nm) UPLCMS; retention time: 0.88 min; (M+H$^+$) 439.3.

Example 171

1-Azabicyclo[3.2.2]nonan-4-yl (2-(4'-(2-methoxyethoxy)-[1,1'-biphenyl]-3-yl)propan-2-yl)carbamate Using General Procedure H and the reaction inputs 2-(4'-(2-methoxyethoxy)-[1,1'-biphenyl]-3-yl)-2-methylpropanoic acid (prepared as described in Example 170) and Intermediate 3, the title compound was prepared as a tan solid. $^1$H NMR (400 MHz, DMSO-d$_6$) δ 7.60-7.19 (m, 7H), 7.03 (d, J=8.8 Hz, 2H), 4.66-4.55 (m, 1H), 4.17-4.09 (m, 2H), 3.72-3.63 (m, 2H), 3.32 (s, 3H), 3.02-2.40 (m, 5H), 1.98-1.30 (m, 3H) ppm. $^{13}$C NMR (100 MHz, DMSO-d$_6$) δ 158.0, 154.3, 148.9, 139.4, 133.1, 128.5, 127.7, 123.8, 123.2, 122.7, 114.8, 77.0, 70.4, 67.0, 58.2, 54.5, 51.4, 47.6, 44.7, 30.6, 29.9, 24.7, 22.1, 18.6 ppm. Purity: 97.0%, 93.9% (210 & 254 nm) UPLCMS; retention time: 0.89 min; (M+H$^+$) 453.3.

Example 172

Quinuclidin-3-yl (2-(4'-(3-methoxypropoxy)-[1,1'-biphenyl]-4-yl)propan-2-yl)carbamate To a stirred solution of 4-iodophenol (10.05 g, 45.68 mmol) in acetonitrile (100 mL) was added potassium carbonate (6.95 g, 50.2 mmol) and 1-chloro-3-methoxypropane (6.4 mL, 57.1 mmol). The mixture was heated at reflux overnight and then concentrated. The residue was taken up in water and extracted with ethyl acetate. The combined extracts were washed with aqueous sodium bicarbonate solution, dried (Na$_2$SO$_4$) and concentrated. The crude material was purified by flash chromatography over silica using a hexane/ethyl acetate eluant to afford 1-iodo-4-(3-methoxypropoxy)benzene as a colorless oil (4.39 g, 33%). This intermediate and ethyl 2-methyl-2-(4-(4,4,5,5-tetramethyl-1,3,2-dioxaborolan-2-yl)phenyl)propanoate were reacted according to General Procedure F to generate ethyl 2-(4'-(3-methoxypropoxy)-[1,1'-biphenyl]-4-yl)-2-methylpropanoate. To a stirred solution of this compound (0.693 g, 1.94 mmol) in 1:1:1 (v/v/v) tetrahydrofuran/ethanol/water (10 mL) was added lithium hydroxide monohydrate (0.326 g, 7.77 mmol). The mixture was heated at reflux overnight and then concentrated. The residue was dissolved in water, treated with 1N hydrochloric acid (10 mL) and extracted with ethyl acetate. The combined organic layers were washed with brine, dried (Na$_2$SO$_4$) and concentrated to afford 2-(4'-(3-methoxypropoxy)-[1,1'-biphenyl]-4-yl)-2-methylpropanoic acid as a waxy, off-white solid (0.630 g, 99%). This intermediate and quinuclidin-3-ol were reacted according to General Procedure H to generate the title compound as a glassy, colorless solid (62%). $^1$H NMR (400 MHz, DMSO-d$_6$) δ 7.61-7.29 (m, 7H), 7.00 (d, J=8.8 Hz, 2H), 4.47-4.36 (m, 1H), 4.05 (t, J=6.4 Hz, 2H), 3.48 (t, J=6.3 Hz, 2H), 3.26 (s, 3H), 3.10-2.25 (m, 6H), 2.04-1.74 (m, 4H), 1.65-1.23 (m, 9H) ppm. $^{13}$C NMR (100 MHz, DMSO-d$_6$) δ 158.0, 154.5, 146.7, 137.4, 132.4, 127.5, 125.7, 125.2, 114.8, 69.9, 68.5, 64.6, 57.9, 55.4, 54.2, 46.9, 46.0, 29.4, 29.0, 25.2, 24.1, 19.2 ppm. Purity: 97.7%, 98.2% (210 & 254 nm) UPLCMS; retention time: 0.96 min; (M+H$^+$) 453.5.

Example 173

1-(2-(4'-(3-Methoxypropoxy)-[1,1'-biphenyl]-4-yl)propan-2-yl)-3-(3-methylquinuclidin-3-yl)urea Using General Procedure H and the reaction inputs 2-(4'-(3-methoxypropoxy)-[1,1'-biphenyl]-4-yl)-2-methylpropanoic acid (prepared as described in Example 172) and Intermediate 1, the title compound was prepared as a white solid. $^1$H NMR (400 MHz, DMSO-d$_6$) δ 7.56 (d, J=8.8 Hz, 2H), 7.51 (d, J=8.4 Hz, 2H), 7.38 (d, J=8.4 Hz, 2H), 7.00 (d, J=8.8 Hz, 2H), 6.17 (br s, 1H), 5.79 (br s, 1H), 4.05 (t, J=6.4 Hz, 2H), 3.48 (t, J=6.3 Hz, 2H), 3.26 (s, 3H), 2.74-2.51 (m, 6H), 2.01-1.74 (m, 4H), 1.68-1.45 (m, 7H), 1.44-1.21 (m, 5H) ppm. $^{13}$C NMR (100 MHz, DMSO-d$_6$) δ 158.0, 156.9, 147.7, 137.2, 132.4, 127.5, 125.6, 125.3, 114.8, 68.5, 64.6, 63.4, 57.9, 53.8, 50.7, 46.1, 46.0, 30.3, 29.9, 29.0, 25.1, 22.8, 22.2 ppm. Purity: 98.0%, 98.1% (210 & 254 nm) UPLCMS; retention time: 0.94 min; (M+H$^+$) 466.5.

Example 174

N-(2-(4'-(3-Methoxypropoxy)-[1,1'-biphenyl]-4-yl)propan-2-yl)-1,4-diazabicyclo[3.2.2]nonane-4-carboxamide Using General Procedure H and the reaction inputs 2-(4'-(3-methoxypropoxy)-[1,1'-biphenyl]-4-yl)-2-methylpropanoic acid (prepared as described in Example 172) and Intermediate 6, the title compound was prepared as a white solid. $^1$H NMR (400 MHz, DMSO-d$_6$) δ 7.56 (d, J=8.8 Hz, 2H), 7.49 (d, J=8.4 Hz, 2H), 7.36 (d, J=8.4 Hz, 2H), 7.00 (d, J=8.8 Hz, 2H), 6.11 (s, 1H), 4.22-4.16 (m, 1H), 4.05 (t, J=6.4 Hz, 2H), 3.52-3.44 (m, 6H), 3.26 (s, 3H), 2.96-2.73 (m, 6H), 2.01-1.81 (m, 4H), 1.65-1.48 (d, 8H) ppm. $^{13}$C NMR (100 MHz, DMSO-d$_6$) δ 157.9, 155.4, 148.1, 136.9, 132.6, 127.5, 125.5, 125.2, 114.8, 68.5, 64.6, 57.9, 57.5, 54.5, 46.6, 46.0, 41.5, 30.2, 29.0, 27.0 ppm. Purity: 100%, 100% (210 & 254 nm) UPLCMS; retention time: 0.88 min; (M+H$^+$) 452.5.

Example 175

Quinuclidin-3-yl (2-(4'-(2-methoxyethoxy)-[1,1'-biphenyl]-3-yl)propan-2-yl)carbamate Exchanging ethyl 2-(4-bromophenyl)-2-methylpropanoate for ethyl 1-(4-bromophenyl)cyclopropanecarboxylate, the reaction sequence outlined in Example 18 was used to prepare 1-(4'-(3-methoxypropoxy)-[1,1'-biphenyl]-4-yl)cyclopropanecarboxylic acid. This intermediate and quinuclidin-3-ol were reacted according to General Procedure H to generate the title compound as a glassy, colorless solid. $^1$H NMR (7:3 rotomer mixture) (400 MHz, DMSO-d$_6$) δ 8.01 (br s, 0.7H), 7.77 (br s, 0.3H), 7.59-7.47 (m, 4H), 7.28-7.16 (m, 2H), 6.99 (d, J=8.8 Hz, 2H), 4.57-4.47 (m, 1H), 4.05 (t, J=6.4 Hz, 2H), 3.48 (t, J=6.4 Hz, 2H), 3.25 (s, 3H), 3.18-2.89 (m, 1H), 2.81-2.25 (m, 6H), 2.00-1.03 (m, 7H) ppm. $^{13}$C NMR (major rotomer) (100 MHz, DMSO-d$_6$) δ 158.0, 156.0, 142.4, 137.2, 132.3, 127.5, 125.8, 125.1, 114.8, 70.4, 68.5, 64.6, 57.9, 55.4, 46.9, 45.9, 34.3, 28.9, 25.3, 24.2, 19.2, 18.0 ppm. Purity: 100%, 100% (210 & 254 nm) UPLCMS; retention time: 0.91 min; (M+H$^+$) 451.6.

Example 176

1-(1-(4'-(3-Methoxypropoxy)-[1,1'-biphenyl]-4-yl)cyclopropyl)-3-(3-methylquinuclidin-3-yl)urea Using General Procedure H and the reaction inputs 1-(4'-(3-methoxypropoxy)-[1,1'-biphenyl]-4-yl)cyclopropanecarboxylic acid (prepared as described in Example 175) and Intermediate 1, the title compound was prepared as an off-white solid. $^1$H NMR (400 MHz, DMSO-d$_6$) δ 7.55 (d, J=8.8 Hz, 2H), 7.50 (d, J=8.4 Hz, 2H), 7.18 (d, J=8.4 Hz, 2H), 6.99 (d, J=8.8 Hz, 2H), 6.63 (br s, 1H), 5.62 (br s, 1H), 4.05 (t, J=6.3 Hz, 2H), 3.48 (t, J=6.3 Hz, 2H), 3.25 (s, 3H), 2.77-2.52 (m, 6H), 2.00-1.88 (m, 3H), 1.76-1.55 (m, 2H), 1.43-1.07 (m, 9H) ppm. $^{13}$C NMR (100 MHz, DMSO-d$_6$) δ 158.0, 157.3, 143.5, 136.9, 132.3, 127.4, 125.7, 124.8, 114.8, 68.5, 64.6, 63.4, 57.9, 50.9, 46.2, 46.0, 33.8, 30.4, 29.0, 25.0, 22.9, 22.3, 18.8 ppm. Purity: 97.6%, 98.2% (210 & 254 nm) UPLCMS; retention time: 0.87 min; (M+H$^+$) 464.6.

Example 177

1-(1-(4'-(3-Methoxypropoxy)-[1,1'-biphenyl]-4-yl)cyclopropyl)-3-(4-methyl-1-azabicyclo[3.2.2]nonan-4-yl)urea Using General Procedure H and the reaction inputs 1-(4'-(3-methoxypropoxy)-[1,1'-biphenyl]-4-yl)cyclopropanecarboxylic acid (prepared as described in Example 175) and Intermediate 5, the title compound was prepared as an off-white solid. $^1$H NMR (400 MHz, DMSO-d$_6$) δ 7.55 (d, J=8.6 Hz, 2H), 7.50 (d, J=8.4 Hz, 2H), 7.20 (d, J=8.3 Hz, 2H), 6.99 (d, J=8.6 Hz, 2H), 6.69 (br s, 1H), 5.56 (br s, 1H), 4.05 (t, J=6.3 Hz, 2H), 3.48 (t, J=6.3 Hz, 2H), 3.25 (s, 3H), 2.87-2.52 (m, 6H), 2.16-2.09 (m, 1H), 2.0-1.91 (m, 2H), 1.80-1.60 (m, 3H), 1.55-1.88 (m, 10H) ppm. $^{13}$C NMR (100 MHz, DMSO-d$_6$) δ 158.0, 157.2, 143.4, 136.9, 132.3, 127.5, 125.7, 124.8, 114.8, 68.5, 64.6, 57.9, 57.4, 52.8, 47.8, 45.0, 36.3, 33.9, 29.0, 26.1, 24.4, 23.9, 18.9, 18.7 ppm. Purity: 98.0%, 98.3% (210 & 254 nm) UPLCMS; retention time: 0.87 min; (M+H$^+$) 478.6.

Example 178

1-Azabicyclo[3.2.2]nonan-4-yl (1-(4'-(3-methoxypropoxy)-[1,1'-biphenyl]-4-yl)cyclopropyl)carbamate Using General Procedure H and the reaction inputs 1-(4'-(3-methoxypropoxy)-[1,1'-biphenyl]-4-yl)cyclopropanecarboxylic acid (prepared as described in Example 175) and Intermediate 3, the title compound was prepared as a glassy, colorless solid. $^1$H NMR (3:1 rotomer mixture) (400 MHz, DMSO-d$_6$) δ 7.96 (br s, 0.75H), 7.71 (br s, 0.25H), 7.27-7.15 (m, 2H), 6.99 (d, J=8.4 Hz, 1H), 4.75-4.68 (m, 1H), 4.05 (t, J=6.3 Hz, 2H), 3.48 (t, J=6.3 Hz, 2H), 3.25 (s, 3H), 3.00-2.58 (m, 6H), 2.01-1.39 (m, 9H), 1.20-1.08 (m, 4H) ppm. $^{13}$C NMR (major rotomer) (100 MHz, DMSO-d$_6$) δ 158.0, 155.6, 142.4, 137.2, 132.3, 127.5, 125.8, 125.2, 114.8, 77.4, 68.5, 64.6, 57.9, 51.4, 47.7, 44.5, 34.3, 33.5, 30.5, 28.9, 24.6, 22.0, 18.0 ppm. Purity: 100%, 100% (210 & 254 nm) UPLCMS; retention time: 0.92 min; (M+H$^+$) 465.6.

Example 179

Quinuclidin-3-yl (2-(4'-(2-(1H-pyrazol-1-yl)ethoxy)-[1,1'-biphenyl]-4-yl)propan-2-yl)carbamate Using General Procedure F and the reaction inputs ethyl 2-methyl-2-(4-(4,4,5,5-tetramethyl-1,3,2-dioxaborolan-2-yl)phenyl)propanoate and 1-(2-(4-bromophenoxy)ethyl)pyrazole, ethyl 2-(4'-(2-(1H-pyrazol-1-yl)ethoxy)-[1,1'-biphenyl]-4-yl)-2-methylpropanoate was prepared as a yellow oil. To a stirred solution of this compound (3.09 g, 8.16 mmol) in 1:1:1 (v/v/v) tetrahydrofuran/ethanol/water (40 mL) was added lithium hydroxide monohydrate (1.37 g, 57.1 mmol). The mixture was left for 6 days and then concentrated. The residue was dissolved in water and washed with diethyl ether. The aqueous layer was then treated with 1N hydrochloric acid (57 mL) and extracted with ethyl acetate. The combined organic layers were dried (Na$_2$SO$_4$) and concentrated. The resulting solid was triturated with diethyl ether to afford 2-(4'-(2-(1H-pyrazol-1-yl)ethoxy)-[1,1'-biphenyl]-4-yl)-2-methylpropanoic acid as a tan solid (1.18 g, 41%). This intermediate and quinuclidin-3-ol were reacted according to General Procedure H to generate the title compound as a white solid. $^1$H NMR (400 MHz, DMSO-d$_6$) δ 7.79 (d, J=2.1 Hz, 1H), 7.62-7.27 (m, 8H), 6.98 (d, J=8.7 Hz, 2H), 6.25 (t, J=2.1 Hz, 1H), 4.51 (t, J=5.3 Hz, 2H), 4.46-4.31 (m, 3H), 3.10-2.20 (m, 6H), 2.14-1.11 (m, 11H) ppm. $^{13}$C NMR (100 MHz, DMSO-d$_6$) δ 157.5, 154.5, 146.8, 138.8, 137.3, 132.8, 130.5, 127.6, 125.7, 125.2, 115.0, 105.1, 70.0, 66.6, 55.4, 54.2, 50.6, 46.9, 45.9, 29.4, 25.2, 24.2, 19.2 ppm. Purity: 100%, 99.5% (210 & 254 nm) UPLCMS; retention time: 1.00 min; (M+H$^+$) 475.4.

Example 180

1-(2-(4'-(2-(1H-Pyrazol-1-yl)ethoxy)-[1,1'-biphenyl]-4-yl)propan-2-yl)-3-(3-methylquinuclidin-3-yl)urea Using General Procedure H and the reaction inputs 2-(4'-(2-(1H-pyrazol-1-yl)ethoxy)-[1,1'-biphenyl]-4-yl)-2-methylpropanoic acid (prepared as described in Example 179) and Intermediate 1, the title compound was prepared as a white solid. $^1$H NMR (400 MHz, DMSO-d$_6$) δ 7.79 (dd, J=2.2, 0.5 Hz, 1H), 7.55 (d, J=8.9 Hz, 2H), 7.50 (d, J=8.6 Hz, 2H), 7.38 (d, J=8.5 Hz, 2H), 6.98 (d, J=8.9 Hz, 2H), 6.25 (t, J=2.2 Hz, 1H), 6.15 (s, 1H), 5.76 (s, 1H), 4.51 (t, J=5.3 Hz, 2H), 4.37 (t, J=5.3 Hz, 2H), 2.71-2.46 (m, 6H), 1.91-1.84 (m, 1H), 1.84-1.72 (m, 1H), 1.65-1.45 (m, 7H), 1.43-1.19 (m, 5H) ppm. $^{13}$C NMR (100 MHz, DMSO-d$_6$) δ 157.5, 156.9, 147.8, 138.8, 137.1, 132.8, 130.5, 127.5, 125.6, 125.3, 115.0, 105.1, 66.6, 63.5, 53.8, 50.7, 50.6, 46.2, 46.1, 30.4, 30.3, 29.9, 25.1, 23.0, 22.3 ppm. Purity: 100%, 99.9% (210 & 254 nm) UPLCMS; retention time: 0.99 min; (M+H$^+$) 488.4.

Example 181

1-(2-(4'-(2-(1H-Pyrazol-1-yl)ethoxy)-[1,1'-biphenyl]-4-yl)propan-2-yl)-3-(4-methyl-1-azabicyclo[3.2.2]nonan-4-yl)urea Using General Procedure H and the reaction inputs 2-(4'-(2-(1H-pyrazol-1-yl)ethoxy)-[1,1'-biphenyl]-4-yl)-2-methylpropanoic acid (prepared as described in Example 179) and Intermediate 5, the title compound was prepared as a white solid. $^1$H NMR (400 MHz, DMSO-d$_6$) δ 7.79 (dd, J=2.2, 0.5 Hz, 1H), 7.58-7.33 (m, 6H), 6.98 (d, J=8.8 Hz, 2H), 6.25 (t, J=2.2 Hz, 1H), 6.21 (s, 1H), 5.72 (br s, 1H), 4.51 (t, J=5.3 Hz, 2H), 4.37 (t, J=5.3 Hz, 2H), 2.91-2.58 (m, 6H), 2.11-2.01 (s, 1H), 1.83-1.14 (m, 15H) ppm. $^{13}$C NMR (100 MHz, DMSO-d$_6$) δ 157.5, 156.8, 147.9, 138.8, 137.1, 132.9, 130.5, 127.6, 125.6, 125.3, 115.0, 105.1, 66.6, 57.2, 53.7, 52.8, 50.6, 48.1, 45.0, 36.2, 30.4, 29.7, 26.2, 24.5, 24.0 ppm. Purity: 100%, 98.8% (210 & 254 nm) UPLCMS; retention time: 0.99 min; (M+H$^+$) 502.4.

Example 182

Quinuclidin-3-yl (2-(4'-(2-(1H-1,2,3-triazol-1-yl)ethoxy)-[1,1'-biphenyl]-4-yl)propan-2-yl)carbamate To a stirred and cooled (0° C.) solution of 2-(4-bromophenoxy)ethanol (10.60 g, 48.8 mmol) and triethylamine (10.2 mL, 73.2 mmol) in methylene chloride (100 mL) was added, dropwise, methanesulfonyl chloride (5.7 mL, 73.2 mmol). The mixture was allowed to warm to room temperature and then stirred overnight. The reaction solution was diluted with methylene chloride and washed with aqueous sodium bicarbonate. The organic layer was dried (Na$_2$SO$_4$) and concentrated to afford crude 2-(4-bromophenoxy)ethyl methanesulfonate as a yellow solid. To a stirred solution of this material in dimethylsulfoxide (50 mL) was added sodium azide (3.81 g, 58.6 mmol). The mixture was left for 3 days and then diluted with water and extracted with ethyl acetate. The organic layer was washed with water and brine, dried (Na$_2$SO$_4$) and then concentrated. The crude material was purified by flash chromatography over silica using a hexane/ethyl acetate eluant to afford 1-(2-azidoethoxy)-4-bromobenzene as a colorless oil (8.66 g, 73% overall). This intermediate (2.24 g, 9.25 mmol) was combined with ethynyltrimethylsilane (6.4 mL, 46 mmol), copper(II) sulfate pentahydrate (0.232 g, 0.929 mmol), sodium ascorbate (0.735 g, 3.71 mmol), N,N-dimethylformamide (30 mL) and water (3 mL). The mixture was heated in a microwave reactor (110° C.) with stirring for 90 minutes. The reaction was filtered through a plug of Celite, which was subsequently washed with ethyl acetate. The combined filtrate was washed with water, aqueous sodium bicarbonate solution and brine and then dried (Na$_2$SO$_4$) and concentrated. The crude was purified by flash chromatography over silica using a hexane/ethyl acetate eluant to afford a mixture of 1-(2-(4-bromophenoxy)ethyl)-1H-1,2,3-triazole and 1-(2-(4-bromophenoxy)ethyl)-4-(trimethylsilyl)-1H-1,2,3-triazole (~70/30 ratio). This material was dissolved in tetrahydrofuran (25 mL) and treated with a 1M solution of tetrabutylammonium fluoride in tetrahydrofuran (3.1 mL). The reaction was stirred overnight, concentrated and purified by flash chromatography over silica using a hexane/ethyl acetate eluant to afford clean 1-(2-(4-bromophenoxy)ethyl)-1H-1,2,3-triazole as white solid (1.81 g, 73% overall). This product and ethyl 2-methyl-2-(4-(4,4,5,5-tetramethyl-1,3,2-dioxaborolan-2-yl)phenyl)propanoate were reacted according to General Procedure F to generate ethyl 2-(4'-(2-(1H-1,2,3-triazol-1-yl)ethoxy)-[1,1'-biphenyl]-4-yl)-2-methylpropanoate. To a stirred solution of this compound (1.83 g, 4.83 mmol) in 1:1:1 (v/v/v) tetrahydrofuran/ethanol/water (20 mL) was added lithium hydroxide (0.809 g, 33.8 mmol). After heating at reflux overnight, the reaction was diluted with water, washed with diethyl ether and treated with 1 N hydrochloric acid (33 mL). The mixture was then extracted with 5:1 (v/v) chloroform/isopropanol and the combined organic layers were dried (Na$_2$SO$_4$) and concentrated. The resulted solid was triturated with diethyl ether to afford 2-(4'-(2-(1H-1,2,3-triazol-1-yl)ethoxy)-[1,1'-biphenyl]-4-yl)-2-methylpropanoic acid as an off-white solid (1.16 g, 69%). This intermediate and quinuclidin-3-ol were reacted according to General Procedure H to generate the title compound as a white solid. $^1$H NMR (400 MHz, DMSO-d$_6$) δ 8.21 (d, J=0.9 Hz, 1H), 7.75 (d, J=0.8 Hz, 1H), 7.63-7.26 (m, 7H), 7.00 (d, J=8.8 Hz, 2H), 4.81 (t, J=5.1 Hz, 2H), 4.49-4.35 (m, 3H), 3.31 (s, 3H), 3.10-2.19 (m, 6H), 2.10-1.12 (m, 11H) ppm. $^{13}$C NMR (100 MHz, DMSO-d$_6$) δ 157.3, 154.5, 146.8, 137.3, 133.3, 133.0, 127.6, 125.8, 125.3, 125.2, 115.0, 69.9, 66.3, 55.4, 54.2, 48.8, 46.9, 45.9, 29.4, 25.3, 24.2, 19.2. ppm. Purity: 100%, 98.9% (210 & 254 nm) UPLCMS; retention time: 0.97 min; (M+H$^+$) 476.4.

Example 183

1-(2-(4'-(2-(1H-1,2,3-Triazol-1-yl)ethoxy)-[1,1'-biphenyl]-4-yl)propan-2-yl)-3-(3-methylquinuclidin-3-yl)urea Using General Procedure H and the reaction inputs 2-(4'-(2-(1H-1,2,3-triazol-1-yl)ethoxy)-[1,1'-biphenyl]-4-yl)-2-methylpropanoic acid (prepared as described in Example 182) and Intermediate 1, the title compound was prepared as a white solid. $^1$H NMR (400 MHz, DMSO-d$_6$) δ 8.21 (d, J=0.9 Hz, 1H), 7.75 (d, J=0.8 Hz, 1H), 7.56 (d, J=8.8 Hz, 2H), 7.50 (d, J=8.5 Hz, 2H), 7.38 (d, J=8.5 Hz, 2H), 7.00 (d, J=8.8 Hz, 2H), 6.16 (br s, 1H), 5.77 (br s, 1H), 4.80 (t, J=5.1 Hz, 2H), 4.45 (t, J=5.2 Hz, 2H), 2.72-2.47 (m, 6H), 1.91-1.73 (m, 2H), 1.66-1.44 (m, 7H), 1.43-1.20 (m, 5H) ppm. $^{13}$C NMR (100 MHz, DMSO-d$_6$) δ 157.3, 156.9, 147.9, 137.0, 133.3, 133.0, 127.6, 125.6, 125.3, 115.0, 66.3, 63.5, 53.8, 50.7, 48.8, 46.2, 46.0, 30.4, 30.3, 29.9, 25.1, 22.9, 22.2 ppm. Purity: 100%, 99.9% (210 & 254 nm) UPLCMS; retention time: 0.95 min; (M+H$^+$) 489.4.

Example 184

1-(2-(4'-(2-(1H-1,2,3-Triazol-1-yl)ethoxy)-[1,1'-biphenyl]-4-yl)propan-2-yl)-3-(3-ethylquinuclidin-3-yl)urea Using General Procedure H and the reaction inputs 2-(4'-(2-(1H-1,2,3-triazol-1-yl)ethoxy)-[1,1'-biphenyl]-4-yl)-2-methylpropanoic acid (prepared as described in Example 182) and Intermediate 2, the title compound was prepared as a white solid. $^1$H NMR (400 MHz, DMSO-d$_6$) δ 8.21 (d, J=0.8 Hz, 1H), 7.75 (d, J=0.7 Hz, 1H), 7.56 (d, J=8.8 Hz, 2H), 7.50 (d, J=8.4 Hz, 2H), 7.39 (d, J=8.4 Hz, 2H), 7.00 (d, J=8.8 Hz, 2H), 6.19 (br s, 1H), 5.73 (br s, 1H), 4.81 (t, J=5.1 Hz, 2H), 4.45 (t, J=5.1 Hz, 2H), 2.83-2.42 (m, 6H), 1.91-1.41 (m, 11H), 1.41-1.20 (m, 2H), 0.74 (t, J=7.3 Hz, 3H) ppm. $^{13}$C NMR (100 MHz, DMSO-d$_6$) δ 157.3, 156.8, 147.9, 137.1, 133.3, 133.0, 127.6, 125.6, 125.3, 115.0, 66.3, 62.8, 53.7, 53.2, 48.8, 46.4, 46.3, 30.4, 29.8, 27.8, 27.7, 22.6, 22.3, 8.0 ppm. Purity: 100%, 99.9% (210 & 254 nm) UPLCMS; retention time: 0.99 min; (M+H$^+$) 503.4.

Example 185

1-(2-(4'-(2-(1H-1,2,3-Triazol-1-yl)ethoxy)-[1,1'-biphenyl]-4-yl)propan-2-yl)-3-(4-methyl-1-azabicyclo[3.2.2]nonan-4-yl)urea Using General Procedure H and the reaction inputs 2-(4'-(2-(1H-1,2,3-triazol-1-yl)ethoxy)-[1,1'-biphenyl]-4-yl)-2-methylpropanoic acid (prepared as described in Example 182) and Intermediate 5, the title compound was prepared as a white solid. $^1$H NMR (400 MHz, DMSO-d$_6$) δ 8.21 (d, J=0.9 Hz, 1H), 7.75 (d, J=0.9 Hz, 1H), 7.56 (d, J=8.8 Hz, 2H), 7.49 (d, J=8.5 Hz, 2H), 7.39 (d, J=8.5 Hz, 2H), 7.00 (d, J=8.8 Hz, 2H), 6.23 (br s, 1H), 5.74 (br s, 1H), 4.80 (t, J=5.1 Hz, 2H), 4.45 (t, J=5.2 Hz, 2H), 2.90-2.61 (m, 6H), 2.11-2.03 (s, 1H), 1.83-1.35 (m, 11H), 1.33-1.16 (m, 4H) ppm. $^{13}$C NMR (100 MHz, DMSO-d$_6$) δ 157.3, 156.8, 147.9, 137.1, 133.3, 133.1, 127.6, 125.6, 125.4, 125.3, 115.0, 66.3, 57.2, 53.7, 52.8, 48.8, 48.1, 45.0, 36.2, 30.4, 29.8, 26.2, 24.5, 24.0 ppm. Purity: 100%, 99.9% (210 & 254 nm) UPLCMS; retention time: 0.96 min; (M+H$^+$) 503.4.

Example 186

Quinuclidin-3-yl (2-(4'-(2-methoxyethoxy)-[1,1'-biphenyl]-3-yl)propan-2-yl)carbamate Exchanging 3-(4-bromophenoxy)propan-1-ol for 2-(4-bromophenoxy)ethanol, the reaction sequence outlined in Example 182 was used to prepare 2-(4'-(3-(1H-1,2,3-triazol-1-yl)propoxy)-[1,1'-biphenyl]-4-yl)-2-methylpropanoic acid. This intermediate and quinuclidin-3-ol were reacted according to General Procedure H to generate the title compound as a glassy, colorless solid. $^1$H NMR (400 MHz, DMSO-d$_6$) δ 8.17 (s, 1H), 7.73 (s, 1H), 7.64-7.24 (m, 7H), 6.99 (d, J=8.7 Hz, 2H), 4.57 (t, J=7.0 Hz, 2H), 4.48-4.32 (m, 1H), 4.01 (t, J=6.0 Hz, 2H), 3.12-2.19 (m, 8H), 2.08-1.13 (m, 11H) ppm. $^{13}$C NMR (100 MHz, DMSO-d$_6$) δ 157.8, 137.4, 133.2, 132.6, 127.6, 125.7, 125.2, 124.8, 114.9, 70.0, 64.5, 55.4, 54.2, 46.9, 46.3, 45.9, 29.5, 29.4, 25.2, 24.2, 19.2 ppm. Purity: 98.5%, 100% (210 & 254 nm) UPLCMS; retention time: 0.81 min; (M+H$^+$) 490.5.

Example 187

1-Azabicyclo[3.2.2]nonan-4-yl (2-(4'-(3-(1H-1,2,3-triazol-1-yl)propoxy)-[1,1'-biphenyl]-4-yl)propan-2-yl)carbamate Using General Procedure H and the reaction inputs 2-(4'-(3-(1H-1,2,3-triazol-1-yl)propoxy)-[1,1'-biphenyl]-4-yl)-2-methylpropanoic acid (prepared as described in Example 186) and Intermediate 3, the title compound was prepared as a pale yellow solid. $^1$H NMR (400 MHz, DMSO-d$_6$) δ 8.17 (s, 1H), 7.74 (s, 1H), 7.64-7.26 (m, 7H), 6.99 (d, J=8.6 Hz, 2H), 4.67-4.50 (m, 3H), 4.01 (t, J=6.0 Hz, 2H), 3.03-2.18 (m, 8H), 2.00-1.28 (m, 13H) ppm. $^{13}$C NMR (100 MHz, DMSO-d$_6$) δ 157.8, 154.2, 146.8, 137.4, 133.2, 132.6, 127.6, 125.7, 125.2, 124.8, 114.9, 77.1, 64.5, 54.1, 51.5, 47.7, 46.3, 44.6, 33.5, 30.6, 29.6, 29.5, 24.7, 22.2 ppm. Purity: 100%, 100% (210 & 254 nm) UPLCMS; retention time: 0.82 min; (M+H$^+$) 504.5.

Example 188

N-(2-(4'-(3-(1H-1,2,3-Triazol-1-yl)propoxy)-[1,1'-biphenyl]-4-yl)propan-2-yl)-1,4-diazabicyclo[3.2.2]nonane-4-carboxamide Using General Procedure H and the reaction inputs 2-(4'-(3-(1H-1,2,3-triazol-1-yl)propoxy)-[1,1'-biphenyl]-4-yl)-2-methylpropanoic acid (prepared as described in Example 186) and Intermediate 6, the title compound was prepared as a white solid. $^1$H NMR (400 MHz, DMSO-d$_6$) δ 8.17 (d, J=0.9 Hz, 1H), 7.73 (d, J=0.9 Hz, 1H), 7.56 (d, J=8.8 Hz, 2H), 7.49 (d, J=8.5 Hz, 2H), 7.36 (d, J=8.5 Hz, 2H), 6.99 (d, J=8.8 Hz, 2H), 6.11 (s, 1H), 4.57 (t, J=7.0 Hz, 2H), 4.22-4.16 (m, 1H), 4.01 (t, J=6.0 Hz, 2H), 3.48 (t, J=5.6 Hz, 2H), 3.02-2.71 (m, 6H), 2.30 (quin, J=6.5 Hz, 2H), 1.94-1.82 (m, 2H), 1.64-1.50 (m, 8H) ppm. $^{13}$C NMR (100 MHz, DMSO-d$_6$) δ 157.7, 155.4, 148.1, 136.8, 133.2, 132.8, 127.5, 125.5, 125.2, 124.8, 114.9, 64.5, 57.5, 54.5, 46.6, 46.3, 46.0, 41.4, 30.2, 29.5, 27.0 ppm. Purity: 97.4%, 99.3% (210 & 254 nm) UPLCMS; retention time: 0.75 min; (M+H$^+$) 489.5.

Example 189

Quinuclidin-3-yl (2-(4'-(3-cyanopropoxy)-[1,1'-biphenyl]-4-yl)propan-2-yl)carbamate To a stirred solution of 4-bromophenol (17.1 g, 98.8 mmol) in acetonitrile (150 mL) was added 1-bromobutylnitrile (12.3 mL, 124 mmol) and potassium carbonate (15.0 g, 109 mmol). The mixture was heated to reflux overnight, cooled and concentrated. The residue was taken up in water and extracted with ethyl acetate. The combined extracts were dried (Na$_2$SO$_4$) and concentrated and the crude material was purified by flash chromatography over silica using a hexane/ethyl acetate eluant to afford 4-(4-bromophenoxy)butanenitrile as a white solid (20.8 g, 88%). To a stirred solution of this product in N,N-dimethylformamide (100 mL), was added bis(pinacolato)diboron (4.60 g, 18.1 mmol), potassium acetate (7.41 g, 75.5 mmol) and [1,1'-bis(diphenylphosphino)ferrocene]-dichloropalladium(II) complex with dichloromethane (0.616 g, 1.04 mmol). The mixture was heated to reflux overnight and then concentrated. The residue was taken up in ethyl acetate and washed with water and brine. The organic layer was dried (Na$_2$SO$_4$) and concentrated and the crude product was purified by flash chromatography over silica using a hexane/ethyl acetate eluant to afford 4-(4-(4,4,5,5-tetramethyl-1,3,2-dioxaborolan-2-yl)phenoxy)butanenitrile as a white solid (3.43 g, 79%). This product and quinuclidin-3-yl (2-(4-bromophenyl)propan-2-yl)carbamate (prepared by reacting quinuclidin-3-ol and 2-(4-bromophenyl)propan-2-amine using General Procedure H) were reacted according to General Procedure F to generate the title compound as a white solid. $^1$H NMR (400 MHz, DMSO-d$_6$) δ 7.67-7.26 (m, 7H), 7.02 (d, J=8.8 Hz, 2H), 4.50-4.33 (m, 1H), 4.08 (t, J=6.0 Hz, 2H), 3.14-2.18 (m, 8H), 2.04 (quin, J=6.7 Hz, 2H), 1.94-1.70 (m, 11H) ppm. $^{13}$C NMR (100 MHz, DMSO-d$_6$) δ 157.7, 154.5, 146.8, 137.4, 132.7, 127.6, 125.7, 125.2, 120.2, 114.9, 70.0, 65.8, 55.4, 54.2, 46.9, 45.9, 29.4, 25.3, 24.7, 24.2, 19.2, 13.4 ppm. Purity: 100%, 98.9% (210 & 254 nm) UPLCMS; retention time: 0.88 min; (M+H$^+$) 448.6.

Example 190

Quinuclidin-3-yl (2-(4'-(cyanomethoxy)-[1,1'-biphenyl]-4-yl)propan-2-yl)carbamate Using General Procedure F and the reaction inputs quinuclidin-3-yl (2-(4-bromophenyl)propan-2-yl)carbamate (prepared by reacting quinuclidin-3-ol and 2-(4-bromophenyl)propan-2-amine using General Procedure H) and 4-(cyanomethoxy)phenylboronic acid, the title compound was prepared as a pale amber solid. $^1$H NMR (400 MHz, DMSO-d$_6$) δ 7.65 (d, J=8.2 Hz, 2H), 7.60-7.31 (m, 5H), 7.15 (d, J=8.9 Hz, 2H), 5.21 (s, 2H), 4.53-4.30 (m, 1H), 3.18-2.19 (m, 6H), 2.05-1.18 (m, 11H) ppm. $^{13}$C NMR (100 MHz, DMSO-d$_6$) δ 155.8, 154.6, 147.2, 137.2, 134.4, 127.8, 126.0, 125.3, 116.7, 115.3, 70.0, 55.4, 54.2, 53.5, 46.9, 45.9, 29.4, 25.2, 24.2, 19.2 ppm. Purity: 100%, 100% (210 & 254 nm) UPLCMS; retention time: 0.85 min; (M+H$^+$) 420.3.

Example 191

Quinuclidin-3-yl (2-(4'-((3-methyloxetan-3-yl)methoxy)-[1,1'-biphenyl]-4-yl)propan-2-yl)carbamate To a stirred solution of 4-bromophenol (3.61 g, 20.8 mmol) in N,N-dimethylformamide (100 mL) was added sodium hydride (60% dispersion in mineral oil; 0.917 g, 22.9 mmol). After 30 minutes 3-(chloromethyl)-3-methyloxetane was added. The reaction heated to 80° C. overnight and then concentrated. The residue was taken up in ethyl acetate and washed with water and brine. The organic layer was dried (Na$_2$SO$_4$) and concentrated and the crude product was purified by flash chromatography over silica using a hexane/ethyl acetate eluant to afford 3-((4-bromophenoxy)methyl)-3-methyloxetane as a colorless oil (4.64 g, 87%). This product and ethyl 2-methyl-2-(4-(4,4,5,5-tetramethyl-1,3,2-dioxaborolan-2-yl)phenyl)propanoate were reacted according to General Procedure F to generate ethyl 2-methyl-2-(4'-((3-methyloxetan-3-yl)methoxy)-[1,1'-biphenyl]-4-yl)propanoate. To a stirred solution of this compound (1.37 g, 3.72 mmol) in 1:1:1 (v/v/v) tetrahydrofuran/ethanol/water (20 mL) was added lithium hydroxide monohydrate (0.780 g, 18.6 mmol). After heating at reflux overnight, the reaction was diluted with water, washed with diethyl ether and treated with 1 N hydrochloric acid (20 mL). The mixture was then extracted with ethyl acetate and the combined organic layers were dried (Na$_2$SO$_4$) and concentrated to afford 2-methyl-2-(4'-((3-methyloxetan-3-yl)methoxy)-[1,1'-biphenyl]-4-yl)propanoic acid as an off-white solid (1.20 g, 95%). This intermediate and quinuclidin-3-ol were reacted according to General Procedure H to generate the title compound as a white solid. $^1$H NMR (400 MHz, DMSO-d$_6$) δ 7.64-7.29 (m, 7H), 7.06 (d, J=8.9 Hz, 2H), 4.51 (d, J=5.7 Hz, 2H), 4.46-4.35 (m, 1H), 4.32 (d, J=5.8 Hz, 2H), 4.09 (s, 2H), 3.15-2.35 (m, 6H), 2.06-1.21 (s, 14H) ppm. $^{13}$C NMR (100 MHz, DMSO-d$_6$) δ 158.3, 154.6, 146.6, 137.4, 132.6, 127.5, 125.7, 125.2, 115.0, 78.6, 72.6, 70.0, 55.4, 54.2, 46.9, 45.9, 39.0, 29.4, 25.3, 24.2, 21.0, 19.2 ppm. Purity: 100%, 100% (210 & 254 nm) UPLCMS; retention time: 0.93 min; (M+H$^+$) 465.4.

Example 192

1-Azabicyclo[3.2.2]nonan-4-yl (2-(4'-((3-methyloxetan-3-yl)methoxy)-[1,1'-biphenyl]-4-yl)propan-2-yl)carbamate Using General Procedure H and the reaction inputs 2-methyl-2-(4'-((3-methyloxetan-3-yl)methoxy)-[1,1'-biphenyl]-4-yl)propanoic acid (prepared as described in Example 191) and Intermediate 3, the title compound was prepared as a pale amber solid. $^1$H NMR (400 MHz, DMSO-d$_6$) δ 7.58 (d, J=8.4 Hz, 2H), 7.53 (d, J=8.5 Hz, 2H), 7.47 (br s, 1H), 7.37 (d, J=8.1 Hz, 2H), 7.06 (d, J=8.8 Hz, 2H), 4.66-4.54 (m, 1H), 4.51 (d, J=5.7 Hz, 2H), 4.32 (d, J=5.8 Hz, 2H), 4.09 (s, 2H), 3.09-2.55 (m, 6H), 1.98-1.28 (m, 16H) ppm. $^{13}$C NMR (100 MHz, DMSO-d$_6$) δ 158.3, 154.1, 146.8, 137.3, 132.7, 127.5, 125.7, 125.2, 115.0, 78.6, 77.1, 72.6, 54.1, 51.4, 47.7, 44.6, 39.0, 33.5, 30.6, 29.6, 24.7, 22.2, 21.0 pm. Purity: 100%, 100% (210 & 254 nm) UPLCMS; retention time: 0.94 min; (M+H$^+$) 479.4.

Example 193

N-(2-(4'-((3-Methyloxetan-3-yl)methoxy)-[1,1'-biphenyl]-4-yl)propan-2-yl)-1,4-diazabicyclo[3.2.2]nonane-4-carboxamide Using General Procedure H and the reaction inputs 2-methyl-2-(4'-((3-methyloxetan-3-yl)methoxy)-[1,1'-biphenyl]-4-yl)propanoic acid (prepared as described in Example 191) and Intermediate 6, the title compound was prepared as a pale amber solid. $^1$H NMR (400 MHz, DMSO-d$_6$) δ 7.58 (d, J=8.7 Hz, 2H), 7.50 (d, J=8.4 Hz, 2H), 7.36 (d, J=8.4 Hz, 2H), 7.05 (d, J=8.7 Hz, 2H), 6.12 (s, 1H), 4.51 (d, J=5.7 Hz, 2H), 4.32 (d, J=5.8 Hz, 2H), 4.23-4.15 (m, 1H), 4.08 (s, 2H), 3.49 (t, J=5.5 Hz, 2H), 3.01-2.60 (m, 6H), 1.94-1.80 (m, 2H), 1.66-1.47 (m, 8H), 1.38 (s, 3H) ppm. $^{13}$C NMR (100 MHz, DMSO-d$_6$) δ 158.2, 155.4, 148.1, 136.8, 132.8, 127.5, 125.5, 125.2, 115.0, 78.6, 72.6, 57.5, 54.5, 46.6, 46.0, 41.5, 39.0, 30.2, 27.0, 21.0 ppm. Purity: 100%, 100% (210 & 254 nm) UPLCMS; retention time: 0.88 min; (M+H$^+$) 464.4.

Example 194

Quinuclidin-3-yl (2-(4'-(2-(oxetan-3-yl)ethoxy)-[1,1'-biphenyl]-4-yl)propan-2-yl)carbamate To a stirred solution of 2-(oxetan-3-yl)ethanol (4.07 g, 39.9 mmol) in methylene chloride (200 mL) was added triethylamine (5.8 mL, 41.6 mmol) and p-toluenesulfonyl chloride (8.36 g, 43.8 mmol). The reaction was stirred overnight and then washed with 0.2 N hydrochloric acid and aqueous sodium bicarbonate solution. The organic layer was dried (Na$_2$SO$_4$) and concentrated and the resulting crude product was purified by flash chromatography over silica using a hexane/ethyl acetate eluant to afford 2-(oxetan-3-yl)ethyl 4-methylbenzenesulfonate as a colorless oil (6.65 g, 65% overall). To a stirred solution of this product (3.00 g, 11.7 mmol) in acetone (45 mL) was added 4-bromophenol (1.69 g, 9.77 mmol) and potassium carbonate (1.69 g, 12.2 mmol). The reaction was heated to reflux overnight, cooled and filtered. The filtrate was concentrated onto silica and subjected to flash chromatography over silica using a hexane/ethyl acetate eluant to afford 3-(2-(4-bromophenoxy)ethyl)oxetane as a white solid (2.43 g, 97%). This product and ethyl 2-methyl-2-(4-(4,4,5,5-tetramethyl-1,3,2-dioxaborolan-2-yl)phenyl)propanoate were reacted according to General Procedure F to generate ethyl 2-methyl-2-(4'-(2-(oxetan-3-yl)ethoxy)-[1,1'-biphenyl]-4-yl)propanoate. To a stirred solution of this compound (1.32 g, 3.58 mmol) in 1:1:1 (v/v/v) tetrahydrofuran/ethanol/water (25 mL) was added lithium hydroxide monohydrate (0.752 g, 17.9 mmol). After stirring at room temperature overnight, the reaction heated at reflux for 4 hours. At this time, the mixture concentrated and the residue was dissolved in water. The solution was washed with diethyl ether and then treated with 1 N hydrochloric acid (20 mL). The mixture was extracted with ethyl acetate and the combined organic layers were dried (Na$_2$SO$_4$) and concentrated to afford 2-methyl-2-(4'-(2-(oxetan-3-yl)ethoxy)-[1,1'-biphenyl]-4-yl)propanoic acid as an off-white solid (1.18 g, 97%). This intermediate and quinuclidin-3-ol were reacted according to General Procedure H to generate the title compound as a pale amber solid. $^1$H NMR (400 MHz, DMSO-d$_6$) δ 7.63-7.28 (m, 7H), 6.97 (d, J=8.9 Hz, 2H), 4.67 (dd, J=7.9, 5.9 Hz, 2H), 4.47-4.32 (m, 3H), 3.97 (t, J=6.3 Hz, 2H), 3.21-3.07 (m, 1H), 3.07-2.18 (m, 6H), 2.15-1.12 (m, 13H) ppm. $^{13}$C NMR (100 MHz, DMSO-d$_6$) δ 157.9, 154.5, 146.7, 137.4, 132.4, 127.5, 125.7, 125.2, 114.8, 76.2, 70.0, 65.9, 55.4, 54.2, 46.9, 45.9, 32.6, 32.4, 29.4, 25.3, 24.2, 19.2 ppm. Purity: 100%, 99.6% (210 & 254 nm) UPLCMS; retention time: 0.93 min; (M+H$^+$) 465.

Example 195

1-Azabicyclo[3.2.2]nonan-4-yl (2-(4'-(2-(oxetan-3-yl)ethoxy)-[1,1'-biphenyl]-4-yl)propan-2-yl)carbamate Using General Procedure H and the reaction inputs 2-methyl-2-(4'-(2-(oxetan-3-yl)ethoxy)-[1,1'-biphenyl]-4-yl)propanoic acid (prepared as described in Example 194) and Intermediate 3, the title compound was prepared as a pale amber solid. $^1$H NMR (400 MHz, DMSO-d$_6$) δ 7.61-7.26 (m, 7H), 6.97 (d, J=8.7 Hz, 2H), 4.67 (dd, J=7.9, 5.9 Hz, 2H), 4.64-4.56 (m, 1H), 4.37 (t, J=6.1 Hz, 2H), 3.98 (t, J=6.2 Hz, 2H), 3.21-3.07 (m, 1H), 3.03-2.33 (m, 6H), 2.13-2.03 (m, 2H), 2.00-1.31 (m, 13H) ppm. $^{13}$C NMR (100 MHz, DMSO-d$_6$) δ 157.9, 154.2, 146.8, 137.4, 132.4, 127.5, 125.7, 125.2, 114.8, 77.1, 76.2, 65.9, 54.1, 51.5, 47.7, 44.6, 33.5, 32.5, 32.4, 30.6, 29.6, 24.7, 22.2 ppm. Purity: 100%, 100% (210 & 254 nm) UPLCMS; retention time: 0.94 min; (M+H$^+$) 479.

Example 196

N-(2-(4'-(2-(Oxetan-3-yl)ethoxy)-[1,1'-biphenyl]-4-yl)propan-2-yl)-1,4-diazabicyclo[3.2.2]nonane-4-carboxamide Using General Procedure H and the reaction inputs 2-methyl-2-(4'-(2-(oxetan-3-yl)ethoxy)-[1,1'-biphenyl]-4-yl)propanoic acid (prepared as described in Example 194) and Intermediate 6, the title compound was prepared as a tan solid. $^1$H NMR (400 MHz, DMSO-d$_6$) δ 7.55 (d, J=8.7 Hz, 2H), 7.48 (d, J=8.2 Hz, 2H), 7.36 (d, J=8.2 Hz, 2H), 6.97 (d, J=8.7 Hz, 2H), 6.12 (s, 1H), 4.67 (dd, J=7.8, 5.9 Hz, 2H), 4.36 (t, J=6.1 Hz, 2H), 4.24-4.14 (m, 1H), 3.97 (t, J=6.1 Hz, 2H), 3.56-3.40 (m, 2H), 3.21-3.06 (m, 1H), 2.98-2.71 (m, 6H), 2.14-2.02 (m, 2H), 1.95-1.81 (m, 2H), 1.66-1.50 (m, 8H) ppm. $^{13}$C NMR (100 MHz, DMSO-d$_6$) δ 157.8, 155.4, 148.1, 136.9, 132.6, 127.5, 125.5, 125.2, 114.8, 76.2, 65.8, 57.5, 54.5, 46.6, 46.0, 41.4, 32.6, 32.4, 30.2, 27.0 ppm. Purity: 100%, 100% (210 & 254 nm) UPLCMS; retention time: 0.87 min; (M+H$^+$) 464.

Example 197

Quinuclidin-3-yl (2-(4'-((2-methoxyethoxy)methyl)-[1,1'-biphenyl]-4-yl)propan-2-yl)carbamate To a stirred solution of 2-methoxyethanol (2.60 mL, 32.9 mmol) in tetrahydrofuran (160 mL) was added sodium hydride (60% dispersion in mineral oil; 1.50 g, 36.2 mmol). The mixture was stirred for 30 minutes before adding 4-bromobenzyl bromide (8.64 g, 34.6 mmol). After overnight stirring, the reaction was concentrated. The residue was taken up in ethyl acetate, washed with aqueous sodium bicarbonate solution and brine, dried (Na$_2$SO$_4$) and concentrated. The resulting yellow oil was purified by flash chromatography over silica using a hexane/ethyl acetate eluant to afford 1-bromo-4-((2-methoxyethoxy)methyl)benzene as a colorless oil (6.43 g, 80%). This product and ethyl 2-methyl-2-(4-(4,4,5,5-tetramethyl-1,3,2-dioxaborolan-2-yl)phenyl)propanoate were reacted according to General Procedure F to generate ethyl 2-(4'-((2-methoxyethoxy)methyl)-[1,1'-biphenyl]-4-yl)-2-methylpropanoate. To a stirred solution of this compound (0.759 g, 2.13 mmol) in 1:1:1 (v/v/v) tetrahydrofuran/ethanol/water (25 mL) was added lithium hydroxide (0.255 g, 10.6 mmol). After heating at reflux overnight, the reaction was concentrated and the residue was dissolved in water. The solution was washed with diethyl ether and then treated with 1 N hydrochloric acid (20 mL). The mixture was extracted with ethyl acetate and the combined organic layers were dried (Na$_2$SO$_4$) and concentrated to afford 2-(4'-((2-methoxyethoxy)methyl)-[1,1'-biphenyl]-4-yl)-2-methylpropanoic acid as an off-white solid (0.657 g, 93%). This intermediate and quinuclidin-3-ol were reacted according to General Procedure H to generate the title compound as a soft, pale beige solid. $^1$H NMR (400 MHz, DMSO-d$_6$) δ 7.68-7.52 (m, 5H), 7.48-7.34 (m, 4H), 4.52 (s, 1H), 4.46-4.37 (m, 1H), 3.63-3.53 (m, 2H), 3.53-3.48 (m, 2H), 3.27 (s, 3H), 3.08-2.29 (m, 6H), 2.03-1.20 (m, 11H) ppm. $^{13}$C NMR (100 MHz, DMSO-d$_6$) δ 154.4, 147.4, 139.1, 137.5, 132.4, 128.1, 126.3, 126.2, 125.3, 71.7, 71.3, 69.2, 69.0, 58.1, 54.9, 54.2, 46.7, 45.7, 29.4, 25.0, 23.3, 18.7 ppm. Purity: 100%, 100% (210 & 254 nm) UPLCMS; retention time: 0.91 min; (M+H$^+$) 453.5.

Example 198

1-(2-(4'-((2-Methoxyethoxy)methyl)-[1,1'-biphenyl]-4-yl)propan-2-yl)-3-(3-methylquinuclidin-3-yl)urea Using General Procedure H and the reaction inputs 2-(4'-((2-methoxyethoxy)methyl)-[1,1'-biphenyl]-4-yl)-2-methylpropanoic acid (prepared as described in Example 197) and Intermediate 1, the title compound was prepared as a white solid. $^1$H NMR (400 MHz, DMSO-d$_6$) δ 7.63 (d, J=8.2 Hz, 2H), 7.57 (d, J=8.5 Hz, 2H), 7.40 (dd, J=10.3, 8.4 Hz, 4H), 6.17 (s, 1H), 5.77 (s, 1H), 4.52 (s, 2H), 3.61-3.55 (m, 2H), 3.53-2.48 (m, 2H), 3.27 (s, 3H), 2.71-2.48 (m, 6H), 1.91-1.85 (m, 1H), 1.84-1.73 (m, 1H), 1.66-1.46 (m, 7H), 1.43-1.20 (m, 5H) ppm. $^{13}$C NMR (100 MHz, DMSO-d$_6$) δ 156.9, 148.5, 139.2, 137.4, 137.2, 128.0, 126.3, 126.0, 125.4, 71.7, 71.3, 69.0, 63.5, 58.1, 53.8, 50.7, 46.2, 46.1, 30.4, 30.3, 29.9, 25.1, 23.0, 22.3 ppm. Purity: 100%, 99.5% (210 & 254 nm) UPLCMS; retention time: 0.89 min; (M+H$^+$) 466.6.

Example 199

1-(3-Ethylquinuclidin-3-yl)-3-(2-(4'-((2-methoxyethoxy)methyl)-[1,1'-biphenyl]-4-yl)propan-2-yl)urea Using General Procedure H and the reaction inputs 2-(4'-((2-methoxyethoxy)methyl)-[1,1'-biphenyl]-4-yl)-2-methylpropanoic acid (prepared as described in Example 197) and Intermediate 2, the title compound was prepared as a white solid. $^1$H NMR (400 MHz, DMSO-d$_6$) δ 7.62 (d, J=8.2 Hz, 2H), 7.56 (d, J=8.5 Hz, 2H), 7.42 (d, J=8.5 Hz, 2H), 7.39 (d, J=8.2 Hz, 2H), 6.20 (s, 1H), 5.73 (s, 1H), 4.52 (s, 2H), 3.64-3.55 (m, 2H), 3.55-3.45 (m, 2H), 3.27 (s, 3H), 2.78-2.52 (m, 6H), 1.90-1.71 (m, 3H), 1.71-1.45 (m, 8H), 1.39-1.21 (m, 2H), 0.75 (t, J=7.3 Hz, 3H) ppm. $^{13}$C NMR (100 MHz, DMSO-d$_6$) δ 156.7, 148.5, 139.2, 137.4, 137.3, 128.0, 126.3, 126.0, 125.4, 71.7, 71.3, 69.0, 62.9, 58.1, 53.8, 53.2, 46.5, 46.3, 30.4, 29.8, 27.8, 27.7, 22.6, 22.3, 8.0 ppm. Purity: 100%, 100% (210 & 254 nm) UPLCMS; retention time: 0.88 min; (M+H$^+$) 480.6.

Example 200

1-Azabicyclo[3.2.2]nonan-4-yl (2-(4'-((2-methoxyethoxy)methyl)-[1,1'-biphenyl]-4-yl)propan-2-yl)carbamate Using General Procedure H and the reaction inputs 2-(4'-((2-methoxyethoxy)methyl)-[1,1'-biphenyl]-4-yl)-2-methylpropanoic acid (prepared as described in Example 197) and Intermediate 3, the title compound was prepared as a soft amber solid. $^1$H NMR (400 MHz, DMSO-d$_6$) δ 7.62 (d, J=8.0 Hz, 2H), 7.57 (d, J=8.4 Hz, 2H), 7.49 (br s, 1H), 7.45-7.35 (m, 4H), 4.65-4.56 (m, 1H), 4.52 (s, 2H), 3.61-3.55 (m, 2H), 3.53-3.47 (m, 2H), 3.27 (s, 3H), 2.99-2.45 (m, 6H), 1.96-1.34 (m, 13H) ppm. $^{13}$C NMR (100 MHz, DMSO-d$_6$) δ 154.2, 139.1, 137.5, 137.4, 128.0, 126.3, 126.1, 125.3, 77.1, 71.7, 71.3, 69.0, 58.1, 54.1, 51.4, 47.6, 44.6, 33.5, 30.6, 29.6, 24.7, 22.2 ppm. Purity: 100%, 100% (210 & 254 nm) UPLCMS; retention time: 0.87 min; (M+H$^+$) 467.6.

Example 201

1-(2-(4'-((2-Methoxyethoxy)methyl)-[1,1'-biphenyl]-4-yl)propan-2-yl)-3-(4-methyl-1-azabicyclo[3.2.2]nonan-4-yl)urea Using General Procedure H and the reaction inputs 2-(4'-((2-methoxyethoxy)methyl)-[1,1'-biphenyl]-4-yl)-2-methylpropanoic acid (prepared as described in Example 197) and Intermediate 5, the title compound was prepared as a glassy, colorless solid. $^1$H NMR (400 MHz, DMSO-d$_6$) δ 7.62 (d, J=8.2 Hz, 2H), 7.56 (d, J=8.4 Hz, 2H), 7.43 (d, J=8.6 Hz, 2H), 7.39 (d, J=8.0 Hz, 2H), 6.24 (br s, 1H), 5.74 (br s, 1H), 4.52 (s, 2H), 3.65-3.55 (m, 2H), 3.55-3.47 (m, 2H), 3.27 (s, 3H), 2.93-2.62 (m, 6H), 2.12-2.04 (m, 1H), 1.84-1.35 (m, 11H), 1.35-1.17 (m, 4H) ppm. $^{13}$C NMR (100 MHz, DMSO-d$_6$) δ 156.8, 148.6, 139.2, 137.4, 137.3, 128.0, 126.3, 126.0, 125.4, 71.7, 71.3, 69.0, 58.1, 57.2, 53.7, 52.8, 48.1, 45.0, 36.2, 30.4, 29.8, 26.2, 24.4, 23.9 ppm. Purity: 100%, 100% (210 & 254 nm) UPLCMS; retention time: 0.86 min; (M+H$^+$) 480.6.

Example 202

N-(2-(4'-((2-Methoxyethoxy)methyl)-[1,1'-biphenyl]-4-yl)propan-2-yl)-1,4-diazabicyclo[3.2.2]nonane-4-carboxamide Using General Procedure H and the reaction inputs 2-(4'-((2-methoxyethoxy)methyl)-[1,1'-biphenyl]-4-yl)-2-methylpropanoic acid (prepared as described in Example 197) and Intermediate 6, the title compound was prepared as an off-white solid. $^1$H NMR (400 MHz, DMSO-d$_6$) δ 7.62 (d, J=8.2 Hz, 2H), 7.55 (d, J=8.4 Hz, 2H), 7.39 (d, J=8.3 Hz, 4H), 6.14 (s, 1H), 4.52 (s, 2H), 4.22-4.16 (m, 1H), 3.65-3.54 (m, 2H), 3.54-3.44 (m, 4H), 3.27 (s, 3H), 3.00-2.67 (m, 6H), 1.94-1.82 (m, 2H), 1.65-1.50 (m, 8H) ppm. $^{13}$C NMR (100 MHz, DMSO-d$_6$) δ 155.4, 148.9, 139.3, 137.3, 136.9, 128.0, 126.3, 125.9, 125.3, 71.7, 71.3, 69.0, 58.1, 57.5, 54.5, 46.6, 46.0, 41.4, 30.2, 27.0 ppm. Purity: 90.8%, 91.5% (210 & 254 nm) UPLCMS; retention time: 0.80 min; (M+H$^+$) 452.5.

Example 203

Quinuclidin-3-yl (2-(4'-((2-methoxyethoxy)methyl)-[1,1'-biphenyl]-3-yl)propan-2-yl)carbamate Exchanging ethyl 2-methyl-2-(4-(4,4,5,5-tetramethyl-1,3,2-dioxaborolan-2-yl)phenyl)-propanoate for ethyl 1-(4-(4,4,5,5-tetramethyl-1,3,2-dioxaborolan-2-yl)phenyl)-cyclopropanecarboxylate, the reaction sequence outlined in Example 197 was used to prepare 1-(4'-((2-methoxyethoxy)methyl)-[1,1'-biphenyl]-4-yl)cyclopropanecarboxylic acid. This intermediate and quinuclidin-3-ol were reacted according to General Procedure H to generate the title compound as a glassy, colorless solid. $^1$H NMR (7:3 rotamer mixture) (400 MHz, DMSO-d$_6$) δ 8.03 (br s, 0.7H), 7.79 (br s, 0.3H), 7.68-7.49 (m, 4H), 7.39 (d, J=8.0 Hz, 2H), 7.34-7.15 (m, 2H), 7.32-7.08 (m, 2H), 4.52 (br s, 3H), 3.62-3.54 (m, 2H), 3.54-3.45 (m, 2H), 3.26 (s, 3H), 3.14-2.87 (m, 1H), 2.83-2.24 (m, 6H), 1.95-1.00 (m, 9H) ppm. $^{13}$C NMR major rotamer (100 MHz, DMSO-d$_6$) δ 157.9, 154.5, 146.8, 137.4, 132.5, 127.5, 125.7, 125.2, 114.8, 70.4, 69.9, 66.9, 58.1, 55.4, 54.2, 46.9, 45.9, 29.4, 25.3, 24.2, 19.2 ppm. Purity: 100%, 99.0% (210 & 254 nm) UPLCMS; retention time: 0.83 min; (M+H$^+$) 451.6.

Example 204

1-Azabicyclo[3.2.2]nonan-4-yl (1-(4'-((2-methoxyethoxy)methyl)-[1,1'-biphenyl]-4-yl)cyclopropyl)carbamate Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 3, the title compound was prepared as a glassy, colorless solid. $^1$H NMR (7:3 rotamer mixture) (400 MHz, DMSO-d$_6$) δ 7.97 (br s, 0.7H), 7.72 (br s, 0.3H), 7.62 (d, J=8.3 Hz, 2H), 7.57 (d, J=8.2 Hz, 2H), 7.39 (d, J=8.3 Hz, 2H), 7.30-7.18 (m, 2H), 4.75-4.67 (m, 1H), 4.52 (s, 2H), 3.64-3.54 (m, 2H), 3.54-3.43 (m, 2H), 3.26 (s, 3H), 3.02-2.55 (m, 6H), 1.99-1.37 (m, 7H), 1.25-1.09 (m, 4H) ppm. $^{13}$C NMR (major rotamer) (100 MHz, DMSO-d$_6$) δ 155.7, 143.3, 139.0, 137.4, 137.2, 128.0, 126.3, 126.2, 125.2, 77.5, 71.7, 71.3, 69.0, 58.1, 51.4, 47.7, 44.5, 34.3, 33.5, 30.6, 24.7, 22.2, 18.1 ppm. Purity: 100%, 100% (210 & 254 nm) UPLCMS; retention time: 0.84 min; (M+H$^+$) 465.5.

Example 205

1-(1-(4'-((2-Methoxyethoxy)methyl)-[1,1'-biphenyl]-4-yl)cyclopropyl)-3-(3-methylquinuclidin-3-yl)urea Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 1, the title compound was prepared as a white solid. $^1$H NMR (400 MHz, DMSO-d$_6$) δ 7.62 (d, J=8.3 Hz, 2H), 7.56 (d, J=8.5 Hz, 2H), 7.38 (d, J=8.3 Hz, 2H), 7.21 (d, J=8.4 Hz, 2H), 6.64 (br s, 1H), 5.63 (br s, 1H), 4.51 (s, 2H), 3.66-3.54 (m, 2H), 3.54-3.45 (m, 2H), 3.26 (s, 3H), 2.80-2.53 (m, 6H), 1.95-1.89 (m, 1H), 1.76-1.56 (m, 2H), 1.44-1.08 (m, 9H) ppm. $^{13}$C NMR (100 MHz, DMSO-d$_6$) δ 157.3, 144.3, 139.0, 137.4, 136.9, 128.0, 126.2, 126.1, 124.8, 71.7, 71.3, 68.9, 63.4, 58.1, 50.9, 46.2, 46.0, 33.9, 30.4, 25.0, 22.9, 22.3, 19.0 ppm. Purity: 100%, 100% (210 & 254 nm) UPLCMS; retention time: 0.80 min; (M+H$^+$) 464.6.

Example 206

1-(3-Ethylquinuclidin-3-yl)-3-(1-(4'-((2-methoxyethoxy)methyl)-[1,1'-biphenyl]-4-yl)cyclopropyl) urea Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 2, the title compound was prepared as an off-white solid. $^1$H NMR (400 MHz, DMSO-d$_6$) δ 7.62 (d, J=8.2 Hz, 2H), 7.56 (d, J=8.4 Hz, 2H), 7.38 (d, J=8.2 Hz, 2H), 7.22 (d, J=8.4 Hz, 2H), 6.66 (br s, 1H), 5.58 (br s, 1H), 4.51 (s, 2H), 3.66-3.54 (m, 2H), 3.54-3.46 (m, 2H), 3.26 (s, 3H), 2.83-2.53 (m, 6H), 1.97-1.84 (m, 2H), 1.77-1.50 (m, 3H), 1.40-1.05 (m, 6H), 0.73 (t, J=7.2 Hz, 3H) ppm. $^{13}$C NMR (100 MHz, DMSO-d$_6$) δ 157.1, 144.3, 139.0, 137.4, 136.9, 128.0, 126.2, 126.1, 124.8, 71.7, 71.3, 68.9, 62.8, 58.1, 53.5, 46.4, 46.2, 33.9, 27.8, 27.7, 22.6, 22.2, 19.0, 7.9 ppm. Purity: 100%, 99.6% (210 & 254 nm) UPLCMS; retention time: 0.83 min; (M+H$^+$) 478.6.

Example 207

1-(1-(4'-((2-Methoxyethoxy)methyl)-[1,1'-biphenyl]-4-yl)cyclopropyl)-3-(4-methyl-1-azabicyclo[3.2.2]nonan-4-yl)urea Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 5, the title compound was prepared as a glassy, colorless solid. $^1$H NMR (400 MHz, DMSO-d$_6$) δ 7.62 (d, J=8.3 Hz, 2H), 7.56 (d, J=8.4 Hz, 2H), 7.38 (d, J=8.3 Hz, 2H), 7.23 (d, J=8.3 Hz, 2H), 6.70 (br s, 1H), 5.57 (br s, 1H), 4.51 (s, 2H), 3.62-3.55 (m, 2H), 3.55-3.44 (m, 2H), 3.26 (s, 3H), 2.95-2.56 (m, 6H), 2.17-2.08 (m, 1H), 1.81-1.60 (m, 3H), 1.55-1.38 (m, 2H), 1.38-1.07 (m, 8H) ppm. $^{13}$C NMR (100 MHz, DMSO-d$_6$) δ 157.2, 144.5, 139.0, 137.4, 137.0, 128.0, 126.2, 126.1, 124.9, 71.7, 71.3, 68.9, 58.1, 57.4, 52.8, 47.9, 45.1, 39.2, 36.4, 33.9, 26.1, 24.4, 24.0, 19.0, 18.8 ppm. Purity: 100%, 100% (210 & 254 nm) UPLCMS; retention time: 0.79 min; (M+H$^+$) 478.6 (M+1).

Example 208

1-(3-Ethylquinuclidin-3-yl)-3-(1-(4'-((2-methoxyethoxy)methyl)-[1,1'-biphenyl]-4-yl)cyclopropyl) urea (Single Enantiomer A)

Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 13, the title compound was prepared as an off-white solid. NMR data matched that of Example 52. Purity: 100%, 100% (210 & 254 nm) UPLCMS; retention time: 0.84 min; (M+H$^+$) 478.4.

Example 209

1-(3-Ethylquinuclidin-3-yl)-3-(1-(4'-((2-methoxyethoxy)methyl)-[1,1'-biphenyl]-4-yl)cyclopropyl) urea (Single Enantiomer B)

Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 14, the title compound was prepared as an off-white solid. NMR data matched that of Example 52. Purity: 100%, 99.7% (210 & 254 nm) UPLCMS; retention time: 0.84 min; (M+H$^+$) 478.4.

Example 210

(S)-1-(1-(4'-((2-Methoxyethoxy)methyl)-[1,1'-biphenyl]-4-yl)cyclopropyl)-3-(3-methylquinuclidin-3-yl) urea Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 11, the title compound was prepared as an off-white solid. NMR data matched that of Example 51. Purity: 100%, 99.4% (210 & 254 nm) UPLCMS; retention time: 0.79 min; (M+H$^+$) 464.4.

Example 211

(R)-1-(1-(4'-((2-Methoxyethoxy)methyl)-[1,1'-biphenyl]-4-yl)cyclopropyl)-3-(3-methylquinuclidin-3-yl) urea Using General Procedure H and the reaction inputs 1-(4'-((2-methoxyethoxy)methyl)-[1,1'-biphenyl]-4-yl)cyclopropanecarboxylic acid (prepared as described in Example 203) and Intermediate 12, the title compound was prepared as an off-white solid. NMR data matched that of Example 51. Purity: 100%, 100% (210 & 254 nm) UPLCMS; retention time: 0.79 min; (M+H$^+$) 464.3.

Example 212

1-Azabicyclo[3.2.2]nonan-4-yl (1-(4'-(3-methoxypropyl)-[1,1'-biphenyl]-4-yl)cyclopropyl)carbamate Using General Procedure F and the reaction inputs ethyl 1-(4-(4,4,5,5-tetramethyl-1,3,2-dioxaborolan-2-yl)phenyl)-cyclopropanecarboxylate and 1-bromo-4-(3-methoxypropyl)benzene, ethyl 1-(4'-(3-methoxypropyl)-[1,1'-biphenyl]-4-yl)cyclopropanecarboxylate was prepared as a pale yellow oil. To a stirred solution of this compound (1.99 g, 5.88 mmol) in 1:1:1 (v/v/v) tetrahydrofuran/ethanol/water (30 mL) was added lithium hydroxide (0.704 g, 29.4 mmol). The mixture was heated at reflux overnight and then concentrated. The residue was dissolved in water and washed with diethyl ether. The aqueous layer was then treated with 1N hydrochloric acid (30 mL) and extracted with ethyl acetate. The combined organic layers were dried (Na$_2$SO$_4$) and concentrated to afford 1-(4'-(3-methoxypropyl)-[1,1'-biphenyl]-4-yl)cyclopropanecarboxylic acid as a white solid (1.53 g, 84%). This intermediate and Intermediate 3 were reacted according to General Procedure H to generate the title compound as a white solid. ¹H NMR (7:3 rotamer mixture) (400 MHz, DMSO-$d_6$) δ 7.96 (br s, 0.75H), 7.72 (br s, 0.25H), 7.54 (d, J=8.2 Hz, 4H), 7.26 (d, J=8.1 Hz, 2H), 7.20 (d, J=8.2 Hz, 2H), 4.76-4.67 (m, 1H), 3.34 (t, J=6.4 Hz, 3H), 3.24 (s, 3H), 3.00-2.56 (m, 8H), 1.99-1.39 (m, 9H), 1.27-1.08 (m, 4H) ppm. ¹³C NMR (major rotamer) (100 MHz, DMSO-$d_6$) δ 155.6, 143.0, 140.8, 137.4, 128.8, 126.3, 126.1, 125.2, 77.5, 71.1, 57.8, 51.4, 47.7, 44.5, 34.3, 33.5, 31.3, 30.7, 30.5, 24.6, 22.1, 18.1 ppm. Purity: 97.5%, 98.0% (210 & 254 nm) UPLCMS; retention time: 0.95 min; (M+H⁺) 449.5.

Example 213

1-(1-(4'-(3-Methoxypropyl)-[1,1'-biphenyl]-4-yl)cyclopropyl)-3-(4-methyl-1-azabicyclo[3.2.2]nonan-4-yl)urea Using General Procedure H and the reaction inputs 1-(4'-(3-methoxypropyl)-[1,1'-biphenyl]-4-yl)cyclopropanecarboxylic acid (prepared as described in Example 212) and Intermediate 5, the title compound was prepared as a white solid. ¹H NMR (400 MHz, DMSO-$d_6$) δ 7.54 (dd, J=8.2, 2.5 Hz, 4H), 7.26 (d, J=8.0 Hz, 2H), 7.22 (d, J=8.2 Hz, 2H), 6.71 (br s, 1H), 5.57 (br s, 1H), 3.33 (t, J=6.4 Hz, 3H), 3.24 (s, 3H), 2.89-2.48 (m, 8H), 2.18-2.08 (m, 1H), 1.88-1.58 (m, 5H), 1.56-1.04 (m, 10H) ppm. ¹³C NMR (100 MHz, DMSO-$d_6$) δ 157.2, 144.0, 140.7, 137.4, 137.2, 128.8, 126.3, 126.0, 124.8, 71.1, 57.8, 57.4, 52.8, 47.9, 45.0, 39.2, 36.4, 33.9, 31.3, 30.8, 26.1, 24.5, 24.1, 19.0, 18.8 ppm. Purity: 100%, 99.5% (210 & 254 nm) UPLCMS; retention time: 0.90 min; (M+H⁺) 462.6.

Example 214

1-(1-(4'-(3-Methoxypropyl)-[1,1'-biphenyl]-4-yl)cyclopropyl)-3-(3-methylquinuclidin-3-yl)urea Using General Procedure H and the reaction inputs 1-(4'-(3-methoxypropyl)-[1,1'-biphenyl]-4-yl)cyclopropanecarboxylic acid (prepared as described in Example 212) and Intermediate 1, the title compound was prepared as a white solid. ¹H NMR (400 MHz, DMSO-$d_6$) δ 7.54 (dd, J=8.4, 2.2 Hz, 4H), 7.26 (d, J=8.2 Hz, 2H), 7.20 (d, J=8.4 Hz, 2H), 6.64 (br s, 1H), 5.63 (br s, 1H), 3.34 (t, J=6.4 Hz, 3H), 3.24 (s, 3H), 2.77-2.52 (m, 8H), 1.95-1.89 (m, 1H), 1.86-1.76 (m, 2H), 1.76-1.56 (m, 2H), 1.44-1.08 (m, 9H) ppm. ¹³C NMR (100 MHz, DMSO-$d_6$) δ 157.3, 144.0, 140.7, 137.4, 137.1, 128.8, 126.3, 126.0, 124.8, 71.1, 63.4, 57.8, 50.9, 46.2, 46.0, 33.9, 31.3, 30.8, 30.4, 25.0, 22.9, 22.2, 18.9 ppm. Purity: LCMS 100%, 99.6% (210 & 254 nm) UPLCMS; retention time: 0.91 min; (M+H⁺) 448.6.

Example 215

1-(3-Ethylquinuclidin-3-yl)-3-(1-(4'-(3-methoxypropyl)-[1,1'-biphenyl]-4-yl)cyclopropyl)urea Using General Procedure H and the reaction inputs 1-(4'-(3-methoxypropyl)-[1,1'-biphenyl]-4-yl)cyclopropanecarboxylic acid (prepared as described in Example 212) and Intermediate 2, the title compound was prepared as a white solid. ¹H NMR (400 MHz, DMSO-$d_6$) δ 7.58-7.50 (m, 4H), 7.26 (d, J=8.2 Hz, 2H), 7.21 (d, J=8.4 Hz, 2H), 6.66 (br s, 1H), 5.58 (br s, 1H), 3.34 (t, J=6.4 Hz, 3H), 3.24 (s, 3H), 2.72-2.52 (m, 8H), 1.98-1.49 (m, 7H), 1.41-1.07 (m, 6H), 0.73 (t, J=7.2 Hz, 3H) ppm. ¹³C NMR (100 MHz, DMSO-$d_6$) δ 157.1, 144.0, 140.7, 137.4, 137.1, 128.8, 126.3, 126.0, 124.7, 71.1, 62.8, 57.8, 53.4, 46.4, 46.2, 33.8, 31.3, 30.8, 27.8, 27.7, 22.6, 22.2, 18.9, 7.9 ppm. Purity: 100%, 99.9% (210 & 254 nm) UPLCMS; retention time: 0.95 min; (M+H⁺) 462.6.

Example 216

Quinuclidin-3-yl (1-(4'-((pyridin-3-ylmethoxy)methyl)-[1,1'-biphenyl]-4-yl)cyclopropyl)carbamate To a stirred solution of 3-pyridinemethanol (2.00 g, 18.3 mmol) in tetrahydrofuran (80 mL) was added sodium hydride (60% dispersion; 0.806 g, 20.2 mmol). After 2 hours, 4-bromobenzylbromide (4.80 g, 19.2 mmol) was added and the mixture was stirred overnight. The reaction was then concentrated and partitioned between water and ethyl acetate. The organic layer was combined with a second ethyl acetate extract, dried (Na₂SO₄) and concentrated. The crude product was purified by flash chromatography over silica using a hexane/ethyl acetate eluant to afford 3-(((4-bromobenzyl)oxy)methyl)pyridine as an amber oil (3.67 g, 72%). This product and ethyl 1-(4-(4,4,5,5-tetramethyl-1,3,2-dioxaborolan-2-yl)phenyl)-cyclopropanecarboxylate were reacted according to General Procedure F to generate ethyl 1-(4'-((pyridin-3-ylmethoxy)methyl)-[1,1'-biphenyl]-4-yl)cyclopropanecarboxylate. To a stirred solution of this compound (1.81 g, 4.67 mmol) in 1:1:1 (v/v/v) tetrahydrofuran/ethanol/water (30 mL) was added lithium hydroxide monohydrate (0.980 g, 23.4 mmol). After stirring at room temperature overnight, the reaction was concentrated and the residue was dissolved in water. The solution was washed with diethyl ether and then treated with 1 N hydrochloric acid (23.4 mL). The mixture was extracted with 4:1 (v/v) chloroform/isopropanol and the combined organic layers were dried (Na₂SO₄) and concentrated to afford 1-(4'-((pyridin-3-ylmethoxy)methyl)-[1,1'-biphenyl]-4-yl)cyclopropanecarboxylic acid as a beige solid (1.68 g, 100%). This intermediate and quinuclidin-3-ol were reacted according to General Procedure H to generate the title compound as an off-white solid. ¹H NMR (400 MHz, DMSO-$d_6$) δ 8.59 (br s, 1H), 8.54-8.49 (m, 1H), 8.05 (br s, 1H), 7.84-7.74 (m, 1H), 7.68-7.52 (m, 4H), 7.48-7.35 (m, 3H), 7.34-7.17 (m, 2H), 4.64-4.47 (m, 5H), 3.14-2.89 (m, 1H), 2.82-2.24 (m, 5H), 1.94-1.67 (m, 2H), 1.65-1.04 (m, 7H) ppm. ¹³C NMR (100 MHz, DMSO-$d_6$) δ 156.0, 148.9, 148.8, 143.3, 139.2, 137.2, 137.1, 135.4, 133.8, 128.2, 126.4, 126.3, 125.2, 123.5, 71.4, 70.4, 69.0, 55.5, 46.9, 46.0, 34.3, 25.3, 24.3, 19.3, 18.2 ppm. Purity: 100%, 100% (210 nm & 254 nm) UPLCMS; retention time: 0.65 min; (M+H⁺) 484.

Example 217

1-(3-Ethylquinuclidin-3-yl)-3-(1-(4'-((pyridin-3-ylmethoxy)methyl)-[1,1'-biphenyl]-4-yl)cyclopropyl)urea Using General Procedure H and the reaction inputs 1-(4'-((pyridin-3-ylmethoxy)methyl)-[1,1'-biphenyl]-4-yl)cyclopropanecarboxylic acid (prepared as described in Example 216) and Intermediate 2, the title compound was prepared as a pale amber solid. ¹H NMR (400 MHz, DMSO-$d_6$) δ 8.62-8.56 (m, 1H), 8.54-8.49 (m, 1H), 7.82-7.75 (m, 1H), 7.64 (d, J=8.1 Hz, 2H), 7.57 (d, J=8.4 Hz, 2H), 7.43 (d, J=8.1 Hz, 2H), 7.39 (dd, J=7.8, 4.8 Hz, 1H), 7.23 (d, J=8.4 Hz, 2H), 4.59 (br s, 4H), 2.80-2.50 (m, 6H), 1.98-1.84 (m, 2H), 1.79-1.48 (m, 3H), 1.41-1.07 (m, 6H), 0.74 (t, J=7.0 Hz, 3H)

ppm. ¹³C NMR (100 MHz, DMSO-d₆) δ 157.1, 148.9, 148.8, 139.2, 137.0, 136.9, 135.4, 133.8, 128.2, 126.3, 126.1, 124.8, 123.5, 71.4, 69.0, 62.8, 53.5, 46.4, 46.3, 33.9, 27.8, 27.7, 22.3, 19.0, 8.0 ppm. Purity: 100%, 99.6% (210 & 254 nm) UPLCMS; retention time: 0.66 min; (M+H⁺) 511.

Example 218

1-(3-Propylquinuclidin-3-yl)-3-(1-(4'-((pyridin-3-ylmethoxy)methyl)-[1,1'-biphenyl]-4-yl)cyclopropyl)urea Using General Procedure H and the reaction inputs 1-(4'-((pyridin-3-ylmethoxy)methyl)-[1,1'-biphenyl]-4-yl)cyclopropanecarboxylic acid (prepared as described in Example 216) and Intermediate 17, the title compound was prepared as a pale amber solid. ¹H NMR (400 MHz, DMSO-d₆) δ 8.59 (d, J=2.0 Hz, 1H), 8.52 (dd, J=4.8, 1.6 Hz, 1H), 7.81-7.76 (m, 1H), 7.63 (d, J=8.2 Hz, 2H), 7.55 (d, J=8.4 Hz, 2H), 7.43 (d, J=8.2 Hz, 2H), 7.41-7.37 (m, 1H), 7.22 (d, J=8.4 Hz, 2H), 6.67 (br s, 1H), 5.61 (br s, 1H), 4.59 (s, 4H), 2.81-2.70 (m, 1H), 2.70-2.51 (m, 5H), 1.95-1.78 (m, 2H), 1.77-1.49 (m, 3H), 1.41-1.06 (m, 8H), 0.87 (t, J=7.2 Hz, 3H) ppm. ¹³C NMR (100 MHz, DMSO-d₆) δ 157.2, 148.8, 148.8, 139.2, 137.1, 136.9, 135.4, 133.8, 128.2, 126.1, 124.8, 123.5, 71.4, 69.0, 63.1, 53.4, 46.4, 46.3, 37.8, 33.9, 28.2, 22.7, 22.3, 19.0, 18.9, 16.7, 14.5 ppm. Purity: 100%, 100% (210 & 254 nm) UPLCMS; retention time: 0.70 min; (M+H⁺) 525.

Example 219

Quinuclidin-3-yl (1-(4'-((pyrimidin-5-ylmethoxy)methyl)-[1,1'-biphenyl]-4-yl)cyclopropyl)carbamate Exchanging 3-pyridinemethanol for 5-pyrimidinemethanol, the reaction sequence outlined in Example 216 was used to prepare 1-(4'-((pyrimidin-5-ylmethoxy)methyl)-[1,1'-biphenyl]-4-yl)cyclopropanecarboxylic acid. This compound and quinuclidin-3-ol were reacted according to General Procedure H to generate the title compound as an off-white solid. ¹H NMR (400 MHz, DMSO-d₆) δ 9.14 (s, 1H), 8.82 (s, 2H), 8.05 (br s, 1H), 7.64 (d, J=8.1 Hz, 2H), 7.58 (d, J=7.9 Hz, 2H), 7.45 (d, J=8.1 Hz, 2H), 7.33-7.17 (m, 2H), 4.63 (s, 2H), 4.62 (s, 2H), 4.58-4.48 (m, 1H), 3.15-2.89 (m, 1H), 2.81-2.25 (m, 5H), 1.95-1.02 (m, 9H) ppm. ¹³C NMR (100 MHz, DMSO-d₆) δ 157.7, 156.2, 156.0, 143.3, 139.2, 137.1, 136.9, 131.8, 128.2, 126.4, 126.3, 125.2, 71.7, 70.4, 66.8, 55.5, 46.9, 46.0, 34.3, 25.3, 24.2, 19.2, 18.2 ppm. Purity: 100%, 99.3% (210 & 254 nm) UPLCMS; retention time: 0.78 min; (M+H⁺) 485.

Example 220

1-(3-Ethylquinuclidin-3-yl)-3-(1-(4'-((pyrimidin-5-ylmethoxy)methyl)-[1,1'-biphenyl]-4-yl)cyclopropyl)urea Using General Procedure H and the reaction inputs 1-(4'-((pyrimidin-5-ylmethoxy)methyl)-[1,1'-biphenyl]-4-yl)cyclopropanecarboxylic acid (prepared as described in Example 219) and Intermediate 2, the title compound was prepared as an off-white solid. ¹H NMR (400 MHz, DMSO-d₆) δ 9.14 (s, 1H), 8.82 (s, 2H), 7.64 (d, J=8.2 Hz, 2H), 7.57 (d, J=8.4 Hz, 2H), 7.44 (d, J=8.2 Hz, 2H), 7.23 (d, J=8.4 Hz, 2H), 6.68 (br s, 1H), 5.60 (br s, 1H), 6.63 (s, 2H), 4.62 (s, 2H), 2.79-2.51 (m, 6H), 1.97-1.84 (m, 2H), 1.78-1.50 (m, 3H), 1.41-1.07 (m, 6H), 0.74 (t, J=7.0 Hz, 3H) ppm. ¹³C NMR (100 MHz, DMSO-d₆) δ 157.7, 157.1, 156.2, 144.3, 139.2, 136.9, 136.8, 131.8, 128.2, 126.4, 126.1, 124.8, 71.7, 66.8, 62.8, 53.5, 46.4, 46.2, 33.9, 27.8, 27.7, 22.6, 22.2, 19.0 ppm. Purity: 100%, 98.7% (210 & 254 nm) UPLCMS; retention time: 0.78 min; (M+H⁺) 512.

Example 221

1-Azabicyclo[3.2.2]nonan-4-yl (1-(4'-((pyrimidin-5-ylmethoxy)methyl)-[1,1'-biphenyl]-4-yl)cyclopropyl)carbamate Using General Procedure H and the reaction inputs 1-(4'-((pyrimidin-5-ylmethoxy)methyl)-[1,1'-biphenyl]-4-yl)cyclopropanecarboxylic acid (prepared as described in Example 219) and Intermediate 3, the title compound was prepared as an off-white solid. ¹H NMR (400 MHz, DMSO-d₆) δ 9.14 (s, 1H), 8.82 (s, 2H), 7.99 (br s, 1H), 7.64 (d, J=8.2 Hz, 2H), 7.58 (d, J=8.2 Hz, 2H), 7.45 (d, J=8.2 Hz, 2H), 7.31-7.17 (m, 2H), 4.77-4.68 (m, 1H), 4.63 (s, 2H), 4.62 (s, 2H), 3.00-2.55 (m, 6H), 2.00-1.35 (m, 7H), 1.17 (br s, 4H) ppm. ¹³C NMR (100 MHz, DMSO-d₆) δ 157.7, 156.2, 155.7, 143.3, 139.2, 137.1, 136.9, 131.8, 128.2, 126.4, 126.2, 125.2, 77.5, 71.7, 66.8, 51.4, 47.7, 44.5, 34.4, 33.5, 30.6, 24.7, 22.2, 18.2 ppm. Purity: 100%, 99.2% (210 & 254 nm) UPLCMS; retention time: 0.79 min; (M+H⁺) 499.

Example 222

1-(2-(4'-(3-Methoxypropyl)-[1,1'-biphenyl]-4-yl)propan-2-yl)-3-(3-methylquinuclidin-3-yl)urea Exchanging ethyl 1-(4-(4,4,5,5-tetramethyl-1,3,2-dioxaborolan-2-yl)phenyl)-cyclopropanecarboxylate for ethyl 2-methyl-2-(4-(4,4,5,5-tetramethyl-1,3,2-dioxaborolan-2-yl)phenyl)-propanoate, the reaction sequence outlined in Example 212 was used to prepare 2-(4'-(3-methoxypropyl)-[1,1'-biphenyl]-4-yl)-2-methylpropanoic acid. This compound and Intermediate 1 were reacted according to General Procedure H to generate the title compound as a white solid. ¹H NMR (400 MHz, DMSO-d₆) δ 7.63-7.47 (m, 4H), 7.41 (d, J=8.5 Hz, 2H), 7.27 (d, J=8.2 Hz, 2H), 6.18 (br s, 1H), 5.79 (br s, 1H), 3.34 (t, J=6.4 Hz, 2H), 3.24 (s, 3H), 2.74-2.52 (m, 8H), 1.91-1.74 (m, 4H), 1.67-1.47 (m, 7H), 1.44-1.20 (m, 5H) ppm. ¹³C NMR (100 MHz, DMSO-d₆) δ 156.9, 148.2, 140.7, 137.6, 137.5, 128.8, 126.4, 125.9, 125.3, 71.2, 63.4, 57.8, 53.8, 50.7, 46.1, 46.0, 31.3, 30.8, 30.3, 29.9, 25.1, 22.9, 22.2 ppm. Purity: 99.9%, 98.1% (210 & 254 nm) UPLCMS; retention time: 0.97 min; (M+H⁺) 450.5.

Example 223

Quinuclidin-3-yl (2-(4'-(hydroxymethyl)-[1,1'-biphenyl]-4-yl)propan-2-yl)carbamate Using General Procedure F and the reaction inputs ethyl 2-(4-bromophenyl)-2-methylpropanoate and 4-formylphenylboronic acid, ethyl 2-(4'-formyl-[1,1'-biphenyl]-4-yl)-2-methylpropanoate was prepared as a pale amber solid. This intermediate and quinuclidin-3-ol were reacted according to General Procedure H to generate quinuclidin-3-yl (2-(4'-formyl-[1,1'-biphenyl]-4-yl)propan-2-yl)carbamate as foamy, yellow solid. To a stirred solution of this material (0.755 g, 1.92 mmol) in 2:1 (v/v) tetrahydrofuran/ethanol (15 mL) was added sodium borohydride (0.073 g, 1.93 mmol). After 45 minutes, the reaction was diluted with water and extracted with chloroform. The combined extracts were dried (Na$_2$SO$_4$) and concentrated onto silica. Flash chromatography over silica using a chloroform/methanol/ammonia eluant provided the title compound as a white solid (0.323 g, 43%). $^1$H NMR (400 MHz, DMSO-d$_6$) δ 7.66-7.29 (m, 9H), 5.18 (t, J=5.7 Hz, 1H), 4.53 (d, J=5.7 Hz, 2H), 4.46-4.37 (m, 1H), 3.11-2.19 (m, 6H), 2.11-1.10 (m, 11H) ppm. $^{13}$C NMR (100 MHz, DMSO-d$_6$) δ 154.7, 147.3, 141.5, 138.4, 137.7, 127.0, 126.2, 126.1, 125.3, 70.0, 62.6, 55.4, 54.2, 46.9, 45.9, 29.4, 25.3, 24.2, 19.2 ppm. Purity: 97.5%, 99.1% (210 & 254 nm) UPLCMS; retention time: 0.73 min; (M+H$^+$) 395.

Example 224

1-(2-(4'-(2-Hydroxyethyl)-[1,1'-biphenyl]-4-yl)propan-2-yl)-3-(3-propylquinuclidin-3-yl)urea Using General Procedure F and the reaction inputs 1-(2-(benzyloxy)ethyl)-4-bromobenzene and ethyl 2-methyl-2-(4-(4,4,5,5-tetramethyl-1,3,2-dioxaborolan-2-yl)phenyl) propanoate, ethyl 2-(4'-(2-(benzyloxy)ethyl)-[1,1'-biphenyl]-4-yl)-2-methylpropanoate was prepared as a colorless gum. To a stirred solution of this compound (1.34 g, 3.33 mmol) in 1:1:1 (v/v/v) tetrahydrofuran/ethanol/water (18 mL) was added lithium hydroxide monohydrate (0.698 g, 16.6 mmol). After heating at reflux overnight, the reaction was concentrated and partitioned between water and diethyl ether. The resulting emulsion was extracted repeatedly with 0.2 N aqueous sodium hydroxide solution (5×50 mL). The clear portion of the aqueous layer was removed each time. The combined aqueous layers were then treated with 1.0 N hydrochloric acid (80 mL) and the resulting suspension of white solid was extracted with ethyl acetate. The combined organic layers were dried (Na$_2$SO$_4$) and concentrated to afford 2-(4'-(2-(benzyloxy)ethyl)-[1,1'-biphenyl]-4-yl)-2-methylpropanoic acid as a white solid (1.20 g, 96%). This compound and Intermediate 17 were reacted according to General Procedure H to generate 1-(2-(4'-(2-(benzyloxy) ethyl)-[1,1'-biphenyl]-4-yl)propan-2-yl)-3-(3-propylquinuclidin-3-yl)urea as a colorless, foamy solid. To a stirred solution of this material (0.435 g, 0.806 mmol) in methanol was added 1.0 N hydrochloric acid (1 mL) and 10% palladium on carbon (50% water; 0.087 g). The mixture was cycled between vacuum and a nitrogen purge several times, refilling with hydrogen after the last evacuation. After 1.25 hours the reaction was filtered through Celite and concentrated. The residue was taken up in aqueous sodium carbonate solution and extracted with 4:1 (v/v) chloroform/isopropanol. The combined extracts were dried (Na$_2$SO$_4$) and concentrated onto silica. Flash chromatography over silica using a chloroform/methanol/ammonia gradient provided the purified title compound as foamy, colorless solid (0.296 g, 82%). $^1$H NMR (400 MHz, DMSO-d$_6$) δ 7.56-7.47 (m, 4H), 7.44-7.37 (m, 2H), 7.33-7.26 (m, 2H), 6.19 (s, 1H), 5.74 (s, 1H), 4.65 (br s, 1H), 3.63 (t, J=7.0 Hz, 2H), 2.79-2.46 (m, 8H), 1.89-1.82 (m, 1H), 1.82-1.68 (m, 2H), 1.67-1.42 (m, 8H), 1.40-1.14 (m, 4H), 0.86 (t, J=7.2 Hz, 3H) ppm. $^{13}$C NMR (100 MHz, DMSO-d$_6$) δ 156.8, 148.3, 138.5, 137.8, 137.5, 129.4, 126.2, 125.9, 125.3, 63.1, 62.1, 53.7, 53.1, 46.4, 46.3, 38.6, 37.8, 30.6, 29.6, 28.2, 22.6, 22.2, 16.7, 14.5 ppm. Purity: 100%, 99.0% (210 & 254 nm) UPLCMS; retention time: 0.83 min; (M+H$^+$) 450.

Example 225

1-(3-Ethylquinuclidin-3-yl)-3-(2-(4'-(2-hydroxyethyl)-[1,1'-biphenyl]-4-yl)propan-2-yl)urea Exchanging Intermediate 17 for Intermediate 2, the reaction sequence outlined in Example 224 was used to prepare the title compound as an off-white solid. $^1$H NMR (400 MHz, DMSO-d$_6$) δ 7.62-7.36 (m, 6H), 7.34-7.21 (m, 2H), 6.22 (br s, 1H), 5.78 (br s, 1H), 4.66 (br s, 1H), 3.63 (t, J=7.0 Hz, 2H), 2.83-2.43 (m, 8H), 1.93-1.18 (m, 13H), 0.75 (t, J=7.4 Hz, 3H) ppm. $^{13}$C NMR (100 MHz, DMSO-d$_6$) δ 156.8, 148.2, 138.5, 137.7, 137.5, 129.4, 126.2, 125.9, 125.3, 62.7, 62.1, 53.8, 53.2, 46.4, 46.2, 38.6, 30.4, 29.8, 27.7, 22.4, 22.1, 8.0 ppm. Purity: 100%, 98.0% (210 & 254 nm) UPLCMS; retention time: 0.79 min; (M+H$^+$) 436.

Example 226

Quinuclidin-3-yl (2-(4'-(2-hydroxyethyl)-[1,1'-biphenyl]-4-yl)propan-2-yl)carbamate Exchanging Intermediate 17 for quinuclidin-3-ol, the reaction sequence outlined in Example 224 was used to prepare the title compound as a colorless solid. $^1$H NMR (400 MHz, DMSO-d$_6$) δ 7.85-7.63 (m, 1H), 7.63-7.19 (m, 8H), 4.78-4.62 (m, 2H), 3.71-2.78 (m, 8H), 2.76 (t, J=6.8 Hz, 2H), 2.26-1.96 (m, 2H), 1.96-1.40 (m, 9H) ppm. $^{13}$C NMR (100 MHz, DMSO-d$_6$) δ 153.8, 146.8, 138.7, 137.9, 137.6, 129.4, 126.3, 126.1, 125.3, 66.2, 62.1, 54.4, 52.8, 45.4, 44.5, 38.6, 29.5, 29.2, 24.0, 19.9, 16.6 ppm. Purity: 100%, 100% (210 & 254 nm) UPLCMS; retention time: 0.75 min; (M+H$^+$) 409.

Example 227

Quinuclidin-3-yl (2-(4'-(2-(1H-1,2,3-triazol-4-yl) ethyl)-[1,1'-biphenyl]-4-yl)propan-2-yl)carbamate To a stirred solution of 1-bromo-4-(but-3-yn-1-yl)benzene (1.73 g, 8.27 mmol) in a mixture of tert-butanol (76 mL) and water (24 mL) was added benzyl azide (1.14 g, 9.13 mmol), L-sodium ascorbate (0.164 g, 0.828 mmol) and copper(II) sulfate pentahydrate (0.103 g, 0.413 mmol). After 2 days, more benzyl azide was added (0.25 mL, 2.00 mmol) and the reaction was stirred for another night. The reaction was then concentrated and the residue was taken up in aqueous sodium bicarbonate solution and extracted with ethyl acetate. The combined extracts were dried (Na$_2$SO$_4$) and concentrated onto silica. Flash chromatography over silica using a hexane/ethyl acetate eluant provided 1-benzyl-4-(4-bromophenethyl)-1H-1,2,3-triazole as white solid (1.17 g, 41%). This compound and ethyl 2-methyl-2-(4-(4,4,5,5-tetramethyl-1,3,2-dioxaborolan-2-yl)phenyl)propanoate were reacted according to General Procedure F to generate ethyl 2-(4'-(2-(1-benzyl-1H-1,2,3-triazol-4-yl)ethyl)-[1,1'-biphenyl]-4-yl)-2-methylpropanoate as a white solid. To a stirred solution of this compound (1.22 g, 2.69 mmol) in 2:3:3 (v/v/v) water/tetrahydrofuran/ethanol (32 mL) was added lithium hydroxide monohydrate (0.564 g, 13.4 mmol). After heating at reflux overnight, the reaction was concentrated and the residue was dissolved in water. The solution was washed with diethyl ether and then treated with 1 N hydrochloric acid (13.4 mL). The resulting milky suspension was extracted with ethyl acetate and the combined organic layers were dried (Na$_2$SO$_4$) and concentrated to afford 2-(4'-(2-(1-benzyl-1H-1,2,3-triazol-4-yl)ethyl)-[1, 1'-biphenyl]-4-yl)-2-methylpropanoic acid as a white solid (1.16 g, 100%). This compound and quinuclidin-3-ol were reacted according to General Procedure H to generate quinuclidin-3-yl (2-(4'-(2-(1-benzyl-1H-1,2,3-triazol-4-yl)ethyl)-[1,1'-biphenyl]-4-yl)propan-2-yl)carbamate as a foamy, colorless solid. To a stirred solution of this intermediate (0.450 g, 0.819 mmol) in methanol (20 mL) was added 1.0 N hydrochloric acid (1 mL) and 10% palladium on carbon (50% water; 0.225 g). The mixture was cycled between vacuum and a nitrogen purge several times, refilling with hydrogen after the last evacuation. After 7 hours, the reaction filtered through Celite and concentrated. The residue was purified by flash chromatography over silica using a chloroform/methanol/ammonia gradient to afford the title compound as a foamy, colorless solid (0.332 g, 88%). $^1$H NMR (400 MHz, DMSO-$d_6$) δ 7.63-7.25 (m, 10H), 4.48-4.35 (m, 1H), 3.09-2.19 (m, 10H), 2.10-1.02 (m, 11H) ppm. $^{13}$C NMR (100 MHz, DMSO-$d_6$) δ 154.5, 147.2, 144.0, 140.1, 137.7, 137.6, 129.3, 128.9, 126.4, 126.1, 125.3, 70.0, 55.4, 54.2, 46.9, 45.9, 34.2, 29.4, 26.0, 25.3, 24.2, 19.2 ppm. Purity: 100%, 100% (210 & 254 nm) UPLCMS; retention time: 0.83 min; (M+H$^+$) 460.

Example 228

1-Azabicyclo[3.2.2]nonan-4-yl (2-(4'-(2-(1H-1,2,3-triazol-4-yl)ethyl)-[1,1'-biphenyl]-4-yl)propan-2-yl)carbamate Exchanging quinuclidin-3-ol for Intermediate 3, the reaction sequence outlined in Example 227 was used to prepare the title compound as a colorless solid. $^1$H NMR (400 MHz, DMSO-$d_6$) δ 14.69 (br s, 1H), 7.59 (s, 1H), 7.55 (d, J=8.4 Hz, 4H), 7.48 (br s, 1H), 7.39 (d, J=8.1 Hz, 2H), 7.30 (d, J=8.3 Hz, 2H), 4.65-4.55 (m, 1H), 3.04-2.42 (m, 10H), 2.01-1.31 (m, 13H) ppm. $^{13}$C NMR (100 MHz, DMSO-$d_6$) δ 154.2, 147.3, 144.1, 140.1, 137.8, 137.6, 129.3, 128.9, 126.4, 126.0, 125.3, 77.0, 54.1, 51.4, 47.7, 44.6, 34.2, 33.4, 30.5, 26.0, 24.5, 22.0 ppm. Purity: 100%, 100% (210 & 254 nm) UPLCMS; retention time: 0.83 min; (M+H$^+$) 474.

Example 229

Quinuclidin-3-yl (2-(4'-(morpholinomethyl)-[1,1'-biphenyl]-4-yl)propan-2-yl)carbamate Using General Procedure F and the reaction inputs ethyl 2-(4-bromophenyl)-2-methylpropanoate and 4-(4-morpholinomethyl)phenylboronic acid, ethyl 2-methyl-2-(4'-(morpholinomethyl)-[1,1'-biphenyl]-4-yl)propanoate was prepared as an amber oil. To a stirred solution of this compound (2.86 g, 7.79 mmol) in 1:1:1 (v/v/v) tetrahydrofuran/ethanol/water (40 mL) was added lithium hydroxide (1.31 g, 54.5 mmol). After heating at reflux overnight, the reaction was diluted with water and washed with diethyl ether. The aqueous layer was treated with 1.0 N hydrochloric acid (56 mL) and extracted with 4:1 (v/v) chloroform/isopropanol. The combined extracts were dried (Na$_2$SO$_4$) and concentrated. The residue was triturated with diethyl ether to afford 2-methyl-2-(4'-(morpholinomethyl)-[1,1'-biphenyl]-4-yl)propanoic acid as a tan solid (2.50 g, 95%). This compound and quinuclidin-3-ol were reacted according to General Procedure H to generate the title compound as an off-white solid. $^1$H NMR (400 MHz, DMSO-$d_6$) δ 7.67-7.26 (m, 9H), 4.50-4.34 (m, 1H), 3.58 (t, J=4.6 Hz, 4H), 3.49 (s, 2H), 3.10-2.22 (m, 8H), 2.07-1.18 (m, 11H) ppm. $^{13}$C NMR (100 MHz, DMSO-$d_6$) δ 154.6, 147.4, 138.7, 137.6, 136.8, 129.4, 126.3, 126.1, 125.3, 70.0, 66.2, 62.1, 55.4, 54.2, 53.2, 46.9, 46.0, 29.4, 25.2, 24.2, 19.2 ppm. Purity: 96.5%, 98.9% (210 & 254 nm) UPLCMS; retention time: 0.50 min; ((M+H$^+$)/2) 232.9.

Example 230

N-(2-(4'-(Morpholinomethyl)-[1,1'-biphenyl]-4-yl)propan-2-yl)-1,4-diazabicyclo[3.2.2]nonane-4-carboxamide Using General Procedure H and the reaction inputs 2-methyl-2-(4'-(morpholinomethyl)-[1,1'-biphenyl]-4-yl)propanoic acid (prepared as described in Example 229) and Intermediate 6, the title compound was prepared as a colorless solid. $^1$H NMR (400 MHz, DMSO-$d_6$) δ 7.59 (d, J=8.1 Hz, 2H), 7.54 (d, J=8.3 Hz, 2H), 7.44-7.32 (m, 4H), 6.16 (br s, 1H), 4.24-4.16 (m, 1H), 3.62-3.54 (m, 2H), 3.54-3.43 (m, 4H), 3.00-2.72 (m, 6H), 2.44-2.29 (m, 4H), 1.95-1.82 (m, 2H), 1.66-1.49 (m, 8H) ppm. $^{13}$C NMR (100 MHz, DMSO-$d_6$) δ 155.4, 148.7, 138.9, 137.0, 136.7, 129.4, 126.3, 125.9, 125.3, 66.2, 62.1, 57.4, 54.6, 53.2, 46.5, 45.9, 41.2, 30.2, 26.8 ppm. Purity: 97.2%, 99.9% (210 & 254 nm) UPLCMS; retention time: 0.44 min; ((M+1)/2) 232.4.

Example 231

Quinuclidin-3-yl (2-(4'-morpholino-[1,1'-biphenyl]-4-yl)propan-2-yl)carbamate

Using General Procedure F and the reaction inputs ethyl 2-(4-bromophenyl)-2-methylpropanoate and 4-(4-(4,4,5,5-tetramethyl-1,3,2-dioxaborolan-2-yl)phenyl)-morpholine, ethyl 2-methyl-2-(4'-morpholino-[1,1'-biphenyl]-4-yl)propanoate was prepared as a white solid. To a stirred solution of this compound (3.32 g, 9.39 mmol) in 1:1:1 (v/v/v) tetrahydrofuran/ethanol/water (50 mL) was added lithium hydroxide (1.57 g, 65.6 mmol). After heating at reflux for 3 hours, the reaction was diluted with water and washed with diethyl ether. The aqueous layer was acidified to pH~5 with 1.0 N hydrochloric acid and extracted with ethyl acetate. The combined extracts were filtered free of solid and concentrated to afford 2-methyl-2-(4'-morpholino-[1,1'-biphenyl]-4-yl)propanoic acid (2.62 g, 86%). This compound and quinuclidin-3-ol were reacted according to General Procedure H to generate the title compound as an off-white solid. $^1$H NMR (400 MHz, DMSO-$d_6$) δ 7.56-7.40 (m, 6H), 6.96 (d, J=8.8 Hz, 2H), 5.19 (br s, 1H), 4.70-4.54 (m, 1H), 3.92-3.83 (m, 4H), 3.27-2.41 (m, 10H), 2.09-1.28 (m, 11H) ppm. $^{13}$C NMR (100 MHz, DMSO-$d_6$) δ 155.2, 151.0, 147.1, 138.3, 131.3, 127.6, 126.1, 125.9, 116.0, 70.6, 66.8, 56.0, 54.7, 48.9, 46.6, 30.1, 30.0, 25.9, 24.8, 19.8 ppm. Purity: 100%, 100% (210 & 254 nm) UPLCMS; retention time: 1.02 min; (M+H$^+$) 450.4.

Example 232

1-(3-Methylquinuclidin-3-yl)-3-(2-(4'-morpholino-[1,1'-biphenyl]-4-yl)propan-2-yl)urea Using General Procedure H and the reaction inputs 2-methyl-2-(4'-morpholino-[1,1'-biphenyl]-4-yl)propanoic acid (prepared as described in Example 231) and Intermediate 1, the title compound was prepared as a white solid. $^1$H NMR (400 MHz, CDCl$_3$) δ 7.57-7.40 (m, 6H), 6.96 (d, J=8.8 Hz, 2H), 5.19 (br s, 1H), 4.71-4.53 (m, 1H), 3.93-3.82 (m, 4H), 3.27-2.11 (m, 10H), 2.09-1.25 (m, 11H) ppm. $^{13}$C NMR (100 MHz, DMSO-d$_6$) δ 156.9, 150.2, 147.4, 137.4, 130.7, 126.9, 125.3, 115.3, 66.1, 63.6, 53.8, 50.7, 48.3, 46.2, 46.1, 30.4, 30.3, 29.9, 25.1, 23.0, 22.3 ppm. Purity: 100%, 99.9% (210 & 254 nm) UPLCMS; retention time: 0.82 min; 463.1 (M+1).

Example 233

1-(4-Methyl-1-azabicyclo[3.2.2]nonan-4-yl)-3-(2-(4'-morpholino-[1,1'-biphenyl]-4-yl)propan-2-yl)urea Using General Procedure H and the reaction inputs 2-methyl-2-(4'-morpholino-[1,1'-biphenyl]-4-yl)propanoic acid (prepared as described in Example 231) and Intermediate 5, the title compound was prepared as an off-white solid. $^1$H NMR (400 MHz, DMSO-d$_6$) δ 7.58-7.44 (m, 4H), 7.38 (d, J=8.4 Hz, 2H), 7.01 (d, J=8.6 Hz, 2H), 6.21 (br s, 1H), 5.72 (br s, 1H), 3.85-3.63 (m, 4H), 3.23-3.02 (m, 4H), 2.94-2.63 (m, 6H), 2.12-2.03 (m, 1H), 1.84-1.35 (m, 11H), 1.35-1.17 (m, 4H) ppm. $^{13}$C NMR (100 MHz, DMSO-d$_6$) δ 156.8, 150.2, 147.5, 137.4, 130.7, 126.9, 125.3, 125.3, 115.3, 66.1, 57.2, 53.7, 52.8, 48.3, 48.1, 45.0, 36.2, 30.4, 29.8, 26.2, 24.5, 24.0 ppm. Purity: 100%, 98.8% (210 & 254 nm) UPLCMS; retention time: 0.83 min; (M+H$^+$) 477.1.

Example 234

1-(3-Ethylquinuclidin-3-yl)-3-(2-(4'-morpholino-[1,1'-biphenyl]-4-yl)propan-2-yl)urea Using General Procedure H and the reaction inputs 2-methyl-2-(4'-morpholino-[1,1'-biphenyl]-4-yl)propanoic acid (prepared as described in Example 231) and Intermediate 2, the title compound was prepared as a foamy, colorless solid. $^1$H NMR (400 MHz, DMSO-d$_6$) δ 7.52 (d, J=8.9 Hz, 2H), 7.49 (d, J=8.5 Hz, 2H), 7.38 (d, J=8.5 Hz, 2H), 7.01 (d, J=8.9 Hz, 2H), 6.17 (br s, 1H), 5.71 (br s, 1H), 3.80-3.69 (m, 4H), 3.20-3.08 (m, 4H), 2.84-2.53 (m, 6H), 1.92-1.41 (m, 11H), 1.41-1.19 (m, 2H), 0.74 (t, J=7.3 Hz, 3H) ppm. $^{13}$C NMR (100 MHz, DMSO-d$_6$) δ 156.8, 150.2, 147.4, 137.4, 130.7, 126.9, 125.3, 115.3, 66.1, 62.9, 53.7, 53.2, 48.3, 46.5, 46.3, 30.4, 29.8, 27.8, 27.7, 22.6, 22.3, 8.0 ppm. Purity: 100%, 99.9% (210 & 254 nm) UPLCMS; retention time: 1.03 min; (M+H$^+$) 477.4.

Example 235

Quinuclidin-3-yl (2-(4'-(methylsulfonyl)-[1,1'-biphenyl]-4-yl)propan-2-yl)carbamate Using General Procedure F and the reaction inputs ethyl 2-methyl-2-(4-(4,4,5,5-tetramethyl-1,3,2-dioxaborolan-2-yl)phenyl)propanoate and 4-bromophenyl methyl sulfone, ethyl 2-methyl-2-(4'-(methylsulfonyl)-[1,1'-biphenyl]-4-yl)propanoate was prepared as a white solid. To a stirred solution of this compound (1.03 g, 2.97 mmol) in 1:1:1 (v/v/v) tetrahydrofuran/ethanol/water (18 mL) was added lithium hydroxide monohydrate (0.624 g, 14.9 mmol). After stirring at room temperature overnight, the reaction was heated at reflux for 3 hours, cooled and concentrated. The residue was dissolved in water and washed with diethyl ether. The aqueous layer was treated with 1.0 N hydrochloric acid (20 mL) and extracted with 4:1 (v/v) chloroform/isopropanol. The combined extracts were dried (Na$_2$SO$_4$) and concentrated to afford 2-methyl-2-(4'-(methylsulfonyl)-[1,1'-biphenyl]-4-yl)propanoic acid as an off-white solid (0.954 g, 100%). This compound and quinuclidin-3-ol were reacted according to General Procedure H to generate the title compound as an off-white solid. $^1$H NMR (400 MHz, DMSO-d$_6$) δ 8.02-7.96 (m, 2H), 7.96-7.87 (m, 2H), 7.73-7.42 (m, 5H), 4.56-4.46 (m, 1H), 3.30-3.10 (m, 1H), 3.25 (s, 3H), 3.00-2.52 (m, 5H), 2.03-1.80 (m, 2H), 1.76-1.33 (m, 9H) ppm. $^{13}$C NMR (100 MHz, DMSO-d$_6$) δ 154.3, 148.7, 144.9, 139.4, 136.0, 127.6, 127.3, 126.8, 125.6, 68.8, 54.6, 54.3, 46.5, 45.5, 43.6, 29.3, 24.8, 22.8, 18.4 ppm. Purity: 100%, 100% (210 & 254 nm) UPLCMS; retention time: 0.74 min; (M+H$^+$) 443.

Example 236

1-(3-Ethylquinuclidin-3-yl)-3-(2-(4'-(methylsulfonyl)-[1,1'-biphenyl]-4-yl)propan-2-yl)urea Using General Procedure H and the reaction inputs 2-methyl-2-(4'-(methylsulfonyl)-[1,1'-biphenyl]-4-yl)propanoic acid (prepared as described in Example 235) and Intermediate 2, the title compound was prepared as an off-white solid. $^1$H NMR (400 MHz, DMSO-d$_6$) δ 8.01-7.96 (m, 2H), 7.96-7.90 (m, 2H), 7.70-7.63 (m, 2H), 7.52-7.45 (m, 2H), 6.30 (br s, 1H), 5.86 (br s, 1H), 3.25 (s, 3H), 2.80-2.52 (m, 6H), 1.93-1.74 (m, 3H), 1.71-1.44 (m, 8H), 1.43-1.25 (m, 2H), 0.76 (t, J=7.3 Hz, 3H) ppm. $^{13}$C NMR (100 MHz, DMSO-d$_6$) δ 156.8, 150.0, 145.0, 139.3, 135.7, 127.6, 127.3, 126.6, 125.6, 62.5, 53.8, 53.2, 46.3, 46.1, 43.6, 30.4, 29.8, 27.7, 27.7, 22.3, 22.0, 8.0 ppm. Purity: 100%, 100% (210 & 254 nm) UPLCMS; retention time: 0.76 min; (M+H$^+$) 470.

Example 237

1-(2-(4'-(Methylsulfonyl)-[1,1'-biphenyl]-4-yl)propan-2-yl)-3-(3-propylquinuclidin-3-yl)urea Using General Procedure H and the reaction inputs 2-methyl-2-(4'-(methylsulfonyl)-[1,1'-biphenyl]-4-yl)propanoic acid (prepared as described in Example 235) and Intermediate 17, the title compound was prepared as an off-white solid. $^1$H NMR (400 MHz, DMSO-d$_6$) δ 8.02-7.96 (m, 2H), 7.95-7.88 (m, 2H), 7.68-7.61 (m, 2H), 7.51-7.44 (m, 2H), 6.24 (br s, 1H), 5.76 (br s, 1H), 3.25 (s, 3H), 2.73-2.45 (m, 6H), 1.89-1.83 (m, 1H), 1.83-1.68 (m, 2H), 1.68-1.45 (m, 2H), 1.41-1.14 (m, 4H), 0.86 (t, J=7.2 Hz, 3H) ppm. $^{13}$C NMR (100 MHz, DMSO-d$_6$) δ 156.8, 150.0, 145.0, 139.3, 135.7, 127.6, 127.3, 126.6, 125.6, 63.1, 53.8, 53.2, 46.5, 46.3, 43.6, 37.8, 30.6, 29.6, 28.2, 22.7, 22.3, 16.7, 14.6 ppm. Purity: 100%, 100% (210 & 254 nm) UPLCMS; retention time: 0.81 min; (M+H$^+$) 484.

Example 238

Quinuclidin-3-yl (2-(4'-((cyclopropylmethyl)sulfonyl)-[1,1'-biphenyl]-4-yl)propan-2-yl)carbamate Using General Procedure F and the reaction inputs ethyl 2-methyl-2-(4-(4,4,5,5-tetramethyl-1,3,2-dioxaborolan-2-yl)phenyl)propanoate and 1-bromo-4-((cyclopropylmethyl)sulfonyl)benzene, ethyl 2-(4'-((cyclopropylmethyl)sulfonyl)-[1,1'-biphenyl]-4-yl)-2-methylpropanoate was prepared as an amber gum. To a stirred solution of this compound (1.93 g, 4.99 mmol) in 1:1:1 (v/v/v) tetrahydrofuran/ethanol/water (36 mL) was added lithium hydroxide monohydrate (1.05 g, 25.0 mmol). After stirring at room temperature overnight, the reaction was heated at reflux for 2 hours, cooled and concentrated. The residue was dissolved in water and washed with diethyl ether. The aqueous layer was treated with 1.0 N hydrochloric acid (27 mL) and extracted with ethyl acetate. The combined extracts were dried (Na$_2$SO$_4$) and concentrated to afford 2-(4'-((cyclopropylmethyl)sulfonyl)-[1,1'-biphenyl]-4-yl)-2-methylpropanoic acid as an off-white solid (1.81 g, 100%). This compound and quinuclidin-3-ol were reacted according to General Procedure H to generate the title compound as an off-white solid. $^1$H NMR (400 MHz, DMSO-d$_6$) δ 8.01-7.85 (m, 4H), 7.71 (d, J=8.1 Hz, 2H), 7.65-7.33 (m, 3H), 4.49-4.36 (m, 1H), 3.29 (d, J=7.1 Hz, 2H), 3.11-2.24 (m, 6H), 2.10-1.15 (m, 11H), 0.97-0.78 (m, 1H), 0.53-0.41 (m, 2H), 0.20-0.08 (m, 2H) ppm. $^{13}$C NMR (100 MHz, DMSO-d$_6$) δ 154.5, 148.9, 144.9, 137.9, 135.9, 128.6, 127.1, 126.8, 125.5, 70.1, 59.4, 55.4, 54.2, 46.9, 45.9, 29.3, 25.2, 24.1, 19.2, 4.6, 3.8 ppm. Purity: 100%, 100% (210 & 254 nm) UPLCMS; retention time: 0.85 min; (M+H$^+$) 483.

Example 239

1-(2-(4'-((Cyclopropylmethyl)sulfonyl)-[1,1'-biphenyl]-4-yl)propan-2-yl)-3-(3-ethylquinuclidin-3-yl) urea Using General Procedure H and the reaction inputs 2-(4'-((cyclopropylmethyl)sulfonyl)-[1,1'-biphenyl]-4-yl)-2-methylpropanoic acid (prepared as described in Example 238) and Intermediate 2, the title compound was prepared as a white solid. $^1$H NMR (400 MHz, DMSO-d$_6$) δ 7.99-7.89 (m, 4H), 7.68 (d, J=8.6 Hz, 2H), 7.48 (d, J=8.4 Hz, 2H), 6.26 (s, 1H), 5.79 (s, 1H), 3.29 (d, J=7.1 Hz, 2H), 2.74-2.48 (m, 6H), 1.92-1.73 (m, 3H), 1.71-1.47 (m, 8H), 1.41-1.21 (m, 2H), 0.93-0.81 (m, 1H), 0.76 (t, J=7.3 Hz, 3H), 0.51-0.42 (m, 2H), 0.18-0.10 (m, 2H) ppm. $^{13}$C NMR (100 MHz, DMSO-d$_6$) δ 156.7, 150.1, 144.9, 137.8, 135.6, 128.6, 127.1, 126.6, 125.6, 62.7, 59.4, 53.8, 53.2, 46.4, 46.2, 30.4, 27.8, 27.7, 22.5, 22.2, 8.0, 4.6, 3.8 ppm. Purity: 100%, 98.8% (210 & 254 nm) UPLCMS; retention time: 0.87 min; (M+H$^+$) 510.

Example 240

1-(2-(4'-((Cyclopropylmethyl)sulfonyl)-[1,1'-biphenyl]-4-yl)propan-2-yl)-3-(3-methylquinuclidin-3-yl) urea Using General Procedure H and the reaction inputs 2-(4'-((cyclopropylmethyl)sulfonyl)-[1,1'-biphenyl]-4-yl)-2-methylpropanoic acid (prepared as described in Example 238) and Intermediate 1, the title compound was prepared as a white solid. $^1$H NMR (400 MHz, DMSO-d$_6$) δ 7.98-7.90 (m, 4H), 7.69 (d, J=8.5 Hz, 2H), 7.48 (d, J=8.2 Hz, 2H), 6.24 (s, 1H), 5.82 (s, 1H), 3.29 (d, J=7.1 Hz, 2H), 2.74-2.51 (m, 6H), 1.92-1.74 (m, 2H), 1.67-1.47 (m, 7H), 1.44-1.20 (m, 5H), 0.93-0.82 (m, 1H), 0.51-0.42 (m, 2H), 0.18-0.10 (m, 2H) ppm. $^{13}$C NMR (100 MHz, DMSO-d$_6$) δ 156.9, 150.0, 144.9, 137.8, 135.6, 128.6, 127.1, 126.6, 125.6, 63.4, 59.4, 53.9, 50.7, 46.1, 46.0, 30.4, 30.3, 29.9, 25.1, 22.9, 22.2, 4.6, 3.8 ppm. Purity: 100%, 98.7% (210 & 254 nm) UPLCMS; retention time: 0.84 min; (M+H$^+$) 496.

Example 241

1-Azabicyclo[3.2.2]nonan-4-yl (2-(4'-((cyclopropylmethyl)sulfonyl)-[1,1'-biphenyl]-4-yl)propan-2-yl) carbamate Using General Procedure H and the reaction inputs 2-(4'-((cyclopropylmethyl)sulfonyl)-[1,1'-biphenyl]-4-yl)-2-methylpropanoic acid (prepared as described in Example 238) and Intermediate 3, the title compound was prepared as a beige solid. $^1$H NMR (400 MHz, DMSO-d$_6$) δ 8.00-7.87 (m, 4H), 7.70 (d, J=8.1 Hz, 2H), 7.53 (br s, 1H), 7.46 (d, J=7.9 Hz, 2H), 4.65-4.56 (m, 1H), 3.29 (d, J=7.1 Hz, 2H), 3.01-2.41 (m, 6H), 1.99-1.31 (m, 13H), 0.94-0.80 (m, 1H), 0.51-0.41 (m, 2H), 0.17-0.10 (m, 2H) ppm. $^{13}$C NMR (100 MHz, DMSO-d$_6$) δ 154.2, 149.0, 144.9, 137.8, 135.9, 128.6, 127.1, 126.7, 125.6, 77.1, 59.3, 54.2, 47.7, 44.6, 40.1, 33.5, 30.6, 29.5, 24.7, 22.1, 4.6, 3.8 ppm. Purity: 100%, 100% (210 & 254 nm) UPLCMS; retention time: 0.86 min; (M+H$^+$) 497.

Example 242

Quinuclidin-3-yl (2-(4'-((3-methoxypropyl)sulfonyl)-[1,1'-biphenyl]-4-yl)propan-2-yl)carbamate Using General Procedure F and the reaction inputs ethyl 2-methyl-2-(4-(4,4,5,5-tetramethyl-1,3,2-dioxaborolan-2-yl)phenyl)propanoate and 1-bromo-4-((3-methoxypropyl)sulfonyl)benzene, ethyl 2-(4'-((3-methoxypropyl)sulfonyl)-[1,1'-biphenyl]-4-yl)-2-methylpropanoate was prepared as a yellow oil. To a stirred solution of this compound (1.43 g, 3.54 mmol) in 1:1:1 (v/v/v) tetrahydrofuran/ethanol/water (20 mL) was added lithium hydroxide (0.302 g, 12.6 mmol). After stirring at 50° C. overnight, the reaction was cooled and concentrated. The residue was dissolved in water and washed with diethyl ether. The aqueous layer was treated with 1.0 N hydrochloric acid (20 mL) and extracted with ethyl acetate. The combined extracts were dried (Na$_2$SO$_4$) and concentrated to afford 2-(4'-((3-methoxypropyl)sulfonyl)-[1,1'-biphenyl]-4-yl)-2-methylpropanoic acid as a white solid (1.12 g, 84%). This compound and quinuclidin-3-ol were reacted according to General Procedure H to generate the title compound as a white solid. $^1$H NMR (400 MHz, DMSO-d$_6$) δ 8.01-7.85 (m, 4H), 7.77 (m, 5H), 4.50-4.36 (m, 1H), 3.42-3.25 (m, 4H), 3.17 (s, 3H), 3.11-2.25 (m, 6H), 2.11-1.70 (m, 4H), 1.70-1.16 (m, 9H) ppm. $^{13}$C NMR (100 MHz, DMSO-d$_6$) δ 154.5, 148.9, 145.1, 137.4, 135.9, 128.3, 127.4, 126.8, 125.6, 69.9, 69.4, 57.8, 55.3, 54.2, 52.0, 46.9, 45.9, 29.3, 25.2, 24.1, 22.8, 19.1 ppm. Purity: LCMS 99.9%, 99.9% (210 & 254 nm) UPLCMS; retention time: 0.81 min; (M+H$^+$) 501.5.

Example 243

1-(3-Ethylquinuclidin-3-yl)-3-(2-(4'-((3-methoxypropyl)sulfonyl)-[1,1'-biphenyl]-4-yl)propan-2-yl) urea Using General Procedure H and the reaction inputs 2-methyl-2-(4'-(methylsulfonyl)-[1,1'-biphenyl]-4-yl) propanoic acid (prepared as described in Example 242) and Intermediate 2, the title compound was prepared as a white solid. $^1$H NMR (400 MHz, DMSO-d$_6$) δ 8.07-7.81 (m, 4H), 7.68 (d, J=8.5 Hz, 2H), 7.49 (d, J=8.5 Hz, 2H), 6.27 (s, 1H), 5.81 (s, 1H), 3.43-3.24 (m, 4H), 3.17 (s, 3H), 2.83-2.54 (m, 6H), 1.92-1.74 (m, 5H), 1.71-1.47 (m, 8H), 1.42-1.24 (m, 2H), 0.76 (t, J=7.3 Hz, 3H) ppm. $^{13}$C NMR (100 MHz, DMSO-d$_6$) δ 156.7, 150.1, 145.1, 137.3, 135.6, 128.3, 127.1, 126.6, 125.6, 69.4, 62.6, 57.8, 53.8, 53.2, 52.1, 46.4, 46.2, 30.4, 29.8, 27.7, 27.7, 22.8, 22.4, 22.1, 8.0 ppm. Purity: 99.9%, 99.9% (210 & 254 nm) UPLCMS; retention time: 0.83 min; (M+H$^+$) 528.6.

Example 244

1-(2-(4'-((3-Methoxypropyl)sulfonyl)-[1,1'-biphenyl]-4-yl)propan-2-yl)-3-(3-propylquinuclidin-3-yl)urea Using General Procedure H and the reaction inputs 2-methyl-2-(4'-(methylsulfonyl)-[1,1'-biphenyl]-4-yl)propanoic acid (prepared as described in Example 242) and Intermediate 17, the title compound was prepared as a white solid. $^1$H NMR (400 MHz, DMSO-d$_6$) δ 8.12-7.86 (m, 4H), 7.66 (d, J=8.1 Hz, 2H), 7.48 (d, J=8.3 Hz, 2H), 6.53 (br s, 1H), 6.33 (br s, 1H), 3.40-3.27 (m, 4H), 3.17 (s, 3H), 3.10-2.66 (m, 6H), 2.03-1.90 (m, 2H), 1.90-1.36 (m, 13H), 1.32-1.13 (m, 2H), 0.87 (t, J=7.2 Hz, 3H) ppm. $^{13}$C NMR (100 MHz, DMSO-d$_6$) δ 156.9, 150.0, 145.2, 137.3, 135.6, 128.4, 127.3, 126.6, 125.6, 69.4, 60.6, 57.8, 53.9, 52.8, 52.0, 45.7, 45.4, 37.5, 30.8, 29.3, 27.4, 22.8, 20.6, 20.3, 16.5, 14.4 ppm. Purity: 99.9%, 99.9% (210 & 254 nm) UPLCMS; retention time: 0.87 min; (M+H$^+$) 542.6.

Example 245

Quinuclidin-3-yl (2-(4'-((3,3-dimethylbutyl)sulfonyl)-[1,1'-biphenyl]-4-yl)propan-2-yl)carbamate To a stirred solution of 4-bromothiophenol (6.36 g, 33.6 mmol) in N,N-dimethylformamide (70 mL) was added sodium hydride (60% dispersion in mineral oil; 1.48 g, 37.0 mmol). After 40 minutes, 1-chloro-3,3-dimethylbutane (5.6 mL, 40.3 mmol) was added and the mixture was left stirring overnight. The reaction was then concentrated and the residue was taken up in ethyl acetate. The solution was washed with water, dried (Na$_2$SO$_4$) and concentrated. The crude product was purified by flash chromatography over silica using a hexane/ethyl acetate gradient to afford (4-bromophenyl)(3,3-dimethylbutyl)sulfane as a colorless oil (8.71 g, 95%). To a stirred solution of this compound (8.69 g, 31.8 mmol) in methylene chloride (130 mL), was added, portion wise over 20 minutes, 3-chloroperbenzoic acid (77%; 14.97 g, 66.80 mmol). The resulting suspension was stirred at room temperature overnight and then washed with aqueous 0.5 N sodium hydroxide solution. The organic layer was dried (Na$_2$SO$_4$) and concentrated to afford 1-bromo-4-((3,3-dimethylbutyl)sulfonyl)benzene, which was used without purification, as a white solid (9.82 g, 100%). This compound and ethyl 2-methyl-2-(4-(4,4,5,5-tetramethyl-1,3,2-dioxaborolan-2-yl)phenyl)propanoate were reacted according to General Procedure F to generate ethyl 2-(4'-((3,3-dimethylbutyl)sulfonyl)-[1,1'-biphenyl]-4-yl)-2-methylpropanoate. To a stirred solution of this intermediate (2.17 g, 5.21 mmol) in 1:1:1 (v/v/v) tetrahydrofuran/ethanol/water (36 mL) was added lithium hydroxide monohydrate (1.09 g, 26.0 mmol). After stirring at room temperature overnight, the reaction was heated at reflux for 2.5 hours, cooled and concentrated. The residue was dissolved in water and washed with diethyl ether. The aqueous layer was treated with 1.0 N hydrochloric acid (30 mL) and extracted with ethyl acetate. The combined extracts were dried (Na$_2$SO$_4$) and concentrated to afford 2-(4'-((3,3-dimethylbutyl)sulfonyl)-[1,1'-biphenyl]-4-yl)-2-methylpropanoic acid as a white solid (1.94 g, 96%). This compound and quinuclidin-3-ol were reacted according to General Procedure H to generate the title compound as a white solid. $^1$H NMR (400 MHz, DMSO-d$_6$) δ 8.00 (m, 4H), 7.71 (d, J=8.3 Hz, 2H), 7.63-7.39 (m, 3H), 4.46-4.39 (m, 1H), 3.33-3.24 (m, 2H), 3.10-2.31 (m, 6H), 2.05-1.72 (m, 2H), 1.67-1.24 (m, 11H), 0.84 (s, 9H) ppm. $^{13}$C NMR (100 MHz, DMSO-d$_6$) δ 154.5, 149.0, 144.9, 137.6, 135.9, 128.3, 127.3, 126.8, 125.6, 70.0, 55.4, 54.2, 51.5, 46.9, 45.9, 35.3, 29.8, 29.3, 28.7, 25.3, 24.2, 19.2 ppm. Purity: 100%, 100% (210 & 254 nm) UPLCMS; retention time: 1.02 min; (M+H$^+$) 513.

Example 246

1-(2-(4'-((3,3-Dimethylbutyl)sulfonyl)-[1,1'-biphenyl]-4-yl)propan-2-yl)-3-(3-methylquinuclidin-3-yl)urea Using General Procedure H and the reaction inputs 2-(4'-((3,3-dimethylbutyl)sulfonyl)-[1,1'-biphenyl]-4-yl)-2-methylpropanoic acid (prepared as described in Example 245) and Intermediate 1, the title compound was prepared as a white solid. $^1$H NMR (400 MHz, DMSO-d$_6$) δ 8.00-7.91 (m, 4H), 7.69 (d, J=8.4 Hz, 2H), 7.48 (d, J=8.4 Hz, 2H), 6.23 (s, 1H), 5.81 (s, 1H), 3.32-3.24 (m, 2H), 2.72-2.52 (m, 6H), 1.91-1.74 (m, 2H), 1.43-1.44 (m, 9H), 1.43-1.22 (m, 5H), 0.84 (s, 9H) ppm. $^{13}$C NMR (100 MHz, DMSO-d$_6$) δ 156.9, 150.1, 145.0, 137.5, 135.6, 128.3, 127.2, 126.6, 125.6, 63.5, 53.9, 51.5, 50.7, 46.2, 46.0, 35.3, 30.4, 30.3, 29.9, 29.8, 28.7, 25.1, 22.9, 22.3 ppm. Purity: 100%, 100% (210 & 254 nm) UPLCMS; retention time: 1.00 min; (M+H$^+$) 526.

Example 247

1-(2-(4'-((3,3-Dimethylbutyl)sulfonyl)-[1,1'-biphenyl]-4-yl)propan-2-yl)-3-(3-ethylquinuclidin-3-yl)urea Using General Procedure H and the reaction inputs 2-(4'-((3,3-dimethylbutyl)sulfonyl)-[1,1'-biphenyl]-4-yl)-2-methylpropanoic acid (prepared as described in Example 245) and Intermediate 2, the title compound was prepared as a white solid. $^1$H NMR (400 MHz, DMSO-d$_6$) δ 8.00-7.90 (m, 4H), 7.68 (d, J=8.5 Hz, 2H), 7.48 (d, J=8.5 Hz, 2H), 6.25 (s, 1H), 5.78 (s, 1H), 3.33-3.24 (m, 2H), 2.75-2.50 (m, 6H), 1.92-1.73 (m, 3H), 1.71-1.42 (m, 10H), 1.42-1.20 (m, 2H), 0.84 (s, 9H), 0.76 (t, J=7.2 Hz, 3H) ppm. $^{13}$C NMR (100 MHz, DMSO-d$_6$) δ 156.7, 150.1, 145.0, 137.5, 135.6, 128.3, 127.2, 126.6, 125.6, 62.8, 53.8, 53.2, 51.5, 46.4, 46.2, 35.3, 30.4, 29.8, 29.8, 28.7, 27.8, 27.7, 22.5, 22.2, 8.0 ppm. Purity: 100%, 98.6% (210 & 254 nm) UPLCMS; retention time: 1.03 min; (M+H$^+$) 540.

Example 248

1-(2-(4'-((3,3-Dimethylbutyl)sulfonyl)-[1,1'-biphenyl]-4-yl)propan-2-yl)-3-(4-methyl-1-azabicyclo[3.2.2]nonan-4-yl)urea Using General Procedure H and the reaction inputs 2-(4'-((3,3-dimethylbutyl)sulfonyl)-[1,1'-biphenyl]-4-yl)-2-methylpropanoic acid (prepared as described in Example 245) and Intermediate 5, the title compound was prepared as a white solid. $^1$H NMR (400 MHz, DMSO-d$_6$) δ 7.99-7.90 (m, 4H), 7.68 (d, J=8.4 Hz, 2H), 7.49 (d, J=8.4 Hz, 2H), 6.31 (s, 1H), 5.79 (s, 1H), 3.33-3.23 (m, 2H), 2.93-2.65 (m, 6H), 2.12-2.05 (m, 1H), 1.85-1.35 (m, 13H), 1.34-1.19 (m, 4H), 0.85 (s, 9H) ppm. $^{13}$C NMR (100 MHz, DMSO-d$_6$) δ 156.8, 150.1, 145.0, 137.5, 135.6, 128.3, 127.4, 126.6, 125.7, 57.2, 53.8, 52.7, 51.5, 48.0, 45.0, 39.1, 36.2, 35.3, 30.4, 29.8, 29.7, 28.7, 26.2, 24.3, 23.8 ppm. Purity: 100%, 100% (210 & 254 nm) UPLCMS; retention time: 1.01 min; (M+H$^+$) 540.

Example 249

Quinuclidin-3-yl (2-(4'-(((1-(methoxymethyl)cyclopropyl)methyl)sulfonyl)-[1,1'-biphenyl]-4-yl)propan-2-yl)carbamate To a stirred and cooled (0° C.) solution of (1-(methoxymethyl)cyclopropyl)methanol (3.65 g, 31.4 mmol) and triethylamine (5.5 mL, 39.5 mmol) in methylene chloride (100 mL) was added, dropwise, methanesulfonyl chloride (2.7 mL, 34.7 mmol). After 2 hours, the reaction solution was washed with an aqueous sodium bicarbonate solution. The organic layer was combined with methylene chloride back extracts of the aqueous layer, dried ($Na_2SO_4$) and concentrated. The crude (1-(methoxymethyl)cyclopropyl)methyl methanesulfonate, which was used without purification, was afforded as a pale amber oil (6.15 g, 100%). To a stirred solution of 4-bromothiophenol (4.98 g, 26.3 mmol) in N,N-dimethylformamide (60 mL) was added sodium hydride (60% dispersion in mineral oil; 1.21 g, 31.6 mmol). After 1 hour, a solution of the mesylate intermediate in N,N-dimethylformamide (20 mL) was added and the mixture was stirred for 3 days at room temperature. The reaction was then concentrated and the residue was taken up in ethyl acetate, washed with water, dried ($Na_2SO_4$) and concentrated. The resulting faint amber oil was purified by flash chromatography over silica using a hexane/ethyl acetate gradient to afford (4-bromophenyl)((1-(methoxymethyl)cyclopropyl)methyl)sulfane as a colorless oil (6.98 g, 92%). To a stirred solution of this material (6.97 g, 24.3 mmol) in methylene chloride (100 mL) was added, portion wise, 3-chloroperbenzoic acid (77%; 11.42 g, 50.96 mmol). The resulting suspension was stirred at room temperature overnight and then washed with aqueous 0.5 N sodium hydroxide solution. The organic layer was dried ($Na_2SO_4$) and concentrated to afford 1-bromo-4-(((1-(methoxymethyl)cyclopropyl)methyl)sulfonyl)benzene, which was used without purification, as a white solid (9.82 g, 100%). This compound and ethyl 2-methyl-2-(4-(4,4,5,5-tetramethyl-1,3,2-dioxaborolan-2-yl)phenyl)propanoate were reacted according to General Procedure F to generate ethyl 2-(4'-(((1-(methoxymethyl)cyclopropyl)methyl)sulfonyl)-[1,1'-biphenyl]-4-yl)-2-methylpropanoate. To a stirred solution of this intermediate (3.54 g, 9.11 mmol) in 1:1:1 (v/v/v) tetrahydrofuran/ethanol/water (60 mL) was added lithium hydroxide monohydrate (1.34 g, 31.9 mmol). After heating at reflux overnight, the reaction was cooled and concentrated. The residue was dissolved in water and washed with diethyl ether. The aqueous layer was treated with 1.0 N hydrochloric acid (40 mL) and extracted with ethyl acetate. The combined extracts were dried ($Na_2SO_4$) and concentrated to afford 2-(4'-(((1-(methoxymethyl)cyclopropyl)methyl)sulfonyl)-[1,1'-biphenyl]-4-yl)-2-methylpropanoic acid as a white solid (3.21 g, 88%). This compound and quinuclidin-3-ol were reacted according to General Procedure H to generate the title compound as an off-white solid. $^1$H NMR (400 MHz, DMSO-$d_6$) δ 8.02-7.85 (m, 4H), 7.71 (d, J=8.0 Hz, 2H), 7.65-7.38 (m, 3H), 4.50-4.36 (m, 1H), 3.40 (s, 2H), 3.18 (s, 2H), 3.13 (s, 3H), 3.13-2.24 (m, 6H), 2.09-1.20 (m, 11H), 0.53-0.37 (m, 4H) ppm. $^{13}$C NMR (100 MHz, DMSO-$d_6$) δ 154.5, 149.0, 145.0, 138.7, 135.8, 128.4, 127.2, 126.8, 125.6, 75.3, 69.9, 58.8, 57.8, 55.3, 54.2, 46.9, 45.9, 29.3, 25.2, 24.1, 19.1, 15.8, 9.5 ppm. Purity: 100%, 100% (210 & 254 nm) UPLCMS; retention time: 0.85 min; (M+H$^+$) 527.

Example 250

1-(3-Ethylquinuclidin-3-yl)-3-(2-(4'-(((1-(methoxymethyl)cyclopropyl)methyl)sulfonyl)-[1,1'-biphenyl]-4-yl)propan-2-yl)urea Using General Procedure H and the reaction inputs 2-(4'-(((1-(methoxymethyl)cyclopropyl)methyl)sulfonyl)-[1,1'-biphenyl]-4-yl)-2-methylpropanoic acid (prepared as described in Example 249) and Intermediate 2, the title compound was prepared as a white solid. $^1$H NMR (400 MHz, DMSO-$d_6$) δ 7.98-7.90 (m, 4H), 7.68 (d, J=8.4 Hz, 2H), 7.48 (d, J=8.4 Hz, 2H), 6.25 (s, 1H), 5.77 (s, 1H), 3.39 (s, 2H), 3.18 (s, 2H), 3.13 (s, 3H), 2.73-2.47 (m, 6H), 1.92-1.72 (m, 3H), 1.71-1.46 (m, 8H), 1.41-1.20 (m, 2H), 0.76 (t, J=7.2 Hz, 3H), 0.51-0.39 (m, 4H) ppm. $^{13}$C NMR (100 MHz, DMSO-$d_6$) δ 156.7, 150.1, 145.0, 138.7, 135.5, 128.4, 127.2, 126.6, 125.6, 75.3, 62.8, 58.9, 57.8, 53.8, 53.3, 46.5, 46.3, 30.4, 29.8, 27.8, 27.7, 22.6, 22.3, 15.8, 9.5, 8.0 ppm. Purity: 97.6%, 100% (210 & 254 nm) UPLCMS; retention time: 0.86 min; (M+H$^+$) 554.

Example 251

1-(2-(4'-(((1-(Methoxymethyl)cyclopropyl)methyl)sulfonyl)-[1,1'-biphenyl]-4-yl)propan-2-yl)-3-(3-propylquinuclidin-3-yl)urea Using General Procedure H and the reaction inputs 2-(4'-(((1-(methoxymethyl)cyclopropyl)methyl)sulfonyl)-[1,1'-biphenyl]-4-yl)-2-methylpropanoic acid (prepared as described in Example 249) and Intermediate 17, the title compound was prepared as a white solid. $^1$H NMR (400 MHz, DMSO-$d_6$) δ 7.98-7.89 (m, 4H), 7.66 (d, J=8.4 Hz, 2H), 7.48 (d, J=8.4 Hz, 2H), 6.24 (s, 1H), 5.76 (s, 1H), 3.39 (s, 2H), 3.17 (s, 2H), 3.13 (s, 3H), 2.74-2.46 (m, 6H), 1.90-1.83 (m, 1H), 1.83-1.68 (m, 2H), 1.68-1.43 (m, 8H), 1.40-1.13 (m, 4H), 0.85 (t, J=7.1 Hz, 3H), 0.52-0.38 (m, 4H) ppm. $^{13}$C NMR (100 MHz, DMSO-$d_6$) δ 156.8, 150.1, 145.1, 138.7, 135.6, 128.4, 127.2, 126.6, 125.6, 75.3, 63.1, 58.9, 57.8, 53.8, 53.2, 46.4, 46.3, 37.8, 30.6, 29.6, 28.2, 22.7, 22.3, 16.7, 15.8, 14.5, 9.5 ppm. Purity: 100%, 100% (210 & 254 nm) UPLCMS; retention time: 0.90 min; (M+H$^+$) 568.

Example 252

Quinuclidin-3-yl (2-(4'-(methylcarbamoyl)-[1,1'-biphenyl]-4-yl)propan-2-yl)carbamate To stirred solution of 4-bromobenzoic acid (6.00 g, 29.8 mmol) in methylene chloride (80 mL) was added N-(3-dimethylaminopropyl)-N'-ethylcarbodiimide hydrochloride (6.30 g, 32.9 mmol), 4-(dimethylamino)pyridine (7.70 g, 63.0 mmol) and methylamine hydrochloride (2.23 g, 33.0 mmol). The mixture was stirred overnight and then washed with 1.0 N hydrochloric acid, dried ($Na_2SO_4$) and concentrated. The crude material was purified by flash chromatography over silica using a hexane/ethyl acetate eluant to afford 4-bromo-N-methylbenzamide as a white solid (5.80 g, 90%). To a stirred solution of this compound (4.00 g, 18.9 mmol) in 1,4-dioxane (10 mL) was added bis(pinacolato)diboron (11.9 g, 46.8 mmol), potassium acetate (5.50 g, 56.1 mmol) and [1,1'-bis(diphenylphosphino)ferrocene]-dichloropalladium(II) (0.410 g, 0.560 mmol). The mixture was heated at 90° C. overnight, filtered and concentrated. The residue was purified by flash chromatography over silica using a hexane/ethyl acetate eluant to afford N-methyl-4-(4, 4,5,5-tetramethyl-1,3,2-dioxaborolan-2-yl)benzamide as a white solid (4.50 g, 91%). This compound and ethyl 2-(4-bromophenyl)-2-methylpropanoate were reacted according to General Procedure F to generate ethyl 2-methyl-2-(4'-50 (methylcarbamoyl)-[1,1'-biphenyl]-4-yl)propanoate as an off-white solid. To a stirred solution of this intermediate (1.00 g, 3.07 mmol) in a mixture of tetrahydrofuran (4 mL), methanol (8 mL) and water (3 mL) was added solid sodium hydroxide (0.640 g, 16.0 mmol). After stirring at room temperature overnight, the reaction was concentrated and taken up in water. The solution was made acidic (pH~6) with 1 N hydrochloric acid and extracted with ethyl acetate. The combined extracts were washed with brine, dried ($Na_2SO_4$) and concentrated to afford 2-methyl-2-(4'-(methylcarbamoyl)-[1,1'-biphenyl]-4-yl)propanoic acid as a white solid (0.950 g, 100%). This compound was used without purification and reacted with quinuclidin-3-ol according to General Procedure I to generate the title compound as an off-white solid. $^1$H NMR (500 MHz, DMSO-$d_6$) δ 8.47 (q, J=4.5 Hz, 1H), 7.91 (d, J=8.5 Hz, 2H), 7.74 (d, J=6.5 Hz, 2H), 7.67-7.65 (d, J=8.5 Hz, 2H), 7.60 (s, 1H), 7.44 (d, J=6.5 Hz, 2H), 4.43 (m, 1H), 3.76 (m, 1H), 2.81-2.63 (m, 7H), 2.47-2.36 (m, 1H), 1.85 (m, 2H), 1.56-1.34 (m, 9H) ppm. $^{13}$C NMR (125 MHz, $CD_3OD$) δ 170.4, 156.9, 149.1, 145.3, 139.2, 134.1, 128.8, 127.9, 126.7, 71.4, 56.1, 55.9, 48.0, 47.0, 30.0, 29.9, 27.0, 26.5, 24.6, 20.0 ppm. Purity: 100% (214 & 254 nm) LCMS; retention time: 1.72 min; (M+H$^+$) 422.3.

Example 253

N-Methyl-4'-(2-(3-(3-methylquinuclidin-3-yl)ureido) propan-2-yl)-[1,1'-biphenyl]-4-carboxamide Using General Procedure I and the reaction inputs 2-methyl-2-(4'-(methylcarbamoyl)-[1,1'-biphenyl]-4-yl)propanoic acid (prepared as described in Example 252) and Intermediate 1, the title compound was prepared. $^1$H NMR (500 MHz, DMSO-$d_6$) δ 8.47 (q, J=4.5 Hz, 1H), 7.90 (d, J=9.0 Hz, 2H), 7.74 (d, J=9.0 Hz, 2H), 7.64 (d, J=8.0 Hz, 2H), 7.44 (d, J=9.0 Hz, 2H), 6.20 (s, 1H), 5.79 (s, 1H), 2.80 (d, J=4.5 Hz, 3H), 2.67-2.52 (m, 6H), 1.88-1.78 (m, 2H), 1.61-1.25 (m, 12H) ppm. $^{13}$C NMR (125 MHz, DMSO-$d_6$) δ 166.3, 156.9, 149.2, 142.4, 136.5, 133.0, 127.7, 126.3, 126.2, 125.4, 63.5, 53.8, 50.7, 46.2, 46.1, 30.4, 29.9, 26.3, 25.1, 223.0, 22.3 ppm. Purity: >95% (214 & 254 nm) LCMS; retention time: 1.32 min; (M+H$^+$) 435.3.

Example 254

1-Azabicyclo[3.2.2]nonan-4-yl (2-(4'-(methylcarbamoyl)-[1,1'-biphenyl]-4-yl)propan-2-yl)carbamate Using General Procedure I and the reaction inputs 2-methyl-2-(4'-(methylcarbamoyl)-[1,1'-biphenyl]-4-yl)propanoic acid (prepared as described in Example 252) and Intermediate 3, the title compound was prepared. $^1$H NMR (500 MHz, CDCl$_3$) δ 7.83-7.81 (d, J=8.5 Hz, 2H), 7.64-7.62 (d, J=8.5 Hz, 2H), 7.58-7.56 (d, J=8.0 Hz, 2H), 750-7.48 (d, J=8.0 Hz, 2H), 6.22 (s, 1H), 5.15 (s, 1H), 4.78-4.77 (m, 1H), 3.16-2.62 (m, 9H), 2.07-1.55 (m, 13H) ppm. $^{13}$C NMR (125 MHz, CDCl$_3$) δ 168.0, 154.2, 147.0, 143.7, 138.2, 133.2, 127.4, 127.1, 127.0, 125.4, 78.1, 55.0, 51.6, 48.0, 46.3, 33.6, 30.4, 29.6, 26.9, 26.4, 24.6, 22.0 ppm. Purity: >97% (214 & 254 nm) LCMS; retention time: 1.70 min; (M+H$^+$) 436.3.

Example 255

N-Methyl-4'-(2-(3-(4-methyl-1-aza-bicyclo[3.2.2] nonan-4-yl)ureido)propan-2-yl)biphenyl-4-carboxamide Using General Procedure I and the reaction inputs 2-methyl-2-(4'-(methylcarbamoyl)-[1,1'-biphenyl]-4-yl)propanoic acid (prepared as described in Example 252) and Intermediate 5, the title compound was prepared. $^1$H NMR (500 MHz, DMSO-$d_6$) δ 8.48-8.47 (q, J=4.5 Hz, 1H), 7.91-7.90 (d, J=8.5 Hz, 2H), 7.75-7.73 (d, J=8.5 Hz, 2H), 7.64-7.62 (d, J=8.5 Hz, 2H), 7.46-7.44 (d, J=9.0 Hz, 2H), 6.26 (s, 1H), 5.75 (s, 1H), 2.87-2.69 (m, 9H), 2.07 (m, 1H), 1.79-1.25 (m, 15H) ppm. $^{13}$C NMR (125 MHz, CDCl$_3$) δ 168.0, 156.8, 146.3, 143.2, 139.2, 133.5, 127.7, 127.3, 127.1, 126.2, 58.7, 54.6, 52.6, 48.3, 45.2, 39.5, 36.5, 31.2, 29.6, 26.9, 26.1, 24.3, 23.8 ppm. Purity: 96.8%, 95.1% (214 nm & 254 nm) UPLCMS; retention time: 1.17 min; (M+H$^+$) 449.3.

Example 256

N-(2-(4'-(Methylcarbamoyl)biphenyl-4-yl)propan-2-yl)-1,4-diazabicyclo[3.2.2]nonane-4-carboxamide Using General Procedure I and the reaction inputs 2-methyl-2-(4'-(methylcarbamoyl)-[1,1'-biphenyl]-4-yl)propanoic acid (prepared as described in Example 252) and Intermediate 6, the title compound was prepared. $^1$H NMR (500 MHz, CDCl$_3$) δ 7.81-7.80 (d, J=8.5 Hz, 2H), 7.63-7.62 (d, J=8.0 Hz, 2H), 7.58-7.55 (d, J=8.0 Hz, 2H), 7.48-7.46 (d, J=8.5 Hz, 2H), 6.28-6.27 (q, J=5.0 Hz, 1H), 4.78 (s, 1H), 4.02 (m, 1H), 3.63 (t, J=5.5 Hz, 2H), 3.14-3.08 (m, 2H), 3.03-2.98 (m, 7H), 2.07-2.01 (m, 2H), 1.80-1.70 (m, 8H) ppm. $^{13}$C NMR (125 MHz, CDCl$_3$) δ 168.1, 155.6, 148.1, 143.9, 137.9, 133.1, 127.3, 127.1, 127.0, 125.3, 57.6, 55.3, 48.1, 46.2, 41.3, 30.2, 27.4, 26.9 ppm. Purity: >99% (214 & 254 nm) LCMS; retention time: 1.13 min; (M+H$^+$) 421.1.

Example 257

Quinuclidin-3-yl 2-(4'-(dimethylcarbamoyl)biphenyl-4-yl)propan-2-ylcarbamate

Exchanging methylamine hydrochloride for dimethylamine hydrochloride, the reaction sequence outlined in Example 252 was used to prepare 2-(4'-(dimethylcarbamoyl)-[1,1'-biphenyl]-4-yl)-2-methylpropanoic acid. This intermediate and quinuclidin-3-ol were reacted according to General Procedure I to generate the title compound. $^1$H NMR (500 MHz, DMSO-$d_6$) δ 7.70 (d, J=7.0 Hz, 2H), 7.63 (d, J=8.0 Hz, 2H), 7.59 (s, 1H), 7.48 (d, J=8.0 Hz, 2H), 7.44 (d, J=7.0 Hz, 2H), 4.42 (m, 1H), 3.00-2.96 (m, 7H), 2.72-2.55 (m, 3H), 2.46-1.98 (m, 2H), 1.84-1.75 (m, 2H), 1.56-1.24 (m, 9H) ppm. $^{13}$C NMR (125 MHz, CDCl$_3$) δ 171.5, 154.5, 146.6, 142.0, 138.6, 135.0, 127.7, 127.1, 126.9, 125.4, 71.0, 55.5, 55.1, 47.3, 46.4, 39.7, 35.4, 29.3, 25.3, 24.5, 19.4 ppm. Purity: >99% (214 & 254 nm) LCMS; retention time: 1.79 min; (M+H$^+$) 436.3.

Example 258

N,N-Dimethyl-4'-(2-(3-(3-methylquinuclidin-3-yl) ureido)propan-2-yl)biphenyl-4-carboxamide Using General Procedure I and the reaction inputs 2-(4'-(dimethylcarbamoyl)-[1,1'-biphenyl]-4-yl)-2-methylpropanoic acid (prepared as described in Example 257) and Intermediate 1, the title compound was prepared. $^1$H NMR (500 MHz, CDCl$_3$) δ 7.60-7.59 (m, 6H), 7.50-7.49 (d, J=8.5 Hz, 2H), 4.88 (br s, 1H), 4.33 (br s, 1H), 3.14 (s, 3H), 3.04 (s, 3H), 2.73-2.66 (m, 5H), 2.17 (m, 1H), 1.92-1.64 (m, 8H), 1.45-1.22 (m, 6H) ppm. $^{13}$C NMR (125 MHz, CDCl$_3$) δ 171.6, 157.1, 146.7, 141.9, 138.9, 135.0, 127.6, 127.4, 127.0, 125.9, 63.5, 54.5, 52.0, 46.5, 46.2, 39.7, 35.5, 30.6, 30.3, 25.0, 23.0, 22.2 ppm. Purity: >98% (214 & 254 nm) LCMS; retention time: 1.38 min; (M+H$^+$) 449.3.

Example 259

1-Azabicyclo[3.2.2]nonan-4-yl 2-(4'-(dimethylcarbamoyl)biphenyl-4-yl)propan-2-ylcarbamate Using General Procedure I and the reaction inputs 2-(4'-(dimethylcarbamoyl)-[1,1'-biphenyl]-4-yl)-2-methylpropanoic acid (prepared as described in Example 257) and Intermediate 3, the title compound was prepared. $^1$H NMR (500 MHz, CDCl$_3$) δ 7.61-7.59 (d, J=8.0 Hz, 2H), 7.56-7.54 (d, J=8.0 Hz, 2H), 7.49-7.47 (m, 4H), 5.20 (s, 1H), 4.78-4.77 (m, 1H), 3.13-2.72 (m, 12H), 2.28 (m, 1H), 2.05-1.18 (m, 12H) ppm. $^{13}$C NMR (125 MHz, CDCl$_3$) δ 171.5, 154.3, 146.8, 142.1, 138.5, 135.0, 127.7, 127.1, 126.8, 125.4, 78.1, 55.0, 51.7, 48.3, 45.0, 39.6, 35.4, 33.7, 31.0, 30.7, 29.7, 24.9, 22.3 ppm. Purity: 100% (214 & 254 nm) UPLC; retention time: 1.39 min; (M+H$^+$) 450.3.

Example 260

N-(2-(4'-(Dimethylcarbamoyl)biphenyl-4-yl)propan-2-yl)-1,4-diazabicyclo[3.2.2]nonane-4-carboxamide Using General Procedure I and the reaction inputs 2-(4'-(dimethylcarbamoyl)-[1,1'-biphenyl]-4-yl)-2-methylpropanoic acid (prepared as described in Example 257) and Intermediate 6, the title compound was prepared. $^1$H NMR (500 MHz, CDCl$_3$) δ 7.61-7.60 (d, J=8.5 Hz, 2H), 7.56-7.55 (d, J=8.5 Hz, 2H), 7.48-7.46 (m, 4H), 4.78 (s, 1H), 4.04 (m, 1H), 3.64 (t, J=6.0 Hz, 2H), 3.15-2.99 (m, 12H), 2.08-2.03 (m, 2H), 1.81-1.73 (m, 8H) ppm. $^{13}$C NMR (125 MHz, CDCl$_3$) δ 171.6, 155.6, 147.9, 142.2, 138.1, 134.8, 127.6, 127.1, 126.9, 125.3, 57.6, 55.3, 48.0, 46.2, 41.3, 39.7, 35.4, 30.2, 27.4 ppm. Purity: 100% (214 & 254 nm) UPLC; retention time: 1.35 min; (M+H$^+$) 435.4.

Example 261

N,N-Dimethyl-4'-(2-(3-(4-methyl-1-azabicyclo[3.2.2]nonan-4-yl)ureido)propan-2-yl)biphenyl-4-carboxamide Using General Procedure I and the reaction inputs 2-(4'-(dimethylcarbamoyl)-[1,1'-biphenyl]-4-yl)-2-methylpropanoic acid (prepared as described in Example 257) and Intermediate 5, the title compound was prepared. $^1$H NMR (400 MHz, CDCl$_3$) δ 7.62-7.58 (m, 6H), 7.51-7.49 (d, J=8.4 Hz, 2H), 4.74 (s, 1H), 4.07 (s, 1H), 3.14 (s, 3H), 3.05 (s, 3H), 2.91-2.70 (m, 4H), 2.51-2.28 (m, 2H), 2.17-2.17 (m, 1H), 1.84-1.50 (m, 10H), 1.47-1.15 (m, 5H) ppm. $^{13}$C NMR (100 MHz, CDCl$_3$) δ 171.5, 157.0, 146.4, 141.8, 139.2, 135.2, 127.7, 127.5, 127.0, 126.1, 58.6, 54.5, 52.7, 48.2, 45.2, 39.7, 39.5, 36.5, 35.4, 31.1, 29.8, 26.1, 24.3, 23.8 ppm. Purity: >95% (214 & 254 nm) LCMS; retention time: 1.35 min; (M+H$^+$) 463.3.

Example 262

Quinuclidin-3-yl 2-(4'-(piperidine-1-carbonyl)biphenyl-4-yl)propan-2-ylcarbamate Exchanging methylamine hydrochloride for piperidine, the reaction sequence outlined in Example 252 was used to prepare 2-methyl-2-(4'-(piperidine-1-carbonyl)-[1,1'-biphenyl]-4-yl)propanoic acid. This intermediate and quinuclidin-3-ol were reacted according to General Procedure I to generate the title compound. $^1$H NMR (500 MHz, CDCl$_3$) δ 7.52-7.51 (d, J=7.5 Hz, 2H), 7.48-7.47 (d, J=8.0 Hz, 2H), 7.42-7.37 (m, 4H), 5.26 (s, 1H), 4.55 (m, 1H), 3.65 (m, 2H), 3.33 (m, 2H), 3.09-2.33 (m, 6H), 2.19-1.77 (m, 2H), 1.63-1.32 (m, 15H) ppm. $^{13}$C NMR (125 MHz, CDCl$_3$) δ 170.2, 154.6, 146.6, 141.9, 138.6, 135.1, 127.4, 127.1, 126.9, 125.4, 71.0, 55.6, 55.0, 48.9, 47.4, 46.4, 43.2, 29.7, 26.6, 25.6, 25.4, 24.6, 19.5 ppm. Purity: >99% (214 & 254 nm) LCMS; retention time: 1.11 min; (M+H$^+$) 476.3.

Example 263

1-Azabicyclo[3.2.2]nonan-4-yl 2-(4'-(piperidine-1-carbonyl)biphenyl-4-yl)propan-2-ylcarbamate Using General Procedure I and the reaction inputs 2-methyl-2-(4'-(piperidine-1-carbonyl)-[1,1'-biphenyl]-4-yl)propanoic acid (prepared as described in Example 262) and Intermediate 3, the title compound was prepared. $^1$H NMR (500 MHz, CDCl$_3$) δ 7.60-7.58 (d, J=8.0 Hz, 2H), 7.56-7.54 (d, J=8.0 Hz, 2H), 7.49-7.45 (m, 4H), 5.20 (s, 1H), 4.78 (m, 1H), 3.73 (m, 2H), 3.41 (m, 2H), 3.10-2.49 (m, 7H), 2.05-1.36 (m, 18H) ppm. $^{13}$C NMR (125 MHz, CDCl$_3$) δ 170.2, 154.2, 146.7, 141.9, 138.6, 135.1, 127.4, 127.1, 127.0, 125.4, 78.2, 55.0, 51.6, 48.9, 48.2, 44.9, 43.2, 33.6, 30.6, 29.6, 26.6, 25.7, 24.6, 22.1 ppm. Purity: >99% (214 & 254 nm) LCMS; retention time: 1.34 min; (M+H$^+$) 490.2.

Example 264

1-(3-Ethylquinuclidin-3-yl)-3-(2-(4'-(piperidine-1-carbonyl)biphenyl-4-yl)propan-2-yl)urea Using General Procedure I and the reaction inputs 2-methyl-2-(4'-(piperidine-1-carbonyl)-[1,1'-biphenyl]-4-yl)propanoic acid (prepared as described in Example 262) and Intermediate 2, the title compound was prepared. $^1$H NMR (500 MHz, CDCl$_3$) δ 7.50-7.45 (m, 6H), 7.38-7.37 (d, J 7.5 Hz, 2H), 5.12 (s, 1H), 4.26 (s, 1H), 3.66-4.34 (m, 4H), 2.61-2.37 (m, 6H), 1.88-1.10 (m, 19H), 0.59 (t, J 7.5 Hz, 3H) ppm. $^{13}$C NMR (125 MHz, CDCl$_3$) δ 167.2, 155.7, 145.4, 140.7, 138.1, 134.2, 126.5, 126.4, 126.0, 125.0, 62.1, 53.8, 53.4, 45.6, 29.7, 29.2, 27.1, 27.0, 23.6, 21.8, 21.4, 7.0 ppm. Purity: >99% (214 & 254 nm) LCMS; retention time: 1.13 min; (M+H$^+$) 503.4.

Example 265

Quinuclidin-3-yl 2-(4'-(morpholine-4-carbonyl)biphenyl-4-yl)propan-2-ylcarbamate Exchanging methylamine hydrochloride for morpholine, the reaction sequence outlined in Example 252 was used to prepare 2-methyl-2-(4'-(morpholine-4-carbonyl)-[1,1'-biphenyl]-4-yl)propanoic acid. This intermediate and quinuclidin-3-ol were reacted according to General Procedure I to generate the title compound. $^1$H NMR (500 MHz, CDCl$_3$) δ

7.62-7.60 (d, J=7.5 Hz, 2H), 7.56-7.54 (d, J=8.5 Hz, 2H), 7.50-7.46 (m, 4H), 5.29 (s, 1H), 4.63 (m, 1H), 3.73-3.54 (m, 8H), 3.17-2.53 (m, 6H), 2.28-2.17 (m, 2H), 1.98-1.40 (m, 9H) ppm. $^{13}$C NMR (125 MHz, CDCl$_3$) δ 170.3, 154.5, 146.7, 142.4, 138.4, 133.9, 127.7, 127.1, 125.4, 71.0, 66.9, 55.5, 55.0, 48.4, 47.3, 46.2, 42.7, 29.4, 25.3, 24.5, 19.5 ppm. Purity: >99% (214 & 254 nm) LCMS; retention time: 1.21 min; (M+H$^+$) 478.3.

Example 266

1-Azabicyclo[3.2.2]nonan-4-yl 2-(4'-(morpholine-4-carbonyl)biphenyl-4-yl)propan-2-ylcarbamate Using General Procedure I and the reaction inputs 2-methyl-2-(4'-(morpholine-4-carbonyl)-[1,1'-biphenyl]-4-yl)propanoic acid (prepared as described in Example 265) and Intermediate 3, the title compound was prepared. $^1$H NMR (500 MHz, CDCl$_3$) δ 7.62-7.61 (d, J=8.0 Hz, 2H), 7.55-7.54 (d, J=8.0 Hz, 2H), 7.49-7.47 (m, 4H), 5.20 (s, 1H), 4.78-4.77 (m, 1H), 3.76-3.54 (m, 8H), 3.09-2.72 (m, 6H), 2.27-1.53 (m, 13H) ppm. $^{13}$C NMR (125 MHz, CDCl$_3$) δ 170.3, 154.3, 146.9, 142.5, 138.4, 133.9, 127.7, 127.1, 126.9, 125.4, 78.3, 66.9, 55.0, 51.7, 48.2, 44.9, 42.5, 33.7, 30.6, 29.5, 28.7, 24.8, 22.2 ppm. Purity: >99% (214 & 254 nm) LCMS; retention time: 1.22 min; (M+H$^+$) 492.3.

Example 267

1-(3-Methylquinuclidin-3-yl)-3-(2-(4'-(morpholine-4-carbonyl)biphenyl-4-yl)propan-2-yl)urea Using General Procedure I and the reaction inputs 2-methyl-2-(4'-(morpholine-4-carbonyl)-[1,1'-biphenyl]-4-yl)propanoic acid (prepared as described in Example 265) and Intermediate 1, the title compound was prepared. $^1$H NMR (500 MHz, CDCl$_3$) δ 7.61-7.53 (m, 6H), 7.48-7.47 (d, J=7.5 Hz, 2H), 5.14 (s, 1H), 4.42 (s, 1H), 3.77-3.53 (m, 8H), 2.73-2.43 (m, 6H), 1.86 (m, 1H), 1.64-1.63 (m, 7H), 1.38-1.18 (m, 6H) ppm. $^{13}$C NMR (125 MHz, CDCl$_3$) δ 171.5, 157.0, 146.4, 141.8, 139.2, 135.2, 127.7, 127.0, 126.1, 125.1, 58.6, 54.5, 52.7, 48.2, 45.2, 39.7, 39.5, 36.5, 35.4, 31.1, 29.8, 26.1, 24.3, 23.8 ppm. Purity: 100% (214 & 254 nm) LCMS; retention time: 1.32 min; (M+H$^+$) 491.3.

Example 268

1-(4-Methyl-1-azabicyclo[3.2.2]nonan-4-yl)-3-(2-(4'-(morpholine-4-carbonyl)biphenyl-4-yl)propan-2-yl)urea Using General Procedure I and the reaction inputs 2-methyl-2-(4'-(morpholine-4-carbonyl)-[1,1'-biphenyl]-4-yl)propanoic acid (prepared as described in Example 265) and Intermediate 5, the title compound was prepared. $^1$H NMR (500 MHz, CDCl$_3$) δ 7.64-7.60 (m, 6H), 7.49-7.48 (d, J=8.5 Hz, 2H), 4.76 (s, 1H), 4.07 (s, 1H), 3.75-3.54 (m, 8H), 2.89-2.70 (m, 4H), 2.47-2.18 (m, 3H), 1.70-1.63 (m, 8H), 1.54-1.15 (m, 7H) ppm. $^{13}$C NMR (125 MHz, CDCl$_3$) δ 170.2, 156.9, 146.2, 142.0, 139.3, 134.2, 127.8, 127.6, 127.2, 126.2, 66.9, 58.7, 54.6, 52.5, 48.3, 45.0, 39.3, 36.4, 31.4, 29.5, 26.1, 24.0, 23.7 ppm. Purity: >99% (214 & 254 nm) LCMS; retention time: 1.34 min; (M+H$^+$) 505.2.

Example 269

N-(2-(4'-(Morpholine-4-carbonyl)biphenyl-4-yl)propan-2-yl)-1,4-diazabicyclo[3.2.2]nonane-4-carboxamide Using General Procedure I and the reaction inputs 2-methyl-2-(4'-(morpholine-4-carbonyl)-[1,1'-biphenyl]-4-yl)propanoic acid (prepared as described in Example 265) and Intermediate 5, the title compound was prepared. $^1$H NMR (500 MHz, CDCl$_3$) δ 7.62-7.61 (d, J=8.0 Hz, 2H), 7.55-7.54 (d, J=8.5 Hz, 2H), 7.48-7.46 (m, 4H), 4.77 (s, 1H), 4.04 (m, 1H), 3.74-3.48 (m, 10H), 3.15-3.09 (m, 2H), 3.04-2.99 (m, 4H), 2.17-3.03 (m, 2H), 1.78-1.63 (m, 8H) ppm. $^{13}$C NMR (125 MHz, CDCl$_3$) δ 170.4, 155.5, 148.0, 142.7, 137.9, 133.7, 127.7, 127.1, 127.1, 125.3, 66.9, 57.6, 55.3, 48.0, 46.2, 41.3, 30.2, 27.4 ppm. Purity: >96% (214 & 254 nm) LCMS; retention time: 1.34 min; (M+H$^+$) 477.3.

Example 270

Quinuclidin-3-yl 2-(4'-(4,4-difluoropiperidine-1-carbonyl)biphenyl-4-yl)propan-2-ylcarbamate Exchanging methylamine hydrochloride for 4,4-difluoropiperidine, the reaction sequence outlined in Example 252 was used to prepare 2-(4'-(4,4-difluoropiperidine-1-carbonyl)-[1,1'-biphenyl]-4-yl)-2-methylpropanoic acid. This intermediate and quinuclidin-3-ol were reacted according to General Procedure I to generate the title compound. $^1$H NMR (500 MHz, CDCl$_3$) δ 7.63-7.61 (d, J=8.5 Hz, 2H), 7.57-7.55 (d, J=8.5 Hz, 2H), 7.51-7.47 (m, 4H), 5.21 (s, 1H), 4.63 (m, 1H), 3.86-3.65 (m, 4H), 3.17-2.67 (m, 5H), 2.17-2.00 (m, 6H), 1.84-1.36 (m, 10H) ppm. $^{13}$C NMR (125 MHz, CDCl$_3$) δ 170.5, 154.5, 146.8, 142.7, 138.4, 133.8, 127.5, 127.2, 127.1, 125.4, 121.6 (t, J=241 Hz), 71.0, 55.6, 55.1, 47.4, 46.3, 34.4, 29.5, 25.4, 24.5, 19.5 ppm. Purity: >99% (214 & 254 nm) LCMS; retention time: 1.47 min; (M+H$^+$) 512.2.

Example 271

1-Azabicyclo[3.2.2]nonan-4-yl 2-(4'-(4,4-difluoropiperidine-1-carbonyl)biphenyl-4-yl)propan-2-ylcarbamate Using General Procedure I and the reaction inputs 2-(4'-(4,4-difluoropiperidine-1-carbonyl)-[1,1'-biphenyl]-4-yl)-2-methylpropanoic acid (prepared as described in Example 270) and Intermediate 3, the title compound was prepared. $^1$H NMR (500 MHz, CDCl$_3$) δ 7.63-7.61 (d, J 8.0 Hz, 2H), 7.56-7.54 (d, J 8.5 Hz, 2H), 7.50-7.47 (m, 4H), 5.19 (s, 1H), 4.79-4.77 (m, 1H), 3.84-3.66 (m, 4H), 3.09-2.72 (m, 6H), 2.41-2.32 (m, 1H), 2.17-1.54 (m, 16H) ppm. $^{13}$C NMR (125 MHz, CDCl$_3$) δ 170, 154.2, 146.9, 142.7, 138.3, 133.8, 127.5, 127.2, 127.1, 125.4, 121.5 (t, J=241 Hz), 78.2, 55.0, 51.7, 48.2, 45.0, 39.4, 34.2, 33.7, 30.6, 29.6, 24.8, 22.2 ppm. Purity: >97% (214 & 254 nm) LCMS; retention time: 1.14 min; (M+H$^+$) 526.3.

Example 272

1-(2-(4'-(4,4-Difluoropiperidine-1-carbonyl)biphenyl-4-yl)propan-2-yl)-3-(3-ethylquinuclidin-3-yl)urea Using General Procedure I and the reaction inputs 2-(4'-(4,4-difluoropiperidine-1-carbonyl)-[1,1'-biphenyl]-4-yl)-2- methylpropanoic acid (prepared as described in Example 270) and Intermediate 2, the title compound was prepared. $^1$H NMR (500 MHz, CDCl$_3$) δ 7.62-7.57 (m, 6H), 7.49 (d, J=8.0 Hz, 2H), 5.06 (s, 1H), 4.15 (s, 1H), 3.88-3.42 (m, 4H), 2.71-2.39 (m, 6H), 2.04-1.57 (m, 14H), 1.37-1.15 (m, 3H), 0.66 (t, J=7.0 Hz, 3H) ppm. $^{13}$C NMR (125 MHz, CDCl$_3$) δ 170.5, 156.6, 146.3, 142.4, 139.1, 134.1, 127.6, 127.5, 127.2, 126.1, 121.5 (t, J=241 Hz), 63.1, 54.9, 54.5, 46.6, 30.8, 30.1, 28.0, 28.0, 22.7, 22.3, 7.9 ppm. Purity: >99% (214 & 254 nm) LCMS; retention time: 1.13 min; (M+H$^+$) 539.3.

Example 273

Quinuclidin-3-yl 2-(4'-(3,3-difluoroazetidine-1-carbonyl)biphenyl-4-yl)propan-2-ylcarbamate Exchanging methylamine hydrochloride for 3,3-difluoroazetidine hydrochloride, the reaction sequence outlined in Example 252 was used to prepare 2-(4'-(3,3-difluoroazetidine-1-carbonyl)-[1,1'-biphenyl]-4-yl)-2-methylpropanoic acid. This intermediate and quinuclidin-3-ol were reacted according to General Procedure I to generate the title compound. $^1$H NMR (500 MHz, CDCl$_3$) δ 7.72-7.71 (d, J=8.0 Hz, 2H), 7.66-7.64 (d, J=8.0 Hz, 2H), 7.59-7.51 (m, 4H), 5.21 (s, 1H), 4.64-4.56 (m, 5H), 3.19-2.27 (m, 6H), 2.12-1.99 (m, 3H), 1.86-1.41 (m, 8H) ppm. $^{13}$C NMR (125 MHz, CDCl$_3$) δ 170.6 (t, J=3.0 Hz), 154.5, 147.9, 147.2, 144.2, 138.1, 130.6, 128.5, 127.2, 125.5, 115.4 (t, J=272 Hz), 71.0, 55.6, 55.0, 47.3, 46.4, 29.6, 29.5, 25.4, 24.5, 19.5 ppm. Purity: >98% (214 & 254 nm) LCMS; retention time: 1.29 min; (M+H$^+$) 484.2.

Example 274

1-Aza-bicyclo[3.2.2]nonan-4-yl 2-(4'-(3,3-difluoroazetidine-1-carbonyl)biphenyl-4-yl)propan-2-ylcarbamate Using General Procedure I and the reaction inputs 2-(4'-(3,3-difluoroazetidine-1-carbonyl)-[1,1'-biphenyl]-4-yl)-2-methylpropanoic acid (prepared as described in Example 273) and Intermediate 3, the title compound was prepared. $^1$H NMR (500 MHz, CDCl$_3$) δ 7.73-7.71 (d, J=8.5 Hz, 2H), 7.66-7.65 (d, J=8.0 Hz, 2H), 7.59-7.57 (d, J=8.0 Hz, 2H), 7.52-7.50 (m, J=8.0 Hz, 2H), 5.14 (s, 1H), 4.82-4.78 (m, 1H), 4.59 (t, J=12.0 Hz, 4H), 3.13-2.76 (m, 6H), 2.08-1.55 (m, 13H) ppm. $^{13}$C NMR (125 MHz, CDCl$_3$) δ 170.6, 154.2, 147.2, 144.3, 138.0, 130.6, 128.5, 127.1, 125.5, 115.4 (t, J=340 Hz), 78.1, 55.0, 51.6, 48.1, 44.9, 33.6, 30.4, 29.6, 24.6, 22.0 ppm. Purity: >99% (214 & 254 nm) LCMS; retention time: 1.46 min; (M+H$^+$) 498.3.

Example 275

1-(2-(4'-(3,3-Difluoroazetidine-1-carbonyl)biphenyl-4-yl)propan-2-yl)-3-(3-ethylquinuclidin-3-yl)urea Using General Procedure I and the reaction inputs 2-(4'-(3,3-difluoroazetidine-1-carbonyl)-[1,1'-biphenyl]-4-yl)-2-methylpropanoic acid (prepared as described in Example 273) and Intermediate 2, the title compound was prepared. $^1$H NMR (500 MHz, CDCl$_3$) δ 7.73-7.61 (m, 8H), 4.89 (s, 1H), 4.58 (t, J=12.0 Hz, 4H), 4.04 (s, 1H), 2.71-2.18 (m, 6H), 1.97-1.20 (m, 13H), 0.66 (t, J=7.5 Hz, 3H) ppm. $^{13}$C NMR (125 MHz, CDCl$_3$) δ 170.6 (t, J=3.0 Hz), 156.4, 146.4, 143.9, 138.9, 130.9, 128.6, 127.7, 127.2, 126.2, 115.3 (t, J=272 Hz), 62.9, 55.0, 54.5, 50.6, 46.5, 30.7, 28.0, 28.0, 22.6, 22.6, 7.9 ppm. Purity: >99% (214 & 254 nm) LCMS; retention time: 1.46 min; (M+H$^+$) 511.3.

Example 276

1-(4-Methyl-1-azabicyclo[3.2.2]nonan-4-yl)-3-(2-(3-(3-(morpholine-4-carbonyl)phenoxy)phenyl)propan-2-yl)urea To stirred solution of 3-hydroxybenzoic acid (8.28 g, 59.9 mmol) in N,N-dimethylformamide (150 mL) was added N-(3-dimethylaminopropyl)-N'-ethylcarbodiimide hydrochloride (6.30 g, 32.9 mmol), N,N-diisopropylethylamine (17.0 g, 132 mmol), 1-hydroxybenzotriazole hydrate (8.80 g, 66.0 mmol) and morpholine (5.75 g, 66.0 mmol). The mixture was stirred overnight and then diluted with water and extracted with ethyl acetate. The combined extracts were washed with brine, dried (Na$_2$SO$_4$) and concentrated. The crude material was purified by flash chromatography over silica using a hexane/ethyl acetate eluant to afford (3-hydroxyphenyl)(morpholino)methanone as a white solid (5.80 g, 47%). To a stirred solution of this compound (5.00 g, 24.1 mmol) in N,N-dimethylformamide (100 mL) was added ethyl 2-(3-bromophenyl)-2-methylpropanoate (8.00 g, 31.1 mmol), cesium carbonate (15.7 g, 48.2 mmol), copper(I) iodide (1.40 g, 7.35 mmol) and 2-(dimethylamino) acetic acid hydrochloride (2.10 g, 14.5 mmol). The mixture was heated at 120° C. overnight. After cooling, the reaction was diluted with water and extracted with ethyl acetate. The combined extracts were washed with brine, dried (Na$_2$SO$_4$) and concentrated. The crude material was purified by flash chromatography over silica using a hexane/ethyl acetate eluant to afford ethyl 2-methyl-2-(3-(3-(morpholine-4-carbonyl)phenoxy)phenyl)propanoate as a viscous, colorless oil (4.40 g, 46%). To a stirred solution of this intermediate (4.40 g, 11.5 mmol) in 1:1 (v/v) methanol/water (40 mL) was added solid sodium hydroxide (2.30 g, 57.5 mmol). After stirring for 6 hours, the reaction was concentrated and taken up in water. The solution was made acidic (pH~6) with 1 N hydrochloric acid and extracted with ethyl acetate. The combined extracts were washed with brine, dried (Na$_2$SO$_4$) and concentrated to afford 2-methyl-2-(3-(3-(morpholine-4-carbonyl)phenoxy)phenyl)propanoic acid as a white solid (3.60 g, 85%). This compound was used without purification and reacted with Intermediate 5 according to General Procedure I to generate the title compound as an off-white solid. $^1$H NMR (500 MHz, CDCl$_3$) δ 7.39-7.34 (m, 2H), 7.29-7.23 (m, 2H), 7.13-7.12 (d, J=7.5 Hz, 1H), 7.06-7.022 (m, 2H), 6.92-6.90 (m, 1H), 4.78 (s, 1H), 4.17 (s, 1H), 3.76-3.47 (m, 8H), 2.94-2.44 (m, 6H), 2.18 (m, 1H), 1.71-1.48 (m, 10H), 1.36-1.21 (m, 5H) ppm. $^{13}$C NMR (125 MHz, CDCl$_3$) δ 169.5, 157.3, 157.0, 156.7, 149.4, 137.0, 130.3, 130.1, 121.7, 120.7, 119.8, 117.6, 117.3, 116.7, 66.8, 58.7, 54.7, 52.8, 48.2, 45.3, 42.6, 39.5, 36.5, 31.0, 29.7, 26.0, 24.4, 23.9 ppm. Purity: >97% (214 & 254 nm) LCMS; retention time: 1.78 min; (M+H$^+$) 521.3.

Example 277

1-(3-Methylquinuclidin-3-yl)-3-(2-(3-(3-(morpholine-4-carbonyl)phenoxy)phenyl)propan-2-yl)urea Using General Procedure I and the reaction inputs 2-methyl-2-(3-(3-(morpholine-4-carbonyl)phenoxy)phenyl)propanoic acid (prepared as described in Example 276) and Intermediate 1, the title compound was prepared. $^1$H NMR (500 MHz, CDCl$_3$) δ 7.39-7.34 (m, 2H), 7.28-7.27 (m, 2H), 7.13-7.12 (d, J=7.5 Hz, 1H), 7.06-7.02 (m, 2H), 6.92-6.91 (m, 1H), 4.73 (s, 1H), 4.14 (s, 1H), 3.77-3.46 (m, 8H), 2.75-2.49 (m, 6H), 1.95-1.60 (m, 8H), 1.42-1.26 (m, 6H) ppm. $^{13}$C NMR (125 MHz, CDCl$_3$) δ 169.6, 157.4, 156.9, 156.7, 149.4, 137.0, 130.2, 130.2, 121.6, 120.7, 119.7, 117.7, 117.2, 116.7, 66.8, 63.6, 54.7, 52.2, 46.5, 46.3, 30.7, 30.5, 30.1, 24.9, 23.1, 22.4 ppm. Purity: >99% (214 & 254 nm) LCMS; retention time: 1.76 min; (M+H$^+$) 507.3.

Example 278

1-Aza-bicyclo[3.2.2]nonan-4-yl 2-(3-(3-(morpholine-4-carbonyl)phenoxy)phenyl)propan-2-ylcarbamate Using General Procedure I and the reaction inputs 2-methyl-2-(3-(3-(morpholine-4-carbonyl)phenoxy)phenyl) propanoic acid (prepared as described in Example 276) and Intermediate 3, the title compound was prepared. $^1$H NMR (500 MHz, CDCl$_3$) δ 7.35-7.28 (m, 2H), 7.19-7.04 (m, 5H), 6.87-6.87 (m, 1H), 5.10 (s, 1H), 4.77 (m, 1H), 3.76-3.45 (m, 8H), 3.09-2.46 (m, 6H), 2.18-1.31 (m, 13H) ppm. $^{13}$C NMR (125 MHz, CDCl$_3$) δ 169.6, 157.7, 156.3, 154.1, 149.7, 137.0, 130.0, 129.7, 121.4, 120.4, 119.5, 117.3, 117.0, 116.4, 78.0, 66.8, 55.0, 51.5, 48.0, 44.9, 42.5, 33.4, 30.3, 30.2, 29.3, 29.4, 24.6, 21.9 ppm. Purity: >99% (214 & 254 nm) LCMS; retention time: 1.40 min; (M+H$^+$) 508.3.

Example 279

Quinuclidin-3-yl 2-(3-(3-(morpholine-4-carbonyl) phenoxy)phenyl)propan-2-ylcarbamate Using General Procedure I and the reaction inputs 2-methyl-2-(3-(3-(morpholine-4-carbonyl)phenoxy)phenyl) propanoic acid (prepared as described in Example 276) and quinuclidin-3-ol, the title compound was prepared. $^1$H NMR (500 MHz, CDCl$_3$) δ 7.37-7.28 (m, 2H), 7.20-7.03 (m, 5H), 6.86-6.85 (d, J=8.0 Hz, 1H), 5.19 (s, 1H), 4.61 (m, 1H), 3.75-3.16 (m, 8H), 2.83-2.37 (m, 6H), 1.95-1.12 (m, 11H) ppm. $^{13}$C NMR (125 MHz, CDCl$_3$) δ 169.6, 157.6, 156.3, 154.4, 149.7, 137.0, 130.1, 129.7, 121.431, 120.4, 119.5, 117.2, 117.0, 116.3, 70.9, 66.8, 55.5, 55.0, 48.1, 47.2, 46.4, 42.5, 30.5, 29.5, 29.3, 25.3, 24.5, 19.5 ppm. Purity: >97% (214 & 254 nm) LCMS; retention time: 1.39 min; (M+H$^+$) 494.2.

Example 280

1-(3-Methylquinuclidin-3-yl)-3-(2-(4-(4-(morpholine-4-carbonyl)phenoxy)phenyl)propan-2-yl)urea Exchanging ethyl 2-(3-bromophenyl)-2-methylpropanoate for ethyl 2-(4-bromophenyl)-2-methylpropanoate and 3-hydroxybenzoic acid for 4-hydroxybenzoic acid, the reaction sequence outlined in Example 276 was used to prepare 2-methyl-2-(4-(4-(morpholine-4-carbonyl)phenoxy)phenyl) propanoic acid. This intermediate and quinuclidin-3-ol were reacted according to General Procedure I to generate the title compound. $^1$H NMR (500 MHz, CDCl$_3$) δ 7.51-7.49 (d, J=9.0 Hz, 2H), 7.42-7.40 (d, J=9.0 Hz, 2H), 7.05-7.00 (m, 4H), 4.82 (s, 1H), 4.21 (s, 1H), 3.72-3.48 (m, 8H), 2.78-2.51 (m, 6H), 1.86-1.89 (m, 1H), 1.72-1.65 (m, 1H), 1.64-1.62 (d, J=8.0 Hz, 6H), 1.49-1.40 (m, 2H), 1.37 (s, 3H), 1.31-1.25 (m, 1H) ppm. $^{13}$C NMR (125 MHz, CDCl$_3$) δ 170.0, 158.7, 156.9, 155.2, 142.4, 129.8, 129.2, 127.0, 119.5, 118.2, 66.8, 63.4, 54.4, 52.1, 46.5, 46.2, 30.7, 30.4, 24.9, 22.9, 22.2 ppm. Purity: >100% LCMS (214 & 254 nm) LCMS; retention time: 1.73 min; (M+H$^+$) 507.3.

Example 281

1-(4-Methyl-1-azabicyclo[3.2.2]nonan-4-yl)-3-(2-(4-(4-(morpholine-4-carbonyl)phenoxy)phenyl)propan-2-yl)urea Using General Procedure I and the reaction inputs 2-methyl-2-(4-(4-(morpholine-4-carbonyl)phenoxy)phenyl) propanoic acid (prepared as described in Example 280) and Intermediate 5, the title compound was prepared. $^1$H NMR (500 MHz, CDCl$_3$) δ 7.52-7.51 (d, J=8.0 Hz, 2H), 7.42-7.41 (d, J=7.5 Hz, 2H), 7.04-7.01 (m, 4H), 4.90 (s, 1H), 4.29 (s, 1H), 3.72-3.57 (m, 8H), 2.97-2.56 (m, 6H), 2.23 (m, 1H), 1.75-1.55 (m, 10H), 1.42-1.24 (m, 5H) ppm. $^{13}$C NMR (125 MHz, CDCl$_3$) δ 170.0, 158.7, 156.951, 155.2, 142.7, 129.8, 129.2, 127.0, 119.4, 118.3, 66.8, 58.4, 54.4, 52.8, 48.4, 45.2, 39.0, 36.3, 31.0, 30.0, 26.1, 24.0, 23.5 ppm. Purity: >98% (214 & 254 nm) LCMS; retention time: 1.72 min; (M+H$^+$) 521.3.

Example 282

1-Azabicyclo[3.2.2]nonan-4-yl 2-(4-(4-(morpholine-4-carbonyl)phenoxy)phenyl)propan-2-ylcarbamate Using General Procedure I and the reaction inputs 2-methyl-2-(4-(4-(morpholine-4-carbonyl)phenoxy)phenyl) propanoic acid (prepared as described in Example 280) and Intermediate 3, the title compound was prepared. $^1$H NMR (500 MHz, CDCl$_3$) δ 7.42-7.38 (m, 4H), 7.03-6.98 (m, 4H), 5.15 (s, 1H), 4.83 (m, 1H), 3.72-3.49 (m, 8H), 3.12-2.97 (m, 6H), 2.24-1.68 (m, 13H) ppm. $^{13}$C NMR (125 MHz, CDCl$_3$) δ 170.3, 158.8, 154.9, 153.7, 142.5, 129.7, 129.2, 126.4, 119.1, 118.2, 66.9, 55.0, 51.0, 47.3, 45.3, 32.5, 30.6, 29.4, 28.7, 22.9, 20.0 ppm. Purity: >98% (214 & 254 nm) LCMS; retention time: 1.72 min; (M+H$^+$) 508.3.

Example 283

Quinuclidin-3-yl 2-(4-(4-(dimethylcarbamoyl)phenoxy)phenyl)propan-2-ylcarbamate

Exchanging ethyl 2-(3-bromophenyl)-2-methylpropanoate for ethyl 2-(4-bromophenyl)-2-methylpropanoate, 3-hydroxybenzoic acid for 4-hydroxybenzoic acid, and morpholine for dimethylamine hydrochloride, the reaction sequence outlined in Example 276 was used to prepare 2-(4-(4-(dimethylcarbamoyl)phenoxy)phenyl)-2-methylpropanoic acid. This intermediate and quinuclidin-3-ol were reacted according to General Procedure I to generate the title compound. $^1$H NMR (500 MHz, CDCl$_3$) δ 7.42-7.37 (m, 4H), 6.99-6.96 (m, 4H), 5.24 (s, 1H), 4.65-4.62 (m, 1H), 3.17-3.02 (m, 7H), 2.88-2.61 (m, 5H), 1.99-1.39 (m, 11H) ppm. $^{13}$C NMR (125 MHz, CDCl$_3$) δ 171.2, 158.5, 154.9, 154.5, 142.6, 130.8, 129.1, 126.3, 119.1, 117.9, 70.8, 55.5, 54.9, 47.3, 46.3, 39.7, 35.5, 29.6, 25.3, 24.4, 19.4 ppm. Purity: >97% (214 & 254 nm) LCMS; retention time: 1.89 min; (M+H$^+$) 452.3.

Example 284

N,N-Dimethyl-4-(4-(2-(3-(3-methylquinuclidin-3-yl) ureido)propan-2-yl)phenoxy)benzamide Using General Procedure I and the reaction inputs 2-(4-(4-(dimethylcarbamoyl)phenoxy)phenyl)-2-methylpropanoic acid (prepared as described in Example 283) and Intermediate 1, the title compound was prepared. $^1$H NMR (500 MHz, CDCl$_3$) δ 7.48 (d, J=8.5 Hz, 2H), 7.42 (d, J=8.5 Hz, 2H), 7.02-6.99 (m, 4H), 5.00 (s, 1H), 4.48 (s, 1H), 3.11-3.04 (m, 6H), 2.78-2.62 (m, 6H), 1.72 (m, 1H), 1.72-1.68 (m, 1H), 1.62-1.60 (m, 6H), 1.49-1.46 (m, 2H), 1.38 (s, 3H), 1.32-1.25 (m, 1H) ppm. $^{13}$C NMR (125 MHz, CDCl$_3$) δ 171.2, 158.4, 157.0, 155.3, 142.4, 130.9, 129.1, 127.0, 119.4, 118.1, 63.1, 54.4, 52.0, 46.5, 46.2, 39.8, 35.5, 30.6, 30.6, 30.4, 24.9, 22.8, 22.1 ppm. Purity: >99% (214 & 254 nm) LCMS; retention time: 1.22 min; (M+H$^+$) 465.2.

Example 285

N,N-Dimethyl-4-(4-(2-(3-(4-methyl-1-azabicyclo [3.2.2]nonan-4-yl)ureido)propan-2-yl)phenoxy)benzamide Using General Procedure I and the reaction inputs 2-(4-(4-(dimethylcarbamoyl)phenoxy)phenyl)-2-methylpropanoic acid (prepared as described in Example 283) and Intermediate 5, the title compound was prepared. $^1$H NMR (500 MHz, CDCl$_3$) δ 7.43-7.41 (d, J=8.5 Hz, 2H), 7.38-7.36 (d, J=8.5 Hz, 2H), 6.97-6.94 (m, 4H), 5.35 (s, 1H), 4.79 (s, 1H), 3.07-2.68 (m, 12H), 2.21 (m, 1H), 1.68-1.28 (m, 15H) ppm. $^{13}$C NMR (125 MHz, CDCl$_3$) δ 171.2, 158.5, 157.1, 155.1, 143.0, 130.7, 129.03 126.9, 119.243, 118.078, 58.253, 54.305, 52.771, 48.292, 45.203, 39.738, 38.770, 36.243, 35.5, 30.8, 30.2, 26.1, 23.9, 23.3 ppm. Purity: >96% LCMS (214 & 254 nm) LCMS; retention time: 1.23 min; (M+H$^+$) 479.3.

Example 286

1-Azabicyclo[3.2.2]nonan-4-yl 2-(4-(4-(dimethylcarbamoyl)phenoxy)phenyl)propan-2-ylcarbamate Using General Procedure I and the reaction inputs 2-(4-(4-(dimethylcarbamoyl)phenoxy)phenyl)-2-methylpropanoic acid (prepared as described in Example 283) and Intermediate 3, the title compound was prepared. $^1$H NMR (500 MHz, CDCl$_3$) δ 7.43-7.38 (m, 4H), 7.02-6.98 (m, 4H), 5.08 (s, 1H), 4.82-4.78 (m, 1H), 3.11-2.75 (m, 12H), 2.09-1.55 (m, 13H) ppm. $^{13}$C NMR (125 MHz, CDCl$_3$) δ 171.2, 158.5, 154.9, 154.1, 142.7, 130.8, 129.1, 126.4, 119.0, 118.1, 77.9, 54.8, 51.6, 48.1, 45.0, 39.7, 35.5, 33.5, 30.3, 29.6, 24.5, 21.9 ppm. Purity: >98% (214 & 254 nm) LCMS; retention time: 1.73 min; (M+H$^+$) 466.3.

Example 287

Quinuclidin-3-yl 2-(4-(4-(dimethylcarbamoyl)phenoxy)phenyl)propan-2-ylcarbamate

Exchanging morpholine for dimethylamine hydrochloride, the reaction sequence outlined in Example 276 was used to prepare 2-(3-(3-(dimethylcarbamoyl)phenoxy)phenyl)-2-methylpropanoic acid. This intermediate and quinuclidin-3-ol were reacted according to General Procedure I to generate the title compound. $^1$H NMR (500 MHz, CDCl$_3$) δ 7.34 (t, J=8.0 Hz, 1H), 7.21 (t, J=8.0 Hz, 1H), 7.18-7.17 (d, J=8.5 Hz, 1H), 7.13-7.10 (m, 2H), 7.04-7.00 (m, 2H), 6.86 (m, 1H), 5.20 (s, 1H), 4.62 (m, 1H), 3.16-2.33 (m, 12H), 1.96-1.36 (m, 11H) ppm. $^{13}$C NMR (125 MHz, CDCl$_3$) δ 170.8, 157.4, 156.6, 154.4, 149.6, 138.0, 129.9, 130.0, 121.5, 120.2, 119.4, 117.2, 117.1, 116.2, 71.0, 55.5, 55.1, 47.3, 46.4, 39.5, 35.3, 29.5, 25.3, 24.5, 19.5 ppm. Purity: >99% (214 & 254 nm) LCMS; retention time: 1.82 min; (M+H$^+$) 452.3.

Example 288

1-Aza-bicyclo[3.2.2]nonan-4-yl 2-(3-(3-(dimethylcarbamoyl)phenoxy)phenyl)propan-2-ylcarbamate Using General Procedure I and the reaction inputs 2-(3-(3-(dimethylcarbamoyl)phenoxy)phenyl)-2-methylpropanoic acid (prepared as described in Example 287) and Intermediate 3, the title compound was prepared. $^1$H NMR (500 MHz, CDCl$_3$) δ 7.34-7.28 (m, 2H), 7.18-7.10 (m, 3H), 7.04-7.02 (m, 2H), 6.87-6.85 (m, 1H), 5.11 (s, 1H), 4.78-4.75 (m, 1H), 3.09-2.63 (m, 12H), 2.03-1.18 (m, 13H) ppm. $^{13}$C NMR (125 MHz, CDCl$_3$) δ 170.8, 157.4, 156.5, 154.106, 149.7, 138.0, 129.8, 129.7, 124.8, 121.5, 120.2, 119.3, 117.2, 116.2, 78.1, 55.0, 51.6, 48.1, 45.0, 39.5, 35.3, 33.5, 30.4, 30.2, 29.5, 29.4, 24.6, 21.9 ppm. Purity: >99% (214 & 254 nm) LCMS; retention time: 1.39 min; (M+H$^+$) 466.3.

Example 289

N,N-Dimethyl-3-(3-(2-(3-(3-methylquinuclidin-3-yl) ureido)propan-2-yl)phenoxy)benzamide Using General Procedure I and the reaction inputs 2-(3-(3-(dimethylcarbamoyl)phenoxy)phenyl)-2-methylpropanoic acid (prepared as described in Example 287) and Intermediate 1, the title compound was prepared. $^1$H NMR (500 MHz, CDCl$_3$) δ 7.38-7.33 (m, 2H), 7.28-7.21 (m, 2H), 7.15-7.13 (d, J=7.5 Hz, 1H), 7.04-7.03 (m, 2H), 6.93-6.91 (m, 1H), 4.82 (br s, 1H), 4.30 (br s, 1H), 3.10 (s, 3H), 2.99 (s, 3H), 2.72-2.47 (m, 6H), 1.83-1.60 (m, 8H), 1.46-1.23 (m, 6H) ppm. $^{13}$C NMR (125 MHz, CDCl$_3$) δ 170.8, 157.2, 157.0, 156.8, 149.5, 138.0, 130.2, 130.0, 121.6, 120.6, 119.6, 117.6, 117.1, 116.5, 63.4, 54.7, 52.1, 46.5, 46.3, 39.5, 35.3, 30.7, 30.5, 30.0, 24.9, 23.0, 22.2 ppm. Purity: >97% (214 & 254 nm) LCMS; retention time: 1.83 min; (M+H$^+$) 465.4.

Example 290

N,N-Dimethyl-4-(4-(2-(3-(4-methyl-1-aza-bicyclo [3.2.2]nonan-4-yl)ureido)propan-2-yl)phenoxy)benzamide Using General Procedure I and the reaction inputs 2-(3-(3-(dimethylcarbamoyl)phenoxy)phenyl)-2-methylpropanoic acid (prepared as described in Example 287) and Intermediate 5, the title compound was prepared. $^1$H NMR (500 MHz, CDCl$_3$) δ 7.37-7.31 (m, 2H), 7.28-7.25 (m, 1H), 7.21 (t, J=2.0 Hz, 1H), 7.14-7.12 (d, J=7.5 Hz, 1H), 7.04-7.01 (m, 2H), 6.91-6.89 (m, 1H), 4.91 (s, 1H), 4.32 (s, 1H), 3.08 (s, 3H), 2.98 (s, 3H), 2.90-2.74 (m, 4H), 2.59-2.44 (m, 2H), 2.18-2.17 (m, 1H), 1.69-1.21 (m, 15H) ppm. $^{13}$C NMR (125 MHz, CDCl$_3$) δ 170.8, 157.1, 157.1, 156.8, 149.5, 138.0, 130.2, 130.0, 121.7, 120.6, 119.6, 117.5, 117.2, 116.5, 58.6, 54.7, 52.8, 48.1, 45.3, 39.5, 39.4, 36.4, 35.3, 30.8, 29.8, 26.0, 24.3, 23.8 ppm. Purity: >99% (214 & 254 nm) LCMS; retention time: 1.77 min; (M+H$^+$) 479.4.

Example 291

Quinuclidin-3-yl 2-(4-(4-(methylcarbamoyl)phenoxy)phenyl)propan-2-ylcarbamate

Exchanging ethyl 2-(3-bromophenyl)-2-methylpropanoate for ethyl 2-(4-bromophenyl)-2-methylpropanoate, 3-hydroxybenzoic acid for 4-hydroxybenzoic acid, and morpholine for methylamine hydrochloride, the reaction sequence outlined in Example 276 was used to prepare 2-methyl-2-(4-(4-(methylcarbamoyl)phenoxy)phenyl)propanoic acid. This intermediate and quinuclidin-3-ol were reacted according to General Procedure I to generate the title compound. $^1$H NMR (500 MHz, CDCl$_3$) δ 7.74 (d, J=9.0 Hz, 2H), 7.42 (d, J=9.0 Hz, 2H), 7.02-6.99 (m, 4H), 6.15 (s, 1H), 5.13 (s, 1H), 4.67-4.64 (m, 1H), 3.19-2.70 (m, 9H), 1.97-1.38 (m, 11H) ppm. $^{13}$C NMR (125 MHz, CDCl$_3$) δ 167.6, 160.2, 154.6, 154.4, 142.8, 129.1, 128.8, 126.4, 119.3, 117.8, 71.0, 55.5, 54.9, 47.2, 46.3, 30.9, 29.6, 26.8, 25.3, 24.4, 19.5 ppm. Purity: >99% (214 & 254 nm) LCMS; retention time: 1.75 min; (M+H$^+$) 438.3.

Example 292

1-Aza-bicyclo[3.2.2]nonan-4-yl 2-(4-(4-(methylcarbamoyl)phenoxy)phenyl)propan-2-ylcarbamate Using General Procedure I and the reaction inputs 2-methyl-2-(4-(4-(methylcarbamoyl)phenoxy)phenyl)propanoic acid (prepared as described in Example 291) and Intermediate 3, the title compound was prepared. $^1$H NMR (500 MHz, CDCl$_3$) δ 7.75-7.73 (d, J=8.5 Hz, 2H), 7.41-7.40 (d, J=8.5 Hz, 2H), 7.00-6.98 (m, 4H), 6.17 (br s, 1H), 5.09 (s, 1H), 4.81-4.77 (m, 1H), 3.11-2.73 (m, 9H), 2.10-1.521 (m, 13H) ppm. $^{13}$C NMR (125 MHz, CDCl$_3$) δ 167.6, 160.2, 154.5, 143.0, 129.1, 128.7, 126.4, 119.3, 117.8, 78.2, 54.8, 51.7, 48.2, 45.0, 33.6, 30.6, 29.7, 26.8, 24.8, 22.2 ppm. Purity: >99% (214 & 254 nm) LCMS; retention time: 1.19 min; (M+1) 452.2.

Example 293

N-Methyl-4-(4-(2-(3-(3-methylquinuclidin-3-yl)ureido)propan-2-yl)phenoxy)benzamide Using General Procedure I and the reaction inputs 2-methyl-2-(4-(4-(methylcarbamoyl)phenoxy)phenyl)propanoic acid (prepared as described in Example 291) and Intermediate 1, the title compound was prepared. $^1$H NMR (500 MHz, CDCl$_3$) δ 7.77-7.75 (d, J=8.5 Hz, 2H), 7.53-7.51 (d, J=8.5 Hz, 2H), 7.06-7.00 (m, 4H), 6.15 (br s, 1H), 4.73 (br s, 1H), 4.12 (br s, 1H), 3.03-3.02 (d, J=5.0 Hz, 3H), 2.79-2.52 (m, 6H), 1.86-1.64 (m, 8H), 1.49-1.22 (m, 6H) ppm. $^{13}$C NMR (125 MHz, CDCl$_3$) δ 167.5, 159.9, 156.8, 155.3, 142.1, 129.4, 128.8, 127.2, 119.7, 118.0, 63.6, 54.5, 52.2, 46.5, 46.3, 30.8, 30.7, 30.3, 26.9, 24.9, 23.0, 22.3 ppm. Purity: >99% (214 & 254 nm) LCMS; retention time: 1.18 min; (M+1) 451.2.

Example 294

N-Methyl-4-(4-(2-(3-(4-methyl-1-aza-bicyclo[3.2.2]nonan-4-yl)ureido)propan-2-yl)phenoxy)benzamide Using General Procedure I and the reaction inputs 2-methyl-2-(4-(4-(methylcarbamoyl)phenoxy)phenyl)propanoic acid (prepared as described in Example 291) and Intermediate 5, the title compound was prepared. $^1$H NMR (500 MHz, CDCl$_3$) δ 7.77-7.75 (d, J=8.0 Hz, 2H), 7.55-7.53 (d, J=9.0 Hz, 2H), 7.07-7.05 (d, J=8.5 Hz, 2H), 7.03-7.01 (d, J=9.0 Hz, 2H), 6.17 (m, 1H), 4.67 (s, 1H), 4.03 (s, 1H), 3.03-3.02 (d, J=4.5 Hz, 3H), 2.95-2.83 (m, 4H), 2.58-2.38 (m, 2H), 2.19 (m, 1H), 1.75-1.51 (m, 10H), 1.42-1.19 (m, 5H) ppm. $^{13}$C NMR (125 MHz, CDCl$_3$) δ 167.5, 159.8, 156.8, 155.5, 142.0, 129.5, 128.8, 127.2, 119.7, 118.1, 58.7, 54.4, 52.8, 48.2, 45.4, 39.5, 36.5, 31.3, 29.8, 26.9, 26.0, 24.3, 23.8 ppm. Purity: >96% (214 & 254 nm) LCMS; retention time: 1.19 min; (M+1) 465.2.

Example 295

2-(3-(3-(Methylcarbamoyl)phenoxy)phenyl)propan-2-ylcarbamate

Exchanging morpholine for methylamine hydrochloride, the reaction sequence outlined in Example 276 was used to prepare 2-methyl-2-(3-(3-(methylcarbamoyl)phenoxy)phenyl)propanoic acid. This intermediate and quinuclidin-3-ol were reacted according to General Procedure I to generate the title compound. $^1$H NMR (500 MHz, DMSO$_{d6}$) δ 8.47 (s, 1H), 7.60-7.59 (d, J=7.5 Hz, 1H), 7.52 (s, 1H), 7.47-7.44 (m, 2H), 7.33 (t, J=7.5 Hz, 1H), 7.15-7.09 (m, 2H), 6.98-6.83 (m, 2H), 4.40 (m, 1H), 2.98-2.37 (m, 9H), 1.76-1.24 (m, 11H) ppm. $^{13}$C NMR (125 MHz, CDCl$_3$) δ 167.9, 157.8, 156.2, 154.6, 149.1, 136.6, 129.9, 121.8, 121.2, 120.6, 117.7, 116.4, 115.7, 115.5, 71.0, 55.3, 47.2, 46.4, 29.7, 26.8, 25.3, 24.4, 19.4 ppm. Purity: >99% (214 & 254 nm) LCMS; retention time: 1.20 min; (M+H$^+$) 438.2.

Example 296

N-Methyl-3-(3-(2-(3-(3-methylquinuclidin-3-yl)ureido)propan-2-yl)phenoxy)benzamide Using General Procedure I and the reaction inputs 2-methyl-2-(3-(3-(methylcarbamoyl)phenoxy)phenyl)propanoic acid (prepared as described in Example 295) and Intermediate 1, the title compound was prepared. $^1$H NMR (500 MHz, CDCl$_3$) δ 7.60-7.59 (d, J=8.0 Hz, 1H), 7.42 (t, J=8.0 Hz, 1H), 7.36 (t, J=8.0 Hz, 1H), 7.26-7.13 (m, 5H), 6.90-6.88 (d, J=7.5 Hz, 1H), 4.78 (br s, 1H), 4.23 (br s, 1H), 2.95-2.94 (d, J=4.5 Hz, 3H), 2.69-2.32 (m, 6H), 1.95 (m, 2H), 1.64 (s, 3H), 1.60 (s, 3H), 1.45-1.41 (m, 2H), 1.33 (s, 3H), 1.24-1.18 (m, 1H) ppm. $^{13}$C NMR (125 MHz, CDCl$_3$) δ 167.8, 157.2, 156.9, 156.9, 149.4, 136.7, 130.2, 130.0, 122.4, 121.8, 120.9, 117.4, 116.6, 116.2, 63.7, 54.8, 52.0, 46.7, 46.1, 30.8, 30.3, 29.8, 26.9, 24.7, 22.9, 22.2 ppm. Purity: >99% (214 & 254 nm) LCMS; retention time: 1.79 min; (M+H$^+$) 451.3.

Example 297

N-Methyl-3-(3-(2-(3-(4-methyl-1-aza-bicyclo[3.2.2]nonan-4-yl)ureido)propan-2-yl)phenoxy)benzamide Using General Procedure I and the reaction inputs 2-methyl-2-(3-(3-(methylcarbamoyl)phenoxy)phenyl)propanoic acid (prepared as described in Example 295) and Intermediate 5, the title compound was prepared. $^1$H NMR (500 MHz, CDCl$_3$) δ 7.69-7.67 (m, 2H), 7.44 (t, J=8.0 Hz, 1H), 7.37-7.33 (m, 2H), 7.24-7.21 (m, 3H), 6.90-6.88 (dd, J=8.0 & 2.0 Hz, 1H), 4.82 (s, 1H), 4.31 (s, 1H), 2.91-2.81 (m, 7H), 2.48-2.18 (m, 2H), 1.76-1.49 (m, 9H), 1.37-1.22 (m, 7H) ppm. $^{13}$C NMR (125 MHz, CDCl$_3$) δ 167.7, 157.2, 156.9, 156.6, 149.3, 136.5, 130.3, 130.2, 122.9, 122.0, 120.5, 117.0, 117.0, 115.7, 58.4, 54.8, 52.8, 49.0, 44.7, 39.3, 36.4, 32.1, 28.7, 27.0, 26.4, 24.5, 23.8 ppm. Purity: >98% (214 & 254 nm) LCMS; retention time: 1.74 min; (M+H$^+$) 465.4.

Example 298

1-Aza-bicyclo[3.2.2]nonan-4-yl 2-(3-(3-(methylcarbamoyl)phenoxy)phenyl)propan-2-ylcarbamate Using General Procedure I and the reaction inputs 2-methyl-2-(3-(3-(methylcarbamoyl)phenoxy)phenyl)propanoic acid (prepared as described in Example 295) and Intermediate 3, the title compound was prepared. $^1$H NMR (500 MHz, CDCl$_3$) δ 7.55-7.54 (m, 1H), 7.41-7.35 (m, 2H), 7.19-6.78 (m, 6H), 5.10 (s, 1H), 4.65 (m, 1H), 3.04-2.70 (m, 9H), 1.96-1.43 (m, 13H) ppm. $^{13}$C NMR (125 MHz, CDCl$_3$) δ 167.7, 158.0, 156.0, 154.3, 149.1, 136.4, 129.9, 121.7, 121.1, 120.7, 117.8, 116.8, 115.2, 78.2, 55.2, 51.5, 47.9, 44.9, 33.4, 30.4, 29.8, 29.7, 26.8, 24.6, 21.9 ppm. Purity: >97% (214 & 254 nm) LCMS; retention time: 1.77 min; (M+H$^+$) 452.3.

Example 299

1-Aza-bicyclo[3.2.2]nonan-4-yl 2-(4-(4-(piperidine-1-carbonyl)phenoxy)phenyl) propan-2-ylcarbamate Exchanging ethyl 2-(3-bromophenyl)-2-methylpropanoate for ethyl 2-(4-bromophenyl)-2-methylpropanoate, 3-hydroxybenzoic acid for 4-hydroxybenzoic acid, and morpholine for piperidine, the reaction sequence outlined in Example 276 was used to prepare 2-methyl-2-(4-(4-(piperidine-1-carbonyl)phenoxy)phenyl)propanoic acid. This compound and Intermediate 3 were reacted according to General Procedure I to generate the title compound. $^1$H NMR (500 MHz, CDCl$_3$) δ 7.39-7.37 (m, 4H), 7.00-6.97 (m, 4H), 5.11 (s, 1H), 4.80-4.76 (m, 1H), 3.70-3.41 (m, 4H), 3.09-2.72 (m, 6H), 2.16 (m, 1H), 2.04-1.55 (m, 18H) ppm. $^{13}$C NMR (125 MHz, CDCl$_3$) δ 169.9, 158.4, 154.9, 154.2, 142.7, 131.0, 128.8, 126.4, 119.0, 118.1, 78.4, 54.8, 51.7, 49.0, 48.1, 45.0, 43.3, 33.6, 30.6, 29.6, 26.3, 25.9, 24.8, 24.6, 22.1 ppm. Purity: >96% (214 & 254 nm) LCMS; retention time: 1.49 min; (M+H$^+$) 506.3.

Example 300

1-(4-Methyl-1-aza-bicyclo[3.2.2]nonan-4-yl)-3-(2-(4-(4-(piperidine-1-50 carbonyl)phenoxy)phenyl) propan-2-yl)urea Using General Procedure I and the reaction inputs 2-methyl-2-(4-(4-(piperidine-1-carbonyl)phenoxy)phenyl)propanoic acid (prepared as described in Example 299) and Intermediate 5, the title compound was prepared. $^1$H NMR (500 MHz, CDCl$_3$) δ 7.48-7.47 (d, J=8.5 Hz, 2H), 7.39-7.37 (d, J=8.0 Hz, 2H) 7.02-6.99 (m, 4H), 4.94 (s, 1H), 4.29 (s, 1H), 3.69-3.39 (m, 4H), 2.93-2.43 (m, 6H), 2.17 (m, 1H), 1.70-1.35 (m, 21H) ppm. $^{13}$C NMR (125 MHz, CDCl$_3$) δ 169.9, 158.2, 156.9, 155.6, 142.2, 131.2, 128.8, 127.0, 119.3, 118.3, 58.6, 54.4, 52.8, 48.9, 48.2, 45.4, 43.0, 39.4, 36.5, 31.0, 30.0, 26.2, 26.0, 24.5, 24.3, 23.8 ppm. Purity: >97% (214 & 254 nm) LCMS; retention time: 1.34 min; (M+H$^+$) 519.3.

Example 301

1-Azabicyclo[3.2.2]nonan-4-yl 2-(4-(4-(4,4-difluoropiperidine-1-carbonyl)phenoxy)phenyl)propan-2-ylcarbamate Exchanging ethyl 2-(3-bromophenyl)-2-methylpropanoate for ethyl 2-(4-bromophenyl)-2-methylpropanoate, 3-hydroxybenzoic acid for 4-hydroxybenzoic acid, and morpholine for 4,4-difluoropiperidine, the reaction sequence outlined in Example 276 was used to prepare 2-(4-(4-(4,4-difluoropiperidine-1-carbonyl)phenoxy)phenyl)-2-methylpropanoic acid. This compound and Intermediate 3 were reacted according to General Procedure I to generate the title compound. $^1$H NMR (500 MHz, CDCl$_3$) δ 7.40-7.38 (m, 4H), 7.02-6.91 (m, 4H), 5.19 (s, 1H), 4.80-4.78 (m, 1H), 3.84-3.73 (m, 4H), 3.22-2.75 (m, 6H), 2.17-1.47 (m, 17H) ppm. $^{13}$C NMR (125 MHz, CDCl$_3$) δ 170.2, 159.1, 154.6, 153.9, 142.8, 129.5, 129.0, 126.4, 121.5 (t, J=241 Hz), 119.2, 118.1, 78.0, 54.9, 51.2, 47.7, 45.1, 34.4, 33.0, 29.5, 23.7, 20.9 ppm. Purity: >98% (214 & 254 nm) LCMS; retention time: 1.92 min; (M+H$^+$) 542.4.

Example 302

1-(2-(4-(4-(4,4-Difluoropiperidine-1-carbonyl)phenoxy)phenyl)propan-2-yl)-3-(4-methyl-1-azabicyclo[3.2.2]nonan-4-yl)urea Using General Procedure I and the reaction inputs 2-(4-(4-(4,4-difluoropiperidine-1-carbonyl)phenoxy)phenyl)-2-methylpropanoic acid (prepared as described in Example 301) and Intermediate 5, the title compound was prepared. $^1$H NMR (500 MHz, CDCl$_3$) δ 7.49-7.47 (d, J=8.5 Hz, 2H), 7.40-7.38 (d, J=8.5 Hz, 2H), 7.01-6.99 (m, 4H), 5.09 (s, 1H), 4.44 (s, 1H), 3.82-3.71 (m, 4H), 2.95-2.52 (m, 6H), 2.20-1.97 (m, 5H), 1.74-1.23 (m, 15H) ppm. $^{13}$C NMR (125 MHz, CDCl$_3$) δ 170.2, 158.9, 156.9, 155.2, 142.6, 129.7, 129.0, 127.1, 121.4 (t, J=241 Hz), 119.5, 118.3, 58.5, 54.4, 52.8, 48.3, 45.2, 39.1, 36.4, 34.2, 31.0, 30.0, 26.1, 24.1, 23.6 ppm. Purity: >99% (214 & 254 nm) LCMS; retention time: 1.84 min; (M+H$^+$) 555.4.

Example 303

1-(2-(4-(4-(3,3-Difluoroazetidine-1-carbonyl)phenoxy)phenyl)propan-2-yl)-3-(4-methyl-1-aza-bicyclo[3.2.2]nonan-4-yl)urea Exchanging ethyl 2-(3-bromophenyl)-2-methylpropanoate for ethyl 2-(4-bromophenyl)-2-methylpropanoate, 3-hydroxybenzoic acid for 4-hydroxybenzoic acid, and morpholine for 3,3-difluoroazetidine hydrochloride, the reaction sequence outlined in Example 276 was used to prepare 2-(4-(4-(3,3-difluoroazetidine-1-carbonyl)phenoxy)phenyl)-2-50 methylpropanoic acid. This compound and Intermediate 5 were reacted according to General Procedure I to generate the title compound. $^1$H NMR (500 MHz, CDCl$_3$) δ 7.66-7.63 (m, 2H), 7.55-7.53 (d, J=9.0 Hz, 2H), 7.06-7.01 (m, 4H), 4.56 (t, J=12.0 Hz, 4H), 3.08-2.76 (m, 5H), 2.31 (m, 1H), 1.79-1.61 (m, 11H), 1.44-1.27 (m, 6H) ppm. $^{13}$C NMR (125 MHz, CDCl$_3$) δ 187.9, 170.2, 160.4, 156.7, 154.9, 130.1, 127.2, 126.6, 119.9, 117.9, 115.3, 71.6, 58.4, 54.4, 52.9, 48.6, 45.0, 36.2, 31.1, 30.0, 26.1, 23.0 ppm. Purity: >98% (214 & 254 nm) LCMS; retention time: 1.30 min; (M+H$^+$) 527.3.

Example 304

Quinuclidin-3-yl 2-(4-(4-phenylpiperazine-1-carbonyl)phenyl)propan-2-ylcarbamate To a stirred solution of 2-(4-bromophenyl)propan-2-amine (1.00 g, 4.67 mmol) in methylene chloride (10 mL) was added di-tert-butyl dicarbonate (6.10 g, 27.9 mmol) and triethylamine (1.3 mL, 9.3 mmol). The mixture was stirred overnight and then concentrated. The residue was purified by flash chromatography over silica using a hexane/ethyl acetate gradient to afford tert-butyl (2-(4-bromophenyl)propan-2-yl)carbamate as a light yellow solid (1.25 g, 85%). To a stirred and cooled (−78° C.) solution of this compound (1.80 g, 5.75 mmol) in tetrahydrofuran (320 mL) was added a 1.6 M solution of n-butyllithium in hexane (5.4 mL, 8.6 mmol). After stirring at −78° C. for 1 hour, carbon dioxide gas was slowly bubbled through the reaction for 1.5 hours. The mixture was then allowed to warm to −10° C., quenched with the addition of water and partitioned between ethyl acetate and water. The aqueous phase was acidified with the addition of 1 N hydrochloric acid and extracted with ethyl acetate. The combined extracts were dried ($Na_2SO_4$) and concentrated to afford 4-(2-((tert-butoxycarbonyl)amino)propan-2-yl)benzoic acid as a white solid (1.20 g, 75%). To a stirred solution of this intermediate (1.20 g, 4.30 mmol) in tetrahydrofuran (20 mL) was added carbonyl diimidazole (1.05 g, 6.44 mmol) and, 1 hour later, 1-phenylpiperazine (1.05 g, 6.44 mmol). The reaction was stirred for an additional 2 hours before diluting with ethyl acetate and washing with, in order, aqueous citric acid solution, water and aqueous sodium carbonate solution. The organic layer was dried ($Na_2SO_4$) and concentrated. The crude material was purified by flash chromatography over silica using a hexane/ethyl acetate gradient to afford tert-butyl (2-(4-(4-phenylpiperazine-1-carbonyl)phenyl)propan-2-yl)carbamate as a white solid (1.23 g, 68%). To a stirred solution of this compound (1.20 g, 2.84 mmol) in methylene chloride (8 mL) was added trifluoroacetic acid (5 mL). After 2 hours the reaction was concentrated and partitioned between aqueous 4 N sodium hydroxide solution and ethyl acetate. The organic layer was combined with additional ethyl acetate extracts, washed with brine, dried ($Na_2SO_4$) and concentrated to afford (4-(2-aminopropan-2-yl)phenyl)(4-phenylpiperazin-1-yl)methanone as a white solid (0.850 g, 93%). To a stirred suspension of this intermediate (0.200 g, 0.618 mmol) in water (3 mL) and concentrated hydrochloric acid (0.3 mL) was added toluene (3 mL). The mixture was cooled (0° C.) and treated with, simultaneously over 1 hour, solutions of triphosgene (0.275 g, 0.928 mmol) in toluene (3 mL) and saturated, aqueous sodium bicarbonate (5 mL). Following the additions, the reaction was stirred for an additional 30 minutes before the upper toluene layer was removed and dried ($Na_2SO_4$). At the same time, a stirred solution of quinuclidin-3-ol (0.200 g, 0.573 mmol) in tetrahydrofuran (2 mL) was treated with sodium hydride (60% dispersion in mineral oil; 0.046 g, 1.15 mmol). This mixture was stirred for 1 hour and then added to the solution of crude isocyanate in toluene. The reaction was stirred overnight, quenched with the addition of an aqueous ammonium chloride solution (10 mL) and extracted with 4:1 (v/v) chloroform/isopropanol. The combined extracts were dried ($Na_2SO_4$) and concentrated. The residue was purified by flash chromatography over reversed phase silica to afford the title compound as a white solid (0.110 g, 37%). $^1$H NMR (500 MHz, $CDCl_3$) δ 7.48-7.42 (m, 4H), 7.32-7.28 (m, 2H), 6.96-6.91 (m, 3H), 5.18 (s, 1H), 4.65-4.63 (m, 1H), 3.94-3.64 (m, 4H), 3.20-2.71 (m, 9H), 2.32-1.86 (m, 3H), 1.68-1.42 (m, 9H) ppm. $^{13}$C NMR (125 MHz, $CDCl_3$) δ 170.3, 154.5, 150.9, 148.9, 133.8, 129.2, 127.3, 125.0, 120.6, 116.7, 71.1, 55.6, 55.2, 49.7, 47.3, 46.4, 42.2, 29.6, 25.4, 24.5, 19.5 ppm. Purity: >99% (214 & 254 nm) LCMS; retention time: 1.25 min; (M+1) 477.2.

Example 305

N-(2-(4-(4-(Methylcarbamoyl)phenoxy)phenyl)propan-2-yl)-1,4-diazabicyclo[3.2.2]nonane-4-carboxamide Exchanging quinuclidin-3-ol for Intermediate 3, the reaction sequence outlined in Example 304 was used to prepare the title compound. $^1$H NMR (500 MHz, $CDCl_3$) δ 7.47-7.46 (d, J=8.0 Hz, 2H), 7.43-7.41 (d, J=8.0 Hz, 2H), 7.32-7.29 (m, 2H), 6.96-6.91 (m, 3H), 5.11 (s, 1H), 4.80-4.77 (m, 1H), 3.94-3.65 (m, 4H), 3.25-2.76 (m, 10H), 2.07-1.55 (m, 13H) ppm. $^{13}$C NMR (125 MHz, $CDCl_3$) δ 170.4, 154.1, 150.9, 149.0, 133.7, 129.3, 127.3, 125.0, 120.6, 116.7, 78.4, 55.1, 51.7, 50.0, 48.2, 45.0, 42.2, 33.6, 30.6, 29.7, 29.5, 24.8, 22.1 ppm. Purity: >98% (214 & 254 nm) LCMS; retention time: 1.25 min; (M+H$^+$) 491.2.

Example 306

1-(3-Ethylquinuclidin-3-yl)-3-(2-(4-(4-phenylpiperazine-1-carbonyl)phenyl)propan-2-yl)urea Exchanging quinuclidin-3-ol for Intermediate 2, the reaction sequence outlined in Example 304 was used to prepare the title compound. $^1$H NMR (500 MHz, $CDCl_3$) δ 7.52-7.50 (d, J=8.0 Hz, 2H), 7.43-7.42 (d, J=8.5 Hz, 2H), 7.32-7.29 (m, 2H), 6.96-6.92 (m, 3H), 5.11 (s, 1H), 4.54 (br s, 1H), 3.94-3.63 (m, 4H), 3.27-3.13 (m, 4H), 2.77-2.69 (m, 6H), 2.03-1.80 (m, 3H), 1.69-1.30 (m, 10H), 0.73 (t, J=7.0 Hz, 3H) ppm. $^{13}$C NMR (125 MHz, $CDCl_3$) δ 170.2, 156.6, 150.8, 149.4, 133.9, 129.3, 127.4, 125.6, 120.7, 116.8, 62.9, 54.7, 49.7, 47.7, 46.7, 46.6, 42.2, 30.5, 28.1, 22.6, 22.3, 8.0 ppm. Purity: >99% (214 & 254 nm) LCMS; retention time: 1.16 min; (M+H$^+$) 504.3.

Example 307

Quinuclidin-3-yl 2-(4-(6-(2-methoxyethoxy)pyridin-3-yl)phenyl)propan-2-ylcarbamate To a stirred solution of 5-bromopyridin-2-ol (3.00 g, 17.2 mmol) in N,N-dimethylformamide (30 mL) was added 1-chloro-2-methoxyethane (2.45 g, 26.0 mmol) and potassium carbonate (4.80 g, 34.7 mmol. The reaction was heated overnight at 90° C. for 8 hours, cooled to room temperature and diluted with water. The mixture was extracted with ethyl acetate and the combined extracts were washed with brine, dried ($Na_2SO_4$) and concentrated. The residue was purified by flash chromatography over silica using a hexane/ethyl acetate gradient to afford 5-bromo-2-(2-methoxyethoxy)pyridine as a light yellow solid (1.70 g, 43%). This compound and ethyl 2-methyl-2-(4-(4,4,5,5-tetramethyl-1,3,2-dioxaborolan-2-yl)phenyl)propanoate were reacted according to General Procedure F to generate to afford ethyl 2-(4-(6-(2-methoxyethoxy)pyridin-3-yl)phenyl)-2-methylpropanoate. To a stirred solution of this intermediate (0.800 g, 2.43 mmol) in 1:1 (v/v) water/methanol (10 mL) was added solid sodium hydroxide (0.300 g, 7.50 mmol). After heating at 88° C. for 2 hours, the reaction was concentrated and taken up in water. The solution was made acidic (pH~6) with 1 N hydrochloric acid and extracted with ethyl acetate. The combined extracts were washed with brine, dried (Na$_2$SO$_4$) and concentrated to afford 2-(4-(6-(2-methoxyethoxy)pyridin-3-yl)phenyl)-2-methylpropanoic acid as a yellow solid (0.600 g, 78%). This compound was used without purification and reacted with quinuclidin-3-ol according to General Procedure I to generate the title compound as a yellow solid. $^1$H NMR (500 MHz, CDCl$_3$) δ 7.63-7.61 (dd, J=9.0 Hz & 2.0 Hz, 1H), 7.57-7.57 (d, J=2.5 Hz, 1H), 7.47-7.45 (d, J=8.5 Hz, 2H), 7.39-7.37 (d, J=8.0 Hz, 2H), 6.66-6.64 (d, J=9.0 Hz, 1H), 5.20 (s, 1H), 4.64-4.63 (m, 1H), 4.19 (t, J=5.0 Hz, 1H), 3.71 (t, J=5.0 Hz, 1H), 3.34 (s, 1H), 3.17-2.62 (m, 6H), 2.18-1.40 (m, 11H) ppm. $^{13}$C NMR (125 MHz, CDCl$_3$) δ 161.9, 154.4, 146.0, 139.4, 136.3, 134.9, 125.8, 125.5, 120.5, 119.2, 71.0, 70.4, 59.0, 55.6, 55.0, 50.0, 47.4, 46.4, 30.9, 29.6, 25.4, 24.6, 19.5 ppm. Purity: >96% (214 & 254 nm) LCMS; retention time: 1.66 min; (M+H$^+$) 440.3.

Example 308

Quinuclidin-3-yl 2-(4-(5-(2-methoxyethoxy)pyridin-2-yl)phenyl)propan-2-ylcarbamate To a stirred solution of 6-chloropyridin-3-ol (3.00 g, 23.0 mmol) in N,N-dimethylformamide (30 mL) was added 1-chloro-2-methoxyethane (3.30 g, 34.5 mmol), potassium carbonate (6.40 g, 46.0 mmol) and potassium iodide (0.200 g, 1.20 mmol). The reaction was heated overnight at 100° C., cooled to room temperature and diluted with water. The mixture was extracted with ethyl acetate and the combined extracts were washed with brine, dried (Na$_2$SO$_4$) and concentrated. The residue was purified by flash chromatography over silica using a hexane/ethyl acetate gradient to afford 2-chloro-5-(2-methoxyethoxy)pyridine as a yellow oil (3.80 g, 88%). This compound (0.570 g, 3.00 mmol, ethyl 2-methyl-2-(4-(4,4,5,5-tetramethyl-1,3,2-dioxaborolan-2-yl)phenyl)propanoate (1.10 g, 3.60 mmol), potassium carbonate (1.20 g, 8.68 mmol), [1,1'-bis(diphenylphosphino)ferrocene]dichloropalladium(II) (0.110 g, 0.150 mmol) and 5:1 (v/v) 1,4-dioxane/water (3 mL) were loaded into a microwave reaction vessel. The reaction was stirred and heated (130° C.) under microwave irradiation for 2 hours. After cooling, the reaction was diluted with water and extracted with ethyl acetate. The combined extracts were washed with brine, dried (Na$_2$SO$_4$) and concentrated. The residue was purified by flash chromatography over silica using a hexane/ethyl acetate eluant to afford ethyl 2-(4-(5-(2-methoxyethoxy)pyridin-2-yl)phenyl)-2-methylpropanoate as a yellow solid (0.520 g, 52%). To a stirred solution of this intermediate (0.520 g, 1.58 mmol) in a mixture of water (3 mL), methanol (4 mL) and tetrahydrofuran (4 mL) was added solid sodium hydroxide (0.253 g, 6.32 mmol). After stirring overnight, the reaction was concentrated and taken up in water. The solution was made acidic (pH~6) with 1 N hydrochloric acid and extracted with ethyl acetate. The combined extracts were washed with brine, dried (Na$_2$SO$_4$) and concentrated to afford 2-(4-(5-(2-methoxyethoxy)pyridin-2-yl)phenyl)-2-methylpropanoic acid as a white solid (0.500 g, 100%). This compound was used without purification and reacted with quinuclidin-3-ol according to General Procedure I to generate the title compound as a yellow solid. $^1$H NMR (500 MHz, CDCl$_3$) δ 8.33-8.32 (d, J=2.5 Hz, 1H), 7.82-7.80 (d, J=8.5 Hz, 2H), 7.57-7.55 (d, J=9.0 Hz, 1H), 7.41-7.40 (d, J=8.0 Hz, 2H), 7.22-7.20 (m, 1H), 5.24 (s, 1H), 4.55 (m, 1H), 4.13 (t, J=4.5 Hz, 2H), 3.71 (t, J=4.5 Hz, 2H), 3.39 (s, 3H), 3.09-1.97 (m, 7H), 1.90-0.99 (m, 10H) ppm. $^{13}$C NMR (125 MHz, CDCl$_3$) δ 154.5, 154.0, 150.0, 147.1, 137.5, 137.4, 126.4, 125.1, 122.1, 120.6, 70.9, 67.8, 59.3, 55.6, 55.1, 47.4, 46.4, 29.7, 29.5, 29.2, 25.4, 24.5, 19.5 ppm. Purity: >96% (214 & 254 nm) LCMS; retention time: 1.09 min; (M+H$^+$) 440.2.

Example 309

Quinuclidin-3-yl 2-(3-(5-(2-methoxyethoxy)pyridin-2-yl)phenyl)propan-2-ylcarbamate Exchanging ethyl 2-methyl-2-(4-(4,4,5,5-tetramethyl-1,3,2-dioxaborolan-2-yl)phenyl)propanoate for ethyl 2-methyl-2-(3-(4,4,5,5-tetramethyl-1,3,2-dioxaborolan-2-yl)phenyl)propanoate, the reaction sequence outlined in Example 304 was used to prepare 2-(3-(5-(2-methoxyethoxy)pyridin-2-yl)phenyl)-2-methylpropanoic acid. This compound was reacted with quinuclidin-3-ol according to General Procedure I to generate the title compound. $^1$H NMR (500 MHz, CDCl$_3$) δ 8.41-8.41 (d, J=3.0 Hz, 1H), 8.01 (s, 1H), 7.75-7.74 (d, J=11.5 Hz, 1H), 7.65-7.63 (d, J=9.0 Hz, 1H), 7.43-7.39 (m, 2H), 7.31-7.29 (dd, J=9.0 Hz & 3.0 Hz, 1H), 5.20 (s, 1H), 4.62 (s, 1H), 4.21 (t, J=4.5 Hz, 2H), 3.79 (t, J=4.5 Hz, 2H), 3.48 (s, 3H), 3.17-2.45 (m, 6H), 2.03-0.99 (m, 11H) ppm. $^{13}$C NMR (125 MHz, CDCl$_3$) δ 154.1, 150.4, 148.3, 147.5, 139.2, 137.5, 128.7, 124.8, 123.0, 122.2, 121.0, 70.9, 67.8, 59.3, 55.6, 55.4, 47.4, 46.4, 46.3, 29.5, 29.3, 25.4, 24.6, 19.5 ppm. Purity: >99% (214 & 254 nm) LCMS; retention time: 1.89 min; (M+H$^+$) 440.3.

Example 310

1-Azabicyclo[3.2.2]nonan-4-yl 2-(4-(5-(2-methoxyethoxy)pyridin-2-yl)phenyl)propan-2-ylcarbamate Using General Procedure I and the reaction inputs 2-(4-(5-(2-methoxyethoxy)pyridin-2-yl)phenyl)-2-methylpropanoic acid (prepared as described in Example 308) and Intermediate 3, the title compound was prepared. $^1$H NMR (500 MHz, CDCl$_3$) δ 8.40-8.40 (d, J=2.8 Hz, 1H), 7.89-7.87 (d, J=8.4 Hz, 2H), 7.64-7.62 (d, J=8.8 Hz, 1H), 7.48-7.46 (d, J=8.0 Hz, 2H), 7.30-7.27 (m, 1H), 5.20 (s, 1H), 4.79-4.76 (m, 1H), 4.20 (t, J=4.4 Hz, 2H), 3.78 (t, J=4.4 Hz, 2H), 3.46 (s, 3H), 3.07-2.71 (m, 6H), 2.37 (m, 1H), 2.03-1.52 (m, 12H) ppm. $^{13}$C NMR (125 MHz, CDCl$_3$) δ 154.3, 154.0, 150.1, 147.2, 137.5, 137.4, 126.3, 125.2, 122.2, 120.6, 78.2, 70.9, 67.8, 59.3, 55.0, 51.7, 48.2, 45.1, 33.6, 30.6, 29.4, 24.8, 22.2 ppm. Purity: >99% LCMS (214 & 254 nm) LCMS; retention time: 1.10 min; (M+H$^+$) 454.2.

Example 311

1-Azabicyclo[3.2.2]nonan-4-yl 2-(3-(5-(2-methoxyethoxy)pyridin-2-yl)phenyl)propan-2-ylcarbamate Using General Procedure I and the reaction inputs 2-(3-(5-(2-methoxyethoxy)pyridin-2-yl)phenyl)-2-methylpropanoic acid (prepared as described in Example 309) and Intermediate 3, the title compound was prepared. $^1$H NMR (500 MHz, CDCl$_3$) δ 8.41-8.41 (d, J=3.0 Hz, 1H), 8.00 (s, 1H), 7.75-7.74 (m, 1H), 7.65-7.63 (d, J=8.5 Hz, 1H), 7.41-7.40 (m, 2H), 7.31-7.29 (m, 1H), 5.16 (s, 1H), 4.77 (m, 1H), 4.22 (t, J=4.5 Hz, 2H), 3.80 (t, J=4.5 Hz, 2H), 3.48 (s, 3H), 3.10-2.62 (m, 6H), 2.16-1.53 (m, 13H) ppm. $^{13}$C NMR (125 MHz, CDCl$_3$) δ 154.3, 154.1, 150.4, 147.6, 146.5, 139.1, 137.5, 128.7, 124.774, 123.056, 122.156, 120.914, 77.938, 70.896, 67.819, 59.309, 55.355, 51.605, 50.7, 48.1, 45.1, 33.5, 30.4, 29.4, 24.6, 22.0 ppm. Purity: >96% (214 & 254 nm) LCMS; retention time: 0.94 min; (M+H$^+$) 454.3.

Example 312

Quinuclidin-3-yl (2-(3-(6-(3-methoxypropoxy) pyridazin-3-yl)phenyl)propan-2-yl)carbamate To a stirred solution of 3-methoxy-1-propanol (5.0 mL, 52 mmol) in N,N-dimethylformamide (300 mL) was added sodium hydride (60% dispersion in mineral oil; 3.14 g, 78.4 mmol). After 2 hours, 3,6-dichloropyridazine (7.79 g, 52.3 mmol) was added. The reaction was stirred at room temperature overnight, concentrated and partitioned between chloroform and water. The organic layer was washed with aqueous sodium bicarbonate solution and brine, dried (Na$_2$SO$_4$) and concentrated. The residue was purified by flash chromatography over silica using a hexane/ethyl acetate gradient to afford 3-chloro-6-(3-methoxypropoxy) pyridazine as a pale yellow oil (8.05 g, 76%). A stirred suspension of this compound (1.77 g, 5.58 mmol), ethyl 2-methyl-2-(3-(4,4,5,5-tetramethyl-1,3,2-dioxaborolan-2-yl)phenyl)propanoate (1.77 g, 5.58 mmol) and potassium carbonate (4.90 g, 35.5 mmol) in 4:1 (v/v) N,N-dimethylformamide/water (75 mL) was deoxygenated by bubbling nitrogen through the mixture for several minutes. Bis(triphenylphosphine)palladium(II) dichloride (0.089 g, 0.127 mmol) was added and the reaction was heated at 100° C. for 6 hours. At this time, the reaction was concentrated and partitioned between ethyl acetate and water. The organic layer was washed with aqueous sodium bicarbonate solution and brine, dried (Na$_2$SO$_4$) and concentrated. The crude material was purified by flash chromatography over silica using a hexane/ethyl acetate gradient to afford ethyl 2-(3-(6-(3-methoxypropoxy)pyridazin-3-yl)phenyl)-2-methylpropanoate as a colorless oil (1.58 g, 87%). To a stirred solution of this compound (1.58 g, 4.41 mmol) in 1:1:1 (v/v/v) tetrahydrofuran/ethanol/water (30 mL) was added lithium hydroxide monohydrate (0.925 g, 22.0 mmol). After heating at reflux overnight, the reaction was cooled and concentrated. The residue was dissolved in water and washed with diethyl ether. The aqueous layer was treated with 1.0 N hydrochloric acid (22 mL) and extracted with ethyl acetate. The combined extracts were dried (Na$_2$SO$_4$) and concentrated to afford 2-(3-(6-(3-methoxypropoxy) pyridazin-3-yl)phenyl)-2-methylpropanoic acid as a colorless solid (1.41 g, 97%). This compound and quinuclidin-3-ol were reacted according to General Procedure H to generate the title compound as a pale tan solid. $^1$H NMR (400 MHz, DMSO-d$_6$) δ 8.20-7.99 (m, 2H), 7.91-7.76 (m, 1H), 7.67-7.34 (m, 3H), 7.30 (d, J=9.2 Hz, 1H), 4.53 (t, J=6.4 Hz, 2H), 4.47-4.34 (m, 1H), 3.51 (t, J=6.2 Hz, 2H), 3.27 (s, 3H), 3.11-2.15 (m, 6H), 2.13-1.10 (m, 13H) ppm. $^{13}$C NMR (100 MHz, DMSO-d$_6$) δ 163.9, 154.8, 154.6, 149.0, 135.6, 128.6, 127.8, 125.8, 124.0, 122.8, 117.6, 70.0, 68.5, 64.1, 57.9, 55.3, 54.5, 46.9, 45.9, 29.4, 28.6, 25.2, 24.2, 19.2 ppm. Purity: 97.8%, 98.7% (210 & 254 nm) UPLCMS; retention time: 0.76 min; (M+H$^+$) 455.3.

Example 313

1-Azabicyclo[3.2.2]nonan-4-yl (2-(3-(6-(3-methoxypropoxy)pyridazin-3-yl)phenyl)propan-2-yl)carbamate Using General Procedure H and the reaction inputs 2-(3-(6-(3-methoxypropoxy)pyridazin-3-yl)phenyl)-2-methyl- propanoic acid (prepared as described in Example 312) and Intermediate 3, the title compound was prepared. $^1$H NMR (400 MHz, DMSO-d$_6$) δ 8.10 (d, J=9.3 Hz, 1H), 8.06 (br s, 1H), 7.98-7.74 (m, 1H), 7.53 (br s, 1H), 7.46-7.35 (m, 2H), 7.30 (d, J=9.3 Hz, 1H), 4.64-4.48 (m, 3H), 3.51 (t, J=6.3 Hz, 2H), 3.27 (s, 3H), 3.01-2.36 (m, 6H), 2.04 (quin, J=6.4 Hz, 2H), 1.97-1.28 (m, 13H) ppm. $^{13}$C NMR (100 MHz, DMSO-d$_6$) δ 163.9, 154.8, 154.3, 149.0, 135.6, 128.5, 127.7, 125.8, 124.0, 122.8, 117.6, 77.1, 68.5, 64.1, 57.9, 54.4, 51.4, 47.7, 44.6, 33.4, 30.6, 29.6, 28.6, 24.7, 22.2 ppm. Purity: >99.9%, 99.5% (210 & 254 nm) UPLCMS; retention time: 0.76 min; (M+H$^+$) 469.4.

Example 314

N-(2-(3-(6-(3-Methoxypropoxy)pyridazin-3-yl)phenyl)propan-2-yl)-1,4-diazabicyclo[3.2.2]nonane-4-carboxamide Using General Procedure H and the reaction inputs 2-(3-(6-(3-methoxypropoxy)pyridazin-3-yl)phenyl)-2-methylpropanoic acid (prepared as described in Example 312) and Intermediate 6, the title compound was prepared. $^1$H NMR (400 MHz, DMSO-d$_6$) δ 8.09 (d, J=9.3 Hz, 1H), 8.07-8.03 (m, 1H), 7.82-7.71 (m, 1H), 7.48-7.34 (m, 2H), 7.29 (d, J=9.3 Hz, 1H), 6.21 (br s, 1H), 4.53 (t, J=6.5 Hz, 2H), 4.22-4.14 (m, 1H), 3.61-3.44 (m, 4H), 3.27 (s, 3H), 2.96-2.67 (m, 6H), 2.04 (quin, J=6.4 Hz, 2H), 1.95-1.81 (m, 2H), 1.66-1.49 (m, 8H) ppm. $^{13}$C NMR (100 MHz, DMSO-d$_6$) δ 163.9, 155.4, 155.0, 150.4, 135.3, 128.3, 127.7, 125.9, 123.5, 122.8, 117.6, 68.5, 64.1, 57.9, 57.5, 54.8, 46.6, 45.9, 41.5, 30.2, 28.6, 27.0 ppm. Purity: >99.9%, 99.1% (210 & 254 nm) UPLCMS; retention time: 0.70 min; (M+H$^+$) 454.4.

Example 315

Quinuclidin-3-yl (2-(3-(5-(3-methoxypropoxy) pyrazin-2-yl)phenyl)propan-2-yl)carbamate To a stirred solution of 3-methoxy-1-propanol (3.2 mL, 34 mmol) in N,N-dimethylformamide (200 mL) was added sodium hydride (60% dispersion in mineral oil; 2.02 g, 50.6 mmol). After 30 minutes, 2,5-dichloropyrazine (5.03 g, 33.7 mmol) was added. The reaction was stirred at room temperature overnight, concentrated and partitioned between ethyl acetate and water. The organic layer was washed with aqueous sodium bicarbonate solution and brine, dried (Na$_2$SO$_4$) and concentrated. The residue was purified by flash chromatography over silica using a hexane/ethyl acetate gradient to afford 2-chloro-5-(3-methoxypropoxy) pyrazine as a colorless oil (4.47 g, 65%). A stirred suspension of this compound (1.00 g, 4.94 mmol), ethyl 2-methyl-2-(3-(4,4,5,5-tetramethyl-1,3,2-dioxaborolan-2-yl)phenyl) propanoate (1.73 g, 5.43 mmol) and potassium carbonate (4.78 g, 34.6 mmol) in 4:1 (v/v) N,N-dimethylformamide/water (75 mL) was deoxygenated by bubbling nitrogen through the mixture for several minutes. Bis(triphenylphosphine)palladium(II) dichloride (0.087 g, 0.124 mmol) was added and the reaction was heated at 100° C. for 6 hours. At this time, the reaction was concentrated and partitioned between ethyl acetate and water. The organic layer was washed with aqueous sodium bicarbonate solution and brine, dried (Na$_2$SO$_4$) and concentrated. The crude material was purified by flash chromatography over silica using a hexane/ethyl acetate gradient to afford ethyl 2-(3-(5-(3-methoxypropoxy)pyrazin-2-yl)phenyl)-2-methylpropanoate as a colorless oil (1.37 g, 77%). To a stirred solution of this compound (1.37 g, 3.81 mmol) in 1:1:1 (v/v/v) tetrahydrofuran/ethanol/water (25 mL) was added lithium hydroxide monohydrate (0.800 g, 19.1 mmol). After heating at reflux overnight, the reaction was cooled and concentrated. The residue was dissolved in water and washed with diethyl ether. The aqueous layer was treated with 1.0 N hydrochloric acid (19 mL) and extracted with ethyl acetate. The combined extracts were dried ($Na_2SO_4$) and concentrated to afford 2-(3-(5-(3-methoxypropoxy)pyrazin-2-yl)phenyl)-2-methylpropanoic acid as a colorless solid (1.20 g, 95%). This compound and quinuclidin-3-ol were reacted according to General Procedure H to generate the title compound as a pale amber solid. $^1$H NMR (400 MHz, DMSO-$d_6$) δ 8.74 (d, J=1.3 Hz, 1H), 8.36 (br s, 1H), 8.03 (br s, 1H), 7.86-7.77 (m, 1H), 7.57 (br s, 1H), 7.49-7.32 (m, 2H), 4.44-4.35 (m, 3H), 3.49 (t, J=6.3 Hz, 2H), 3.26 (s, 3H), 3.06-2.23 (m, 6H), 2.00 (quin, J=6.4 Hz, 2H), 1.95-1.19 (m, 10H) ppm. $^{13}$C NMR (100 MHz, DMSO-$d_6$) δ 158.9, 154.6, 149.1, 144.4, 137.5, 135.5, 134.2, 128.5, 125.2, 123.3, 122.3, 70.1, 68.5, 63.5, 57.9, 55.4, 54.5, 46.9, 45.9, 29.5, 28.6, 25.2, 24.2, 19.2 ppm. Purity: >99.9%, 98.7% (210 & 254 nm) UPLCMS; retention time: 0.84 min; (M+H$^+$) 455.4.

Example 316

1-Azabicyclo[3.2.2]nonan-4-yl (2-(3-(5-(3-methoxypropoxy)pyrazin-2-yl)phenyl)propan-2-yl)carbamate Using General Procedure H and the reaction inputs 2-(3-(5-(3-methoxypropoxy)pyrazin-2-yl)phenyl)-2-methylpropanoic acid (prepared as described in Example 315) and Intermediate 3, the title compound was prepared. $^1$H NMR (400 MHz, DMSO-$d_6$) δ 8.73 (d, J=1.3 Hz, 1H), 8.40-8.33 (m, 1H), 8.00 (br s, 1H), 7.85-7.76 (m, 1H), 7.52 (br s, 1H), 7.46-7.33 (m, 2H), 4.64-4.53 (s, 1H), 4.40 (t, J=6.5 Hz, 2H), 3.49 (t, J=6.3 Hz, 2H), 3.26 (s, 3H), 3.00-2.33 (m, 6H), 2.00 (quin, J=6.5 Hz, 2H), 1.95-1.26 (m, 13H) ppm. $^{13}$C NMR (100 MHz, DMSO-$d_6$) δ158.8, 154.2, 149.0, 144.5, 137.5, 135.5, 134.2, 128.5, 125.2, 123.3, 122.4, 77.1, 68.5, 63.5, 57.9, 54.4, 51.4, 47.9, 44.7, 33.5, 30.6, 29.7, 29.5, 28.6, 24.7, 22.2 ppm. Purity: >99.9%, >99.9% (210 & 254 nm) UPLCMS; retention time: 0.85 min; (M+H$^+$) 469.4.

Example 317

N-(2-(3-(5-(3-Methoxypropoxy)pyrazin-2-yl)phenyl) propan-2-yl)-1,4-diazabicyclo[3.2.2]nonane-4-carboxamide Using General Procedure H and the reaction inputs 2-(3-(5-(3-methoxypropoxy)pyrazin-2-yl)phenyl)-2-methylpropanoic acid (prepared as described in Example 315) and Intermediate 6, the title compound was prepared. $^1$H NMR (400 MHz, DMSO-$d_6$) δ 8.72 (d, J=1.4 Hz, 1H), 8.35 (d, J=1.4 Hz, 1H), 7.98 (s, 1H), 7.80-7.74 (m, 1H), 7.37 (d, J=4.8 Hz, 2H), 6.19 (br s, 1H), 4.39 (t, J=6.5 Hz, 2H), 4.18 (s, 1H), 3.49 (t, J=6.2 Hz, 4H), 3.26 (s, 3H), 3.04-2.66 (m, 6H), 2.00 (quin, J=6.4 Hz, 2H), 1.95-1.82 (m, 2H), 1.66-1.49 (m, 8H) ppm. $^{13}$C NMR (100 MHz, DMSO-$d_6$) δ 158.8, 155.4, 150.4, 144.7, 137.4, 135.3, 134.1, 128.3, 125.2, 122.9, 122.4, 68.5, 63.5, 57.9, 57.6, 54.8, 46.7, 45.9, 41.5, 30.2, 28.6, 27.0 ppm. Purity: 95.4%, 97.7% (210 & 254 nm) UPLCMS; retention time: 0.78 min; (M+H$^+$) 454.4.

Example 318

Quinuclidin-3-yl (2-(3-(6-ethoxypyridazin-3-yl)phenyl)propan-2-yl)carbamate

Exchanging 3-methoxy-1-propanol for ethanol, the reaction sequence outlined in Example 312 was used to prepare the title compound. $^1$H NMR (400 MHz, DMSO-$d_6$) δ 8.17-8.02 (m, 2H), 7.87-7.80 (m, 1H), 7.65-7.34 (m, 3H), 7.28 (d, J=9.3 Hz, 1H), 4.54 (q, J=7.0 Hz, 2H), 4.45-4.33 (m, 1H), 3.12-2.18 (m, 6H), 2.05-1.10 (m, 14H) ppm. $^{13}$C NMR (100 MHz, DMSO-$d_6$) δ 163.9, 154.7, 154.6, 149.0, 135.6, 128.6, 127.7, 125.8, 124.0, 122.7, 117.6, 70.1, 62.7, 55.3, 54.5, 46.9, 45.9, 29.4, 25.2, 24.2, 19.2, 14.4 ppm. Purity: >99.9%, 99.5% (210 & 254 nm) UPLCMS; retention time: 0.78 min; (M+H$^+$) 411.3.

Example 319

1-Azabicyclo[3.2.2]nonan-4-yl (2-(3-(6-ethoxypyridazin-3-yl)phenyl)propan-2-yl)carbamate Exchanging 3-methoxy-1-propanol for ethanol and quinuclidin-3-ol for Intermediate 3, the reaction sequence outlined in Example 312 was used to prepare the title compound. $^1$H NMR (400 MHz, DMSO-$d_6$) δ 8.10 (d, J=9.3 Hz, 1H), 8.07 (br s, 1H), 7.86-7.79 (m, 1H), 7.60-7.37 (m, 3H), 7.28 (d, J=9.3 Hz, 1H), 4.64-4.55 (m, 1H), 4.54 (q, J=7.0 Hz, 2H), 3.01-2.34 (m, 6H), 1.98-1.21 (m, 3H) ppm. $^{13}$C NMR (100 MHz, DMSO-$d_6$) δ 163.9, 154.7, 154.2, 149.1, 135.6, 128.5, 127.7, 125.8, 123.9, 122.8, 117.5, 77.1, 62.7, 54.4, 51.4, 47.6, 44.7, 33.4, 30.6, 29.6, 24.7, 22.1, 14.4 ppm. Purity: >99.9%, 99.4% (210 & 254 nm) UPLCMS; retention time: 0.79 min; (M+H$^+$) 425.3.

Example 320

Quinuclidin-3-yl (2-(4-(5-(3-methoxypropoxy) pyrazin-2-yl)phenyl)propan-2-yl)carbamate Exchanging ethyl 2-methyl-2-(3-(4,4,5,5-tetramethyl-1,3,2-dioxaborolan-2-yl)phenyl)propanoate for ethyl 2-methyl-2-(4-(4,4,5,5-tetramethyl-1,3,2-dioxaborolan-2-yl)phenyl) propanoate, the reaction sequence outlined in Example 315 was used to prepare the title compound. $^1$H NMR (400 MHz, DMSO-$d_6$) δ 8.74 (d, J=1.2 Hz, 1H), 8.35 (d, J=1.3 Hz, 1H), 7.93 (d, J=7.9 Hz, 2H), 7.56 (br s, 1H), 7.45 (d, J=7.5 Hz, 2H), 4.55-4.30 (m, 3H), 3.49 (t, J=6.3 Hz, 2H), 3.26 (s, 3H), 3.08-2.24 (m, 6H), 2.00 (quin, J=6.4 Hz, 2H), 1.92-1.19 (m, 11H) ppm. $^{13}$C NMR (100 MHz, DMSO-$d_6$) δ 158.8, 154.5, 148.9, 144.2, 137.3, 134.2, 133.7, 125.5, 125.2, 70.0, 68.5, 63.4, 57.9, 55.4, 54.3, 46.9, 45.9, 29.3, 28.6, 25.2, 24.2, 19.2 ppm. Purity: >99.9%, >99.9% (210 & 254 nm) UPLCMS; retention time: 0.86 min; (M+H$^+$) 455.4.

Example 321

1-Azabicyclo[3.2.2]nonan-4-yl (2-(4-(5-(3-methoxypropoxy)pyrazin-2-yl)phenyl)propan-2-yl)carbamate Exchanging ethyl 2-methyl-2-(3-(4,4,5,5-tetramethyl-1,3,2-dioxaborolan-2-yl)phenyl)propanoate for ethyl 2-methyl-2-(4-(4,4,5,5-tetramethyl-1,3,2-dioxaborolan-2-yl)phenyl) propanoate and quinuclidin-3-ol for Intermediate 3, the reaction sequence outlined in Example 315 was used to prepare the title compound. $^1$H NMR (400 MHz, DMSO-$d_6$) δ 8.74 (d, J=1.2 Hz, 1H), 8.35 (d, J=1.3 Hz, 1H), 7.92 (d, J=8.4 Hz, 2H), 7.51 (br s, 1H), 7.43 (d, J=8.2 Hz, 2H), 4.65-4.55 (m, 1H), 4.39 (t, J=6.5 Hz, 2H), 3.49 (t, J=6.3 Hz, 2H), 3.26 (s, 3H), 3.01-2.41 (m, 6H), 2.00 (quin, J=6.4 Hz, 2H), 1.95-1.30 (m, 13H) ppm. $^{13}$C NMR (100 MHz, DMSO-$d_6$) δ 158.8, 154.2, 148.9, 144.2, 137.3, 134.2, 133.6, 125.4, 125.3, 77.1, 68.5, 63.4, 57.9, 54.2, 51.4, 47.7, 44.6, 33.4, 30.6, 29.5, 28.6, 24.7, 22.2 ppm. Purity: 98.8%, >99.9% (210 & 254 nm) UPLCMS; retention time: 0.87 min; (M+H$^+$) 469.4.

Example 322

N-(2-(4-(5-(3-methoxypropoxy)pyrazin-2-yl)phenyl)propan-2-yl)-1,4-diazabicyclo[3.2.2]nonane-4-carboxamide Exchanging ethyl 2-methyl-2-(3-(4,4,5,5-tetramethyl-1,3,2-dioxaborolan-2-yl)phenyl)propanoate for ethyl 2-methyl-2-(4-(4,4,5,5-tetramethyl-1,3,2-dioxaborolan-2-yl)phenyl)propanoate and quinuclidin-3-ol for Intermediate 6, the reaction sequence outlined in Example 315 was used to prepare the title compound. $^1$H NMR (400 MHz, DMSO-d$_6$) δ 8.73 (d, J=1.4 Hz, 1H), 8.35 (d, J=1.4 Hz, 1H), 7.89 (d, J=8.5 Hz, 2H), 7.42 (d, J=8.5 Hz, 2H), 6.17 (s, 1H), 4.39 (t, J=6.5 Hz, 2H), 4.22-4.16 (m, 1H), 3.49 (t, J=6.2 Hz, 4H), 3.26 (s, 3H), 3.09-2.70 (m, 6H), 2.00 (quin, J=6.4 Hz, 2H), 1.94-1.82 (m, 2H), 1.65-1.49 (m, 8H) ppm. $^{13}$C NMR (100 MHz, DMSO-d$_6$) δ 158.7, 155.4, 150.3, 144.4, 137.2, 134.2, 133.1, 125.3, 125.2, 68.5, 63.4, 57.9, 57.5, 54.6, 46.6, 46.0, 41.5, 30.1, 28.6, 27.0 ppm. Purity: >99.9%, >99.9% (210 & 254 nm) UPLCMS; retention time: 0.80 min; (M+H$^+$) 454.4.

Example 323

Quinuclidin-3-yl (2-(3-(5-(3-methoxypropoxy)pyrimidin-2-yl)phenyl)propan-2-yl)carbamate To a stirred solution 2-chloropyrimidin-5-ol (5.04 g, 38.6 mmol) in N,N-dimethylformamide (25 mL) was added 1-bromo-3-methoxypropane (10.8 mL, 96.5 mmol) and potassium carbonate (12.26 g, 88.74 mmol). The mixture was heated at 60° C. overnight, concentrated and partitioned between ethyl acetate and aqueous sodium bicarbonate solution. The organic layer was washed with brine, dried (Na$_2$SO$_4$) and concentrated. The residue was purified by flash chromatography over silica using a hexane/ethyl acetate gradient to afford 2-chloro-5-(3-methoxypropoxy)pyrimidine as a white solid (4.90 g, 63%). This compound and ethyl 2-methyl-2-(3-(4,4,5,5-tetramethyl-1,3,2-dioxaborolan-2-yl)phenyl)propanoate were reacted according to General Procedure F to afford ethyl 2-(3-(5-(3-methoxypropoxy)pyrimidin-2-yl)phenyl)-2-methylpropanoate. To a stirred solution of this intermediate (1.93 g, 5.38 mmol) in 1:1:1 (v/v/v) tetrahydrofuran/ethanol/water (36 mL) was added lithium hydroxide monohydrate (1.13 g, 26.9 mmol). After heating at reflux overnight, the reaction was cooled and concentrated. The residue was dissolved in water and washed with diethyl ether. The aqueous layer was treated with 1.0 N hydrochloric acid (27 mL) and extracted with ethyl acetate. The combined extracts were dried (Na$_2$SO$_4$) and concentrated to afford 2-(3-(5-(3-methoxypropoxy)pyrimidin-2-yl)phenyl)-2-methylpropanoic acid as a colorless solid (1.49 g, 84%). This compound and quinuclidin-3-ol were reacted according to General Procedure H to generate the title compound as an off-white solid. $^1$H NMR (400 MHz, DMSO-d$_6$) δ 8.63 (br s, 2H), 8.36 (br s, 1H), 8.15-8.09 (m, 1H), 7.61 (br s, 1H), 7.50-7.37 (m, 2H), 4.44-4.35 (m, 1H), 4.24 (t, J=6.4 Hz, 2H), 3.50 (t, J=6.3 Hz, 2H), 3.26 (s, 3H), 3.07-2.23 (m, 6H), 2.00 (quin, J=6.4 Hz, 2H), 1.93-1.21 (m, 11H) ppm. $^{13}$C NMR (100 MHz, DMSO-d$_6$) δ 156.4, 154.6, 151.4, 148.7, 144.0, 136.7, 128.3, 126.3, 124.7, 123.5, 70.0, 68.2, 65.8, 58.0, 55.4, 54.4, 47.0, 45.9, 29.5, 28.8, 25.2, 24.2, 19.2 ppm. Purity: 96.8%, 97.9% (210 & 254 nm) UPLCMS; retention time: 0.79 min; (M+H$^+$) 455.4.

Example 324

1-Azabicyclo[3.2.2]nonan-4-yl (2-(3-(5-(3-methoxypropoxy)pyrimidin-2-yl)phenyl)propan-2-yl)carbamate Using General Procedure H and the reaction inputs 2-(3-(5-(3-methoxypropoxy)pyrimidin-2-yl)phenyl)-2-methylpropanoic acid (prepared as described in Example 323) and Intermediate 3, the title compound was prepared. $^1$H NMR (400 MHz, DMSO-d$_6$) δ 8.63 (s, 2H), 8.34 (br s, 1H), 8.15-8.09 (m, 1H), 7.50 (br s, 1H), 7.46-7.36 (m, 2H), 4.63-4.53 (m, 1H), 4.24 (t, J=6.4 Hz, 2H), 3.50 (t, J=6.3 Hz, 2H), 3.26 (s, 3H), 2.99-2.32 (m, 6H), 2.01 (quin, J=6.6 Hz, 2H), 1.96-1.29 (m, 11H) ppm. $^{13}$C NMR (100 MHz, DMSO-d$_6$) δ 156.5, 154.2, 151.4, 148.7, 144.0, 136.7, 128.2, 126.3, 124.6, 123.6, 77.1, 68.2, 65.8, 58.0, 54.3, 51.5, 47.7, 44.6, 33.4, 30.6, 29.7, 29.4, 28.8, 24.7, 22.2 ppm. Purity: 96.8%, 98.2% (210 & 254 nm) UPLCMS; retention time: 0.80 min; (M+H$^+$) 469.4.

Example 325

1-(3-Ethylquinuclidin-3-yl)-3-(4-(4-(2-methoxyethyl)phenyl)-2-methylbut-3-yn-2-yl)urea To a stirred solution of 1-bromo-4-(2-methoxyethyl)benzene (2.09 g, 9.73 mmol) in diisopropylamine (10 mL) was added copper(I) iodide (0.185 g, 0.973 mmol) and tert-butyl (2-methylbut-3-yn-2-yl)carbamate (2.14 g, 11.7 mmol). Nitrogen was bubbled through the mixture for several minutes and then bis(triphenylphosphine)palladium(II) dichloride (0.342 g, 0.487 mmol) was added. The reaction was heated at reflux overnight, diluted with ethyl acetate and water and filtered through a plug of Celite. The organic layer of the filtrate was washed with aqueous sodium bicarbonate solution and brine, dried (Na$_2$SO$_4$) and concentrated. The residue was purified by flash chromatography over silica using a hexane/ethyl acetate gradient to afford tert-butyl (4-(4-(2-methoxyethyl)phenyl)-2-methylbut-3-yn-2-yl)carbamate as an orange oil (2.22 g, 72%). To a stirred solution of this compound (2.22 g, 6.99 mmol) in 1,4-dioxane (20 mL) was added a 4 M solution of hydrogen chloride in 1,4-dioxane (20 mL). After overnight stirring, the reaction was concentrated and partitioned between 1 N hydrochloric acid and diethyl ether. The aqueous layer was made basic (pH~10) with the addition of concentrated ammonium hydroxide and extracted with ethyl acetate. The combined extracts were dried (Na$_2$SO$_4$) and concentrated to afford 4-(4-(2-methoxyethyl)phenyl)-2-methylbut-3-yn-2-amine as a yellow oil (1.07 g, 70%). This compound and Intermediate 2 were reacted according to General Procedure J to generate the title compound as a white solid. $^1$H NMR (400 MHz, DMSO-d$_6$) δ 7.28-7.16 (m, 4H), 5.99 (br s, 1H), 5.75 (br s, 1H), 3.52 (t, J=6.7 Hz, 2H), 3.23 (s, 3H), 2.80 (t, J=6.7 Hz, 2H), 2.77-2.50 (m, 6H), 2.00-1.86 (m, 2H), 1.86-1.66 (m, 2H), 1.66-1.47 (m, 7H), 1.44-1.20 (m, 2H), 0.73 (t, J=7.3 Hz, 3H) ppm. $^{13}$C NMR (100 MHz, DMSO-d$_6$) δ 156.8, 139.3, 131.0, 129.0, 120.5, 94.8, 79.3, 72.4, 62.7, 57.8, 53.4, 46.6, 46.4, 46.3, 35.1, 29.8, 29.8, 27.8, 27.7, 22.5, 22.2, 8.0 ppm. Purity: >99.9%, >99.9% (210 & 254 nm) UPLCMS; retention time: 0.86 min; (M+H$^+$) 398.5.

Example 326

1-(4-(4-(2-Methoxyethyl)phenyl)-2-methylbut-3-yn-2-yl)-3-(3-propylquinuclidin-3-yl)urea Using General Procedure J and the reaction inputs 4-(4-(2-methoxyethyl)phenyl)-2-methylbut-3-yn-2-amine (prepared as described in Example 325) and Intermediate 17, the title compound was prepared. $^1$H NMR (400 MHz, DMSO-$d_6$) δ 7.27-7.16 (m, 4H), 5.95 (br s, 1H), 5.73 (br s, 1H), 3.51 (t, J=6.8 Hz, 2H), 3.22 (s, 3H), 2.79 (t, J=6.8 Hz, 2H), 2.76-2.50 (m, 6H), 1.96-1.91 (m, 1H), 1.91-1.66 (m, 2H), 1.66-1.46 (m, 7H), 1.43-1.09 (m, 2H), 0.83 (t, J=7.3 Hz, 3H) ppm. $^{13}$C NMR (100 MHz, DMSO-$d_6$) δ 156.8, 139.3, 131.0, 128.9, 120.5, 94.8, 79.3, 72.4, 63.1, 57.8, 53.3, 46.6, 46.4, 46.3, 37.9, 35.1, 29.8, 29.7, 28.2, 22.6, 22.3, 16.7, 14.6 ppm. Purity: >99.9%, >99.9% (210 & 254 nm) UPLCMS; retention time: 0.91 min; (M+H$^+$) 412.6.

Example 327

1-(3-Ethylquinuclidin-3-yl)-3-(4-(4-(methoxymethyl)phenyl)-2-methylbut-3-yn-2-yl)urea Exchanging 1-bromo-4-(2-methoxyethyl)benzene for 1-bromo-4-(methoxymethyl)benzene, the reaction sequence outlined in Example 325 was used to prepare the title compound. $^1$H NMR (400 MHz, DMSO-$d_6$) δ 7.49-7.15 (m, 4H), 5.99 (br s, 1H), 5.74 (br s, 1H), 4.40 (s, 2H), 3.28 (s, 3H), 2.84-2.55 (m, 6H), 2.02-1.85 (m, 2H), 1.85-1.63 (m, 2H), 1.63-1.46 (m, 7H), 1.45-1.19 (m, 2H), 0.73 (t, J=7.3 Hz, 3H) ppm. $^{13}$C NMR (100 MHz, DMSO-$d_6$) δ 156.8, 138.3, 131.0, 127.5, 121.9, 95.2, 79.2, 73.1, 62.8, 57.6, 53.4, 46.6, 46.4, 46.3, 29.8, 29.7, 27.8, 27.7, 22.6, 22.2, 8.0 ppm. Purity: 100%, 100% (210 & 254 nm) UPLCMS; retention time: 0.82 min; (M+H$^+$) 384.5.

Example 328

1-(4-(4-(Methoxymethyl)phenyl)-2-methylbut-3-yn-2-yl)-3-(3-propylquinuclidin-3-yl)urea Exchanging 1-bromo-4-(2-methoxyethyl)benzene for 1-bromo-4-(methoxymethyl)benzene and Intermediate 2 for Intermediate 17, the reaction sequence outlined in Example 325 was used to prepare the title compound. $^1$H NMR (400 MHz, DMSO-$d_6$) δ 7.40-7.19 (m, 4H), 5.96 (br s, 1H), 5.72 (br s, 1H), 4.40 (s, 2H), 3.28 (s, 3H), 2.80-2.52 (m, 6H), 1.97-1.92 (m, 1H), 1.92-1.79 (m, 1H), 1.79-1.64 (m, 2H), 1.64-1.44 (m, 7H), 1.42-1.31 (m, 1H), 1.31-1.09 (m, 3H), 0.82 (t, J=7.3 Hz, 3H) ppm. $^{13}$C NMR (100 MHz, DMSO-$d_6$) δ 156.8, 138.3, 131.0, 127.5, 121.9, 95.2, 79.2, 73.1, 63.1, 57.5, 53.3, 46.6, 46.4, 46.3, 37.9, 29.8, 29.7, 28.2, 22.6, 22.3, 16.7, 14.6 ppm. Purity: 100%, 100% (210 & 254 nm) UPLCMS; retention time: 0.88 min; (M+H$^+$) 398.5.

Example 329

Quinuclidin-3-yl (4-(4-(2-methoxyethoxy)phenyl)-2-methylbut-3-yn-2-yl)carbamate Exchanging 1-bromo-4-(2-methoxyethyl)benzene for 1-bromo-4-(2-methoxyethoxy)benzene and Intermediate 2 for quinuclidin-3-ol, the reaction sequence outlined in Example 325 was used to prepare the title compound. $^1$H NMR (400 MHz, DMSO-$d_6$) δ 7.35 (br s, 1H), 7.26 (d, J=8.8 Hz, 2H), 6.91 (d, J=8.8 Hz, 2H), 4.63-4.51 (s, 1H), 4.13-4.05 (m, 2H), 3.68-3.60 (m, 2H), 3.30 (s, 3H), 3.13-3.03 (m, 1H), 2.77-2.41 (m, 5H), 1.92-1.71 (m, 2H), 1.64-1.40 (m, 8H), 1.36-1.24 (m, 1H) ppm. $^{13}$C NMR (100 MHz, DMSO-$d_6$) δ 158.2, 148.8, 132.7, 129.9, 114.7, 114.6, 92.7, 79.4, 70.2, 67.0, 58.1, 55.5, 46.9, 46.8, 46.0, 29.4, 25.3, 24.2, 19.3 ppm. Purity: 100%, 100% (210 & 254 nm) UPLCMS; retention time: 0.76 min; (M+H$^+$) 387.5.

Example 330

1-(4-(4-(2-Methoxyethoxy)phenyl)-2-methylbut-3-yn-2-yl)-3-(3-propylquinuclidin-3-yl)urea Exchanging 1-bromo-4-(2-methoxyethyl)benzene for 1-bromo-4-(2-methoxyethoxy)benzene and Intermediate 2 for Intermediate 17, the reaction sequence outlined in Example 325 was used to prepare the title compound. $^1$H NMR (400 MHz, DMSO-$d_6$) δ 7.24 (d, J=8.6 Hz, 2H), 6.91 (d, J=8.6 Hz, 2H), 5.93 (br s, 1H), 5.71 (br s, 1H), 4.19-3.97 (m, 2H), 3.80-3.58 (m, 2H), 3.30 (s, 3H), 2.83-2.50 (m, 6H), 1.99-1.45 (m, 11H), 1.45-1.07 (m, 4H), 0.83 (t, J=7.2 Hz, 3H) ppm. $^{13}$C NMR (100 MHz, DMSO-$d_6$) δ 158.2, 156.8, 132.6, 114.9, 114.6, 93.7, 79.2, 70.3, 67.0, 63.0, 58.1, 53.3, 46.6, 46.4, 46.3, 37.8, 29.9, 29.8, 28.2, 22.6, 22.2, 16.7, 14.6 ppm. Purity: 100%, 100% (210 & 254 nm) UPLCMS; retention time: 0.79 min; (M+H$^+$) 478.6.

Example 331

Quinuclidin-3-yl (4-(4-(3-methoxypropoxy)phenyl)-2-methylbut-3-yn-2-yl)carbamate Exchanging 1-bromo-4-(2-methoxyethyl)benzene for 1-bromo-4-(3-methoxypropoxy)benzene and Intermediate 2 for quinuclidin-3-ol, the reaction sequence outlined in Example 325 was used to prepare the title compound. $^1$H NMR (400 MHz, DMSO-$d_6$) δ 7.35 (s, 1H), 7.29-7.18 (m, 2H), 6.95-6.76 (m, 2H), 4.57 (s, 1H), 4.01 (t, J=6.4 Hz, 2H), 3.45 (t, J=6.3 Hz, 2H), 3.24 (s, 3H), 3.1-2.99 (m, 1H), 2.76-2.43 (m, 5H), 1.97-1.72 (m, 4H), 1.63-1.40 (m, 8H), 1.35-1.25 (m, 1H) ppm. $^{13}$C NMR (100 MHz, DMSO-$d_6$) δ 158.3, 158.3, 132.7, 132.6, 114.6, 114.6, 92.7, 79.4, 68.4, 64.7, 57.9, 55.5, 46.9, 46.8, 45.9, 29.5, 28.8, 25.3, 24.2, 19.3 ppm. Purity: 100%, 100% (210 & 254 nm) UPLCMS; retention time: 0.85 min; (M+H$^+$) 401.5.

Example 332

1-(3-Ethylquinuclidin-3-yl)-3-(2-methyl-4-(4-((pyridin-3-ylmethoxy)methyl)phenyl)but-3-yn-2-yl)urea Exchanging 1-bromo-4-(2-methoxyethyl)benzene for 3-(((4-bromobenzyl)oxy)methyl)pyridine (prepared as described in Example 215), the reaction sequence outlined in Example 325 was used to prepare the title compound. $^1$H NMR (400 MHz, DMSO-$d_6$) δ 8.72-8.36 (m, 2H), 7.89-7.65 (m, 1H), 7.59-7.07 (m, 5H), 6.08 (br s, 1H), 5.89 (br s, 1H), 4.56 (br s, 4H), 2.94-2.37 (m, 6H), 2.15-1.12 (m, 13H), 0.74 (br s, 3H) ppm. $^{13}$C NMR (100 MHz, DMSO-$d_6$) δ 156.8, 148.9, 148.8, 138.1, 135.4, 133.7, 131.1, 127.6, 123.5, 122.0, 95.3, 79.2, 71.2, 69.1, 62.1, 53.4, 46.6, 46.2, 46.0, 29.8, 29.7, 27.7, 27.5, 22.0, 21.7, 7.9 ppm. Purity: 99.9%, 99.6% (210 & 254 nm) UPLCMS; retention time: 0.61 min; ((M+2H$^+$)/2) 231.4.

Example 333

1-(2-Methyl-4-(4-((pyridin-3-ylmethoxy)methyl)phenyl)but-3-yn-2-yl)-3-(3-propylquinuclidin-3-yl)urea

Exchanging 1-bromo-4-(2-methoxyethyl)benzene for 3-(((4-bromobenzyl)oxy)methyl)pyridine (prepared as described in Example 215) and Intermediate 2 for Intermediate 17, the reaction sequence outlined in Example 325 was used to prepare the title compound. $^1$H NMR (400 MHz, DMSO-$d_6$) δ 8.79-8.38 (m, 2H), 7.77 (d, J=7.6 Hz, 1H), 7.53-7.10 (m, 5H), 6.04 (br s, 1H), 5.84 (br s, 1H), 4.56 (br s, 4H), 2.94-2.47 (m, 6H), 2.06-1.00 (m, 15H), 0.83 (t, J=7.1 Hz, 3H) ppm. $^{13}$C NMR (100 MHz, DMSO-$d_6$) δ 156.9, 148.9, 148.8, 138.1, 135.4, 133.6, 131.1, 127.5, 123.5, 122.0, 95.3, 79.2, 71.2, 69.1, 62.7, 53.2, 46.6, 46.3, 46.2, 37.8, 29.8, 29.7, 28.1, 22.3, 22.0, 16.6, 14.5 ppm. Purity: 99.9%, 99.9% (210 & 254 nm) UPLCMS; retention time: 0.67 min; (M+H$^+$) 475.5.

Example 334

Quinuclidin-3-yl (4-(4-((3,3-dimethylbutyl)sulfonyl)phenyl)-2-methylbut-3-yn-2-yl)carbamate

Exchanging 1-bromo-4-(2-methoxyethyl)benzene for 1-bromo-4-((3,3-dimethylbutyl)sulfonyl)benzene (prepared as described in Example 245) and Intermediate 2 for quinuclidin-3-ol, the reaction sequence outlined in Example 325 was used to prepare the title compound. $^1$H NMR (400 MHz, DMSO-$d_6$) δ 7.88 (d, J=8.5 Hz, 2H), 7.60 (d, J=8.5 Hz, 2H), 7.51 (br s, 1H), 4.64-4.57 (m, 1H), 3.30-3.21 (m, 2H), 2.80-2.50 (m, 5H), 1.95-1.87 (m, 1H), 1.86-1.74 (m, 1H), 1.65-1.43 (m, 8H), 1.43-1.27 (m, 3H), 0.81 (s, 9H) ppm. $^{13}$C NMR (100 MHz, DMSO-$d_6$) δ 154.5, 138.0, 132.0, 128.0, 128.0, 98.1, 78.4, 70.3, 55.3, 51.3, 46.8, 46.8, 45.9, 35.4, 29.8, 29.1, 28.6, 25.2, 24.0, 19.1 ppm. Purity: 90.0%, 99.6% (210 & 254 nm) UPLCMS; retention time: 0.95 min; (M+1) 461.

Example 335

1-Azabicyclo[3.2.2]nonan-4-yl (4-(4-((3,3-dimethylbutyl)sulfonyl)phenyl)-2-methylbut-3-yn-2-yl)carbamate

Exchanging 1-bromo-4-(2-methoxyethyl)benzene for 1-bromo-4-((3,3-dimethylbutyl)sulfonyl)benzene (prepared as described in Example 245) and Intermediate 2 for Intermediate 3, the reaction sequence outlined in Example 325 was used to prepare the title compound. $^1$H NMR (400 MHz, DMSO-$d_6$) δ 7.88 (d, J=8.5 Hz, 2H), 7.60 (d, J=8.5 Hz, 2H), 7.44 (br s, 1H), 4.80-4.72 (m, 1H), 3.30-3.22 (m, 2H), 2.98-2.62 (m, 6H), 2.01-1.50 (m, 12H), 1.47-1.33 (m, 3H), 0.81 (s, 9H) ppm. $^{13}$C NMR (100 MHz, DMSO-$d_6$) δ 154.2, 138.0, 132.0, 128.0, 128.0, 98.2, 78.4, 77.6, 51.4, 51.3, 47.7, 46.7, 44.6, 35.5, 33.4, 30.6, 29.8, 29.2, 28.6, 24.6, 22.1 ppm. Purity: 100%, 100% (210 & 254 nm) UPLCMS; retention time: 0.96 min; (M+1) 475.

Example 336

1-(4-(4-((3,3-Dimethylbutyl)sulfonyl)phenyl)-2-methylbut-3-yn-2-yl)-3-(4-methyl-1-azabicyclo[3.2.2]nonan-4-yl)urea

Exchanging 1-bromo-4-(2-methoxyethyl)benzene for 1-bromo-4-((3,3-dimethylbutyl)sulfonyl)benzene (prepared as described in Example 245) and Intermediate 2 for Intermediate 5, the reaction sequence outlined in Example 325 was used to prepare the title compound. $^1$H NMR (400 MHz, DMSO-$d_6$) δ 7.88 (d, J=8.5 Hz, 2H), 7.57 (d, J=8.5 Hz, 2H), 6.15 (s, 1H), 5.79 (s, 1H), 3.30-3.20 (m, 2H), 2.90-2.70 (m, 6H), 2.23-2.17 (m, 1H), 1.88-1.64 (m, 3H), 1.62-1.42 (m, 8H), 1.42-1.25 (m, 6H), 0.81 (s, 9H) ppm. $^{13}$C NMR (100 MHz, DMSO-$d_6$) δ 156.7, 137.8, 131.9, 128.3, 128.0, 99.5, 78.1, 57.3, 52.7, 51.3, 48.0, 46.4, 44.9, 38.9, 36.2, 35.4, 29.8, 29.7, 29.5, 28.6, 26.1, 24.1, 23.7 ppm. Purity: 100%, 100% (210 & 254 nm) UPLCMS; retention time: 0.94 min; (M+1) 488.

Example 337

1-(4-(4-((3,3-Dimethylbutyl)sulfonyl)phenyl)-2-methylbut-3-yn-2-yl)-3-(3-methylquinuclidin-3-yl)urea

Exchanging 1-bromo-4-(2-methoxyethyl)benzene for 1-bromo-4-((3,3-dimethylbutyl)sulfonyl)benzene (prepared as described in Example 245) and Intermediate 2 for Intermediate 1, the reaction sequence outlined in Example 325 was used to prepare the title compound. $^1$H NMR (400 MHz, DMSO-$d_6$) δ 7.88 (d, J=8.5 Hz, 2H), 7.58 (d, J=8.5 Hz, 2H), 6.04 (s, 1H), 5.77 (s, 1H), 3.29-3.21 (m, 2H), 2.75-2.56 (m, 6H), 1.96-1.91 (m, 1H), 1.81-1.51 (m, 8H), 1.45-1.33 (m, 7H), 0.81 (s, 9H) ppm. $^{13}$C NMR (100 MHz, DMSO-$d_6$) δ 156.7, 137.9, 131.9, 128.3, 128.0, 99.4, 78.1, 63.4, 51.3, 50.9, 46.5, 46.2, 46.0, 35.4, 30.4, 29.6, 29.5, 28.6, 25.0, 22.9, 22.2 ppm. Purity: 97.8%, 99.2% (210 & 254 nm) UPLCMS; retention time: 0.93 min; (M+1) 474.

Example 338

1-(4-(4-((3,3-Dimethylbutyl)sulfonyl)phenyl)-2-methylbut-3-yn-2-yl)-3-(3-ethylquinuclidin-3-yl)urea

Exchanging 1-bromo-4-(2-methoxyethyl)benzene for 1-bromo-4-((3,3-dimethylbutyl)sulfonyl)benzene (prepared as described in Example 245), the reaction sequence outlined in Example 325 was used to prepare the title compound. $^1$H NMR (400 MHz, DMSO-$d_6$) δ 7.88 (d, J=8.5 Hz, 2H), 7.57 (d, J=8.5 Hz, 2H), 6.04 (s, 1H), 5.74 (s, 1H), 3.29-3.21 (m, 2H), 2.76-2.53 (m, 6H), 1.98-1.87 (m, 2H), 1.80-1.67 (m, 2H), 1.65-1.49 (m, 7H), 1.42-1.20 (m, 4H), 0.81 (s, 9H), 0.73 (t, J=7.3 Hz, 3H) ppm. $^{13}$C NMR (100 MHz, DMSO-$d_6$) δ 156.7, 137.9, 131.9, 128.2, 128.0, 99.4, 78.1, 62.8, 53.5, 51.3, 46.5, 46.4, 46.3, 35.4, 29.8, 29.6, 29.5, 28.6, 27.8, 27.7, 22.6, 22.3, 8.0 ppm. Purity: 97.5%, 98.3% (210 & 254 nm) UPLCMS; retention time: 0.96 min; (M+1) 488.

Example 339

1-(4-(4-(1-Methoxy-2-methylpropan-2-yl)phenyl)-2-methylbut-3-yn-2-yl)-3-(3-methylquinuclidin-3-yl)urea

To a stirred and cooled (0° C.) suspension of lithium aluminum hydride (1.81 g, 47.7 mmol) in tetrahydrofuran (100 mL) was added a solution of ethyl 2-(4-bromophenyl)-2-methylpropanoate (11.25 g, 41.47 mmol) in tetrahydrofuran (40 mL), dropwise over 15 minutes. The reaction was stirred cold for 1 hour before quenching with the slow addition of ethyl acetate (~15 mL). After another 30 minutes, the reaction was diluted with 1 N hydrochloric acid and extracted with ethyl acetate. The combined extracts were washed with 1 N hydrochloric acid and brine, dried ($Na_2SO_4$) and concentrated to afford 2-(4-bromophenyl)-2-methylpropan-1-ol as a white solid (9.50 g, 100%). To a stirred solution of the crude alcohol (1.92 g, 8.38 mmol) in N,N-dimethylformamide (17 mL) was added sodium hydride (60% dispersion in mineral oil; 0.402 g, 10.1 mmol). After 20 minutes, iodomethane (0.70 mL, 10.9 mmol) was added, dropwise, via syringe. The reaction was stirred overnight, concentrated and partitioned between ethyl acetate and water. The organic layer was washed with aqueous sodium bicarbonate solution and brine, dried ($Na_2SO_4$) and concentrated. The crude product was purified by flash chromatography over silica using a hexane/ethyl acetate gradient to afford 1-bromo-4-(1-methoxy-2-methylpropan-2-yl)benzene as a colorless oil (1.26 g, 62%). Exchanging 1-bromo-4-(2-methoxyethyl)benzene for the this intermediate and Intermediate 2 for Intermediate 1, the reaction sequence outlined in Example 325 was used to prepare the title compound. $^1$H NMR (400 MHz, DMSO-$d_6$) δ 7.34 (d, J=8.5 Hz, 2H), 7.25 (d, J=8.5 Hz, 2H), 5.99 (s, 1H), 5.80 (s, 1H), 3.34 (s, 2H), 3.19 (s, 3H), 2.82-2.57 (m, 6H), 1.96-1.90 (m, 1H), 1.83-1.73 (m, 1H), 1.71-1.60 (m, 1H), 1.55 (d, J=5.0 Hz, 1H), 1.47-1.18 (m, 11H) ppm. $^{13}$C NMR (100 MHz, DMSO-$d_6$) δ 156.7, 147.6, 130.7, 126.2, 120.2, 94.7, 81.6, 79.3, 63.2, 58.6, 50.8, 46.6, 46.1, 45.9, 38.8, 30.4, 29.8, 29.8, 25.8, 25.0, 22.7, 22.1 ppm. Purity: 100%, 99.5% (210 & 254 nm) UPLCMS; retention time: 0.94 min; (M+H$^+$) 412.5.

Example 340

Quinuclidin-3-yl (2-(2-(4-(3-methoxypropoxy)phenyl)thiazol-4-yl)-propan-2-yl)carbamate To a stirred suspension of 4-methoxythiobenzamide (9.99 g, 59.7 mmol) in ethanol (75 mL) was added ethyl 4-chloroacetoacetate (8.1 mL, 60 mmol). The mixture was heated at reflux for 4 hours before cooling, adding additional ethyl 4-chloroacetoacetate (0.81 mL, 6.0 mmol) and returning to reflux. After 4 more hours of heating the reaction was concentrated and partitioned between ethyl acetate and aqueous sodium bicarbonate solution. The organic layer was combined with additional ethyl acetate extracts, dried ($Na_2SO_4$) and concentrated. The crude product was purified by flash chromatography over silica using a hexane/ethyl acetate gradient to afford ethyl 2-(2-(4-methoxyphenyl)thiazol-4-yl)acetate as a pale amber oil (14.51 g, 87%). To a stirred solution of this compound (14.48 g, 52.2 mmol) in N,N-dimethylformamide (125 mL) was added sodium hydride (60% dispersion in mineral oil; 6.27 g, 157 mmol), portion wise over 15 minutes. The resulting red suspension was cooled (0° C.) and treated, dropwise over 10 minutes, with iodomethane (9.80 mL, 157 mmol). The cooling bath was removed and the reaction was allowed to stir 4 hours before concentrating and partitioning the residue between ethyl acetate and water. The organic layer was washed twice more with water, dried ($Na_2SO_4$) and concentrated. The residue was purified by flash chromatography over silica using a hexane/ethyl acetate gradient to afford ethyl 2-(2-(4-methoxyphenyl)thiazol-4-yl)-2-methylpropanoate as a pale amber oil (14.12 g, 89%). To a stirred solution of this intermediate (14.12 g, 46.24 mmol) in methylene chloride (250 mL) was added boron tribromide (11.0 mL, 116 mmol), dropwise over 5 minutes. After stirring overnight, the reaction was quenched by the slow addition of methanol (~20 mL) and then concentrated. The residue was taken up in methanol (250 mL) and concentrated sulfuric acid (7.0 mL). The stirred solution was heated at reflux for 2 hours, concentrated and partitioned between ethyl acetate and aqueous sodium bicarbonate solution. The organic layer was combined with a second ethyl acetate extract of the aqueous layer, dried ($Na_2SO_4$) and concentrated to afford methyl 2-(2-(4-hydroxyphenyl)thiazol-4-yl)-2-methylpropanoate as a white solid (12.56 g, 98%). To a stirred solution of 1-bromo-3-methoxypropane (1.66 g, 10.8 mmol) in acetone (30 mL) was added the phenol intermediate (2.00 g, 7.21 mmol) and potassium carbonate (1.25 g, 9.04 mmol). The mixture was heated overnight at reflux, filtered and concentrated. The residue was purified by flash chromatography over silica using a hexane/ethyl acetate gradient to afford methyl 2-(2-(4-(3-methoxypropoxy)phenyl)thiazol-4-yl)-2-methylpropanoate as a faint amber gum (2.47 g, 98%). To a stirred solution of this compound (2.45 g, 7.01 mmol) in 1:1:1 (v/v/v) tetrahydrofuran/ethanol/water (45 mL) was added lithium hydroxide monohydrate (1.47 g, 35.0 mmol). After overnight stirring, the reaction was concentrated and partitioned between water and diethyl ether. The aqueous layer was treated with 1.0 N hydrochloric acid (40 mL) and extracted with ethyl acetate. The combined extracts were dried ($Na_2SO_4$) and concentrated to afford 2-(2-(4-(3-methoxypropoxy)phenyl)thiazol-4-yl)-2-methylpropanoic acid as a white solid (2.19 g, 93%). This compound and quinuclidin-3-ol were reacted according to General Procedure H to generate the title compound as a soft, faint amber solid. $^1$H NMR (400 MHz, DMSO-$d_6$) δ 7.82 (d, J=8.9 Hz, 2H), 7.36 (br s, 1H), 7.24 (br s, 1H), 7.03 (d, J=8.9 Hz, 2H), 4.49-4.41 (m, 1H), 4.07 (t, J=6.4 Hz, 2H), 3.48 (t, J=6.4 Hz, 2H), 3.26 (s, 3H), 3.09-2.26 (m, 6H), 2.02-1.91 (m, 2H), 1.91-1.03 (m, 11H) ppm. $^{13}$C NMR (100 MHz, DMSO-$d_6$) δ 165.8, 162.4, 160.0, 154.6, 127.5, 126.1, 114.9, 112.1, 70.1, 68.4, 64.8, 57.9, 55.4, 53.5, 46.9, 45.9, 28.9, 28.3, 25.2, 24.2, 19.2 ppm. Purity: 100%, 100% (210 & 254 nm) UPLCMS; retention time: 0.87 min; (M+H$^+$) 460.

Example 341

1-Azabicyclo[3.2.2]nonan-4-yl (2-(2-(4-(3-methoxypropoxy)phenyl)thiazol-4-yl)propan-2-yl)carbamate Using General Procedure H and the reaction inputs 2-(2-(4-(3-methoxypropoxy)phenyl)thiazol-4-yl)-2-methylpropanoic acid (prepared as described in Example 340) and Intermediate 3, the title compound was prepared. $^1$H NMR (400 MHz, DMSO-$d_6$) δ 7.81 (d, J=8.8 Hz, 2H), 7.29 (br s, 1H), 7.21 (s, 1H), 7.03 (d, J=8.8 Hz, 2H), 4.68-4.60 (m, 1H), 4.07 (t, J=6.4 Hz, 2H), 3.48 (t, J=6.3 Hz, 2H), 3.26 (s, 3H), 3.00-2.51 (m, 6H), 2.03-1.30 (m, 15H) ppm. $^{13}$C NMR (100 MHz, DMSO-$d_6$) δ 165.7, 163.0, 160.0, 154.3, 127.5, 126.2, 114.9, 112.1, 77.1, 68.4, 64.8, 57.9, 53.4, 51.4, 47.7, 44.7, 33.4, 30.6, 28.9, 28.3, 24.7, 22.1 ppm. Purity: 100%, 100% (210 & 254 nm) UPLCMS; retention time: 0.88 min; (M+H$^+$) 474.

Example 342

N-(2-(2-(4-(3-Methoxypropoxy)phenyl)thiazol-4-yl) propan-2-yl)-1,4-diazabicyclo[3.2.2]nonane-4-carboxamide Using General Procedure H and the reaction inputs 2-(2-(4-(3-methoxypropoxy)phenyl)thiazol-4-yl)-2-methylpropanoic acid (prepared as described in Example 340) and Intermediate 6, the title compound was prepared. $^1$H NMR (400 MHz, DMSO-$d_6$) δ 7.81 (d, J=8.8 Hz, 2H), 7.19 (s, 1H), 7.03 (d, J=8.8 Hz, 2H), 6.08 (s, 1H), 4.16-4.11 (m, 1H), 4.08 (t, J=6.5 Hz, 2H), 3.54-3.44 (m, 4H), 3.26 (s, 3H), 2.95-2.74 (m, 6H), 2.01-1.88 (m, 4H), 1.69-1.53 (m, 8H) ppm. $^{13}$C NMR (100 MHz, DMSO-$d_6$) δ 165.4, 164.2, 160.0, 155.6, 127.4, 126.2, 114.9, 111.6, 68.4, 64.8, 57.9, 57.5, 54.0, 46.9, 45.9, 41.3, 28.9, 28.8, 26.9 ppm. Purity: 100%, 100% (210 & 254 nm) UPLCMS; retention time: 0.82 min; (M+H$^+$) 459.

Example 343

Quinuclidin-3-yl (2-(2-(4-(2-methoxyethoxy)phenyl) thiazol-4-yl)propan-2-yl)carbamate To a stirred solution of 2-bromoethyl methyl ether (1.88 g, 13.5 mmol) in acetone was added methyl 2-(2-(4-hydroxyphenyl)thiazol-4-yl)-2-methylpropanoate (prepared as described in Example 185; 2.00 g, 7.21 mmol) and potassium carbonate (1.56 g, 11.3 mmol). After heating at reflux overnight, the mixture was treated with additional 2-bromoethyl methyl ether (1.88 g, 13.5 mmol) and potassium carbonate (1.56 g, 11.3 mmol). The reaction was heated at reflux for a second night, filtered and concentrated.

The residue was purified by flash chromatography over silica using a hexane/ethyl acetate gradient to afford methyl 2-(2-(4-(2-methoxyethoxy)phenyl)thiazol-4-yl)-2-methylpropanoate as a white solid (2.71 g, 90%). To a stirred solution of this compound (2.71 g, 8.08 mmol) in 1:1:1 (v/v/v) tetrahydrofuran/ethanol/water (50 mL) was added lithium hydroxide monohydrate (1.70 g, 40.5 mmol). After overnight stirring, the reaction was concentrated and partitioned between water and diethyl ether. The aqueous layer was treated with 1.0 N hydrochloric acid (41 mL) and extracted with ethyl acetate. The combined extracts were dried (Na$_2$SO$_4$) and concentrated to afford 2-(2-(4-(2-methoxyethoxy)phenyl)thiazol-4-yl)-2-methylpropanoic acid as a white solid (2.57 g, 99%). This compound and quinuclidin-3-ol were reacted according to General Procedure H to generate the title compound as a pale amber solid. $^1$H NMR (400 MHz, DMSO-$d_6$) δ 7.82 (d, J=8.8 Hz, 2H), 7.36 (br s, 1H), 7.24 (br s, 1H), 7.04 (d, J=8.8 Hz, 2H), 4.49-4.41 (m, 1H), 4.19-4.12 (m, 2H), 3.71-3.65 (m, 2H), 3.32 (s, 3H), 3.11-2.87 (m, 1H), 2.86-2.19 (m, 5H), 1.92-1.16 (m, 11H) ppm. $^{13}$C NMR (100 MHz, DMSO-$d_6$) δ 165.7, 162.9, 159.9, 154.6, 127.5, 126.2, 114.9, 112.2, 70.3, 70.1, 67.1, 58.2, 55.4, 53.5, 46.9, 45.9, 28.3, 25.2, 24.3, 19.2 ppm. Purity: 100%, 100% (210 & 254 nm) UPLCMS; retention time: 0.85 min; (M+H$^+$) 446.

Example 344

1-Azabicyclo[3.2.2]nonan-4-yl (2-(2-(4-(2-methoxyethoxy)phenyl)thiazol-4-yl)propan-2-yl)carbamate Using General Procedure H and the reaction inputs 2-(2-(4-(2-methoxyethoxy)phenyl)thiazol-4-yl)-2-methylpropanoic acid (prepared as described in Example 343) and Intermediate 3, the title compound was prepared. $^1$H NMR (400 MHz, DMSO-$d_6$) δ 7.81 (d, J=8.8 Hz, 2H), 7.29 (br s, 1H), 7.21 (br s, 1H), 7.04 (d, J=8.8 Hz, 2H), 4.67-4.60 (m, 1H), 4.18-4.12 (m, 2H), 3.71-3.65 (m, 2H), 3.32 (s, 3H), 3.00-2.50 (m, 6H), 1.99-1.25 (m, 13H) ppm. $^{13}$C NMR (100 MHz, DMSO-$d_6$) δ 165.7, 163.0, 159.9, 154.3, 127.5, 126.2, 114.9, 112.1, 77.1, 70.3, 67.1, 58.2, 53.4, 51.4, 47.6, 44.7, 33.4, 30.6, 28.3, 24.7, 22.1 ppm. Purity: 100%, 100% (210 & 254 nm) UPLCMS; retention time: 0.86 min; (M+H$^+$) 460.

Example 345

N-(2-(2-(4-(2-Methoxyethoxy)phenyl)thiazol-4-yl) propan-2-yl)-1,4-diazabicyclo[3.2.2]nonane-4-carboxamide Using General Procedure H and the reaction inputs 2-(2-(4-(2-methoxyethoxy)phenyl)thiazol-4-yl)-2-methylpropanoic acid (prepared as described in Example 343) and Intermediate 6, the title compound was prepared. $^1$H NMR (400 MHz, DMSO-$d_6$) δ 7.82 (d, J=8.8 Hz, 2H), 7.20 (s, 1H), 7.05 (d, J=8.8 Hz, 2H), 6.09 (s, 1H), 4.20-4.10 (m, 3H), 3.71-3.65 (m, 2H), 3.54-3.47 (m, 2H), 3.32 (s, 3H), 2.96-2.73 (m, 6H), 2.00-1.88 (m, 2H), 1.70-1.53 (m, 8H) ppm. $^{13}$C NMR (100 MHz, DMSO-$d_6$) δ 165.4, 164.2, 159.9, 155.6, 127.4, 126.3, 114.9, 111.7, 70.3, 67.1, 58.2, 57.5, 54.0, 46.9, 45.9, 41.2, 28.8, 26.8 ppm. Purity: 100%, 100% (210 & 254 nm) UPLCMS; retention time: 0.79 min; (M+H$^+$) 445.

Example 346

Quinuclidin-3-yl 2-(5-(4-(2-methoxyethoxy)phenyl) pyridin-2-yl)propan-2-ylcarbamate Using General Procedure F and the reaction inputs 5-bromopicolinonitrile and 2-(4-(2-methoxyethoxy)phenyl)-4,4,5,5-tetramethyl-1,3,2-dioxaborolane, 5-(4-(2-methoxyethoxy)phenyl)picolinonitrile was prepared. Cercium trichloride (8.05, 21.6 mmol) was loaded into a flask and dried by heating (170° C.) under vacuum for 3 hours. The solid was taken up in tetrahydrofuran (20 mL) and stirred vigorously for 30 minutes. The suspension was cooled to −78° C. and treated, dropwise, with a 3.0 M solution of methyllithium in diethyl ether (7.2 mL, 21.6 mmol). Following addition, the reaction was stirred at −78° C. for 1 hour before adding a solution of the above arylborate (1.83 g, 7.20 mmol) in tetrahydrofuran (20 mL). The mixture was maintained at −78° C. for 2 hours and then allowed to warm to room temperature. At this time, the reaction was quenched by the addition of aqueous ammonium hydroxide (10 mL) and filtered through a plug of Celite. The filtrate was extracted with ethyl acetate and the combined extracts were washed with brine, dried (Na$_2$SO$_4$) and concentrated. The residue was purified by flash chromatography over silica using ethyl acetate eluant to afford 2-(5-(4-(2-methoxyethoxy)phenyl)pyridin-2-yl)propan-2-amine as a yellow solid (0.800 g, 39%). To a stirred suspension of this intermediate (0.500 g, 1.75 mmol) in water (10 mL) and concentrated hydrochloric acid (0.44 mL) was added toluene (10 mL). The mixture was cooled (0° C.) and treated with, simultaneously over 1 hour, solutions of triphosgene (0.776 g, 2.62 mmol) in toluene (10 mL) and sodium bicarbonate (2.2 g, 26 mmol) in water (20 mL). Following the additions, the reaction was stirred for an additional 30 minutes before the upper toluene layer was removed and dried (Na$_2$SO$_4$). At the same time, a stirred solution of quinuclidin-3-ol (0.445 g, 3.64 mmol) in tetrahydrofuran (10 mL) was treated with sodium hydride (60% dispersion in mineral oil; 0.154 g, 3.85 mmol). This mixture was stirred for 5 minutes and then added to the solution of crude isocyanate in toluene. The reaction was stirred for 10 minutes, quenched with the addition of brine (5 mL) and extracted with ethyl acetate.

The combined extracts were dried (Na$_2$SO$_4$) and concentrated. The residue was purified by flash chromatography over reversed phase silica to afford the title compound as a light yellow solid (0.100 g, 13%). $^1$H NMR (500 MHz, CDCl$_3$) δ 8.70-8.70 (d, J=2.0 Hz, 1H), 7.83-7.81 (m, 1H), 7.49-7.47 (d, J=9.0 Hz, 2H), 7.45-7.43 (d, J=8.0 Hz, 1H), 7.03-7.01 (d, J=8.5 Hz, 2H), 6.63 (br s, 1H), 4.68-4.66 (m, 1H), 4.16 (t, J=5.0 Hz, 2H), 3.77 (t, J=5.0 Hz, 2H), 3.45 (s, 3H), 3.19-2.70 (m, 6H), 2.15-1.89 (m, 2H), 1.76 (s, 6H), 1.73-1.36 (m, 3H) ppm. $^{13}$C NMR (125 MHz, CDCl$_3$) δ 162.7, 158.9, 154.9, 145.9, 134.8, 134.3, 130.1, 128.1, 119.2, 115.2, 71.0, 70.8, 67.4, 59.2, 55.9, 55.7, 47.4, 46.5, 46.4, 27.9, 25.4, 24.6, 19.5 ppm. Purity: >99% (214 & 254 nm) LCMS; retention time: 1.32 min; (M+H$^+$) 440.2.

Example 347

1-Azabicyclo[3.2.2]nonan-4-yl 2-(5-(4-(2-methoxyethoxy)phenyl)pyridin-2-yl)propan-2-ylcarbamate Exchanging quinuclidin-3-ol for Intermediate 3, the reaction sequence outlined in Example 346 was used to prepare the title compound. $^1$H NMR (500 MHz, CDCl$_3$) δ 8.71 (s, 1H), 7.85-7.83 (m, 1H), 7.50 (d, J=8.5 Hz, 2H), 7.45 (d, J=8.5 Hz, 1H), 7.04 (d, J=8.5 Hz, 2H), 6.54 (s, 1H), 4.85-4.82 (m, 1H), 4.18 (t, J=4.5 Hz, 2H), 3.79 (t, J=4.5 Hz, 2H), 3.46 (s, 3H), 3.12-2.76 (m, 6H), 2.35-1.43 (m, 13H) ppm. $^{13}$C NMR (125 MHz, CDCl$_3$) δ 162.7, 158.9, 154.6, 145.9, 134.9, 134.3, 130.1, 128.1, 119.2, 115.2, 77.9, 71.0, 67.4, 59.2, 56.0, 51.6, 48.1, 45.0, 33.5, 30.4, 29.7, 28.0, 24.7, 22.0 ppm. Purity: >97% (214 & 254 nm) LCMS; retention time: 1.02 min; (M+H$^+$) 454.2.

Example 348

1-Azabicyclo[3.2.2]nonan-4-yl 2-(5-(4-(2-methoxyethoxy)phenyl)pyridin-2-yl)propan-2-ylcarbamate (Single Enantiomer A)

Using General Procedure F and the reaction inputs methyl 2-(5-bromopyridin-2-yl)-2-methylpropanoate (Org. Lett. 2005, 7(21), 4585-4588) and 4-(2-methoxyethoxy)phenylboronic acid, methyl 2-(5-(4-(2-methoxyethoxy)phenyl)pyridin-2-yl)-2-methylpropanoate was prepared. To a stirred solution of this compound (7.00 g, 21.3 mmol) in 1:1:1 (v/v/v) tetrahydrofuran/ethanol/water (135 mL) was added lithium hydroxide monohydrate (2.68 g, 63.9 mmol). After overnight stirring, the reaction was concentrated and partitioned between water and diethyl ether. The aqueous layer was treated with 1.04 N hydrochloric acid (61.4 mL) and extracted with ethyl acetate. The combined extracts were dried (Na$_2$SO$_4$) and concentrated to afford 2-(5-(4-(2-methoxyethoxy)phenyl)pyridin-2-yl)-2-methylpropanoic acid as an off-white solid (5.90 g, 88%). This compound and Intermediate 15 were reacted according to General Procedure H to generate the title compound as an off-white solid. $^1$H NMR (400 MHz, DMSO-d$_6$) δ 8.74 (d, J=2.1 Hz, 1H), 7.96 (dd, J=8.3, 2.4 Hz, 1H), 7.63 (d, J=8.3 Hz, 2H), 7.51 (br s, 1H), 7.44 (d, J=8.3 Hz, 1H), 7.06 (d, J=8.8 Hz, 2H), 4.69-4.57 (m, 1H), 4.17-4.11 (m, 2H), 3.71-3.65 (m, 2H), 3.32 (s, 3H), 3.00-242 (m, 6H), 1.98-1.33 (m, 13H) ppm. $^{13}$C NMR (100 MHz, DMSO-d$_6$) δ 163.9, 158.5, 154.2, 145.4, 134.0, 132.8, 129.4, 127.8, 119.0, 115.1, 77.2, 70.4, 67.0, 58.2, 56.1, 51.4, 47.8, 44.6, 33.5, 30.6, 28.2, 24.7, 22.2 ppm. Purity: 100%, 100% (210 & 254 nm) UPLCMS; retention time: 0.65 min; (M+H$^+$) 454.4.

Example 349

1-Azabicyclo[3.2.2]nonan-4-yl 2-(5-(4-(2-methoxyethoxy)phenyl)pyridin-2-yl)propan-2-ylcarbamate (Single Enantiomer B)

Exchanging Intermediate 15 for Intermediate 16, the reaction sequence outlined in Example 348 was used to prepare the title compound. NMR data matched that of Example 348. Purity: 100%, 99.4% (210 & 254 nm) UPLCMS; retention time: 0.65 min; (M+H$^+$) 454.4.

Example 350

Inhibition of glucosylceramide synthase activity for certain compounds of the invention were measured with 1) a microsomal assay that directly measures the conversion of ceramide to glucosylceramide by HPLC and 2) second, cell based, phenotypic assay that monitors cell surface expression of the downstream lipid GM3 by antibody mediated immunofluorescence. The cell based assay was performed in two different cell types, B16 and C32. Cell viability was also assessed in the second, cell-based assay.

Results of these assays are set forth in Table 1 below. The "Compound Number" in the table corresponds to the compound disclosed in the Example of the same number. The results of the microsomal assay are expressed as "GCS IC50", which represents the concentration of the compound causing 50% inhibition of glucosylceramide synthase activity. The results of the cell based assays (performed in two different cell systems, i.e. B16 mouse melanoma or C32 human melanoma cells) are expressed as "GM3 B16 IC50" or "GM3 C32 IC50" for the B16 assay and the C32 assay, respectively. These values represent the concentration of the compound causing 50% inhibition of GM3 expression on the cell surface. The results of the viability assays are expressed as "Viability, B16 IC50" or "Viability, C32 IC50", respectively. These values represent the concentration of the compound causing 50% cell death. Values greater than 10 represent a lack of cell death.

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 1 | 4-([1,1'-Biphenyl]-4-yl)-N-(3-methylquinuclidin-3-yl)piperazine-1-carboxamide | 1 | 0.719 | 1.26 | 0.109 | 7.16 | 10. |
| 2 | 4-([1,1'-Biphenyl]-4-yl)-N-(quinuclidin-3-yl)piperazine-1-carboxamide | 2 | 6.93 | 1.6 | 0.667 | 5.28 | 7.58 |
| 3 | 4-([1,1'-Biphenyl]-4-yl)-N-(1-azabicyclo[3.2.2]nonan-4-yl)piperazine-1-carboxamide | 3 | 10.9 | 6.84 | 1.0 | 4.18 | 2.51 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 4 | 4-([1,1'-Biphenyl]-4-yl)-N-(4-methyl-1-azabicyclo[3.2.2]nonan-4-yl)piperazine-1-carboxamide | 4 | 1.0 | 1.38 | 0.0625 | 6.16 | 6.31 |
| 5 | (4-([1,1'-Biphenyl]-4-yl)piperazin-1-yl)(1,4-diazabicyclo[3.2.2]nonan-4-yl)methanone | 5 | 30. | 2.0 | 2.0 | 2.0 | 2.0 |
| 6 | Quinuclidin-3-yl 4-([1,1'-biphenyl]-4-yl)piperazine-1-carboxylate | 6 | 5.6 | 3.52 | 1.0 | 5.21 | 4.12 |
| 7 | 4-Phenyl-N-(quinuclidin-3-yl)piperazine-1-carboxamide | 7 | 12.2 | >10 | 7.08 | 10. | 10. |
| 8 | N-(1-Azabicyclo[3.2.2]nonan-4-yl)-4-phenylpiperazine-1-carboxamide | 8 | 3.31 | >10 | 0.518 | 10. | 10. |
| 9 | N-(3-Methylquinuclidin-3-yl)-4-phenylpiperazine-1-carboxamide | 9 | 12.2 | >10 | 7.59 | 10. | 10. |
| 10 | N-(4-Methyl-1-azabicyclo[3.2.2]nonan-4-yl)-4-phenylpiperazine-1-carboxamide | 10 | 14.7 | >10 | 4.24 | 10. | 10. |
| 11 | 1,4-Diazabicyclo[3.2.2]nonan-4-yl(4-phenylpiperazin-1-yl)methanone | 11 | 20.8 | >10 | >10 | 10. | 10. |
| 12 | Quinuclidin-3-yl 4-phenylpiperazine-1-carboxylate | 12 | 12.2 | >10 | >10 | 10. | 10. |
| 13 | 4-([1,1'-Biphenyl]-3-yl)-N-(quinuclidin-3-yl)piperazine-1-carboxamide | 13 | 2.47 | 6.8 | 0.697 | 8.59 | 10. |
| 14 | 4-([1,1'-Biphenyl]-3-yl)-N-(1-azabicyclo[3.2.2]nonan-4-yl)piperazine-1-carboxamide | 14 | 0.705 | 3.39 | 0.108 | 6.79 | 10. |
| 15 | 4-([1,1'-Biphenyl]-3-yl)-N-(3-methylquinuclidin-3-yl)piperazine-1-carboxamide | 15 | 0.839 | 0.368 | 0.172 | 10. | 10. |
| 16 | 4-([1,1'-Biphenyl]-3-yl)-N-(4-methyl-1-azabicyclo[3.2.2]nonan-4-yl)piperazine-1-carboxamide | 16 | 0.0495 | 0.181 | 0.0124 | 6.76 | 1.0 |
| 17 | (4-([1,1'-Biphenyl]-3-yl)piperazin-1-yl)(1,4-diazabicyclo[3.2.2]nonan-4-yl)methanone | 17 | 12.2 | 6.31 | 6.36 | 10. | 10. |
| 18 | Quinuclidin-3-yl 4-([1,1'-biphenyl]-3-yl)piperazine-1-carboxylate | 18 | 0.551 | 2.04 | 0.563 | 8.36 | 10. |
| 19 | 1-Azabicyclo[3.2.2]nonan-4-yl 4-([1,1'-biphenyl]-3-yl)piperazine-1-carboxylate | 19 | 2.67 | 1.48 | 0.456 | 7.09 | 9.09 |
| 20 | 1-Azabicyclo[3.2.2]nonan-3-yl 4-(1,1'-biphenyl]-3-yl)piperazine-1-carboxylate | 20 | 16.6 | 4.47 | 10.7 | 7.71 | 15.1 |
| 21 | 4-([1,1'-Biphenyl]-3-yl)-N-(3-ethylquinuclidin-3-yl)piperazine-1-carboxamide | 21 | 0.288 | 0.168 | 0.0252 | 7.23 | 3.16 |
| 22 | 4-(4'-Fluoro-[1,1'-biphenyl]-3-yl)-N-(4-methyl-1-azabicyclo[3.2.2]nonan-4-yl)piperazine-1-carboxamide | 22 | 0.613 | 0.629 | 0.0411 | 7.06 | 1.0 |
| 23 | N-(3-Ethylquinuclidin-3-yl)-4-(4'-fluoro-[1,1'-biphenyl]-3-yl)piperazine-1-carboxamide | 23 | 1.58 | 0.351 | 0.0909 | 7.07 | 3.16 |
| 24 | 1-Azabicyclo[3.2.2]nonan-4-yl 4-(4'-fluoro-[1,1'-biphenyl]-3-yl)piperazine-1-carboxylate | 24 | 9.52 | 1.68 | 1.08 | 3.61 | 3.98 |
| 25 | 1-Azabicyclo[3.2.2]nonan-3-yl 4-(4'-fluoro-[1,1'-biphenyl]-3-yl)piperazine-1-carboxylate | 25 | 3.48 | 4.86 | 9.38 | 5.39 | 5.41 |
| 26 | N-(4-Methyl-1-azabicyclo[3.2.2]nonan-4-yl)-4-(3-(pyrimidin-2-yl)phenyl)piperazine-1-carboxamide | 26 | 6.9 | >10 | 0.36 | 10. | 10. |
| 27 | N-(4-Methyl-1-azabicyclo[3.2.2]nonan-4-yl)-4-(3-(pyrimidin-5-yl)phenyl)piperazine-1-carboxamide | 27 | 16.5 | >10 | 0.798 | 10. | 10. |
| 28 | 4-(3-Isopropylphenyl)-N-(4-methyl-1-azabicyclo[3.2.2]nonan-4-yl)piperazine-1-carboxamide | 28 | 1.59 | 1.44 | 0.0866 | 10. | 3.16 |
| 29 | 4-(3-Cyclohexylphenyl)-N-(4-methyl-1-azabicyclo[3.2.2]nonan-4-yl)piperazine-1-carboxamide | 29 | 0.309 | 2.66 | 0.0382 | 7.81 | 1.0 |
| 30 | 4-([1,1'-Biphenyl]-3-yl)-2-methyl-N-(4-methyl-1-azabicyclo[3.2.2]nonan-4-yl)piperazine-1-carboxamide | 30 | 0.376 | 0.864 | 0.0639 | 7.64 | 1.0 |
| 31 | 4-([1,1'-Biphenyl]-3-yl)-3-methyl-N-(4-methyl-1-azabicyclo[3.2.2]nonan-4-yl)piperazine-1-carboxamide | 31 | 0.00406 | 0.0707 | 0.00151 | 7.62 | 1.0 |
| 32 | 4-([1,1'-Biphenyl]-3-yl)-3-methyl-N-(4-methyl-1-azabicyclo[3.2.2]nonan-4-yl)piperazine-1-carboxamide | 32 | 0.544 | 0.462 | 0.0465 | 7.29 | 3.16 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 33 | 1-(4'-Fluoro-[1,1'-biphenyl]-3-yl)-N-(3-methylquinuclidin-3-yl)piperidine-4-carboxamide | 33 | 0.0221 | 0.237 | 0.00502 | 6.91 | 1.0 |
| 34 | 1-(4'-Fluoro-[1,1'-biphenyl]-3-yl)-N-(4-methyl-1-azabicyclo[3.2.2]nonan-4-yl)piperidine-4-carboxamide | 34 | 0.00478 | 0.079 | 0.000872 | 4.72 | 0.316 |
| 35 | 1-([1,1'-Biphenyl]-3-yl)-N-(3-methylquinuclidin-3-yl)piperidine-4-carboxamide | 35 | 0.0496 | 0.149 | 0.00711 | 7.31 | 1.0 |
| 36 | 1-([1,1'-Biphenyl]-3-yl)-N-(4-methyl-1-azabicyclo[3.2.2]nonan-4-yl)piperidine-4-carboxamide | 36 | 0.0103 | 0.136 | 0.0025 | 7.57 | 1.0 |
| 37 | 1-([1,1'-Biphenyl]-4-yl)-N-(3-methylquinuclidin-3-yl)piperidine-4-carboxamide | 37 | 1.55 | 1.8 | 0.131 | 7.05 | 6.9 |
| 38 | 1-([1,1'-Biphenyl]-4-yl)-N-(4-methyl-1-azabicyclo[3.2.2]nonan-4-yl)piperidine-4-carboxamide | 38 | 1.05 | 2.6 | 0.0894 | 6.62 | 6.74 |
| 39 | N-(4-Methyl-1-azabicyclo[3.2.2]nonan-4-yl)-1-(3-(pyrimidin-2-yl)phenyl)piperidine-4-carboxamide | 39 | 1.8 | 7.24 | 0.126 | 10. | 3.16 |
| 40 | N-(4-Methyl-1-azabicyclo[3.2.2]nonan-4-yl)-1-(3-(pyrimidin-5-yl)phenyl)piperidine-4-carboxamide | 40 | 0.291 | 5.5 | 0.0152 | 0.0713 | 1.0 |
| 41 | 1-(4-(4-Fluorophenyl)pyrimidin-2-yl)-N-(4-methyl-1-azabicyclo[3.2.2]nonan-4-yl)piperidine-4-carboxamide | 41 | 0.00114 | 0.0097 | 0.000124 | 6.44 | 0.020 |
| 42 | 1-(4-(4-Fluorophenyl)pyrimidin-2-yl)-N-(4-methyl-1-azabicyclo[3.2.2]nonan-4-yl)piperidine-4-carboxamide (single enantiomer A) | 42 | 0.0941 | 0.918 | 0.00982 | 7.66 | 4.64 |
| 43 | 1-(4-(4-Fluorophenyl)pyrimidin-2-yl)-N-(4-methyl-1-azabicyclo[3.2.2]nonan-4-yl)piperidine-4-carboxamide (single enantiomer B) | 43 | 0.00125 | 0.00654 | 0.0000655 | 7.14 | 8.92 |
| 44 | 1-(4-(4-Fluorophenyl)pyrimidin-2-yl)-N-(3-methylquinuclidin-3-yl)piperidine-4-carboxamide | 44 | 0.00124 | 0.0499 | 0.000205 | 9.27 | 0.316 |
| 45 | 1-(4-(4-Fluorophenyl)pyrimidin-2-yl)-N-(quinuclidin-3-yl)piperidine-4-carboxamide | 45 | 0.00267 | 0.125 | 0.000457 | 10. | 1.0 |
| 46 | 1-(6-(4-Fluorophenyl)pyrazin-2-yl)-N-(4-methyl-1-azabicyclo[3.2.2]nonan-4-yl)piperidine-4-carboxamide | 46 | 0.00279 | 0.0766 | 0.000425 | 7.31 | 0.316 |
| 47 | 1-(6-(4-Fluorophenyl)pyrazin-2-yl)-N-(4-methyl-1-azabicyclo[3.2.2]nonan-4-yl)piperidine-4-carboxamide (single enantiomer A) | 47 | 0.258 | 2.19 | 0.050 | 7.83 | 3.16 |
| 48 | 1-(6-(4-Fluorophenyl)pyrazin-2-yl)-N-(4-methyl-1-azabicyclo[3.2.2]nonan-4-yl)piperidine-4-carboxamide (single enantiomer B) | 48 | 0.00161 | 0.0477 | 0.000096 | 7.76 | 0.00517 |
| 49 | 1-(6-(4-Fluorophenyl)pyrazin-2-yl)-N-(3-methylquinuclidin-3-yl)piperidine-4-carboxamide | 49 | 0.0041 | 0.145 | 0.000822 | 8.16 | 1.0 |
| 50 | 1-(4-(4-Fluorophenyl)-1,3,5-triazin-2-yl)-N-(4-methyl-1-azabicyclo[3.2.2]nonan-4-yl)piperidine-4-carboxamide | 50 | 0.0325 | 0.162 | 0.000708 | 10. | 3.16 |
| 51 | 1-(2-(4-Fluorophenyl)pyrimidin-4-yl)-N-(4-methyl-1-azabicyclo[3.2.2]nonan-4-yl)piperidine-4-carboxamide | 51 | 0.0466 | 0.335 | 0.00388 | 8.26 | 3.16 |
| 52 | 4-([1,1'-Biphenyl]-3-yl)-N-(4-methyl-1-azabicyclo[3.2.2]nonan-4-yl)piperidine-1-carboxamide | 52 | 0.503 | 1.06 | 0.337 | 7.36 | 8.64 |
| 53 | 4-([1,1'-Biphenyl]-4-yl)-N-(4-methyl-1-azabicyclo[3.2.2]nonan-4-yl)piperidine-1-carboxamide | 53 | 2.21 | 1.24 | 0.175 | 6.74 | 6.29 |
| 54 | 1-(5-Fluoro-4-(4-fluorophenyl)pyrimidin-2-yl)-N-(3-methylquinuclidin-3-yl)piperidine-4-carboxamide | 54 | 0.000734 | 0.106 | 0.0000902 | 5.13 | 8.04 |
| 55 | 1-(5-Fluoro-4-(4-fluorophenyl)pyrimidin-2-yl)-N-(4-methyl-1-azabicyclo[3.2.2]nonan-4-yl)piperidine-4-carboxamide | 55 | 0.000736 | 0.0475 | 0.0000479 | 3.74 | 0.10 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 56 | 1-(5-Fluoro-4-(4-(2-methoxyethoxy)phenyl)pyrimidin-2-yl)-N-(4-methyl-1-azabicyclo[3.2.2]nonan-4-yl)piperidine-4-carboxamide | 56 | 0.00463 | 0.0209 | 0.000173 | 6.76 | 7.42 |
| 57 | 1-(5-Fluoro-4-(4-(2-methoxyethoxy)phenyl)pyrimidin-2-yl)-N-(3-methylquinuclidin-3-yl)piperidine-4-carboxamide | 57 | 0.00241 | 0.0693 | 0.000169 | 10. | 1.0 |
| 58 | 1-(5-Fluoro-4-(4-((2-methoxyethoxy)methyl)phenyl)pyrimidin-2-yl)-N-(4-methyl-1-azabicyclo[3.2.2]nonan-4-yl)piperidine-4-carboxamide | 58 | 0.00339 | 0.0405 | 0.00017 | 10. | 1.0 |
| 59 | 1-(5-Fluoro-4-(4-((2-methoxyethoxy)methyl)phenyl)pyrimidin-2-yl)-N-(3-methylquinuclidin-3-yl)piperidine-4-carboxamide | 59 | 0.00918 | 0.152 | 0.000339 | 10. | 0.464 |
| 60 | 1-(5-Fluoro-4-(4-(methoxymethyl)phenyl)pyrimidin-2-yl)-N-(4-methyl-1-azabicyclo[3.2.2]nonan-4-yl)piperidine-4-carboxamide | 60 | 0.00168 | 0.0155 | 0.0001 | 3.5 | 0.0464 |
| 61 | 1-(5-Fluoro-4-(4-(methoxymethyl)phenyl)pyrimidin-2-yl)-N-(3-methylquinuclidin-3-yl)piperidine-4-carboxamide | 61 | 0.00141 | 0.0524 | 0.00013 | 8.54 | 0.0464 |
| 62 | 1-(5-Fluoro-4-(4-(3-methoxypropoxy)phenyl)pyrimidin-2-yl)-N-(4-methyl-1-azabicyclo[3.2.2]nonan-4-yl)piperidine-4-carboxamide | 62 | 0.000931 | 0.0105 | 0.000109 | 2.39 | 0.10 |
| 63 | 1-(5-Fluoro-4-(4-(3-methoxypropoxy)phenyl)pyrimidin-2-yl)-N-(3-methylquinuclidin-3-yl)piperidine-4-carboxamide | 63 | 0.000586 | 0.0408 | 0.0000988 | 3.52 | 0.10 |
| 64 | 1-(4-(3,4-Difluorophenyl)pyrimidin-2-yl)-N-(4-methyl-1-azabicyclo[3.2.2]nonan-4-yl)piperidine-4-carboxamide | 64 | 0.0017 | 0.0329 | 0.000062 | 3.42 | 5.53 |
| 65 | 1-(4-(3,5-Difluorophenyl)pyrimidin-2-yl)-N-(4-methyl-1-azabicyclo[3.2.2]nonan-4-yl)piperidine-4-carboxamide | 65 | 0.00131 | 0.0561 | 0.0000934 | 4.14 | 0.215 |
| 66 | 1-(4-(4-(2-Methoxyethoxy)phenyl)pyrimidin-2-yl)-N-(4-methyl-1-azabicyclo[3.2.2]nonan-4-yl)piperidine-4-carboxamide | 66 | 0.00317 | 0.0693 | 0.000329 | 8.2 | 0.215 |
| 67 | 1-(4-(4-(3-Methoxypropoxy)phenyl)pyrimidin-2-yl)-N-(4-methyl-1-azabicyclo[3.2.2]nonan-4-yl)piperidine-4-carboxamide | 67 | 0.00188 | 0.00724 | 0.000114 | 4.95 | 1.0 |
| 68 | 1-(4'-(2-Methoxyethoxy)-[1,1'-biphenyl]-3-yl)-N-(4-methyl-1-azabicyclo[3.2.2]nonan-4-yl)piperidine-4-carboxamide | 68 | 0.0213 | 0.132 | 0.00353 | 7.12 | 3.16 |
| 69 | 1-(4'-((2-Methoxyethoxy)methyl)-[1,1'-biphenyl]-3-yl)-N-(4-methyl-1-azabicyclo[3.2.2]nonan-4-yl)piperidine-4-carboxamide | 69 | 0.0362 | 0.303 | 0.00464 | 4.64 | 1.0 |
| 70 | 1-(4-(4-(Methoxymethyl)phenyl)pyrimidin-2-yl)-N-(4-methyl-1-azabicyclo[3.2.2]nonan-4-yl)piperidine-4-carboxamide | 70 | 0.00396 | 0.0156 | 0.0000905 | 1.0 | 1.0 |
| 71 | 1-(4-(4-(2-Fluoroethoxy)phenyl)pyrimidin-2-yl)-N-(4-methyl-1-azabicyclo[3.2.2]nonan-4-yl)piperidine-4-carboxamide | 71 | 0.00248 | 0.00429 | 0.000126 | 2.15 | 0.010 |
| 72 | 1-(4-(4-(3-Methoxypropoxy)phenyl)pyrimidin-2-yl)-N-(quinuclidin-3-yl)piperidine-4-carboxamide | 72 | 0.00116 | 0.0795 | 0.00026 | 8.63 | 0.464 |
| 73 | 1-(4-(4-(Methoxymethyl)phenyl)pyrimidin-2-yl)-N-(3-methylquinuclidin-3-yl)piperidine-4-carboxamide | 73 | 0.00346 | 0.0474 | 0.00025 | 4.64 | 0.631 |
| 74 | 1-(4-(4-((2-Methoxyethoxy)methyl)phenyl)pyrimidin-2-yl)-N-(4-methyl-1-azabicyclo[3.2.2]nonan-4-yl)piperidine-4-carboxamide | 74 | 0.0128 | 0.0325 | 0.00071 | 10. | 0.215 |

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 75 | 4-Fluoro-1-(4-(4-(methoxymethyl)phenyl)pyrimidin-2-yl)-N-(4-methyl-1-azabicyclo[3.2.2]nonan-4-yl)piperidine-4-carboxamide | 75 | 0.00283 | 0.0489 | 0.000383 | 5.27 | 0.316 |
| 76 | 4-Fluoro-1-(4-(4-(3-methoxypropoxy)phenyl)pyrimidin-2-yl)-N-(3-methylquinuclidin-3-yl)piperidine-4-carboxamide | 76 | 0.00134 | 0.0587 | 0.000141 | 3.87 | 1.0 |
| 77 | 4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide | 77 | 0.00167 | 0.0863 | 0.000316 | 3.76 | 0.316 |
| 78 | 4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide (single enantiomer A) | 78 | 0.0647 | 3.12 | 0.00487 | 3.54 | 1.0 |
| 79 | 4-Fluoro-1-(5-fluoro-4-(4-((2-methoxyethoxy)methyl)phenyl)pyrimidin-2-yl)-N-(4-methyl-1-azabicyclo[3.2.2]nonan-4-yl)piperidine-4-carboxamide (single enantiomer B) | 79 | 0.0018 | 0.109 | 0.000191 | 4.28 | 0.215 |
| 80 | 4-Fluoro-1-(4-(4-(methoxymethyl)phenyl)pyrimidin-2-yl)-N-(3-methylquinuclidin-3-yl)piperidine-4-carboxamide | 80 | 0.0040 | 0.0685 | 0.000525 | 10. | 0.215 |
| 81 | (S)-4-Fluoro-1-(4-(4-(methoxymethyl)phenyl)pyrimidin-2-yl)-N-(3-methylquinuclidin-3-yl)piperidine-4-carboxamide | 81 | 0.0023 | 0.0481 | 0.000222 | 10. | 0.316 |
| 82 | 4-Fluoro-1-(4-(4-(3-methoxypropoxy)phenyl)pyrimidin-2-yl)-N-(4-methyl-1-azabicyclo[3.2.2]nonan-4-yl)piperidine-4-carboxamide | 82 | 0.00126 | 0.0421 | 0.000128 | 2.79 | 1.0 |
| 83 | 4-Fluoro-1-(4-(4-((2-methoxyethoxy)methyl)phenyl)pyrimidin-2-yl)-N-(3-methylquinuclidin-3-yl)piperidine-4-carboxamide | 83 | 0.0134 | 0.119 | 0.00113 | 10. | 1.0 |
| 84 | (S)-4-Fluoro-1-(4-(4-((2-methoxyethoxy)methyl)phenyl)pyrimidin-2-yl)-N-(3-methylquinuclidin-3-yl)piperidine-4-carboxamide | 84 | 0.00535 | 0.0903 | 0.000621 | 10. | 1.0 |
| 85 | 4-Fluoro-1-(4-(4-(2-methoxyethoxy)phenyl)pyrimidin-2-yl)-N-(3-methylquinuclidin-3-yl)piperidine-4-carboxamide | 85 | 0.0105 | 0.0799 | 0.000389 | 10. | 0.316 |
| 86 | (S)-4-Fluoro-1-(4-(4-(2-methoxyethoxy)phenyl)pyrimidin-2-yl)-N-(3-methylquinuclidin-3-yl)piperidine-4-carboxamide | 86 | 0.00346 | 0.048 | 0.000241 | 10. | 1.0 |
| 87 | 4-Fluoro-1-(4-(4-(2-fluoroethoxy)phenyl)pyrimidin-2-yl)-N-(quinuclidin-3-yl)piperidine-4-carboxamide | 87 | 0.00191 | 0.0643 | 0.000177 | 8.91 | 0.215 |
| 88 | (S)-4-Fluoro-1-(4-(4-(2-fluoroethoxy)phenyl)pyrimidin-2-yl)-N-(quinuclidin-3-yl)piperidine-4-carboxamide | 88 | 0.00168 | 0.0568 | 0.000252 | 10. | 1.0 |
| 89 | 4-Fluoro-1-(4-(4-((2-methoxyethoxy)methyl)phenyl)pyrimidin-2-yl)-N-(4-methyl-1-azabicyclo[3.2.2]nonan-4-yl)piperidine-4-carboxamide | 89 | 0.00823 | 0.109 | 0.00117 | 9.47 | 0.316 |
| 90 | 4-Fluoro-1-(4-(4-(2-fluoroethoxy)phenyl)pyrimidin-2-yl)-N-(4-methyl-1-azabicyclo[3.2.2]nonan-4-yl)piperidine-4-carboxamide | 90 | 0.00226 | 0.0134 | 0.0000953 | 3.06 | 0.215 |
| 91 | 4-Fluoro-1-(5-fluoro-4-(4-(2-methoxyethoxy)phenyl)pyrimidin-2-yl)-N-(4-methyl-1-azabicyclo[3.2.2]nonan-4-yl)piperidine-4-carboxamide | 91 | 0.00204 | 0.0714 | 0.000117 | 2.66 | 0.10 |
| 92 | 4-Fluoro-1-(4-(4-(2-fluoroethoxy)phenyl)pyrimidin-2-yl)-N-(3-methylquinuclidin-3-yl)piperidine-4-carboxamide | 92 | 0.00146 | 0.029 | 0.000106 | 6.83 | 0.10 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
| --- | --- | --- | --- | --- | --- | --- | --- |
| 93 | 4-Fluoro-1-(4-(4-(2-methoxyethoxy)phenyl)pyrimidin-2-yl)-N-(4-methyl-1-azabicyclo[3.2.2]nonan-4-yl)piperidine-4-carboxamide | 93 | 0.00396 | 0.0439 | 0.000261 | 3.96 | 0.316 |
| 94 | 4-Fluoro-1-(4-(4-fluorophenyl)pyrimidin-2-yl)-N-(4-methyl-1-azabicyclo[3.2.2]nonan-4-yl)piperidine-4-carboxamide | 94 | 0.000736 | 0.0144 | 0.0000964 | 2.1 | 0.0464 |
| 95 | 4-Fluoro-1-(4-(4-fluorophenyl)pyrimidin-2-yl)-N-(3-methylquinuclidin-3-yl)piperidine-4-carboxamide | 95 | 0.000585 | 0.020 | 0.0000836 | 4.69 | 0.0316 |
| 96 | 1-(4-(4-(Methoxymethyl)phenyl)pyrimidin-2-yl)-4-methyl-N-(4-methyl-1-azabicyclo[3.2.2]nonan-4-yl)piperidine-4-carboxamide | 96 | 0.0070 | 0.145 | 0.000804 | 3.39 | 1.0 |
| 97 | 1-(4-(4-((2-Methoxyethoxy)methyl)phenyl)pyrimidin-2-yl)-4-methyl-N-(4-methyl-1-azabicyclo[3.2.2]nonan-4-yl)piperidine-4-carboxamide | 97 | 0.0134 | 0.285 | 0.00136 | 10. | 1.0 |
| 98 | 1-(4-(4-((2-Methoxyethoxy)methyl)phenyl)pyrimidin-2-yl)-4-methyl-N-(3-methylquinuclidin-3-yl)piperidine-4-carboxamide | 98 | 0.0769 | 1.91 | 0.00813 | 8.19 | 1.0 |
| 99 | 1-(4-(4-Fluorophenyl)pyrimidin-2-yl)-4-hydroxy-N-(4-methyl-1-azabicyclo[3.2.2]nonan-4-yl)piperidine-4-carboxamide | 99 | 0.00223 | 0.012 | 0.0000552 | 3.78 | 0.0464 |
| 100 | 1-(4-(4-Fluorophenyl)pyrimidin-2-yl)-4-methoxy-N-(4-methyl-1-azabicyclo[3.2.2]nonan-4-yl)piperidine-4-carboxamide | 100 | 0.00368 | 0.0265 | 0.000109 | 1.9 | 1.0 |
| 101 | 4-Methoxy-1-(4-(4-(3-methoxypropoxy)phenyl)pyrimidin-2-yl)-N-(4-methyl-1-azabicyclo[3.2.2]nonan-4-yl)piperidine-4-carboxamide | 101 | 0.00338 | 0.0785 | 0.000436 | 2.03 | 1.0 |
| 102 | 1-(5-Fluoro-4-(4-(2-fluoroethoxy)phenyl)pyrimidin-2-yl)-4-methoxy-N-(4-methyl-1-azabicyclo[3.2.2]nonan-4-yl)piperidine-4-carboxamide | 102 | 0.00103 | 0.0929 | 0.000258 | 2.85 | 0.10 |
| 103 | 1-(4-(4-(2-Fluoroethoxy)phenyl)pyrimidin-2-yl)-4-methoxy-N-(4-methyl-1-azabicyclo[3.2.2]nonan-4-yl)piperidine-4-carboxamide | 103 | 0.00365 | 0.0738 | 0.00029 | 3.11 | 0.316 |
| 104 | 1-(4-(4-Fluorophenyl)-5-(2-methoxyethoxy)pyrimidin-2-yl)-N-(4-methyl-1-azabicyclo[3.2.2]nonan-4-yl)piperidine-4-carboxamide | 104 | 0.0251 | 0.0513 | 0.0030 | 10. | 1.0 |
| 105 | 1-(4-(4-Fluorophenyl)-6-(2-methoxyethoxy)pyrimidin-2-yl)-N-(4-methyl-1-azabicyclo[3.2.2]nonan-4-yl)piperidine-4-carboxamide | 105 | 0.0105 | 0.272 | 0.0020 | 3.66 | 1.0 |
| 106 | 1-(4-(4-Fluorophenyl)pyridin-2-yl)-N-(4-methyl-1-azabicyclo[3.2.2]nonan-4-yl)piperidine-4-carboxamide | 106 | 0.000858 | 0.0153 | 0.000095 | 6.97 | 9.02 |
| 107 | 1-(5-(4-Fluorophenyl)pyridin-3-yl)-N-(4-methyl-1-azabicyclo[3.2.2]nonan-4-yl)piperidine-4-carboxamide | 107 | 0.00476 | 0.299 | 0.000935 | 10. | 0.0785 |
| 108 | 1-(2-(4-Fluorophenyl)pyridin-4-yl)-N-(4-methyl-1-azabicyclo[3.2.2]nonan-4-yl)piperidine-4-carboxamide | 108 | 0.0808 | 1.08 | 0.0541 | 5.65 | 3.16 |
| 109 | 1-(4-(4-Fluorophenyl)pyrimidin-2-yl)-N-methyl-N-(quinuclidin-3-yl)piperidine-4-carboxamide | 109 | 0.0401 | 2.23 | 0.00899 | 9.53 | 3.16 |
| 110 | 1-Azabicyclo[3.2.2]nonan-4-yl 1-(4-(4-fluorophenyl)pyrimidin-2-yl)piperidine-4-carboxylate | 110 | 0.00122 | 0.528 | 0.00239 | 3.81 | 1.0 |
| 111 | 1-(5-Fluoro-4-(4-(3-methoxypropoxy)phenyl)pyrimidin-2-yl)-N-(4-methyl-1-azabicyclo[3.2.2]nonan-4-yl)azetidine-3-carboxamide | 111 | 0.0020 | 0.119 | 0.00019 | 3.65 | 1.0 |
| 112 | 1-(5-Fluoro-4-(4-fluorophenyl)pyrimidin-2-yl)-N-(4-methyl-1-azabicyclo[3.2.2]nonan-4-yl)azetidine-3-carboxamide | 112 | 0.00737 | 0.122 | 0.000238 | 7.24 | 0.316 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 113 | 1-(4-(4-Fluorophenyl)pyrimidin-2-yl)-N-(4-methyl-1-azabicyclo[3.2.2]nonan-4-yl)azetidine-3-carboxamide | 113 | 0.00831 | 0.546 | 0.000884 | 10. | 0.316 |
| 114 | 1-(4'-Fluoro-[1,1'-biphenyl]-3-yl)-N-(4-methyl-1-azabicyclo[3.2.2]nonan-4-yl)azetidine-3-carboxamide | 114 | 0.051 | 0.272 | 0.0111 | 3.46 | 1.0 |
| 115 | 1-(4-(4-Fluorophenoxy)pyrimidin-2-yl)-N-(4-methyl-1-azabicyclo[3.2.2]nonan-4-yl)piperidine-4-carboxamide | 115 | 0.00245 | 0.00894 | 0.00014 | 9.3 | 0.0464 |
| 116 | 4-Fluoro-1-(4-(4-fluorophenoxy)pyrimidin-2-yl)-N-(4-methyl-1-azabicyclo[3.2.2]nonan-4-yl)piperidine-4-carboxamide | 116 | 0.00143 | 0.0159 | 0.000155 | 5.72 | 0.10 |
| 117 | 4-Fluoro-1-(4-(4-fluorophenoxy)-1,3,5-triazin-2-yl)-N-(4-methyl-1-azabicyclo[3.2.2]nonan-4-yl)piperidine-4-carboxamide | 117 | 0.168 | 0.0884 | 0.00905 | 10. | 1.0 |
| 118 | 4-Fluoro-1-(4-(4-fluorophenoxy)-1,3,5-triazin-2-yl)-N-(4-methyl-1-azabicyclo[3.2.2]nonan-4-yl)piperidine-4-carboxamide | 118 | 0.00254 | 0.0634 | 0.00116 | 4.64 | 1.0 |
| 119 | 1-(4-(4-Cyanophenoxy)pyrimidin-2-yl)-4-fluoro-N-(3-methylquinuclidin-3-yl)piperidine-4-carboxamide | 119 | 0.00671 | 0.0544 | 0.000476 | 10. | 0.316 |
| 120 | 1-(4-(4-Cyanophenoxy)pyrimidin-2-yl)-4-fluoro-N-(4-methyl-1-azabicyclo[3.2.2]nonan-4-yl)piperidine-4-carboxamide | 120 | 0.00412 | 0.0188 | 0.000332 | 10. | 0.316 |
| 121 | 1-(4-(4-Fluorophenoxy)pyrimidin-2-yl)-N-(3-methylquinuclidin-3-yl)piperidine-4-carboxamide | 121 | 0.00133 | 0.0263 | 0.000093 | 7.65 | 0.10 |
| 122 | 1-(5-Cyano-4-(4-fluorophenoxy)pyrimidin-2-yl)-4-fluoro-N-(3-methylquinuclidin-3-yl)piperidine-4-carboxamide | 122 | 0.00441 | 0.112 | 0.000639 | 10. | 0.316 |
| 123 | 4-Fluoro-N-(4-methyl-1-azabicyclo[3.2.2]nonan-4-yl)-1-(4-((tetrahydro-2H-pyran-4-yl)oxy)pyrimidin-2-yl)piperidine-4-carboxamide | 123 | 0.0423 | 0.226 | 0.00226 | 10. | 1.0 |
| 124 | 4-Fluoro-1-(4-((4-fluorobenzyl)oxy)pyrimidin-2-yl)-N-(4-methyl-1-azabicyclo[3.2.2]nonan-4-yl)piperidine-4-carboxamide | 124 | 0.000553 | 0.0178 | 0.0000849 | 3.42 | 0.10 |
| 125 | 4-Fluoro-1-(4-((4-fluorobenzyl)oxy)pyrimidin-2-yl)-N-(3-methylquinuclidin-3-yl)piperidine-4-carboxamide | 125 | 0.000643 | 0.0177 | 0.0000509 | 4.29 | 0.158 |
| 126 | 4-Fluoro-1-(6-(4-fluorophenoxy)pyrazin-2-yl)-N-(4-methyl-1-azabicyclo[3.2.2]nonan-4-yl)piperidine-4-carboxamide | 126 | 0.00157 | 0.036 | 0.000726 | 6.26 | 1.0 |
| 127 | 4-Fluoro-1-(5-(4-fluorophenoxy)pyridin-3-yl)-N-(4-methyl-1-azabicyclo[3.2.2]nonan-4-yl)piperidine-4-carboxamide | 127 | 0.00227 | 0.106 | 0.000569 | 6.98 | 0.316 |
| 128 | 4-Fluoro-1-(4-((4-fluorobenzyl)oxy)-1,3,5-triazin-2-yl)-N-(4-methyl-1-azabicyclo[3.2.2]nonan-4-yl)piperidine-4-carboxamide | 128 | 0.0198 | 0.654 | 0.0034 | 10. | 1.0 |
| 129 | 4-Fluoro-1-(5-(4-fluorophenoxy)pyrimidin-2-yl)-N-(3-methylquinuclidin-3-yl)piperidine-4-carboxamide | 129 | 0.00427 | 0.0978 | 0.00038 | 8.26 | 0.316 |
| 130 | 1-(5-(4-Fluorophenoxy)pyrimidin-2-yl)-N-(4-methyl-1-azabicyclo[3.2.2]nonan-4-yl)piperidine-4-carboxamide | 130 | 0.000889 | 0.0169 | 0.000156 | 5.67 | 0.316 |
| 131 | 4-Fluoro-1-(5-(4-(2-methoxyethoxy)phenoxy)pyrimidin-2-yl)-N-(3-methylquinuclidin-3-yl)piperidine-4-carboxamide | 131 | 0.00681 | 0.0527 | 0.000858 | 10. | 1.0 |
| 132 | 4-Fluoro-1-(5-((4-fluorobenzyl)oxy)pyrimidin-2-yl)-N-(4-methyl-1-azabicyclo[3.2.2]nonan-4-yl)piperidine-4-carboxamide | 132 | 0.0107 | 0.115 | 0.00265 | 4.59 | 1.0 |
| 133 | 4-Fluoro-1-(5-(4-fluorophenoxy)pyrazin-2-yl)-N-(3-methylquinuclidin-3-yl)piperidine-4-carboxamide | 133 | 0.0459 | 0.467 | 0.00483 | 10. | 1.0 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
| --- | --- | --- | --- | --- | --- | --- | --- |
| 134 | 4-Fluoro-1-(6-(4-fluorophenoxy)pyridazin-3-yl)-N-(4-methyl-1-azabicyclo[3.2.2]nonan-4-yl)piperidine-4-carboxamide | 134 | 0.0145 | 0.343 | 0.00283 | 10. | 1.0 |
| 135 | 4-Fluoro-1-(4-((4-fluorophenoxy)methyl)pyrimidin-2-yl)-N-(3-methylquinuclidin-3-yl)piperidine-4-carboxamide | 135 | 0.00138 | 0.0317 | 0.000132 | 8.25 | 0.0464 |
| 136 | 4-Fluoro-1-(5-(4-fluorobenzyl)pyrimidin-2-yl)-N-(3-methylquinuclidin-3-yl)piperidine-4-carboxamide | 136 | 0.0079 | 0.0249 | 0.000716 | 10. | 1.0 |
| 137 | (3R)-3-Methyl-N-(4-methyl-1-azabicyclo[3.2.2]nonan-4-yl-4-(4-phenylpyrimidin-2-yl)piperazine-1-carboxamide (single enantiomer B) | 137 | 0.0032 | 0.0501 | 0.000198 | 5.72 | 1.0 |
| 138 | (3R)-3-Methyl-N-(4-methyl-1-azabicyclo[3.2.2]nonan-4-yl)-4-(4-phenylpyrimidin-2-yl)piperazine-1-carboxamide(single enantiomer A) | 138 | 0.902 | >10 | 0.0636 | 9.31 | 3.16 |
| 139 | (3S)-3-Methyl-N-(4-methyl-1-azabicyclo[3.2.2]nonan-4-yl)-4-(4-phenylpyrimidin-2-yl)piperazine-1-carboxamide (single enantiomer B) | 139 | 0.0173 | 0.067 | 0.00137 | 5.25 | 3.16 |
| 140 | (3S)-3-Methyl-N-(4-methyl-1-azabicyclo[3.2.2]nonan-4-yl)-4-(4-phenylpyrimidin-2-yl)piperazine-1-carboxamide (single enantiomer A) | 140 | 0.0469 | 9.08 | 0.574 | 6.49 | 3.16 |
| 141 | 3-Methyl-N-(4-methyl-1-azabicyclo[3.2.2]nonan-4-yl)-4-(4-phenylpyrimidin-2-yl)piperazine-1-carboxamide | 141 | 0.00596 | 0.209 | 0.000888 | 4.67 | 0.316 |
| 142 | 3-Ethyl-N-(4-methyl-1-azabicyclo[3.2.2]nonan-4-yl)-4-(4-phenylpyrimidin-2-yl)piperazine-1-carboxamide | 142 | 0.00769 | 0.10 | 0.000861 | 5.34 | 9.21 |
| 143 | 3-Ethyl-N-(4-methyl-1-azabicyclo[3.2.2]nonan-4-yl)-4-(4-phenylpyrimidin-2-yl)piperazine-1-carboxamide | 143 | 0.00179 | 0.0523 | 0.000304 | 3.11 | 3.16 |
| 144 | 3-(Methoxymethyl)-N-(4-methyl-1-azabicyclo[3.2.2]nonan-4-yl)-4-(4-phenylpyrimidin-2-yl)piperazine-1-carboxamide | 144 | 0.0673 | 0.529 | 0.00633 | 10. | 1.0 |
| 145 | 4-(4-(4-Fluorophenyl)pyrimidin-2-yl)-3-methyl-N-(4-methyl-1-azabicyclo[3.2.2]nonan-4-yl)piperazine-1-carboxamide | 145 | 0.00801 | 0.0763 | 0.000507 | 6.98 | 0.316 |
| 146 | 4-(4-(4-Fluorophenyl)pyrimidin-2-yl)-3-methyl-N-(4-methyl-1-azabicyclo[3.2.2]nonan-4-yl)piperazine-1-carboxamide | 146 | 0.0166 | 0.11 | 0.000559 | 6.37 | 1.0 |
| 147 | cis-3,5-Dimethyl-N-(4-methyl-1-azabicyclo[3.2.2]nonan-4-yl)-4-(4-phenylpyrimidin-2-yl)piperazine-1-carboxamide | 147 | 0.00545 | 0.096 | 0.0010 | 3.51 | 1.0 |
| 148 | 4-(5-Fluoro-4-(methoxymethyl)phenyl)pyrimidin-2-yl)-3-isopropyl-N-(4-methyl-1-azabicyclo[3.2.2]nonan-4-yl)piperazine-1-carboxamide | 148 | 0.0174 | 0.39 | 0.00859 | 3.46 | 1.0 |
| 149 | 4-(4-(4-(Methoxymethyl)phenyl)pyrimidin-2-yl)-N-(4-methyl-1-azabicyclo[3.2.2]nonan-4-yl)-3-(trifluoromethyl)piperazine-1-carboxamide | 149 | 0.0109 | 0.279 | 0.0015 | 4.31 | 1.0 |
| 150 | 3-(Difluoromethyl)-4-(4-(4-(methoxymethyl)phenyl)pyrimidin-2-yl)-N-(4-methyl-1-azabicyclo[3.2.2]nonan-4-yl)piperazine-1-carboxamide | 150 | 0.023 | 0.195 | 0.00106 | 5.44 | 1.0 |
| 151 | 3-Isopropyl-4-(4-(4-(methoxymethyl)phenyl)-1,3,5-triazin-2-yl)-N-(4-methyl-1-azabicyclo[3.2.2]nonan-4-yl)piperazine-1-carboxamide | 151 | 0.324 | 1.82 | 0.0956 | 9.84 | 1.0 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 152 | (3R)-4-(5-(4-Fluorophenoxy)pyrimidin-2-yl)-3-methyl-N-(4-methyl-1-azabicyclo[3.2.2]nonan-4-yl)piperazine-1-carboxamide | 152 | 0.00288 | 0.0763 | 0.000439 | 6.77 | 0.316 |
| 153 | 3-Ethynyl-4-(4-(methoxymethyl)phenyl)pyrimidin-2-yl)-N-(4-methyl-1-azabicyclo[3.2.2]nonan-4-yl)piperazine-1-carboxamide | 153 | 0.0534 | 2.64 | 0.0117 | 10. | 1.0 |
| 154 | 1-Azabicyclo[3.2.2]nonan-4-yl 3-methyl-4-(4-phenylpyrimidin-2-yl)piperazine-1-carboxylate | 154 | 0.057 | 1.93 | 0.0165 | 2.84 | 1.0 |
| 155 | Quinuclidin-3-yl(2-(4'-(2-methoxyethoxy)-[1,1'-biphenyl]-4-yl)propan-2-yl)carbamate | 155 | 0.00348 | 0.0386 | 0.000657 | 1.0 | 0.215 |
| 156 | (S)-Quinuclidin-3-yl (2-(4'-(2-methoxyethoxy)-[1,1'-biphenyl]-4-yl)propan-2-yl)carbamate | 156 | 0.00414 | 0.0437 | 0.00131 | 4.74 | 0.763 |
| 157 | (R)-1-(2-(4'-(2-Methoxyethoxy)-[1,1'-biphenyl]-4-yl)propan-2-yl)-3-(3-methylquinuclidin-3-yl)urea | 157 | 0.228 | 0.538 | 0.042 | 3.16 | 3.16 |
| 158 | (S)-1-(2-(4'-(2-Methoxyethoxy)-[1,1'-biphenyl]-4-yl)propan-2-yl)-3-(3-methylquinuclidin-3-yl)urea | 158 | 0.00285 | 0.00762 | 0.000529 | 0.631 | 0.631 |
| 159 | 1-(3-Ethylquinuclidin-3-yl)-3-(2-(4'-(2-methoxyethoxy)-[1,1'-biphenyl]-4-yl)propan-2-yl)urea | 159 | 0.0056 | 0.00446 | 0.000636 | 1.0 | 1.0 |
| 160 | 1-(2-(4'-(2-Methoxyethoxy)-[1,1'-biphenyl]-4-yl)propan-2-yl)-3-(4-methyl-1-azabicyclo[3.2.2]nonan-4-yl)urea | 160 | 0.00391 | 0.0019 | 0.000544 | 1.0 | 1.0 |
| 161 | N-(2-(4'-(2-Methoxyethoxy)-[1,1'-biphenyl]-4-yl)propan-2-yl)-1,4-diazabicyclo[3.2.2]nonane-4-carboxamide | 161 | 0.25 | 0.311 | 0.0327 | 3.16 | 3.16 |
| 162 | 1-(1-(4'-(2-Methoxyethoxy)-[1,1'-biphenyl]-4-yl)cyclopropyl)-3-(quinuclidin-3-yl)urea | 162 | 0.0281 | 0.0727 | 0.00221 | 3.54 | 1.0 |
| 163 | 1-(1-(4'-(2-Methoxyethoxy)-[1,1'-biphenyl]-4-yl)cyclopropyl)-3-(3-methylquinuclidin-3-yl)urea | 163 | 0.00849 | 0.00657 | 0.000539 | 1.0 | 0.173 |
| 164 | 1-(3-Ethylquinuclidin-3-yl)-3-(1-(4'-(2-methoxyethoxy)-[1,1'-biphenyl]-4-yl)cyclopropyl)urea | 164 | 0.00616 | 0.00251 | 0.000205 | 1.0 | 0.173 |
| 165 | 1-(1-(4'-(2-Methoxyethoxy)-[1,1'-biphenyl]-4-yl)cyclopropyl)-3-(4-methyl-1-azabicyclo[3.2.2]nonan-4-yl)urea | 165 | 0.00415 | 0.000516 | 0.00024 | 0.316 | 0.0316 |
| 166 | Quinuclidin-3-yl (1-(4'-(2-methoxyethoxy)-[1,1'-biphenyl]-4-yl)cyclopropyl)carbamate | 166 | 0.00569 | 0.0219 | 0.00181 | 0.316 | 0.215 |
| 167 | Quinuclidin-3-yl (2-(3'-(2-methoxyethoxy)-[1,1'-biphenyl]-4-yl)propan-2-yl)carbamate | 167 | 0.0104 | 0.109 | 0.00531 | 10. | 1.0 |
| 168 | 1-Azabicyclo[3.2.2]nonan-4-yl (2-(3'-(2-methoxyethoxy)-[1,1'-biphenyl]-4-yl)propan-2-yl)carbamate | 168 | 0.00556 | 0.0793 | 0.00334 | 10. | 1.0 |
| 169 | N-(2-(3'-(2-Methoxyethoxy)-[1,1'-biphenyl]-4-yl)propan-2-yl)-1,4-diazabicyclo[3.2.2]nonane-4-carboxamide | 169 | 0.257 | 0.283 | 0.018 | 10. | 1.0 |
| 170 | Quinuclidin-3-yl (2-(4'-(2-methoxyethoxy)-[1,1'-biphenyl]-3-yl)propan-2-yl)carbamate | 170 | 0.0267 | 0.0295 | 0.00494 | 10. | 10. |
| 171 | 1-Azabicyclo[3.2.2]nonan-4-yl (2-(4'-(2-methoxyethoxy)-[1,1'-biphenyl]-3-yl)propan-2-yl)carbamate | 171 | 0.0325 | 0.0119 | 0.00145 | 0.0746 | 3.98 |
| 172 | Quinuclidin-3-yl (2-(4'-(3-methoxypropoxy)-[1,1'-biphenyl]-4-yl)propan-2-yl)carbamate | 172 | 0.00241 | 0.0666 | 0.00156 | 8.29 | 10. |
| 173 | 1-(2-(4'-(3-Methoxypropoxy)-[1,1'-biphenyl]-4-yl)propan-2-yl)-3-(3-methylquinuclidin-3-yl)urea | 173 | 0.00198 | 0.0203 | 0.000766 | 10. | 10. |
| 174 | N-(2-(4'-(3-Methoxypropoxy)-[1,1'-biphenyl]-4-yl)propan-2-yl)-1,4-diazabicyclo[3.2.2]nonane-4-carboxamide | 174 | 0.134 | 0.386 | 0.0225 | 10. | 1.0 |
| 175 | Quinuclidin-3-yl (2-(4'-(2-methoxyethoxy)-[1,1'-biphenyl]-3-yl)propan-2-yl)carbamate | 175 | 0.0025 | 0.0713 | 0.00187 | 10. | 9.0 |
| 176 | 1-(1-(4'-(3-Methoxypropoxy)-[1,1'-biphenyl]-4-yl)cyclopropyl)-3-(3-methylquinuclidin-3-yl)urea | 176 | 0.0041 | 0.022 | 0.00147 | 10. | 10. |
| 177 | 1-(1-(4'-(3-Methoxypropoxy)-[1,1'-biphenyl]-4-yl)cyclopropyl)-3-(4-methyl-1-azabicyclo[3.2.2]nonan-4-yl)urea | 177 | 0.00159 | 0.00175 | 0.000497 | 10. | 10. |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
| --- | --- | --- | --- | --- | --- | --- | --- |
| 178 | 1-Azabicyclo[3.2.2]nonan-4-yl(1-(4'-(3-methoxypropoxy)-[1,1'-biphenyl]-4-yl)cyclopropyl)carbamate | 178 | 0.00354 | 0.0679 | 0.00261 | 10. | 7.1 |
| 179 | Quinuclidin-3-yl (2-(4'-(2-(1H-pyrazol-1-yl)ethoxy)-[1,1'-biphenyl]-4-yl)propan-2-yl)carbamate | 179 | 0.00673 | 0.0952 | 0.00499 | 8.73 | 3.16 |
| 180 | 1-(2-(4'-(2-(1H-Pyrazol-1-yl)ethoxy)-[1,1'-biphenyl]-4-yl)propan-2-yl)-3-(3-methylquinuclidin-3-yl)urea | 180 | 0.0053 | 0.0463 | 0.00181 | 3.16 | 3.16 |
| 181 | 1-(2-(4'-(2-(1H-Pyrazol-1-yl)ethoxy)-[1,1'-biphenyl]-4-yl)propan-2-yl)-3-(4-methyl-1-azabicyclo[3.2.2]nonan-4-yl)urea | 181 | 0.00233 | 0.00515 | 0.000587 | 1.0 | 1.0 |
| 182 | Quinuclidin-3-yl (2-(4'-(2-(1H-1,2,3-triazol-1-yl)ethoxy)-[1,1'-biphenyl]-4-yl)propan-2-yl)carbamate | 182 | 0.0431 | 0.388 | 0.0131 | 3.16 | 1.0 |
| 183 | 1-(2-(4'-(2-(1H-1,2,3-Triazol-1-yl)ethoxy)-[1,1'-biphenyl]-4-yl)propan-2-yl)-3-(3-methylquinuclidin-3-yl)urea | 183 | 0.0316 | 0.969 | 0.0102 | 5.62 | 2.51 |
| 184 | 1-(2-(4'-(2-(1H-1,2,3-Triazol-1-yl)ethoxy)-[1,1'-biphenyl]-4-yl)propan-2-yl)-3-(3-ethylquinuclidin-3-yl)urea | 184 | 0.0211 | 0.188 | 0.00346 | 3.16 | 1.0 |
| 185 | 1-(2-(4'-(2-(1H-1,2,3-Triazol-1-yl)ethoxy)-[1,1'-biphenyl]-4-yl)propan-2-yl)-3-(4-methyl-1-azabicyclo[3.2.2]nonan-4-yl)urea | 185 | 0.0129 | 0.0999 | 0.00387 | 3.16 | 1.0 |
| 186 | Quinuclidin-3-yl (2-(4'-(2-methoxyethoxy)-[1,1'-biphenyl]-3-yl)propan-2-yl)carbamate | 186 | 0.045 | 0.157 | 0.0107 | 10. | 1.0 |
| 187 | 1-Azabicyclo[3.2.2]nonan-4-yl (2-(4'-(3-(1H-1,2,3-triazol-1-yl)propoxy)-[1,1'-biphenyl]-4-yl)propan-2-yl)carbamate | 187 | 0.0202 | 0.106 | 0.00774 | 10. | 1.0 |
| 188 | N-(2-(4'-(3-(1H-1,2,3-Triazol-1-yl)propoxy)-[1,1'-biphenyl]-4-yl)propan-2-yl)-1,4-diazabicyclo[3.2.2]nonane-4-carboxamide | 188 | 0.597 | 0.365 | 0.0774 | 10. | 1.0 |
| 189 | Quinuclidin-3-yl (2-(4'-(3-cyanopropoxy)-[1,1'-biphenyl]-4-yl)propan-2-yl)carbamate | 189 | 0.00957 | 0.0865 | 0.00322 | 10. | 8.47 |
| 190 | Quinuclidin-3-yl (2-(4'-(cyanomethoxy)-[1,1'-biphenyl]-4-yl)propan-2-yl)carbamate | 190 | 0.00259 | 0.0477 | 0.000775 | 10. | 1.0 |
| 191 | Quinuclidin-3-yl (2-(4'-((3-methyloxetan-3-yl)methoxy)-[1,1'-biphenyl]-4-yl)propan-2-yl)carbamate | 191 | 0.0072 | 0.0718 | 0.00324 | 5.25 | 1.0 |
| 192 | 1-Azabicyclo[3.2.2]nonan-4-yl (2-(4'-((3-methyloxetan-3-yl)methoxy)-[1,1'-biphenyl]-4-yl)propan-2-yl)carbamate | 192 | 0.00569 | 0.0816 | 0.00186 | 5.84 | 1.0 |
| 193 | 1-Azabicyclo[3.2.2]nonan-4-yl (2-(4'-((3-methyloxetan-3-yl)methoxy)-[1,1'-biphenyl]-4-yl)propan-2-yl)carbamate | 193 | 0.297 | 0.318 | 0.0447 | 10. | 10. |
| 194 | Quinuclidin-3-yl (2-(4'-(2-(oxetan-3-yl)ethoxy)-[1,1'-biphenyl]-4-yl)propan-2-yl)carbamate | 194 | 0.0105 | 0.115 | 0.00406 | 9.93 | 1.0 |
| 195 | 1-Azabicyclo[3.2.2]nonan-4-yl (2-(4'-(2-(oxetan-3-yl)ethoxy)-[1,1'-biphenyl]-4-yl)propan-2-yl)carbamate | 195 | 0.00567 | 0.0948 | 0.00101 | 8.03 | 0.10 |
| 196 | N-(2-(4'-(2-(Oxetan-3-yl)ethoxy)-[1,1'-biphenyl]-4-yl)propan-2-yl)-1,4-diazabicyclo[3.2.2]nonane-4-carboxamide | 196 | 0.538 | 0.274 | 0.0283 | 10. | 1.0 |
| 197 | Quinuclidin-3-yl (2-(4'-((2-methoxyethoxy)methyl)-[1,1'-biphenyl]-4-yl)propan-2-yl)carbamate | 197 | 0.0322 | 0.309 | 0.00967 | 10. | 10. |
| 198 | 1-(2-(4'-((2-Methoxyethoxy)methyl)-[1,1'-biphenyl]-4-yl)propan-2-yl)-3-(3-methylquinuclidin-3-yl)urea | 198 | 0.0252 | 0.118 | 0.00324 | 10. | 10. |
| 199 | 1-(3-Ethylquinuclidin-3-yl)-3-(2-(4'-((2-methoxyethoxy)methyl)-[1,1'-biphenyl]-4-yl)propan-2-yl)urea | 199 | 0.0147 | 0.0317 | 0.0018 | 1.0 | 1.0 |
| 200 | 1-Azabicyclo[3.2.2]nonan-4-yl (2-(4'-((2-methoxyethoxy)methyl)-[1,1'-biphenyl]-4-yl)propan-2-yl)carbamate | 200 | 0.024 | 0.22 | 0.00616 | 10. | 1.0 |
| 201 | 1-(2-(4'-((2-Methoxyethoxy)methyl)-[1,1'-biphenyl]-4-yl)propan-2-yl)-3-(4-methyl-1-azabicyclo[3.2.2]nonan-4-yl)urea | 201 | 0.0139 | 0.023 | 0.00076 | 10. | 0.316 |
| 202 | N-(2-(4'-((2-Methoxyethoxy)methyl)-[1,1'-biphenyl]-4-yl)propan-2-yl)-1,4-diazabicyclo[3.2.2]nonane-4-carboxamide | 202 | 2.35 | 0.933 | 0.154 | 10. | 10. |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 203 | Quinuclidin-3-yl (2-(4'-((2-methoxyethoxy)methyl)-[1,1'-biphenyl]-3-yl)propan-2-yl)carbamate | 203 | 0.0296 | 0.0963 | 0.00653 | 10. | 1.78 |
| 204 | 1-Azabicyclo[3.2.2]nonan-4-yl (1-(4'-((2-methoxyethoxy)methyl)-[1,1'-biphenyl]-4-yl)cyclopropyl)carbamate | 204 | 0.0433 | 0.0993 | 0.00826 | 10. | 1.47 |
| 205 | 1-(1-(4'-((2-Methoxyethoxy)methyl)-[1,1'-biphenyl]-4-yl)cyclopropyl)-3-(3-methylquinuclidin-3-yl)urea | 205 | 0.0515 | 0.156 | 0.00531 | 10. | 1.78 |
| 206 | 1-(3-Ethylquinuclidin-3-yl)-3-(1-(4'-((2-methoxyethoxy)methyl)-[1,1'-biphenyl]-4-yl)cyclopropyl)urea | 206 | 0.0278 | 0.0596 | 0.00266 | 10. | 1.78 |
| 207 | 1-(1-(4'-((2-Methoxyethoxy)methyl)-[1,1'-biphenyl]-4-yl)cyclopropyl)-3-(4-methyl-1-azabicyclo[3.2.2]nonan-4-yl)urea | 207 | 0.0123 | 0.0313 | 0.00139 | 10. | 1.78 |
| 208 | 1-(3-Ethylquinuclidin-3-yl)-3-(1-(4'-((2-methoxyethoxy)methyl)-[1,1'-biphenyl]-4-yl)cyclopropyl)urea (single enantiomer A) | 208 | 2.71 | 0.988 | 0.0739 | 10. | 10. |
| 209 | 1-(3-Ethylquinuclidin-3-yl)-3-(1-(4'-((2-methoxyethoxy)methyl)-[1,1'-biphenyl]-4-yl)cyclopropyl)urea (single enantiomer B) | 209 | 0.0174 | 0.0392 | 0.00105 | 10. | 1.78 |
| 210 | (S)-1-(1-(4'-((2-Methoxyethoxy)methyl)-[1,1'-biphenyl]-4-yl)cyclopropyl)-3-(3-methylquinuclidin-3-yl)urea | 210 | 0.0502 | 0.087 | 0.00334 | 10. | 10. |
| 211 | (R)-1-(1-(4'-((2-Methoxyethoxy)methyl)-[1,1'-biphenyl]-4-yl)cyclopropyl)-3-(3-methylquinuclidin-3-yl)urea | 211 | 0.938 | 0.683 | 0.072 | 10. | 3.16 |
| 212 | 1-Azabicyclo[3.2.2]nonan-4-yl(1-(4'-(3-methoxypropyl)-[1,1'-biphenyl]-4-yl)cyclopropyl)carbamate | 212 | 0.00385 | 0.0479 | 0.00253 | 6.36 | 10. |
| 213 | 1-(1-(4'-(3-Methoxypropyl)-[1,1'-biphenyl]-4-yl)cyclopropyl)-3-(4-methyl-1-azabicyclo[3.2.2]nonan-4-yl)urea | 213 | 0.00112 | 0.0059 | 0.00035 | 9.22 | 10. |
| 214 | 1-(1-(4'-(3-Methoxypropyl)-[1,1'-biphenyl]-4-yl)cyclopropyl)-3-(3-methylquinuclidin-3-yl)urea | 214 | 0.00329 | 0.0329 | 0.00126 | 10. | 10. |
| 215 | 1-(3-Ethylquinuclidin-3-y])-3-(1-(4'-(3-methoxypropyl)-[1,1'-biphenyl]-4-yl)cyclopropyl)urea | 215 | 0.00248 | 0.0162 | 0.000542 | 7.55 | 10. |
| 216 | Quinuclidin-3-yl (1-(4'-((pyridin-3-ylmethoxy)methyl)-[1,1'-biphenyl]-4-yl)cyclopropyl)carbamate | 216 | 0.00933 | 0.201 | 0.0111 | 7.94 | 10. |
| 217 | 1-(3-Ethylquinuclidin-3-yl)-3-(1-(4'-((pyridin-3-ylmethoxy)methyl)-[1,1'-biphenyl]-4-yl)cyclopropyl)urea | 217 | 0.0133 | 0.168 | 0.00402 | 10. | 10. |
| 218 | 1-(3-Propylquinuclidin-3-yl)-3-(1-(4'-((pyridin-3-ylmethoxy)methyl)-[1,1'-biphenyl]-4-yl)cyclopropyl)urea | 218 | 0.011 | 0.0809 | 0.00297 | 7.95 | 10. |
| 219 | Quinuclidin-3-yl (1-(4'-((pyrimidin-5-ylmethoxy)methyl)-[1,1'-biphenyl]-4-yl)cyclopropyl)carbamate | 219 | 0.0466 | 0.118 | 0.0209 | 10. | 10. |
| 220 | 1-(3-Ethylquinuclidin-3-yl)-3-(1-(4'-((pyrimidin-5-ylmethoxy)methyl)-[1,1'-biphenyl]-4-yl)cyclopropyl)urea | 220 | 0.0516 | 0.114 | 0.00606 | 10. | 3.16 |
| 221 | 1-Azabicyclo[3.2.2]nonan-4-yl (1-(4'-((pyrimidin-5-ylmethoxy)methyl)-[1,1'-biphenyl]-4-yl)cyclopropyl)carbamate | 221 | 0.0521 | 0.0992 | 0.0211 | 10. | 10. |
| 222 | 1-(2-(4'-(3-Methoxypropyl)-[1,1'-biphenyl]-4-yl)propan-2-yl)-3-(3-methylquinuclidin-3-yl)urea | 222 | 0.0017 | 0.0307 | 0.000758 | 10. | 10. |
| 223 | Quinuclidin-3-yl(2-(4'-(hydroxymethyl)-[1,1'-biphenyl]-4-yl)propan-2-yl)carbamate | 223 | 0.454 | 0.881 | 0.0216 | 10. | 10. |
| 224 | 1-(2-(4'-(2-Hydroxyethyl)-[1,1'-biphenyl]-4-yl)propan-2-yl)-3-(3-propylquinuclidin-3-yl)urea | 224 | 0.0202 | 0.0643 | 0.0016 | 10. | 10. |
| 225 | 1-(3-Ethylquinuclidin-3-yl)-3-(2-(4'-(2-hydroxyethyl)-[1,1'-biphenyl]-4-yl)propan-2-yl)urea | 225 | 0.0294 | 0.229 | 0.00192 | 10. | 10. |
| 226 | Quinuclidin-3-yl (2-(4'-(2-hydroxyethyl)-[1,1'-biphenyl]-4-yl)propan-2-yl)carbamate | 226 | 0.148 | 0.656 | 0.0223 | 10. | 10. |
| 227 | Quinuclidin-3-yl (2-(4'-(2-(1H-1,2,3-triazol-4-yl)ethyl)-[1,1'-biphenyl]-4-yl)propan-2-yl)carbamate | 227 | 0.027 | 0.122 | 0.0104 | 10. | 1.0 |

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 228 | 1-Azabicyclo[3.2.2]nonan-4-yl (2-(4'-(2-(1H-1,2,3-triazol-4-yl)ethyl)-[1,1'-biphenyl]-4-yl)propan-2-yl)carbamate | 228 | 0.0182 | 0.0808 | 0.00608 | 7.65 | 3.16 |
| 229 | Quinuclidin-3-yl (2-(4'-(morpholinomethyl)-[1,1'-biphenyl]-4-yl)propan-2-yl)carbamate | 229 | 0.158 | 0.524 | 0.0532 | 10. | 10. |
| 230 | N-(2-(4'-(Morpholinomethyl)-[1,1'-biphenyl]-4-yl)propan-2-yl)-1,4-diazabicyclo[3.2.2]nonane-4-carboxamide | 230 | 2.28 | 1.79 | 0.417 | 10. | 10. |
| 231 | Quinuclidin-3-yl (2-(4'-morpholino-[1,1'-biphenyl]-4-yl)propan-2-yl)carbamate | 231 | 0.071 | 0.23 | 0.015 | 2.0 | 2.0 |
| 232 | 1-(3-Methylquinuclidin-3-yl)-3-(2-(4'-morpholino-[1,1'-biphenyl]-4-yl)propan-2-yl)urea | 232 | 0.0309 | 0.0642 | 0.00717 | 1.0 | 1.0 |
| 233 | 1-(4-Methyl-1-azabicyclo[3.2.2]nonan-4-yl)-3-(2-(4'-morpholino-[1,1'-biphenyl]-4-yl)propan-2-yl)urea | 233 | 0.00568 | 0.00551 | 0.000726 | 1.0 | 1.0 |
| 234 | 1-(3-Ethylquinuclidin-3-yl)-3-(2-(4'-morpholino-[1,1'-biphenyl]-4-yl)propan-2-yl)urea | 234 | 0.0146 | 0.0326 | 0.00181 | 1.0 | 1.0 |
| 235 | Quinuclidin-3-yl (2-(4'-(methylsulfonyl)-[1,1'-biphenyl]-4-yl)propan-2-yl)carbamate | 235 | 0.111 | 0.118 | 0.0199 | 10. | 10. |
| 236 | 1-(3-Ethylquinuclidin-3-yl)-3-(2-(4'-(methylsulfonyl)-[1,1'-biphenyl]-4-yl)propan-2-yl)urea | 236 | 0.0538 | 0.0744 | 0.00946 | 10. | 10. |
| 237 | 1-(2-(4'-(Methylsulfonyl-[1,1'-biphenyl]-4-yl)propan-2-yl)-3-(3-propylquinuclidin-3-yl)urea | 237 | 0.0354 | 0.0329 | 0.00671 | 10. | 10. |
| 238 | Quinuclidin-3-yl (2-(4'-((cyclopropylmethyl)sulfonyl)-[1,1'-biphenyl]-4-yl)propan-2-yl)carbamate | 238 | 0.0154 | 0.0501 | 0.00445 | 10. | 1.0 |
| 239 | 1-(2-(4'-((Cyclopropylmethyl)sulfonyl)-[1,1'-biphenyl]-4-yl)propan-2-yl)-3-(3-ethylquinuclidin-3-yl)urea | 239 | 0.00987 | 0.0285 | 0.00321 | 10. | 1.0 |
| 240 | 1-(2-(4'-((Cyclopropylmethyl)sulfonyl)-[1,1'-biphenyl]-4-yl)propan-2-yl)-3-(3-methylquinuclidin-3-yl)urea | 240 | 0.0133 | 0.0865 | 0.00597 | 10. | 1.0 |
| 241 | 1-Azabicyclo[3.2.2]nonan-4-yl (2-(4'-((cyclopropylmethyl)sulfonyl)-[1,1'-biphenyl]-4-yl)propan-2-yl)carbamate | 241 | 0.00423 | 0.0122 | 0.00144 | 10. | 3.16 |
| 242 | Quinuclidin-3-yl (2-(4'-((3-methoxypropyl)sulfonyl)-[1,1'-biphenyl]-4-yl)propan-2-yl)carbamate | 242 | 0.0325 | 0.0825 | 0.0102 | 10. | 3.16 |
| 243 | 1-(3-Ethylquinuclidin-3-yl)-3-(2-(4'-((3-methoxypropyl)sulfonyl)-[1,1'-biphenyl]-4-yl)propan-2-yl)urea | 243 | 0.0328 | 0.0573 | 0.00749 | 10. | 3.16 |
| 244 | 1-(2-(4'-((3-Methoxypropyl)sulfonyl)-[1,1'-biphenyl]-4-yl)propan-2-yl)-3-(3-propylquinuclidin-3-yl)urea | 244 | 0.0371 | 0.0341 | 0.00699 | 10. | 3.16 |
| 245 | Quinuclidin-3-yl (2-(4'-((3,3-dimethylbutyl)sulfonyl)-[1,1'-biphenyl]-4-yl)propan-2-yl)carbamate | 245 | 0.00185 | 0.0663 | 0.000716 | 6.74 | 0.316 |
| 246 | 1-(2-(4'-((3,3-Dimethylbutyl)sulfonyl)-[1,1'-biphenyl]-4-yl)propan-2-yl)-3-(3-methylquinuclidin-3-yl)urea | 246 | 0.0017 | 0.0114 | 0.000624 | 10. | 1.0 |
| 247 | 1-(2-(4'-((3,3-Dimethylbutyl)sulfonyl)-[1,1'-biphenyl]-4-yl)propan-2-yl)-3-(3-ethylquinuclidin-3-yl)urea | 247 | 0.00166 | 0.00428 | 0.000396 | 6.64 | 1.0 |
| 248 | 1-(2-(4'-((3,3-Dimethylbutyl)sulfonyl)-[1,1'-biphenyl]-4-yl)propan-2-yl)-3-(4-methyl-1-azabicyclo[3.2.2]nonan-4-yl)urea | 248 | 0.000804 | 0.00684 | 0.000315 | 7.73 | 1.0 |
| 249 | Quinuclidin-3-yl (2-(4'-(((1-(methoxymethyl)cyclopropyl)methyl)sulfonyl)-[1,1'-biphenyl]-4-yl)propan-2-yl)carbamate | 249 | 0.0535 | 0.247 | 0.00582 | 10. | 2.15 |
| 250 | 1-(3-Ethylquinuclidin-3-yl)-3-(2-(4'-(((1-(methoxymethyl)cyclopropyl)methyl)sulfonyl)-[1,1'-biphenyl]-4-yl)propan-2-yl)urea | 250 | 0.0201 | 0.0845 | 0.00441 | 10. | 1.0 |
| 251 | 1-(2-(4'-(((1-(Methoxymethyl)cyclopropyl)methyl)sulfonyl)-[1,1'-biphenyl]-4-yl)propan-2-yl)-3-(3-propylquinuclidin-3-yl)urea | 251 | 0.021 | 0.0475 | 0.00501 | 10. | 1.0 |
| 252 | Quinuclidin-3-yl (2-(4'-(methylcarbamoyl)-[1,1'-biphenyl]-4-yl)propan-2-yl)carbamate | 252 | 1.84 | 1.5 | 0.22 | 10. | 10. |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
| --- | --- | --- | --- | --- | --- | --- | --- |
| 253 | N-Methyl-4'-(2-(3-(3-methylquinuclidin-3-yl)ureido)propan-2-yl)-[1,1'-biphenyl]-4-carboxamide | 253 | 0.751 | 2.0 | 0.201 | 2.0 | 2.0 |
| 254 | 1-Azabicyclo[3.2.2]nonan-4-yl (2-(4'-(methylcarbamoyl)-[1,1'-biphenyl]-4-yl)propan-2-yl)carbamate | 254 | 0.60 | 0.65 | 0.0638 | 10. | 10. |
| 255 | N-Methyl-4'-(2-(3-(4-methyl-1-aza-bicyclo[3.2.2]nonan-4-yl)ureido)propan-2-yl)biphenyl-4-carboxamide | 255 | 0.0469 | 3.42 | 0.0201 | 6.79 | 1.0 |
| 256 | N-(2-(4'-(Methylcarbamoyl)biphenyl-4-yl)propan-2-yl)-1,4-diazabicyclo[3.2.2]nonane-4-carboxamide | 256 | 12.3 | 4.44 | 0.729 | 10. | 10. |
| 257 | Quinuclidin-3-yl 2-(4'-(dimethylcarbamoyl)biphenyl-4-yl)propan-2-ylcarbamate | 257 | 0.365 | 0.786 | 0.0772 | 10. | 10. |
| 258 | N,N-Dimethyl-4'-(2-(3-(3-methylquinuclidin-3-yl)ureido)propan-2-yl)biphenyl-4-carboxamide | 258 | 0.281 | 2.34 | 0.049 | 10. | 10. |
| 259 | 1-Azabicyclo[3.2.2]nonan-4-yl 2-(4'-(dimethylcarbamoyl)biphenyl-4-yl)propan-2-ylcarbamate | 259 | 0.134 | 0.179 | 0.0205 | 10. | 10. |
| 260 | N-(2-(4'-(Dimethylcarbamoyl)biphenyl-4-yl)propan-2-yl)-1,4-diazabicyclo[3.2.2]nonane-4-carboxamide | 260 | 8.55 | 1.64 | 0.302 | 10. | 10. |
| 261 | N,N-Dimethyl-4'-(2-(3-(4-methyl-1-azabicyclo[3.2.2]nonan-4-yl)ureido)propan-2-yl)biphenyl-4-carboxamide | 261 | 0.0608 | 0.354 | 0.0141 | 10. | 3.16 |
| 262 | Quinuclidin-3-yl 2-(4'-(piperidine-1-carbonyl)biphenyl-4-yl)propan-2-ylcarbamate | 262 | 0.0196 | 0.112 | 0.0035 | 10. | 1.0 |
| 263 | 1-Azabicyclo[3.2.2]nonan-4-yl 2-(4'-(piperidine-1-carbonyl)biphenyl-4-yl)propan-2-ylcarbamate | 263 | 0.0145 | 0.075 | 0.00301 | 10. | 1.0 |
| 264 | 1-(3-Ethylquinuclidin-3-yl)-3-(2-(4'-(piperidine-1-carbonyl)biphenyl-4-yl)propan-2-yl)urea | 264 | 0.0137 | 0.0674 | 0.00213 | 10. | 1.0 |
| 265 | Quinuclidin-3-yl 2-(4'-(morpholine-4-carbonyl)biphenyl-4-yl)propan-2-ylcarbamate | 265 | 0.48 | 0.454 | 0.0399 | 10. | 2.15 |
| 266 | 1-Azabicyclo[3.2.2]nonan-4-yl 2-(4'-(morpholine-4-carbonyl)biphenyl-4-yl)propan-2-ylcarbamate | 266 | 0.399 | 0.284 | 0.0227 | 10. | 1.0 |
| 267 | 1-(3-Methylquinuclidin-3-yl)-3-(2-(4'-(morpholine-4-carbonyl)biphenyl-4-yl)propan-2-yl)urea | 267 | 0.363 | 2.77 | 0.119 | 0.565 | 10. |
| 268 | 1-(4-Methyl-1-azabicyclo[3.2.2]nonan-4-yl)-3-(2-(4'-(morpholine-4-carbonyl)biphenyl-4-yl)propan-2-yl)urea | 268 | 0.166 | 0.648 | 0.0315 | 10. | 1.0 |
| 269 | N-(2-(4'-(Morpholine-4-carbonyl)biphenyl-4-yl)propan-2-yl)-1,4-diazabicyclo[3.2.2]nonane-4-carboxamide | 269 | 23. | 2.16 | 0.518 | 10. | 10. |
| 270 | Quinuclidin-3-yl 2-(4'-(4,4-difluoropiperidine-1-carbonyl)biphenyl-4-yl)propan-2-ylcarbamate | 270 | 0.025 | 0.067 | 0.00356 | 10. | 1.0 |
| 271 | 1-Azabicyclo[3.2.2]nonan-4-yl 2-(4'-(4,4-difluoropiperidine-1-carbonyl)biphenyl-4-yl)propan-2-ylcarbamate | 271 | 0.00942 | 0.0607 | 0.00264 | 10. | 0.316 |
| 272 | 1-(2-(4'-(4,4-Difluoropiperidine-1-carbonyl)biphenyl-4-yl)propan-2-yl)-3-(3-ethylquinuclidin-3-yl)urea | 272 | 0.0164 | 0.0249 | 0.00215 | 10. | 1.0 |
| 273 | Quinuclidin-3-yl 2-(4'-(3,3-difluoroazetidine-1-carbonyl)biphenyl-4-yl)propan-2-ylcarbamate | 273 | 0.108 | 0.074 | 0.0106 | 10. | 3.16 |
| 274 | 1-Aza-bicyclo[3.2.2]nonan-4-yl 2-(4'-(3,3-difluoroazetidine-1-carbonyl)biphenyl-4-yl)propan-2-ylcarbamate | 274 | 0.0304 | 0.0673 | 0.00478 | 10. | 1.0 |
| 275 | 1-(2-(4'-(3,3-Difluoroazetidine-1-carbonyl)biphenyl-4-yl)propan-2-yl)-3-(3-ethylquinuclidin-3-yl)urea | 275 | 0.0756 | 0.0554 | 0.00292 | 10. | 1.0 |
| 276 | 1-(4-Methyl-1-azabicyclo[3.2.2]nonan-4-yl)-3-(2-(3-(3-(morpholine-4-carbonyl)phenoxy)phenyl)propan-2-yl)urea | 276 | 0.020 | 1.53 | 0.0296 | 10. | 3.16 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 277 | 1-(3-Methylquinuclidin-3-yl)-3-(2-(3-(3-(morpholine-4-carbonyl)phenoxy)phenyl)propan-2-yl)urea | 277 | 0.0917 | 2.03 | 0.0801 | 10. | 10. |
| 278 | 1-Aza-bicyclo[3.2.2]nonan-4-yl 2-(3-(3-(morpholine-4-carbonyl)phenoxy)phenyl)propan-2-ylcarbamate | 278 | 0.593 | 1.44 | 0.053 | 10. | 10. |
| 279 | Quinuclidin-3-yl 2-(3-(3-(morpholine-4-carbonyl)phenoxy)phenyl)propan-2-ylcarbamate | 279 | 4.33 | 3.92 | 0.217 | 10. | 3.16 |
| 280 | 1-(3-Methylquinuclidin-3-yl)-3-(2-(4-(4-(morpholine-4-carbonyl)phenoxy)phenyl)propan-2-yl)urea | 280 | 0.164 | 1.94 | 0.0491 | 10. | 1.0 |
| 281 | 1-(4-Methyl-1-azabicyclo[3.2.2]nonan-4-yl)-3-(2-(4-(4-(morpholine-4-carbonyl)phenoxy)phenyl)propan-2-yl)urea | 281 | 0.0316 | 0.44 | 0.00779 | 10. | 1.0 |
| 282 | 1-Azabicyclo[3.2.2]nonan-4-yl 2-(4-(4-(morpholine-4-carbonyl)phenoxy)phenyl)propan-2-ylcarbamate | 282 | 0.479 | 0.66 | 0.0404 | 10. | 3.16 |
| 283 | Quinuclidin-3-yl 2-(4-(4-(dimethylcarbamoyl)phenoxy)phenyl)propan-2-ylcarbamate | 283 | 0.606 | 1.03 | 0.114 | 10. | 10. |
| 284 | N,N-Dimethyl-4-(4-(2-(3-(3-methylquinuclidin-3-yl)ureido)propan-2-yl)phenoxy)benzamide | 284 | 0.201 | 3.78 | 0.0607 | 10. | 10. |
| 285 | N,N-Dimethyl-4-(4-(2-(3-(4-methyl-1-azabicyclo[3.2.2]nonan-4-yl)ureido)propan-2-yl)phenoxy)benzamide | 285 | 0.0163 | 0.725 | 0.00648 | 10. | 1.0 |
| 286 | 1-Azabicyclo[3.2.2]nonan-4-yl 2-(4-(4-(dimethylcarbamoyl)phenoxy)phenyl)propan-2-ylcarbamate | 286 | 0.437 | 0.793 | 0.0316 | 10. | 10. |
| 287 | Quinuclidin-3-yl 2-(4-(4-(dimethylcarbamoyl)phenoxy)phenyl)propan-2-ylcarbamate | 287 | 1.33 | 2.2 | 0.229 | 10. | 3.16 |
| 288 | 1-Aza-bicyclo[3.2.2]nonan-4-yl 2-(3-(3-(dimethylcarbamoyl)phenoxy)phenyl)propan-2-ylcarbamate | 288 | 0.203 | 1.18 | 0.0502 | 10. | 10. |
| 289 | N,N-Dimethyl-3-(3-(2-(3-(3-methylquinuclidin-3-yl)ureido)propan-2-yl)phenoxy)benzamide | 289 | 0.104 | 1.41 | 0.0917 | 9.26 | 10. |
| 290 | N,N-Dimethyl-4-(4-(2-(3-(4-methyl-1-aza-bicyclo[3.2.2]nonan-4-yl)ureido)propan-2-yl)phenoxy)benzamide | 290 | 0.0191 | 2.58 | 0.0268 | 10. | 3.16 |
| 291 | Quinuclidin-3-yl 2-(4-(4-(methylcarbamoyl)phenoxy)phenyl)propan-2-ylcarbamate | 291 | 1.91 | 2.31 | 0.0902 | 10. | 3.16 |
| 292 | 1-Aza-bicyclo[3.2.2]nonan-4-yl 2-(4-(4-(methylcarbamoyl)phenoxy)phenyl)propan-2-ylcarbamate | 292 | 0.207 | 1.22 | 0.0412 | 10. | 10. |
| 293 | N-Methyl-4-(4-(2-(3-(3-methylquinuclidin-3-yl)ureido)propan-2-yl)phenoxy)benzamide | 293 | 0.186 | 5.37 | 0.046 | 10. | 1.0 |
| 294 | N-Methyl-4-(4-(2-(3-(4-methyl-1-aza-bicyclo[3.2.2]nonan-4-yl)ureido)propan-2-yl)phenoxy)benzamide | 294 | 0.0124 | 0.843 | 0.00706 | 10. | 1.0 |
| 295 | 2-(3-(3-(Methylcarbamoyl)phenoxy)phenyl)propan-2-ylcarbamate | 295 | 1.02 | 1.75 | 0.147 | 10. | 10. |
| 296 | N-Methyl-3-(3-(2-(3-(3-methylquinuclidin-3-yl)ureido)propan-2-yl)phenoxy)benzamide | 296 | 0.20 | 5.47 | 0.155 | 10. | 10. |
| 297 | N-Methyl-3-(3-(2-(3-(4-methyl-1-aza-bicyclo[3.2.2]nonan-4-yl)ureido)propan-2-yl)phenoxy)benzamide | 297 | 0.0102 | 1.37 | 0.0132 | 10. | 1.0 |
| 298 | 1-Aza-bicyclo[3.2.2]nonan-4-yl 2-(3-(3-(methylcarbamoyl)phenoxy)phenyl)propan-2-ylcarbamate | 298 | 0.138 | 1.1 | 0.0308 | 10. | 3.16 |
| 299 | 1-Aza-bicyclo[3.2.2]nonan-4-yl 2-(4-(4-(piperidine-1-carbonyl)phenoxy)phenyl)propan-2-ylcarbamate | 299 | 0.0154 | 0.192 | 0.00367 | 10. | 1.0 |
| 300 | 1-(4-Methyl-1-aza-bicyclo[3.2.2]nonan-4-yl)-3-(2-(4-(4-(piperidine-1-carbonyl)phenoxy)phenyl)propan-2-yl)urea | 300 | 0.00685 | 0.0876 | 0.00154 | 10. | 0.316 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 301 | 1-Azabicyclo[3.2.2]nonan-4-yl 2-(4-(4-(4,4-difluoropiperidine-1-carbonyl)phenoxy)phenyl)propan-2-ylcarbamate | 301 | 0.0172 | 0.0494 | 0.00339 | 10. | 1.0 |
| 302 | 1-(2-(4-(4-(4,4-Difluoropiperidine-1-carbonyl)phenoxy)phenyl)propan-2-yl)-3-(4-methyl-1-azabicyclo[3.2.2]nonan-4-yl)urea | 302 | 0.00422 | 0.0317 | 0.00147 | 10. | 1.0 |
| 303 | 1-(2-(4-(4-(3,3-Difluoroazetidine-1-carbonyl)phenoxy)phenyl)propan-2-yl)-3-(4-methyl-1-aza-bicyclo[3.2.2]nonan-4-yl)urea | 303 | 0.00763 | 0.0389 | 0.00124 | 10. | 0.316 |
| 304 | Quinuclidin-3-yl 2-(4-(4-phenylpiperazine-1-carbonyl)phenyl)propan-2-ylcarbamate | 304 | 1.73 | 0.355 | 0.0959 | 10. | 10. |
| 305 | N-(2-(4-(4-(Methylcarbamoyl)phenoxy)phenyl)propan-2-yl)-1,4-diaza-bicyclo[3.2.2]nonane-4-carboxamide | 305 | 0.399 | 0.299 | 0.0195 | 10. | 1.0 |
| 306 | 1-(3-Ethylquinuclidin-3-yl)-3-(2-(4-(4-phenylpiperazine-1-carbonyl)phenyl)propan-2-yl)urea | 306 | 0.0951 | 0.257 | 0.032 | 10. | 3.16 |
| 307 | Quinuclidin-3-yl 2-(4-(6-(2-methoxyethoxy)pyridin-3-yl)phenyl)propan-2-ylcarbamate | 307 | 0.735 | 4.34 | 0.0972 | 10. | 10. |
| 309 | Quinuclidin-3-yl 2-(4-(6-(2-methoxyethoxy)pyridin-3-yl)phenyl)propan-2-ylcarbamate | 309 | 0.106 | 0.188 | 0.014 | 10. | 3.16 |
| 308 | Quinuclidin-3-yl 2-(4-(5-(2-methoxyethoxy)pyridin-2-yl)phenyl)propan-2-ylcarbamate | 308 | 0.254 | 0.314 | 0.0358 | 7.77 | 1.0 |
| 312 | Quinuclidin-3-yl (2-(3-(6-(3-methoxypropoxy)pyridazin-3-yl)phenyl)propan-2-yl)carbamate | 312 | 1.66 | 1.34 | 0.103 | 10. | 1.0 |
| 313 | 1-Azabicyclo[3.2.2]nonan-4-yl (2-(3-(6-(3-methoxypropoxy)pyridazin-3-yl)phenyl)propan-2-yl)carbamate | 313 | 0.0889 | 0.47 | 0.0107 | 10. | 10. |
| 314 | N-(2-(3-(6-(3-Methoxypropoxy)pyridazin-3-yl)phenyl)propan-2-yl)-1,4-diazabicyclo[3.2.2]nonane-4-carboxamide | 314 | 2.63 | 4.91 | 0.118 | 10. | 10. |
| 315 | Quinuclidin-3-yl (2-(3-(5-(3-methoxypropoxy)pyrazin-2-yl)phenyl)propan-2-yl)carbamate | 315 | 0.197 | 0.435 | 0.0259 | 10. | 1.0 |
| 316 | 1-Azabicyclo[3.2.2]nonan-4-yl (2-(3-(5-(3-methoxypropoxy)pyrazin-2-yl)phenyl)propan-2-yl)carbamate | 316 | 0.028 | 0.152 | 0.00439 | 10. | 10. |
| 317 | N-(2-(3-(5-(3-Methoxypropoxy)pyrazin-2-yl)phenyl)propan-2-yl)-1,4-diazabicyclo[3.2.2]nonane-4-carboxamide | 317 | 0.295 | 0.656 | 0.0291 | 10. | 1.0 |
| 318 | Quinuclidin-3-yl (2-(3-(6-ethoxypyridazin-3-yl)phenyl)propan-2-yl)carbamate | 318 | 1.46 | 0.635 | 0.0699 | #NUM! | 1.0 |
| 319 | 1-Azabicyclo[3.2.2]nonan-4-yl (2-(3-(6-ethoxypyridazin-3-yl)phenyl)propan-2-yl)carbamate | 319 | 0.075 | 0.121 | 0.00804 | 10. | 10. |
| 310 | 1-Azabicyclo[3.2.2]nonan-4-yl 2-(4-(5-(2-methoxyethoxy)pyridin-2-yl)phenyl)propan-2-ylcarbamate | 310 | 0.123 | 0.145 | 0.0121 | 10. | 3.16 |
| 320 | Quinuclidin-3-yl (2-(4-(5-(3-methoxypropoxy)pyrazin-2-yl)phenyl)propan-2-yl)carbamate | 320 | 0.131 | 0.201 | 0.0112 | 10. | 1.0 |
| 321 | 1-Azabicyclo[3.2.2]nonan-4-yl (2-(4-(5-(3-methoxypropoxy)pyrazin-2-yl)phenyl)propan-2-yl)carbamate | 321 | 0.0461 | 0.108 | 0.00639 | 10. | 1.0 |
| 322 | N-(2-(4-(5-(3-methoxypropoxy)pyrazin-2-yl)phenyl)propan-2-yl)-1,4-diazabicyclo[3.2.2]nonane-4-carboxamide | 322 | 1.07 | 1.44 | 0.0999 | 10. | 1.0 |
| 311 | 1-Azabicyclo[3.2.2]nonan-4-yl 2-(3-(5-(2-methoxyethoxy)pyridin-2-yl)phenyl)propan-2-ylcarbamate | 311 | 0.076 | 0.103 | 0.0085 | 10. | 3.16 |
| 323 | Quinuclidin-3-yl (2-(3-(5-(3-methoxypropoxy)pyrimidin-2-yl)phenyl)propan-2-yl)carbamate | 323 | 1.16 | 0.508 | 0.0488 | 10. | 1.0 |
| 324 | 1-Azabicyclo[3.2.2]nonan-4-yl (2-(3-(5-(3-methoxypropoxy)pyrimidin-2-yl)phenyl)propan-2-yl)carbamate | 324 | 0.0969 | 0.157 | 0.00849 | 10. | 1.0 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
| --- | --- | --- | --- | --- | --- | --- | --- |
| 325 | 1-(3-Ethylquinuclidin-3-yl)-3-(4-(4-(2-methoxyethyl)phenyl)-2-methylbut-3-yn-2-yl)urea | 325 | 0.092 | 0.399 | 0.00794 | 10. | 10. |
| 326 | 1-(4-(4-(2-Methoxyethyl)phenyl)-2-methylbut-3-yn-2-yl)-3-(3-propylquinuclidin-3-yl)urea | 326 | 0.0266 | 0.123 | 0.00429 | 3.16 | 3.16 |
| 327 | 1-(3-Ethylquinuclidin-3-yl)-3-(4-(4-(methoxymethyl)phenyl)-2-methylbut-3-yn-2-yl)urea | 327 | 0.0962 | 0.343 | 0.0147 | 10. | 10. |
| 328 | 1-(4-(4-(Methoxymethyl)phenyl)-2-methylbut-3-yn-2-yl)-3-(3-propylquinuclidin-3-yl)urea | 328 | 0.0251 | 0.115 | 0.00332 | 3.16 | 3.16 |
| 329 | Quinuclidin-3-yl (4-(4-(2-methoxyethoxy)phenyl)-2-methylbut-3-yn-2-yl)carbamate | 329 | 3.14 | 2.7 | 0.284 | 10. | 10. |
| 330 | 1-(4-(4-(2-Methoxyethoxy)phenyl)-2-methylbut-3-yn-2-yl)-3-(3-propylquinuclidin-3-yl)urea | 330 | 0.104 | 0.203 | 0.00641 | 10. | 3.16 |
| 331 | Quinuclidin-3-yl (4-(4-(3-methoxypropoxy)phenyl)-2-methylbut-3-yn-2-yl)carbamate | 331 | 1.33 | 1.76 | 0.118 | 10. | 10. |
| 332 | 1-(3-Ethylquinuclidin-3-yl)-3-(2-methyl-4-(4-((pyridin-3-ylmethoxy)methyl)phenyl)but-3-yn-2-yl)urea | 332 | 0.0494 | 0.945 | 0.0155 | 10. | 10. |
| 333 | 1-(2-Methyl-4-(4-((pyridin-3-ylmethoxy)methyl)phenyl)but-3-yn-2-yl)-3-(3-propylquinuclidin-3-yl)urea | 333 | 0.0161 | 0.413 | 0.00618 | 10. | 3.16 |
| 334 | Quinuclidin-3-yl (4-(4-((3,3-dimethylbutyl)sulfonyl)phenyl)-2-methylbut-3-yn-2-yl)carbamate | 334 | 0.0802 | 0.317 | 0.0118 | 3.28 | 10. |
| 335 | 1-Azabicyclo[3.2.2]nonan-4-yl (4-(4-((3,3-dimethylbutyl)sulfonyl)phenyl)-2-methylbut-3-yn-2-yl)carbamate | 335 | 0.0146 | 0.193 | 0.00432 | 2.15 | 1.0 |
| 336 | 1-(4-(4-((3,3-Dimethylbutyl)sulfonyl)phenyl)-2-methylbut-3-yn-2-yl)-3-(4-methyl-1-azabicyclo[3.2.2]nonan-4-yl)urea | 336 | 0.0012 | 0.0388 | 0.000902 | 10. | 10. |
| 337 | 1-(4-(4-((3,3-Dimethylbutyl)sulfonyl)phenyl)-2-methylbut-3-yn-2-yl)-3-(3-methylquinuclidin-3-yl)urea | 337 | 0.0145 | 0.0941 | 0.00254 | 2.15 | 1.0 |
| 338 | 1-(4-(4-((3,3-Dimethylbutyl)sulfonyl)phenyl)-2-methylbut-3-yn-2-yl)-3-(3-ethylquinuclidin-3-yl)urea | 338 | 0.00445 | 0.0721 | 0.000984 | 2.15 | 1.0 |
| 339 | 1-(4-(4-(1-Methoxy-2-methylpropan-2-yl)phenyl)-2-methylbut-3-yn-2-yl)-3-(3-methylquinuclidin-3-yl)urea | 339 | 0.136 | 0.72 | 0.0257 | 10. | 10. |
| 340 | Quinuclidin-3-yl (2-(2-(4-(3-methoxypropoxy)phenyl)thiazol-4-yl)-propan-2-yl)carbamate | 340 | 0.17 | 0.197 | 0.0426 | 10. | 10. |
| 341 | 1-Azabicyclo[3.2.2]nonan-4-yl (2-(2-(4-(3-methoxypropoxy)phenyl)thiazol-4-yl)propan-2-yl)carbamate | 341 | 0.0193 | 0.0904 | 0.00719 | 10. | 10. |
| 342 | N-(2-(2-(4-(3-Methoxypropoxy)phenyl)thiazol-4-yl)propan-2-yl)-1,4-diazabicyclo[3.2.2]nonane-4-carboxamide | 342 | 0.666 | 0.393 | 0.0851 | 10. | 10. |
| 343 | Quinuclidin-3-yl (2-(2-(4-(2-methoxyethoxy)phenyl)thiazol-4-yl)propan-2-yl)carbamate | 343 | 0.36 | 0.106 | 0.0198 | 10. | 1.0 |
| 344 | 1-Azabicyclo[3.2.2]nonan-4-yl (2-(2-(4-(2-methoxyethoxy)phenyl)thiazol-4-yl)propan-2-yl)carbamate | 344 | 0.0658 | 0.0564 | 0.00876 | 10. | 1.0 |
| 345 | N-(2-(2-(4-(2-Methoxyethoxy)phenyl)thiazol-4-yl)propan-2-yl)-1,4-diazabicyclo[3.2.2]nonane-4-carboxamide | 345 | 2.54 | 0.369 | 0.091 | 10. | 3.16 |
| 346 | Quinuclidin-3-yl 2-(5-(4-(2-methoxyethoxy)phenyl)pyridin-2-yl)propan-2-ylcarbamate | 346 | 0.0507 | 0.266 | 0.0111 | 10. | 3.16 |
| 347 | 1-Azabicyclo[3.2.2]nonan-4-yl 2-(5-(4-(2-methoxyethoxy)phenyl)pyridin-2-yl)propan-2-ylcarbamate | 347 | 0.0368 | 0.15 | 0.00582 | 10. | 1.41 |

-continued

| Compound Number | Compound Name | Example Number | GCS IC50 (uM) | GM3 B16 IC50 (uM) | GM3 C32 IC50 (uM) | Viability, B16 IC50 (uM) | Viability, C32 IC50 (uM) |
|---|---|---|---|---|---|---|---|
| 348 | 1-Azabicyclo[3.2.2]nonan-4-yl 2-(5-(4-(2-methoxyethoxy)phenyl)pyridin-2-yl)propan-2-ylcarbamate (single enantiomer A) | 348 | 0.0278 | 0.0872 | 0.00352 | 10. | 1.0 |
| 349 | 1-Azabicyclo[3.2.2]nonan-4-yl 2-(5-(4-(2-methoxyethoxy)phenyl)pyridin-2-yl)propan-2-ylcarbamate (single enantiomer B) | 349 | 0.25 | 0.233 | 0.0144 | 10. | 1.0 |

Example 351

Glucosylceramide Synthase Inhibition in a Model of Polycystic Kidney Disease

Mice homozygous for the Nek8jck mutation develop polycystic kidney disease ("jck mice"). Histology reveals that the kidneys of some 3 day old pups from heterozygous parents had small isolated cysts lined by cuboidal epithelial cells, and 15 day old pups had cysts lined by flattened epithelia. Disease is progressive but not evident by kidney palpation until at least 4 to 5 weeks of age. Homozygotes generally remain active until shortly before death and usually die between 20 and 25 weeks of age. Homozygous females are fertile but do not consistently care for their litters; homozygous males are fertile but decreased fertility is reported after 15 weeks of age. No histologic abnormalities are found in the liver, spleen, or pancreas. (Atala et al., 1993).

To evaluate the effects of a GCS inhibitor on polycystic kidney disease, Compound 156, (S)-quinuclidin-3-yl (2-(4'-(2-methoxyethoxy)-[1,1'-biphenyl]-4-yl)propan-2-yl)carbamate was administered in the feed of jck mice at doses of 15, 30 and 50 mg/kg. A second compound, quinuclidin-3-yl (2-(4'-fluoro-[1,1'-biphenyl]-3-yl)propan-2-yl)carbamate (hereinafter "GZ 161") was administered in the feed of jck mice at a dose of 60 mg/kg.

Administration of the compound was started between 3 and 4 weeks of age, and continued until the mice were sacrificed at 9 weeks of age. The effect of the compounds on the disease phenotype was evaluated by measurement of body weight, blood urea nitrogen ("BUN"), and serum GL1. Additional effects on kidney/body weight (K/BW), cyst volume, BUN, kidney GL1, and serum GL1 were also measured at the end of life time point of the study.

Figure 3:
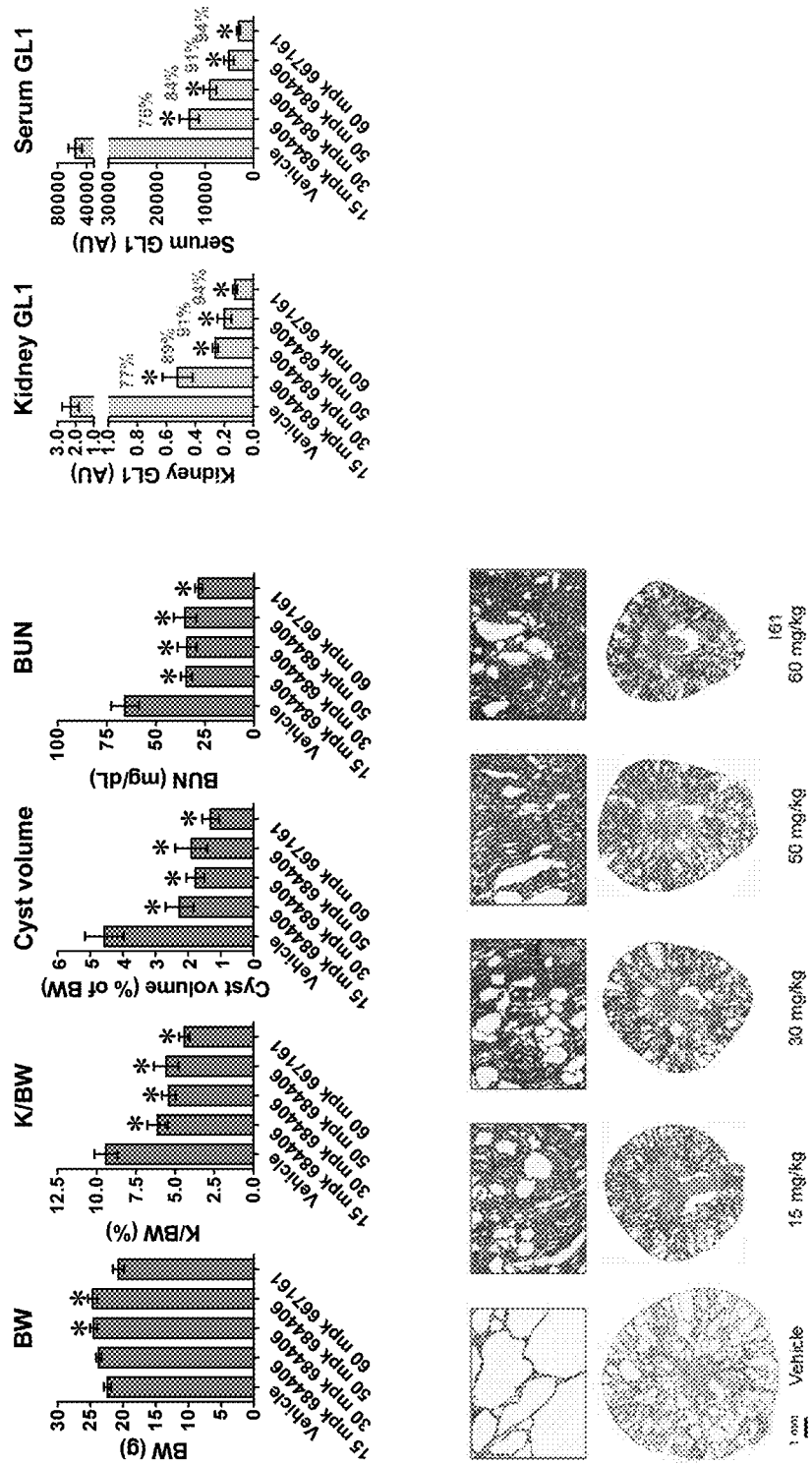
FIG. 3 presents the effects of a GCS inhibitor, (S)-Quinuclidin-3-yl (2-(4'-(2-methoxyethoxy)-[1,1'-biphenyl]-4-yl)propan-2-yl)carbamate, in a mouse model of polycystic kidney disease, jck mice, at several dose levels.

As demonstrated in FIG. 3, Compound 156 caused a dose-dependent inhibition of GL1 that is associated with reduced cyst growth and preservation of kidney function.

The dose dependent reductions are provided graphically as well as numerically wherein the percentages expressed are the percent reductions in the GL1 levels as compared to the vehicle control groups. FIG. 3 demonstrates the body weight measurements between the vehicle control group, the three doses of Compound 156 groups tested, and the GZ 161 group, wherein the 30 mg/kg and 50 mg/kg doses Compound 156 are statistically different from the vehicle control group. FIG. 3 also demonstrates the kidney to body weight measurements between the vehicle control group, the three doses of Compound 156 groups tested, and the GZ 161 group, wherein all of the Compound 156 groups and the GZ 161 groups are statistically different from the vehicle control group. FIG. 3 also demonstrates the cyst volume and the BUN measurements between the vehicle control group, the three doses of Compound 156 tested, and the GZ 161 group, wherein all of the GZ 406 groups and the Compound 156 groups are statistically different from the vehicle control group.

The invention claimed is:

1. A compound of the formula

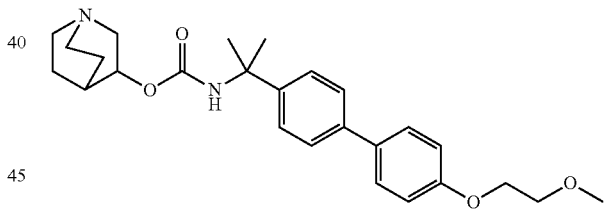

or a pharmaceutically acceptable salt thereof.

2. A pharmaceutical composition comprising an effective amount of a compound according to claim 1 and at least one pharmaceutically acceptable carrier.

* * * * *